US008367709B2

(12) United States Patent
Pinto et al.

(10) Patent No.: US 8,367,709 B2
(45) Date of Patent: Feb. 5, 2013

(54) DIPEPTIDE ANALOGS AS COAGULATION FACTOR INHIBITORS

(75) Inventors: Donald J. P. Pinto, Churchville, PA (US); Mimi L. Quan, Yardley, PA (US); Leon M. Smith, II, Somerset, NJ (US); Michael J. Orwat, New Hope, PA (US); Paul J. Gilligan, Wilmington, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 352 days.

(21) Appl. No.: 12/663,861

(22) PCT Filed: Jun. 11, 2008

(86) PCT No.: PCT/US2008/066506
§ 371 (c)(1),
(2), (4) Date: Dec. 10, 2009

(87) PCT Pub. No.: WO2008/157162
PCT Pub. Date: Dec. 24, 2008

(65) Prior Publication Data
US 2010/0173899 A1 Jul. 8, 2010

Related U.S. Application Data

(60) Provisional application No. 60/943,791, filed on Jun. 13, 2007, provisional application No. 61/049,516, filed on May 1, 2008.

(51) Int. Cl.
*A01N 43/64* (2006.01)
*A61K 31/41* (2006.01)
(52) U.S. Cl. ..................... 514/381; 548/253
(58) Field of Classification Search .................. 548/253
See application file for complete search history.

(56) References Cited

U.S. PATENT DOCUMENTS

| 7,429,604 B2 | 9/2008 | Corte et al. |
| 7,453,002 B2 | 11/2008 | Hangeland et al. |
| 7,459,564 B2 | 12/2008 | Corte et al. |
| 7,626,039 B2 | 12/2009 | Pinto et al. |
| 2004/0180855 A1 | 9/2004 | Schumacher et al. |
| 2009/0181983 A1 | 7/2009 | Corte |
| 2009/0253766 A1 | 10/2009 | Han |

FOREIGN PATENT DOCUMENTS

| BE | 667776 | * | 2/1966 |
| EP | 622361 A1 | * | 11/1994 |
| WO | WO02/064559 A2 | | 8/2002 |
| WO | WO2004/032834 A2 | | 4/2004 |

OTHER PUBLICATIONS

I.W. Elliott et al., 27 Journal of Organic Chemistry 3302-3305 (1961).*
U.S. Appl. No. 12/518,111, filed Dec. 30, 2007, Pinto.

Bouma, B. N. et al., "Thrombin-Activatable Fibrinolysis Inhibitor (TAFI, Plasma Procarboxypeptidase B, Procarboxypeptidase R, Procarboxypeptidase U)", Thrombosis Research, vol. 101, pp. 329-354 (2001).
Chan, J.C.Y. et al., "The Characterization of Mice with a Targeted Combined Deficiency of Protein C and Factor XI", American J. of Pathology, vol. 158(2), pp. 469-479 (2001).
Coleman, R. "Contact Activation Pathway: inflammatory, Fibrinolytic, Anticoagulant, Antiadhesive, and Antiagiogenic Activities", Hemostasis and Thrombosis, Chapter 6, pp. 103-122 (2001).
Gailani, D., "Activation of Factor IX by Factor Xia", Trends Cardiovascular Medicine, vol. 10(5), pp. 198-204 (2000).
Gruber, A. et al., "Factor XI-dependence of surface-and tissue factor-initiated thrombus propagation in primates", Blood, vol. 102(3), pp. 953-955 (2003).
Hoffman, M., "A cell-based model of coagulation and the role of factor VIIa", Blood Reviews, vol. 17, pp. S1-S5, (2003).
Howard, N. et al., "Application of Fragment Screening and Fragment Linking to the Discovery of Novel Thrombin Inhibitors", J. Med. Chem., vol. 49, pp. 1346-1355 (2006).
Kleinschnitz, C. et al., "Targeting coagulation factor XII provides protection from pathological thrombosis in cerebral ischemia without interfering with hemostasis", The J. of Experimental Medicine, vol. 203(3), pp. 513-518 (2006).
Renné, T. et al., "Defective thrombus formation in mice lacking coagulation factor XII", The J. of Experimental Medicine, vol. 202(2), pp. 271-281 (2005).
Rosen, E. et al., "FXI is Essential for Thrombus Formation Following FeCl$_3$-induced Injury of the Carotid Artery in the Mouse", Thromb Haemost, vol. 87, pp. 774-776 (2002).

(Continued)

*Primary Examiner* — James O Wilson
*Assistant Examiner* — Alexander R Pagano
(74) *Attorney, Agent, or Firm* — Hong Liu

(57) ABSTRACT

Disclosed are novel dipeptide analogs compounds of Formula (I), (II) or (III):

or a stereoisomer, a tautomer, a pharmaceutically acceptable salt, a solvate, or a prodrug thereof, which are inhibitors of factor XIa and/or plasma kallikrein, compositions containing them, and methods of using them, for example, for the treatment or prophylaxis of thrombotic diseases.

11 Claims, No Drawings

OTHER PUBLICATIONS

Schmaier, A. H., "Contact Activation", Chapter 5, Thrombosis and Hemorrhage, pp. 105-128 (1998).

Shariat-Madar, Z. et al., "Bradykinin B2 receptor knockout mice are protected from thrombosis by increased nitric oxide and prostacyclin", Blood, vol. 108, pp. 192-199 (2006).

Walsh, P., "Platelets and Factor XI Bypass the Contact System of Blood Coagulation", Thrombosis and Haemostasis, vol. 82(2), pp. 234-242 (1999).

Wang, X. et al., "Effects of factor IX or factor XI deficiency of ferric chloride-induced carotid artery occlusion in mice", J. of Thrombosis and Haemostasis, vol. 3, pp. 695-702 (2005).

* cited by examiner

DIPEPTIDE ANALOGS AS COAGULATION FACTOR INHIBITORS

CROSS-REFERENCE TO RELATED APPLICATIONS

The present application is a 371 application of PCT/US2008/066506 filed Jun. 11, 2008, which claims priority benefit of U.S. provisional application Ser. No. 60/943,791, filed Jun. 13, 2007; and Ser. No. 61/049,516, filed May 1, 2008, each of which is incorporated by reference herein.

FIELD OF THE INVENTION

The present invention provides novel dipeptide analogs that inhibit factor XIa and/or plasma kallikrein, compositions containing them, and methods of using them, for example, for the treatment or prophylaxis of thromboembolic disorders.

BACKGROUND OF THE INVENTION

Thromboembolic diseases remain the leading cause of death in developed countries despite the availability of anticoagulants such as warfarin (Coumadin®), heparin, low molecular weight heparins (LMWH), and synthetic pentasaccharides and antiplatelet agents such as aspirin and clopidogrel (Plavix®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor XIa (FXIa). Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Walsh, P. N. Thromb. Haemostasis. 1999, 82, 234-242.) The resulting burst of thrombin converts fibrinogen to fibrin that polymerizes to form the structural framework of a blood clot, and activates platelets, which are a key cellular component of coagulation (Hoffman, M. Blood Reviews 2003, 17, S1-S5). Therefore, factor XIa plays a key role in propagating this amplification loop and is thus an attractive target for anti-thrombotic therapy.

SUMMARY OF THE INVENTION

The present invention provides dipeptide analogs that are useful as selective inhibitors of serine protease enzymes, especially factor XIa and/or plasma kallikrein, or stereoisomers, tautomers, pharmaceutically acceptable salts, solvates, or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for the treatment or prophylaxis of thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment or prophylaxis of a thromboembolic disorder.

These and other features of the invention will be set forth in expanded form as the disclosure continues.

DETAILED DESCRIPTION OF THE INVENTION

I. Compounds of the Invention

In a first aspect, the present invention provides, inter alia, compounds of Formula (I), (II), or (III):

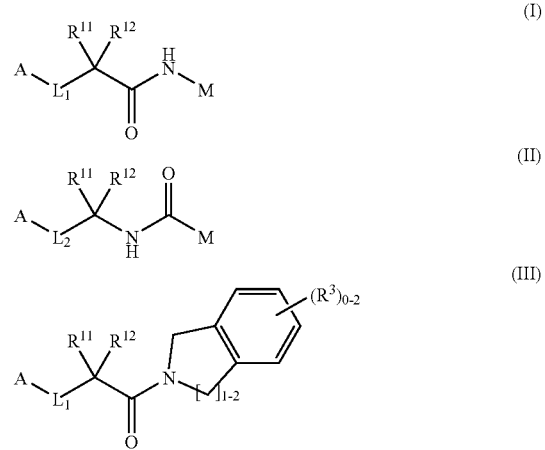

or a stereoisomer, a tautomer, a pharmaceutically acceptable salt, a solvate, or a prodrug thereof, wherein:

A is a $C_{3-10}$ carbocycle further substituted with 0-3 $R^1$ or a 5- to 10-membered heterocycle comprising: carbon atoms and 1-4 heteroatoms selected from N, $NR^{13}$, O, and $S(O)_p$, wherein said heterocycle is substituted with 0-3 $R^1$;

provided that when A is a heterocycle containing one or more nitrogen atoms, then A is not attached to L via any of the nitrogen atoms on the A ring;

$L_1$ is —CH($R^5$)CH$_2$C(O)NH—, —CH(NR$^7$R$^8$)CH$_2$C(O) NH—, —C($R^5$)═CHC(O)NH—, —CH═C($R^5$)C(O) NH—, —C($R^5$)═C($R^5$)C(O)NH—, —CH$_2$C(O)NHCH$_2$—, —C≡CC(O)NH—, —CH$_2$NHC(O)NH—, —C(O) NHCH$_2$CH$_2$—, —CH($R^5$)CH$_2$SO$_2$NH—, —C($R^5$)

=CHSO₂NH—, —CH₂SO₂NHCH₂—, —SO₂NHCH₂CH₂—, —NHNHC(O)CH₂—, —CH₂C(O)NHNH—, —CH($R^5$)CH₂CH₂N$R^{10}$—, —CH₂NHC(O)CH₂—, —NHC(O)CH₂CH₂—, —N($R^7$)CH₂C(O)NH—, —NHC(O)NHCH₂—, —NHC(O)OCH₂—, —CH₂NHSO₂CH₂—, —NHSO₂CH₂CH₂—, —CH₂OC(O)NH—, —OCH₂C(O)NH—, or —S(O)$_p$CH₂C(O)NH—;

L₂ is —NHNHC(O)CH₂—, —CH($R^5$)CH₂NHC(O)—, —CH(N$R^7R^8$)CH₂NHC(O)—, —C($R^5$)=CHNHC(O)—, —CH₂NHC(O)CH₂—, —C≡CNHC(O)—, —NHC(O)CH₂CH₂—, —CH($R^5$)CH₂NHSO₂—, —C($R^5$)=CHNHSO₂—, —CH₂NHSO₂CH₂—, —NHSO₂CH₂CH₂—, —CH₂NHNHC(O)—, —CONHNHC(O)—, or —COCH₂NHC(O)—;

M is —(CH₂)$_r$—C$_{3-10}$ carbocycle substituted with 0-3 $R^3$ or a —(CH₂)$_r$-5- to 12-membered heterocycle comprising: carbon atoms and 1-4 heteroatoms selected from N, N$R^{13}$, O, and S(O)$_p$, wherein said heterocycle is substituted with 0-3 $R^3$;

$R^1$ is, independently at each occurrence, =O, F, Cl, Br, OCF₃, CF₃, CHF₂, OCF₃, CN, NO₂, —(CH₂)$_r$O$R^a$, —(CH₂)$_r$S$R^a$, —(CH₂)$_r$C(O)$R^a$, —(CH₂)$_r$C(O)O$R^a$, —(CH₂)$_r$OC(O)$R^a$, —(CH₂)$_r$N$R^7R^8$, —C(=N$R^8$)N$R^8R^9$, —(CH₂)$_r$C(O)N$R^8R^9$, —(CH₂)$_r$N$R^8$C(O)$R^c$, —(CH₂)$_r$N$R^8$C(O)O$R^c$, —CO₂(CH₂)$_r$N$R^7R^8$, —N$R^8$C(O)N$R^8R^c$, —S(O)$_p$N$R^8R^9$, —(CH₂)$_r$N$R^8$C(O)N$R^8R^c$, —(CH₂)$_r$S(O)$_p$N$R^8R^9$, —(CH₂)$_r$N$R^8$S(O)$_p$$R^c$, —(CH₂)$_r$S(O)$R^c$, —(CH₂)$_r$S(O)₂$R^c$, C$_{1-6}$ alkyl substituted with 0-1 $R^2$, —(CH₂)$_r$-3-7 membered carbocycle optionally substituted with 0-2 $R^{2a}$, or —(CH₂)$_r$-5-7 membered heterocycle comprising carbon atoms and 1-4 heteroatoms selected from N, N$R^{13}$, O, and S(O)$_p$, wherein said heterocycle is substituted with 0-2 $R^{2a}$;

$R^2$ is F, OCF₃, CF₃, O$R^a$, S$R^a$, CN, —N$R^7R^8$, —C(O)N$R^8R^9$, —N$R^8$C(O)$R^c$, —N$R^8$C(O)O$R^c$, —N$R^8$C(O)N$R^8R^c$, —S(O)$_p$N$R^8R^9$, —N$R^8$SO₂$R^c$, or —(CF₂)$_r$CF₃;

$R^{2a}$ is, independently at each occurrence, =O, F, Br, Cl, OCF₃, CF₃, —(CH₂)$_r$O$R^a$, —(CH₂)$_r$S$R^a$, —(CH₂)$_r$CN, —(CH₂)$_r$N$R^7R^8$, —(CH₂)$_r$C(O)O$R^a$, —(CH₂)$_r$OC(O)$R^a$, —(CH₂)$_r$C(O)N$R^8R^9$, —(CH₂)$_r$N$R^8$C(O)$R^c$, —(CH₂)$_r$N$R^8$C(O)O$R^c$, —(CH₂)$_r$S(O)$_p$N$R^8R^9$, —(CH₂)$_r$N$R^8$SO₂$R^c$, C$_{1-4}$ alkyl or —(CF₂)$_r$CF₃;

$R^3$ is, independently at each occurrence, =O, F, Cl, Br, I, OCF₃, CF₃, —(CH₂)$_r$CN, NO₂, —(CH₂)$_r$O$R^{3b}$, —(CH₂)$_r$S$R^{3b}$, —(CH₂)$_r$N$R^7R^8$, —(CH₂)$_r$NHC(O)N$R^8R^9$, —C(=N$R^8$)N$R^8R^9$, —(C=NH)NHO$R^{3b}$, —(CH₂)$_r$C(O)O$R^{3b}$, —C(O)C$_{1-4}$ alkyl, —SO₂NH$R^{3b}$, —SO₂NHCO$R^{3c}$, —SO₂NHCO₂$R^{3c}$, —CONHSO₂$R^{3c}$, —(CH₂)$_r$N$R^8$C(O)$R^{3b}$, —(CH₂)$_r$N$R^8$CO₂$R^{3c}$, —(CH₂)$_r$S(O)$_p$N$R^8R^9$, —(CH₂)$_r$N$R^8$S(O)$_p$$R^{3c}$, —NHSO₂CF₃, —S(O)$R^{3c}$, —S(O)₂$R^{3c}$, —(CH₂)$_r$OC(O)$R^{3b}$, —(CH₂)$_r$C(O)(CH₂)$_r$N$R^8R^9$, —(CH₂)$_r$OC(O)N$R^8R^9$, —NHCOCF₃, —CONHO$R^{3b}$, —(CH₂)$_r$P(O)(OH)₂, —(CH₂)$_r$P(O)(OC$_{1-4}$ alkyl)₂, C$_{1-4}$ haloalkyl, C$_{1-4}$ haloalkyloxy-, C$_{1-6}$ alkyl substituted by $R^{3e}$, C$_{2-6}$ alkenyl substituted by $R^{3e}$, C$_{1-6}$ alkynyl substituted by $R^{3e}$, C$_{3-6}$ cycloalkyl substituted by 0-1 $R^{3d}$, —(CH₂)$_r$—C$_{3-10}$ carbocycle substituted by 0-3 $R^{3d}$ or —(CH₂)$_r$-5- to 10-membered heterocycle comprising: carbon atoms and 1-4 heteroatoms selected from N, O, and S(O)$_p$, wherein said heterocycle is substituted with 0-3 $R^{3d}$;

alternately, when two $R^3$ groups are substituted on adjacent atoms, they can be taken together with the atoms to which they are attached to form a C$_{3-10}$ carbocycle substituted with 0-2 $R^{3d}$, or a 5- to 10-membered heterocycle comprising: carbon atoms and 1-4 heteroatoms selected from N, O, and S(O)$_p$, wherein said heterocycle is substituted with 0-2 $R^{3d}$;

$R^{3b}$ is, independently at each occurrence, H, C$_{1-6}$ alkyl substituted with 0-2 $R^{3d}$, C$_{2-6}$ alkenyl substituted with 0-2 $R^{3d}$, C$_{2-6}$ alkynyl substituted with 0-2 $R^{3d}$, —(CH₂)$_r$—C$_{3-10}$ carbocycle substituted with 0-3 $R^{3d}$, or —(CH₂)$_r$-5- to 10-membered heterocycle comprising: carbon atoms and 1-4 heteroatoms selected from N, O, and S(O)$_p$, wherein said heterocycle is substituted with 0-3 $R^{3d}$;

$R^{3c}$ is, independently at each occurrence, C$_{1-6}$ alkyl substituted with 0-2 $R^{3d}$, C$_{2-6}$ alkenyl substituted with 0-2 $R^{3d}$, C$_{2-6}$ alkynyl substituted with 0-2 $R^{3d}$, —(CH₂)$_r$—C$_{3-10}$ carbocycle substituted with 0-3 $R^{3d}$, or —(CH₂)$_r$-5- to 10-membered heterocycle comprising: carbon atoms and 1-4 heteroatoms selected from N, O, and S(O)$_p$, wherein said heterocycle is substituted with 0-3 $R^{3d}$;

$R^{3d}$ is, independently at each occurrence, =O, F, Cl, Br, CN, NO₂, —(CH₂)$_r$N$R^7R^8$, —(CH₂)$_r$O$R^a$, —C(O)$R^a$, —C(O)O$R^a$, —OC(O)$R^a$, —N$R^8$C(O)$R^c$, —C(O)N$R^8R^9$, —S(O)₂N$R^8R^9$, —N$R^8$S(O)₂N$R^8R^9$, —N$R^8$S(O)₂$R^c$, —S(O)$_p$$R^c$, —(CF₂)$_r$CF₃, —(CH₂)$_r$P(O)(OH)₂, —(CH₂)$_r$P(O)(OC$_{1-4}$ alkyl)₂, C$_{1-6}$ alkyl substituted with 0-2 $R^e$, C$_{2-6}$ alkenyl substituted with 0-2 $R^e$, C$_{2-6}$ alkynyl substituted with 0-2 $R^e$, —(CH₂)$_r$—C$_{3-10}$ carbocycle substituted with 0-3 $R^d$, or —(CH₂)$_r$-5- to 10-membered heterocycle comprising: carbon atoms and 1-4 heteroatoms selected from N, O, and S(O)$_p$, wherein said heterocycle is substituted with 0-3 $R^d$;

$R^{3e}$ is, independently at each occurrence, —(CH₂)$_r$O$R^a$, F, =O, CN, NO₂, —(CH₂)$_r$N$R^7R^8$, —C(O)$R^a$, —C(O)O$R^a$, —OC(O)$R^a$, —N$R^8$C(O)$R^e$, —C(O)N$R^8R^9$, —S(O)₂N$R^8R^9$, —N$R^8$S(O)₂N$R^8R^9$, —N$R^8$S(O)₂$R^e$, —S(O)$_p$$R^e$, —(CF₂)$_r$CF₃, —(CH₂)$_r$—C$_{3-10}$ carbocycle substituted with 0-3 $R^d$, or —(CH₂)$_r$-5- to 10-membered heterocycle comprising: carbon atoms and 1-4 heteroatoms selected from N, O, and S(O)$_p$, wherein said heterocycle is substituted with 0-3 $R^d$;

$R^5$ is, independently at each occurrence, H, F, CF₃, —(CH₂)$_r$O$R^a$, —(CH₂)$_r$N$R^7R^8$, —S(O)$_p$N$R^8R^9$, —(CH₂)$_r$CO₂$R^a$, —(CH₂)$_r$CONR$^8R^9$, or C$_{1-4}$ alkyl;

$R^7$ is, independently at each occurrence, H, C$_{1-6}$ alkyl, —(CH₂)$_n$—C$_{3-10}$ carbocycle, —(CH₂)$_n$-(5- to 10-membered heteroaryl), —C(O)$R^e$, —CHO, —C(O)₂$R^e$, —S(O)₂$R^c$, —CON$R^8R^c$, —OCONH$R^c$, —C(O)O—(C$_{1-4}$ alkyl)OC(O)—(C$_{1-4}$ alkyl), or —C(O)O—(C$_{1-4}$ alkyl)OC(O)—(C$_{6-10}$ aryl); wherein said alkyl, carbocycle, heteroaryl, and aryl are substituted with 0-2 $R^f$; wherein said heteroaryl comprises: carbon atoms and 1-4 heteroatoms selected from N, O, and S(O)$_p$;

$R^8$ is, independently at each occurrence, H, C$_{1-6}$ alkyl, —(CH₂)$_n$-phenyl, or —(CH₂)$_n$-5- to 10-membered heterocycle comprising: carbon atoms and 1-4 heteroatoms selected from N, O, and S(O)$_p$; wherein said alkyl, phenyl and heterocycle are optionally substituted with 0-2 $R^f$;

alternatively, $R^7$ and $R^8$, when attached to the same nitrogen, combine to form a 5- to 10-membered heterocycle comprising: carbon atoms and 0-3 additional heteroatoms selected from N, O, and S(O)$_p$, wherein said heterocycle is substituted with 0-2 $R^f$;

$R^9$ is, independently at each occurrence, H, C$_{1-6}$ alkyl, or —(CH₂)$_n$-phenyl; wherein said alkyl and phenyl are optionally substituted with 0-2 $R^f$;

alternatively, $R^8$ and $R^9$, when attached to the same nitrogen, combine to form a 5- to 12-membered heterocycle comprising: carbon atoms and 0-2 additional heteroatoms selected from N, O, and S(O)$_p$, wherein said heterocycle is substituted with 0-2 $R^d$;

$R^{10}$ is, independently at each occurrence, H or C$_{1-6}$ alkyl substituted with 0-3 $R^{10a}$;

$R^{10a}$ is, independently at each occurrence, H, =O, $C_{1-4}$ alkyl, $OR^a$, $SR^a$, F, $CF_3$, CN, $NO_2$, —C(O)$R^a$, —C(O)O$R^a$, —C(O)$NR^8R^9$, —$NR^8$C(O)$R^c$, —S(O)$_p$$NR^8R^9$, —$NR^8$S(O)$_p$$R^c$, or —S(O)$_p$$R^c$;

$R^{11}$ is $C_{1-4}$ haloalkyl, —C(O)$NR^8R^9$, —$CH_2$C(O)$NR^8R^9$, —$CH_2CH_2$C(O)$NR^8R^9$, —C(O)$R^a$, —$CH_2$C(O)$R^a$, —$CH_2CH_2$C(O)$R^a$, —C(O)O$R^a$, —$CH_2$C(O)O$R^a$, —$CH_2CH_2$C(O)O$R^a$, $C_{1-6}$ alkyl substituted with 0-3 $R^{11c}$, $C_{2-6}$ alkenyl substituted with 0-3 $R^{11a}$, $C_{2-6}$ alkynyl substituted with 0-3 $R^{11a}$, —(CH$_2$)$_r$—$C_{3-10}$ carbocycle substituted with 0-3 $R^{11b}$, or —(CH$_2$)$_r$-5- to 10-membered heterocycle comprising: carbon atoms and 1-4 heteroatoms selected from N, O, and S(O)$_p$, wherein said heterocycle is substituted with 0-3 $R^{11b}$;

$R^{11a}$ is independently at each occurrence =O, $OR^a$, $SR^a$, F, $CF_3$, CN, $NO_2$, —C(O)$R^a$, —C(O)O$R^a$, —$NR^7R^8$, —C(O)$NR^8R^9$, —$NR^8$C(O)$R^c$, —$NR^8$C(O)O$R^c$, —$NR^8$CHO, —S(O)$_p$$NR^8R^9$, —$NR^8$S(O)$_p$$R^c$, —S(O)$_p$$R^c$, $C_{1-4}$ alkyl, $C_{3-6}$ cycloalkyl, $C_{1-4}$ haloalkyl, $C_{1-4}$ haloalkyloxy-, —(CH$_2$)$_r$—$C_{3-10}$ carbocycle substituted with 0-3 $R^d$, or —(CH$_2$)$_r$-5- to 10-membered heterocycle comprising carbon atoms and 1-4 heteroatoms selected from N, O, and S(O)$_p$, and substituted with 0-3 $R^d$;

$R^{11b}$ is, independently at each occurrence, =O, =$NR^8$, $OR^a$, —$CH_2OR^a$, F, Cl, Br, CN, $NO_2$, $CF_3$, $OCF_3$, $OCHF_2$, —C(CH$_3$)$_2$O$R^a$, —C(O)$R^a$, —C(O)O$R^a$, —$NR^7R^8$, —C(O)$NR^8R^9$, —$NR^7$C(O)$R^b$, —$NR^8$C(O)$_2R^c$, —S(O)$_p$$NR^8R^9$, —$NR^8$S(O)$_p$$R^c$, —S(O)$_p$$R^c$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, —(CH$_2$)$_r$—$C_{3-10}$ carbocycle substituted with 0-3 $R^d$, or —(CH$_2$)$_r$-5- to 10-membered heterocycle comprising carbon atoms and 1-4 heteroatoms selected from N, O, and S(O)$_p$, and substituted with 0-3 $R^d$;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and S(O)$_p$ and substituted with 0-2 $R^g$;

$R^{11c}$ is independently at each occurrence =O, $OR^a$, $SR^a$, F, $CF_3$, CN, $NO_2$, —$NR^7R^8$, —$NR^8$C(O)$R^c$, —$NR^8$C(O)O$R^c$, —$NR^8$CHO, —NHC(NH$_2$)=N(NO$_2$), —C(=$NR^8$)$NR^8R^9$, —S(O)$_p$$NR^8R^9$, —$NR^8$S(O)$_p$$R^c$, —S(O)$_p$$R^c$, $C_{1-4}$ alkyl, $C_{3-6}$ cycloalkyl, $C_{1-4}$ haloalkyl, $C_{1-4}$ haloalkyloxy-, —(CH$_2$)$_r$—$C_{3-10}$ carbocycle substituted with 0-3 $R^d$, or —(CH$_2$)$_r$-5- to 10-membered heterocycle comprising carbon atoms and 1-4 heteroatoms selected from N, O, and S(O)$_p$, and substituted with 0-3 $R^d$;

$R^{12}$ is, independently at each occurrence, H, F, or $C_{1-4}$ alkyl;

$R^{13}$ is, independently at each occurrence, H, $C_{1-4}$ alkyl, $CO_2R^a$, or benzyl;

$R^a$ is, independently at each occurrence, H, $CF_3$, $C_{1-6}$ alkyl, —(CH$_2$)$_r$—$C_{3-7}$ cycloalkyl, —(CH$_2$)$_r$—$C_{6-10}$ aryl, or —(CH$_2$)$_r$-5- to 10-membered heterocycle comprising carbon atoms and 1-4 heteroatoms selected from N, O, and S(O)$_p$, wherein said cycloalkyl, aryl or heterocycle groups are optionally substituted with 0-2 $R^f$;

$R^b$ is, independently at each occurrence, $CF_3$, OH, $C_{1-4}$ alkoxy, $C_{1-6}$ alkyl, —(CH$_2$)$_r$—$C_{3-10}$ carbocycle substituted with 0-2 $R^d$, or —(CH$_2$)$_r$-5- to 10-membered heterocycle comprising: carbon atoms and 1-4 heteroatoms selected from N, O, and S(O)$_p$ and substituted with 0-3 $R^d$;

$R^c$ is, independently at each occurrence, $CF_3$, $C_{1-6}$ alkyl substituted with 0-2 $R^f$, $C_{3-6}$ cycloalkyl substituted with 0-2 $R^f$, $C_{6-10}$ aryl, 5- to 10-membered heteroaryl, (C$_{6-10}$ aryl)-$C_{1-4}$ alkyl, or (5- to 10-membered heteroaryl)-$C_{1-4}$ alkyl, wherein said aryl is substituted with 0-3 $R^f$ and said heteroaryl comprises: carbon atoms and 1-4 heteroatoms selected from N, O, and S(O)$_p$ and substituted with 0-3 $R^f$;

$R^d$ is, independently at each occurrence, H, =O, =$NR^8$, $OR^a$, F, Cl, Br, I, CN, $NO_2$, —$NR^7R^8$, —C(O)$R^a$, —C(O)O$R^a$, —OC(O)$R^a$, —$NR^8$C(O)$R^e$, —C(O)$NR^8R^9$, —SO$_2$$NR^8R^9$, —$NR^8$SO$_2$$NR^8R^9$, —$NR^8$SO$_2$—$C_{1-4}$ alkyl, —$NR^8$SO$_2CF_3$, —$NR^8$SO$_2$-phenyl, —S(O)$_2$$CF_3$, —S(O)$_p$—$C_{1-4}$ alkyl, —S(O)$_p$-phenyl, —(CF$_2$)$_r$$CF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^e$ is, independently at each occurrence, =O, $OR^a$, F, Cl, Br, I, CN, $NO_2$, —$NR^7R^8$, —C(O)$R^a$, —C(O)O$R^a$, —$NR^8$C(O)$R^e$, —C(O)$NR^8R^9$, —SO$_2$$NR^8R^9$, —$NR^8$SO$_2$$NR^8R^9$, —$NR^8$SO$_2$—$C_{1-4}$ alkyl, —$NR^8$SO$_2CF_3$, —$NR^8$SO$_2$-phenyl, —S(O)$_2$$CF_3$, —S(O)$_p$—$C_{1-4}$ alkyl, —S(O)$_p$-phenyl, or —(CF$_2$)$_r$$CF_3$;

$R^f$ is, independently at each occurrence, H, =O, —(CH$_2$)$_r$O$R^g$, F, Cl, Br, I, CN, $NO_2$, —$NR^gR^g$, —C(O)$R^g$, —C(O)O$R^g$, —$NR^g$C(O)$R^g$, —C(O)$NR^gR^g$, —SO$_2$$NR^gR^g$, —$NR^g$SO$_2$$NR^gR^g$, —$NR^g$SO$_2$—$C_{1-4}$ alkyl, —$NR^g$SO$_2CF_3$, —$NR^g$SO$_2$-phenyl, —S(O)$_2$$CF_3$, —S(O)$_p$—$C_{1-4}$ alkyl, —S(O)$_p$-phenyl, —(CF$_2$)$_r$$CF_3$, $C_{1-6}$ alkyl, $C_{2-6}$ alkenyl, $C_{2-6}$ alkynyl, —(CH$_2$)$_n$-phenyl, or —(CH$_2$)$_n$-5- to 10-membered heterocycle comprising carbon atoms and 1-4 heteroatoms selected from N, O, and S(O)$_p$;

$R^g$ is, independently at each occurrence, H, $C_{1-6}$ alkyl, or —(CH$_2$)$_n$-phenyl;

n, at each occurrence, is selected from 0, 1, 2, 3, and 4;

p, at each occurrence, is selected from 0, 1, and 2; and r, at each occurrence, is selected from 0, 1, 2, 3, and 4.

In a second aspect, the present invention includes compounds of Formula (I), (II), or (III), or a stereoisomer, a tautomer, a pharmaceutically acceptable salt, a solvate, or a prodrug thereof, within the scope of the first aspect wherein:

$L_1$ is —CH($R^5$)$CH_2$C(O)NH—, —CH($NR^7R^8$)$CH_2$C(O)NH—, —C($R^5$)=CHC(O)NH—, —CH=C($R^5$)C(O)NH—, —C≡CC(O)NH—, —$CH_2$NHC(O)NH—, —NHNHC(O)$CH_2$—, —CH($R^5$)$CH_2CH_2NR^{10}$—, —$CH_2$NHC(O)$CH_2$—, —NHC(O)O$CH_2$—, O$CH_2$C(O)NH—, or —S(O)$_p$$CH_2$C(O)NH—;

$L_2$ is —CH($R^5$)$CH_2$NHC(O)—, —C($R^5$)=CHNHC(O)—, —$CH_2$NHC(O)$CH_2$—, —C≡CNHC(O)—, —$CH_2$NHNHC(O)—, —CONHNHC(O)—, or —COCH$_2$NHC(O)—;

A is substituted with 0-3 $R^1$ and selected from the group consisting of: $C_{3-7}$ cycloalkyl, phenyl, naphthyl, 1,2,3,4-tetrahydronaphthyl, pyrrolidinyl, pyridyl, indazolyl, indolyl, imidazolyl, furanyl, thienyl, benzimidazolyl, benzisoxazolyl, benzothiazolyl, benzothiophenyl, 3,4-methylenedioxy-phenyl, oxazolyl, isoxazolyl, thiazolyl, isothiazolyl, and pyrazolyl; and M is substituted with 0-3 $R^3$ and selected from the group consisting of: cyclohexyl, phenyl, benzyl, pyridyl, pyrimidinyl, pyrazinyl, furanyl, thienyl, pyrrolyl, pyrazolyl, imidazolyl, oxazolyl, thiazolyl, thiadiazolyl, indolyl, indolinyl, isoindolyl, indazolyl, benzofuranyl, benzothienyl, benzimidazolyl, benzothiazolyl, benzoisothiazolyl, benzoxazolyl, benzisoxazolyl, tetrahydroisoquinolinyl, dihydroisoquinolinyl, isoquinolinyl, tetrahydroquinolinyl, dihydroquinolinyl, quinolinyl,

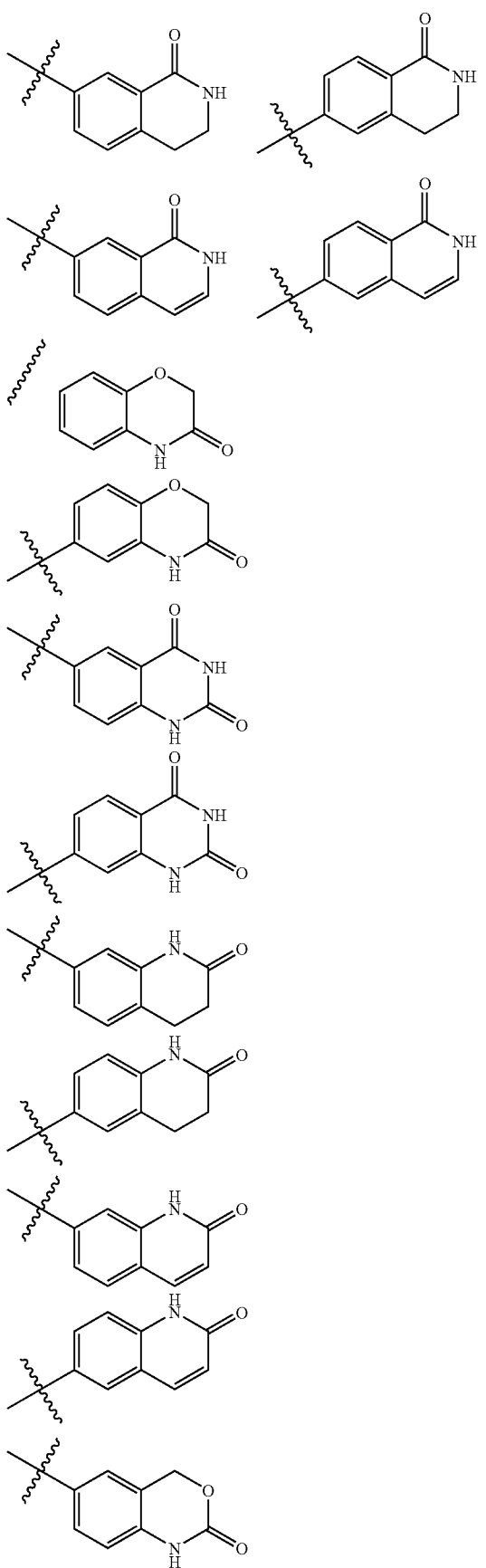
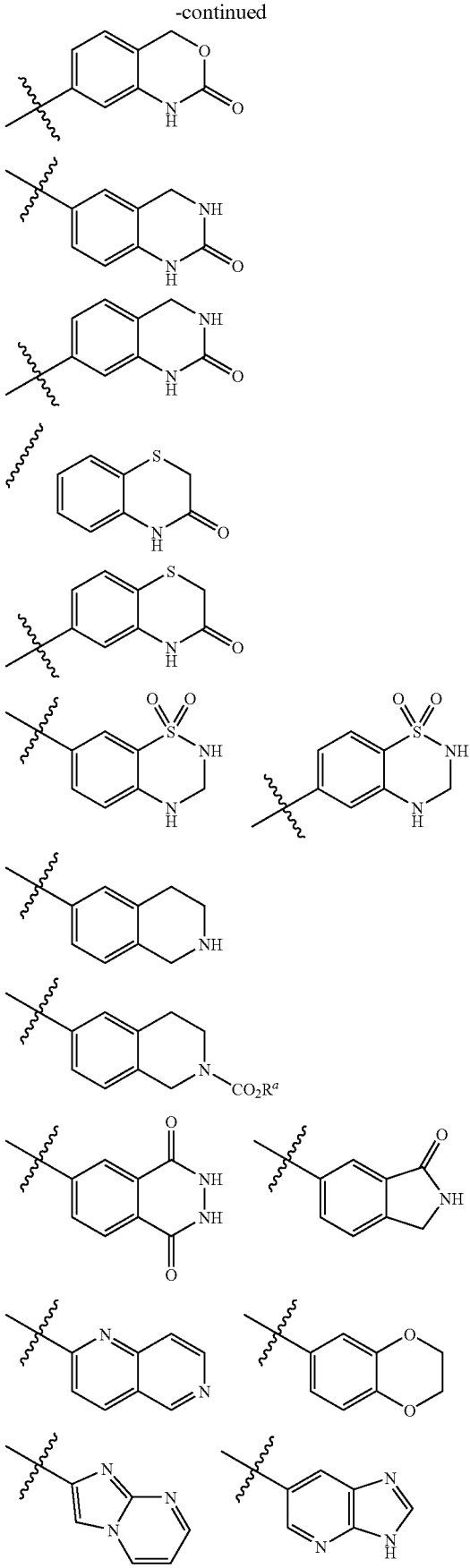

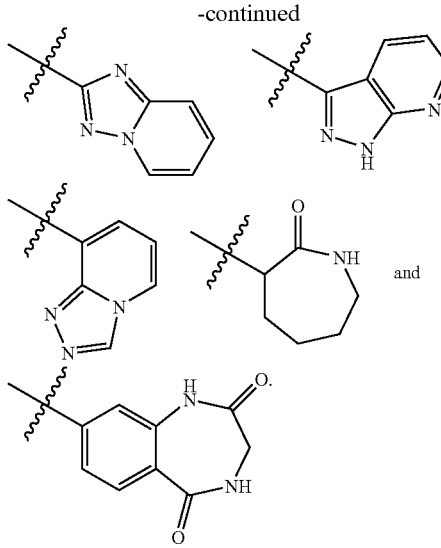

and

In a third aspect, the present invention includes compounds of Formula (I) or (II), or a stereoisomer, a tautomer, a pharmaceutically acceptable salt, a solvate, or a prodrug thereof, within the scope of the first aspect wherein:

$L_1$ is —CH(Me)CH$_2$C(O)NH—, —CH$_2$CH$_2$C(O)NH—, —C(Me)=CHC(O)NH—, —CH=C(Me)C(O)NH—, —CH=CHC(O)NH—, —C≡CC(O)NH—, —CH$_2$NHC(O)NH—, —NHNHC(O)CH$_2$—, —CH$_2$C(O)NHNH—, —CH$_2$CH$_2$CH$_2$NR$^{10}$—, —CH$_2$NHC(O)CH$_2$—, —NHC(O)OCH$_2$—, —OCH$_2$C(O)NH—, —CH$_2$OC(O)NH—, or —S(O)$_p$CH$_2$C(O)NH—;

$L_2$ is —CH(Me)CH$_2$NHC(O)—, —CH$_2$CH$_2$NHC(O)—, —CH=CHNHC(O)—, —C(Me)=CHNHC(O)—, —CH$_2$NHNHC(O)—, —CH$_2$NHC(O)CH$_2$—, —C≡CNHC(O)—, —CONHNHC(O)—, or —COCH$_2$NHC(O)—;

$R^1$ is, independently at each occurrence, F, Cl, Br, CF$_3$, OCF$_3$, NO$_2$, CN, —(CH$_2$)$_r$OR$^a$, —(CH$_2$)$_r$SR$^a$, —(CH$_2$)$_r$COR$^a$, —(CH$_2$)$_r$C(O)OR$^a$, —(CH$_2$)$_r$C(O)NR$^8$R$^9$, —C(=NH)NH$_2$, —(CH$_2$)$_r$NR$^8$C(O)R$^c$, —(CH$_2$)$_r$NR$^8$C(O)OR$^c$, —CO$_2$(CH$_2$)$_2$NR$^7$R$^8$, —(CH$_2$)$_r$NR$^8$C(O)NR$^8$R$^c$, —(CH$_2$)$_r$S(O)$_p$NR$^8$R$^9$, —(CH$_2$)$_r$NR$^8$SO$_2$R$^c$, —(CH$_2$)$_r$NR$^7$R$^8$, —(CH$_2$)$_r$S(O)R$^c$, —(CH$_2$)$_r$S(O)$_2$R$^c$, C$_{1-6}$ alkyl substituted with 0-1 R$^{1a}$, or a 5-7 membered heterocycle comprising carbon atoms and 1-4 heteroatoms selected from N, NR$^{13}$, O, and S(O)$_p$, wherein said heterocycle is substituted with 0-2 R$^{1b}$;

$R^{11}$ is C$_{1-4}$ haloalkyl, —CH$_2$C(O)NR$^8$R$^9$, —CH$_2$CH$_2$C(O)NR$^8$R$^9$, —CH$_2$C(O)R$^a$, —CH$_2$CH$_2$C(O)R$^a$, —CH$_2$C(O)OR$^a$, —CH$_2$CH$_2$C(O)OR$^a$, C$_{1-6}$ alkyl substituted with 0-2 R$^{11c}$, —(CH$_2$)$_r$-C$_{3-7}$ cycloalkyl substituted with 0-2 R$^{11b}$, —(CH$_2$)$_r$-indanyl substituted with 0-2 R$^{11b}$, —(CH$_2$)$_r$-indenyl substituted with 0-2 R$^{11b}$, —(CH$_2$)$_r$-phenyl substituted with 0-2 R$^{11b}$, —(CH$_2$)$_r$-naphthyl substituted with 0-2 R$^{11b}$, or —(CH$_2$)$_r$-5- to 10-membered heterocycle comprising carbon atoms and 1-4 heteroatoms selected from N, O, and S(O)$_p$, wherein said heterocycle is substituted with 0-2 R$^{11b}$; and $R^{12}$ is H.

In a fourth aspect, the present invention includes compounds of Formula (I) or (II), or a stereoisomer, a tautomer, a pharmaceutically acceptable salt, a solvate, or a prodrug thereof, within the scope of the above aspects wherein:

A is phenyl substituted with 0-3 R$^1$;

$L_1$ is —CH$_2$CH$_2$C(O)NH—, —CH=CHC(O)NH—, —C≡CC(O)NH—, —CH$_2$NHC(O)NH—, —OCH$_2$C(O)NH—, —SCH$_2$C(O)NH—, —S(O)CH$_2$C(O)NH—, or —S(O)$_2$CH$_2$C(O)NH—;

$L_2$ is —CH$_2$CH$_2$NHC(O)— or —CH=CHNHC(O)—;

M is substituted with 0-2 R$^3$ and is selected from the group consisting of: cyclohexyl, phenyl, pyridyl, pyrimidinyl, thienyl, thiazolyl,

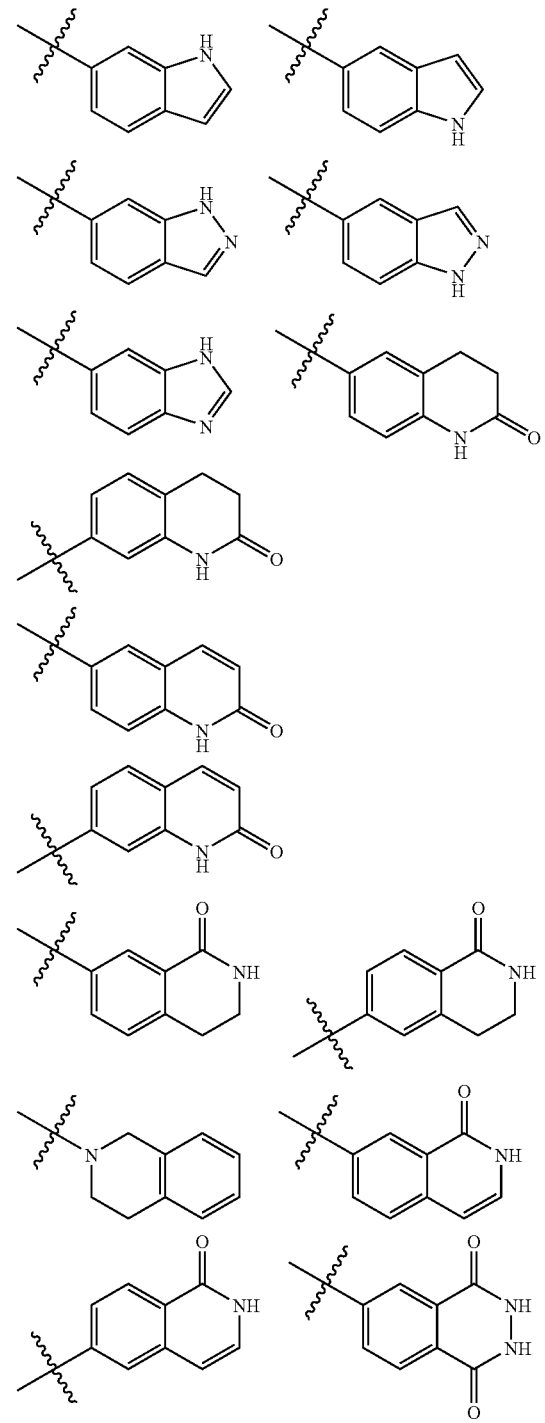

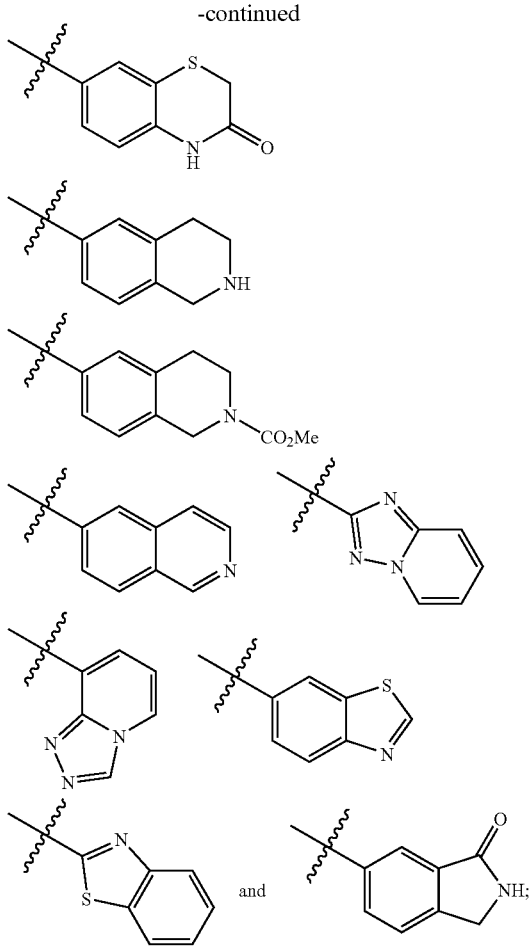

and

R[1] is, independently at each occurrence, F, Cl, Br, $CF_3$, $OCF_3$, $OR^a$, $SR^a$, —$CH_2OR^a$, —$CH_2SR^a$, $SO_2Me$, $SO_2NH_2$, CN, $NR^7R^8$, —$CH_2NR^7R^8$, $NO_2$, $COR^a$, $C(O)OR^a$, —$CH_2C(O)OR^a$, —C(=NH)$NH_2$, —$C(O)NR^8R^9$, —$CH_2C(O)NR^8R^9$, —$NR^8C(O)R^c$, —$CH_2NR^8C(O)R^c$, —$NR^8C(O)OR^c$, —$CH_2NR^8C(O)OR^c$, —$CO_2(CH_2)_2NR^7R^8$, —$NR^8C(O)NR^8R^c$, —$CH_2NR^8C(O)NR^8R^c$, —$NR^8SO_2R^c$, —$CH_2NR^8SO_2R^c$, $C_{1-6}$ alkyl substituted with 0-1 $R^{1a}$, or a 5-7 membered heterocycle comprising carbon atoms and 1-4 heteroatoms selected from N, $NR^{13}$, O, and $S(O)_p$, wherein said heterocycle is substituted with 0-2 $R^{1b}$; and $R^3$ is, independently at each occurrence, =O, F, Cl, Br, $OCF_3$, $CF_3$, CN, —$CH_2CN$, $OR^{3b}$, —$CH_2OR^{3b}$, $SR^{3b}$, —$CH_2SR^{3b}$, —$C(O)C_{1-4}$ alkyl, —$OC(O)(C_{1-4}$ alkyl), —$(CH_2)_rC(O)OR^{3b}$, —$(CH_2)_rNR^7R^8$, $C(O)NR^8R^9$, —$CH_2C(O)NR^8R^9$, —$NR^8C(O)R^{3b}$, —$CH_2NR^8C(O)R^{3b}$, —$NR^8CO_2R^{3c}$, —$CH_2NR^8CO_2R^{3c}$, —C(=NH)$NH_2$, —C(=NH)NHOH, —NHC(O)$NR^8R^9$, —$CH_2NHC(O)NR^8R^9$, —$SO_2NR^8R^9$, —$NHSO_2R^{3c}$, —$CONHSO_2R^{3c}$, $P(O)(OH)_2$, $P(O)(OC_{1-4}$ alkyl$)_2$, —$CH_2P(O)(OH)_2$, —$CH_2P(O)(OC_{1-4}$ alkyl$)_2$, $C_{1-4}$ alkyl, or —$(CH_2)_r$-5- to 6-membered heterocycle comprising: carbon atoms and 1-4 heteroatoms selected from N, O, and $S(O)_p$, wherein said heterocycle is substituted with 0-1 $R^{3d}$.

In a fifth aspect, the present invention includes compounds of Formula (I) or (II), or a stereoisomer, a tautomer, a pharmaceutically acceptable salt, a solvate, or a prodrug thereof, within the scope of the above aspects wherein:

$R^1$ is, independently at each occurrence, F, Cl, Br, Me, Et, OMe, $CF_3$, $OCF_3$, CN, $NH_2$, $CO_2H$, $CO_2Me$, $CO_2Et$, $CO_2$(t-Bu), C(O)Me, —$CH_2CO_2H$, —$CH_2CO_2Me$, —$CH_2CO_2Et$, —$CH_2NH_2$, —$CONH_2$, —CONHMe, —NHCOMe, —$NHCO_2Me$, —$NHCO_2$(t-Bu), —$CO_2(CH_2)_2NEt_2$, —$NHCO_2(CH_2)_2N(Me)_2$, —$SO_2NH_2$, —C(=NH)$NH_2$, pyrazol-1-yl, 3-carboxy-pyrazol-1-yl, 4-carboxy-pyrazol-1-yl, 4-(ethoxycarbonyl)-pyrazol-1-yl, 1,2,3-triazol-1-yl, 1,2,4-triazol-1-yl, 1,3,4-triazol-1-yl, 1,2,3-triazol-2-yl, 4-carboxy-1,2,3-triazol-1-yl, 4-(ethoxycarbonyl)-1,2,3-triazol-1-yl, tetrazol-1-yl, tetrazol-5-yl, 5-Me-tetrazol-1-yl, 5-$CF_3$-tetrazol-1-yl, 5-$NH_2$-tetrazol-1-yl, 5-$NH_2$-1,3,4-oxadiazol-2-yl, 2-oxo-1,3,4-trizaolyl-5-yl, 4-aminocarbonyl-1,2,3-triazol-1-yl, 4-dimethylaminocarbonyl-1,2,3-triazol-1-yl, or 4-hydroxymethyl-1,2,3-triazol-1-yl; and $R^3$ is, independently at each occurrence, F, Cl, Me, $CF_3$, $OCF_3$, OH, CN, $NH_2$, $CO_2H$, $CO_2Me$, $CO_2Et$, $CO_2$(t-Bu), —$CH_2CO_2H$, —$CH_2CO_2Me$, —$CH_2CO_2Et$, —$CONH_2$, —$CON(Me)_2$, —NHCOMe, —$NHCO_2Me$, —$NHCO_2$(t-Bu), —(C=NH)$NH_2$, —(C=NH)NHOH, —$CONHCH_2CO_2H$, —CON(Me)$CH_2CO_2H$, —CONH$(CH_2)_2CO_2H$, —CONH$(CH_2)_2CO_2Et$, —CONH$(CH_2)_3CO_2H$, —CONH$(CH_2)_3CO_2Et$, —$CO_2(CH_2)_2NEt_2$, —$CO_2(CH_2)_3N(Bu)_2$, —$CH_2NHCO_2Me$, —$NHCO_2(CH_2)_2OMe$, —$CH_2NHCO_2(CH_2)_2OMe$, —$NHCO_2(CH_2)_2CO_2H$, —$NHCO_2(CH_2)_2CO_2Me$, —$NHCO_2(CH_2)_2CO_2Et$, —$NHCO_2(CH_2)_2N(Me)_2$, —$CH_2NHCONH_2$, —NHCONH$(CH_2)_2CO_2H$, —NHCONH$(CH_2)_2CO_2Me$, —NHCONH$(CH_2)_3CO_2Me$, —$CONHSO_2Me$, —$SO_2NH_2$, $P(O)(OH)_2$, $P(O)(OEt)_2$, —$CH_2P(O)(OH)_2$, —$CH_2P(O)(OEt)_2$, 2-(N,N-dimethylaminomethyl)-phenyl, pyridin-4-yl-, tetrahydrofuran-2-ylmethoxy-, 2-oxo-piperidin-1-yl, 2-oxo-2H-pyridin-1-yl, imidazol-1-yl, 2-(N,N-dimethylaminomethyl)-imidazol-1-yl, 1,2,4-triazol-1-yl, tetrazol-1-yl, tetrazol-5-yl,

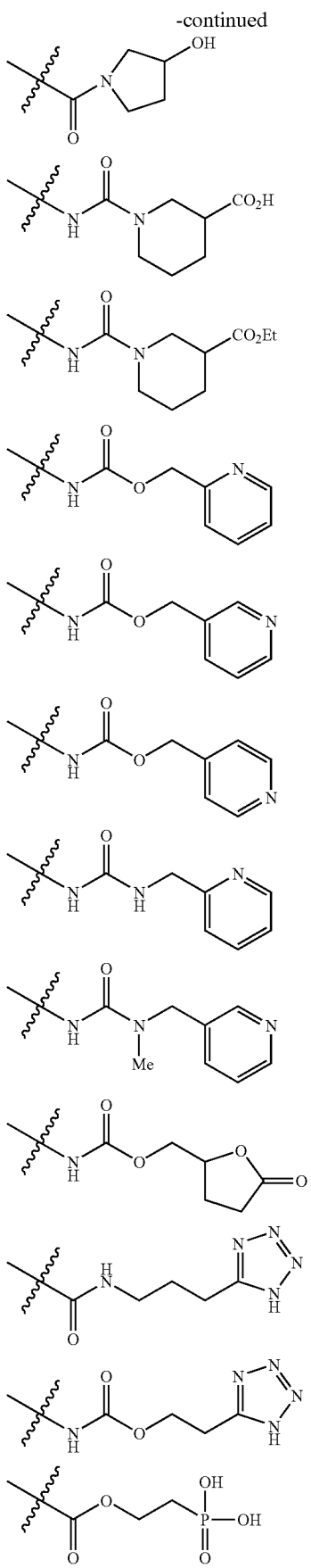
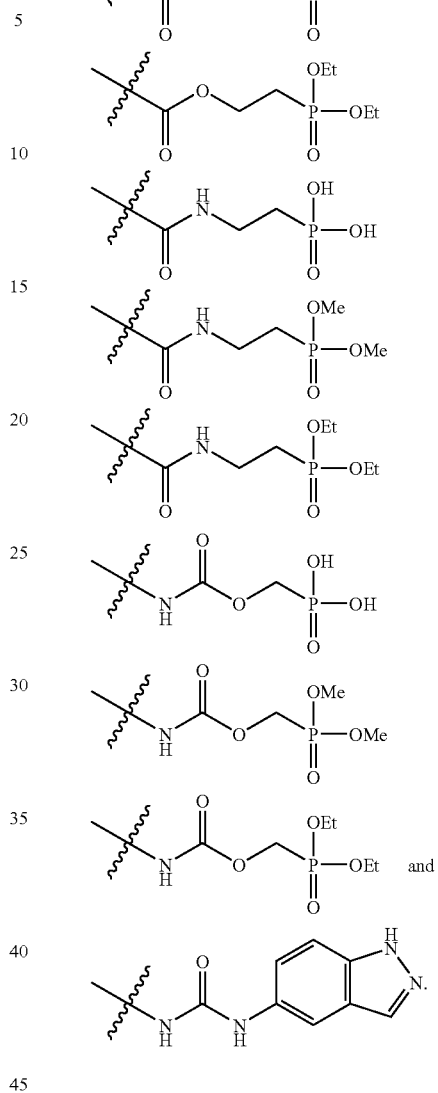
In a sixth aspect, the present invention includes a compound of Formula (Ia) or (IIa):
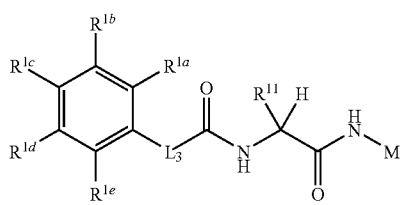
(Ia)
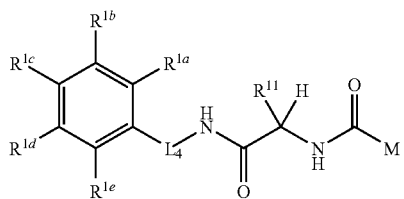
(IIa)

or a stereoisomer, a tautomer, a pharmaceutically acceptable salt, a solvate, or a prodrug thereof, wherein:

$L_3$ is —$CH_2CH_2$—, —CH=CH—, —C≡C— or —S(O)$CH_2$—;

$L_4$ is —$CH_2CH_2$—, —CH=CH—, —C≡C—, —CONH—, or —COCH$_2$—;

M is substituted with 0-2 $R^3$ and is selected from the group consisting of: cyclohexyl, phenyl, pyridyl, pyrimidinyl, thienyl thiazolyl,

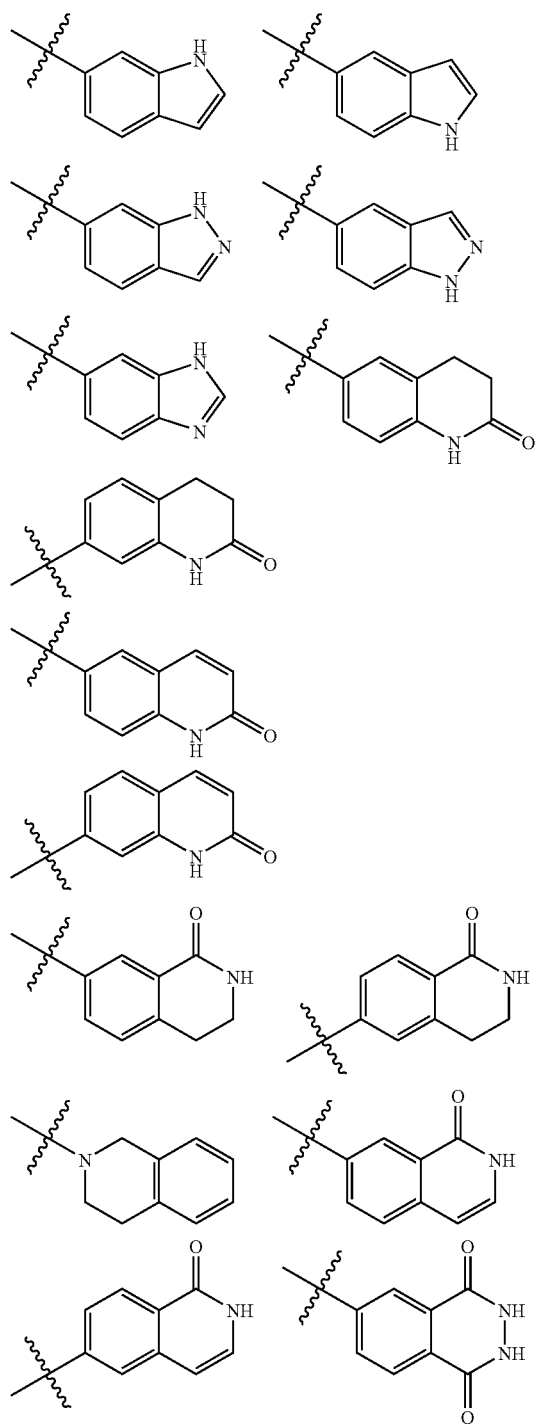
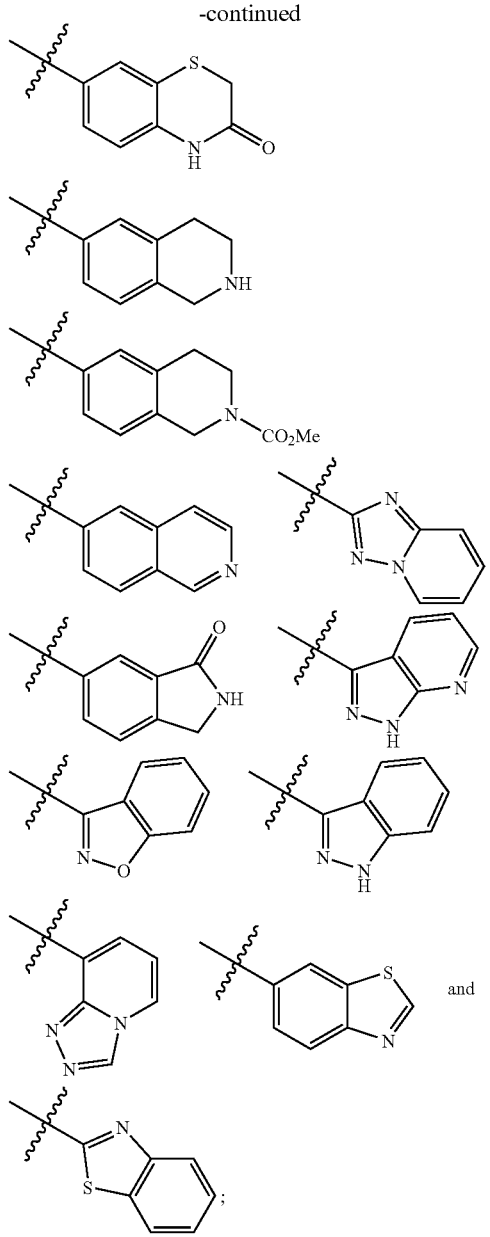

$R^{1a}$ is, independently at each occurrence, H, F, C(O)Me, —$CH_2NH_2$, 1,2,3-triazol-1-yl, 1,2,4-triazol-1-yl, 1,3,4-triazol-1-yl, 1,2,3-triazol-2-yl, 4-carboxy-1,2,3-triazol-1-yl, 4-(ethoxycarbonyl)-1,2,3-triazol-1-yl, tetrazol-1-yl, tetrazol-5-yl, 5-Me-tetrazol-1-yl, or 5-CF$_3$-tetrazol-1-yl;

$R^{1b}$, $R^{1c}$, $R^{1d}$, are, independently at each occurrence, H, F, Cl, Br, Me, Et, OMe, CF$_3$, OCF$_3$, CN, NH$_2$, CO$_2$H, CO$_2$Me, CO$_2$Et, CO$_2$(t-Bu), C(O)Me, —CH$_2$CO$_2$H, —CH$_2$CO$_2$Me, —CH$_2$CO$_2$Et, —CH$_2$NH$_2$, —CONH$_2$, —CONHMe, —NHCOMe, —NHCO$_2$Me, —NHCO$_2$(t-Bu), —CO$_2$(CH$_2$)$_2$NEt$_2$, —NHCO$_2$(CH$_2$)$_2$N(Me)$_2$, —SO$_2$NH$_2$, —C(=NH)NH$_2$;

$R^{1e}$ is, independently at each occurrence, H or F;

$R^3$ is, independently at each occurrence, F, Cl, Me, CF$_3$, OCF$_3$, OH, CN, NH$_2$, CO$_2$H, CO$_2$Me, CO$_2$Et, CO$_2$(t-Bu), —CH$_2$CO$_2$H, —CH$_2$CO$_2$Me, —CH$_2$CO$_2$Et, —CONH$_2$, —CON(Me)$_2$, —NHCOMe, —NHCO$_2$Me, —NHCO$_2$(t-Bu), —(C=NH)NH$_2$, —(C=NH)NHOH, —CONHCH$_2$CO$_2$H, —CON(Me)CH$_2$CO$_2$H, —CONH (CH$_2$)$_2$CO$_2$H, —CONH(CH$_2$)$_2$CO$_2$Et, —CONH(CH$_2$)$_3$CO$_2$H, —CONH(CH$_2$)$_3$CO$_2$Et, —CO$_2$(CH$_2$)$_2$NEt$_2$, —CO$_2$(CH$_2$)$_3$N(Bu)$_2$, —CH$_2$NHCO$_2$Me, —NHCO$_2$(CH$_2$)$_2$OMe, —CH$_2$NHCO$_2$(CH$_2$)$_2$OMe, —NHCO$_2$(CH$_2$)$_2$CO$_2$H, —NHCO$_2$(CH$_2$)$_2$CO$_2$Me, —NHCO$_2$(CH$_2$)$_2$CO$_2$Et, —NHCO$_2$(CH$_2$)$_2$N(Me)$_2$, —CH$_2$NHCONH$_2$, —NHCONH(CH$_2$)$_2$CO$_2$H, —NHCONH(CH$_2$)$_2$CO$_2$Me, —NHCONH(CH$_2$)$_3$CO$_2$Me, —CONHSO$_2$Me, —SO$_2$NH$_2$, P(O)(OH)$_2$, P(O)(OEt)$_2$, —CH$_2$P(O)(OH)$_2$, —CH$_2$P(O)(OEt)$_2$, 2-(N,N-dimethylaminomethyl)-phenyl, pyridin-4-yl-, tetrahydrofuran-2-ylmethoxy-, 2-oxo-piperidin-1-yl, 2-oxo-2H-pyridin-1-yl, imidazol-1-yl, 2-(N,N-dimethylaminomethyl)-imidazol-1-yl, 1,2,4-triazol-1-yl, tetrazol-1-yl, tetrazol-5-yl,

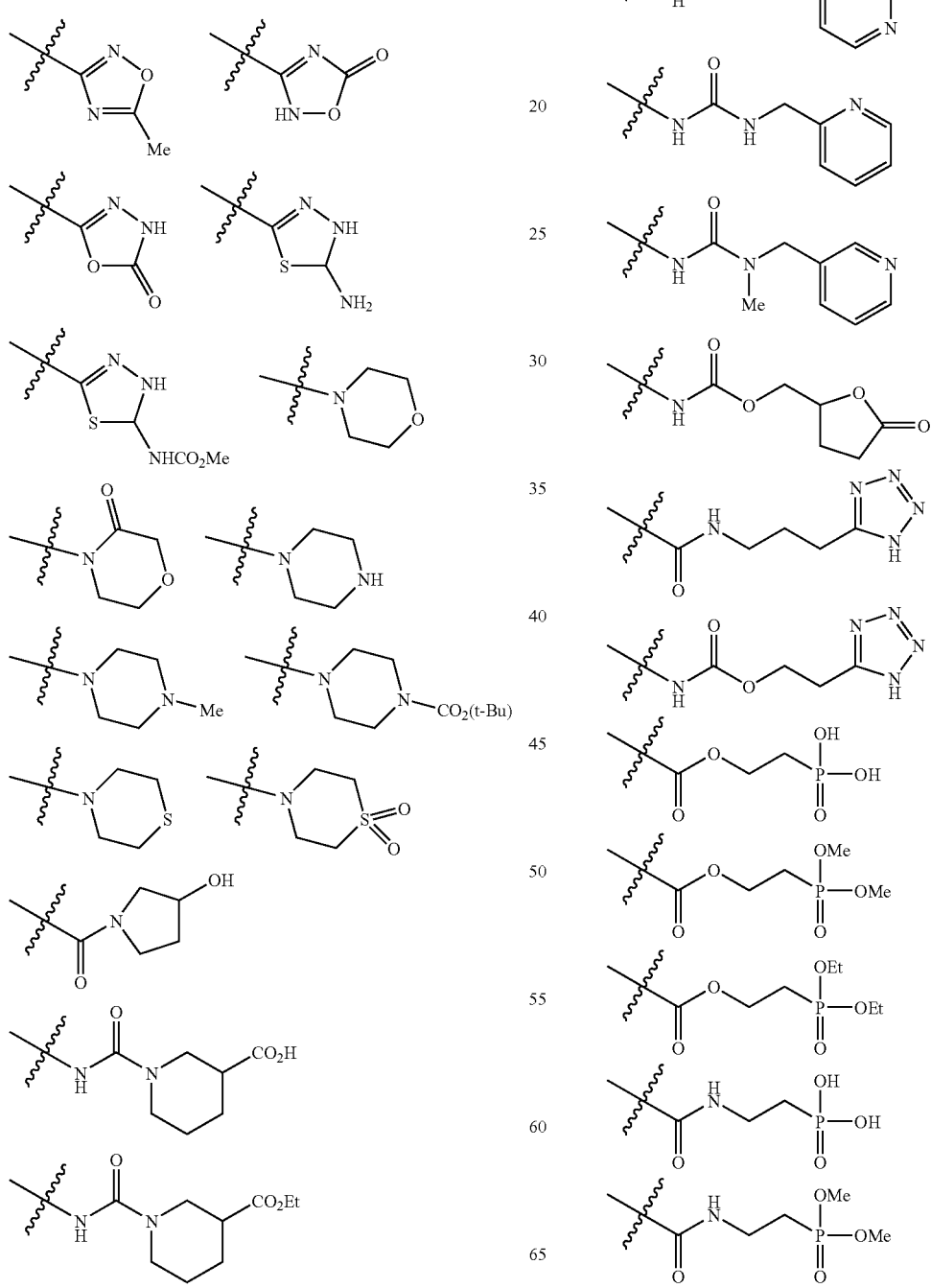

-continued

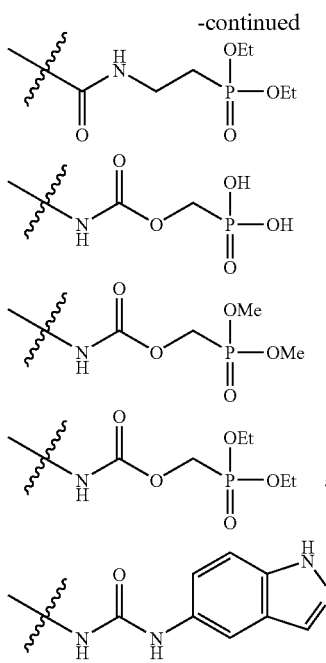

R$^{11}$ is methyl, ethyl, neopentyl, —CH$_2$CO$_2$H, —CH$_2$CO$_2$Me, —CH$_2$CONMe, —CH$_2$CF$_3$, —CH$_2$CH$_2$CF$_3$, —CH$_2$CH$_2$SMe, —CH$_2$S(t-Bu), —CH$_2$CH$_2$S(O)Me, —CH$_2$CH$_2$S(O)$_2$Me, —(CH$_2$)$_4$N(Me)$_2$, —CH$_2$C(O)N(Me)(CH$_2$)$_2$N(Me)$_2$, —(CH$_2$)$_3$NHC(NH$_2$)=N(NO$_2$), (2-morpholinoethyl)carbamoylmethyl, phenylcarbamoylmethyl, benzyl, 2-fluorobenzyl, 3-fluorobenzyl, 4-fluorobenzyl, 3,5-difluorobenzyl, 3-carboxybenzyl, 3-carbamoylbenzyl, 3-(N-methylcarbamoyl)-benzyl, 3-methoxycarbonylbenzyl, 3-methylcarbonylamino-benzyl, 3-(isopropyl-methyl-carbamoyl)-benzyl, 3-(methyl-phenyl-carbamoyl)-benzyl, 3-(N,N-dimethylcarbamoyl)-benzyl, 3-(morpholin-4-ylcarbonyl)benzyl, phenethyl, thien-2-ylmethyl, (dimethylamino)-carbonylmethyl, benzyloxymethyl, benzylthiomethyl, 1-naphthylmethyl, 2-naphthylmethyl, thiazol-2-ylmethyl, thiazol-4-ylmethyl, pyrid-2-ylmethyl, pyrid-3-ylmethyl, pyrid-4-ylmethyl, N-oxide-pyrid-2-ylmethyl, N-oxide-pyrid-3-ylmethyl, N-oxide-pyrid-4-ylmethyl, (2-hydroxy-pyrid-5-yl)methyl, (benzyloxycarbonyl)methyl, (1-methylpyrazol-3-yl)methyl, (1-methylpyrazol-5-yl)methyl, (3-methylpyrazol-5-yl)methyl, (1-ethylpyrazol-3-yl)methyl, 3-pyrazolylmethyl, [1-(4-methoxybenzyl)-pyrazol-3-yl]methyl, (1,5-dimethylpyrazol-3-yl)methyl, (1,3-dimethylpyrazol-5-yl)methyl, [1-(4-methoxybenzyl)-5-methyl-pyrazol-3-yl]methyl, (3-trifluoromethylpyrazol-5-yl)methyl, [1-(4-methoxybenzyl)-3-trifluoromethylpyrazol-5-yl]methyl, (1-(2-hydroxyethyl)-5-methyl-1H-pyrazol-3-yl)methyl, (1-methyl-5-(methylsulfinyl)-1H-pyrazol-3-yl)methyl, (1-methyl-5-(methylsulfonyl)-1H-pyrazol-3-yl)methyl, 1H-imidazol-4-ylmethyl, 1-methyl-1H-imidazol-4-ylmethyl, 1-methyl-1H-imidazol-5-ylmethyl, azetidin-3-ylmethyl, (1-acetyl-azetidin-3-yl)methyl, (1-CO$_2$Me-azetidin-3-yl)methyl, pyrrolidin-2-ylmethyl, pyrrolidin-3-ylmethyl, (1-acetyl-pyrrolidin-3-yl)methyl, (1-CO$_2$Me-pyrrolidin-3-yl)methyl, (3-(2-ethoxyethoxy)pyrrolidin-1-yl)carbonylmethyl, (1-benzoylpyrrolidin-3-yl)methyl, pyrrolidin-1-ylcarbonylmethyl, 2-methoxypyrrolidin-1-ylcarbonylmethyl, piperidin-3-ylmethyl, piperidin-4-ylmethyl, piperidin-4-ylethyl, (1-acetyl-piperidin-4-yl)ethyl, (1-CO$_2$Me-piperidin-3-yl)methyl, (1-CO$_2$Me-piperidin-4-yl)methyl, (2-methoxypyridin-3-yl)methyl, (2-methoxypyridin-5-yl)methyl, (4-(methoxycarbonyl)-oxazol-2-yl)methyl, morpholin-4-ylcarbonylmethyl, (2,6-dimethyl-morpholin-4-yl)carbonylmethyl, N-((5-methylpyrazin-2-yl)methyl)-aminocarbonylmethyl, 4-methylpiperazin-1-ylcarbonylmethyl, piperazin-1-ylcarbonylmethyl, 4-methylcarbonylpiperazin-1-ylcarbonylmethyl, tetrahydro-2H-pyran-4-ylmethyl, (1,1-dioxo-1λ$^6$-thiomorpholin-4-yl)methyl, (1,1-dioxo-1λ$^6$-thiomorpholin-4-yl)carbonylmethyl, N-(pyrazin-2-ylmethyl)aminocarbonylmethyl, 1H-indol-3-yl, quinoxalin-2-ylmethyl,

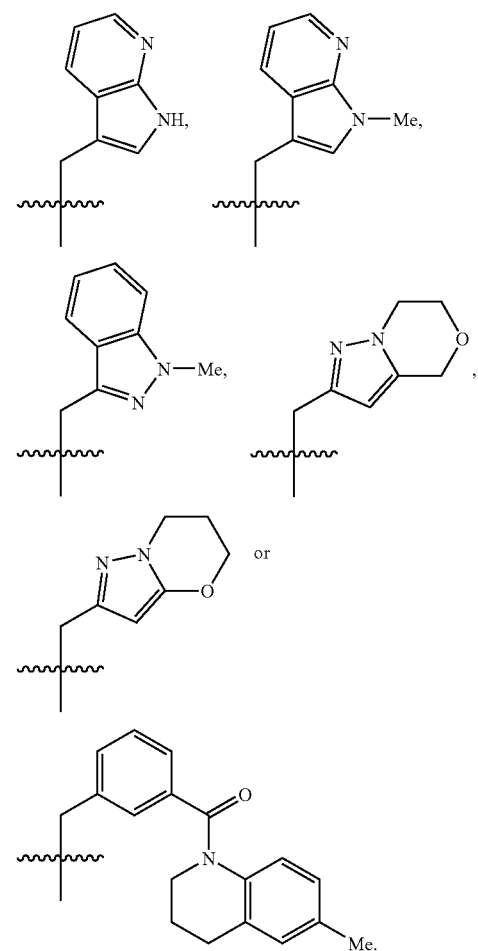

In a seventh aspect, the present invention includes a compound of Formula (Ib) or (IIb):

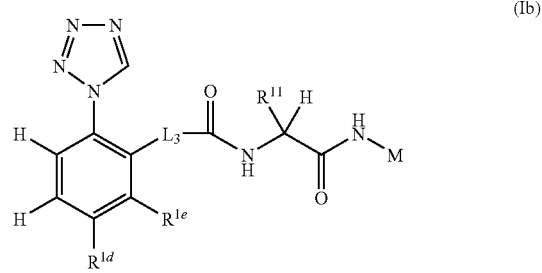

(Ib)

-continued (IIb)

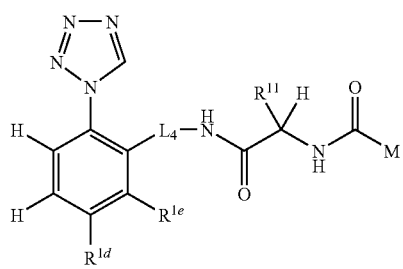

or a stereoisomer, a tautomer, a pharmaceutically acceptable salt, a solvate, or a prodrug thereof, within the scope of the above aspects wherein:
$R^{1d}$ is, independently at each occurrence, Cl or Me; and
$R^{1e}$ is, independently at each occurrence, H or F.

In an eighth aspect, the present invention includes a compound of Formula (Ic) or (IIc):

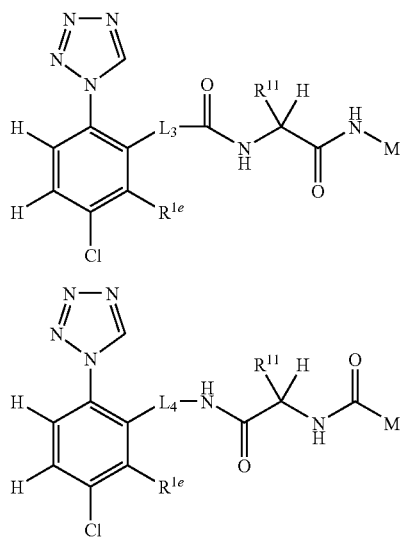

or a stereoisomer, a tautomer, a pharmaceutically acceptable salt, a solvate, or a prodrug thereof, within the scope of the above aspects, wherein:
$R^{1e}$ is, independently at each occurrence, H or F.

In a ninth aspect, the present invention includes compounds of Formula (Ib), (IIb), (Ic) or (IIc), or a stereoisomer, a tautomer, a pharmaceutically acceptable salt, a solvate, or a prodrug thereof, within the scope of the seventh or eighth aspect, wherein:
$L_3$ is —CH$_2$CH$_2$—, —CH=CH—, —C≡C— or —S(O)CH$_2$—;
$L_4$ is —CH$_2$CH$_2$—, —CH=CH—, or —COCH$_2$—;
M is substituted with 0-2 $R^3$ and is selected from the group consisting of: phenyl, pyridyl, thienyl,

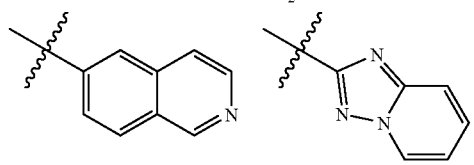

-continued

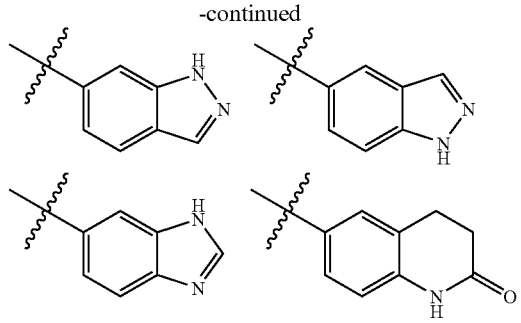

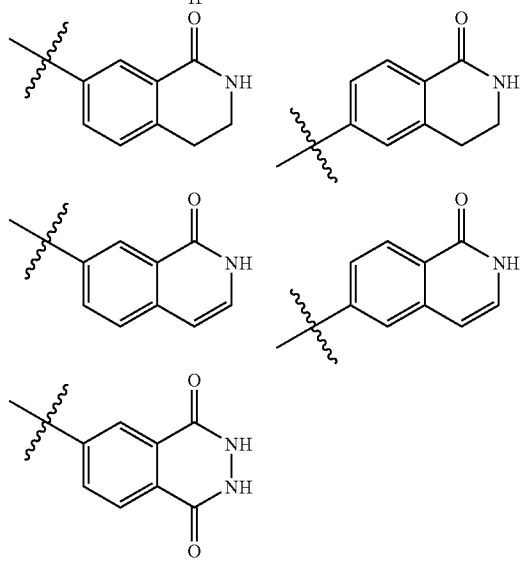

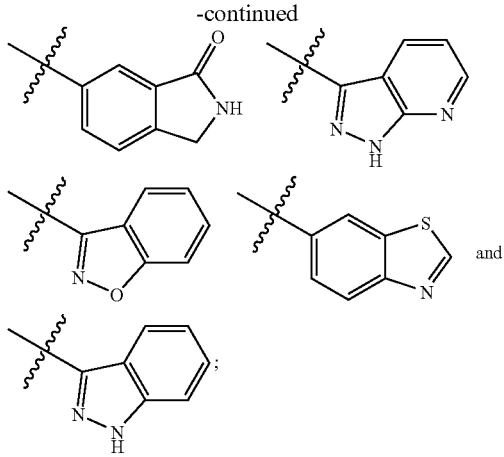

R³ is, independently at each occurrence, F, Cl, Me, CF₃, OH, CN, NH₂, CO₂H, CO₂Me, —CH₂CO₂H, —CH₂CO₂Me, —CH₂CO₂Et, —CONH₂, —CON(Me)₂, —NHCOMe, —NHCO₂Me, —(C=NH)NHOH, —CONHCH₂CO₂H, —CON(Me)CH₂CO₂H, —CONH(CH₂)₂CO₂H, —CONH(CH₂)₂CO₂Et, —CONH(CH₂)₃CO₂H, —CONH(CH₂)₃CO₂Et, —CO₂(CH₂)₂N(Et)₂, —CO₂(CH₂)₃N(Bu)₂, —CH₂NHCO₂Me, —NHCO₂(CH₂)₂OMe, —CH₂NHCO₂(CH₂)₂OMe, —NHCO₂(CH₂)₂CO₂H, —NHCO₂(CH₂)₂CO₂Me, —NHCO₂(CH₂)₂CO₂Et, —NHCO₂(CH₂)₂N(Me)₂, —CH₂NHCONH₂, —NHCONH(CH₂)₂CO₂H, —NHCONH(CH₂)₂CO₂Me, —NHCONH(CH₂)₃CO₂Me, —CONHSO₂Me, —SO₂NH₂, P(O)(OH)₂, P(O)(OEt)₂, —CH₂P(O)(OH)₂, —CH₂P(O)(OEt)₂, pyridin-4-yl-, tetrahydrofuran-2-ylmethoxy-, 2-oxo-piperidin-1-yl, imidazol-1-yl, 1,2,4-triazol-1-yl, tetrazol-1-yl, tetrazol-5-yl,

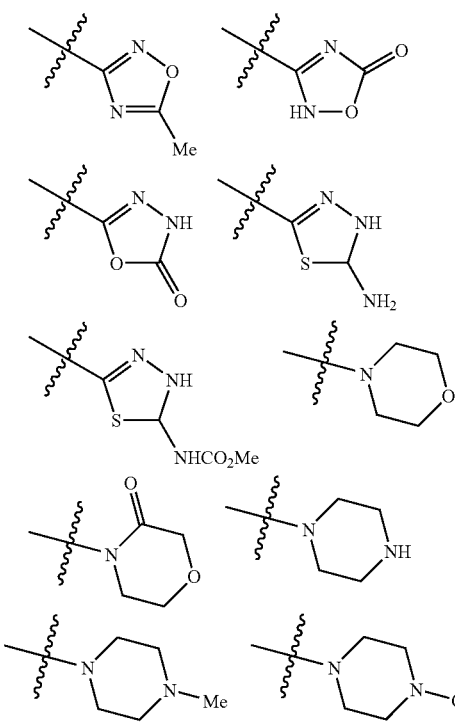

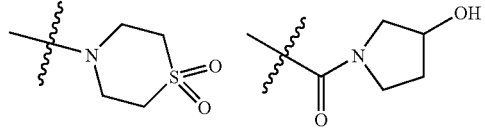

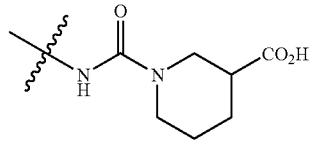

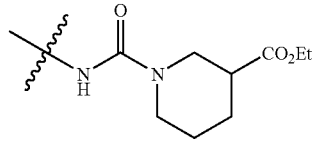

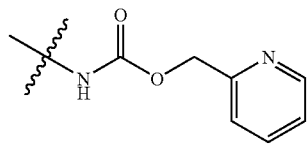

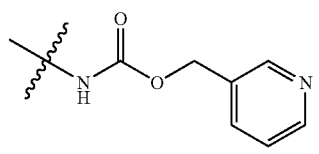

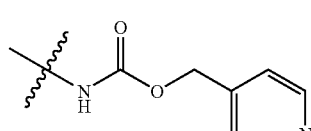

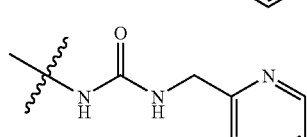

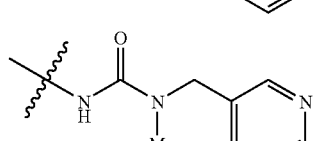

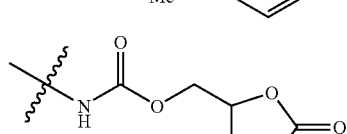

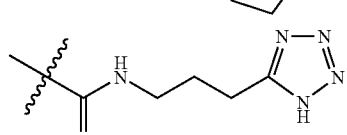

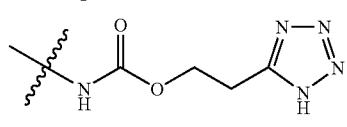

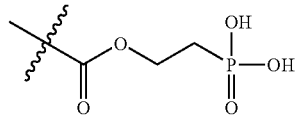

-continued

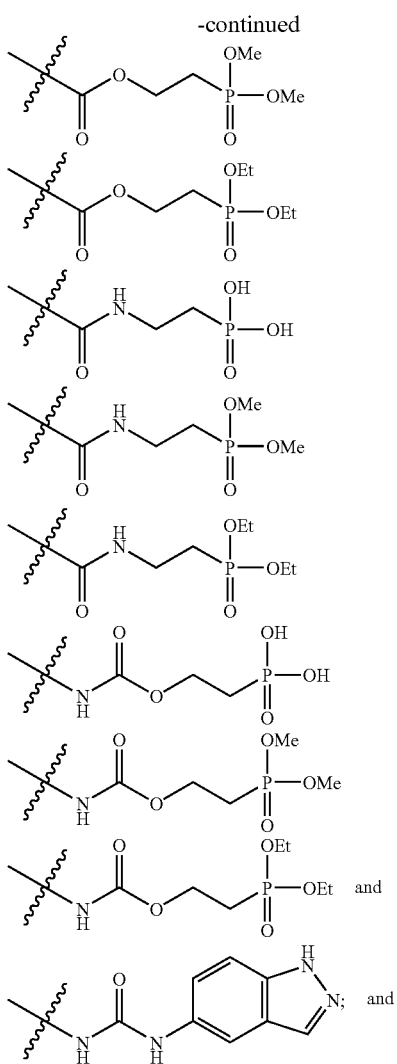

R$^{11}$ is neopentyl, —CH$_2$CO$_2$H, —CH$_2$CO$_2$Me, —CH$_2$CF$_3$, —CH$_2$CH$_2$CF$_3$, —CH$_2$CH$_2$SMe, —CH$_2$S(t-Bu), —CH$_2$CH$_2$S(O)Me, —CH$_2$CH$_2$S(O)$_2$Me, —(CH$_2$)$_4$N(Me)$_2$, —CH$_2$C(O)N(Me)(CH$_2$)$_2$N(Me)$_2$, —(CH$_2$)$_3$NHC(NH$_2$)=N(NO$_2$), phenylcarbamoylmethyl, benzyl, 2-fluorobenzyl, 3-fluorobenzyl, 4-fluorobenzyl, 3,5-difluorobenzyl, 3-carboxybenzyl, 3-carbamoylbenzyl, 3-(morpholin-4-ylcarbonyl)benzyl, phenethyl, (dimethylamino)-carbonylmethyl, 3-(N,N-dimethylcarbamoyl)-benzyl, thien-2-ylmethyl, (1-methylpyrazol-3-yl)methyl, (1,3-dimethylpyrazol-5-yl)methyl, (1,5-dimethylpyrazol-3-yl)methyl, (1-ethylpyrazol-3-yl)methyl, (1-(2-hydroxyethyl)-5-methyl-1H-pyrazol-3-yl)methyl, (1-methyl-5-(methylsulfinyl)-1H-pyrazol-3-yl)methyl, (1-methyl-5-(methylsulfonyl)-1H-pyrazol-3-yl)methyl, thiazol-2-ylmethyl, thiazol-4-ylmethyl, 1H-imidazol-4-ylmethyl, 1-methyl-1H-imidazol-4-ylmethyl, 1-methyl-1H-imidazol-5-ylmethyl, azetidin-3-ylmethyl, (1-acetyl-azetidin-3-yl)methyl, (1-CO$_2$Me-azetidin-3-yl)methyl, pyrrolidin-2-ylmethyl, pyrrolidin-3-ylmethyl, (1-acetyl-pyrrolidin-3-yl)methyl, (1-CO$_2$Me-pyrrolidin-3-yl)methyl, (3-(2-ethoxyethoxy)pyrrolidin-1-yl)carbonylmethyl, (1-benzoylpyrrolidin-3-yl)methyl, piperidin-3-ylmethyl, piperidin-4-ylmethyl, piperidin-4-ylethyl, (1-acetyl-piperidin-4-yl)ethyl, (1-CO$_2$Me-piperidin-3-yl)methyl, (1-CO$_2$Me-piperidin-4-yl)methyl, tetrahydro-2H-pyran-4-ylmethyl, pyrid-2-ylmethyl, pyrid-3-ylmethyl, pyrid-4-ylmethyl, N-oxide-pyrid-2-ylmethyl, N-oxide-pyrid-3-ylmethyl, N-oxide-pyrid-4-ylmethyl, (2-hydroxy-pyrid-5-yl)methyl, morpholin-4-ylcarbonylmethyl, 4-methylpiperazin-1-ylcarbonylmethyl, 4-methylcarbonylpiperazin-1-ylcarbonylmethyl, (1,1-dioxo-1λ$^6$-thiomorpholin-4-yl)methyl, (1,1-dioxo-1λ$^6$-thiomorpholin-4-yl)carbonylmethyl, N-(pyrazin-2-ylmethyl)aminocarbonylmethyl, 1H-indol-3-yl, quinoxalin-2-ylmethyl,

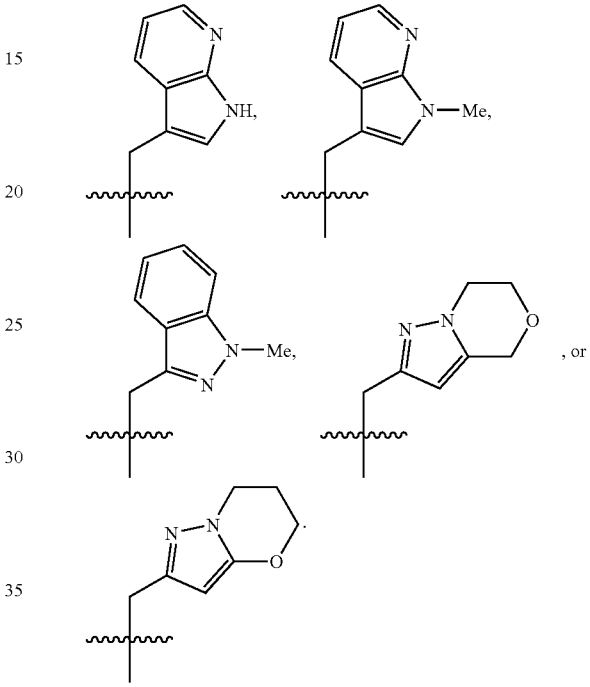

In a tenth aspect, the present invention includes compounds of Formula (Ib), (IIb), (Ic) or (IIc), or a stereoisomer, a tautomer, a pharmaceutically acceptable salt, a solvate, or a prodrug thereof, within the scope of the ninth aspect, wherein:

M is substituted with 0-2 R$^3$ and is selected from the group consisting of: phenyl, pyridyl, thienyl,

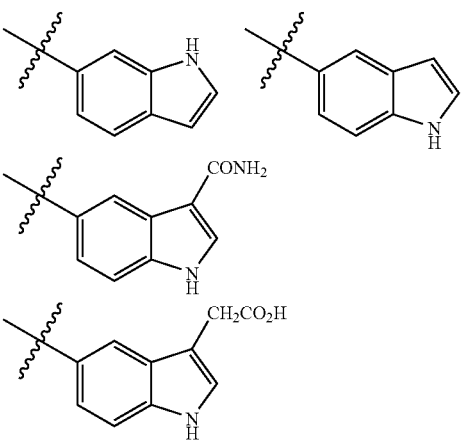

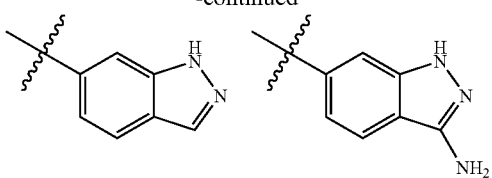

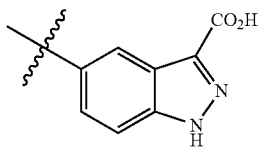

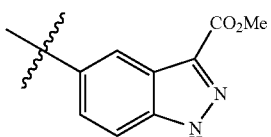

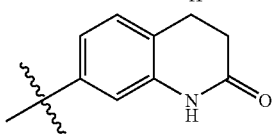

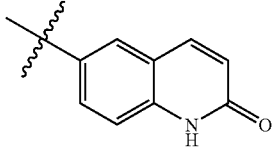

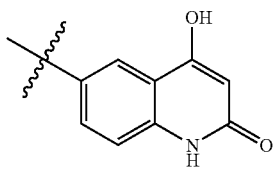

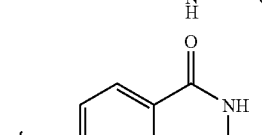

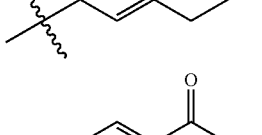

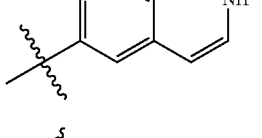

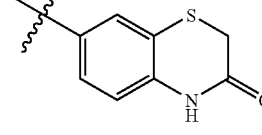

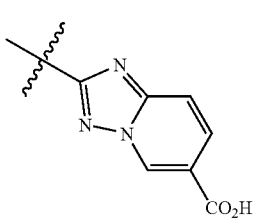

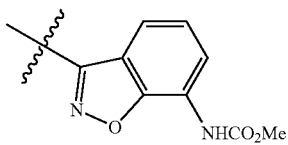

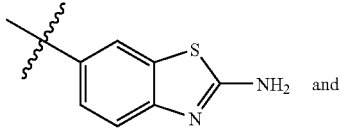

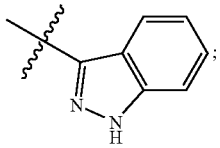

$R^3$ is, independently at each occurrence, F, Cl, CN, $CO_2H$, $CO_2Me$, —$CH_2CO_2H$, —$CONH_2$, —$NHCO_2Me$, —(C=NH)NHOH, —$CONHCH_2CO_2H$, —$CONH(CH_2)_2CO_2H$, —$CONH(CH_2)_3CO_2H$, —$CONH(CH_2)_3CO_2Et$, —$CH_2NHCO_2Me$, —$NHCO_2(CH_2)_2OMe$, —$CH_2NHCO_2(CH_2)_2OMe$, —$NHCO_2(CH_2)_2CO_2H$, —$NHCO_2(CH_2)_2CO_2Me$, —$NHCO_2(CH_2)_2CO_2Et$, —$CH_2NHCONH_2$, —$NHCONH(CH_2)_2CO_2H$, —$NHCONH(CH_2)_2CO_2Me$, —$NHCONH(CH_2)_3CO_2Me$, —$CONHSO_2Me$, $P(O)(OH)_2$, $P(O)(OEt)_2$, —$CH_2P(O)(OH)_2$, —$CH_2P(O)(OEt)_2$, pyridin-4-yl-, tetrahydrofuran-2-ylmethoxy-, imidazol-1-yl, 1,2,4-triazol-1-yl, tetrazol-1-yl, tetrazol-5-yl,

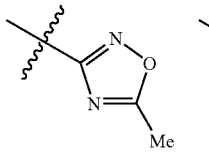

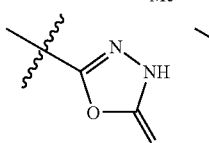

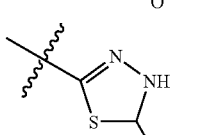

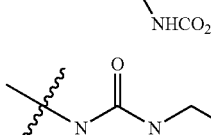

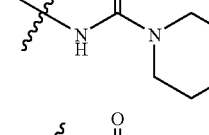

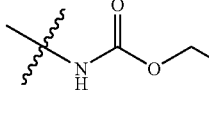

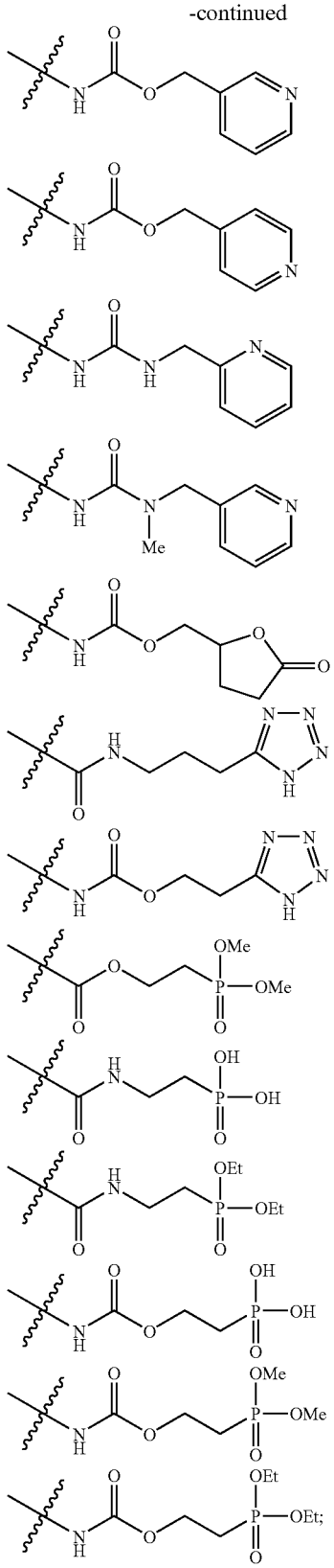

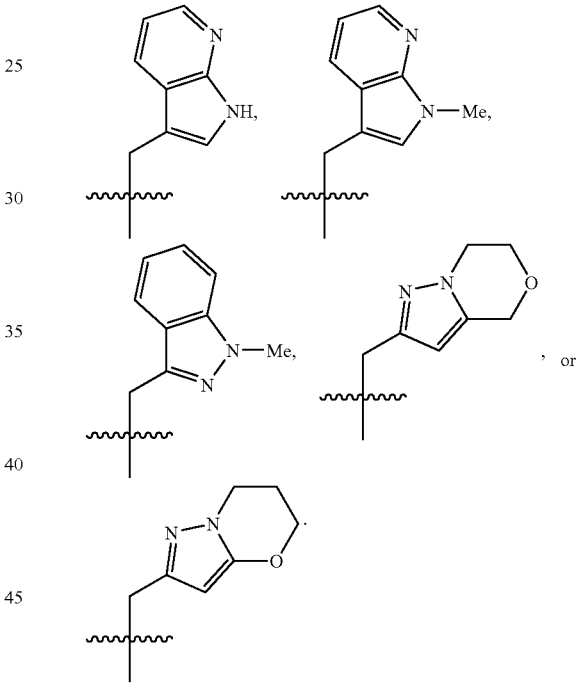

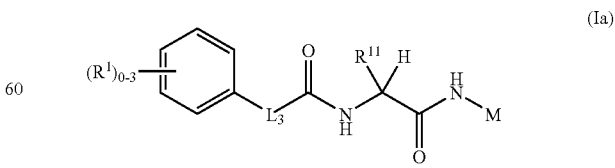

zyl, 3-carboxybenzyl, 3-carbamoylbenzyl, 3-(morpholin-4-ylcarbonyl)benzyl, (dimethylamino)-carbonylmethyl, thien-2-ylmethyl, (1-methylpyrazol-3-yl)methyl, (1,3-dimethylpyrazol-5-yl)methyl, (1,5-dimethylpyrazol-3-yl) methyl, (1-ethylpyrazol-3-yl)methyl, (1-(2-hydroxyethyl)-5-methyl-1H-pyrazol-3-yl)methyl, thiazol-2-ylmethyl, thiazol-4-ylmethyl, 1H-imidazol-4-ylmethyl, 1-methyl-1H-imidazol-4-ylmethyl, 1-methyl-1H-imidazol-5-ylmethyl, azetidin-3-ylmethyl, (1-acetyl-azetidin-3-yl)methyl, (1-$CO_2$Me-azetidin-3-yl)methyl, (3-(2-ethoxyethoxy)pyrrolidin-1-yl)carbonylmethyl, (1-benzoylpyrrolidin-3-yl)methyl, piperidin-3-ylmethyl, piperidin-4-ylmethyl, piperidin-4-ylethyl, (1-acetyl-piperidin-4-yl)ethyl, (1-$CO_2$Me-piperidin-3-yl)methyl, (1-$CO_2$Me-piperidin-4-yl)methyl, tetrahydro-2H-pyran-4-ylmethyl, pyrid-2-ylmethyl, pyrid-3-ylmethyl, pyrid-4-ylmethyl, (2-hydroxy-pyrid-5-yl)methyl, (1,1-dioxo-1$\lambda^6$-thiomorpholin-4-yl)methyl, (1,1-dioxo-1$\lambda^6$-thiomorpholin-4-yl)carbonylmethyl, N-(pyrazin-2-ylmethyl)aminocarbonylmethyl, 1H-indol-3-yl, quinoxalin-2-ylmethyl, In an eleventh aspect, the present invention provides a compound selected from the exemplified examples or stereoisomers, tautomers, pharmaceutically acceptable salts, solvates, or prodrugs thereof.

In another aspect, the present invention includes a compound of Formula (Ia):

or its stereoisomers, tautomers, pharmaceutically acceptable salts, solvates, or prodrugs thereof: wherein:

$L_3$ is —$CH_2CH_2$—, or —CH=CH—;

$R^{11}$ is —$CH_2CO_2$Me, —$CH_2CH_2CF_3$, —$CH_2CH_2$SMe, —$CH_2CH_2$S(O)Me, —$CH_2CH_2$S(O)$_2$Me, —$(CH_2)_4$N(Me)$_2$, —$(CH_2)_3$NHC(NH$_2$)=N(NO$_2$), benzyl, 2-fluorobenzyl, 3-fluorobenzyl, 4-fluorobenzyl, 3,5-difluoroben- M is substituted with 0-2 $R^3$ and is selected from the group: cyclohexyl, phenyl, pyridyl, thienyl and thiazolyl;
alternatively, M is selected from the group:

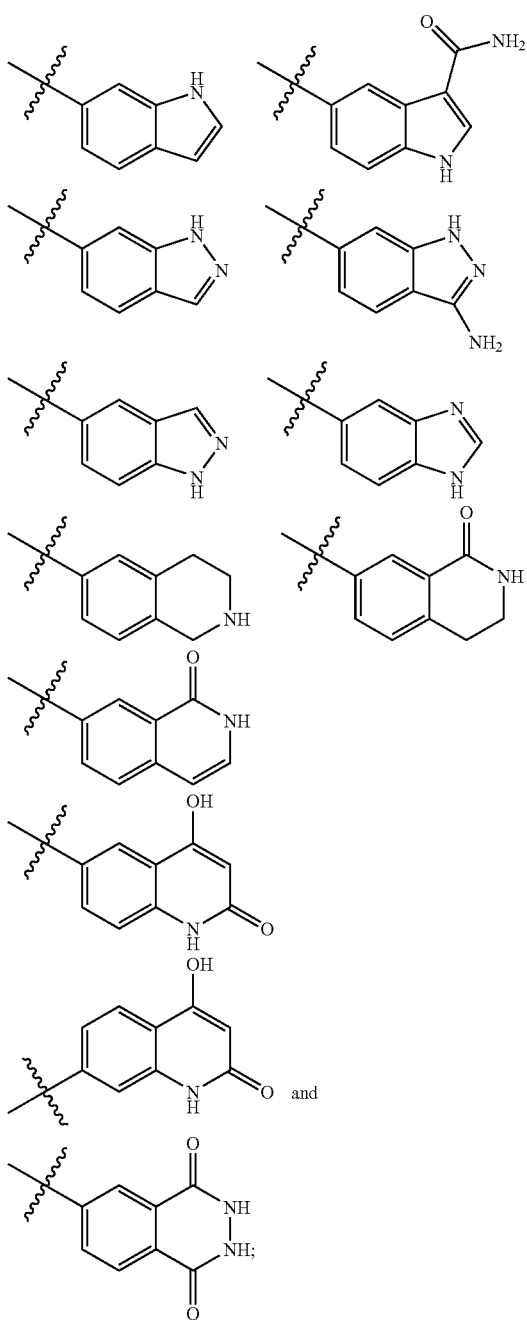

and $R^1$ is, independently at each occurrence, F, Cl, Br, Me, Et, OMe, $CF_3$, $OCF_3$, CN, $NH_2$, $CO_2H$, $CO_2Me$, $CO_2Et$, $CO_2$(t-Bu), C(O)Me, —$CH_2CO_2H$, —$CH_2CO_2Me$, —$CH_2CO_2Et$, —$CH_2NH_2$, —$CONH_2$, —NHCOMe, —$NHCO_2Me$, —$NHCO_2$(t-Bu), —$CO_2(CH_2)_2NEt_2$, —$NHCO_2(CH_2)_2N(Me)_2$, —$SO_2NH_2$, —C(=NH)$NH_2$, pyrazol-1-yl, 3-carboxy-pyrazol-1-yl, 4-carboxy-pyrazol-1-yl, 1,2,3-triazol-1-yl, 1,2,4-triazol-1-yl, 1,3,4-triazol-1-yl, 1,2,3-triazol-2-yl, 4-carboxy-1,2,3-triazol-1-yl, 4-(ethoxycarbonyl)-1,2,3-triazol-1-yl, tetrazol-1-yl, tetrazol-5-yl, 5-Me-tetrazol-1-yl, 5-$CF_3$-tetrazol-1-yl, 5-amino-1,3,4-oxadiazol-2-yl, 2-oxo-1,3,4-trizaolyl-5-yl, 4-aminocarbonyl-1,2,3-triazol-1-yl, 4-dimethylaminocarbonyl-1,2,3-triazol-1-yl, or 4-hydroxymethyl-1,2,3-triazol-1-yl;

$R^3$ is, independently at each occurrence, F, Cl, CN, $NH_2$, $CO_2H$, $CO_2Me$, $CO_2Et$, $CO_2$(t-Bu), —$CH_2CO_2H$, —$CH_2CO_2Me$, —$CH_2CO_2Et$, —$CONH_2$, —NHCOMe, —$NHCO_2Me$, —$NHCO_2$(t-Bu), —$CO_2(CH_2)_2NEt_2$, —$NHCO_2(CH_2)_2N(Me)_2$, —$SO_2NH_2$, 2-(N,N-dimethylaminomethyl)-phenyl, pyridin-4-yl-, tetrahydrofuran-2-ylmethoxy-, 2-oxo-piperidin-1-yl, 2-oxo-2H-pyridin-1-yl, imidazol-1-yl, 2-(N,N-dimethylaminomethyl)-imidazol-1-yl, 1,2,4-triazol-1-yl, tetrazol-1-yl, tetrazol-5-yl, or 4-methylpiperazin-1-yl;

$R^{11}$ is methyl, ethyl, carboxymethyl, benzyl, 2-fluorobenzyl, 3-fluorobenzyl, 4-fluorobenzyl, 3-carboxybenzyl, 3-carbamoylbenzyl, 3-(N-methylcarbamoyl)-benzyl, 3-methoxycarbonylbenzyl, 3-methylcarbonylamino-benzyl, 3-(isopropyl-methyl-carbamoyl)-benzyl, 3-(methyl-phenyl-carbamoyl)-benzyl, benzyloxymethyl, benzylthiomethyl, 1-naphthylmethyl, 2-naphthylmethyl, thiazol-4-ylmethyl, pyrid-2-ylmethyl, pyrid-3-ylmethyl, pyrid-4-ylmethyl, (benzyloxycarbonyl)methyl, (1-methylpyrazol-3-yl)methyl, (1-methylpyrazol-5-yl)methyl, (3-methylpyrazol-5-yl)methyl, 1-ethylpyrazol-3-ylmethyl, 3-pyrazolylmethyl, [1-(4-methoxybenzyl)-pyrazol-3-yl]methyl, (1,5-dimethylpyrazol-3-yl)methyl, (1,3-dimethylpyrazol-5-yl)methyl, [1-(4-methoxybenzyl)-5-methyl-pyrazol-3-yl]methyl, (3-trifluoromethylpyrazol-5-yl)methyl, [1-(4-methoxybenzyl)-3-trifluoromethylpyrazol-5-yl]methyl, (2-methoxypyridin-3-yl)methyl, (6-methoxypyridin-3-yl)methyl, (4-(methoxycarbonyl)-oxazol-2-yl)methyl, morpholin-4-ylcarbonylmethyl, (2,6-dimethyl-morpholin-4-yl)carbonylmethyl, N-((5-methylpyrazin-2-yl)methyl)-aminocarbonylmethyl, 4-methylpiperazin-1-ylcarbonylmethyl, piperazin-1-ylcarbonylmethyl, 4-methylcarbonylpiperazin-1-ylcarbonylmethyl, pyrrolidin-1-ylcarbonylmethyl, 2-methoxypyrrolidin-1-ylcarbonylmethyl, (1,1-dioxo-1$\lambda^6$-thiomorpholin-4-yl)carbonylmethyl, or

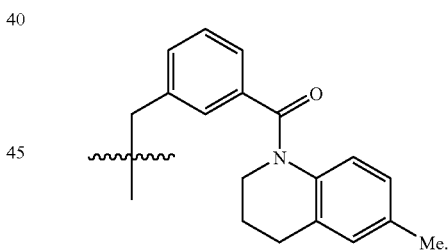

In another aspect, the present invention includes a compound of Formula (Ib):

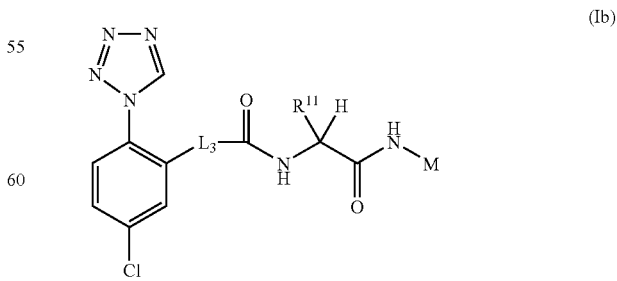

(Ib)

or its stereoisomers, tautomers, pharmaceutically acceptable salts, solvates, or prodrugs thereof: wherein:
$L_3$ is —$CH_2CH_2$— or —CH=CH—;

M is substituted with 0-2 R³ and is selected from the group: phenyl and pyridyl;
alternatively, M is selected from the group:

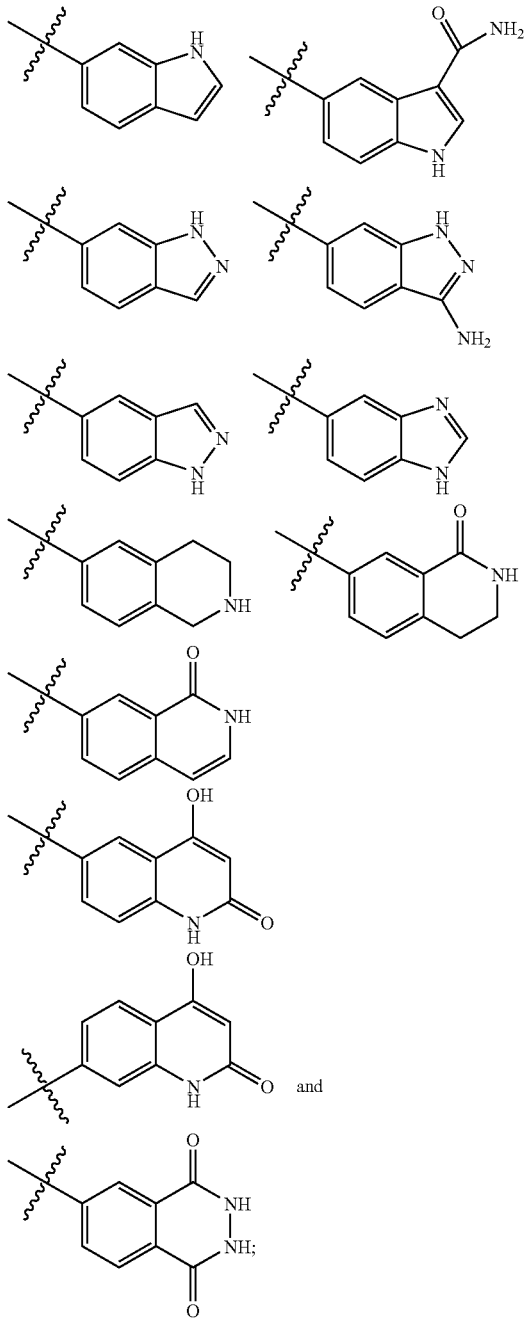

R³ is, independently at each occurrence, F, Cl, CN, NH₂, CO₂H, CO₂Me, CO₂Et, CO₂(t-Bu), —CH₂CO₂H, —CH₂CO₂Me, —CH₂CO₂Et, —CONH₂, —NHCOMe, —NHCO₂Me, —NHCO₂(t-Bu), —CO₂(CH₂)₂NEt₂, —NHCO₂(CH₂)₂N(Me)₂, —SO₂NH₂, pyridin-4-yl-, tetrahydrofuran-2-ylmethoxy-, 2-oxo-piperidin-1-yl, 2-oxo-2H-pyridin-1-yl, imidazol-1-yl, 2-(N,N-dimethylaminomethyl)-imidazol-1-yl, 1,2,4-triazol-1-yl, tetrazol-1-yl, tetrazol-5-yl, or 4-methyl-piperazin-1-yl; and
R¹¹ is methyl, ethyl, —CH₂CO₂Me, —CH₂CO₂H, —CH₂CONMe, benzyl, 2-fluorobenzyl, 3-fluorobenzyl, 1-ethylpyrazol-3-ylmethyl, 1-methyl-pyrazol-3-ylmethyl, 4-methyl-piperazin-1-ylcarbonylmethyl, (1,1-dioxo-1λ⁶-thiomorpholin-4-yl)carbonylmethyl, or morpholinylcarbonylmethyl.

In another aspect, the present invention includes a compound of Formula (IIa):

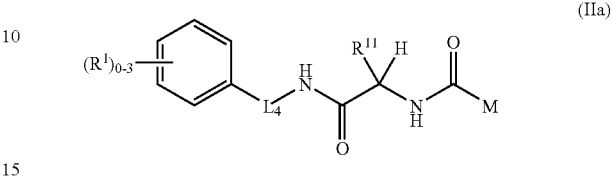

(IIa)

or its stereoisomers, tautomers, pharmaceutically acceptable salts, solvates, or prodrugs thereof: wherein:
L₄ is —CH₂CH₂— or —CH═CH—;
M is substituted with 0-2 R³ and is selected from the group: cyclohexyl, phenyl, pyridyl, thienyl and thiazolyl;
alternatively, M is selected from the group:

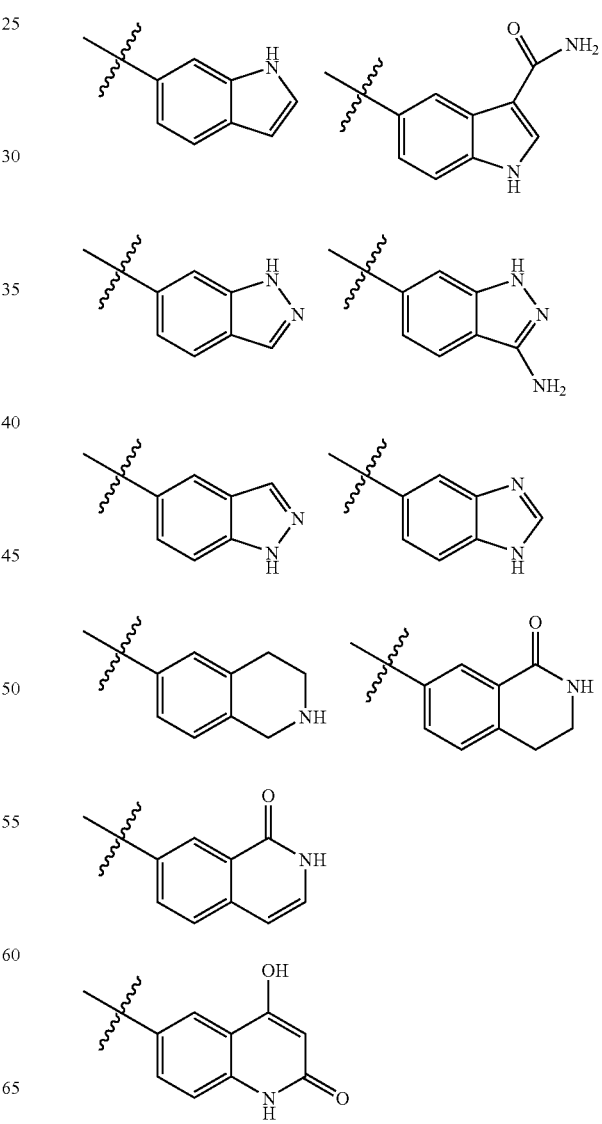

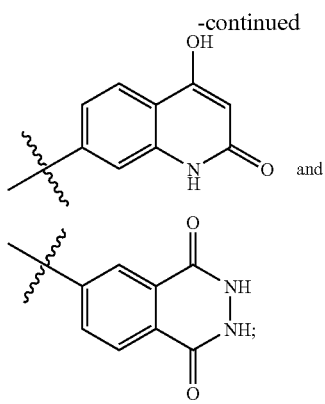 and 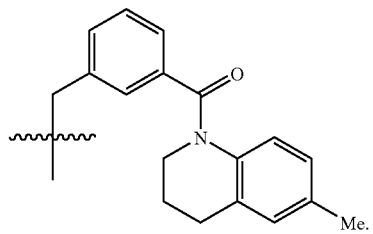 [SMILES: *Cc1cccc(C(=O)N2CCCc3cc(C)ccc32)c1]

R¹ is, independently at each occurrence, F, Cl, Br, Me, Et, OMe, $CF_3$, $OCF_3$, CN, $NH_2$, $CO_2H$, $CO_2Me$, $CO_2Et$, $CO_2$(t-Bu), C(O)Me, —$CH_2CO_2H$, —$CH_2CO_2Me$, —$CH_2CO_2Et$, —$CH_2NH_2$, —$CONH_2$, —$NHCOMe$, —$NHCO_2Me$, —$NHCO_2$(t-Bu), —$CO_2(CH_2)_2NEt_2$, —$NHCO_2(CH_2)_2N(Me)_2$, —$SO_2NH_2$, —C(=NH)$NH_2$, pyrazol-1-yl, 3-carboxy-pyrazol-1-yl, 4-carboxy-pyrazol-1-yl, 1,2,3-triazol-1-yl, 1,2,4-triazol-1-yl, 1,3,4-triazol-1-yl, 1,2,3-triazol-2-yl, 4-carboxy-1,2,3-triazol-1-yl, 4-(ethoxycarbonyl)-1,2,3-triazol-1-yl, tetrazol-1-yl, tetrazol-5-yl, 5-Me-tetrazol-1-yl, 5-$CF_3$-tetrazol-1-yl, 5-amino-1,3,4-oxadiazol-2-yl, 2-oxo-1,3,4-trizaolyl-5-yl, 4-aminocarbonyl-1,2,3-triazol-1-yl, 4-dimethylaminocarbonyl-1,2,3-triazol-1-yl, or 4-hydroxymethyl-1,2,3-triazol-1-yl;

R³ is, independently at each occurrence, F, Cl, CN, $NH_2$, $CO_2H$, $CO_2Me$, $CO_2Et$, $CO_2$(t-Bu), —$CH_2CO_2H$, —$CH_2CO_2Me$, —$CH_2CO_2Et$, —$CONH_2$, —$NHCOMe$, —$NHCO_2Me$, —$NHCO_2$(t-Bu), —$CO_2(CH_2)_2NEt_2$, —$NHCO_2(CH_2)_2N(Me)_2$, —$SO_2NH_2$, 2-(N,N-dimethylaminomethyl)-phenyl, pyridin-4-yl-, tetrahydrofuran-2-ylmethoxy-, 2-oxo-piperidin-1-yl, 2-oxo-2H-pyridin-1-yl, imidazol-1-yl, 2-(N,N-dimethylaminomethyl)-imidazol-1-yl, 1,2,4-triazol-1-yl, tetrazol-1-yl, tetrazol-5-yl, or 4-methylpiperazin-1-yl;

R¹¹ is methyl, ethyl, carboxymethyl, benzyl, 2-fluorobenzyl, 3-fluorobenzyl, 4-fluorobenzyl, 3-carboxybenzyl, 3-carbamoylbenzyl, 3-(N-methylcarbamoyl)-benzyl, 3-methoxycarbonylbenzyl, 3-methylcarbonylamino-benzyl, 3-(isopropyl-methyl-carbamoyl)-benzyl, 3-(methyl-phenyl-carbamoyl)-benzyl, benzyloxymethyl, benzylthiomethyl, 1-naphthylmethyl, 2-naphthylmethyl, thiazol-4-ylmethyl, pyrid-2-ylmethyl, pyrid-3-ylmethyl, pyrid-4-ylmethyl, (benzyloxycarbonyl)methyl, (1-methylpyrazol-3-yl)methyl, (1-methylpyrazol-5-yl)methyl, (3-methylpyrazol-5-yl)methyl, 1-ethylpyrazol-3-ylmethyl, 3-pyrazolylmethyl, [1-(4-methoxybenzyl)-pyrazol-3-yl]methyl, (1,5-dimethylpyrazol-3-yl)methyl, (1,3-dimethylpyrazol-5-yl)methyl, [1-(4-methoxybenzyl)-5-methyl-pyrazol-3-yl]methyl, (3-trifluoromethylpyrazol-5-yl)methyl, [1-(4-methoxybenzyl)-3-trifluoromethylpyrazol-5-yl]methyl, (2-methoxypyridin-3-yl)methyl, (6-methoxypyridin-3-yl)methyl, (4-(methoxycarbonyl)-oxazol-2-yl)methyl, morpholin-4-ylcarbonylmethyl, (2,6-dimethyl-morpholin-4-yl) carbonylmethyl, N-((5-methylpyrazin-2-yl)methyl)-aminocarbonylmethyl, 4-methylpiperazin-1-ylcarbonylmethyl, piperazin-1-ylcarbonylmethyl, 4-methylcarbonylpiperazin-1-ylcarbonylmethyl, pyrrolidin-1-ylcarbonylmethyl, 2-methoxypyrrolidin-1-ylcarbonylmethyl, (1,1-dioxo-1$\lambda^6$-thiomorpholin-4-yl)carbonylmethyl, or

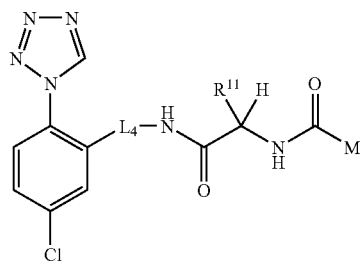

In another aspect, the present invention includes a compound of Formula (IIb):

(IIb)

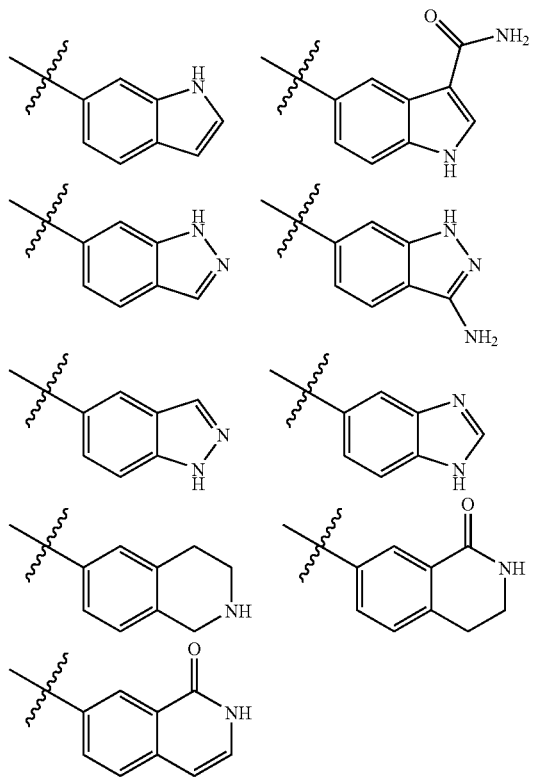

or its stereoisomers, tautomers, pharmaceutically acceptable salts, solvates, or prodrugs thereof: wherein:

$L_4$ is —$CH_2CH_2$— or —CH=CH—;

M is substituted with 0-2 R³ and is selected from the group: phenyl and pyridyl;

alternatively, M is selected from the group:

-continued

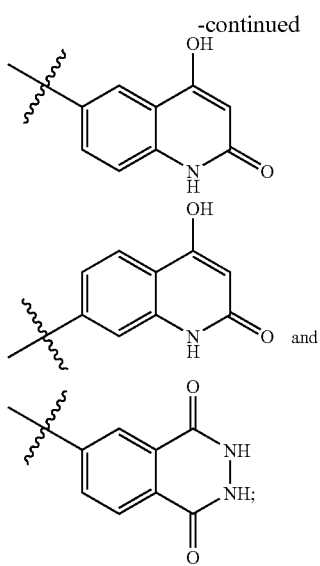

R[3] is, independently at each occurrence, F, Cl, CN, NH$_2$, CO$_2$H, CO$_2$Me, CO$_2$Et, CO$_2$(t-Bu), —CH$_2$CO$_2$H, —CH$_2$CO$_2$Me, —CH$_2$CO$_2$Et, —CONH$_2$, —NHCOMe, —NHCO$_2$Me, —NHCO$_2$(t-Bu), —CO$_2$(CH$_2$)$_2$NEt$_2$, —NHCO$_2$(CH$_2$)$_2$N(Me)$_2$, —SO$_2$NH$_2$, pyridin-4-yl-, tetrahydrofuran-2-ylmethoxy-, 2-oxo-piperidin-1-yl, 2-oxo-2H-pyridin-1-yl, imidazol-1-yl, 2-(N,N-dimethylaminomethyl)-imidazol-1-yl, 1,2,4-triazol-1-yl, tetrazol-1-yl, tetrazol-5-yl, or 4-methyl-piperazin-1-yl; and R[11] is methyl, ethyl, —CH$_2$CO$_2$Me, CH$_2$CO$_2$H, —CH$_2$CONMe, benzyl, 2-fluorobenzyl, 3-fluorobenzyl, 1-ethylpyrazol-3-ylmethyl, 1-methyl-pyrazol-3-ylmethyl, 4-methyl-piperazin-1-ylcarbonylmethyl, (1,1-dioxo-1λ$^6$-thiomorpholin-4-yl)carbonylmethyl, or morpholinylcarbonylmethyl.

In another embodiment, M is phenyl substituted with 0-2 R[3].

In another embodiment, M is pyridyl substituted with 0-2 R[3].

In another embodiment, M is selected from:

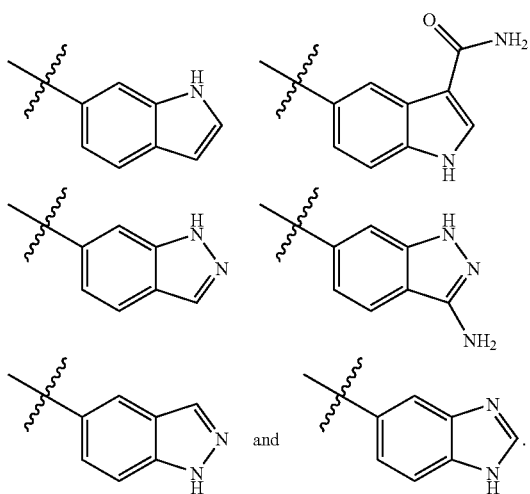

In another embodiment, M is selected from:

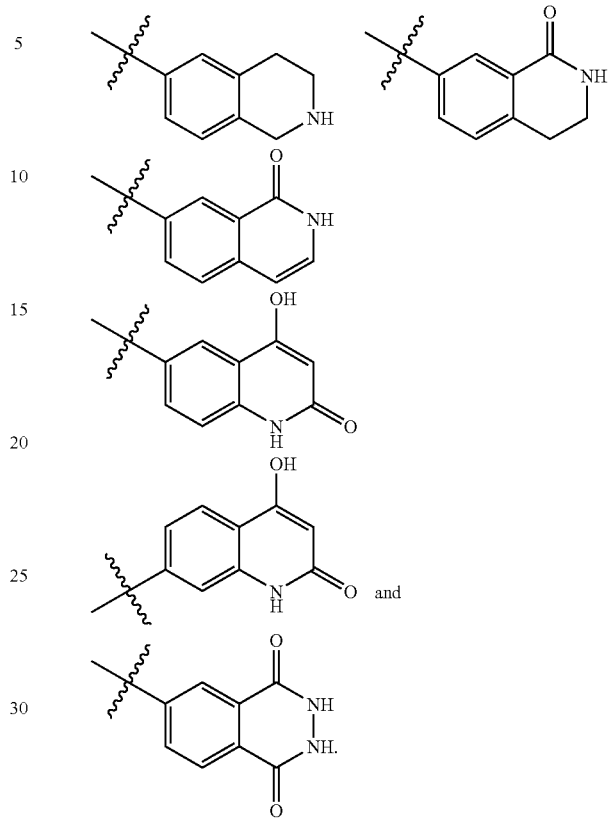

In another embodiment, R[11] is benzyl.
In another embodiment, R[12] is H.

II. Other Embodiments of the Invention

In another embodiment, the present invention provides a composition comprising at least one of the compounds of the present invention or a stereoisomer, tautomer, pharmaceutically acceptable salt, solvate, or prodrug thereof.

In another embodiment, the present invention provides a pharmaceutical composition comprising a pharmaceutically acceptable carrier and at least one of the compounds of the present invention or a stereoisomer, tautomer, pharmaceutically acceptable salt, solvate, or prodrug thereof.

In another embodiment, the present invention provides a pharmaceutical composition, comprising: a pharmaceutically acceptable carrier and a therapeutically effective amount of at least one of the compounds of the present invention or a stereoisomer, tautomer, pharmaceutically acceptable salt, solvate or prodrug thereof.

In another embodiment, the present invention provides a process for making a compound of the present invention or a stereoisomer, tautomer, pharmaceutically acceptable salt, solvate or prodrug thereof.

In another embodiment, the present invention provides an intermediate for making a compound of the present invention or a stereoisomer, tautomer, pharmaceutically acceptable salt, solvate or prodrug thereof.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof. Preferably, the anti-platelet agent(s) are clopidogrel and/or aspirin, or a combination thereof.

In another embodiment, the present invention provides a method for the treatment or prophylaxis of a thromboembolic disorder comprising administering to a patient in need of such treatment or prophylaxis a therapeutically effective amount of at least one of the compounds of the present invention or stereoisomers, tautomers, pharmaceutically acceptable salts, solvates, or prodrugs thereof. Preferably, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders. Preferably, the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a compound of the present invention or stereoisomers, tautomers, pharmaceutically acceptable salts, solvates, or prodrugs thereof, for use in therapy.

In another embodiment, the present invention provides a compound of the present invention or stereoisomers, tautomers, pharmaceutically acceptable salts, solvates, or prodrugs thereof, for use in therapy for the treatment or prophylaxis of a thromboembolic disorder. Preferably, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders. Preferably, the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention also provides the use of a compound of the present invention or stereoisomers, tautomers, pharmaceutically acceptable salts, solvates, or prodrugs thereof, for the manufacture of a medicament for the treatment or prophylaxis of a thromboembolic disorder.

In another embodiment, the present invention provides a method for treating a thromboembolic disorder, comprising: administering to a patient in need thereof a therapeutically effective amount of a first and second therapeutic agent, wherein the first therapeutic agent is a compound of the present invention or a stereoisomer, tautomer, pharmaceutically acceptable salt, solvate or prodrug thereof, and the second therapeutic agent is at least one agent selected from a second factor Xa inhibitor, an anti-coagulant agent, an anti-platelet agent, a thrombin inhibiting agent, a thrombolytic agent, and a fibrinolytic agent. Preferably, the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

In another embodiment, the present invention provides a method for the treatment or prophylaxis of an inflammatory disorder comprising: administering to a patient in need of such treatment or prophylaxis a therapeutically effective amount of at least one of the compounds of the present invention or a stereoisomer, tautomer, pharmaceutically acceptable salt, solvate or prodrug thereof.

In another embodiment, the present invention provides a method for the treatment or prophylaxis of an inflammatory disorder, wherein the inflammatory disorder is selected from the group consisting of sepsis, acute respiratory distress syndrome, and systemic inflammatory response syndrome.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Otically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The molecular weight of compounds of the present invention is preferably less than about 800 grams per mole.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

Alkenyl" or "alkenylene" is intended to include hydrocarbon chains of either straight or branched configuration having the specified number of carbon atoms and one or more carbon-carbon double bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more carbon-carbon triple bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9 or 10-membered carbocyclic ring system that contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in *Hawley's Condensed Chemical Dictionary* (13 ed.), R. J. Lewis, ed., J. Wiley & Sons, Inc., New York (1997). "$C_{6-10}$ aryl" refers to phenyl and naphthyl. Unless otherwise specified, "aryl", "$C_{6-10}$ aryl" or "aromatic residue" may be unsubstituted or substituted with 1 to 3 groups selected from OH, $OCH_3$, Cl, F, Br, I, CN, $NO_2$, $NH_2$, $N(CH_3)$ H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9 or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part of (i.e., within) the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases in which there are quaternary carbon atoms in compounds of the present invention, these can be replaced by silicon atoms, provided they do not form Si—N or Si—O bond.

When any variable occurs more than one time in any constituent or formula for a compound, its definition at each occurrence is independent of its definition at every other occurrence. Thus, for example, if a group is shown to be substituted with 0-3 $R^{3a}$, then said group may optionally be substituted with up to three $R^{3a}$ groups, and at each occurrence $R^{3a}$ is selected independently from the definition of $R^{3a}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18$^{th}$ Edition, Mack Publishing Company, Easton, Pa., 1990, the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull.*, Vol. 32, p. 692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g. acetoxymethyl, pivaloyloxymethyl or propionyloxymethyl), $C_{1-6}$alkoxycarbonyloxy-$C_{1-6}$alkyl (e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of Prodrugs is Well Known in the Art and Described in, for example, *Medicinal Chemistry: Principles and Practice*, ed. F. D. King, The Royal Society of Chemistry, Cambridge, UK, 1994.

Isotopically labeled compounds of the present invention, i.e., wherein one or more of the atoms described are replaced by an isotope of that atom (e.g., $^{12}$C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and insoluble solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
AcOH acetic acid
MeOH methanol
EtOH ethanol
EtOAc ethyl acetate
Et$_2$O diethyl ether
i-PrOH or IPA isopropanol
HOAc acetic acid
BOP reagent benzotriazol-1-yloxytris(dimethylamino) phosphonium hexafluorophosphate
BBr$_3$ boron tribromide
Boc tert-butyloxycarbonyl
cDNA complimentary DNA
CH$_2$Cl$_2$ dichloromethane
CH$_3$CN acetonitrile
ACN acetonitrile
DABCO 1,4-diazabicyclo[2.2.2]octane
DCE 1,2 dichloroethane
DCM dichloromethane
DCC dicyclohexylcarbodiimide
DIEA or DIPEA N,N,-diisopropylethylamine
DME 1,2-dimethoxyethane
DMF dimethyl formamide
DMAP N,N-dimethylaminopyridine
DMSO dimethyl sulfoxide
DPPA diphenyl phosphoryl azide
EDC (or EDC.HCl) or EDCI (or EDCI.HCl) or EDAC 3-ethyl-3'-(dimethylamino)propyl-carbodiimide hydrochloride (or 1-(3-dimethylaminopropyl)-3-ethylcarbodiimide hydrochloride)
EDTA ethylenediaminetetraacetic acid
HATU 0-(7-azabenzotriazol-1-yl)-N,N,N',N'-tetramethyluronium hexafluorophosphate
HCl hydrochloric acid
HEPES 4-(2-hydroxyethyl)piperaxine-1-ethanesulfonic acid
Hex hexane
HOBt or HOBT 1-hydroxybenzotriazole monohydrate
Hunig's base N,N-diisopropylethyl amine
LAH lithium aluminum hydride
LDA Lithium diisopropylamide
LiHMDS Lithium bis(trimethylsilyl)amide
mCPBA or m-CPBA meta-chloroperbenzoic acid
NMM N-methylmorpholine
Pd/C palladium on carbon
PPA polyphosphoric acid
PS polystyrene
PXPd2 bis[di-tert-butyl phosphinous chloride-kP]di-m-chlorodichloro dipalladium
PyBOP (benzotriazol-1-yloxy)tripyrrolidinophosphonium hexafluorophosphate
TEA triethylamine
TFA trifluoroacetic acid
THF tetrahydrofuran
TRIS tris(hydroxymethyl)aminomethane
KOAc potassium acetate
K$_3$PO$_4$ potassium phosphate
MgSO$_4$ magnesium sulfate
NaCl sodium chloride
NaH sodium hydride
NaHCO$_3$ sodium bicarbonate
NaOH sodium hydroxide
Na$_2$SO$_3$ sodium sulfite
Na$_2$SO$_4$ sodium sulfate
NH$_3$ ammonia
NH$_4$Cl ammonium chloride
NH$_4$OH ammonium hydroxide
OTs tosylate, para-toluenesulfonate
PBr$_3$ phosphorous tribromide
Pd(PPh$_3$)$_4$ tetrakis(triphenylphosphine) palladium (0)
(S,S)-EtDuPhosRh(I) (+)-1,2-bis((2S,5S)-2,5-diethylphospholano)benzene (cyclooctadiene)rhodium (I) trifluoromethanesulfonate The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley-Interscience, 3$^{rd}$ Edition, 1999).

Peptide compounds of this invention wherein $L_1$ is —(CH$_2$)$_2$CONH—, —CH═CHCONH—, —C≡CCONH—, —OCH$_2$CONH—, or S(O)$_p$CH$_2$CONH— of formula 1c, can be obtained by the condensation of appropriately substituted carboxylic acids 1a and the amine intermediate 1b with using standard amide bond forming conditions known to one skilled in the art as outlined in Scheme 1A. Reagent combinations which may be employed for the coupling of amines of formula 1b with suitably substituted carboxylic acids include, but are not limited to: BOP-reagent and triethylamine, EDC, HOBt, and N-methylmorpholine, or HATU and Hunig's base (DIPEA). Solvents suitable for this transformation include, but are not limited to tetrahydrofuran and dimethylformamide. Coupling of amines of formula 1b with suitably substituted carboxylic acid chlorides or mixed anhydrides derived from carboxylic acids of formula 1a as shown in Scheme 1A can be carried out in solvents such as methylene chloride or tetrahydrofuran in the presence of a base such as triethylamine, N,N-dimethylaminopyridine (DMAP) or potassium carbonate. It should be recognized by one skilled in the art that the choice of amide bond forming method may be influenced by the nature of the substituents on the group A in 1a, or and that it may be necessary to introduce the final R$^1$ and/or R$^2$ groups on to ring A at a later stage in the synthesis if these groups are not compatible with the coupling method to be used for the formation of the amide bond shown in Scheme 1A.

Scheme 1A

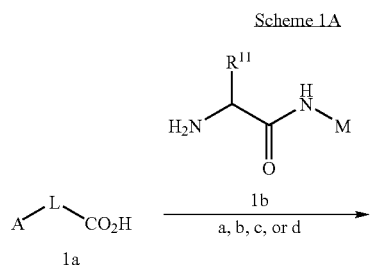

-continued

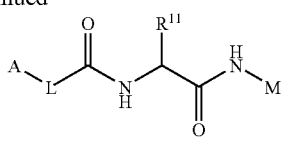

1c

L = —(CH$_2$)$_2$—, —CH═CH—, —C≡C—, —OCH$_2$—, or —S(O)$_p$CH$_2$—.

a: BOP, TEA;
b: EDC, HOBT, NMM;
c: ClCO$_2$(iBu), DIPEA, THF;
d: (i) (COCl)$_2$/DMF or SOCl$_2$ (ii) DMAP, CH$_2$Cl$_2$.

Alternately, as shown in Scheme 1B, acid, 1a is first coupled to a suitable amino ester 1d, followed by deprotection of ester 1e and coupling of the resulting acid to an appropriately functionalized amine, 1f, provide compounds of formula 1c.

Scheme 1B

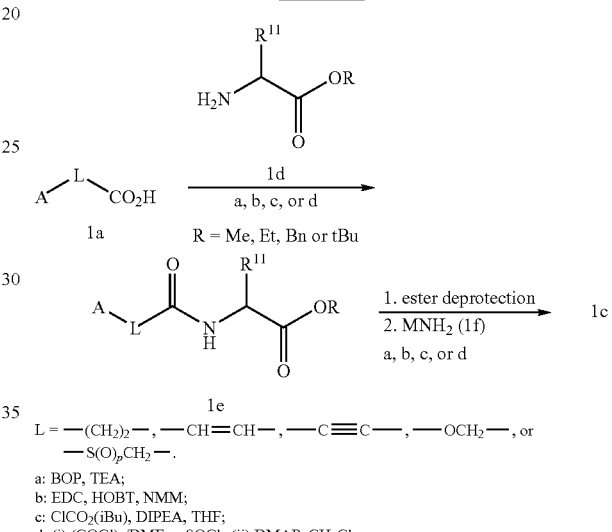

L = —(CH$_2$)$_2$—, —CH═CH—, —C≡C—, —OCH$_2$—, or —S(O)$_p$CH$_2$—.

a: BOP, TEA;
b: EDC, HOBT, NMM;
c: ClCO$_2$(iBu), DIPEA, THF;
d: (i) (COCl)$_2$/DMF or SOCl$_2$ (ii) DMAP, CH$_2$Cl$_2$.

Suitably substituted carboxylic acids 1a where L is —(CH$_2$)$_2$— are either commercially available, or they can be prepared from the corresponding bromides, alcohols, aldehydes, or esters as shown in Scheme 2 using methods known to one skilled in the art.

Scheme 2

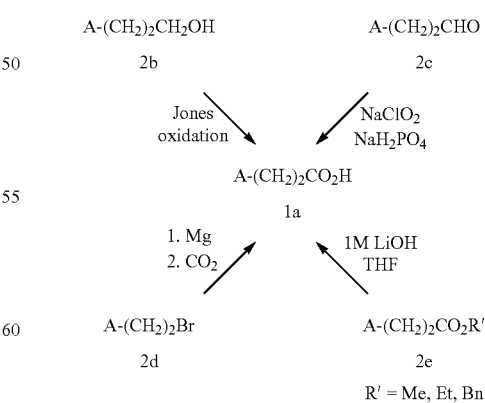

R' = Me, Et, Bn

Additional carboxylic acid intermediates of formulae 3a, 3b, 3c, 3d, 3e, and 3f useful for preparation of amide compounds of this invention can be prepared as outlined in Schemes 3A and 3B.

Scheme 3A

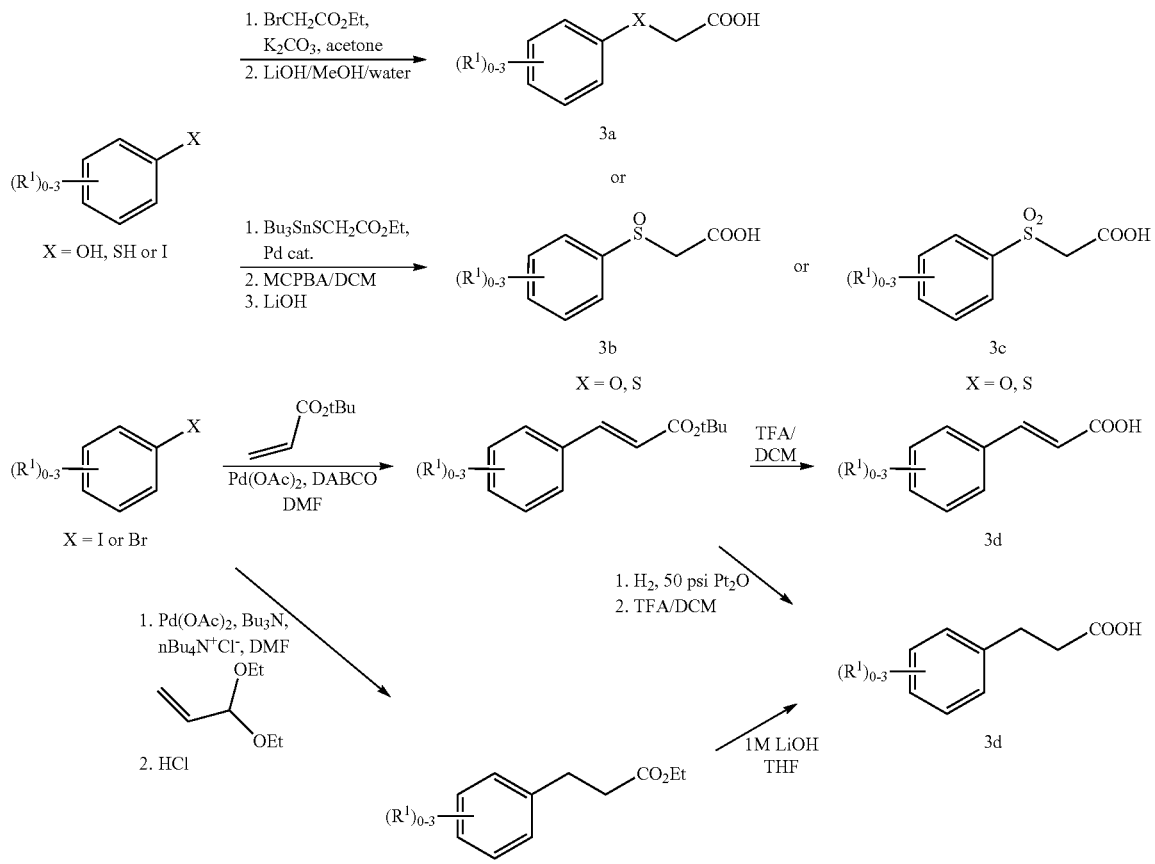

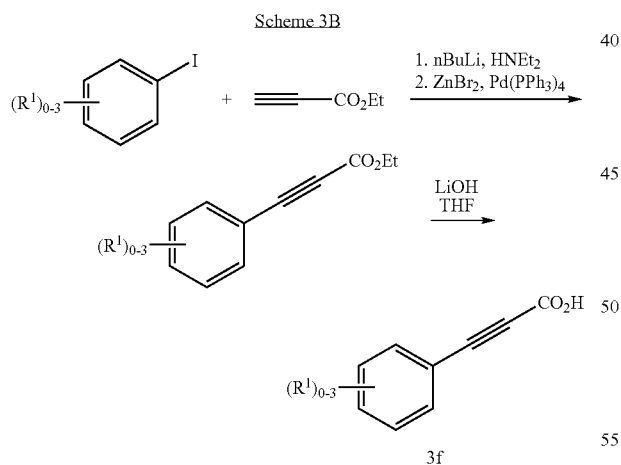

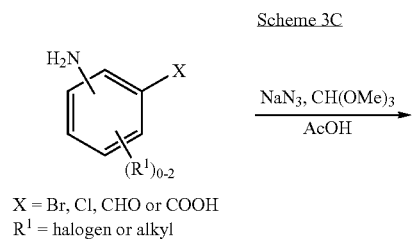

Substitution of suitably functionalized heteroaryl alcohols, bromides and iodides for the phenol, bromo and iodobenzene starting materials in Schemes 3A and 3B will provide additional carboxylic acids useful for the preparation of compound of the instant invention wherein A is a heteroaryl moiety, such as, for example, a pyridine, thiophene, indole, or benzthiazole moiety. Additional starting materials useful for the preparation of the substituted phenyl acrylic or propanoic acids shown in Schemes 3A and 3B, wherein one of the $R^1$ groups is chloro or methyl and another $R^1$ is 1-tetrazolyl, can be prepared from the corresponding anilines by treatment with sodium azide and trimethylorthoformate in acetic acid as shown in Scheme 3C.

Scheme 3C

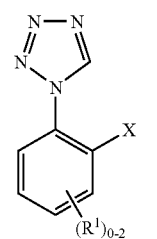

Phenol starting materials useful for preparation of compounds of the invention wherein $L_1$ is —OCH$_2$CONH— can be prepared by the Bayer-Villger reaction of the requisite aldehydes followed by mild hydrolysis as outlined in Scheme 3D.

Scheme 3D

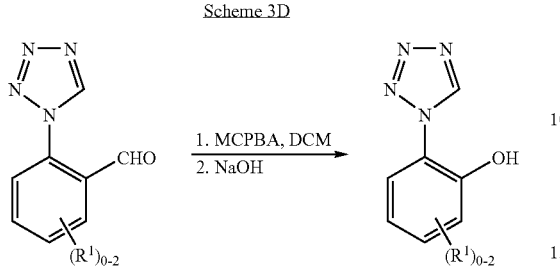

The preparation of the requisite amine intermediates of formula 1b is outlined in Scheme 4. A suitably protected amino acid 4a is condensed with an amine of formula 1f using any of a variety of methods for amide bond formation known to one skilled in the art of organic synthesis. Removal of the amino protecting group from the resulting amide product can be easily accomplished according to procedures outlined in Greene and Wuts (*Protective Groups In Organic Synthesis*, Wiley-Interscience, 3$^{rd}$ Edition, 1999) to afford amines 1b which can be coupled according to Scheme 1A above to afford compounds of this invention.

Scheme 4

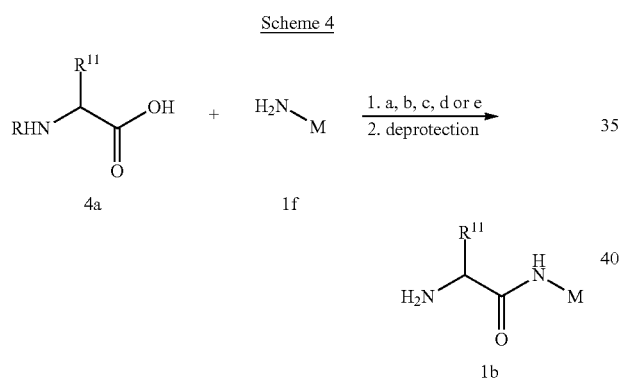

R = Boc, Cbz or other suitable amine protecting group
a: BOP, TEA;
b: EDC, HOBT, NMM;
c: ClCO$_2$(iBu), DIPEA, THF, -10° C.;
d: (i) (COCl)$_2$/DMF or SOCl$_2$ (ii) DMAP, CH$_2$Cl$_2$;
e. POCl$_3$, pyridine, -10° C.

Peptide compounds of this invention wherein $L_1$ is —CH$_2$NHCONH— may be prepared as outlined in Scheme 5. Condensation of an appropriately functionalized amine intermediate 1b, prepared as described above, with a suitably substituted isocyanate 5a in a solvent, such as tetrahydrofuran or methylene chloride, in the presence of a base, such as triethylamine, diisopropylethylamine or potassium carbonate, provides ureas of formula 5d. Alternatively, ureas of formula 5d of this invention can be prepared by condensation of an amine intermediate 1b with carbonyl diimidazole in a solvent such as tetrahydrofuran or N,N-dimethylformamide followed by treatment in situ with an suitably substituted amine 5b. Urea linked compounds of this invention of formula 5d can also be prepared by condensation of amine intermediate 1b with p-nitrophenylchloroformate in the presence of a suitable base such as triethylamine, followed by treatment of the resulting p-nitrophenylcarbamate with an appropriate substituted amine 5b.

Scheme 5

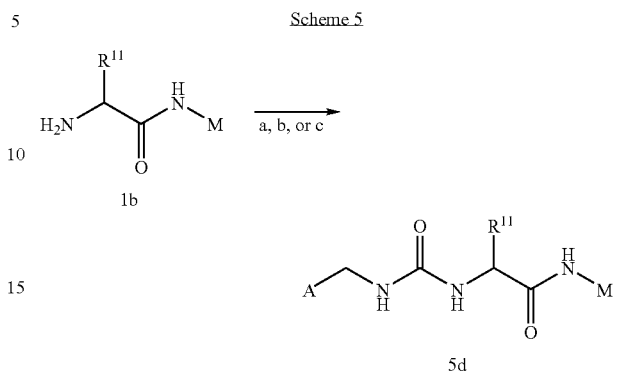

a: A-CH$_2$NCO (5a), Et$_3$N, THF;
b: (i) CDI, Et$_3$N, THF, (ii) ACH$_2$NH$_2$ (5b);
e. p-nitrophenylchloroformate, Et$_3$N, THF, 5b.

Isocyanates of formula 5a used in Scheme 5 above are either commercially available or can be readily prepared from the corresponding amines 5b by treatment with phosgene or by various other methods known in the art (see for example, H. Eckert & B. Forster, *Angew. Chem. Int. Ed.* 1987, 26, 894; H. Knolker & T. Braxmeier, *Synlett*, 1997, 925; S. Porwanski et al. *Tetrahedron Lett.* 2004, 45, 5027). Amines of formula 5b are also available commercially or can be prepared by those knowledgeable in the art from a variety of easily accessible starting materials such as nitriles, aldehydes, alcohols, halides, acids and esters by methods including, but not limited to those outlined in Scheme 6.

Scheme 6

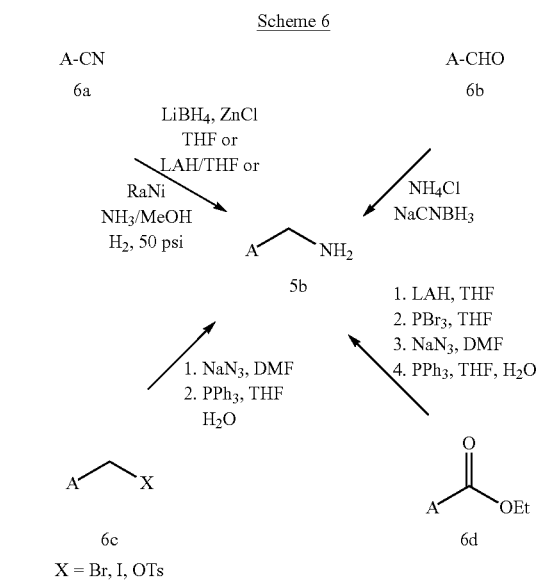

X = Br, I, OTs

Peptide compounds of this invention wherein $L_1$ is —NHNHCONH— of formula 7c may be synthesized similarly as outlined in Scheme 7 by treatment of a suitably functionalized amine intermediate 1b with p-nitrochloroformate as described above followed by treatment of the resulting p-nitrophenylcarbamate 7a with a suitably substituted hydrazine of formula 7b.

Scheme 7

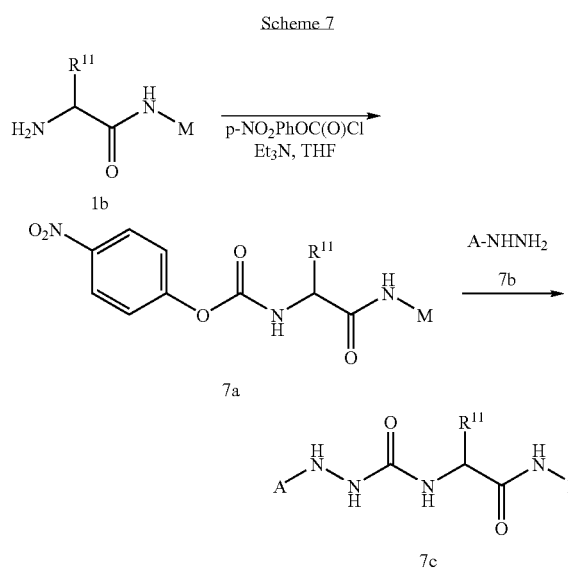

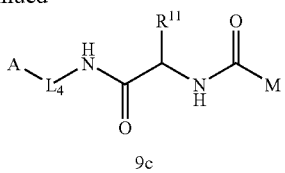

a: BOP, TEA;
b: EDC, HOBT, NMM;
c: ClCO₂(iBu), DIPEA, THF, -10° C.;
d: (i) (COCl)₂/DMF or SOCl₂ (ii) DMAP, CH₂Cl₂.

Scheme 9B

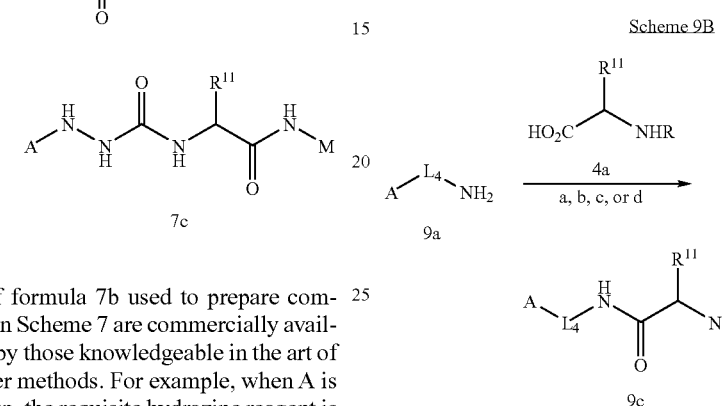

R = Boc, Cbz or other suitable amine protecting group
a: BOP, TEA;
b: EDC, HOBT, NMM;
c: ClCO₂(iBu), DIPEA, THF, -10° C.;
d: (i) (COCl)₂/DMF or SOCl₂ (ii) DMAP, CH₂Cl₂.

Hydrazine reagents of formula 7b used to prepare compounds of this invention in Scheme 7 are commercially available or may be prepared by those knowledgeable in the art of organic synthesis by other methods. For example, when A is an aryl or heteroaryl group, the requisite hydrazine reagent is readily available via diazotization of a starting aryl or heteroarylamine 8a followed by reduction of the resulting diazonium salt with tin chloride to the corresponding arylhydrazine 8b as illustrated in Scheme 8.

Scheme 8

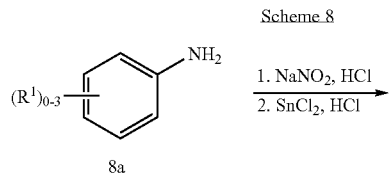

Using methods analogous to those described in Schemes 1A and 1B above, compounds of this invention where $L_2$ is —CH₂CH₂NHCO— or —CH═CHNHCO—, are prepared according to Scheme 9A or 9B starting from a suitably substituted amine of formula 9a.

Phenethylamine starting materials 9a in Scheme 9B wherein $L_4$ is —(CH₂)₂— can be easily obtained by the Curtius rearrangement of the corresponding carboxylic acid, the preparation of which is described in Schemes 3A-D above, as illustrated in Scheme 10A.

Scheme 10A

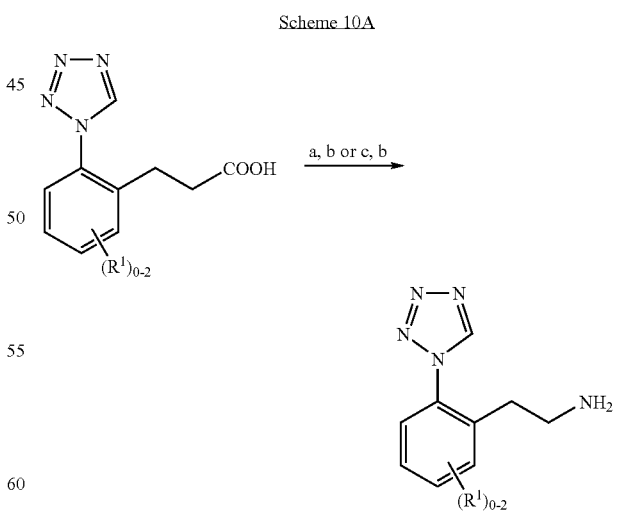

a) DPPA, TEA, t-BuOH, reflux;
b) TFA;
c) Oxalyl Chloride, NaN₃, heat, tBuOH.

Alternatively the phenethylamino derivatives can be easily obtained by the condensation of the corresponding aldhydes

Scheme 9A

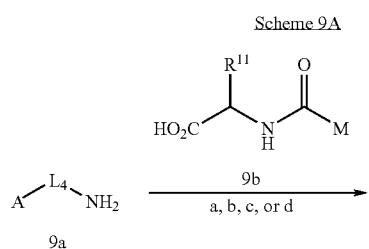

with nitromethane in the presence of ammonium acetate and acetic acid followed by reduction with borane in THF as outlined in Scheme 10B.

Scheme 10B

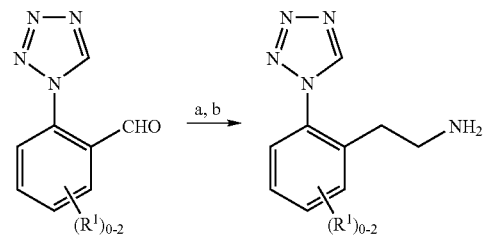

a) CH$_3$NO$_2$, Ammonium acetate, Acetic acid;
b) BH$_3$-THF.

Amine derivatives of formula M-NH$_2$ or their related acid derivatives M-COOH used in the peptide couplings described above to afford compounds of this invention are available through commercial sources or can be easily prepared by those knowledgeable in the art of organic synthesis (for synthetic transformations to amines and carboxylic acids see Larock "Comprehensive Organic Transformations" VCH publishers ISBN 0-89573-710-8).

Chiral amino acid derivatives 1d and 4a useful for the synthesis of compounds of this invention are either commercially available or can be prepared by any of a number of methods known in the art. For example, as shown in Scheme 12, didehydroamino acid derivatives of formula 12c may be reduced to provide protected (S)-amino acids of formula 12d by hydrogenation in the presence of a chiral catalyst such as (S,S)-EtDuPhosRh(I) using a modified procedure of Burk (*J. Am. Chem. Soc.*, 1991, 113, 8518). Didehydroamino acid derivatives of formula 12c can be prepared via several methods, such as for example, a Heck coupling between an aryl iodide, bromide, or triflate of formula 12a and Boc didehydroalanine benzyl ester, using a modified procedure of Carlström, et al. (*Synthesis*, 1989, 414). Alternatively, protected didehydroaminoacids of formula 12c may be prepared by Horner-Emmons type condensation of an aldehyde of formula 12b with Boc-methyl-2-(dimethylphosphono)glycinate, using modifications of literature procedures (Wang, et al. *Tetrahedron*, 2002, 58, 3101). Protected amino acids of formula 12d may also be prepared by alkylation of methyl 2-(diphenylmethyleneamino)acetate with an appropriately substituted benzylbromide in the presence of a chiral cinchonidinium catalyst in a suitable solvent, such as methylene chloride, using a procedure similar to that described by O'Donnell, et al. (*Tetrahedron*, 1999, 55, 6347), followed by mild acidic workup and reprotection of the amino functionality with a Boc group according to methods known to one skilled in the art. Selective deprotection of protected amino ester compounds of formula 12d will furnish either amino esters of formula 1d or N-protected amino acids of formula 4a useful for the synthesis of dipeptide compounds of this invention as outlined in the above schemes. Heteroaryl bromides or iodides 12a, heteroaryl or alkyl aldehydes 12b, and heteroarylalkyl or alkylbromides 12e would lead to additional chiral amino acids useful for the synthesis of additional compounds of this invention. For example, optionally substituted pyrazole carbaldehydes of formula 12b will give compounds of this invention wherein R$^{11}$ is an optionally substituted pyrazolylmethyl group.

Scheme 12

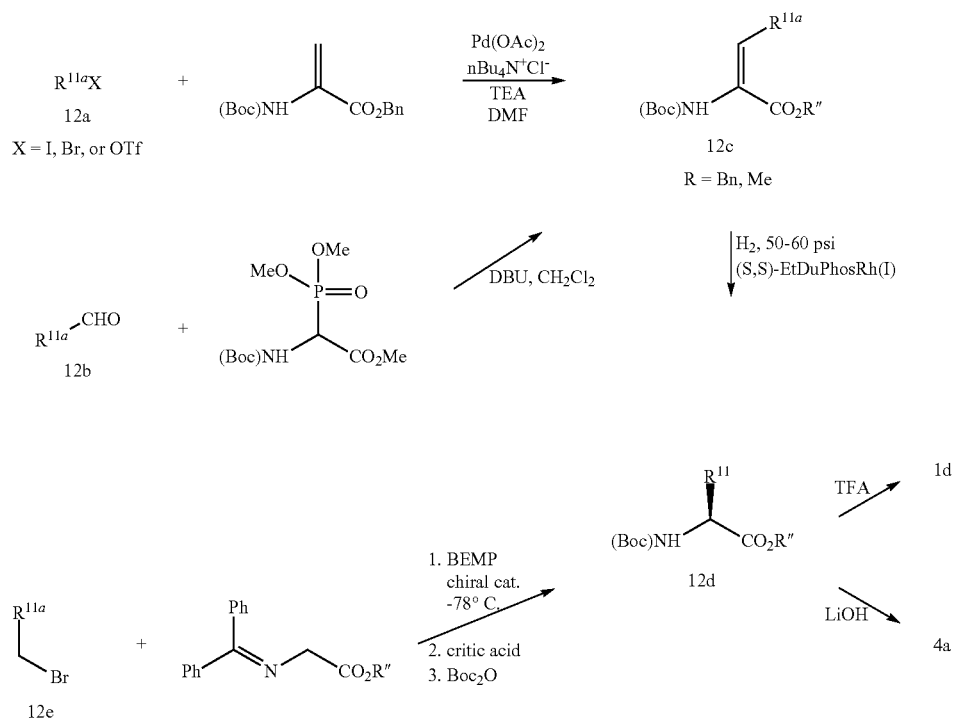

It should be recognized that additional deprotection steps and further functional group manipulations of compounds obtained via Schemes 1-12 above using methods known in the art will then provide additional compounds of this invention.

The compound of the instant invention herein described may have asymmetric center(s). For example, the chiral carbon atom in Formula (Ia) as indicated below, exists in either as S or R configuration.

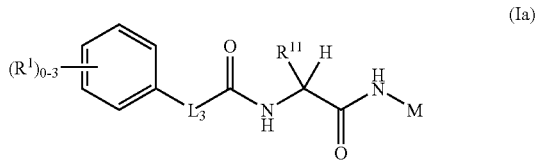
(Ia)

For example, but not limited to therein, in compounds of Formula (I), the following two stereoisomeric configurations are possible:

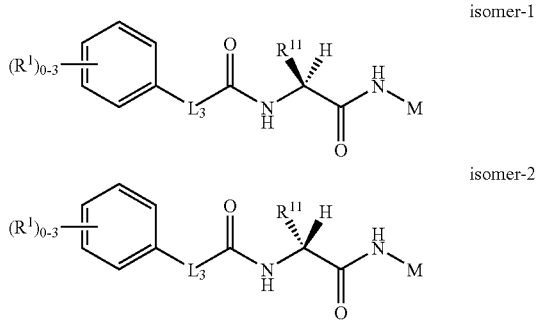
isomer-1 isomer-2

They are collectively, as well as individually, considered part of the invention. In a preferred stereoisomeric embodiment the present invention provides for a stereoisomeric configuration of isomer-1 for Formula (Ia) or tautomer, pharmaceutically acceptable salt, solvate, or prodrug form thereof.

Similarly, the chiral carbon atom in Formula (Ia) as indicated below, exists in either the S or R configuration

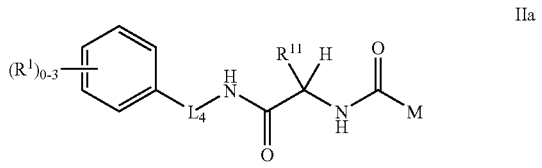
IIa

For example, but not limited to therein, in compounds of Formula (IIa), the following two stereoisomeric configurations are possible:

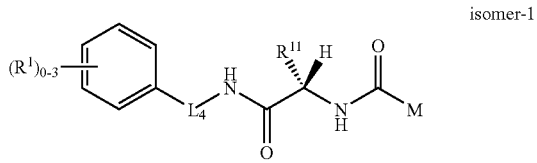
isomer-1

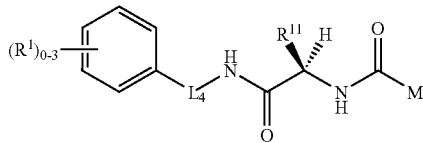
isomer-2

They are collectively, as well as individually, considered part of the invention. In a preferred stereoisomeric embodiment the present invention provides for a stereoisomeric configuration of isomer-1 for Formula (IIa) or tautomer, pharmaceutically acceptable salt, solvate, or prodrug form thereof.

In the following experimental procedures, solution ratios express a volume relationship, unless stated otherwise. NMR chemical shifts (δ) are reported in parts per million (ppm).

Products were analyzed by reverse phase analytical HPLC carried out on a Shimadzu Analytical HPLC system running DiscoveryVP software using Method A: Phenomenex Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B: 10% water, 89.9% methanol, 0.1% TFA, UV 220 nm), or Method B: Phenomenex Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm) or Method C: Phenomenex Luna C18 column (4.6×50 mm or 4.6×75 mm) eluted at 4 mL/min with a 2, 4 or 8 min gradient from 100% A to 100% B (A: 10% methanol, 89.9% water, 0.1% $H_3PO_4$; B: 10% water, 89.9% methanol, 0.1% $H_3PO_4$, UV 220 nm) or Method D: Waters SunFire™ column (3.5 μm C18, 4.6×150 mm) eluted at 1 mL/min with a gradient from 10-100% solvent B for 10 min and then 100% solvent B for 5 min. (A: 95% water, 5% acetonitrile, 0.05% TFA; B: is 5% water, 95% acetonitrile, 0.05% TFA, UV 254 nm)

Purification of intermediates and final products was carried out via either normal or reverse phase chromatography. Normal phase chromatography was carried out using prepacked $SiO_2$ cartridges eluted with gradients of hexanes and ethyl acetate or methylene chloride and methanol. Reverse phase preparative HPLC was carried out using a Shimadzu Preparative HPLC system running DiscoveryVP software using Method A: YMC Sunfire 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: Phenomenex AXIA Luna 5 μm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: Phenomenex Luna 5 μm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: Phenomenex Luna 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm). Alternatively, reverse phase preparative HPLC was carried out using a Varian ProStar Preparative HPLC System running Star 6.2 Chromatography Workstation software using Method E: Dynamax 10 μm C18 41.4×250 mm column with a 30 min gradient at 30 mL/min from 10% B to 100% B (A 98% water, 2% acetonitrile, 0.05% TFA; B: 98% acetonitrile, 2% water, 0.05% TFA, UV 254 nm). LCMS chromatograms were obtained on a Shimadzu HPLC system running DiscoveryVP software, coupled with a Waters ZQ mass spectrometer running MassLynx version 3.5 software using the same columns and conditions as utilized for analytical described above.

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders and include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, and artificial heart valves.

Some conditions contribute to the risk of developing thrombosis. For example, alterations of the vessel wall, changes in the flow of blood, and alterations in the composition of the vascular compartment. These risk factors are collectively known as Virchow's triad. (Hemostasis and Thrombosis, Basic Principles and Clinical practice, page 853, $5^{th}$ Edition, 2006, edited by Colman, R. W. et al. Published by Lippincott Williams & Wilkins)

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy), are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e. heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al. *Blood* 2005, 105, 453-463).

An alternative way of initiation of coagulation is operative when blood is exposed to artificial surfaces (e.g., during hemodialysis, 'on-pump' cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al. *Blood* 2006, 108, 192-199). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al. *J. Exp. Medicine* 2005, 202, 271-281; Kleinschmitz et al. *J. Exp.l Medicine*, 2006, 203, 513-518). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor 1× as its normal macromolecular substrate. (Galiani, D. *Trends Cardiovasc. Med.* 2000, 10, 198-204.)

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al. *Thromb. Res.* 2001, 101, 329-354.) Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride ($FeCl_3$)-induced carotid artery thrombosis (Rosen et al. *Thromb Haemost* 2002, 87, 774-77; Wang et al., *J Thromb Haemost* 2005, 3, 695-702). Also, factor XI deficiency rescues the perinatal lethal phenotype of complete protein C deficiency (Chan et al., *Amer. J. Pathology* 2001, 158, 469-479). Furthermore, baboon cross-reactive, function blocking antibodies to human factor XI protect against baboon arterial venous shunt thrombosis (Gruber et al., *Blood* 2003, 102, 953-955). Evidence for an antithrombotic effect of small molecule inhibitors of factor XIa is also disclosed in published U.S. Patent Application US20040180855A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D. *Frontiers in Bioscience* 2001, 6, 201-207; Gailani, D. et al. *Blood Coagulation and Fibrinolysis* 1997, 8, 134-144.) Taken together, these observations suggest that high levels of inhibition of factor XIa should be well tolerated. This is in contrast to gene targeting experiments with other coagulation factors, excluding factor XII.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al. *Arterioscler. Thromb. Vasc. Biol.* 2000, 20, 2489-2493). A second study establishes a positive correlation between the extent of coronary arteriosclerosis and factor XIa in complex with alpha 1 antitrypsin (Murakami, T. et al. *Arterioscler Thromb Vasc Biol* 1995, 15, 1107-1113.). In another study, Factor XI levels above the 90$^{th}$ percentile in patients were associated with a 2.2-fold increased risk for venous thrombosis (Meijers, J. C. M. et al. *N. Engl. J. Med.* 2000, 342, 696-701.)

Plasma kallikrein is a zymogen of a trypsin-like serine protease and is present in plasma at 35 to 50 µg/mL. The gene structure is similar to that of factor XI. Overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H.; Hathaway, W. E. Screening Tests of Hemostasis. *Disorders of Thrombosis and Hemostasis: a clinical guide*, 2$^{nd}$ edition, McGraw-Hill: New York, 2001 pp. 41-51).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

Pre-clinical studies demonstrated significant antithrombotic effects of small molecule factor XIa inhibitors in rabbit and rat model of arterial thrombosis, at doses that preserved hemostasis. (Wong P. C. et al. *American Heart Association Scientific Sessions*, Nov. 12-15, 2006, Abstract 6118; Schumacher, W. et al. *Journal of Thrombosis and Haemostasis* 2005; Volume 3, Supplement 1: P 1228; Schumacher, W. A. et al. *European Journal of Pharmacology*, in press). Furthermore, it was observed that in vitro prolongation of the aPTT by specific XIa inhibitors is a good predictor of efficacy in our thrombosis models. Thus, the in vitro aPTT test can be used as a surrogate for efficacy in vivo.

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or 'prevention' cover the preventive treatment of a subclinical disease-state in a mammal, particularly in a human, aimed at reducing the probability of the occurance of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurance of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined vide supra).

The term "thromboembolic disorders" as used herein includes arterial cardiovascular thromboembolic disorders, venous cardiovascular or cerebovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a 'big baby', hypertension, low HDL cholesterol, and polycystic ovary syndrome.

Risk factor for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al. *Medicine* (Baltimore) 1999, 78(5):285-291; Levine M. et al. *N Engl J Med* 1996, 334(11):677-681; Blom, J. W. et al. *JAMA:* 2005, 293(6):715-722.) Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e. presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al. *British Journal of Surgery* 2001, 88:913-930.)

A. In Vitro Assays

The effectiveness of compounds of the present invention as inhibitors of the coagulation factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; Chromogenix or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 1-5 nM, recombinant soluble tissue factor at a concentration of 10-40 nM and the synthetic substrate H-D-Ile-Pro-Arg-pNA (S-2288; Chromogenix or BMPM-2; AnaSpec) at a concentration of 0.001-0.0075 M.

Factor IXa determinations were made in 0.005 M calcium chloride, 0.1 M sodium chloride, 0.0001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; Chromogenix) at a concentration of 0.0002-0.00035 M.

Factor XIIa determinations were made in 50 mM HEPES buffer at pH 7.4 containing 145 mM NaCl, 5 mM KCl, and 0.1% PEG 8000. Determinations were made using purified human Factor XIIa at a final concentration of 4 nM (American Diagnostica) and the synthetic substrate Spectrozyme #312 (pyroGlu-Pro-Arg-pNA; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; Chromogenix) at a concentration of 0.00008-0.0004 M. The Km value used for calculation of Ki was 0.00005 to 0.00007 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002-0.00026 M.

The Michaelis constant, $K_m$, for substrate hydrolysis by each protease, was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$(v_o-v_s)/v_s=I/(K_i(1+S/K_m))$ for a competitive inhibitor with one binding site; or $v_s/v_o=A+((B-A)/1+((IC_{50}/(I)^n)))$ and
$K_i=IC_{50}/(1+S/K_m)$ for a competitive inhibitor
where:

$v_o$, is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios >20 are considered selective. Compounds with selectivity ratios >100 are preferred, and compounds with selectivity ratios >500 are more preferred.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5× or IC2×, the inhibitor concentration required to increase the clotting time by 50 or 100 percent, respectively. The IC1.5× or IC2× is found by linear interpolation from relative clotting time versus inhibitor concentration plots using inhibitor concentration that spans the IC1.5× or IC2×.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Illinois). Similarly, clotting times can be determined from laboratory animal species or humans dosed with compounds of the invention.

Activated Partial Thromboplastin Time (aPTT) is determined using Alexin (Trinity Biotech, Ireland) following the directions in the package insert. Plasma (0.05 mL) is warmed to 37° C. for 1 minute. Alexin (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus, Dade-Behring, Illinois) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

a. In Vivo Electrically-Induced Carotid Artery Thrombosis (ECAT) Model

The rabbit ECAT model, described by Wong et al. (*J Pharmacol Exp Ther* 2000, 295, 212-218), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In Vivo Rabbit Arterio-Venous (AV) Shunt Thrombosis Model

The rabbit AV shunt model, described by Wong et al. (Wong, P. C. et al. *J Pharmacol Exp Ther* 2000, 292, 351-357), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm) The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (DeltaGraph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18$^{th}$ Edition, 1990.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intra-musculary, or sub-cutaneously. When administered intra-venous or intra-arterial, the dose can be given continuously or intermittend. Furthermore, formulation can be developed for intramusculary and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 100 milligrams per dosage unit, and the second anti-coagulant in an amount of about 1 to about 50 milligrams per dosage unit.

Where the compounds of the present invention are administered in combination with an anti-platelet agent, by way of general guidance, typically a daily dosage may be about 0.01 to about 25 milligrams of the compound of the present invention and about 50 to about 150 milligrams of the anti-platelet agent, preferably about 0.1 to about 1 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 1 milligrams of the compound of the present invention, per kilogram of patient body weight and, in the case of the thrombolytic agents, the usual dosage of the thrombolyic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (alliskerin) and vasopepsidase inhibitors, an antiarrythmic agent selected from IKur inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX™), synthetic pentasaccharide, direct acting thrombin inhibitors including hirudin and argatroban, as well as other factor VIIa inhibitors, factor IXa inhibitors, factor Xa inhibitors (e.g., Arixtra™, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDS) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDS, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include clopidogrel, ticlopidine, prasugrel, and AZD-6140, cangrelor, and pharmaceutically acceptable salts or prodrugs thereof. Ticlopidine and clopidogrel are also preferred compounds since they are known to be more gentle than aspirin on the gastrointestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvsatatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPAR-gamma modulators (e.g., rosiglitazone), compounds that have multiple functionality for modulating the activities of various combinations of PPARalpha, PPARgamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXRbeta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 μM against the target protease and greater than or equal to 0.1 μM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

EXAMPLES

The following Examples have been prepared, isolated and characterized using the methods disclosed herein. The following Examples demonstrate a partial scope of the invention and are not meant to be limiting of the scope of the invention.

Intermediate 1

(S)-2-(tert-butoxycarbonylamino)-3-(1-methyl-1H-pyrazol-3-yl)propanoic acid

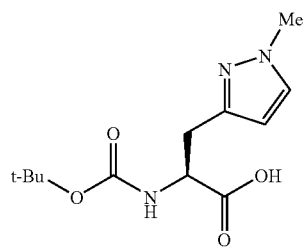 [SMILES: Cn1ccc(C[C@H](NC(=O)OC(C)(C)C)C(=O)O)n1]

Intermediate 1A. (E)-2-tert-butoxycarbonylamino-3-(1-methyl-1H-pyrazol-3-yl)-acrylic acid methyl ester: Boc-methyl-2-(dimethylphosphono)glycinate (1.620 g, 5.45 mmol) was dissolved in $CH_2Cl_2$ (10 mL) and stirred under nitrogen at rt. To this solution was added DBU (0.753 mL, 4.99 mmol) and the mixture was stirred for 10 min, followed by dropwise addition of a solution of 1-methyl-1H-pyrazole-3-carbaldehyde (0.5 g, 4.54 mmol) in $CH_2Cl_2$ (10 mL) over 15-20 min. Stirring was continued at rt overnight. The solvent was removed on a rotary evaporator and the residue was taken up in a mixture of $CH_2Cl_2$/EtOAc, washed with 5% citric acid and brine, then dried over anhydrous sodium sulfate, filtered and evaporated. The residue was dissolved in methylene chloride and charged to a 120 g silica gel cartridge which was eluted with a 30 min gradient from 0-60% EtOAc in hexane to provide the olefin product (0.95 g, 74.4%) as a thick viscous oil. MS: m/z 226.1 [M+H-tBu]$^+$. $^1$H NMR (500 MHz, $CDCl_3$) δ: 8.49 (1H, s), 7.32 (1H, d, J=2.2 Hz), 6.50 (1H, s), 6.28 (1H, d, J=2.2 Hz), 3.94 (3H, s), 3.84 (3H, s), 1.48 (9H, s) ppm.

Intermediate 1B. (S)-2-tert-butoxycarbonylamino-3-(1-methyl-1H-pyrazol-3-yl)-propionic acid methyl ester: Intermediate 1A (0.95 g, 3.38 mmol) was dissolved in MeOH (15 mL) and transferred to a 250 mL hydrogenation flask. The solution was evacuated and flushed with nitrogen three times and then (S,S)-EtDuPhosRh(I) (0.1 g, 0.138 mmol) was added. The flask was connected to a hydrogenation manifold and contents evacuated and flushed with nitrogen three times and then the reaction was stirred at rt under 45-50 psi $H_2$ for 3-3.5 h. An additional 20 mg of catalyst was added as described above and the reaction mixture was stirred under 55 psi $H_2$ at rt overnight. Methanol was removed on a rotary evaporator and the crude product was dissolved in methylene chloride and charged to an 80 g silica gel cartridge which was eluted with a 20 min gradient from 0-60% EtOAc in hexane to provide Intermediate 1B (0.928 g, 97%) as a white oil. MS: m/z 228.2 [M+H-tBu]$^+$. $^1$H NMR (500 MHz, $CHCl_3$) δ: 7.24 (1H, d, J=2.2 Hz), 6.00 (1H, d, J=2.2 Hz), 5.43 (1H, d, J=8.2 Hz), 4.52-4.62 (1H, m), 3.84 (3H, s), 3.72 (3H, s), 2.99-3.21 (2H, m), 1.43 (9H, s) ppm.

Intermediate 1: Intermediate 1B (0.92 g, 3.25 mmol) was dissolved in THF (20 mL) and 1 M lithium hydroxide (5.0 mL, 5.00 mmol) and a little MeOH was added. The resulting reaction mixture was stirred for 3 days at rt under nitrogen. The reaction was diluted with a little water to dissolve the small amount of solid and THF was removed on a rotary evaporator. The reaction was diluted with a 5% citric acid solution to lower the pH<5 and then extracted EtOAc (2×). The combined extracts were washed with brine, dried over anhydrous $Na_2SO_4$, filtered, and evaporated to afford Intermediate 1 (0.79 g, 90%) as a white crystalline solid. MS: m/z 214.1 [M+H-tBu]$^+$; 170.2 [M+H-Boc]$^+$ $^1$H NMR (500 MHz, $CDCl_3$) δ: 7.27 (1H, d, J=2.2 Hz), 6.10 (1H, d, J=2.2 Hz), 5.49 (1H, d, J=6.6 Hz), 4.55 (1H, t, J=6.6 Hz), 3.90 (3H, s), 3.23-3.36 (1H, m), 3.10-3.24 (1H, m), 1.46 (9H, s) ppm.

Intermediate 2

(S)-2-(tert-butoxycarbonylamino)-3-(1-ethyl-1H-pyrazol-3-yl)propanoic acid

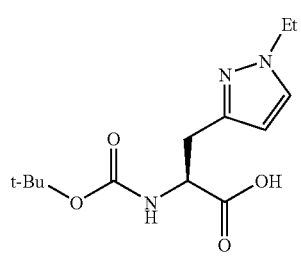 [SMILES: CCn1ccc(C[C@H](NC(=O)OC(C)(C)C)C(=O)O)n1]

The title compound was prepared from 1-ethyl-1H-pyrazole-3-carbaldehyde following the procedure described for Intermediate 1. MS m/z 284.1 [M+H]$^+$ 228.1 [M+H-tBu]$^+$.

Intermediate 3

(S)-2-(tert-butoxycarbonylamino)-3-(1,5-dimethyl-1H-pyrazol-3-yl)propanoic acid

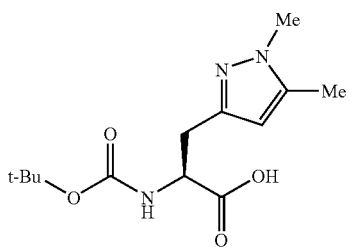 [SMILES: Cc1cc(C[C@H](NC(=O)OC(C)(C)C)C(=O)O)nn1C]

The title compound was prepared from 1,5-dimethyl-1H-pyrazole-3-carbaldehyde following the procedure described for Intermediate 1. 284.2 [M+H]$^+$; 228.1 [M+H-tBu]$^+$.

Intermediate 4

(S)-2-(tert-butoxycarbonylamino)-3-(1,3-dimethyl-1H-pyrazol-5-yl)propanoic acid

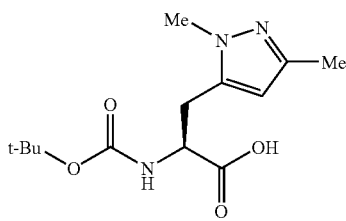 [SMILES: Cc1cc(C[C@H](NC(=O)OC(C)(C)C)C(=O)O)n(C)n1]

The title compound was prepared from 1,3-dimethyl-1H-pyrazole-5-carbaldehyde following the procedure described for Intermediate 1. MS m/z 284.3 [M+H]$^+$; 228.2 [M+H-tBu]$^+$.

Intermediate 5

(E)-3-(5-chloro-2-(4-(ethoxycarbonyl)-1H-1,2,3-triazol-1-yl)phenyl)acrylic acid

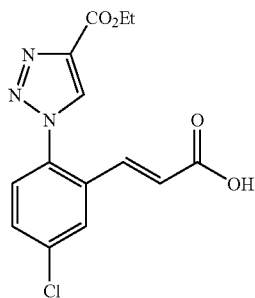 [SMILES: CCOC(=O)c1cn(-c2ccc(Cl)cc2/C=C/C(=O)O)nn1]

Intermediate 5A. 1-azido-4-chloro-2-iodobenzene. Commercially available 4-chloro-2-iodo aniline (1.7 g, 6.71 mmol) was stirred in TFA (10 mL) and water (2 mL). The reaction was homogenous and turned purple. The reaction was cooled to 0° C. and NaNO$_2$ (0.46 g, 6.71 mmol) was added over 0.5 h. To this slurry was added an aqueous solution (2 mL) of sodium azide (0.553 g, 8.51 mmol) dropwise over 0.25 h. The reaction was stirred at 0° C. for 1 h and allowed to warm to rt. The reaction was quenched with water (100 mL) and the solid was filtered and dried under nitrogen to give Intermediate 5A. $^1$H NMR (CDCl$_3$) δ: 7.80 (s, 1H), 7.40 (dd (J=2.4 & 8.7 Hz, 1H), 7.09) d, J=8.6 Hz, 1H) ppm. LCMS m/z 261.4 [M+H]$^+$.

Intermediate 5B. ethyl 1-(4-chloro-2-iodophenyl)-1H-1,2,3-triazole-4-carboxylate. Intermediate 5A (1.54 g, 5.19 mmol) was slurried with ethyl propiolate (5.1 g, 51.9 mmol) in toluene in a small microwave flask. The mixture was heated at 100° C. in a microwave oven for 1.5 h. The reaction was purified directly onto a 80 g silica-gel column (gradient eluton; 10% to 100% EtOAc/Hex). The two regioisomers were separated. The first eluting regioisomer was Intermediate 5B (2.63 g, 95%). $^1$H NMR (CDCl$_3$) δ: 8.41 (s, 1H), 8.05 (d, J=2.2 Hz, 1H), 7.56 (dd, J=2.2 & 8.4 Hz, 1H), 7.43 (d, J=8.5 Hz, 1H), 4.54 (q, 2H), 1.50 (t, 3H) ppm. LCMS 378.0 [M+H]$^+$.

Intermediate 5C. (E)-ethyl 1-(2-(3-tert-butoxy-3-oxoprop-1-enyl)-4-chlorophenyl)-1H-1,2,3-triazole-4-carboxylate.

To degassed DMF (1 mL) was added Intermediate 5B (0.28 g, 0.74 mmol), Pd/C (10%, 0.5 g) and Pd(OAc)$_2$ (0.01 g). The reaction mixture was capped and heated in a sealed vial at 100° C. for 18 h. The reaction mixture was quenched with water (50 mL) and extracted EtOAc (2×100 mL). The combined organic layers were washed with HCl (1N, 50 mL), dried (MgSO$_4$), and concentrated to afford Intermediate 5C (0.31 g) as a brown solid. $^1$H NMR (CDCl$_3$) δ: 8.22 (s, 1H), 7.69 (d, J=2.2 Hz, 1H), 7.46 (dd, J=2.2 & 8.5 Hz, 1H), 7.37 (d, J=8.5 Hz, 1H), 7.15 (d, J=15.8 Hz, 1H), 6.34 (d, J=15.8 Hz, 1H), 4.43 (q, 2H), 1.39 (s, 9H) 1.37 (t, 3H) ppm. LCMS 378.1 [M+H]$^+$.

Intermediate 5. TFA (3 mL) was added to a DCM (5 mL) solution of 105C (0.31 g). The reaction mixture was stirred at rt for 1 h. The reaction was concentrated and then water (100 mL) was added. The reaction was extracted with DCM (2×100 mL), dried (MgSO$_4$), evaporated to afford Intermediate 5D as a white solid (0.21 g, 74%). $^1$H NMR (CDCl$_3$) δ: 8.37 (s, 1H), 7.81 (d, J=2.3 Hz, 1H), 7.57 (dd, J=2.3 & 8.5 Hz, 1H), 7.56 (d, J=8.4 Hz, 1H), 7.32 (d, J=15.8 Hz, 1H), 6.47 (d, J=15.9 Hz, 1H), 4.50 (q, 2H), 1.43 (t, 3H) ppm. LCMS 322.2 [M+H]$^+$.

Intermediate 6

2-(5-chloro-2-(1H-tetrazol-1-yl)phenyl)ethanamine

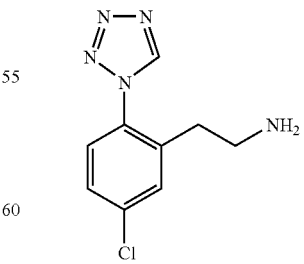

To a cooled (−78° C.) solution of 3-(5-chloro-2-(1H-tetrazol-1-yl)phenyl)propanoic acid tetrazole acid (1.78 g, 7.05 mmol) in THF (20 mL) was added TEA (0.98 mL) followed by ethylchloroformate (0.76 g, 7.05 mmol). After stirring for 0.5 h, ammonia in methanol (60 mL, 2N solution) was added. The reaction turned from heterogenous to homogenous. After 2 h, the reaction was quenched with sat. NaHCO₃ (100 mL) and extracted with EtOAc (2×100 mL). The combined organic layers were washed with HCl (1N, 100 mL), dried and evaporated to give a brown solid (1.65 g). The solid was dissolved in acetonitrile (100 mL) and to this solution was added water (75 mL) and the reaction mixture was then cooled in an ice/acetone bath. To this solution was then added pyridine (1.25 mL) followed by the addition of bis(trifluoroacetoxy)iodobenzene (3.03 g, 7.05 mmol). The reaction was stirred cold for 0.5 h and then the ice bath was removed and the reaction was allowed to warm to rt. The reaction was quenched with water (100 mL) and then extracted with EtOAc (2×100 mL). The combined organic layers were dried and evaporated to give Intermediate 6 (1.5 g, 95%) as a pale yellow solid. ¹H NMR (CDCl₃) δ: 9.11 (s, 1H), 7.54-7.46 (dd, J=1.2 & 8.5 Hz, 1H), 7.39-7.23 (m, 2H), 2.95 (t, 2H), 2.53 (t, 2H) ppm. LCMS 224.2 [M+H]⁺.

Intermediate 7

(E)-3-(3-chloro-2-fluoro-6-(1H-tetrazol-1-yl)phenyl)acrylic acid

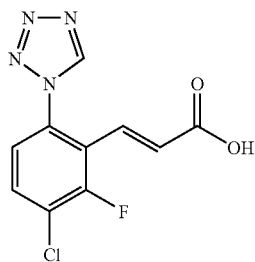 [SMILES: O=C(O)/C=C/c1c(-n2cnnn2)ccc(Cl)c1F]

Intermediate 7A. N-(2-bromo-4-chloro-3-fluorophenyl)-2,2,2-trifluoroacetamide: 2,2,2-trifluoroacetic anhydride (5.77 mL, 41.2 mmol) was added dropwise to a stirring mixture of sodium carbonate (6.19 g, 58.4 mmol) and 4-chloro-3-fluoroaniline (5.0 g, 34.3 mmol) in Et₂O (50 mL) at −10° C. After 1 h, hexane (30 mL) was added and the reaction mixture filtered. The filtrate was washed with ice-water, 10% aq. NaHCO₃ solution, and then brine. The organic phase was treated with activated charcoal, dried over sodium sulfate, filtered through a plug of Celite®, and concentrated to give N-(4-chloro-3-fluorophenyl)-2,2,2-trifluoroacetamide as a white solid. A solution of tert-Butyllithium (1.7M in pentane) (40.4 mL, 68.7 mmol) was added dropwise to N,N,N',N'-tetramethylethylenediamine (10.37 mL, 68.7 mmol) in THF (60 mL) at −78° C. After 1 h, N-(4-chloro-3-fluorophenyl)-2,2,2-trifluoroacetamide in THF (40 mL) was added dropwise to this yellow solution. After stirring for an additional hour, bromine (2.12 mL, 41.2 mmol) was slowly added and the complete mixture stirred for 1.5 h before quenching and neutralized with 1.0N HCl solution (final pH ~6-7). The mixture was brought to rt, treated with brine (100 mL), and THF evaporated. The aqueous layer was extracted with EtOAc (3×). The combined organic extracts were washed with water, saturated NaHCO₃ solution, brine, dried over sodium sulfate, filtered and dry-loaded onto silica gel. Purification by flash chromatography (120 g column; (hexane/EtOAc solvent system) gave Intermediate 7A (3.95 g, 36%) as a slowly solidifying tan solid. ¹H NMR (400 MHz, CDCl₃) δ: 8.42 (1H, br. s.), 8.13 (1H, dd, J=9.09, 1.77 Hz), 7.43-7.49 (1H, m) ppm.

Intermediate 7B. (E)-tert-butyl 3-(3-chloro-2-fluoro-6-(2,2,2-trifluoro-acetamido)phenyl)acrylate: Intermediate 7A (1.0 g, 3.12 mmol), tert-butyl acrylate (3.00 mL, 18.72 mmol), DABCO (0.35 g, 3.12 mmol), K₂CO₃ (1.08 g, 7.80 mmol) were added DMF (10 mL) and degassed 10 min. Palladium (II) acetate (0.035 g, 0.16 mmol) was added and the complete mixture was heated at 110° C. overnight. After cooling to rt, the reaction mixture was filtered through a plug of Celite® and the filter-cake was rinsed with EtOAc (3×30 mL). The combined filtrate was washed with water, brine, dried over sodium sulfate, filtered, and concentrated onto silica gel. Purification by flash chromatography (40 g column; hexane/EtOAc solvent system) gave Intermediate 7B (0.84 g, 73.0%) as an off-white solid. ¹H NMR (400 MHz, CDCl₃) δ 8.15 (1H, br. s.), 7.69 (1H, dd, J=8.84, 1.52 Hz), 7.43-7.49 (2H, m), 6.48-6.55 (1H, m), 1.53 (9H, s) ppm.

Intermediate 7. (E)-3-(3-chloro-2-fluoro-6-(1H-tetrazol-1-yl)phenyl)acrylic acid: To a solution of Intermediate 7B (0.83 g, 2.25 mmol) in ethanol was added 1.0N NaOH solution (11.29 mL, 11.29 mmol). The resulted mixture was stirred at 80° C. for 1 h before cooling to rt and the organics were concentrated. Both the trifluoroacetamide and t-butyl ester groups were removed under these conditions. The remaining aqueous phase was diluted with water and cooled to 0° C., and neutralized (~6-7) with 1.0M HCl solution. The mixture was extracted with EtOAc (3×50 mL). The combined organic extract was washed with brine, dried over sodium sulfate, filtered, and concentrated to give a yellow solid. AcOH (10 mL) was added to a stirring suspension of (E)-3-(6-amino-3-chloro-2-fluorophenyl)acrylic acid, trimethyl orthoformate (0.73 mL, 6.68 mmol), and sodium azide (0.434 g, 6.68 mmol) at 0° C. The reaction was heated at 75° C. for 4 h. After cooling to rt, the reaction mixture was diluted with water, and extracted with EtOAc (3×75 mL). The combined organic extract was washed with brine, dried over sodium sulfate, filtered, and concentrated. The crude material was purified by reverse phase preparative HPLC (ACN/H₂O/TFA). The product fractions were concentrated on a Speedvac to give Intermediate 7 (0.258 g, 43%) as an amber solid. LCMS: m/z 269.1 [M+H]⁺.

Example 1

(S)-ethyl 2-(4-(2-(3-(5-chloro-2-(1H-tetrazol-1-yl)phenyl)propan-amideo)-3-phenylpropanamido)phenyl)acetate

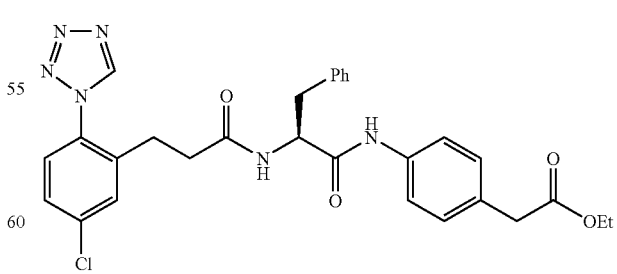

1A. (S)-ethyl 2-(4-(2-(tert-butoxycarbonylamino)-3-phenylpropanamido) phenylacetate: To a solution of (S)-2-(tert-butoxycarbonylamino)-3-phenylpropanoic acid (1.5 g, 5.65 mmol) in DMF (15 mL) was added EDC (2.168 g, 11.31 mmol), HOBT (1.732 g, 11.31 mmol) and DIEA (3.95 mL, 22.62 mmol) and stirred at rt for 15 min. To this mixture was added ethyl 2-(4-aminophenyl)acetate (1.013 g, 5.65 mmol) and stirred overnight under argon. The reaction mixture was diluted with ethylacetate, washed with 10% LiCl solution. The organic layers were pooled, dried over MgSO$_4$ and subjected to flash column chromatography using DCM/MeOH to give 1A. (2.3 g, 95%). LCMS: m/z 427.3 (M+H)$^+$. $^1$H NMR (CD$_3$OD, 400 MHz) δ: 7.35 (d, J=8.25 Hz, 2H) 7.18 (d, J=3.85 Hz, 4H) 7.12 (d, J=7.70 Hz, 3H) 4.34 (t, J=7.15 Hz, 1H) 4.04 (q, J=7.15 Hz, 2H) 3.50 (s, 2H) 3.23 (m, 2H) 3.03 (dd, J=13.47, 6.32 Hz, 1H) 2.85 (dd, J=13.47, 8.52 Hz, 1H) 1.30 (s, 9H) 1.15 (t, J=6.87 Hz, 3H) ppm.

1B. (S)-ethyl 2-(4-(2-amino-3-phenylpropanamido)phenyl)acetate: A solution of 50% TFA in DCM (total volume 25 mL) was prepared separately and added to 1A (2.3 g, 5.39 mmol). The solution was stirred for 30 min and then concentrated, dried under vacuum to give the crude product 1B that was used for the next step without further purification. LCMS: m/z 327.2 (M+H)$^+$. $^1$H NMR (400 MHz, CD$_3$OD) δ: 7.25 (d, J=8.80 Hz, 2H) 7.14-7.18 (m, 2H) 7.09-7.13 (m, 3H) 7.04 (d, J=8.25 Hz, 2H) 3.90-4.02 (m, 3H) 3.41 (s, 2H) 3.06-3.14 (m, 4H) 2.93-3.00 (m, 1H) 1.04 (t, J=7.15 Hz, 3H) ppm.

1C. (E)-3-(5-chloro-2-tetrazol-1-yl-phenyl)-acrylic acid: To a cooled (0° C.) suspension of NaH (0.262 g, 6.56 mmol) in THF (27.3 mL) was added dropwise methyl 2-(dimethoxyphosphoryl)-acetate (1.150 mL, 7.10 mmol). The resulting thick, white suspension was diluted with additional THF (15 mL) to facilitate mixing, then allowed to warm to rt and stirred at rt for 45 min. Next, a slightly cloudy blue solution of 5-chloro-2-tetrazol-1-yl-benzaldehyde (1.14 g, 5.46 mmol), prepared according to a modification of the procedure described by Howard (*J. Med. Chem.*, 2006, 49, 1346.), in THF (8 mL) was added. The yellow/green suspension was stirred vigorously. After 30 min, the reaction was poured into cold sat. ammonium chloride and extracted with EtOAc. The combined organic layers were washed with brine, dried over Na$_2$SO$_4$, filtered and concentrated to give a green/blue solid weighing 1.76 g. The solid was dissolved in EtOAc and filtered through a plug of silica gel, eluting with EtOAc. The green filtrate was concentrated to give a greenish solid weighing 1.36 g. Recrystallization from EtOAc gave an off-white solid weighing 0.476 g. Additional product was obtained by concentrating the filtrate from recrystallization, adding methanol, sonicating, and collecting the solid product by filtration. A total of 0.829 g (57%) of (E)-3-(5-chloro-2-tetrazol-1-yl-phenyl)-acrylic acid methyl ester was obtained. LCMS m/z 265.1 (M+H)$^+$; 287.2 (M+Na)$^+$. $^1$H NMR (CDCl$_3$, 500 MHz) δ: 8.80 (s, 1H), 7.78 (d, J=2.2 Hz, 1H), 7.58 (dd, J=8.8, 2.2 Hz, 1H), 7.42 (d, J=8.2 Hz, 1H), 7.25 (d, J=16.0 Hz, 1H), 6.45 (d, J=16.0 Hz, 1H), 3.78 (s, 3H). To a white suspension of this ester (0.140 g, 0.529 mmol) in MeOH (3.0 mL) was added 1.0 M sodium hydroxide (1.587 ml, 1.587 mmol). The resulting suspension was stirred vigorously at rt for 2.5 h. The yellow suspension was neutralized with 1.0 N HCl (1.60 mL), and concentrated to give a beige solid. The solid was partitioned between 1.0 N HCl and EtOAc, and the layers were separated. The organic layer was washed with brine, dried over Na$_2$SO$_4$, filtered and concentrated to give 0.137 g (100%) of (E)-3-(5-chloro-2-tetrazol-1-yl-phenyl)-acrylic acid as a white solid. LCMS m/z 251.1 (M+H)$^+$. $^1$H NMR (500 MHz, DMSO-d$_6$) δ: 12.72 (s, 1H), 9.87 (s, 1H), 8.24 (d, J=2.2 Hz, 1H), 7.77 (dd, J=8.8, 2.2 Hz, 1H), 7.73 (d, J=8.2 Hz, 1H), 6.98 (d, J=16.0 Hz, 1H), 6.70 (d, J=16.0 Hz, 1H).

1D. 3-(5-chloro-2-tetrazol-1-yl-phenyl)-propionic acid: To a suspension of the acrylic acid (0.030 g, 0.120 mmol) in MeOH (5.0 mL) was added platinum oxide (0.005 g, 0.022 mmol). Hydrogen from a balloon was bubbled through the reaction for 1-2 min and then the reaction was stirred vigorously under a hydrogen atmosphere. Additional amounts of platinum oxide (0.010 g, 0.044 mmol) were added over the course of the reaction. After 27 h, the reaction was filtered, and the filtrate was concentrated to give a brown residue. The residue was dissolved in MeOH, refiltered, and the filtrate was concentrated to give 0.025 g (83%) of 1C as a clear colorless residue. LCMS m/z 253.1 (M+H)$^+$. $^1$H NMR (400 MHz, CD$_3$OD) δ: 9.51 (s, 1H), 7.63 (d, J=2.2 Hz, 1H), 7.48 (dd, J=8.8, 2.2 Hz, 1H), 7.43 (d, J=8.8 Hz, 1H), 2.72 (t, J=7.5 Hz, 2H), 2.55 (t, J=7.5 Hz, 2H).

Example 1: To a solution of 1B (150 mg, 0.594 mmol) in DMF (5 mL) was added EDC (228 mg, 1.187 mmol), HOBT (182 mg, 1.187 mmol) and DIEA (0.415 mL, 2.375 mmol) and stirred for 15 min under argon. To this solution was added 3-(5-chloro-2-(1H-tetrazol-1-yl)phenyl)propanoic acid 1C (194 mg, 0.594 mmol) and stirred at rt under argon overnight. The reaction mixture was diluted with ethylacetate, washed with 10% LiCl solution. The organic layers were pooled, dried over MgSO$_4$ and subjected to flash column chromatography using DCM/MeOH to give the desired product. (185 mg, 55%). LCMS: m/z 561.3 (M+H)$^+$. $^1$H NMR (400 MHz, CD$_3$OD) δ: 9.34 (s, 1H) 7.45 (d, J=2.20 Hz, 1H) 7.27-7.37 (m, 5H) 7.07-7.19 (m, 8H) 4.49-4.63 (m, 1H) 4.04 (q, J=7.15 Hz, 2H) 3.49 (s, 2H) 3.00 (dd, J=13.75, 7.15 Hz, 1H) 2.82 (dd, J=13.75, 8.25 Hz, 1H) 2.52-2.68 (m, 2H) 2.28-2.47 (m, 2H) 1.14 (t, J=7.15 Hz, 3H) ppm. Analytical HPLC RT: 4.49 min (Method A, 4 min gradient).

Example 2

(S)-2-(4-(2-(3-(5-chloro-2-(1H-tetrazol-1-yl)phenyl) propanamideo)-3-phenylpropanamido)phenyl)aceticacid

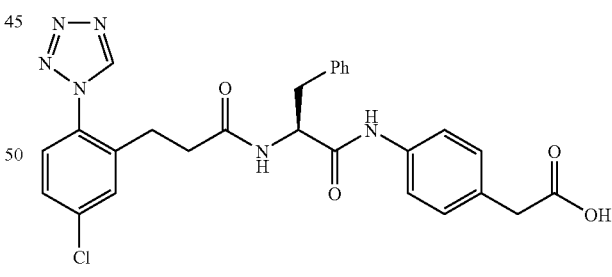

To a solution of Example 1 (170 mg, 0.303 mmol) in THF/water (1.2:1.0) was added lithium hydroxide (21.77 mg, 0.909 mmol) and stirred for 3 h. The reaction mixture was acidified with 2 N HCl and washed with brine, extracted with ethylacetate. The crude product was subjected to column (12 g column) purification using hexane/ethylacetate as the eluants. The desired fractions were pooled together and concentrated to afford Example 2. LCMS: m/z 533.2 (M+H).$^+$ $^1$H NMR (400 MHz, CD$_3$OD) δ: 9.48 (s, 1H) 7.58 (s, 1H) 7.40-7.52 (m, 5H) 7.17-7.34 (m, 6H) 4.78 (m, 1H) 3.58 (s, 2H) 3.32 (m, 3H) 3.11 (dd, J=13.75, 6.60 Hz, 1 H) 2.93 (dd, J=13.75,

Example 3

(4-{(S)-2-[(E)-3-(5-chloro-2-tetrazol-1-yl-phenyl)-acryloylamino]-3-phenyl-propionylamino}-phenyl)-carbamic acid methyl ester

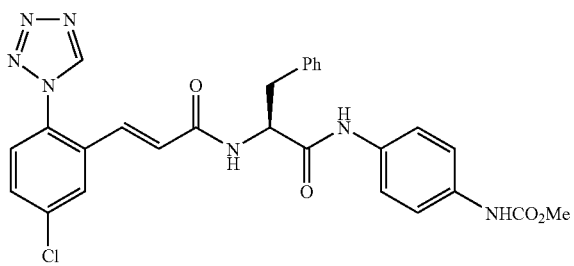

3A. (S)-tert-butyl 1-(4-nitrophenylamino)-1-oxo-3-phenylpropan-2-ylcarbamate: $POCl_3$ (0.4 mL) was added dropwise to a −15° C. pyridine (11 mL) solution of L-phenylalanine (0.82 g, 3.09 mmol) and p-nitroaniline (0.43 g, 3.09 mmol). The reaction mixture was stirred at −15° C. for 30 min. Aliquot showed some starting material present along with product formation. Stirring was continued for an additional 15 min. The reaction was quenched with water (100 mL), and gently acidified with 1N HCl. The organics were extracted with EtOAc (2×100 mL), dried ($MgSO_4$) and concentrated to yellow foam (1.11 g) of 3A. LCMS m/z 386.3 (M+H). $^1$H NMR (400 MHz, $CDCl_3$) δ: 8.16 (d, J=8.8 Hz, 2H), 7.55 (d, J=8.5 Hz, 4H), 733-7.22 (m, 5H), 5.12 (bm, 1H), 4.52 (bs, 1H), 3.20 (m, 2H), 1.43 (s, 9H) ppm.

3B. (S)-tert-butyl 1-(4-aminophenylamino)-1-oxo-3-phenylpropan-2-ylcarbamate: A catalytic amount of Pd/C (10%) was added to a methanol solution of 3A in methanol (50 mL). The reaction was hydrogenated at 60 psi. The reaction product was filtered through a Celite® pad, washed with excess methanol, and concentrated to a yellow solid. LCMS m/z 356.1 (M+H). $^1$H NMR (400 MHz, $CDCl_3$) δ: 7.37-7.24 (m, 5H), 7.12 (d, J=8.6 Hz, 2H), 6.61 (d, J=8.6 Hz, 2H), 5.12 (bs, 1H), 4.40 (bs, 1H), 3.10 (bs, 2H), 3.15 (t, 2H), 1.42 (s, 9H) ppm.

3C. [4-((S)-2-tert-butoxycarbonylamino-3-phenyl-propionylamino)-phenyl]-carbamic acid methyl ester: To a dichloromethane (5 mL) solution of 3B (0.082 g, 0.24 mmol) was added methyl chloroformate (0.02 g, 0.23 mmol) and pyridine (0.5 mL). The reaction mixture was stirred at rt overnight. Aliquat LCMS showed formation of 3C (414, M+H). The reaction was quenched with water (100 mL). The organics were extracted with EtOAc (2×50 mL), washed with HCl (1N), dried ($MgSO_4$), concentrated to a yellow solid (0.095 g) of 3C. LCMS m/z 414.1 (M+H). $^1$H NMR (400 MHz, $CDCl_3$) δ: 7.79 (bs, 1H), 7.28-7.23 (m, 9H), 6.68 (bs, 1H), 5.23 (bd, 1H), 4.46 (bs, 1H), 3.76 (s, 3H), 3.14 (d, 2H), 1.41 (s, 9H) ppm.

Example 3: 3C (0.095 g, 0.23 mmol) dissolved in DCM (5 mL). To this solution was added TFA (1 mL) and stirred at rt for 1 h. The reaction mixture was concentrated and quenched with NaOH (0.05N). The organics were extracted with EtOAc (2×25 mL), dried ($MgSO_4$) and concentrated to afford a colorless solid (0.095 g). LCMS m/z 314.3 (M+H). $^1$H NMR (400 MHz, $CDCl_3$) δ: 9.35 (bs, 1H), 7.51 (d, J=8.8 Hz, 2H), 7.35-7.22 (m, 7H), 6.90 (bs, 1H), 3.75 (s, 3H), 3.41 (m, 2H), 2.82 (m, 1H), 1.87 (bs, 2H) ppm. The solid was re-dissolved in THF (10 mL) and to this solution was added (E)-3-(5-chloro-2-(1H-tetrazol-1-yl)phenyl)acrylic acid 1C (0.075 g, 3.04 mmol) and BOP reagent (0.11 g, 3.04 mmol.) and TEA (0.5 mL). The reaction mixture was stirred at rt for 1 h, was quenched with water (100 mL). The organics were extracted with EtOAc (2×25 mL), dried ($MgSO_4$) and concentrated to a colorless solid, which was then taken up in a mixture of MeOH/ACN/DMF. All solids did not dissolve. The mixture was filtered and washed with excess MeOH. The filtrate was purified via reverse phase HPLC (methanol/water/0.05% TFA gradient). The pure fractions were collected and lyophilized. A colorless solid Example 3 was obtained (0.053 g). LCMS m/z 546.0 (M+H, chlorine isotope). $^1$H NMR (400 MHz, DMSO-$d_6$) δ: 9.80 (s, 1H), 9.47 (bs, 1H), 8.46 (d, J=8.2 Hz, 1H), 7.87 (d, J=2.1 Hz, 1H), 7.67 (m, 2H), 7.40 (d, 2H), 7.32 (d, J=8.9 Hz, 2H), 7.22 (m, 4H), 6.78 (dq, 2H), 4.69 (m, 1H), 3.58 (s, 3H), 3.01 (m, 1H), 2.85 (m, 1H) ppm. Analytical HPLC RT: 5.65 min (Method C, 8 min gradient).

Example 4

(E)-3-(5-chloro-2-tetrazol-1-yl-phenyl)-N—[(S)-1-(4-hydroxy-2-oxo-1,2-dihydro-quinolin-6-ylcarbamoyl)-2-phenyl-ethyl]-acrylamide

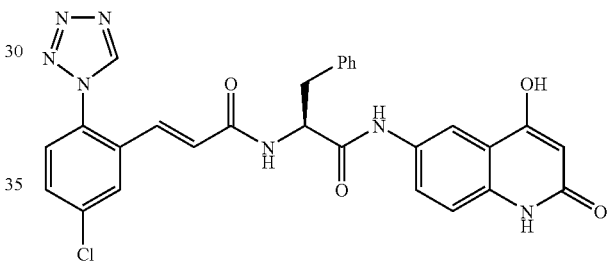

4A. N-[4-((S)-2-tert-butoxycarbonylamino-3-phenyl-propionyl-amino)-phenyl]-malonamic acid tert-butyl ester: To a THF (8 mL) solution of (S)-tert-butyl 1-(4-aminophenylamino)-1-oxo-3-phenylpropan-2-ylcarbamate (3B) (0.141 g, 0.397 mmol) was added 3-tert-butoxy-3-oxopropanoic acid (0.064 g, 0.397 mmol), BOP reagent (0.18 g, 0.39 mmol) and TEA (0.06 mmol). The reaction mixture was stirred at rt overnight, quenched with diluted HCl. The organics were extracted with EtOAc (2×50 mL), dried ($MgSO_4$), and concentrated to a yellow viscous oil product of 4A. LCMS m/z 498.3 (M+H). $^1$H NMR (400 MHz, $CDCl_3$) δ: 9.31 (bs, 1H), 7.79 (t, 1H), 7.49-7.46 (m, 2H), 7.33-7.23 (m, 2H0, 3.37 (s, 2H), 3.18 (d, 2H), 1.51 (s, 9H), 1.28 (s, 9H) ppm.

4B. [(S)-1-(4-hydroxy-2-oxo-1,2-dihydro-quinolin-6-yl-carbamoyl)-2-phenyl-ethyl]-carbamic acid tert-butyl ester: PPA (~0.5 mL) was added to the neat product from 4A. The reaction was heated in an open flask at 130° C. for 3 h. Aliquat was subsequently taken for LCMS and showed the desired product. Water (100 mL) was added but no product precipitate out. The aqueous layer was basified with NaOH (1N) and to this was added 200 mg of $Boc_2O$. The reaction mixture was stirred overnight. Aliquat LCMS showed the presence of the Boc protected material. The basic layer was extracted with EtOAc (2×100 mL), dried ($MgSO_4$) and concentrated. The aqueous layer was acidified with 1N HCl. The organics were extracted with EtOAc (2×100 mL), dried ($MgSO_4$) and concentrated. LCMS of both fractions showed the presence of Boc protected compound. The above product was purified via reverse phase HPLC (methanol/water/0.05% TFA gradient). Pure fractions were lyophilized to obtain a colorless solid (0.11 g). LCMS m/z 424.2 (M+H). $^1$H NMR (400 MHz, CD$_3$OD) δ: 8.06 (d, J=2.3 Hz, 1H), 7.60 (bd, 1H), 7.85 (m, 1H), 7.25-7.08 (m, 6H), 5.84 (s, 1H), 4.36 (m, 1H), 3.08 (m, 1H), 2.88 (m, 1H), 1.23 (s, 9H) ppm.

4C. (S)-2-amino-N-(4-hydroxy-2-oxo-1,2-dihydro-quinolin-6-yl)-3-phenyl-propionamide: Approximately 20 mL of 4N HCl in doxane was added to a methanol solution of 4B. The reaction was stirred for 2 h. Aliquat LCMS: using a 4 min gradient afforded the desired product 4C at 1.79 min RT that corresponds to 324.2 (M+H). The reaction mixture was concentrated and treated with ether to precipitate the salt, which was decanted and put on a high vacuum pump. A colorless solid product 4C was obtained (0.07 g).

Example 4: To a THF solution of 4C (0.045 g, 0.134 mmol) was added (E)-3-(5-chloro-2-(1H-tetrazol-1-yl)phenyl) acrylic acid (0.065 g, 0.26 mmol), PyBOP (0.135 g, 0.26 mmol) and TEA (0.6 mL). The reaction mixture was stirred at rt overnight. The reaction product was concentrated and subsequently quenched with 1N NaOH (25 mL). The basic layer was extracted with DCM (2×25 mL), dried and concentrated to a yellow oil product. LCMS did not show product in this extract. The basic layer from above was acidified with 1N HCl and extracted with EtOAc (2×100 mL), dried (MgSO$_4$) and concentrated to a yellow oil product. LCMS showed the presence of the desired product along with some other impurities. This fraction was purified via reverse phase HPLC (methanol/water/0.05% TFA) on a phenomenex Axia column. The pure fraction collected was concentrated and lyophilized to afford Example 4 as a colorless solid (10 mg). HPLC purity: ~91%. LCMS m/z 556.2 (M+H). $^1$H NMR (400 MHz, CD$_3$OD) δ: 9.55 (s, 1H), 8.15 (m, 1H), 7.98 (d, 1H), 7.68-7.57 (m, 4H), 7.30-7.17 (m, 5H), 7.13 (d, J=15.5 Hz, 1H), 6.82 (d, J=15.5 Hz, 1H), 5.90 (s, 1H), 4.85 (m, 1H), 3.19 (m, 1H), 3.03 (m, 1H) ppm. Analytical HPLC RT: 5.40 min (Method C, 8 min gradient).

Example 5

(E)-3-(5-chloro-2-tetrazol-1-yl-phenyl)-N—[(S)-2-(1-methyl-1H-pyrazol-3-yl)-1-(4-propionylamino-phenylcarbamoyl)-ethyl]-acrylamide

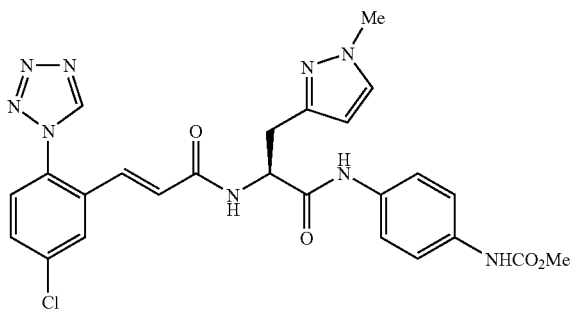

Example 5 (colorless solid, 1% yield overall) was prepared in a similar manner to that described for Example 3. HPLC purity: 91%. LCMS m/z 550.3 (M+H, chlorine isotope). $^1$H NMR (400 MHz, CD$_3$OD) δ: 9.40 (s, 1H), 7.89 (d, J=2.3 Hz, 1H), 7.64 (m, 1H), 7.52 (dd, J=2.3 & 8.5 Hz, 1H), 7.48 (m, 2H), 7.37-7.20 (m, 4H), 7.02 (d, J=15.6 Hz, 1H), 6.69 (d, J=15.6 Hz, 1H), 6.07 (dd, J=2.2 & 8.8 Hz, 2H), 4.70 (m, 1H), 3.71 (s, 3H), 3.65 (s, 3H), 3.05 (m, 2H) ppm. Analytical HPLC RT: 4.55 min (Method C, 8 min gradient).

Example 6

4-{(S)-2-[(E)-3-(5-chloro-2-tetrazol-1-yl-phenyl)-acryloylamino]-3-phenyl-propionylamino}-benzamide

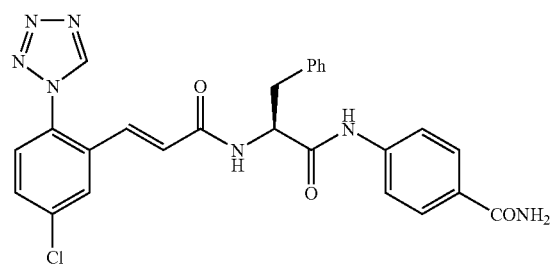 [SMILES: NC(=O)c1ccc(NC(=O)[C@H](Cc2ccccc2)NC(=O)/C=C/c2cc(Cl)ccc2-n2cnnn2)cc1]

Example 6 was prepared was prepared in a similar manner to that described for Example 3. Colorless solid (2% yield). HPLC purity: >92%. LCMS m/z 516.0 (M+H). $^1$H NMR (400 MHz, CD$_3$OD) δ: 9.39 (s, 1H), 7.38 (s, 1H), 7.72 (d, 2H), 7.559 (m, 5H), 7.159 (m, 3H), 7.00 (d, 1H), 6.71 (d, 1H), 4.7 (m, 1H), 3.1 (m, 1H), 3.00 (m, 1H) ppm. Analytical HPLC RT: 5.16 min (Method C, 8 min gradient).

Example 7

(E)-3-(5-chloro-2-tetrazol-1-yl-phenyl)-N—[(S)-1-(4-cyano-phenylcarbamoyl)-2-phenyl-ethyl]-acrylamide

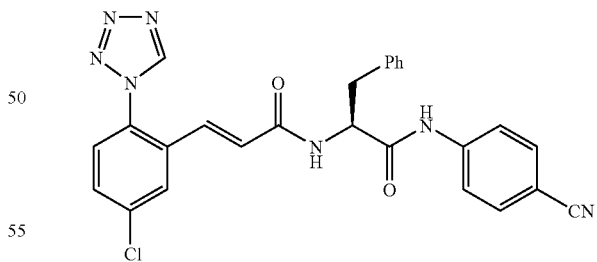

Example 7 (colorless solid, 2%) was prepared by the dehydradion of Example 6 followed by purification via reverse phase HPLC as previously described. HPLC purity: >95%. LCMS m/z 498.0 (M+H)$^+$. $^1$H NMR (400 MHz, CD$_3$OD) δ: 9.39 (s, 1H), 7.86 (d, J=2.3 Hz, 1H), 7.60-7.52 (m, 5H), 7.47 (d, =9.5 Hz, 1H), 7.18 (m, 4H), 7.12 (m, 1H), 7.07 (d, J=15.6 Hz, 1H), 6.67 (d, J=16.6 Hz, 1H), 4.69 (m, 1H), 3.10 (m, 1H), 2.99 (m, 1H) ppm. Analytical HPLC RT: 5.88 min (Method C, 8 min gradient).

Example 8

4-{(S)-2-[(E)-3-(5-chloro-2-tetrazol-1-yl-phenyl)-acryloylamino]-3-phenyl-propionylamino}-benzoic acid

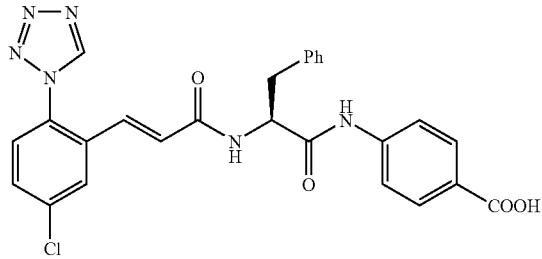 [SMILES: O=C(/C=C/c1cc(Cl)ccc1-n1cnnn1)N[C@@H](Cc1ccccc1)C(=O)Nc1ccc(C(=O)O)cc1]

Example 8 (colorless solid, 7% yield) was prepared following the general procedure adopted for Example 3. HPLC purity: >98%. LCMS m/z 517.3 (M+H, chlorine isotope). $^1$H NMR (400 MHz, CD$_3$OD) δ: 9.39 (s, 1H), 7.86 (m, 3H), 7.56-7.46 (m, 4H), 7.05 (m, 5H), 7.01 (d, J=16.4 Hz, 1H), 6.67 (d, J=15.6 Hz, 1H), 4.70 (m, 1H), 3.10 (m, 1H), 2.95 (m, 1H) ppm. Analytical HPLC RT: 5.70 min (Method C, 8 min gradient).

Example 9

3-{(S)-2-[(E)-3-(5-chloro-2-tetrazol-1-yl-phenyl)-acryloylamino]-3-phenyl-propionylamino}-benzoic acid

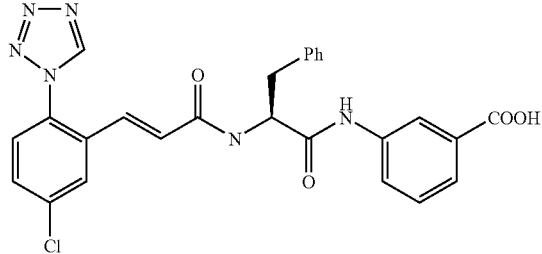 [SMILES: O=C(/C=C/c1cc(Cl)ccc1-n1cnnn1)N[C@@H](Cc1ccccc1)C(=O)Nc1cccc(C(=O)O)c1]

Example 9 was prepared following the general procedure adopted for Example 3. Colorless solid (25% yield). HPLC purity: >98%. LCMS m/z 517.3 (M+H, chlorine isotope). $^1$H NMR (400 MHz, CD$_3$OD) δ: 9.39 (s, 1H), 8.04 (m, 1H), 7.88 (d, J=2.3 Hz, 1H), 7.66-7.59 (m, 3H), 7.56 (dd, J=2.3 & 8.4 Hz, 1H), 7.47 (d, J=8.5 Hz, 1H), 7.32 (t, 1H), 7.18-7.10 (m, 4H), 7.01 (d, J=15.6 Hz, 1H), 6.69 (d, J=15.6 Hz, 1H), 4.70 (m, 1H), 3.20-2.95 (m, 2H) ppm. Analytical HPLC RT: 5.72 min (Method C, 8 min gradient).

Example 10

(4-{(S)-2-[E)-3-(5-chloro-2-tetrazol-1-yl-phenyl)-acryloylamino]-3-phenyl-propionylamino}-cyclohexyl)-carbamic acid methyl ester

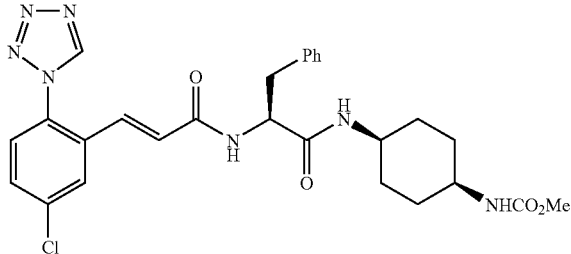

10A. [4-((S)-2-benzyloxycarbonylamino-3-phenyl-propionylamino)-cyclohexyl]-acetic acid tert-butyl ester: To a THF (20 mL) solution of CBz-protected L-phenylalanine (0.458 g, 1.53 mmol) was added tert-butyl (1S,4S)-4-aminocyclohexylcarbamate (0.328 g, 1.51 mmol), BOP reagent (0.577 g, 1.531 mmol) and TEA (0.23 mL). The reaction mixture was stirred at rt overnight. The reaction mixture became homogenous on stirring. The reaction was quenched with diluted HCl (1N, 50 mL). The organics were extracted with EtOAc (2×50 mL), dried (MgSO$_4$) and concentrated to afford 10A as foam (0.766 g, 91%). LCMS m/z 496.1 (M+H). $^1$H NMR (400 MHz, CDCl$_3$) δ: 7.36-7.20 (m, 10H), 5.55 (bs, 1H), 5.40 (bs, 1H), 5.12 (m, 2H), 4.33 (m, 1H), 3.80 (bs, 1H), 3.55 (bs, 1H), 3.20 (m, 2H), 3.00 (m, 1H), 1.62 (m, 5H), 1.44 (s, 9H) ppm.

10B. tert-butyl (1R,4s)-4-((S)-2-amino-3-phenylpropanamido)cyclohexylcarbamate (10A) was dissolved in methanol/ethylacetate (1:1, 20 mL) and to this solution was added 10% Pd/C and hydrogenated at 60 psi overnight. Aliquat showed the formation of 10B. The reaction product was filtered through a Celite® pad and washed with excess water. The solvent was evaporated to afford 10B as an oil product (0.54 g). LCMS shows the desired product at 1.47 min RT that corresponds to 362.4 (M+H). The same product was filtered through a Celite® pad, washed with excess methanol, and concentrated to colorless foam. LCMS m/z 362.5 (M+H). $^1$H NMR (400 MHz, CDCl$_3$/CD$_3$OD) δ: 7.34-7.20 (m, 5H), 4.90 (bs, 1H), 3.85 (bs, 1H), 3.58 (m, 2H), 3.48 (m, 1H), 2.77 (m, 1H), 1.60 (m, 8H), 1.44 (s, 9H) ppm.

10C. (4-{(S)-2-[(E)-3-(5-chloro-2-tetrazol-1-yl-phenyl)-acryloylamino]-3-phenyl-propionylamino}-cyclohexyl)-carbamic acid tert-butyl ester: 10B was coupled with (E)-3-(5-chloro-2-(1H-tetrazol-1-yl)phenyl)acrylic acid using the BOP reagent coupling methodology. The reaction was quenched with water (100 mL). The organics were extracted with EtOAc (2×100 mL), washed with diluted HCl (50 mL) and brine (50 mL). The product was dried (MgSO$_4$) and concentrated to an oil product. A portion of it was treated with TFA (3 mL) in DCM (10 mL). The remaining portion was purified via reverse phase HPLC (MeOH/water/TFA) gradient. The pure fractions were collected, concentrated and lyophilized to obtain a colorless solid. HPLC purity: >98%. LCMS m/z 594.4 (M+H, chlorine isotope). $^1$H NMR (400 MHz, CD$_3$OD) δ: 9.40 (s, 1H), 7.86 (d, J=0.3 Hz, 1H), 7.56 (bd, 1H), 7.56 (dd, J=2.3 & 8.4 Hz, 1H), 7.47 (d, J=8.5 Hz, 1H), 7.19-7.00 (m, 5H), 7.00 (d, J=15.6 z, 1H), 6.66 (d, J=15.6 Hz, 1H), 4.58 (t, 1H), 3.60 (bs, 1H), 3.32 (bs, 1H), 2.98-2.85 (m, 2H), 1.49-1.43 (m, 6H), 1.33 (s, 9H), 1.29 (m, 2H) ppm.

Example 10: 10C was treated with TFA in DCM to remove the Boc protected group, and concentrated and re-dissolved in pyridine. To this solution was added methylchloroformate. The reaction was stirred at rt for 1 h. The reaction was quenched with water. The reaction product was extracted with EtOAc (2×100 mL), dried (MgSO$_4$) and concentrated to an oil product, which was re-dissolved in MeOH and purified via reverse phase HPLC Phenomenex Axia column using MeOH/water/TFA gradient. The pure fraction was collected, concentrated and lyophilized to a colorless solid (26 mg). LCMS m/z 552.4 (M+H, chlorine isotope). HPLC purity: >98%. $^1$H NMR (400 MHz, CD$_3$OD) δ: 9.45 (s, 1H), 7.95 (s, 1H), 7.63 (dd, 1H), 7.56 (d, 1H), 7.54-7.35 (m, 5H), 7.24 (d, J=15.5 Hz, 1H), 6.75 (d, J=15.5 Hz, 1H), 4.66 (t, 1H), 3.70 (bs, 1H), 3.61 (s, 3H), 3.48 (bs, 1H), 3.06-2.87 (m, 2H), 1.64-1.42 (m, 8H) ppm. Analytical HPLC RT: 5.62 min (Method C, 8 min gradient).

Example 11

(4-{(S)-2-[(E)-3-(5-chloro-2-tetrazol-1-yl-phenyl)-acryloylamino]-3-phenyl-propionylamino}-cyclohexyl)-carbamic acid methyl ester

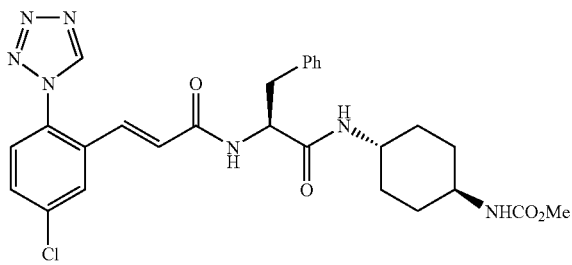

Example 11 was prepared was prepared in a similar manner to that described for Example 10. HPLC purity: 100%. LCMS m/z 594.2 (M+H). $^1$H NMR (400 MHz, DMSO-d$_6$) δ: 9.77 (s, 1H), 8.24 (d, J=8.2 Hz, 1H), 7.85 (m, 2H), 7.65 (m, 2H), 7.21-7.10 (m, 4H), 6.82 (q, 2H), 6.60 (bs, 1H), 4.47 (m, 1H), 3.30 (bs, 1H), 3.05 (bs, 1H), 2.95 (m, 1H), 2.73 (m, 1H), 1.68 (bs, 3H), 1.60 (bd, 1H), 1.30 (s, 9H), 1.12 (m, 6H) ppm. Analytical HPLC RT: 6.38 min (Method C, 8 min gradient).

Example 12

4-{(S)-2-[(E)-3-(5-chloro-2-tetrazol-1-yl-phenyl)-acryloylamino]-3-phenyl-propionylamino}-benzoic acid methyl ester

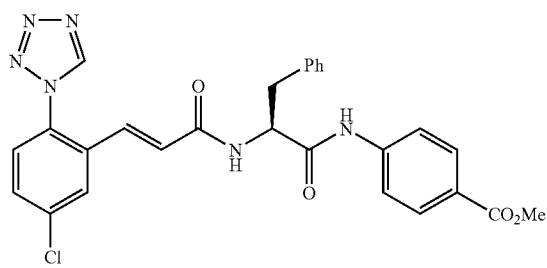 [SMILES: COC(=O)c1ccc(NC(=O)[C@H](Cc2ccccc2)NC(=O)/C=C/c2cc(Cl)ccc2-n2cnnn2)cc1]

Example 12 was prepared in a similar manner to that adopted for Example 3. HPLC purity: 98%. LCMS m/z 531.3 (M+H). $^1$H NMR (400 MHz, CD$_3$OD) δ: 9.77 (s, 1H), 8.54 (d, J=8.0 Hz, 1H), 7.85 (m, 2H), 7.69 (m, 4H), 7.21 (S, 4H), 7.15 (M, 1H), 6.78 (S, 2H), 4.71 (m, 1H), 3.75 (s, 3H), 3.05 (m, 1H), 2.85 (m, 1H) ppm. Analytical HPLC RT: 6.17 min (Method C, 8 min gradient).

Example 13

4-{(S)-2-[(E)-3-(5-chloro-2-tetrazol-1-yl-phenyl)-acryloylamino]-3-phenyl-propionylamino}-benzoic acid methyl ester

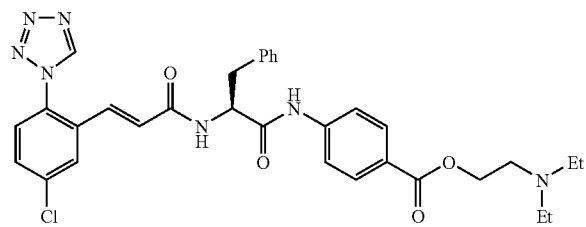 [SMILES: CCN(CC)CCOC(=O)c1ccc(NC(=O)[C@H](Cc2ccccc2)NC(=O)/C=C/c2cc(Cl)ccc2-n2cnnn2)cc1]

Example 13 was prepared in a similar manner to that adopted for Example 3. HPLC purity: 98%. LCMS m/z 616.4 (M+H). $^1$H NMR (400 MHz, CD$_3$OD) δ: 9.52 (s, 1H), 8.11 (m, 3H), 7.66 (d, 3H), 7.57 (d, 1H), 7.28 (m, 5H), 3.60 (m, 1H), 7.18 (m, 1H), 7.07 (d, J=15.5 Hz, 1H), 6.77 (d, J=15.7 Hz, 1H), 4.63 (m, 1H), 3.61 (m, 1H), 3.35 (m, 8H), 3.20 (m, 1H), 3.03 (m, 1H), 1.38 (t, 6H) ppm. Analytical HPLC RT: 4.48 min (Method C, 8 min gradient).

Example 14

(3-chloro-4-{(S)-2-[(E)-3-(5-chloro-2-tetrazol-1-yl-phenyl)-acryloylamino]-3-phenyl-propionylamino}-phenyl)-carbamic acid methyl ester

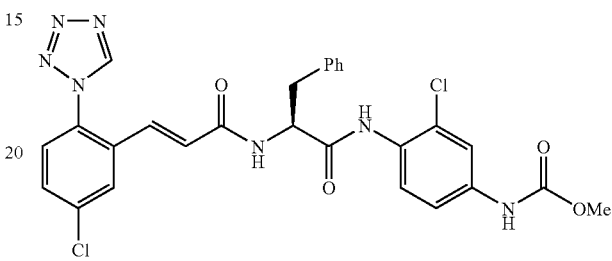

Example 14 was prepared in a similar manner to that adopted for Example 3. HPLC purity: 98%. LCMS m/z 580.2 (M+H). $^1$H NMR (400 MHz, CD$_3$OD) δ: 9.50 (s, 1H), 8.00 (s, 1H), 7.87 (m, 3H), 7.63-7.48 ((m, 6H), 7.40 (s, 1H), 6.95 (d, 1H), 6.85 (d, 1H), 6.07 (s, 1H), 4.75 (t, 1H), 3.70 (s, 3H), 3.10-2.85 (m, 2H). Analytical HPLC RT: 3.05 min (Method A, 4 min gradient).

Example 15

4-{(S)-2-[(E)-3-(3-chloro-2,6-difluoro-phenyl)-acryloylamino]-3-phenyl-propionylamino}-benzoic acid

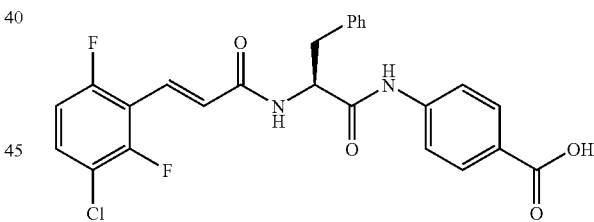

To (E)-3-(3-chloro-2,6-difluoro-phenyl)-acrylic acid (0.064 g, 0.294 mmol), 4-((S)-2-amino-3-phenyl-propionylamino)-benzoic acid tert-butyl ester (0.1 g, 0.294 mmol), PyBOP (0.153 g, 0.294 mmol) in THF (4 mL) was added Hunig'sBase (0.205 mL, 1.175 mmol). The reaction was stirred for 72 h. The reaction was quenched with water (10 mL) and extracted with ethyl acetate (3×20 mL). The combined organic layers were washed with water (10 mL), brine (10 mL) and dried (MgSO$_4$). The crude ester was treated with TFA (2 mL) in DCM (5 mL) for 2 h and then concentrated. Purification by HPLC and freeze-dried afforded Example 15 as a white solid (8 mg, 5.6%). LCMS m/z 485.3 [M+H]$^+$. $^1$H NMR (400 MHz, CD$_3$OD) δ: 7.94-8.00 (m, 2H), 7.63-7.67 (m, 2H), 7.60 (d, J=16.17 Hz, 1H), 7.50-7.57 (m, 1H), 7.27-7.35 (m, 4H), 7.19-7.25 (m, 1H), 7.07-7.15 (m, 1H), 7.02 (d, J=16.17 Hz, 1H), 4.90-4.94 (m, 1H), 3.20-3.28 (m, 1H), 3.09 (dd, J=13.64, 8.08 Hz, 1H) ppm. Analytical HPLC RT: 6.64 min (Method C, 8 min gradient).

Example 16

2-chloro-4-{(S)-2-[(E)-3-(5-chloro-2-tetrazol-1-yl-phenyl)-acryloylamino]-3-phenyl-propionylamino}-benzoic acid

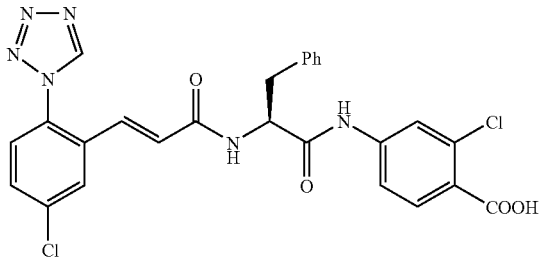 [SMILES: O=C(/C=C/c1cc(Cl)ccc1-n1cnnn1)N[C@@H](Cc1ccccc1)C(=O)Nc1ccc(C(=O)O)c(Cl)c1]

Example 16 was prepared in a similar manner to that adopted for Example 3. Deprotection of the Boc ester protecting group with TFA afforded Example 16 as a colorless solid on purification and lyophilization. HPLC purity: 100%. LCMS m/z 551.3 (M+H). $^1$H NMR (400 MHz, DMSO-d$_6$) δ: 9.77 (s, 1H), 8.56 (d, J=8.0 Hz, 1H), 7.88 (d, J=4.5 Hz, 1H), 7.78 (m, 2H), 7.69-7.63 (m, 2H), 7.47 (dd, J=2.0 & 8.6 Hz, 1H), 7.20 (m, 3H), 7.14 (m, 1H), 6.77 (s, 2H), 4.68 (m, 1H), 3.05 (m, 1H), 2.86 (m, 1H) ppm. Analytical HPLC RT: 5.84 min (Method C, 8 min gradient).

Example 17

(S,E)-ethyl 4-(2-(3-(5-chloro-2-(1H-tetrazol-1-yl)phenyl)acrylamido)-3-phenylpropanamido)-3-fluorobenzoate

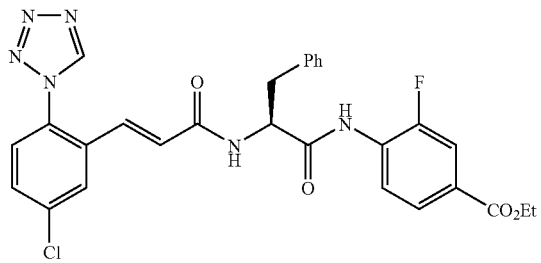 [SMILES: CCOC(=O)c1ccc(NC(=O)[C@H](Cc2ccccc2)NC(=O)/C=C/c2cc(Cl)ccc2-n2cnnn2)c(F)c1]

Example 17 was prepared as a colorless solid following a similar procedure used for Example 3. HPLC purity>97%. LCMS m/z 563.3 (M+H, chlorine isotope). $^1$H NMR (400 MHz, CD$_3$OD) δ: 9.49 (s, 1H), 8.15 (t, J=8.3 Hz, 1H), 7.96 (d, J=3.3 Hz, 1H), 7.80 (dd, J=0.8 & 8.4 Hz, 1H), 7.73 (dd, J=1.8 & 8.2 Hz, 1H), 7.66 (dd, j=2.3 & 8.5 Hz, 1H), 7.29-7.18 (m, 5H), 7.11 (d, J=15.7 Hz, 1H), 6.76 (d, J=15.6 Hz, 1H), 4.98 (t, 1H), 4.38 (q, 2H), 3.25 (m, 1H), 3.06 (m, 1H), 1.39 (t, 3H) ppm. Analytical HPLC RT: 6.64 min (Method C, 8 min gradient).

Example 18

2-{(S)-2-[(E)-3-(5-chloro-2-tetrazol-1-yl-phenyl)-acryloylamino]-3-phenyl-propionylamino}-thiazole-4-carboxylic acid ethyl ester

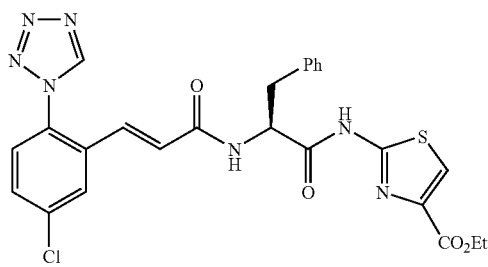 [SMILES: CCOC(=O)c1csc(NC(=O)[C@H](Cc2ccccc2)NC(=O)/C=C/c2cc(Cl)ccc2-n2cnnn2)n1]

Example 18 was prepared following the general procedure adopted for Example 3. HPLC purity: >98%. LCMS m/z 552.3 (M+H, chlorine isotope). $^1$H NMR (400 MHz, CD$_3$OD) δ: 9.48 (s, 1H), 7.96 (m, 2H), 7.68 (dd, J=2.3 & 8.5 Hz, 1H), 7.56 (d, J=8.5 Hz, 1H), 7.28-7.17 (m, 5H), 7.10 (d, J=15.7 Hz, 1H), 6.74 (d, J=15.7 Hz, 1H), 4.92 (t, 1H), 4.37 (q, 2H), 3.27 (m, 1H), 3.10 (m, 1H), 1.37 (t, 3H) ppm. Analytical HPLC RT: 6.13 min (Method C, 8 min gradient).

Example 19

2-{(S)-2-[(E)-3-(5-Chloro-2-tetrazol-1-yl-phenyl)-acryloylamino]-3-phenyl-propionylamino}-thiazole-5-carboxylic acid methyl ester

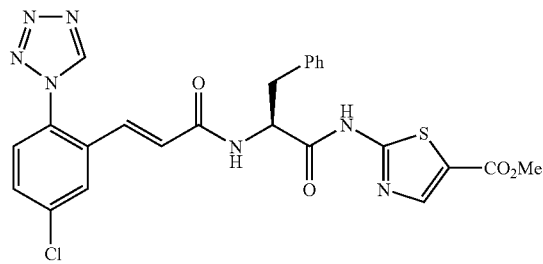 [SMILES: COC(=O)c1cnc(NC(=O)[C@H](Cc2ccccc2)NC(=O)/C=C/c2cc(Cl)ccc2-n2cnnn2)s1]

Example 19 was prepared following the general procedure adopted for Example 3. LCMS m/z 538.2 (M+H, chlorine isotope). $^1$H NMR (400 MHz, DMSO-d$_6$) δ: 9.87 (s, 1H), 8.71 (d, J=7.7 Hz, 1H), 8.18 (s, 1H), 7.97 (d, J=2.2 Hz, 1H), 7.77-7.70 (m, 2H), 7.31-7.19 (m, 6H), 6.82 (dq, 2H), 4.88 (m, 1H), 3.82 (s, 3H), 3.12 (m, 1H), 2.94 (m, 1H) ppm. Analytical HPLC RT: 1.70 min (Method A, 2 min gradient).

Example 20

(E)-3-(5-chloro-2-tetrazol-1-yl-phenyl)-N-{(S)-1-[4-(2-oxo-piperidin-1-yl)-phenylcarbamoyl]-2-phenyl-ethyl}-acrylamide

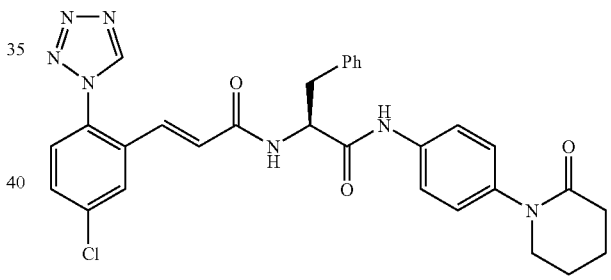

Example 20 (colorless solid) was prepared following the general procedure adopted for Example 3. HPLC purity: >98%. LCMS m/z 570.3 (M+H, chlorine isotope). $^1$H NMR (400 MHz, DMSO-d$_6$) δ: 9.94 (s, 1H), 8.61 (d, J=8.8 Hz, 1H), 8.00 (s, 1H), 7.80 (m, 2H), 7.60 (m, 2H), 7.36 (s, 4H), 7.28 (d, 2H), 6.92 (q, 2H), 4.85 (m, 1H), 3.63 (m, 2H), 3.16 (m, 1H), 3.00 (m, 1H), 2.49 (m, 2H), 1.95 (m, 4H) ppm. Analytical HPLC RT: 5.61 min (Method C, 8 min gradient).

Example 21

2-{(S)-2-[(E)-3-(5-chloro-2-tetrazol-1-yl-phenyl)-acryloylamino]-3-phenyl-propionylamino}-thiazole-5-carboxylic acid

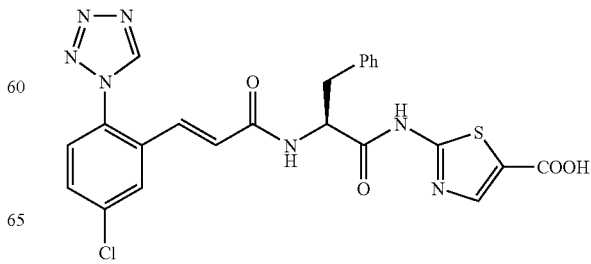

LiOH/THF/water hydrolysis of 2-{(S)-2-[(E)-3-(5-chloro-2-tetrazol-1-yl-phenyl)-acryloylamino]-3-phenyl-propionylamino}-thiazole-5-carboxylic acid ethyl ester (Example 19) afforded Example 21. HPLC purity: >98%. LCMS m/z 524.2 (M+H, chlorine isotope). ¹H NMR (400 MHz, CD₃OD) δ: 9.48 (s, 1H), 8.02 (s, 1H), 7.96 (d, J=2.3 Hz, 1H), 7.68 (dd, J=2.3 & 9.2 Hz, 1H), 7.56 (d, J=8.5 Hz, 1H), 7.31-7.19 (m, 5H), 7.10 (d, J=15.7 Hz, 1H), 6.75 (d, J=15.6 Hz, 1H), 4.9 (t, 1H), 3.30 (m, 1H), 3.11 (m, 1H) ppm. Analytical HPLC RT: 5.48 min (Method C, 8 min gradient).

Example 22

2-{(S)-2-[(E)-3-(5-chloro-2-tetrazol-1-yl-phenyl)-acryloylamino]-3-phenyl-propionylamino}-thiazole-5-carboxylic acid

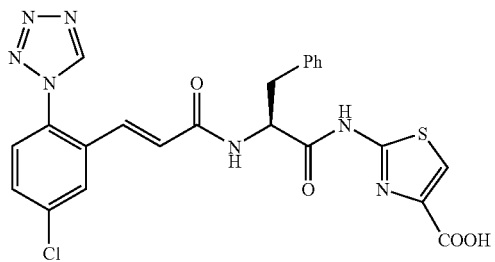 [SMILES: O=C(/C=C/c1cc(Cl)ccc1-n1cnnn1)N[C@@H](Cc1ccccc1)C(=O)Nc1nc(C(=O)O)cs1]

LiOH/THF/water hydrolysis of 2-{(S)-2-[(E)-3-(5-chloro-2-tetrazol-1-yl-phenyl)-acryloylamino]-3-phenyl-propionylamino}-thiazole-4-carboxylic acid ethyl ester (Example 18) afforded Example 22. HPLC purity: >97%. LCMS m/z 524.3 (M+H, chlorine isotope). ¹H NMR (400 MHz, CD₃OD) δ: 9.49 (s, 1H), 7.96 (ds, 2H), 7.72-7.54 (m, 2H), 7.27 (m, 5H), 7.10 (d, J=15.7 Hz, 1H), 6.75 (d, J=15.7 Hz, 1H), 4.90 (m, 1H), 3.27 (m, 1H), 3.11 (m, 1H) ppm. Analytical HPLC RT: 5.58 min (Method C, 8 min gradient).

Example 23

(S,E)-4-(2-(3-(2-acetyl-5-chlorophenyl)acrylamido)-3-phenylpropanamido)benzoic acid

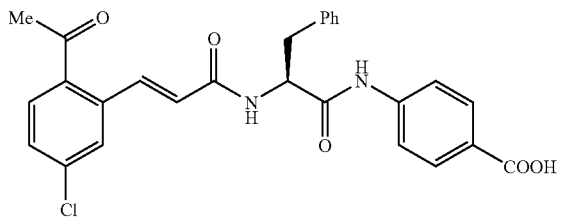 [SMILES: CC(=O)c1ccc(Cl)cc1/C=C/C(=O)N[C@@H](Cc1ccccc1)C(=O)Nc1ccc(C(=O)O)cc1]

Example 23 was prepared in a similar manner to that described for Example 3. Removal of the Boc protecting group with TFA followed by purification and lyophilization of the pure fraction afforded Example 23 as a colorless solid. HPLC purity: >97%. LCMS m/z 491.3 (M+H, chlorine isotope). ¹H NMR (400 MHz, CD₃OD) δ: 7.94 (m, m, 2H), 7.86 (d, J=8.4 Hz, 1H), 7.70 (d, 1H), 7.66 (d, J=8.4 Hz, 2H), 7.51 (dd, J=2.2 & 8.5 Hz, 1H), 7.31-7.18 (m, 5H), 6.56 (d, J=15.5 Hz, 1H), 4.90 (m, 1H), 3.22 (m, 1H0, 3.11 (m, 1H), 2.59 (s, 3H) ppm. Analytical HPLC RT: 6.07 min (Method C, 8 min gradient).

Example 24

(S,E)-N-(1-(4-(1H-imidazol-1-yl)phenylamino)-1-oxo-3-phenylpropan-2-yl)-3-(5-chloro-2-(1H-tetrazol-1-yl)phenyl)acrylamide

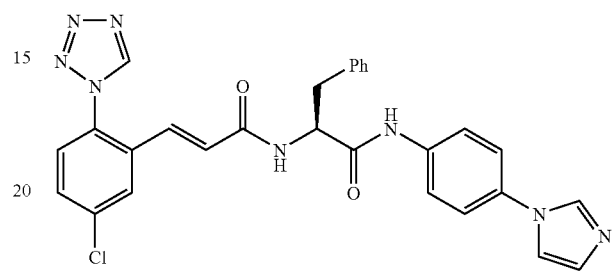

Example 24 was prepared in a similar manner to that described for Example 3. Purification and lyophilization of the pure fraction afforded Example 24 as a colorless solid. HPLC purity: >96%. LCMS m/z 539.3 (M+H, chlorine isotope). ¹H NMR (400 MHz, CD₃OD) δ: 9.50 (s, 1H), 9.39 (s, 1H), 8.02 (d, J=13.3 Hz, 2H), 7.77 (m, 3H), 7.66-7.57 (m, 3H), 7.57 (d, J=8.5 Hz, 1H), 7.29 (m, 4H), 7.21 (m, 1H), 7.11 (d, J=16.6 Hz, 1H), 6.78 (d, J=15.5 Hz, 1H), 4.86 (t, 1H), 3.21 (m, 1H), 3.11 (m, 1H) ppm. Analytical HPLC RT: 4.21 min (Method C, 8 min gradient).

Example 25

(S,E)-3-(5-chloro-2-(1H-tetrazol-1-yl)phenyl)-N-(1-(4-(2-((dimethylamino)methyl)-1H-imidazol-1-yl)-2-fluorophenylamino)-1-oxo-3-phenylpropan-2-yl)acrylamide

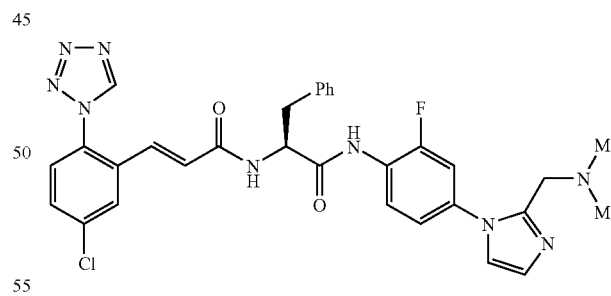

Example 25 was prepared in a similar manner to that described for Example 3. The 4-(2-((dimethylamino)methyl)-1H-imidazol-1-yl)-2-fluoroaniline was prepared as described by Quan (J. Med. Chem., 2005, 48, 1729-1744 and references cited within). Purification and lyophilization of the pure fraction afforded Example 25 as a colorless solid. HPLC purity: >98%. LCMS m/z 614.5 (M+H, chlorine isotope). ¹H NMR (400 MHz, CD₃OD) δ: 9.50 (s, 1H), 8.12 (t, 1H), 7.98 (d, J=2.2 Hz, 1H), 7.67 (dd, J=2.1 & 8.4 Hz, 1H), 7.57 (d, J=8.3 Hz, 1H), 7.44 (s, 1H), 7.40 (dd, J=2.1 & 8.5 Hz, 1H, 7.30-7.12 (m, 7H), 7.12 (d, J=15.6 Hz, 1H), 6.77 (d, J=15.6

Hz, 1H), 4.93 (t, 1H), 4.40 (s, 2H), 3.25 (m, 1H), 3.10 (m, 1H), 2.48 (s, 6H) ppm. Analytical HPLC RT: 4.54 min (Method C, 8 min gradient).

Example 26

(S,E)-3-(5-chloro-2-(1H-tetrazol-1-yl)phenyl)-N-(1-(2'-(((dimethylamino)methyl)-3-fluorobiphenyl-4-ylamino)-1-oxo-3-phenylpropan-2-yl)acrylamide

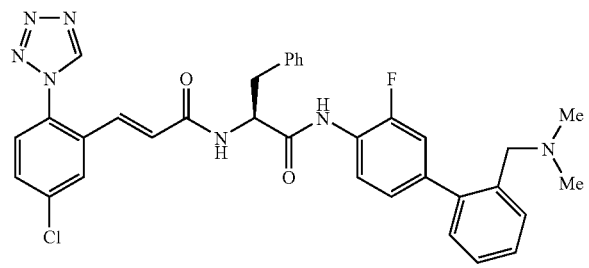 [SMILES: CN(C)Cc1ccccc1-c1ccc(NC(=O)[C@H](Cc2ccccc2)NC(=O)/C=C/c2cc(Cl)ccc2-n2cnnn2)c(F)c1]

Example 26 was prepared in a similar manner to that described for Example 3. Purification and lyophilization of the pure fraction afforded Example 26 as a colorless solid. HPLC purity: >98%. LCMS m/z 624.4 (M+H, chlorine isotope). $^1$H NMR (400 MHz, CD$_3$OD) δ: 9.50 (s, 1H), 8.00 (m, 2H), 7.65 (m, 1H), 7.50 (m, 4H), 7.40 (m, 1H), 7.32-7.10 (m, 8H), 6.80 (d, J=15.5 Hz, 1H), 4.94 (t, 1H), 4.40 (s, 2H), 3.30 (m, 1H), 3.13 (m, 1H), 2.66 (s, 6H) ppm. Analytical HPLC RT: 5.20 min (Method C, 8 min gradient).

Example 27

(S,E)-3-(5-chloro-2-(1H-tetrazol-1-yl)phenyl)-N-(1-(4-(4-methylpiperazin-1-yl)phenylamino)-1-oxo-3-phenylpropan-2-yl)acrylamide

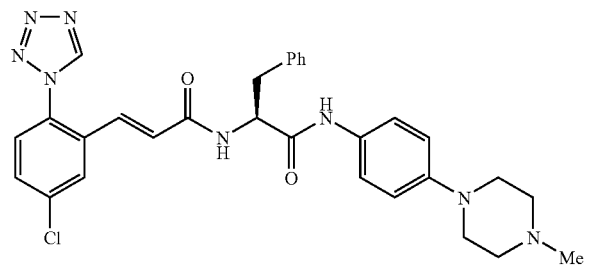 [SMILES: CN1CCN(c2ccc(NC(=O)[C@H](Cc3ccccc3)NC(=O)/C=C/c3cc(Cl)ccc3-n3cnnn3)cc2)CC1]

Example 27 was prepared in a similar manner to that described for Example 3. Purification and lyophilization of the pure fraction afforded Example 27 as a colorless solid. HPLC purity: >98%. LCMS m/z 571.4 (M+H, chlorine isotope). $^1$H NMR (400 MHz, CD$_3$OD) δ: 9.50 (s, 1H), 7.96 (d, J=2.5 Hz, 1H), 7.65 (dd, J=2.5 & 8.2 Hz, 1H), 7.57 (d, J=8.4 Hz, 1H), 7.37 (m, 2H), 7.26-7.17 (m, 3H), 7.10 (d, J=15.7 Hz, 1H), 6.98 (d, J=8.4 Hz, 2H), 6.77 (d, J=15.5 Hz, 1H), 4.75 (m, 1H), 3.80 (bd, 2H), 3.62 (bd, 2H), 3.30 (m, 4H), 3.18 (m, 1H), 3.05 (m, 1H), 2.99 (s, 3H) ppm. Analytical HPLC RT: 4.49 min (Method C, 8 min gradient).

Example 28

(S)-4-(1-(5-chloro-2-(1H-tetrazol-1-yl)phenethylamino)-1-oxo-3-phenylpropan-2-ylcarbamoyl)benzoic acid

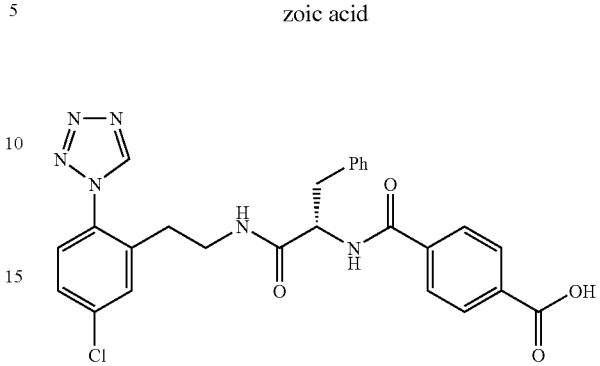

28A. (S)-2-amino-N-(5-chloro-2-(1H-tetrazol-1-yl)phenethyl)-3-phenylpropanamide: To a mixture of 2-(5-chloro-2-(1H-tetrazol-1-yl)phenyl)ethanamine (0.179 g, 0.8 mmol), (S)-2-(tert-butoxycarbonylamino)-3-phenylpropanoic acid (0.233 g, 0.880 mmol), EDC (0.169 g, 0.880 mmol) and HOBt (0.135 g, 0.880 mmol) in DMF (10 mL) was added DIEA (excess, 1.0 mL). The resulted mixture was stirred at rt for 2.5 h. Most of the solvent was removed and the residue was diluted with ethyl acetate, washed with water, 1N HCl, sat. NaHCO$_3$, brine and dried over anhydrous MgSO$_4$ to obtain the desired product as a white solid. LCMS m/z 471.4.

28B. (S)-methyl 4-(1-(5-chloro-2-(1H-tetrazol-1-yl)phenethylamino)-1-oxo-3-phenylpropan-2-ylcarbamoyl)benzoate: A mixture of (S)-tert-butyl 1-(5-chloro-2-(1H-tetrazol-1-yl)phenethylamino)-1-oxo-3-phenylpropan-2-ylcarbamate (106 mg, 0.225 mmol) in 10 mL of 4N HCl in dioxane was stirred at rt for 30 min. LCMS indicated the completion of the reaction. The mixture was concentrated and dried and to this was added (S)-2-amino-N-(5-chloro-2-(1H-tetrazol-1-yl)phenethyl)-3-phenylpropanamide (83 mg, 0.224 mmol), 4-(methoxycarbonyl)benzoic acid (44.4 mg, 0.246 mmol), EDC (47.2 mg, 0.246 mmol) and HOBt (37.7 mg, 0.246 mmol) in DMF under N$_2$ and DIEA (0.8 mL). The resulted mixture was stirred at rt for 2.5 h. Most of the solvent was removed. The residue was diluted with ethyl acetate, washed with water, 1N HCl, sat. NaHCO$_3$ and brine. The mixture was purified with reverse phase HPLC (MeCN/water containing 0.1% TFA system, starting 10% MeCN in water, gradient, to 98% MeCN in water) to obtain 28B as a white solid. LCMS: m/z 533.3 (M+H)$^+$. $^1$H NMR (400 MHz, CD$_3$OD) δ: 9.52 (s, 1H), 8.04 (d, J=8.80 Hz, 2H), 7.81 (d, J=8.31 Hz, 2H), 7.58 (s, 1H), 7.41-7.45 (m, 2H), 7.16-7.24 (m, 5H), 4.66-4.70 (m, 1H), 3.30-3.32 (m, 2H), 3.11-3.16 (m, 1H), 2.95-3.00 (m, 1H), 0.2.53-2.58 (m, 2H), ppm.

Example 28: To a mixture of 28B (21 mg, 0.039 mmol) in THF was added 1N NaOH (1.5 mL). The resulted mixture was stirred at rt for 3.5 h. The mixture was acidified at 0° C. to pH 6 with 1N HCl, purified via reverse phase HPLC (MeCN/water containing 0.1% TFA system, starting 10% MeCN in water, gradient, to 98% MeCN in water). Removal of the solvents provided the desired product as a white solid. LCMS m/z 519.1 (M+H)$^+$. $^1$H NMR (400 MHz, CD$_3$OD) δ: 9.53 (s, 1H), 8.04 (d, J=8.31 Hz, 2H), 7.80 (d, J=8.80 Hz, 2H), 7.58 (s, 1H), 7.41-7.45 (m, 2H), 7.17-7.24 (m, 5H), 4.68 (m, 1H), 3.31-3.33 (m, 2H), 3.11-3.15 (m, 1H), 2.95-3.01 (m, 1H), 2.54-2.57 (m, 2H), ppm. Analytical HPLC RT: 6.86 min (Method C, 8 min gradient, 4.6×75 mm column)

Example 29

5-{(S)-2-[(E)-3-(5-chloro-2-tetrazol-1-yl-phenyl)-acryloylamino]-3-phenyl-propionylamino}-1H-indole-3-carboxylic acid amide

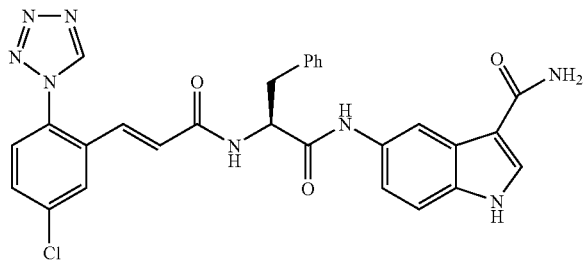 [SMILES: NC(=O)c1c[nH]c2ccc(NC(=O)[C@H](Cc3ccccc3)NC(=O)/C=C/c3cc(Cl)ccc3-n3cnnn3)cc12]

29A. (S)-5-(2-amino-3-phenylpropanamido)-1H-indole-3-carboxamide: (S)-2-(tert-butoxycarbonylamino)-3-phenylpropanoic acid (0.20 g, 0.75 mmol), 5-amino-1H-indole-3-carboxamide hydrochloride (0.16 g, 0.75 mmol), 1-hydroxybenzotriazole hydrate (0.12 g, 0.75 mmol), EDCI (0.29 g, 1.51 mmol), and N-methylmorpholine (0.33 mL, 3.02 mmol) were added to DMF (10 mL) and stirred at rt for 14 h. The reaction mixture was partitioned between water/brine (1:1, 50 mL) and EtOAc (50 mL). The organic layer was washed with brine, dried over sodium sulfate, filtered, and concentrated. Purification by flash column chromatography (40 g column, 100% DCM to 10% MeOH/90% DCM) yielded yellow oil. The Boc group was removed by dissolution in MeOH (5 mL) and treatment with 4.0M HCl in dioxane solution (1 mL) with stirring for 4 h at 25° C. Evaporation to dryness afforded 29A as a free base. LCMS m/z (M+H)$^+$= 323.

Example 29: 29A was dissolved in THF (10 mL) followed by the addition of (E)-3-(5-chloro-2-(1H-tetrazol-1-yl)phenyl)acrylic acid (0.19 g, 0.75 mmol), BOP Reagent (0.33 g, 0.75 mmol), and TEA (0.32 mL, 2.26 mmol) with stirring. After 15 h, the mixture was partitioned between water/brine (1:1, 25 mL) and EtOAc (2×30 mL). The organic layer was washed with brine, dried over sodium sulfate, filtered, and concentrated. Purification by preparative reverse phase yielded Example 29 (40, mg, 9% yield) as a white solid. LCMS m/z 555 (M+H)$^+$. $^1$H NMR (400 MHz, DMSO-d$_6$) δ: 11.41-11.47 (m, 1H), 10.08 (s, 1H), 9.84 (s, 1H), 8.50 (d, J=8.25 Hz, 1H), 8.25-8.30 (m, 1H), 7.99 (d, J=2.75 Hz, 1H), 7.94 (d, J=2.20 Hz, 1H), 7.67-7.78 (m, 2H), 7.45 (dd, J=8.79, 2.20 Hz, 1H), 7.23-7.36 (m, 6H), 7.14-7.24 (m, 1H), 6.78-6.95 (m, 2H), 4.73-4.83 (m, 1H), 3.05-3.14 (m, 1H), 2.85-2.97 (m, 1H) ppm. Analytical HPLC RT: 5.23 min (Method C, 8 min gradient).

Example 30

(E)-3-(5-chloro-2-tetrazol-1-yl-phenyl)-N—[(S)-1-(1H-indazol-5-ylcarbamoyl)-2-phenyl-ethyl]-acrylamide

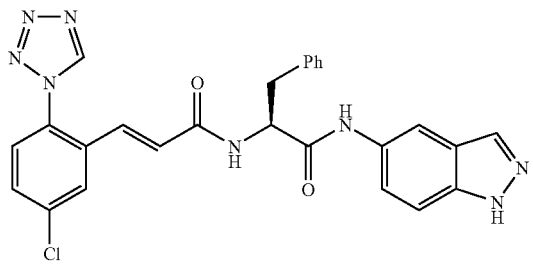 [SMILES: O=C(/C=C/c1cc(Cl)ccc1-n1cnnn1)N[C@@H](Cc1ccccc1)C(=O)Nc1ccc2[nH]ncc2c1]

30A. (S)-2-amino-N-(1H-indazol-5-yl)-3-phenylpropanamide hydrochloride: (S)-2-(tert-butoxycarbonylamino)-3-phenylpropanoic acid (1.0 g, 3.77 mmol) and 5-aminoindazole (0.50 g, 3.77 mmol) were added to pyridine (11 mL) at −15° C. under nitrogen atmosphere. After 5 min, POCl$_3$ (0.18 mL, 1.9 mmol) was added dropwise and stirring continued. After 1 h, the mixture was diluted with water (100 mL), acidified with 1.0M HCl, and extracted with EtOAc (2×75 mL). The combined organic extracts were washed with water, brine, dried over sodium sulfate, filtered, and concentrated. The residue was dissolved in MeOH (20 mL) and treated with 4.0M HCl in dioxane (3 mL) for 3 h before concentrating. Trituration with Et$_2$O, filtration, and drying under vacuum afforded 30A as an HCl salt (0.712 g, 67.4% yield). LCMS m/z 281 [M+H]$^+$.

Example 30: The title compound was obtained in a similar manner described for Example 29 (30 mg, 18%). LCMS m/z 513 [M+H]$^+$. $^1$H NMR (400 MHz, DMSO-d$_6$) δ: 10.16 (s, 1H), 9.84 (s, 1H), 8.56 (d, J=8.24 Hz, 1H), 8.05-8.09 (m, 1H), 7.99-8.03 (m, 1H), 7.93 (d, J=2.20 Hz, 1H), 7.67-7.77 (m, 2H), 7.43-7.50 (m, 1H), 7.33-7.40 (m, 1H), 7.22-7.33 (m, 4H), 7.13-7.22 (m, 1H), 6.77-6.95 (m, 2H), 4.72-4.84 (m, 1H), 3.08 (dd, J=13.47, 5.22 Hz, 1H), 2.87-2.98 (m, 1H) ppm. Analytical HPLC RT: 5.50 min (Method C, 8 min gradient).

Example 31

(E)-3-(5-chloro-2-tetrazol-1-yl-phenyl)-N-{(S)-2-phenyl-1-[4-(1H-tetrazol-5-yl)-phenylcarbamoyl]-ethyl}-acrylamide

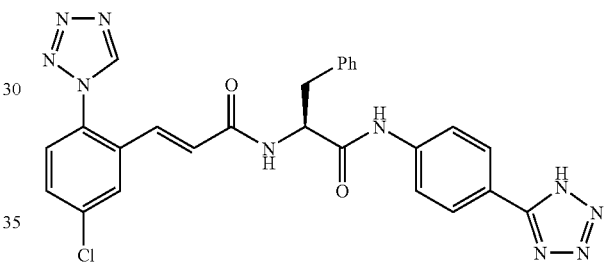

31A. (S)—N-(4-(1H-tetrazol-5-yl)phenyl)-2-amino-3-phenylpropanamide: The title compound was prepared in a similar manner described for Example 3 using 4-(1H-tetrazol-5-yl)aniline as the coupling starting material (75% yield). LCMS (ES+): m/z [M+1] 309.

Example 31: The title compound was prepared in a similar manner described for Examples 3 (11 mg, 14% yield). LCMS m/z 541 [M+H]$^+$. $^1$H NMR (400 MHz, DMSO-d$_6$) δ: 10.43-10.53 (m, 1H), 9.83 (s, 1H), 8.60 (d, J=8.25 Hz, 1H), 7.91-8.01 (m, 3H), 7.68-7.83 (m, 4H), 7.22-7.33 (m, 4H), 7.14-7.23 (m, 1H), 6.75-6.94 (m, 2H), 4.71-4.86 (m, 1H), 3.09 (dd, J=13.74, 4.95 Hz, 1H), 2.86-2.99 (m, 1H) ppm. Analytical HPLC RT: 5.62 min (Method C, 8 min gradient).

Example 32

(E)-3-(5-chloro-2-tetrazol-1-yl-phenyl)-N-{(S)-2-phenyl-1-[3-(1H-tetrazol-5-yl)-phenylcarbamoyl]-ethyl}-acrylamide

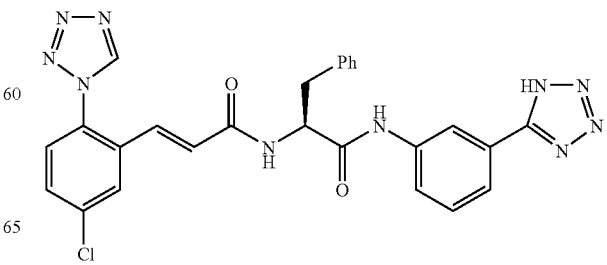

32A. (S)—N-(3-(1H-tetrazol-5-yl)phenyl)-2-amino-3-phenylpropanamide hydrochloride: The title compound was prepared in a similar manner described for Examples 3 and 31 using 3-(1H-tetrazol-5-yl)aniline in place of 5-aminoindazole (49% yield). LCMS m/z 309 [M+H]+.

Example 32: The title compound was prepared in a similar manner described for Examples 29 and 30 (21 mg, 13%). LCMS m/z 541 [M+H]+. 1H NMR (400 MHz, DMSO-d6) δ: 10.46 (s, 1H), 9.84 (s, 1H), 8.60 (d, J=7.70 Hz, 1H), 8.37 (s, 1H), 7.94 (d, J=2.20 Hz, 1H), 7.66-7.79 (m, 4H), 7.54 (t, J=7.70 Hz, 1H), 7.23-7.33 (m, 4H), 7.13-7.24 (m, 1H), 6.77-6.95 (m, 1H), 4.69-4.85 (m, 1H), 3.11 (dd, J=14.02, 5.22 Hz, 1H), 2.86-2.99 (m, 1H) ppm. Analytical HPLC RT: 5.62 min (Method C, 8 min gradient).

Example 33

(E)-N—[(S)-1-(6-acetylamino-pyridin-3-ylcarbamoyl)-2-phenyl-ethyl]-3-(5-chloro-2-tetrazol-1-yl-phenyl)-acrylamide 33A. (S)—N-(6-acetamidopyridin-3-yl)-2-amino-3-phenylpropanamide hydrochloride: (S)-2-(tert-butoxycarbonylamino)-3-phenylpropanoic acid (1.0 g, 3.77 mmol), N-(5-aminopyridin-2-yl)acetamide (0.570 g, 3.8 mmol), PyBOP (1.961 g, 3.8 mmol), and N-methylmorpholine (1.2 mL, 11.3 mmol) were added to THF (38 mL) with stirring. After 15 h, the reaction mixture was concentrated, diluted with EtOAc, washed with water (1×50 mL), 0.05M HCl solution (1×25 mL), saturated bicarbonate solution (1×25 mL), and brine (2×25 mL), dried over sodium sulfate, filtered, and concentrated. The residue was dissolved in MeOH (20 mL) and treated with 4.0M HCl solution. After 30 min, a solid precipitated from the solution. The suspension was further diluted with Et2O, filtered, washed with Et2O, and air-dried. 33A (602 mg, 48% yield) was recovered as a white solid. LCMS m/z 299 [M+H]+. 1H NMR (400 MHz, CD3OD) δ: 8.95 (s, 1H), 8.34 (dd, J=9.34, 2.75 Hz, 1H), 7.51 (d, J=9.34 Hz, 1H), 7.28-7.40 (m, 5H), 4.36 (t, J=7.42 Hz, 1H), 3.34-3.41 (m, 1H), 3.19 (dd, J=14.29, 8.25 Hz, 1H), 2.31 (s, 3H) ppm.

Example 33: The title compound was prepared in a similar manner described for Examples 3 (37 mg, 23% yield). LCMS m/z 531 [M+H]+. 1H NMR (400 MHz, DMSO-d6) δ: 10.24-10.42 (m, 2H), 9.83 (s, 1H), 8.52-8.64 (m, 1H), 8.47 (d, J=2.53 Hz, 1H), 8.00 (d, J=8.84 Hz, 1H), 7.93 (d, J=2.02 Hz, 1H), 7.86 (dd, J=8.97, 2.65 Hz, 1H), 7.67-7.77 (m, 2H), 7.24-7.31 (m, 4H), 7.15-7.22 (m, 1H), 4.69-4.78 (m, 1H), 6.84 (s, 2H), 3.07 (dd, J=13.64, 5.31 Hz, 1H), 2.91 (dd, J=13.77, 9.22 Hz, 1H), 2.05 (s, 3H) ppm. Analytical HPLC RT: 4.96 min (Method C, 8 min gradient).

Example 34

(E)-N—[(S)-1-(6-amino-pyridin-3-ylcarbamoyl)-2-phenyl-ethyl]-3-(5-chloro-2-tetrazol-1-yl-phenyl)-acrylamide

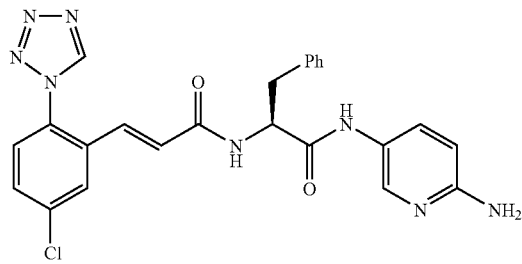 [SMILES: Nc1ccc(NC(=O)[C@H](Cc2ccccc2)NC(=O)/C=C/c2cc(Cl)ccc2-n2cnnn2)cn1]

Example 33 (0.03 g, 0.057 mmol) was added to a microwave reactor tube (20 mL) containing 20% H2SO4 (aq)/MeOH (1:1; 6 mL), sealed, and the mixture was irradiated at 100° C. for 30 min. The mixture was diluted with water and then the excess MeOH was evaporated. The resulting suspension was neutralized with 1.0N NaOH, extracted with EtOAc (2×20 mL), dried over sodium sulfate, filtered, and concentrated. Purification by preparative reverse phase afforded Example 34 (11 mg, 37.8% yield) as a TFA salt. LCMS m/z 489 [M+H]+. 1H NMR: (400 MHz, CD3OD) δ: 9.50 (s, 1H), 8.31 (d, J=2.27 Hz, 1H), 7.96 (d, J=2.27 Hz, 1H), 7.72 (dd, J=9.47, 2.40 Hz, 1H), 7.63-7.68 (m, 1H), 7.52-7.59 (m, 1H), 7.18-7.32 (m, 5H), 7.08 (d, J=15.66 Hz, 1H), 6.96 (d, J=9.35 Hz, 1H), 6.73 (d, J=15.66 Hz, 1H), 4.69 (t, J=7.71 Hz, 1H), 3.11-3.20 (m, 1H), 3.01-3.09 (m, 1H) ppm. Analytical HPLC RT: 4.02 min (Method C, 8 min gradient).

Example 35

(E)-3-(5-chloro-2-tetrazol-1-yl-phenyl)-N—[(S)-2-phenyl-1-(3-sulfamoyl-phenylcarbamoyl)-ethyl]-acrylamide

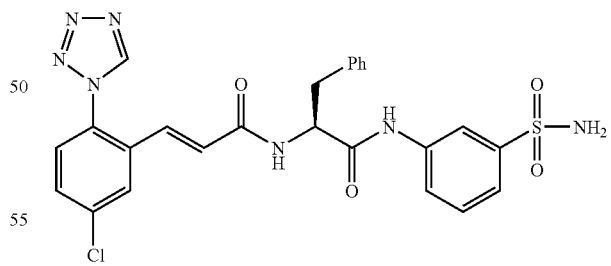

(S)-2-(tert-butoxycarbonylamino)-3-phenylpropanoic acid (0.1 g, 0.38 mmol) and 3-aminobenzenesulfonamide (0.065 g, 0.38 mmol) were added to pyridine (5 mL) at −15° C. under nitrogen atmosphere. After 5 min, POCl3 (0.035 mL, 0.38 mmol) was added dropwise and stirring continued under set conditions. After 1.5 h, the reaction mixture was diluted with water (100 mL), acidified with 1.0M HCl, and extracted with EtOAc (2×75 mL). The combined organic extracts were washed with brine, dried over sodium sulfate, filtered, and concentrated. The resulting residue was diluted with MeOH (5 mL) and treated with 4.0M HCl in dioxane (2.0 mL). After 2 h, the reaction mixture was concentrated to dryness. The amine HCl salt intermediate was dissolved in THF (10 mL), (E)-3-(5-chloro-2-(1H-tetrazol-1-yl)phenyl)acrylic acid (0.094 g, 0.377 mmol), PyBOP (0.196 g, 0.377 mmol), and TEA (0.263 mL, 1.885 mmol) was added with stirring. After 2 h, the reaction mixture was partitioned between water/brine (1:1) and EtOAc. The organic layer was washed with brine, dried over sodium sulfate, filtered, and concentrated. Purification by preparative reverse phase HPLC afforded Example 35 (12 mg, 6% yield). LCMS m/z 553/555 [M+H]$^+$; (ES−): m/z 551 [M−H]. $^1$H NMR: (400 MHz, DMSO-d$_6$) δ: 10.49 (s, 1H), 9.81-9.85 (m, 1H), 8.59 (d, J=8.08 Hz, 1H), 8.11-8.20 (m, 1H), 7.93 (d, J=2.02 Hz, 1H), 7.67-7.80 (m, 3H), 7.47-7.53 (m, 2H), 7.35 (s, 2H), 7.23-7.32 (m, 4H), 7.14-7.23 (m, 1H), 6.76-6.88 (m, 2H), 4.73 (d, J=8.34 Hz, 1H), 3.00-3.16 (m, 1H), 2.83-2.99 (m, 1H), ppm. Analytical HPLC RT: 5.11 min (Method C, 8 min gradient).

Example 36

(E)-3-(5-chloro-2-tetrazol-1-yl-phenyl)-N—[(S)-1-(1,4-dioxo-1,2,3,4-tetrahydro-phthalazin-6-ylcarbamoyl)-2-phenyl-ethyl]-acrylamide

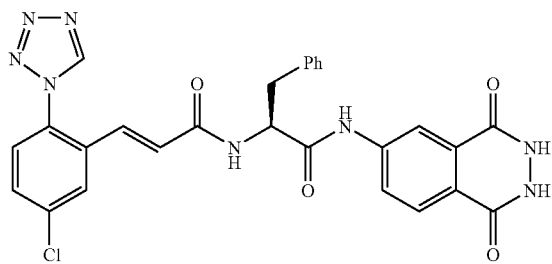 [SMILES: O=C(/C=C/c1cc(Cl)ccc1-n1cnnn1)N[C@@H](Cc1ccccc1)C(=O)Nc1ccc2c(=O)[nH][nH]c(=O)c2c1]

Example 36 (31 mg, 8% yield) as a white solid was prepared using similar procedures to Examples 3. LCMS m/z 557 [M+H]$^+$. $^1$H NMR (400 MHz, CD$_3$OD) δ: 10.40 (s, 1H), 9.50 (s, 1H), 8.69 (d, J=7.58 Hz, 1H), 8.41 (s, 1H), 8.07-8.15 (m, 1H), 7.96 (d, J=2.27 Hz, 1H), 7.93 (dd, J=8.72, 1.89 Hz, 1H), 7.62-7.66 (m, 1H), 7.53-7.57 (m, 1H), 7.16-7.31 (m, 5H), 7.09 (d, J=15.66 Hz, 1H), 6.77 (d, J=15.66 Hz, 1H), 4.87-4.93 (m, 1H), 3.19-3.26 (m, 1H), 3.04-3.12 (m, 1H) ppm. Analytical HPLC RT: 5.45 min (Method C, 8 min gradient).

Example 37

(E)-3-(5-chloro-2-tetrazol-1-yl-phenyl)-N—[(S)-2-phenyl-1-(4-sulfamoyl-phenylcarbamoyl)-ethyl]-acrylamide

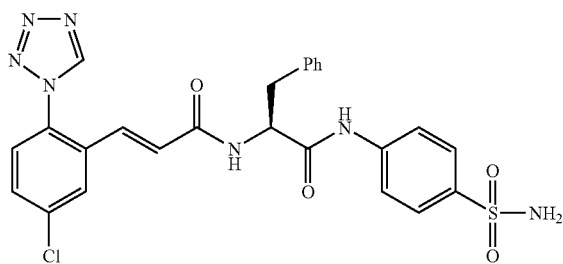 [SMILES: NS(=O)(=O)c1ccc(NC(=O)[C@H](Cc2ccccc2)NC(=O)/C=C/c2cc(Cl)ccc2-n2cnnn2)cc1]

Example 37 (45 mg, 22% yield) as a white solid was prepared using similar procedures to Examples 3. LCMS m/z 552 [M+H]$^+$. $^1$H NMR (400 MHz, CD$_3$OD) δ: 9.49 (s, 1H), 7.96 (d, J=2.02 Hz, 1H), 7.76-7.84 (m, 2H), 7.61-7.67 (m, 3H), 7.52-7.58 (m, 1H), 7.15-7.32 (m, 5H), 7.08 (d, J=15.66 Hz, 1H), 6.75 (d, J=15.66 Hz, 1H), 4.80 (t, J=7.58 Hz, 1H), 3.16 (d, J=7.07 Hz, 1H), 2.98-3.11 (m, 1H) ppm. Analytical HPLC RT: 5.23 min (Method C, 8 min gradient).

Example 38

(E)-3-(5-chloro-2-tetrazol-1-yl-phenyl)-N—[(S)-2-phenyl-1-(4-[1,2,4]triazol-1-yl-phenylcarbamoyl)-ethyl]-acrylamide

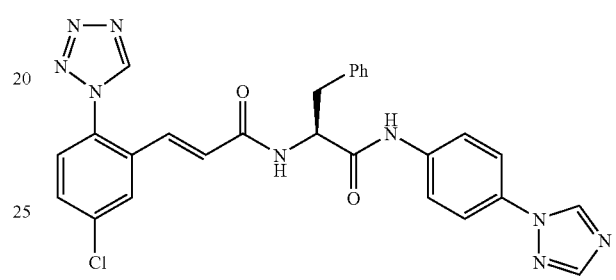

Example 38 (22 mg, 10% yield) as a white solid was prepared using similar procedures to Examples 3. LCMS m/z 540 [M+H]$^+$. $^1$H NMR (400 MHz, DMSO-d$_6$) δ: 10.40 (s, 1H), 9.84 (s, 1H), 9.19 (s, 1H), 8.60 (d, J=8.08 Hz, 1H), 8.20 (s, 1H), 7.93 (d, J=2.27 Hz, 1H), 7.67-7.82 (m, 6H), 7.27 (d, J=4.55 Hz, 4H), 7.14-7.22 (m, 1H), 6.84 (d, J=1.77 Hz, 2H), 4.69-4.85 (m, 1H), 3.09 (dd, J=13.64, 5.31 Hz, 1H), 2.92 (dd, J=13.77, 9.22 Hz, 1H) ppm. Analytical HPLC RT: 5.66 min (Method C, 8 min gradient).

Example 39

(E)-3-(5-chloro-2-tetrazol-1-yl-phenyl)-N—[(S)-2-phenyl-1-(4-tetrazol-1-yl-phenylcarbamoyl)-ethyl]-acrylamide

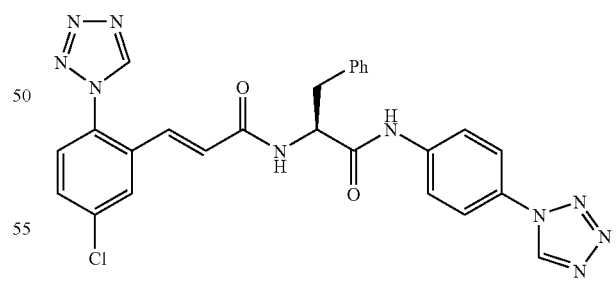

Example 39 (27 mg, 13% yield) as a white solid was prepared using similar procedures to Examples 3. LCMS m/z 541 [M+H]$^+$. (ES−): m/z 539 [M−H]. $^1$H NMR (400 MHz, DMSO-d$_6$) δ: 10.52 (s, 1H), 10.01 (s, 1H), 9.84 (s, 1H), 8.62 (d, J=8.08 Hz, 1H), 7.92-7.97 (m, 1H), 7.68-7.88 (m, 6H), 7.24-7.31 (m, 4H), 7.16-7.23 (m, 1H), 6.81-6.92 (m, 2H), 4.71-4.83 (m, 1H), 3.09 (dd, J=13.89, 5.31 Hz, 1H), 2.93 (dd, J=13.77, 8.97 Hz, 1H) ppm. Analytical HPLC RT: 5.60 min (Method C, 8 min gradient).

Example 40

(E)-3-(5-chloro-2-tetrazol-1-yl-phenyl)-N-{(S)-2-phenyl-1-[4-(tetrahydro-furan-2-ylmethoxy)-phenyl-carbamoyl]-ethyl}-acrylamide

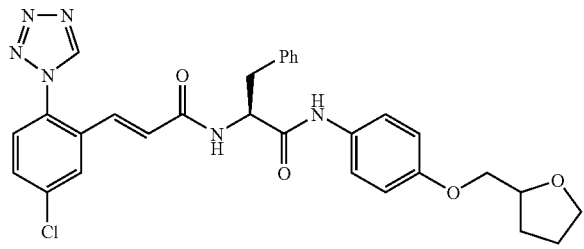 [SMILES: O=C(/C=C/c1cc(Cl)ccc1-n1cnnn1)N[C@@H](Cc1ccccc1)C(=O)Nc1ccc(OCC2CCCO2)cc1]

Example 40 (44 mg, 20% yield) as a white solid was prepared using similar procedures to Example 3. LCMS m/z 573 [M+H]$^+$. $^1$H NMR (400 MHz, CD$_3$OD) δ: 9.50 (s, 1H), 7.97 (d, J=2.20 Hz, 1H), 7.58-7.71 (m, 1H), 7.50-7.57 (m, 1H), 7.14-7.37 (m, 7H), 7.08 (d, J=15.39 Hz, 1H), 6.81-6.91 (m, J=8.79 Hz, 2H), 6.76 (d, J=15.39 Hz, 1H), 4.77 (t, J=7.42 Hz, 1H), 4.17-4.33 (m, J=6.32, 4.12 Hz, 1H), 3.84-3.99 (m, 3H), 3.74-3.84 (m, 1H), 3.09-3.22 (m, 1H), 2.92-3.07 (m, 1H), 1.86-2.15 (m, 3H), 1.78 (dd, J=11.82, 8.52 Hz, 1H) ppm. Analytical HPLC RT: 6.22 min (Method C, 8 min gradient).

Example 41

(E)-3-(5-chloro-2-tetrazol-1-yl-phenyl)-N—[(S)-2-phenyl-1-(4-pyridin-4-yl-phenylcarbamoyl)-ethyl]-acrylamide

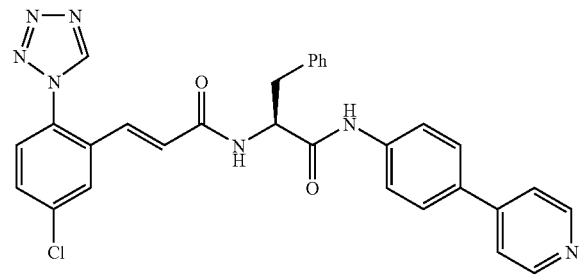 [SMILES: O=C(/C=C/c1cc(Cl)ccc1-n1cnnn1)N[C@@H](Cc1ccccc1)C(=O)Nc1ccc(-c2ccncc2)cc1]

Example 41 (18 mg, 9%) as a TFA salt (white solid) was prepared using similar procedures to Examples 3. LCMS m/z 551 [M+H]$^+$; (ES–): m/z 549 [M–H]. $^1$H NMR (400 MHz, DMSO-d$_6$) δ: 10.35-10.58 (m, 1H), 9.84 (s, 1H), 8.79 (d, J=5.31 Hz, 2H), 8.61 (t, J=8.72 Hz, 1H), 8.03-8.18 (m, 2H), 7.88-8.01 (m, 3H), 7.65-7.85 (m, 4H), 7.13-7.38 (m, 5H), 6.76-6.91 (m, 2H), 4.70-4.84 (m, 1H), 3.04-3.15 (m, 1H), 2.85-3.01 (m, 1H), ppm. Analytical HPLC RT: 4.68 min (Method C, 8 min gradient).

Example 42

(4-{(S)-2-[(E)-3-(5-chloro-2-tetrazol-1-yl-phenyl)-acryloylamino]-3-phenyl-propionylamino}-phenyl)-carbamic acid 2-dimethylamino-ethyl ester

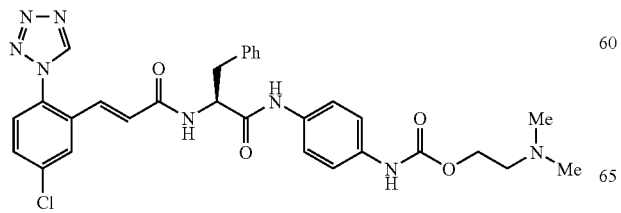

42A. 2-(dimethylamino)ethyl 4-nitrophenylcarbamate: DIPEA (0.53 mL, 3.05 mmol) was added to a solution of 1-isocyanato-4-nitrobenzene (0.50 g, 3.05 mmol) and 2-(dimethylamino)ethanol (0.27 g, 3.05 mmol) in toluene (10 mL) with stirring at 25° C. The reaction mixture was heated at 80° C. After 15 h, the reaction mixture was cooled to rt. The resulting yellow solids were filtered, washed several times with Et$_2$O/hexane (1:1), and dried under vacuum. LCMS m/z 254 [M+H]$^+$.

42B. 2-(dimethylamino)ethyl 4-aminophenylcarbamate: 42A was dissolved in MeOH, treated with 5% Pd/C, and subjected to H$_2$ atmosphere. After 14 h, the reaction mixture was filtered through a plug of Celite®, the filter-cake rinsed with MeOH (3×30 mL), and the combined filtrates were concentrated to afford 42B as yellow oil. LCMS m/z 224 [M+H]$^+$.

42C. (S)-2-(dimethylamino)ethyl 4-(2-amino-3-phenyl-propanamido)phenyl carbamate: PyBOP (1.59 g, 3.05 mmol) was added to a stirring solution of the product from 42B (0.81 g, 3.05 mmol), and DIPEA (0.53 mL, 3.05 mmol) in THF (50 mL). After 3 h, the reaction mixture was partitioned between H$_2$O and EtOAc. The aqueous layer was extracted additional times with EtOAc (2×50 mL). The combined organic extracts were washed with brine, dried over sodium sulfate, filtered, and concentrated. The Boc-group was removed by treatment with 50% TFA/DCM (5 mL) at 25° C. for 2 h. The mixture was diluted with EtOAc and slowly neutralized with saturated NaHCO$_3$ solution. The organic phase was separated, washed with brine, dried over sodium sulfate, filtered, and concentrated to afford 42C (620 mg, 55% yield) as yellow oil. LCMS m/z 371 [M+H]$^+$.

Example 42: PyBOP (0.14 g, 0.27 mmol) was added to a stirring solution of 42C (0.10 g, 0.27 mmol), (E)-3-(5-chloro-2-(1H-tetrazol-1-yl)phenyl)acrylic acid (0.07 g, 0.27 mmol), and DIPEA (0.24 mL, 1.35 mmol) in THF (10 mL). After 1 h, the resulting solids were filtered and rinsed with MeOH. Purification by preparative reverse phase HPLC afforded Example 42 (15 mg, 9% yield) as a white solid. LCMS m/z 603 [M+H]$^+$. $^1$H NMR (400 MHz, DMSO-d$_6$) δ: 10.12 (s, 1H), 9.84 (s, 1H), 8.54 (d, J=8.08 Hz, 1H), 7.92 (d, J=2.02 Hz, 1H), 7.67-7.77 (m, 2H), 7.45-7.52 (m, 2H), 7.34-7.44 (m, 2H), 7.23-7.33 (m, 5H), 7.15-7.23 (m, 1H), 6.76-6.91 (m, 2H), 4.71 (dd, J=8.34, 3.28 Hz, 1H), 4.34-4.44 (m, 2H), 3.40 (s, 2H), 3.05 (dd, J=13.64, 5.05 Hz, 1H), 2.80-2.94 (m, 7H) ppm. Analytical HPLC RT: 4.57 min (Method C, 8 min gradient).

Example 43

(E)-3-(5-chloro-2-tetrazol-1-yl-phenyl)-N-{(S)-2-(3-fluoro-phenyl)-1-[4-(1H-tetrazol-5-yl)-phenylcarbamoyl]-ethyl}-acrylamide

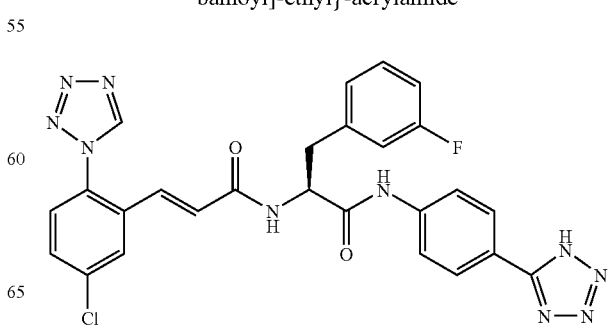

43A. (S)-tert-butyl 1-(4-(1H-tetrazol-5-yl)phenylamino)-3-(3-fluorophenyl)-1-oxopropan-2-ylcarbamate: (S)-2-(tert-butoxycarbonylamino)-3-(3-fluorophenyl)propanoic acid (0.1 g, 0.353 mmol) and 4-(1H-tetrazol-5-yl)aniline (0.057 g, 0.353 mmol) were added to EtOAc (10 mL) at rt. The mixture was treated dropwise with DCC (0.109 g, 0.529 mmol) in EtOAc (5 mL) dropwise at rt. After 18 h, the DCC urea by-product was filtered and the filtercake was rinsed with EtOAc (2×15 mL). The combined filtrate was washed with 5% citric acid (10 mL), brine, dried over sodium sulfate, filtered and concentrated. Purification by flash chromatography (4 g column; 100% DCM to 10% MeOH/90% DCM over 20 min) afforded 43A as an off-white solid. LCMS m/z 427 [M+H]$^+$.

Example 43: 43A was treated with 50% TFA/DCM (3.0 mL) for 45 min before concentrating to dryness. The residue was dissolved in DMF, and (E)-3-(5-chloro-2-(1H-tetrazol-1-yl)phenyl)acrylic acid (0.09 g, 0.35 mmol), 1-hydroxybenzotriazole hydrate (0.05 g, 0.35 mmol), EDCI (0.07 g, 0.35 mmol), and DIPEA (0.31 mL, 1.77 mmol) were added, respectively. After stirring for 14 h, the reaction mixture was partitioned between water/brine (1:1) and EtOAc. The organic layer was washed with brine, dried over sodium sulfate, filtered, and concentrated. Purification by preparative reverse phase HPLC afforded Example 43 (12 mg, 6% yield) as a white solid. LCMS m/z 559 [M+H]$^+$; (ES−): m/z 557 [M−H]. $^1$H NMR (400 MHz, DMSO-d$_6$) δ: 10.51 (s, 1H), 9.84 (s, 1H), 8.67 (d, J=8.25 Hz, 1H), 7.92-8.01 (m, 3H), 7.66-7.82 (m, 4H), 7.26-7.37 (m, 1H), 6.98-7.18 (m, 3H), 6.78-6.88 (m, 1H), 4.77 (d, J=7.70 Hz, 1H), 3.07-3.17 (m, 1H), 2.94 (dd, J=13.74, 9.89 Hz, 1H) ppm. Analytical HPLC RT: 5.76 min (Method C, 8 min gradient).

Example 44

(E)-3-(5-chloro-2-tetrazol-1-yl-phenyl)-N-{(S)-2-(2-fluoro-phenyl)-1-[4-(1H-tetrazol-5-yl)-phenylcarbamoyl]-ethyl}-acrylamide

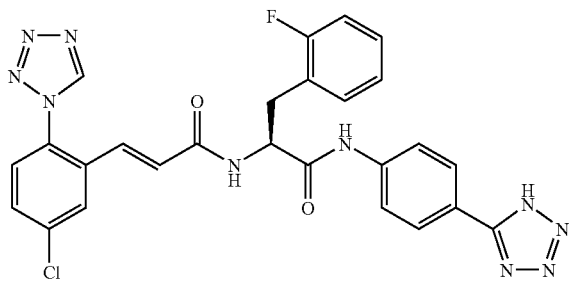 [SMILES: O=C(/C=C/c1cc(Cl)ccc1-n1cnnn1)N[C@@H](Cc1ccccc1F)C(=O)Nc1ccc(-c2nnn[nH]2)cc1]

Example 44 (14 mg, 7% yield) as a white solid was prepared using similar procedures to previously described for Example 43. LCMS m/z 559 [M+H]$^+$; (ES−): m/z 557. [M−H]. $^1$H NMR (400 MHz, DMSO-d$_6$) δ: 10.48 (s, 1H), 9.85 (s, 1H), 8.60 (d, J=8.25 Hz, 1H), 7.88-8.07 (m, 3H), 7.66-7.79 (m, 4H), 7.20-7.35 (m, 2H), 7.02-7.15 (m, 2H), 6.71-6.99 (m, 2H), 4.76-4.89 (m, 1H), 3.06-3.17 (m, 1H), 2.93-3.07 (m, 1H) ppm. Analytical HPLC RT: 5.69 min (Method D).

Example 44B

4-{(S)-2-[(E)-3-(5-chloro-2-tetrazol-1-yl-phenyl)-acryloylamino]-3-methoxycarbonyl-propionylamino}-benzoic acid

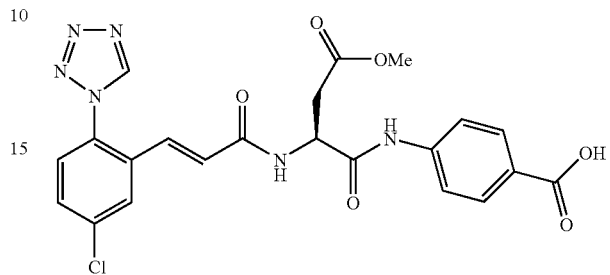

44BA. (S)-tert-butyl 4-(2-(benzyloxycarbonylamino)-4-methoxy-4-oxobutanamido)benzoate: (S)-2-(benzyloxycarbonylamino)-4-methoxy-4-oxobutanoic acid (1.0 g, 3.56 mmol) and tert-butyl 4-aminobenzoate (0.69 g, 3.56 mmol) were added to pyridine (11 mL) at −15° C. under nitrogen atmosphere. After 5 min, POCl$_3$ (0.17 mL, 1.78 mmol) was added dropwise and stirring continued under set conditions. After 1 h, the mixture was diluted with water (100 mL), acidified with 1.0M HCl, and extracted with EtOAc (2×75 mL). The combined organic extracts were washed with water, brine, dried over sodium sulfate, filtered, and concentrated to afford the desired product. LCMS m/z 457 [M+H]$^+$.

44BB. (S,E)-tert-butyl 4-(2-(3-(5-chloro-2-(1H-tetrazol-1-yl)phenyl)acrylamido)-4-methoxy-4-oxobutanamido)benzoate: 44BA was dissolved in MeOH (50 mL), treated with 5% Pd/C, and placed under hydrogen atmosphere (50 psi). After 12 h, the mixture was filtered through a plug of Celite® and the filter-cake was rinsed several times with MeOH. The combined filtrate was concentrated. The resulting oil was dissolved in THF (50 mL) and then (E)-3-(5-chloro-2-(1H-tetrazol-1-yl)phenyl)acrylic acid (0.89 g, 3.56 mmol), BOP (1.57 g, 3.56 mmol), and TEA (1.48 mL, 10.67 mmol) were added at 25° C. with stirring. After 2 h, the reaction mixture was diluted with EtOAc, washed with water and then brine, dried over sodium sulfate, filtered, and concentrated. Purification by flash chromatography (40 g column; (100% hexane/0% EtOAC to 0% hexane over 30 min) afforded 44BB (1.8 g, 55%) as a white solid. LCMS m/z 555 [M+H]$^+$.

Example 44B: 44BB (0.20 g, 0.36 mmol) was treated with a 25% TFA/DCM solution (5 mL) and stirred for 1 h. The mixture was concentrated and purified by preparative reverse phase HPLC to obtain Example 44B (20 mg, 11%) as a white solid. LCMS m/z 499 [M+H]$^+$. $^1$H NMR (400 MHz, CD$_3$OD) δ: 9.51 (s, 1H), 7.96 (d, J=8.59 Hz, 3H), 7.62-7.71 (m, 3H), 7.54-7.59 (m, 1H), 7.16 (d, J=15.66 Hz, 1H), 6.74 (d, J=15.66 Hz, 1H), 4.93-5.01 (m, 1H), 3.68 (s, 3H), 2.91-3.04 (m, 1H), 2.76-2.85 (m, 1H) ppm. Analytical HPLC RT: 5.69 min (Method C, 8 min gradient).

Example 45

4-[(S)-2-[(E)-3-(5-chloro-2-tetrazol-1-yl-phenyl)-acryloylamino]-4-(4-methyl-piperazin-1-yl)-4-oxo-butyrylamino]-benzoic acid

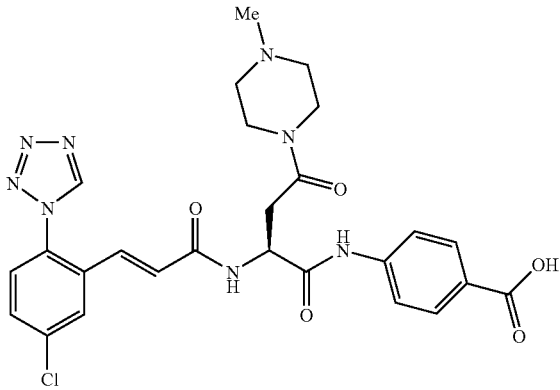 [SMILES: CN1CCN(C(=O)C[C@H](NC(=O)/C=C/c2cc(Cl)ccc2-n2cnnn2)C(=O)Nc2ccc(C(=O)O)cc2)CC1]

45A. (S,E)-4-(4-(tert-butoxycarbonyl)phenylamino)-3-(3-(5-chloro-2-(1H-tetrazol-1-yl)phenyl)acrylamido)-4-oxobutanoic acid: To a solution of 17A (1.8 g, 3.24 mmol) in THF (16 mL) was added lithium hydroxide monohydrate (0.30 g, 7.14 mmol) in H₂O (16 mL). After 1 h, the reaction mixture was acidified to pH 5-6 with 1.0M HCl and extracted with EtOAc (3×40 mL). The combined organic extracts were dried over sodium sulfate, filtered, and concentrated to afford the desired product as an off-white solid. LCMS m/z 541 [M+H]⁺.

Example 45: N-methylmorpholine (0.06 mL, 0.56 mmol) was added to a stirring mixture of 45A (0.20 g, 0.19 mmol), 1-methylpiperazine (0.019 g, 0.19 mmol), 1-hydroxybenzotriazole hydrate (0.028 g, 0.19 mmol), and EDCI (0.064 g, 0.33 mmol) in DMF (5 mL). After 20 h, the reaction mixture was partitioned between water/brine (1:1) and EtOAc. The organic layer was washed with brine, dried over sodium sulfate, filtered, and concentrated. The residue was treated with 50% TFA/DCM for 1 h, concentrated, and purified by preparative reverse-phase HPLC. Example 45 (8 mg, 6% yield) was isolated as a TFA salt (white solid). LCMS m/z 567 [M+H]⁺; (ES−). ¹H NMR (400 MHz, DMSO-d₆) δ: 10.35 (s, 1H), 9.86 (s, 1H), 8.75 (d, J=8.08 Hz, 1H), 7.91-7.96 (m, 1H), 7.83-7.91 (m, 2H), 7.70-7.80 (m, 3H), 7.65 (t, J=7.83 Hz, 2H), 6.71-6.96 (m, 2H), 5.13-5.26 (m, 1H), 3.27-3.54 (m, 3H), 2.93-3.12 (m, 2H), 2.63-2.85 (m, 6H) ppm. Analytical HPLC RT: 3.36 min (Method C, 8 min gradient).

Example 46

4-{(S)-2-[(E)-3-(5-chloro-2-tetrazol-1-yl-phenyl)-acryloylamino]-4-morpholin-4-yl-4-oxo-butyrylamino}-benzoic acid methyl ester

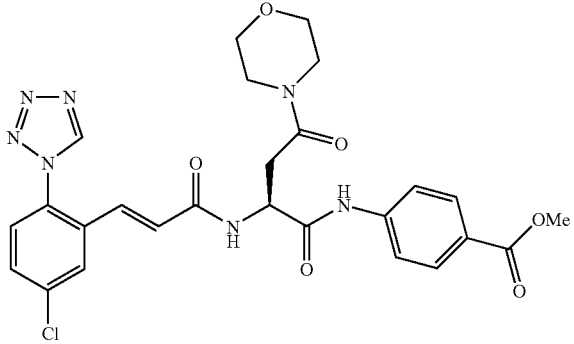 [SMILES: COC(=O)c1ccc(NC(=O)[C@H](CC(=O)N2CCOCC2)NC(=O)/C=C/c2cc(Cl)ccc2-n2cnnn2)cc1]

46A. (S)-3-(tert-butoxycarbonylamino)-4-(4-(methoxycarbonyl)phenylamino)-4-oxobutanoic acid: POCl₃ (1.44 mL, 15.5 mmol) was added dropwise to a stirring solution of (S)-4-(benzyloxy)-2-(tert-butoxycarbonylamino)-4-oxobutanoic acid (5.0 g, 15.5 mmol) and methyl 4-aminobenzoate (2.81 g, 18.6 mmol) in pyridine (60 mL) at −15° C. After 1.5 h, the mixture was diluted with water (100 mL), acidified with 1.0M HCl, and extracted with EtOAc (2×75 mL). The combined organic extracts were washed with brine, dried over sodium sulfate, filtered, and concentrated. The resulting oil was diluted with MeOH (50 mL), 5% Pd/C added, and the suspension was stirred under a H₂ atmosphere (50 psi) for 3 h. The mixture was filtered through a plug of Celite®, the filtercake was rinsed with MeOH, and the combined filtrates were concentrated to afford 46A (3.75 g, 66%) as a white solid. This material was carried forward to subsequent reaction without further purification. LCMS m/z 367 [M+H]⁺.

Example 46: BOP Reagent (0.33 g, 0.75 mmol) was added to a stirring solution of 46A (0.25 g, 0.68 mmol), morpholine (0.06 g, 0.68 mmol), and DIPEA (0.48 mL, 2.73 mmol) in THF (15 mL) at 25° C. After 48 h, the reaction mixture was partitioned between water/brine (1:1) and EtOAc. The organic layer was washed with brine, dried over sodium sulfate, filtered, and concentrated. The resulting residue was diluted with MeOH (5 mL) and treated with 4.0M HCl in dioxane (2.0 mL). After 2 h, the reaction mixture was concentrated, diluted with EtOAc, washed with saturated sodium bicarbonate solution, brine, dried over sodium sulfate, filtered, and concentrated. The free amine was dissolved in THF (10 mL) and then (E)-3-(5-chloro-2-(1H-tetrazol-1-yl)phenyl)acrylic acid (0.17 g, 0.68 mmol), DIPEA (0.48 mL, 2.73 mmol), and BOP Reagent (0.33 g, 0.75 mmol) added, respectively. After 2 h, the mixture was partitioned between water/brine (1:1, 30 mL) and EtOAc (2×30 mL). The organic layer was washed with brine, dried over sodium sulfate, filtered, and concentrated. Purification by preparative reverse phase afforded Example 46 (20 mg, 5% yield) as a white solid. LCMS m/z 568 [M+H]⁺. ¹H NMR (400 MHz, DMSO-d₆) δ: 10.45 (s, 1H), 9.86 (s, 1H), 8.52 (d, J=7.58 Hz, 1H), 7.87-8.00 (m, 3H), 7.65-7.81 (m, 4H), 6.78-6.96 (m, 2H), 4.85 (d, J=7.33 Hz, 1H), 3.81 (s, 3H), 3.38-3.61 (m, 8H), 2.81 (dd, J=11.87, 6.57 Hz, 2H) ppm. Analytical HPLC RT: 5.05 min (Method C, 8 min gradient).

Example 47

4-{(S)-2-[(E)-3-(5-chloro-2-tetrazol-1-yl-phenyl)-acryloylamino]-4-morpholin-4-yl-4-oxo-butyrylamino}-benzoic acid

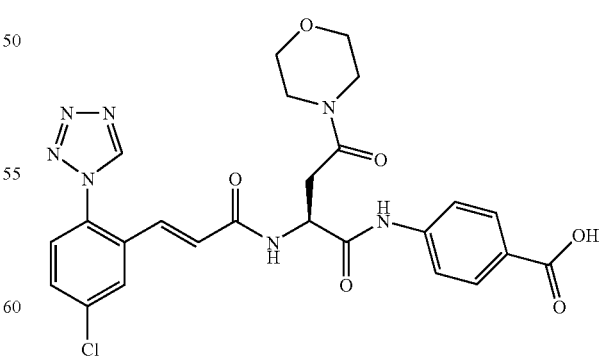

Example 46 (0.10 g, 0.18 mmol) was dissolved in THF (5 mL) and treated with lithium hydroxide monohydrate (0.022 g, 0.53 mmol) in water (5 mL) at 25° C. After stirring for 1.5 h, the mixture was diluted with water (10 mL) and the organics were concentrated. The solution was made acidic with 1.0M HCl and extracted with EtOAc (3×20 mL). The combined organic extracts were washed with brine, dried over sodium sulfate, filtered, and concentrated. Purification by preparative reverse phase afforded the desired product (18 mg, 18%) as a white solid. LCMS m/z 554 [M+H]+. 1H NMR (400 MHz, DMSO-$d_6$) δ: 10.39 (s, 1H), 9.80-9.92 (m, 1H), 8.51 (d, J=7.58 Hz, 1H), 7.93 (d, J=2.02 Hz, 1H), 7.86 (d, J=8.84 Hz, 2H), 7.67-7.77 (m, 4H), 6.77-6.95 (m, 2H), 4.84 (m, 1H), 3.27-3.63 (m, 8H), 2.69-2.89 (m, 2H) ppm. Analytical HPLC RT: 4.28 min (Method C, 8 min gradient).

Example 48

4-[(S)-2-[(E)-3-(5-chloro-2-tetrazol-1-yl-phenyl)-acryloylamino]-4-(1,1-dioxo-1λ6-thiomorpholin-4-yl)-4-oxo-butyrylamino]-benzoic acid methyl ester

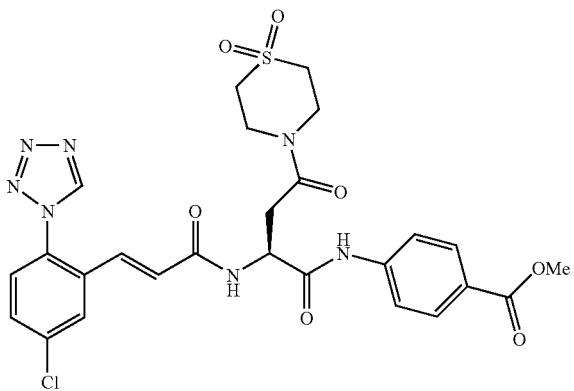 [SMILES: COC(=O)c1ccc(NC(=O)[C@H](CC(=O)N2CCS(=O)(=O)CC2)NC(=O)/C=C/c2cc(Cl)ccc2-n2cnnn2)cc1]

48A. 4-[(S)-2-tert-butoxycarbonylamino-4-(1,1-dioxo-1λ6-thiomorpholin-4-yl)-4-oxo-butyrylamino]-benzoic acid methyl ester: To the mixture of 46A (0.15 g, 0.41 mmol) and thiomorpholine 1,1-dioxide (0.055 g, 0.41 mmol) were added EtOAc (10 mL) at rt. The reaction mixture was treated dropwise with DCC (0.127 g, 0.614 mmol) in EtOAc (5 mL) with stirring. After stirring for 4 days, the DCC urea by-product was filtered and the filtercake was rinsed with EtOAc (2×20 mL). The combined filtrate was washed with 5% citric acid (10 mL), brine, dried over sodium sulfate, filtered and concentrated. Purification by flash chromatography (4 g column; 100% DCM to 10% MeOH/90% DCM over 20 min) afforded 48A as an off-white solid. LCMS m/z 484 [M+H]+. 1H NMR (400 MHz, DMSO-$d_6$) δ: 10.18-10.45 (m, 1H), 7.91 (d, J=8.59 Hz, 2H), 7.71-7.80 (m, 2H), 7.10 (d, J=6.82 Hz, 1H), 4.42-4.55 (m, 1H), 3.84-4.11 (m, 2H), 3.62-3.86 (m, 5H), 2.97-3.14 (m, 4H), 2.66-2.93 (m, 2H), 1.38 (s, 9H) ppm.

Example 48: 48A was treated with 50% TFA/DCM (3.0 mL) for 45 min before concentrating. The residue was dissolved in DMF (5 mL) and HOBt hydrate (0.063 g, 0.41 mmol), EDCI (0.078 g, 0.41 mmol), (E)-3-(5-chloro-2-(1H-tetrazol-1-yl)phenyl)acrylic acid (0.11 g, 0.41 mmol), and DIPEA (0.358 mL, 2.047 mmol) were added, respectively. After 18 h, the reaction mixture was partitioned between water/brine (1:1, 50 mL) and EtOAc (100 mL). The organic layer was washed with brine, dried over sodium sulfate, filtered, and concentrated. Purification by preparative reverse phase HPLC afforded Example 48 as a white solid. LCMS m/z 617 [M+H]+; (ES−): m/z 615. [M−H]. 1H NMR (400 MHz, DMSO-$d_6$) δ: 10.47 (s, 1H), 9.86 (s, 1H), 8.54 (d, J=7.15 Hz, 1H), 7.83-8.04 (m, 3H), 7.63-7.82 (m, 4H), 6.73-7.00 (m, 2H), 4.73-4.94 (m, 1H), 3.75-3.94 (m, 7H), 3.25 (s, 2H), 2.79-3.09 (m, 4H) ppm. Analytical HPLC RT: 4.99 min (Method C, 8 min gradient).

Example 49

(4-{(S)-2-[(E)-3-(5-chloro-2-tetrazol-1-yl-phenyl)-acryloylamino]-propionylamino}-phenyl)-carbamic acid methyl ester

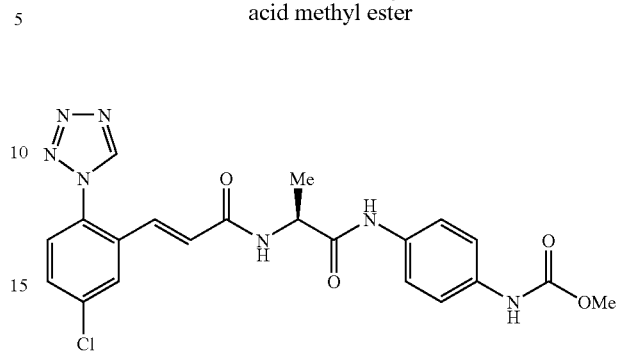

49A. [4-((S)-2-amino-propionylamino)-phenyl]-carbamic acid methyl ester: (S)-tert-butyl 1-(4-aminophenylamino)-1-oxopropan-2-ylcarbamate (0.050 g, 0.18 mmol) and pyridine (0.043 mL, 0.54 mmol) were added to DCM (5 mL) and cooled to 0° C. with stirring. Then, methyl carbonochloridate (0.017 g, 0.18 mmol) was added dropwise and stirring continued at rt. After 1.5 h, the solvent was evaporated, the resulting residue diluted with water (10 mL) and made slightly acidic with 1M HCl (aq). The solution was extracted with EtOAc (3×15 mL), washed with brine, dried over sodium sulfate, filtered, and concentrated. The residue was treated with 50% TFA/DCM (2 mL) for 1 h. Afterwards, the mixture was partitioned between EtOAc and sat. NaHCO3 solution and stirred for 15 min. The organic layer was separated, washed with brine, dried over sodium sulfate, filtered, and concentrated to afford 49A. LCMS m/z 237.2 [M+H]+.

Example 49: 49A (0.046 g, 0.197 mmol), (E)-3-(5-chloro-2-(1H-tetrazol-1-yl)phenyl)acrylic acid (0.049 g, 0.197 mmol), BOP Reagent (0.079 g, 0.179 mmol), and TEA (0.075 mL, 0.537 mmol) were added to THF (10 mL) with stirring. After 2 h, the mixture was poured into water, extracted with EtOAc, washed with brine, dried over sodium sulfate, filtered, and concentrated. Purification by preparative reverse phase HPLC afforded Example 49 (5.5 mg, 6% yield) as a white solid. LCMS m/z 470 [M+H]+. 1H NMR (400 MHz, DMSO-$d_6$) δ: 9.99 (s, 1H), 9.86 (s, 1H), 9.54 (s, 1H), 8.45 (d, J=7.70 Hz, 1H), 7.88-7.99 (m, 1H), 7.66-7.81 (m, 2H), 7.47 (d, J=9.34 Hz, 2H), 7.36 (d, J=8.79 Hz, 2H), 6.80-6.94 (m, 2H), 4.42-4.61 (m, 1H), 3.63 (s, 3H), 1.30 (d, J=6.60 Hz, 3H) ppm. Analytical HPLC RT: 4.48 min (Method C, 8 min gradient).

Example 50

(4-{(S)-2-[(E)-3-(5-chloro-2-tetrazol-1-yl-phenyl)-acryloylamino]-butyrylamino}-phenyl)-carbamic acid methyl ester

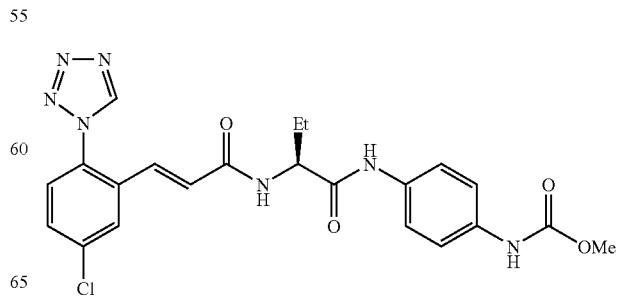

Example 50 (25 mg, 7% yield) was prepared as a colorless solid, following similar procedures to Example 49. LCMS m/z 484 [M+H]+. ¹H NMR (400 MHz, DMSO-d₆) δ: 10.02 (s, 1H), 9.86 (s, 1H), 9.54 (s, 1H), 8.38 (d, J=7.70 Hz, 1H), 7.93 (s, 1H), 7.64-7.80 (m, 2H), 7.48 (d, J=8.79 Hz, 2H), 7.35 (d, J=8.79 Hz, 2H), 6.82-7.01 (m, 2H), 4.34-4.49 (m, 1H), 3.63 (s, 3H), 1.57-1.86 (m, 2H), 0.88 (t, J=7.15 Hz, 3H) ppm. Analytical HPLC RT: 4.85 min (Method C, 8 min gradient).

Example 51

(4-{(S)-2-[(E)-3-(5-chloro-2-tetrazol-1-yl-phenyl)-acryloylamino]-propionylamino}-phenyl)-acetic acid

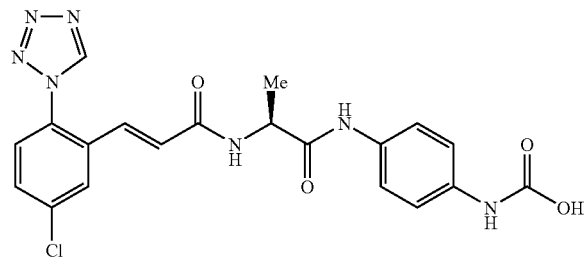 [SMILES: C[C@H](NC(=O)/C=C/c1cc(Cl)ccc1-n1cnnn1)C(=O)Nc1ccc(NC(=O)O)cc1]

51A. [4-((S)-2-tert-butoxycarbonylamino-propionylamino)-phenyl]-acetic acid ethyl ester: (S)-2-(tert-butoxycarbonylamino)propanoic acid (0.10 g, 0.53 mmol), ethyl 2-(4-aminophenyl)acetate (0.11 g, 0.63 mmol), 1-hydroxybenzotriazole hydrate (0.081 g, 0.53 mmol), EDCI (0.15 g, 0.79 mmol), and n-methylmorpholine (0.116 mL, 1.06 mmol) were added to DMF (3 mL) with stirring. After 18 h, the reaction mixture was partitioned between EtOAc (30 mL) and water/brine (1:1, 15 mL). The organic extract was washed with brine, dried over sodium sulfate, filtered, and concentrated to give 51A as yellow oil. LCMS m/z 351 [M+H]+.

Example 51: 51A was treated with 50% TFA/DCM (3 mL) for 2 h. The reaction mixture was partitioned between EtOAc (10 mL) and saturated sodium bicarbonate solution (20 mL) and stirred for 15 min. The organic layer was separated, washed with brine, dried over sodium sulfate, filtered, and concentrated. DMF (3 mL) was added to the residue with stirring followed by (E)-3-(5-chloro-2-(1H-tetrazol-1-yl)phenyl)acrylic acid (0.13 gram, 0.53 mmol), 1-hydroxybenzotriazole hydrate (0.081 g, 0.53 mmol), EDCI (0.12 g, 0.79 mmol), and N-methylmorpholine (0.12 mL, 1.06 mmol), respectively. After 20 h, the reaction mixture was partitioned between EtOAc (15 mL) and water/brine (1:1, 20 mL). The organic extract was washed with brine, dried over sodium sulfate, filtered, and concentrated. The ester was hydrolyzed by dissolution in MeOH (5 mL) and treatment with 1.0N NaOH (1.6 mL, 1.6 mmol). After 1 h, the reaction mixture was liberated of organics, diluted with H₂O (5 mL), acidified with 1.0 M HCl (2.0 mL), and extracted with EtOAc (3×5 mL). Purification by preparative reverse phase HPLC (Phenomenex Luna 10 u 21.2×100 mm; 10 min gradient; MeOH—H₂O-(0.1% TFA) afforded Example 51 (32 mg, 13% yield) as a white solid. LCMS m/z 455 [M+H]+. ¹H NMR (400 MHz, DMSO-d₆) δ: 12.24 (s, 1H), 10.06 (s, 1H), 9.85 (s, 1H), 8.47 (d, J=7.70 Hz, 1H), 7.92 (s, 1H), 7.67-7.81 (m, 2H), 7.50 (d, J=8.79 Hz, 2H), 7.16 (d, J=8.79 Hz, 2H), 6.81-6.92 (m, 2H), 4.47-4.55 (m, 1H), 3.48 (s, 2H), 1.30 (d, J=6.60 Hz, 3H) ppm. Analytical HPLC RT: 4.48 min (Method C, 8 min gradient).

Example 52

(S,E)-4-(2-(3-(5-chloro-2-(1H-tetrazol-1-yl)phenyl)acrylamido)-3-phenylpropanamido)-3-fluorobenzoic acid

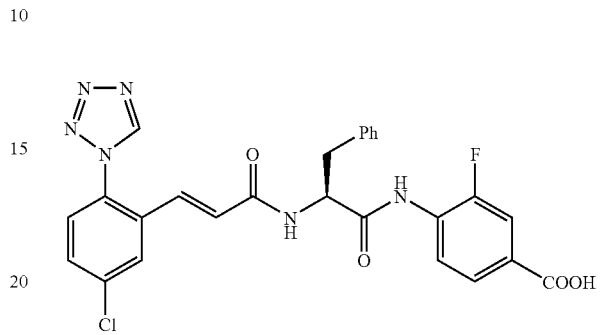

Example 52 was prepared by hydrolysis of Example 17 (0.15 g, 0.266 mmol) with LiOH (0.5 g, 20.8 mmol) in THF water (20 mL, 1:1). Purification via reverse phase HPLC and lyophilization afforded the desired product (Example 52) as a colorless solid. HPLC purity: >98%. LCMS m/z 535.4 (M+H, chlorine isotope). ¹H NMR (400 MHz, CD₃OD) δ: 9.49 (s, 1H), 8.86 (bd, 1H), 8.13-8.04 (m, 2H), 7.96 (d, J=1.8 Hz, 1H), 7.80 (dd, J=1.0 & 8.6 Hz, 1H), 7.73 (dd, J=1.7 & 8.4 Hz, 1H), 7.65 (dd, J=1.7 & 8.5 Hz, 1H), 7.56 (d, J=8.5 Hz, 1H), 7.28-7.07 (m, 4H), 7.11 (d, J=15.6 Hz, 1H), 6.77 (d, J=15.6 Hz, 1H), 5.00 (t, 1H), 3.20 (m, 1H+ TEA), 3.10 (m, 1H), 1.33 (t (TEA salt) ppm. Analytical HPLC RT: 5.90 min (Method C, 8 min gradient).

Example 53

(E)-3-(5-chloro-2-tetrazol-1-yl-phenyl)-N—[(S)-2-phenyl-1-(1,2,3,4-tetrahydro-isoquinolin-6-ylcarbamoyl)-ethyl]-acrylamide

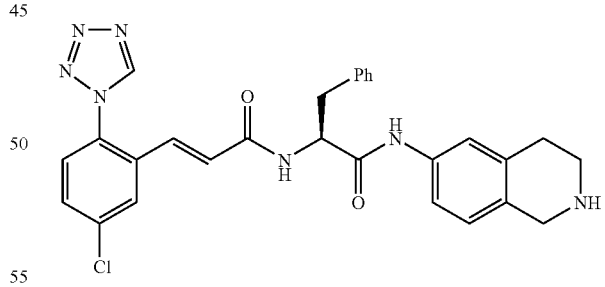

53A. 6-((S)-2-benzyloxycarbonylamino-3-phenyl-propionylamino)-3,4-dihydro-1H-isoquinoline-2-carboxylic acid tert-butyl ester: To tert-butyl 6-amino-3,4-dihydroisoquinoline-2(1H)-carboxylate (0.2 g, 0.805 mmol), CBz-phenylalanine (0.241 g, 0.805 mmol), PyBOP (0.419 g, 0.805 mmol) and THF (8 mL) was added Hunig'sBase (0.141 mL, 0.805 mmol). After 2 h, the reaction mixture was concentrated. The reaction was quenched with water (10 mL). The reaction product was extracted with ethyl acetate (3×20 mL). The combined organic layers were washed with water (10 mL), brine (10 mL) and dried (MgSO₄). Purification by silica gel chromatography using DCM/0-10% MeOH as eluents afforded 0.6 g of 53A. LCMS m/z 530.4 (M+H).+

53B. 6-((S)-2-amino-3-phenyl-propionylamino)-3,4-dihydro-1H-isoquinoline-2-carboxylic acid tert-butyl ester: 53A was hydrogenated with 10% Pd/C in ethanol (20 mL) at 50 psi. After 3 h, the reaction product was filtered through Celite® and the filtrate was concentrated to afford 0.45 g (14.1% yield) foam. LCMS m/z (M−H) 394.4 [M+H]+.

53C. 6-{(S)-2-[(E)-3-(5-chloro-2-tetrazol-1-yl-phenyl)-acryloylamino]-3-phenyl-propionylamino}-3,4-dihydro-1H-isoquinoline-2-carboxylic acid tert-butyl ester: To 53B (0.21 g, 0.531 mmol) was added (E)-3-(5-chloro-2-tetrazol-1-yl-phenyl)-acrylic acid (0.133 g, 0.531 mmol), PyBOP (0.276 g, 0.531 mmol) in THF (5 mL), Hunig'sBase (0.139 ml, 0.796 mmol). After 24 h, the reaction was quenched with water (15 mL) and the reaction product was extracted with ethyl acetate (3×30 mL). The combined organic layers were washed with water (10 mL), brine (10 mL) and dried (MgSO4) to afford 53C. LCMS m/z 628.4 [M+H]+.

Example 53: 53C was placed in DCM (6 mL) and TFA (2 mL) was added. After 24 h, the reaction mixture was concentrated and purified by reverse phase HPLC and freeze-dried to afford Example 53 (41 mg, 14.4% yield). LCMS m/z 528.3 [M+H]+. 1H NMR (400 MHz, CD3OD) δ: 9.49 (s, 1H), 7.95 (d, J=2.27 Hz, 1H), 7.59-7.69 (m, 1H), 7.55 (d, J=8.3 Hz, 1H), 7.44 (s, 1H), 7.30 (d, J=2.02 Hz, 1H), 7.24-7.29 (m, 4H), 7.17-7.22 (m, 1H), 7.13 (d, J=8.59 Hz, 1H), 7.08 (d, J=15.41 Hz, 1H), 6.75 (d, J=15.41 Hz, 1H), 4.73-4.79 (m, 1H), 4.29 (s, 2H), 3.48 (t, J=6.32 Hz, 2H), 3.16 (dd, J=7.07 Hz, 1H), 2.98-3.11 (m, 3H) ppm. Analytical HPLC RT: 4.14 min (Method C, 8 min gradient).

Example 54

6-{(S)-2-[(E)-3-(5-chloro-2-tetrazol-1-yl-phenyl)-acryloylamino]-3-phenyl-propionylamino}-3,4-dihydro-1H-isoquinoline-2-carboxylic acid methyl ester

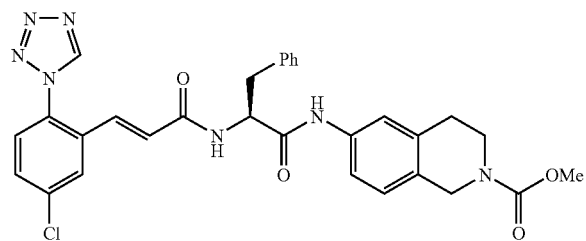 [SMILES: COC(=O)N1CCc2cc(NC(=O)[C@H](Cc3ccccc3)NC(=O)/C=C/c3cc(Cl)ccc3-n3cnnn3)ccc2C1]

To the solution of Example 53 (10 mg, 0.016 mmol) in DCM (2 mL) and pyridine (0.3 mL) was added methyl chloroformate (1.689 μL, 0.022 mmol). After 2 h, the reaction was quenched with water (10 mL). The reaction product was extracted with DCM (3×20 mL). The combined organic layers were washed with brine (10 mL) and dried (MgSO4). Purified by reverse phase HPLC and freeze-drying afforded the title compound (7 mg, 77%) as a white solid. LCMS m/z 586.4 [M+H]+. 1H NMR (400 MHz, CD3OD) δ: 9.51 (s, 1H), 7.96 (d, J=2.27 Hz, 1H), 7.62-7.68 (m, 1H), 7.57 (d, 1H), 7.18-7.33 (m, 7H), 7.09 (d, 1H), 7.04-7.08 (m, 1H), 6.77 (d, J=15.66 Hz, 1H), 4.81 (t, J=7.45 Hz, 1H), 4.56 (s, 2H), 3.74 (s, 3H), 3.66 (t, J=5.94 Hz, 2H), 3.14-3.22 (m, 1H), 3.05 (dd, J=13.52, 7.96 Hz, 1H), 2.81 (t, J=5.94 Hz, 2H) ppm. Analytical HPLC RT: 6.21 min (Method C, 8 min gradient).

Example 55

(E)-N—[(S)-1-(3-amino-1H-indazol-6-ylcarbamoyl)-2-phenyl-ethyl]-3-(5-chloro-2-tetrazol-1-yl-phenyl)-acrylamide

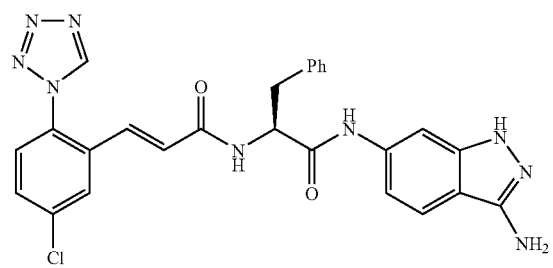 [SMILES: Nc1n[nH]c2cc(NC(=O)[C@H](Cc3ccccc3)NC(=O)/C=C/c3cc(Cl)ccc3-n3cnnn3)ccc12]

55A. 4-amino-2-fluoro-benzonitrile: To 2-fluoro-4-nitrobenzonitrile (8.5 g, 51.2 mmol) was added 10% palladium on carbon (0.5 g) and EtOAc (42.5 mL) and EtOH (170 mL) and the reaction was hydrogenated at 50 psi for 1 h. The reaction was filtered through Celite® and the reaction mixture was concentrated to afford 6.7 g (96% yield) as a light brown solid. LCMS m/z 135.1 [M+H]+.

55B. [(S)-1-(4-cyano-3-fluoro-phenylcarbamoyl)-2-phenyl-ethyl]-carbamic acid tert-butyl ester: To 55A (1.9 g, 13.96 mmol) was added (S)-2-(tert-butoxycarbonylamino)-3-phenylpropanoic acid (3.70 g, 13.96 mmol) in DCM (20 mL) and pyridine (16 mL). The solution was cooled in an ice/acetone bath and added phosphorous oxychloride (1.301 mL, 13.96 mmol). After 2 h, the dark reaction was quenched with 0.1N HCl (20 mL) and water (30 mL). The reaction mixture was extracted with DCM (50 mL). The layers did not separate. CHCl3 (75 mL)/water (50 mL) was added. The combined organic layers were washed with sat'd NaHCO3 (20 mL), brine (20 mL) and dried (MgSO4). Purification by silica gel chromatography using hexanes/ethyl acetate as eluents afforded 55B (1 g, 18% yield) as a tan solid. LCMS m/z 384.3 [M+H]+.

55C. [(S)-1-(3-amino-1H-indazol-6-ylcarbamoyl)-2-phenyl-ethyl]-carbamic acid tert-butyl ester: To 55B (0.5 g, 1.304 mmol) was added EtOH (10 mL) and hydrazine hydrate (0.511 mL, 10.43 mmol). The mixture was heated to 160° C. for 11 min in a microwave. An additional 0.2 mL hydrazine was added and the reaction was reheated for 7 min to completion. The insoluble material was removed by filtration. The filtrate was concentrated. The reaction was then quenched with water (15 mL) and ethyl acetate (40 mL). The organic layer was washed with brine (10 mL) and dried (MgSO4). Filtration and concentration afforded 55C (0.38 g, 66% yield) as a tan solid. LCMS m/z 396.3 [M+H]+.

55D. (S)-2-amino-N-(3-amino-1H-indazol-6-yl)-3-phenyl-propionamide bis TFA salt: 55C was treated with DCM (10.00 mL) and TFA (2 mL). After 1 h, the reaction was concentrated to afford 0.8 g of dark oil. LCMS m/z 296.3 [M+H]+.

55E. (E)-3-(5-chloro-2-tetrazol-1-yl-phenyl)-acrylic acid 2,5-dioxo-pyrrolidin-1-yl ester: To a solution of (E)-3-(5-chloro-2-tetrazol-1-yl-phenyl)-acrylic acid (2 g, 7.98 mmol) in THF (40 mL) and DMF (4.00 mL) was added 1-hydroxypyrrolidine-2,5-dione (1.010 g, 8.78 mmol) and diisopropylcarbodiimide (1.368 mL, 8.78 mmol). After 24 h, a white precipitate was collected and washed with methanol and water. The solid was dried on vacuum to afford 55E (1.8 g, 64% yield) as a white solid. LCMS m/z 348.2 [M+H]⁺.

Example 55: To 55 D (0.5 g, 0.301 mmol) and 55E (0.125 g, 0.361 mmol) in DMF (4 mL) was added Hunig'sBase (0.315 mL, 1.803 mmol). After 24 h, the reaction was quenched with water (15 mL) and ethyl acetate (40 mL). The organic layer was washed with water (10 mL), brine (10 mL) and dried (MgSO₄). Purification by reverse phase HPLC and freeze-drying afforded Example 55 (91 mg, 47.2% yield) as a tan solid. LCMS m/z 528.3 [M+H]⁺. ¹H NMR (400 MHz, CD₃OD) δ: 9.40 (s, 1H), 7.87 (d, J=2.27 Hz, 2H), 7.68 (d, J=8.84 Hz, 1H), 7.53-7.60 (m, 1H), 7.46 (d, J=8.5 Hz, 1H), 7.07-7.22 (m, 5H), 6.99 (d, J=15.66 Hz, 1H), 6.95 (dd, J=8.84, 1.52 Hz, 1H), 6.66 (d, J=15.41 Hz, 1H), 4.65-4.75 (m, 1H), 3.10 (dd, J=13.77, 7.20 Hz, 1H), 2.97 (dd, J=13.64, 8.08 Hz, 1H) ppm. Analytical HPLC RT: 4.45 min (Method C, 8 min gradient).

Example 56

4-{(S)-2-[2-(5-chloro-2-tetrazol-1-yl-benzenesulfinyl)-acetylamino]-3-phenyl-propionylamino}-benzoic acid

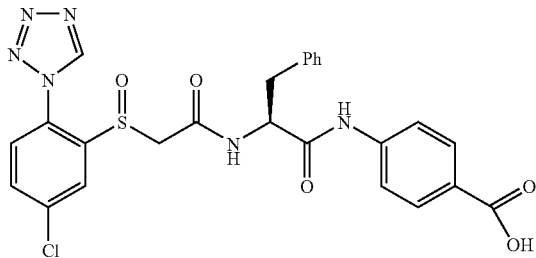 [SMILES: O=C(CS(=O)c1cc(Cl)ccc1-n1cnnn1)N[C@@H](Cc1ccccc1)C(=O)Nc1ccc(C(=O)O)cc1]

56A. 1-(4-chloro-2-iodo-phenyl)-1H-tetrazole: To a 1000 mL 3N flask equipped with a thermometer was added 4-chloro-2-iodoaniline (20 g, 79 mmol) and acetic acid (300 mL) and the mixture was cooled in an ice water bath. Trimethyl orthoformate (26.2 mL, 237 mmol) was added and the reaction was stirred 15 min. Portion-wise, sodium azide (15.90 g, 245 mmol) was added and the resultant thick grey slurry was stirred at rt for 24 h. The reaction was quenched with 800 mL water and stirred 1 h. A grey solid was filtered off and dried under a stream of argon to afford 56A (22.28 g, 92% yield). ¹H NMR (400 MHz, CDCl₃) δ: 7.43 (d, J=8.59 Hz, 1H), 7.58 (dd, J=8.46, 2.15 Hz, 1H), 8.04 (d, J=2.27 Hz, 1H), 8.99 (s, 1H) ppm.

56B. methyl 2-(trimethylstannylthio)acetate: (Dickens et. al, Tet. 1991, 47 (40), 8621) To methyl thioglycolate (1.609 mL, 17.89 mmol) and TEA (2.77 ml, 19.87 mmol) in CCl₄ (100 mL) was added a solution of trimethyltin chloride (3.3 g, 16.56 mmol) in CCl₄ (8 mL). A thick white suspension was stirred for 2 h. The solid was filtered through Celite® and the filtrate was washed (1×) 5% AcOH, (1×) H₂O, (1×) brine, dried (MgSO₄), filtered, and concentrated to afford 4.5 g of 56B as a clear oil that was carried directly on to subsequent steps without purification.

56C. (5-chloro-2-tetrazol-1-yl-phenylsulfanyl)-acetic acid methyl ester: To 56B (1.062 g, 3.95 mmol) was add a solution of 56A (1.1 g, 3.59 mmol) with toluene (15 mL). The mixture was degassed for 10 min. Tetrakis(triphenylphosphine)palladium(0) (0.207 g, 0.179 mmol) was added and the reaction was heated to 110° C. for 24 h. The reaction was cooled and quenched with 10% aq.KF solution. The reaction product was extracted (3×) Et₂O, washed (1×) 10% aq KF, (1×) brine and dried (MgSO₄). Purification by silica gel chromatography using hexanes/ethyl acetate as eluents afforded 56C (0.4 g, 47% with recovered starting material) as a reddish-brown oil. LCMS m/z 285.2 [M+H]⁺. ¹H NMR (400 MHz, CDCl₃) δ: 9.14 (s, 1H), 7.68 (s, 1H), 7.38-7.51 (m, 2H), 3.71 (s, 3H), 3.61 (s, 2H) ppm.

56D. (5-chloro-2-tetrazol-1-yl-benzenesulfinyl)-acetic acid methyl ester: To 56C (0.12 g, 0.421 mmol) was added DCM (10 mL) and mCPBA (0.104 g, 0.421 mmol). After 24 h, the reaction was quenched with sat'd NaHCO₃. The reaction mixture was extracted with DCM (3×20 mL). The combined organic layers were washed with brine and dried (MgSO₄). Purification by silica gel chromatography using DCM/0-10% MeOH as eluents afforded 56D (76 mg, 60% yield) as an oil. LCMS m/z 301.1 [M+H]⁺.

56E. (5-chloro-2-tetrazol-1-yl-benzenesulfinyl)-acetic acid: To 56D (76 mg, 0.253 mmol) in THF (3 mL)/water (3.00 ml) was added LiOH hydrate (10.61 mg, 0.253 mmol). After 1.5 h, the reaction was quenched with 1N HCl (10 mL) and ethyl acetate (30 mL). The organic layer was washed with brine (10 mL) and dried (MgSO₄) and concentrated to afford 56E (72 mg, 100% yield) as a solid; LCMS m/z 287.17 [M+H]⁺.

Example 56: To 56E was added 4-((S)-2-amino-3-phenyl-propionylamino)-benzoic acid tert-butyl ester (86 mg, 0.253 mmol), PyBOP (132 mg, 0.253 mmol), THF (4 mL) and Hunig'sBase (0.044 mL, 0.253 mmol) and the reaction was stirred 24 h. The reaction was quenched with water (10 mL). The reaction mixture extracted with ethyl acetate (3×20 mL). The combined organic layers were washed with water (10 mL), brine (10 mL) and dried (MgSO₄). Purification by silica gel chromatography using DCM/0-10% MeOH as eluents afforded 4-{(S)-2-[2-(5-chloro-2-tetrazol-1-yl-benzenesulfinyl)-acetylamino]-3-phenyl-propionylamino}-benzoic acid tert-butyl ester as a dark oil (LCMS: m/z (M+H)⁺ 609.3), which was directly deprotected with DCM (5 mL)/TFA (2 mL) for 24 h. The reaction was concentrated and purified (2×) by reverse phase HPLC and freeze-dried to afford Example 56 (4 mg, 2.7% yield) as a white solid. LCMS m/z 553.3 [M+H]⁺. ¹H NMR (400 MHz, CD₃OD) δ: 9.70-9.86 (m, 1H), 7.92-8.04 (m, 2H), 7.77-7.88 (m, 2H), 7.71-7.76 (m, 1H), 7.62-7.70 (m, 1H), 7.25-7.31 (m, 5H), 7.16-7.22 (m, 1H), 4.72-4.79 (m, 1H), 4.19-4.32 (m, 1H), 3.82-4.00 (m, 1H), 3.21-3.27 (m, 1H), 2.97-3.08 (m, 1H) ppm. Analytical HPLC RT: 1.09 min (Method A, 2 min gradient).

Example 57

(E)-3-(3-chloro-2,6-difluoro-phenyl)-N—[(S)-1-(1H-indazol-6-ylcarbamoyl)-2-phenyl-ethyl]-acrylamide

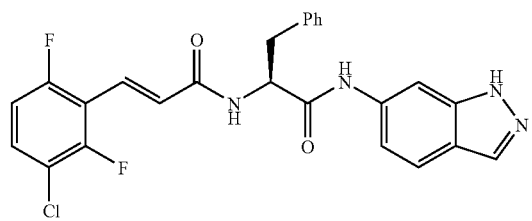 [SMILES: O=C(/C=C/c1c(F)ccc(Cl)c1F)N[C@@H](Cc1ccccc1)C(=O)Nc1ccc2cn[nH]c2c1]

57A. (E)-3-(3-chloro-2,6-difluoro-phenyl)-acrylic acid tert-butyl ester: To 3-chloro-2,6-difluorobenzaldehyde (5 g, 28.3 mmol) was added tert-butyl 2-(dimethoxyphosphoryl) acetate (5.62 mL, 28.3 mmol), THF (25 mL) and potassium carbonate (11.74 g, 85 mmol). The yellow suspension was stirred 72 h. The reaction was quenched with water (30 mL). The reaction product was extracted with ethyl acetate (3×500 mL). The combined organic layers were washed with brine (20 mL) and dried (Na$_2$SO$_4$). Filtration and concentration afforded 57A (97.9 g, 100% yield) as a yellow solid. LCMS m/z 219 (M+H-t-butyl).+ $^1$H NMR (400 MHz, CDCl$_3$) δ: 7.63 (d, J=16.42 Hz, 1H), 7.30-7.40 (m, 1H), 6.85-6.96 (m, 1H), 6.68 (d, J=16.42 Hz, 1H), 1.54 (s, 9H) ppm.

57B. (E)-3-(3-chloro-2,6-difluoro-phenyl)-acrylic acid: To 57A (7.9 g, 28.8 mmol) was added DCM (50 mL) and TFA (10 mL). After 2 h, the reaction mixture was concentrated to afford 57B (6.5 g, 103%) as a solid. LCMS m/z 219.1 [M+H]$^+$. $^1$H NMR (400 MHz, DMSO-d$_6$) δ: 67.67-7.78 (m, 1H), 7.50 (d, J=16.42 Hz, 1H), 7.24-7.33 (m, 1H), p. 59 (d, J=16.42 Hz, 1H) ppm.

57C. [(S)-1-(1H-indazol-6-ylcarbamoyl)-2-phenyl-ethyl]-carbamic acid tert-butyl ester: To 1H-indazol-6-amine (0.5 g, 3.76 mmol) and (S)-2-(tert-butoxycarbonylamino)-3-phenyl-propanoic acid (0.996 g, 3.76 mmol) in pyridine (5 mL) cooled in ice/acetone bath was added POCl$_3$ (0.350 mL, 3.76 mmol). After 1 h, the reaction was quenched with water (15 mL), and dilute 0.1N HCl (15 mL) was added and extracted with ethyl acetate (3×20 mL). The combined organic layers were washed with sat'd NaHCO$_3$ (20 mL), brine (20 mL) and dried (MgSO$_4$). Filtration and concentration afforded 57C (1.1 g, 79%) as a foam. LCMS m/z 381.3 [M+H]$^+$.

57D. (S)-2-amino-N-(1H-indazol-6-yl)-3-phenyl-propionamide: 57C (1.1 g, 2.89 mmol) was treated with DCM (20 mL) and TFA (4 mL). After 1 h, the reaction was concentrated to afford 57D (0.75 g, 93% yield) as a brown solid. LCMS: m/z 281.3 [M+H]$^+$.

Example 57: To 57B (0.055 g, 0.254 mmol), 57D (0.1 g, 0.254 mmol), PyBOP (0.132 g, 0.254 mmol) and THF (4 mL) was added Hunig'sBase (0.177 mL, 1.014 mmol). After 24 h, the reaction was quenched with water (10 mL). The reaction product was extracted with ethyl acetate (3×20 mL). The combined organic layers were washed with water (10 mL), brine (10 mL) and dried (MgSO$_4$). Purification by reverse phase HPLC and freeze-drying afforded Example 57 (32 mg, 26% yield) as a white solid. LCMS m/z 481.2 [M+H]$^+$. $^1$H NMR (400 MHz, CD$_3$OD) δ: 8.05-8.12 (m, 1H), 8.00 (s, 1H), 7.68 (d, J=9.35 Hz, 1H), 7.60 (d, J=16.17 Hz, 1H), 7.49-7.55 (m, 1H), 7.26-7.37 (m, 4H), 7.20-7.26 (m, 1H), 7.05-7.14 (m, 2H), 7.03 (d, 1H), 4.91-4.98 (m, 1H), 3.26 (dd, J=13.64, 6.82 Hz, 1H), 3.11 (dd, J=13.64, 8.08 Hz, 1H) ppm. Analytical HPLC RT: 1.92 min (Method A, 2 min gradient).

Example 58

(E)-3-(5-chloro-2-tetrazol-1-yl-phenyl)-N—[(S)-1-(1H-indazol-6-ylcarbamoyl)-2-phenyl-ethyl]-acrylamide

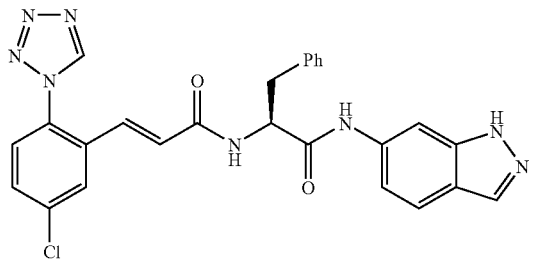 [SMILES: O=C(/C=C/c1cc(Cl)ccc1-n1cnnn1)N[C@@H](Cc1ccccc1)C(=O)Nc1ccc2cn[nH]c2c1]

Example 58 was prepared from 1H-indazol-6-amine as described in previously for Example 3 (17 mg, 8.7% yield) as a white solid. LCMS m/z 513.2 [M+H]$^+$. $^1$H NMR (400 MHz, CD$_3$OD) δ: 9.49 (s, 1H), 8.02 (s, 1H), 7.89-8.01 (m, 2H), 7.60-7.69 (m, 2H), 7.55 (d, J=8.25 Hz, 1H), 7.22-7.32 (m, 4H), 7.15-7.22 (m, 1H), 7.09 (d, J=15.39 Hz, 1H), 7.00 (d, J=6.60 Hz, 1H), 6.77 (d, J=15.94 Hz, 1H), 4.83-4.90 (m, 1H), 3.19-3.26 (m, 1H), 3.06 (dd, J=13.47, 7.97 Hz, 1H) ppm. Analytical HPLC RT: 5.57 min (Method C, 8 min gradient).

Example 59

(E)-N—[(S)-1-(3H-benzoimidazol-5-ylcarbamoyl)-2-phenyl-ethyl]-3-(5-chloro-2-tetrazol-1-yl-phenyl)-acrylamide

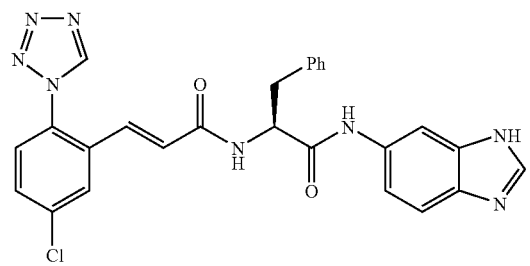 [SMILES: O=C(/C=C/c1cc(Cl)ccc1-n1cnnn1)N[C@@H](Cc1ccccc1)C(=O)Nc1ccc2nc[nH]c2c1]

59A. [(S)-1-(1H-benzoimidazol-5-ylcarbamoyl)-2-phenyl-ethyl]-carbamic acid tert-butyl ester: To 6-nitro-1H-benzo[d]imidazole (0.2 g, 1.226 mmol) was added ethanol (20 mL), conc. HCl (0.5 mL), 10% Pd/C (50 mg). The mixture was hydrogenated at 50 psi. After 1 h, the reaction mixture was filtered through Celite® and concentrated to afford 59A (0.133 g, 64% yield) as a tan solid. LCMS m/z 134.0 [M+H]$^+$.

59B. (S)-2-amino-N-(1H-benzoimidazol-5-yl)-3-phenyl-propionamide: To 59A was added PyBOP (0.412 g, 0.792 mmol), (S)-2-(tert-butoxycarbonylamino)-3-phenylpropanoic acid (0.210 g, 0.792 mmol), THF (5 mL) and Hunig'sBase (0.414 mL, 2.37 mmol). After 24 h, the reaction was quenched with water (10 mL). The reaction mixture was extracted with ethyl acetate (3×25 mL). The combined organic layers were washed with water (10 mL), brine (10 mL) and dried (MgSO$_4$). Filtration and concentration afforded 0.6 g crude oil. LCMS m/z 381.3 [M+H]$^+$. Deprotection with TFA (3 mL) in DCM (6 mL) was complete in 1 h. The reaction product was concentrated to afford 59B (0.45 g) as a dark oil. LCMS: m/z (M+H)$^+$ 281.2. 59B was used in the next step without purification.

Example 59: To crude 59B (0.156 g, 0.556 mmol), (E)-3-(5-chloro-2-tetrazol-1-yl-phenyl)-acrylic acid (0.139 g, 0.556 mmol), PyBOP (0.290 g, 0.556 mmol), THF (7 mL) was added Hunig'sBase (0.486 mL, 2.78 mmol). After 24 h, the reaction was quenched with water (10 mL) and EtOAc (30 mL). The organic layer was washed with water (10 mL), brine (10 mL) and dried (MgSO$_4$). Purification by reverse phase HPLC, then by silica gel chromatography using DCM/0-10% MeOH as eluents and freeze-drying afforded Example 59 (49 mg, 16.8% yield) as a white solid. LCMS m/z 513 [M+H]$^+$. $^1$H NMR (400 MHz, CD$_3$OD) δ: 9.49 (s, 1H), 8.18 (s, 1H), 7.95 (d, 2H), 7.64 (dd, J=8.24, 2.20 Hz, 1H), 7.53 (dd, J=13.74, 8.79 Hz, 2H), 7.22-7.36 (m, 4H), 7.14-7.25 (m, 2H), 7.09 (d, J=15.94 Hz, 1H), 6.77 (d, J=15.39 Hz, 1H), 4.77-4.83 (m, 1H), 3.20 (dd, J=13.74, 7.15 Hz, 1H), 3.06 (dd, J=13.47, 7.97 Hz, 1H) ppm. Analytical HPLC RT: 4.10 min (Method C, 8 min gradient).

Example 60

(E)-3-(5-chloro-2-tetrazol-1-yl-phenyl)-N—[(S)-1-(1H-indol-6-ylcarbamoyl)-2-phenyl-ethyl]-acrylamide

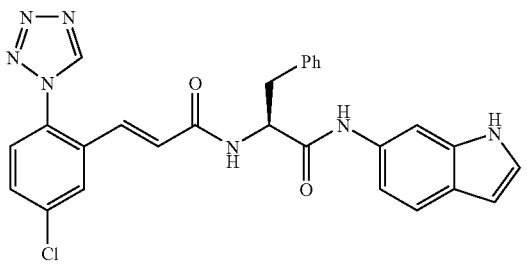 [SMILES: O=C(/C=C/c1cc(Cl)ccc1-n1cnnn1)N[C@@H](Cc1ccccc1)C(=O)Nc1ccc2cc[nH]c2c1]

60A. (S)-2-amino-N-(1H-indol-6-yl)-3-phenyl-propionamide, bis-TFA Salt: The title compound was prepared from 1H-indol-6-amine in a similar manner as previously described for Example 3 as a dark oil. LCMS: m/z (M+H)$^+$ 280.4.

Example 60: To 60A (0.17 g, 0.335 mmol) in THF (5 mL) was added (E)-3-(5-chloro-2-tetrazol-1-yl-phenyl)-acrylic acid 2,5-dioxo-pyrrolidin-1-yl ester (0.117 g, 0.335 mmol) and Hunig'sBase (0.410 mL, 2.345 mmol). After 24 h, the reaction was quenched with water (10 mL) and ethyl acetate (30 mL). The organic layer was washed with water (10 mL), brine (10 mL) and dried (MgSO$_4$). Purification by reverse phase HPLC (2×) and freeze-drying afforded Example 60 (4 mg, 1.9%) as an off-white solid. LCMS m/z 512.3 [M+H]$^+$. $^1$H NMR (400 MHz, CD$_3$OD) δ: 9.69 (s, 1H), 9.40 (s, 1H), 8.45 (d, J=7.83 Hz, 1H), 7.88 (d, J=2.27 Hz, 1H), 7.60 (s, 1H), 7.55 (m, 1H), 7.46 (d, J=8.59 Hz, 1H), 7.33 (d, J=8.34 Hz, 1H), 7.17-7.22 (m, 3H), 7.12 (dd, J=5.94, 2.65 Hz, 1H), 7.08 (d, J=3.28 Hz, 1H), 7.00 (d, J=15.66 Hz, 1H), 6.79 (m, 1H), 6.68 (d, J=15.66 Hz, 1H), 6.28 (d, J=2.27 Hz, 1H), 4.68-4.76 (m, 1H), 3.07-3.15 (m, 1H), 2.96 (dd, J=13.52, 7.71 Hz, 1H) ppm. Analytical HPLC RT: 5.40 min (Method C, 8 min gradient).

Example 61

2-{(S)-2-[(E)-3-(5-chloro-2-tetrazol-1-yl-phenyl)-acryloylamino]-3-phenyl-propionyl}-1,2,3,4-tetrahydro-isoquinoline-5-carboxylic acid

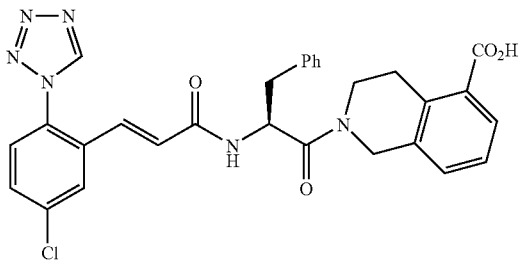 [SMILES: O=C(/C=C/c1cc(Cl)ccc1-n1cnnn1)N[C@@H](Cc1ccccc1)C(=O)N1CCc2c(cccc2C(=O)O)C1]

61A. 2-((S)-2-amino-3-phenyl-propionyl)-1,2,3,4-tetrahydro-isoquinoline-5-carboxylic acid methyl ester TFA salt: The title compound was prepared in a similar manner as previously described for Example 52 using methyl 1,2,3,4-tetrahydroisoquinoline-5-carboxylate, HCl (0.086 g, 0.377 mmol), and (S)-2-(tert-butoxycarbonylamino)-3-phenylpropanoic acid (0.1 g, 0.377 mmol), followed by TFA deprotection to afford 0.49 g crude light brown oil. LCMS m/z 339.4 [M+H]$^+$.

61B. 2-{(S)-2-[(E)-3-(5-chloro-2-tetrazol-1-yl-phenyl)-acryloylamino]-3-phenyl-propionyl}-1,2,3,4-tetrahydro-isoquinoline-5-carboxylic acid methyl ester: To 61A (0.17 g, 0.376 mmol), (E)-3-(5-chloro-2-tetrazol-1-yl-phenyl)-acrylic acid (0.094 g, 0.376 mmol), PyBOP (0.196 g, 0.376 mmol), in THF (7 mL) was added Hunig'sBase (0.197 mL, 1.127 mmol). After 24 h, the reaction was partitioned with EtOAc (40 mL) and water (15 mL) and the layers were separated. The organic layer was washed with water (10 mL), brine (10 mL) and dried (MgSO$_4$). Purification by reverse phase HPLC and silica gel chromatography using DCM/O-10% MeOH as eluents and freeze-drying afforded 61B (54 mg, 23.4% yield) as a white solid. LCMS m/z 571.3 [M+H]$^+$. $^1$H NMR (400 MHz, CD$_3$OD) δ: 9.50 (s, 1H), 7.92-8.01 (m, 1H), 7.70-7.81 (m, J=18.14 Hz, 1H), 7.65 (dd, J=8.25, 2.20 Hz, 1H), 7.56 (d, J=8.79 Hz, 1H), 7.02-7.38 (m, 6H), 6.85-6.96 (m, 1H), 6.72 (d, 1H), 6.74 (d, 1H), 5.11-5.30 (m, 1H), 4.59-4.73 (m, 2H), 4.29 (d, J=15.94 Hz, 1H), 3.82-3.90 (m, 3H), 3.59-3.72 (m, 1H), 3.32-3.52 (m, 2H), 2.94-3.17 (m, 2 H) ppm.

Example 61: To 61B (17 mg, 3.03 mmol) in water (1 mL) and THF (0.5 mL) was added lithium hydroxide (3.56 mg, 0.149 mmol). After 1 h, an additional 10 mg lithium hydroxide was added to complete the reaction. After 1 h, the reaction was acidified with 1N HCl. The reaction mixture was concentrated. Purification by reverse phase HPLC and freeze-drying afforded 3 mg (17.7%) of Example 61 as a white solid. LCMS m/z 557 [M+H]$^+$. $^1$H NMR (400 MHz, CD$_3$OD) δ: 9.52 (s, 1H), 7.98 (dd, J=5.81, 2.27 Hz, 1H), 7.82 (m, 1H), 7.63-7.74 (m, 1H), 7.53-7.61 (m, 1H), 7.25-7.41 (m, 1H), 7.03-7.22 (m, 7H), 6.71-6.82 (m, 1H), 5.16-5.29 (m, 1H), 4.53-4.81 (m, 2H), 3.35-3.88 (m, 4H), 3.10-3.20 (m, 1H), 2.99-3.09 (m, 1H) ppm. Analytical HPLC RT: 5.90 min (Method C, 8 min gradient).

Example 62

(2-{(S)-2-[(E)-3-(5-chloro-2-tetrazol-1-yl-phenyl)-acryloylamino]-3-phenyl-propionyl}-1,2,3,4-tetrahydro-isoquinolin-5-yl)-carbamic acid methyl ester

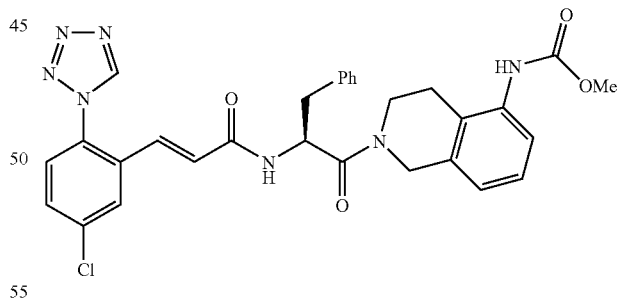

62A. [2-((S)-2-Amino-3-phenyl-propionyl)-1,2,3,4-tetrahydro-isoquinolin-5-yl]-carbamic acid methyl ester TFA Salt: To 1,2,3,4-tetrahydroisoquinolin-5-amine (0.056 g, 0.377 mmol), (S)-2-(tert-butoxycarbonylamino)-3-phenylpropanoic acid (0.1 g, 0.377 mmol), PyBOP (0.196 g, 0.377 mmol) in THF (5 mL) was added Hunig'sBase (0.132 mL, 0.754 mmol). After 1.5 h, the reaction was concentrated and then partitioned with EtOAc (30 mL) and water (15 mL). The layers were separated and organic layer was washed with water (10 mL), brine (10 mL) and dried (MgSO$_4$). 0.26 g of the aniline crude tan foam was collected. LCMS m/z 396.3 [M+H]$^+$. To the crude aniline was added DCM (5.00 mL), pyridine (2 mL) and methyl chloroformate (0.2 mL, 2.58 mmol). After 24 h, the reaction was quenched with water (10 mL). The reaction mixture extracted with ethyl acetate (3×25 mL). The combined organic layers were washed with water (10 mL), brine (10 mL) and dried (MgSO$_4$). 0.28 g of the carbamate brown foam was collected. LCMS: m/z (M+H)$^+$ 454.3. To the Boc intermediate was added DCM (5.00 mL) and TFA (2 mL). After 1 h, the reaction was concentrated to afford 0.31 g of 62A as a dark oil. LCMS m/z 354.3 [M+H]$^+$.

Example 62: 62A (0.17 g, 0.49 mmol) was coupled with (E)-3-(5-chloro-2-tetrazol-1-yl-phenyl)-acrylic acid (0.125 g, 0.49 mmol) in a manner similar to Example 61 and purified by HPLC and freeze-dried to afford Example 62 (89 mg, 29.3% yield) as a white solid. LCMS m/z 586.3 [M+H]$^+$. $^1$H NMR (400 MHz, DMSO-d$_6$) δ: 9.84 (s, 1H), 8.87 (s, 1H), 7.93 (s, 1H), 7.68-7.77 (m, 2H), 7.09-7.32 (m, 7H), 6.83 (s, 2H), 5.02-5.17 (m, 1H), 4.63-4.78 (m, 1H), 4.38-4.56 (m, 1H), 3.40-3.81 (m, 5H), 2.97-3.06 (m, 1H), 2.87 (m, 1H), 2.56-2.71 (m, 2H) ppm. Analytical HPLC RT: 5.90 min (Method C, 8 min gradient).

Example 63

(E)-3-(5-chloro-2-tetrazol-1-yl-phenyl)-N—[(S)-1-(1-oxo-1,2,3,4-tetrahydro-isoquinolin-7-ylcarbamoyl)-2-phenyl-ethyl]-acrylamide

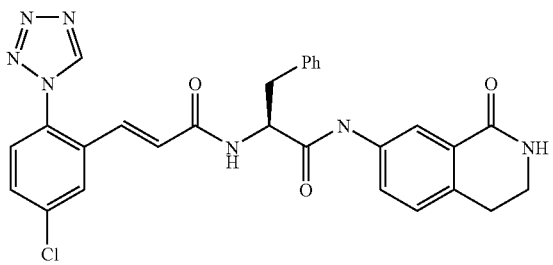 [SMILES: O=C(/C=C/c1cc(Cl)ccc1-n1cnnn1)N[C@@H](Cc1ccccc1)C(=O)Nc1ccc2c(c1)C(=O)NCC2]

63A. [(S)-1-(1-oxo-1,2,3,4-tetrahydro-isoquinolin-7-yl-carbamoyl)-2-phenyl-ethyl]-carbamic acid tert-butyl ester: To a solution of 7-amino-3,4-dihydroisoquinolin-1(2H)-one (0.1 g, 0.617 mmol), (S)-2-(tert-butoxycarbonylamino)-3-phenylpropanoic acid (0.164 g, 0.617 mmol) in pyridine (3 mL) cooled in ice/acetone bath, was added POCl$_3$ (0.057 mL, 0.617 mmol). After 1 h, the deep red reaction was concentrated and quenched with 0.1N HCl (10 mL) and ethyl acetate (30 mL). The organic layer was washed with sat'd NaHCO$_3$ (10 mL), brine (10 mL) and dried (MgSO$_4$). Filtration and concentration afforded 63A (0.135 g, 53%) as a yellow solid. LCMS m/z 408.2. (M−H).

63B. (S)-2-amino-N-(1-oxo-1,2,3,4-tetrahydro-isoquinolin-7-yl)-3-phenyl-propionamide, TFA Salt: To 63A (0.13 g, 0.31 mmol) in DCM (5 mL) was added TFA (2 mL). After 2 h, the reaction was partitioned with sat'd NaHCO$_3$ (20 mL) and ethyl acetate (20 mL). The layers were separated and the aqueous layer was extracted with ethyl acetate (2×20 mL). The combined organic layers were washed with brine (10 mL) and dried (MgSO$_4$) and concentrated to afford 63B (78 mg, 41% yield) as a yellow solid. LCMS m/z 310.3 [M+H]$^+$.

Example 63: 63B (78 mg, 0.252 mmol) was coupled with (E)-3-(5-chloro-2-tetrazol-1-yl-phenyl)-acrylic acid (63 mg, 0.252 mmol) in a manner similar to Example 3 and purified by HPLC and freeze-dried to afford Example 63 (26 mg, 18.9%) as a white solid. LCMS m/z 542.3 [M+H]$^+$. $^1$H NMR (400 MHz, CD$_3$OD) δ: 9.40 (s, 1H), 7.89 (dd, J=9.60, 2.27 Hz, 2H), 7.53-7.60 (m, 2H), 7.46 (d, J=8.59 Hz, 1H), 7.12-7.20 (m, 5H), 7.07-7.13 (m, 1H), 6.99 (d, J=15.66 Hz, 1H), 6.67 (d, J=15.66 Hz, 1H), 4.66-4.76 (m, 1H), 3.34-3.43 (m, 2H), 3.04-3.12 (m, 1 H), 2.95 (dd, J=13.64, 7.83 Hz, 1H), 2.84 (t, J=6.69 Hz, 2H) ppm. Analytical HPLC RT: 1.42 min (Method A, 2 min gradient).

Example 64

(E)-3-(5-chloro-2-tetrazol-1-yl-phenyl)-N—[(S)-1-(1-oxo-1,2-dihydro-isoquinolin-7-ylcarbamoyl)-2-phenyl-ethyl]-acrylamide

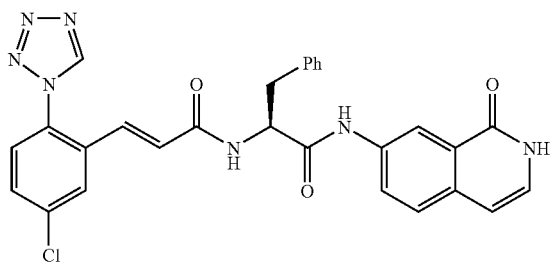 [SMILES: O=C(/C=C/c1cc(Cl)ccc1-n1cnnn1)N[C@@H](Cc1ccccc1)C(=O)Nc1ccc2cc[nH]c(=O)c2c1]

64A. [(S)-1-(1-oxo-1,2-dihydro-isoquinolin-7-ylcarbamoyl)-2-phenyl-ethyl]-carbamic acid tert-butyl ester: 7-Amino-2H-isoquinolin-1-one (75 mg, 0.468 mmol) and (S)-2-(tert-butoxycarbonylamino)-3-phenylpropanoic acid (124 mg, 0.468 mmol) were coupled as in Example 3 to afford 64A (0.18 g, 90% yield) as a yellow oil. LCMS m/z 408.3 [M+H]$^+$.

Example 64: To 64A (0.18 g, 0.44 mmol) in DCM (5 mL) was added TFA (2 mL). After 2 h, the reaction was concentrated to 0.2 g of a red oil, which was coupled with (E)-3-(5-chloro-2-tetrazol-1-yl-phenyl)-acrylic acid (0.113 g, 0.451 mmol) as previously described for Example 3. The crude product was purified by reverse phase HPLC and freeze-dried to afford Example 64 (38 mg, 15.6% yield) as a white solid. LCMS m/z 540.3 [M+H]$^+$. $^1$H NMR (400 MHz, DMSO-d$_6$) δ:), 11.10 (s, 1H), 10.37 (s, 1H), 9.78 (s, 1H), 8.54 (d, J=7.83 Hz, 1H), 8.39 (d, J=1.77 Hz, 1H), 7.88 (d, J=2.02 Hz, 1H), 7.77 (dd, J=8.72, 2.15 Hz, 1H), 7.59-7.71 (m, 2H), 7.53 (d, J=8.59 Hz, 1H), 7.14-7.26 (m, 4H), 7.08-7.14 (m, 1H), 6.96-7.03 (m, 1H), 6.79 (d, J=3.54 Hz, 2H), 6.42 (d, J=7.07 Hz, 1H), 4.65-4.77 (m, 1H), 2.98-3.12 (m, J=9.09 Hz, 1H), 2.80-2.93 (m, J=23.5 Hz, 1H) ppm. Analytical HPLC RT: 1.70 min (Method A, 2 min gradient).

Example 65

(E)-3-(5-chloro-2-tetrazol-1-yl-phenyl)-N—[(S)-1-(2-oxo-1,2,3,4-tetrahydro-quinolin-6-ylcarbamoyl)-2-phenyl-ethyl]-acrylamide

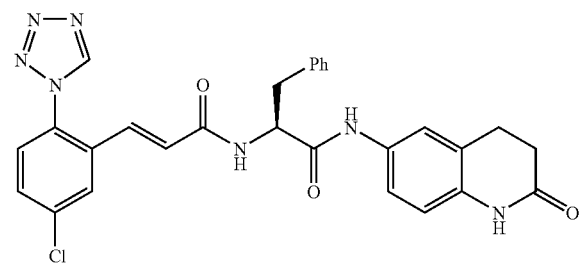 [SMILES: O=C(/C=C/c1cc(Cl)ccc1-n1cnnn1)N[C@@H](Cc1ccccc1)C(=O)Nc1ccc2c(c1)CCC(=O)N2]

65A: Synthesis of (S)-2-amino-N-(2-oxo-1,2,3,4-tetrahydro-quinolin-6-yl)-3-phenyl-propionamide: 6-amino-3,4-dihydroquinolin-2(1H)-one (0.15 g, 0.92 mmol) and (S)-2-(tert-butoxycarbonylamino)-3-phenylpropanoic acid (0.24 g, 0.92 mmol) were coupled and deprotected via TFA to afford 0.17 g (59.4%) of a yellow film. LC/MS m/z 310.3 [M+H]+.

Example 65: To the product of 65A (95 mg, 0.307 mmol), (E)-3-(5-chloro-2-tetrazol-1-yl-phenyl)-acrylic acid 2,5-dioxo-pyrrolidin-1-yl ester (77 mg, 0.307 mmol), PyBOP (160 mg, 0.307 mmol) in THF (4 mL) was added Hunig'sBase (0.161 mL, 0.921 mmol) and the reaction was stirred 24 h. The reaction was quenched with water (10 mL) and extracted with ethyl acetate (3×20 mL). The combined organic layers were washed with brine (10 mL) and dried (MgSO$_4$). Filtration and concentration afforded a solid that was triturated with MeOH (15 mL) to afford Example 65 as a white solid (61 mgs, 36.7%). LC/MS m/z 542.4 [M+H]+. $^1$H NMR (400 MHz, CD$_3$OD) δ: 9.52 (s, 1H), 7.99 (d, J=2.27 Hz, 1H), 7.67 (d, J=8.59 Hz, 1 H), 7.58 (d, J=8.59 Hz, 1H), 7.28-7.35 (m, 5H), 7.20-7.27 (m, 2H), 7.11 (d, J=15.66 Hz, 1H), 6.74-6.82 (m, 2H), 4.80 (t, J=7.45 Hz, 1H), 3.14-3.25 (m, 1H), 3.05 (dd, J=13.52, 7.96 Hz, 1H), 2.93 (t, J=7.58 Hz, 2H), 2.57 (dd, J=8.34, 6.82 Hz, 2H) ppm. Analytical HPLC RT: 5.48 min (Method C, 8 min gradient).

Example 66

(S)—N-(1-(5-chloro-2-(1H-tetrazol-1-yl)phenethylamino)-1-oxo-3-phenylpropan-2-yl)-4-hydroxy-2-oxo-1,2-dihydroquinoline-6-carboxamide

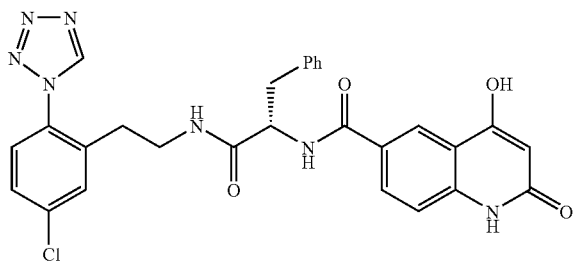 [SMILES: O=C(N[C@@H](Cc1ccccc1)C(=O)NCCc1cc(Cl)ccc1-n1cnnn1)c1ccc2[nH]c(=O)cc(O)c2c1]

66A. (S)-tert-butyl 1-(5-chloro-2-(1H-tetrazol-1-yl)phenethylamino)-1-oxo-3-phenylpropan-2-ylcarbamate: To a solution of 2-(5-chloro-2-(1H-tetrazol-1-yl)phenyl)ethanamine, HCl (48 mg, 0.185 mmol) in DMF (4.0 mL) were added (S)-2-(tert-butoxycarbonylamino)-3-phenylpropanoic acid (49.0 mg, 0.185 mmol), DIEA (0.097 mL, 0.554 mmol), HOBt (14.13 mg, 0.092 mmol) and EDC (42.4 mg, 0.221 mmol) at rt. The reaction mixture was stirred under nitrogen at rt for 5 h. The reaction mixture was diluted with EtOAc, washed with 1M HCl (1×5 mL), sat NaHCO$_3$ (1×5 mL) and sat'd NaCl (1×5 mL). The organic phase was dried over Na$_2$SO$_4$, filtered and concentrated to leave a semi-solid, which was used in next step without further purification. LCMS m/z 471.3 [M+H]+.

66B. (S)-2-amino-N-(5-chloro-2-(1H-tetrazol-1-yl)phenethyl)-3-phenylpropanamide: To 66A (87 mg, 0.185 mmol) was added 4N HCl in dioxane (4.0 mL, 16.00 mmol). The mixture was stirred at rt for 1 h. The solvent was removed under reduced pressure to leave a white residue which was used in next step without further purification.

Example 66: To a solution of 66B (69 mg, 0.186 mmol) in DMF (3.0 mL) were added 4-hydroxy-2-oxo-1,2-dihydroquinoline-6-carboxylic acid (38.2 mg, 0.186 mmol), DIEA (0.1 mL, 0.573 mmol), EDC (42.8 mg, 0.223 mmol) and HOBT (28.5 mg, 0.186 mmol). The reaction mixture was stirred under nitrogen at rt for 3 h. The crude product was purified by HPLC (Phenomenex, C18, 100×30 mm, 5 m column, CH$_3$CN/H$_2$O with 0.1% TFA, 10% to 98% 20 min gradient, flow rate 20 mL/min) The solvent was removed from the desired fraction and the product was dried on lyophilizer to give Example 66 (61.5 mg, 0.110 mmol, 59.2% yield) as a white solid. LCMS m/z 558.3 [M+H]+. HPLC purity 96%. $^1$H NMR (400 MHz, DMSO-d$_6$) δ: 11.48 (s, br. 1H), 11.33 (s, br, 1H), 9.74 (s, 1H), 8.58 (d, br, J=8.35 Hz, 1H), 8.24 (d, J=1.76 Hz, 1H), 8.12 (t, J=5.71 Hz, 1H), 7.84 (dd, J=8.57, 1.98 Hz, 1H), 7.58 (d, J=1.76 Hz, 1H), 7.44-7.54 (m, 2H), 7.10-7.25 (m, 5H), 7.06 (t, J=7.25 Hz, 1H), 5.69 (s, 1H), 4.36-4.66 (m, 1H), 2.97-3.29 (m, 2H), 2.88 (d, J=7.47 Hz, 2H), 2.36-2.56 (m, 2H) ppm. Analytical HPLC RT: 6.60 min (Method C, 8 min gradient, 4.6×75 mm column)

Example 67

(S)-3-(1-(5-chloro-2-(1H-tetrazol-1-yl)phenethylamino)-1-oxo-3-phenylpropan-2-ylcarbamoyl)benzoic acid

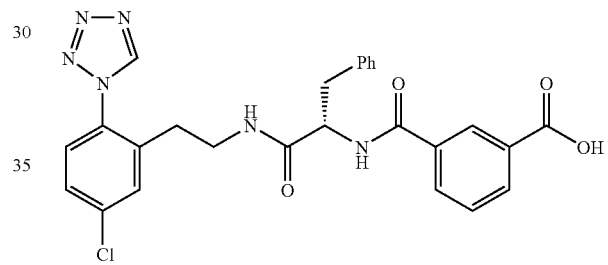

Example 67 was prepared as described previously for Example 56 as a white solid. LC/MS m/z 519.1 (M+H)+. $^1$H NMR (400 MHz, CD$_3$OD) δ: 9.53 (s, 1H), 8.39 (s, 1H), 8.15 (d, J=7.83 Hz, 1H), 7.92 (d, J=7.83 Hz, 1H), 7.52-7.58 (m, 2H), 7.41-7.45 (m, 2H), 7.17-7.25 (m, 5H), 4.66-4.70 (m, 1H), 3.30-3.32 (m, 2H), 3.11-3.15 (m, 1H), 2.96-3.02 (m, 1H), 2.53-2.58 (m, 2H) ppm. Analytical HPLC RT: 6.84 min (Method C, 8 min gradient, 4.6×75 mm column)

Example 68

(S)-methyl 4-(1-(5-chloro-2-(1H-tetrazol-1-yl)phenethylamino)-1-oxo-3-phenylpropan-2-ylcarbamoyl)phenylcarbamate

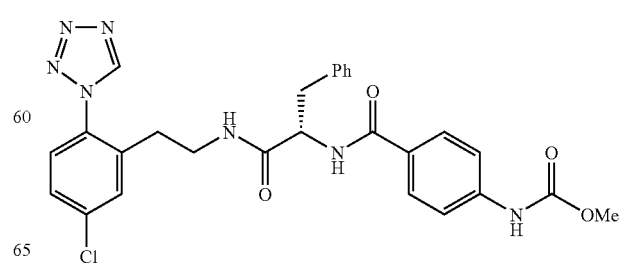

Example 68 was prepared as described previously for Example 28 as a white solid. LC/MS m/z 548.2 (M+H)+. 1H NMR (400 MHz, CD3OD) δ: 9.52 (s, 1H), 7.67 (d, J=8.8 Hz, 2H), 7.57 (d, J=1.96 Hz, 1H), 7.49 (d, J=8.8 Hz, 2H), 7.40-7.42 (m, 2H), 7.16-7.22 (m, 5H), 4.63-4.67 (dd, J=8.8 Hz, J=6.36 Hz, 1H), 3.30-3.34 (m, 2H), 3.75 (s, 3H), 3.09-3.12 (dd, J=13.69 Hz, J=6.36 Hz, 1H), 2.98-3.02 (dd, J=13.69 Hz, J=8.8 Hz, 1H), 2.53-2.56 (m, 2H) ppm. Analytical HPLC RT: 7.02 min (Method C, 8 min gradient, 4.6×75 mm column)

Example 69

(E)-3-(5-chloro-2-tetrazol-1-yl-phenyl)-N—[(S)-1-(2-oxo-1,2,3,4-tetrahydro-quinolin-7-ylcarbamoyl)-2-phenyl-ethyl]-acrylamide

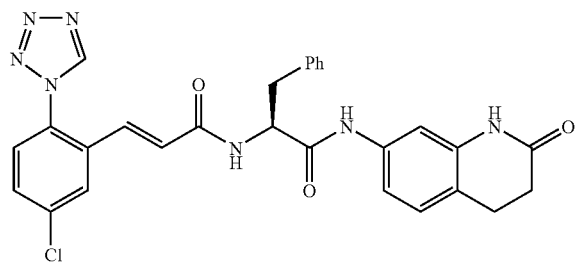 [SMILES: O=C(/C=C/c1cc(Cl)ccc1-n1cnnn1)N[C@@H](Cc1ccccc1)C(=O)Nc1ccc2c(c1)NC(=O)CC2]

Example 69 was prepared in a similar manner as Example 65 as a white solid (12.2 mg, 8%). LCMS m/z 542.4 [M+H]+. 1H NMR (400 MHz, CD3OD) δ: 9.52 (s, 1H), 7.98 (d, J=2.27 Hz, 1H), 7.63-7.69 (m, 1H), 7.58 (d, J=8.59 Hz, 1 H), 7.25-7.32 (m, 4H), 7.18-7.27 (m, 2H), 7.04-7.13 (m, 2H), 6.96 (dd, J=8.08, 2.02 Hz, 1H), 6.78 (d, J=15.66 Hz, 1H), 4.81 (t, J=7.33 Hz, 1H), 3.16-3.24 (m, 1H), 3.01-3.08 (m, 1H), 2.91 (t, J=7.58 Hz, 2H), 2.50-2.61 (m, 2H) ppm. Analytical HPLC RT: 5.70 min (Method C, 8 min gradient).

Example 70

(S)-methyl 4-(1-(5-chloro-2-(1H-tetrazol-1-yl)phenethylamino)-3-(1-methyl-1H-pyrazol-3-yl)-1-oxopropan-2-ylcarbamoyl)phenylcarbamate

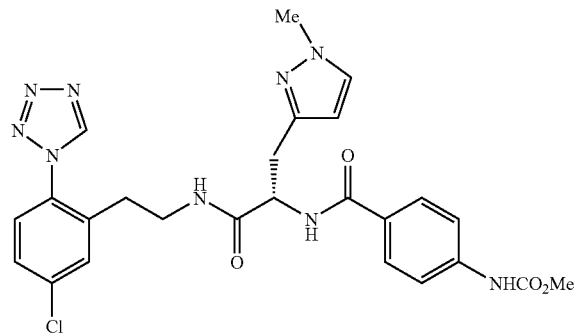

Example 70 was prepared as a colorless solid following a similar procedure used for Example 28 and Example 68. HPLC purity: >98%. LCMS m/z 552.4 (M+H, chlorine isotope). 1H NMR (400 MHz, CD3OD) δ: 9.45 (s, 1H), 7.66 (d, J=8.5 Hz, 2H), 7.51 (d, J=2.2 Hz, 1H), 7.44 (d, J=8.8 Hz, 2H), 7.37-7.30 (m, 3H), 6.01 (d, J=2.3 Hz, 1H), 4.57 (t, 1H), 3.72 (s, 3H), 3.65 (s, 3H), 3.25 (t, 2H), 3.04 (m, 1H), 2.92 (m, 1H), 2.52 (t, 2H) ppm. Analytical HPLC RT: 4.53 min (Method C, 8 min gradient).

Example 71

(S,E)-methyl 3-(2-(3-(5-chloro-2-(1H-tetrazol-1-yl)phenyl)acrylamido)-3-phenylpropanamido)phenylcarbamate

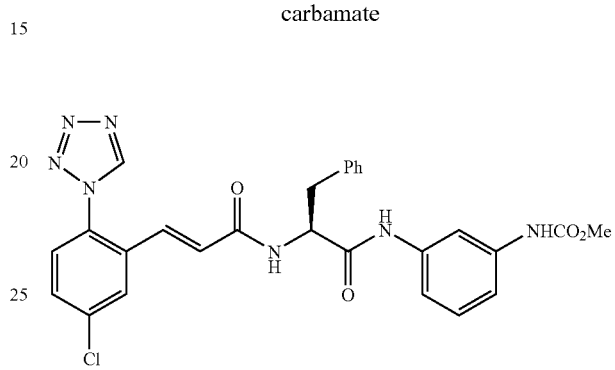

Example 71 was prepared in a similar manner as described for Example 3 (45 mg, 28%). LCMS m/z 546.5 [M+H]+. 1H NMR (400 MHz CD3OD) δ: 9.35 (s, 1H), 7.86 (s, 1H), 7.57 (m, 2H), 7.46 (d, 1H), 7.17 (m, 3H), 7.15-7.03 (m, 3H), 7.00 (d, J=15.6 Hz, 1H), 6.67 (d, J=15.7 Hz, 1H), 4.71 (m, 1H), 3.12 (m, 1H), 2.93 (m, 1H) ppm. Analytical HPLC RT: 5.68 min (Method C, 8 min gradient).

Example 72

(S,E)-3-(5-chloro-2-(1H-tetrazol-1-yl)phenyl)-N-(1-(4-morpholinophenylamino)-1-oxo-3-phenylpropan-2-yl)acrylamide, TFA salt

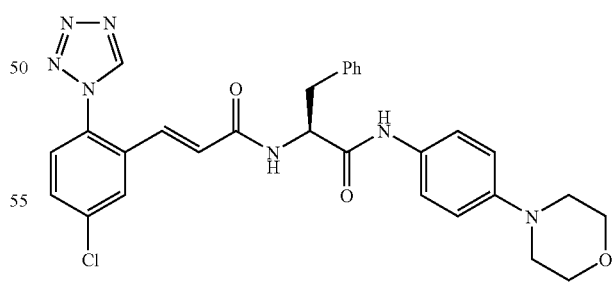

Example 72 was prepared in a similar manner as described for Example 3 (38 mg, 22%). LCMS m/z 558.5 [M+H]+. 1H NMR (400 MHz, DMSO-d6) δ: 8.53 (d, J=8.3 Hz, 1H), 7.94 (d, J=2.1 Hz, 1H), 7.77-7.70 (m, 2H), 7.43 (d, J=9.0 Hz, 2H), 7.27 (m, 6H), 7.21-7.18 (m, 1H), 6.90-6.81 (m, 2H), 4.75 (m, 1H), 3.74 (m, 2H), 3.08 (m, 3H), 2.90 (m, 1H) ppm. Analytical HPLC RT: 5.271 min (Method C, 8 min gradient).

Example 73

(S,E)-3-(5-chloro-2-(1H-tetrazol-1-yl)phenyl)-N-(1-(4-(N-hydroxycarbamimidoyl)phenylamino)-1-oxo-3-phenylpropan-2-yl)acrylamide, TFA salt

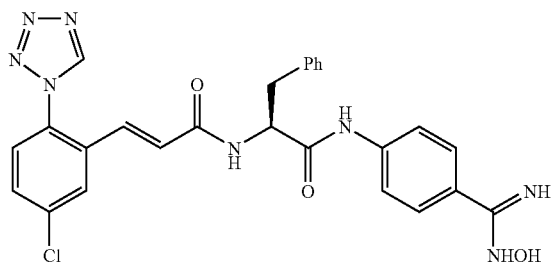

73A. (S)-tert-butyl 1-(4-(N-hydroxycarbamimidoyl)phenylamino)-1-oxo-3-phenylpropan-2-ylcarbamate: To 75 mL ethanol, was added (S)-tert-butyl 1-(4-cyanophenylamino)-1-oxo-3-phenylpropan-2-ylcarbamate (1.64 g, 4.49 mmol, prepared according to Examples 3 and 7), hydroxylamine hydrochloride (0.468 g, 6.73 mmol), and potassium carbonate (5.0 g, 36.2 mmol). The reaction mixture was stirred at rt overnight, concentrated and treated with DCM (200 mL). The product was filtered and concentrated to a foam of 73A. $^1$H NMR (400 MHz, CDCl$_3$) δ: 7.50-7.10 (bm, 9H), 6.70 (d, 1H), 3.50 (m, 1H), 3.20 (bm, 2H), 1.26 (s, 9H). LCMS m/z 399.5 [M+H]$^+$. Analytical HPLC RT: 1.43 min, (Method C, 8 min gradient).

Example 73: HCl in dioxane (4N, 3 mL) was added to a DCM solution of 73A (0.07 g, 0.18 mmol). After 1 h, the reaction mixture was concentrated. To this solid was added THF (10 mL) and DMF (4 mL) followed by 1C (0.04 g, 0.18 mmol), BOP reagent (0.08 g, 0.18 mmol) and TEA (0.2 mL). The reaction mixture was stirred vigorously at rt. After 1 h the reaction was concentrated and directly purified via reverse phase HPLC (methanol/water/TFA gradient). The pure fractions were collected and lyophilized to afford Example 73 as white solid (16 mg, 17%). LCMS m/z 531.5 [M+H]$^+$. $^1$H NMR (400 MHz, CD$_3$OD) δ: 9.08 (s, 1H), 7.78 (m, 1H), 7.68 (d, 1H), 7.56-7.47 (m, 2H), 7.36 (m, 2H), 7.22-7.02 (m, 3H), 7.06 (d, 1H), 6.61 (d, 1H), 4.73 (t, 1H), 3.17 (m, 1H), 3.02 (m, 1H) ppm. Analytical HPLC RT: 4.266 min (Method C, 8 min gradient).

Example 74

(S,E)-3-(5-chloro-2-(1H-tetrazol-1-yl)phenyl)-N-(1-oxo-1-(4-(3-oxomorpholino) phenyl amino)-phenyl-propan-2-yl)acrylamide

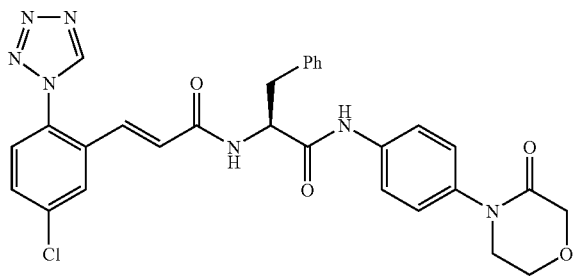 [SMILES: O=C(/C=C/c1cc(Cl)ccc1-n1cnnn1)N[C@@H](Cc1ccccc1)C(=O)Nc1ccc(N2CCOCC2=O)cc1]

Example 74 was prepared in a similar manner as described for Example 3 (5 mg, 2.2%). The 4-(4-aminophenyl)morpholin-3-one was prepared according to the procedures described in Straub (*J. Med. Chem.*, 2005, 48, 5900-5908. LCMS m/z 572.5 [M+H]$^+$. $^1$H NMR (400 MHz DMSO-d$_6$) δ: 8.52 (d, J=8.2 Hz, 1H), 7.87 (d, J=2.1 Hz, 1H), 7.72-7.63 (m, 2H), 7.52 (d, J=8.9 Hz, 2H), 7.26-7.24 (d, J=8.9 Hz, 2H), 7.21-7.20 (m, 4H), 7.15-7.10 (m, 1H), 6.83-6.74 (q(AB), 2H), 4.71 (m, 1H), 4.11 (s, 2H), 3.90 (t, 2H), 3.64 (t, 2H), 3.03 (m, 1H), 2.88 (m, 1H) ppm. Analytical HPLC RT: 5.261 min (Method C, 8 min gradient).

Example 75

(S,E)-3-(5-chloro-2-(1H-tetrazol-1-yl)phenyl)-N-(1-oxo-1-(4-(5-oxo-2,5-dihydro-1,2,4-oxadiazol-3-yl) phenylamino)-3-phenylpropan-2-yl)acrylamide

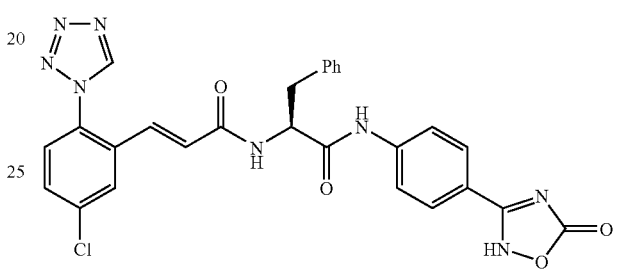

75A. (S)-tert-butyl 1-oxo-1-(4-(5-oxo-2,5-dihydro-1,2,4-oxadiazol-3-yl)phenylamino)-3-phenylpropan-2-ylcarbamate: To a THF (10 mL) solution of 73A (0.18 g, 0.45 mmol), was added CDI (0.07 g, 0.45 mmol) and TEA (0.6 mL). The reaction mixture was stirred at rt overnight. LCMS showed the reaction was partially complete so NaH (60%, 0.1 g) was added and the reaction mixture was stirred for an additional 24 h. The reaction mixture was quenched with water (100 mL) and acidified with HCl (1N). The organics were extracted with EtOAc (2×100 mL), dried (MgSO$_4$) and evaporated to afford 75A as an oil (0.13 g, 65%). LCMS m/z 423.2 [M−H]$^+$. The crude material was used directly into the next step without purification.

Example 75: 75A was converted to the title compound according to the procedures described in Example 73. LCMS m/z 557.5 [M+H]$^+$. $^1$H NMR (400 MHz, DMSO-d$_6$) δ: 9.80 (s, 1H), 8.57 (d, J=8.0 Hz, 1H), 7.88 (d, J=2.1 Hz, 1H), 7.71-7.64 (m, 5H), 7.22 (d, 4H), 7.15-7.11 (m, 1H), 6.78 (s, 2H), 4.73 (m, 1H), 3.04 (m, 1H), 2.85 (m, 1H) ppm. Analytical HPLC RT: 5.745 min (Method C, 8 min gradient).

Example 76

(S,E)-tert-butyl 4-(4-(2-(3-(5-chloro-2-(1H-tetrazol-1-yl)phenyl)acrylamido)-3-phenylpropanamido)phenyl)piperazine-1-carboxylate

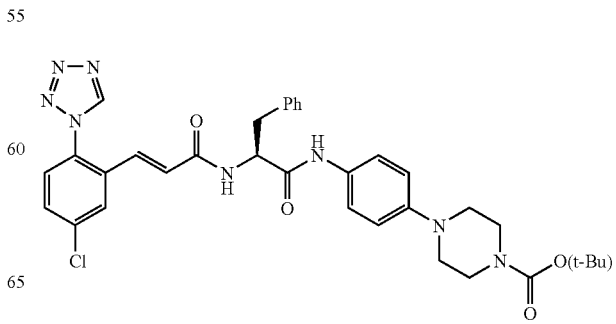

Example 76 was prepared in a similar manner as described for Example 3 (0.16 mg, 80%). LCMS m/z 657.6 [M+H]+. $^1$H NMR (400 MHz, CD$_3$OD) δ: 9.40 (s, 1H), 7.87 (d, J=2.3 Hz, 1H), 7.56 (dd, J=2.4 & 8.5 Hz, 1H), 7.47 (d, J=8.5 Hz, 1H), 7.29 (d, J=9.0 Hz, 2H), 7.17-7.09 (m, 5H), 6.96-6.92 (t, 2H), 6.86 (d, J=15.6 Hz, 1H), 4.67 (t, 1H), 3.51 (bm, 2H), 3.14-2.77 (m, 4H), 1.38 (s, 9H) ppm. Analytical HPLC RT: 6.576 min (Method C, 8 min gradient).

Example 77

(S,E)-3-(5-chloro-2-(1H-tetrazol-1-yl)phenyl)-N-(1-oxo-3-phenyl-1-(4-(piperazin-1-yl)phenylamino)propan-2-yl)acrylamide, Bis-TFA salt

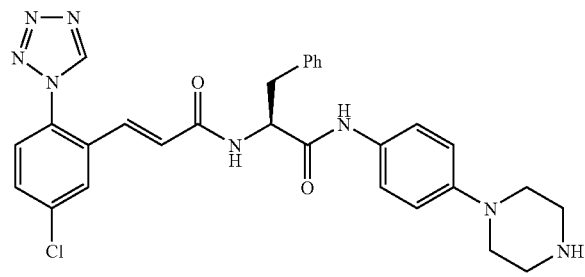 [SMILES: O=C(/C=C/c1cc(Cl)ccc1-n1cnnn1)N[C@@H](Cc1ccccc1)C(=O)Nc1ccc(N2CCNCC2)cc1]

Example 76 was treated with TFA (1 mL) and stirred at rt for 1 h. The reaction mixture was concentrated and purified via reverse phase HPLC. The pure fraction was lyophilized to afford the desired product Example 77 as a white solid (0.11 g, 60%). LCMS m/z 557.5 [M+H]+. $^1$H NMR (400 MHz, CD$_3$OD) δ: 9.49 (s, 1H), 7.96 (s, 1H), 7.65 (dd, J=2.5 & 8.8 Hz, 2H), 7.40 (d, 2H), 7.30-7.15 (m, 4H), 7.10 (d, J=15.6 Hz, 1H), 6.96 (d, J=8.6 Hz, 2H), 6.77 (d, J=15.7 Hz, 1H), 4.909 (bm, 2H overlapp with H$_2$O for CD$_3$OD), 4.78 (t, 1H), 3.82 (bm, 2H overlap with CD$_3$OD peak), 3.10-3.02 (m, 2H) ppm. Analytical HPLC RT 4.193 min (Method C, 8 min gradient).

Example 78

(S,E)-3-(5-chloro-2-(1H-tetrazol-1-yl)phenyl)-N-(1-(4-(5-methyl-1,2,4-oxadiazol-3-yl)phenylamino)-1-oxo-3-phenylpropan-2-yl)acrylamide

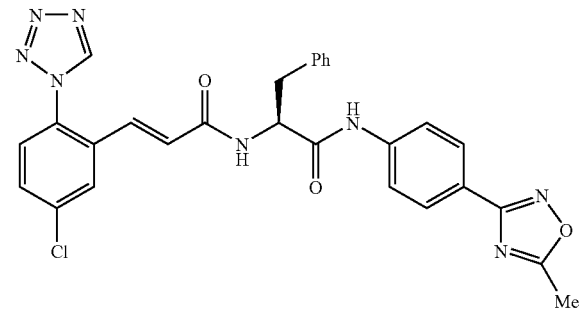 [SMILES: Cc1nc(-c2ccc(NC(=O)[C@H](Cc3ccccc3)NC(=O)/C=C/c3cc(Cl)ccc3-n3cnnn3)cc2)no1]

Example 78 was prepared in a similar manner as described for Example 3 (12 mg, 2%) from commercially available 4-(5-methyl-1,2,4-oxadiazol-3-yl)aniline. LCMS m/z 555.5 [M+H]+. $^1$H NMR (400 MHz, DMSO-d$_6$/CD$_3$OD) δ: 9.46 (s, 1H), 7.90 (d, J=2.3 Hz, 1H), 7.88 (d, J=8.8 Hz, 2H), 7.61-7.56 (m, 2H), 7.51 (d, J=8.5 Hz, 1H), 7.20 (m, 3H), 7.15 (m, 1H), 6.96 (d, J=15.6 Hz, 1H), 6.74 (d, J=15.6 Hz, 1H), 4.75 (t, 1H), 3.13 (m, 1H), 2.95 (m, 1H), 2.54 (s, 3H) ppm. Analytical HPLC RT: 6.116 min (Method C, 8 min gradient).

Example 79

(S,E)-N-(1-(4-carbamimidoylphenylamino)-1-oxo-3-phenylpropan-2-yl)-3-(5-chloro-2-(1H-tetrazol-1-yl)phenyl)acrylamide, TFA salt

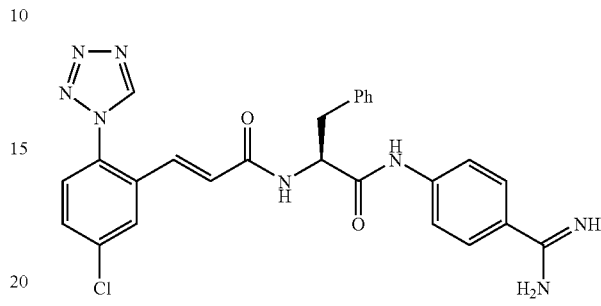

73A (0.5 g, 1.255 mmol) was hydrogenated at 60 psi with 10% Pd/C (50 mg) for 12 h in methanol, AcOH containing a small amount of Ac$_2$O (0.5 mL). The reaction mixture was filtered through a Celite® pad and concentrated to an oil. Approximately 70 mg of the reaction mixture was re-dissolved in methanol (1 mL) and to this was added HCl in dioxane (1 mL). The reaction mixture was stirred at rt for 5 h, concentrated to an oil, then re-dissolved in THF (10 mL). To this solution was added BOP reagent (0.10 g, 0.22 mmol), 1C (0.06 g, 0.22 mmol), and TEA (0.2 mL). The reaction mixture was stirred at rt for 1.5 h, concentrated and purified directly via reverse phase HPLC. The pure fractions corresponding to the desired product were collected and concentrated and lyophilized to give Example 79 as a solid (25 mg, 20%). LCMS m/z 515.5 [M+H]+. $^1$H NMR (400 MHz, CD$_3$OD) δ: 9.51 (s, 1H), 7.97 (d, J=2.2 Hz, 1H), 7.81-7.77 (m, 5H), 7.66 (dd, 1H), 7.59 (d, 1H), 7.49 (d, 1H), 7.28-7.19 (m, 6H), 6.94 (d, J=15.4 Hz, 1H), 4.19 (m, 1H), 3.20 (m, 1H), 3.12 (m, 1H) ppm. Analytical HPLC RT: 3.071 min (Method C, 8 min gradient).

Example 80

(S,E)-3-(5-chloro-2-(1H-tetrazol-1-yl)phenyl)-N-(1-(3-chloro-4-fluorophenylamino)-1-oxo-3-phenylpropan-2-yl)acrylamide

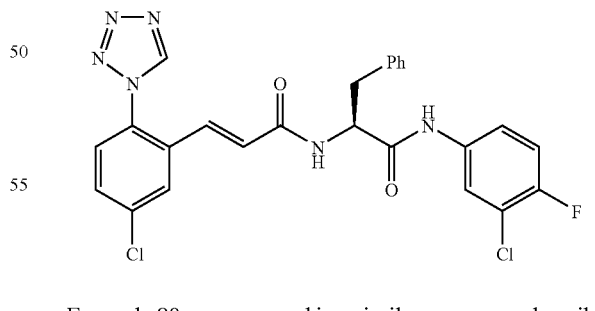

Example 80 was prepared in a similar manner as described for Example 3 (17 mg, 4%). LCMS m/z 525.4 [M+H]+. $^1$H NMR (400 MHz, DMSO-d$_6$) δ: 9.78 (s, 1H), 8.55 (d, J=8.0 Hz, 1H), 7.87 (d, J=2.1 Hz, 1H), 7.81 (dd, J=2.5 Hz & 8.4 hz, 1H), 7.70-7.64 (m, 2H), 7.40-7.36 (m, 1H), 7.32-7.28 (m, 1H), 7.23-7.18 (m, 3H), 7.15-7.02 (m, 1H), 6.77 (s, 2H), 4.67 (m, 1H), 3.03 (m, 1H), 2.87 (m, 1H) ppm. Analytical HPLC RT: 6.570 min (Method C, 8 min gradient).

Example 81

(S,E)-3-(5-chloro-2-(1H-tetrazol-1-yl)phenyl)-N-(1-(4-fluoro-3-methylphenylamino)-1-oxo-3-phenylpropan-2-yl)acrylamide

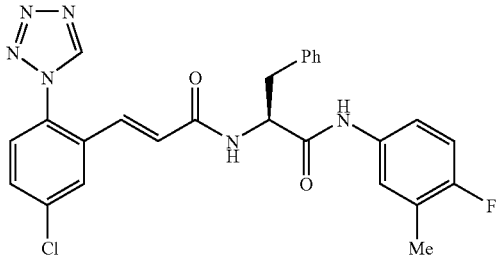 [SMILES: Cc1cc(NC(=O)[C@H](Cc2ccccc2)NC(=O)/C=C/c2cc(Cl)ccc2-n2cnnn2)ccc1F]

Example 81 was prepared in a similar manner as described for Example 3 (17 mg, 4%). LCMS m/z 505.5 [M+H]$^+$. $^1$H NMR (400 MHz DMSO-d$_6$) δ: 9.78 (s, 1H), 8.49 (d, J=8.1 Hz, 1H), 7.87 (d, J=2.1 Hz, 1H), 7.70-7.63 (m, 2H), 7.39 (m, 1H), 7.31 (m, 1H), 7.23-7.19 (m, 3H), 7.15-7.10 (m, 1H), 7.02-6.98 (t, 1H), 6.82-6.73 (d(q), 2H), 4.67 (m, 1H), 3.02 (m, 1H), 2.83 (m, 1H), 2.15 (s, 3H) ppm. Analytical HPLC RT: 6.378 min (Method C, 8 min gradient).

Example 82

(S,E)-ethyl 4-(2-(3-(5-chloro-2-(1H-tetrazol-1-yl)phenyl)acrylamido)-3-phenylpropanamido)benzoate

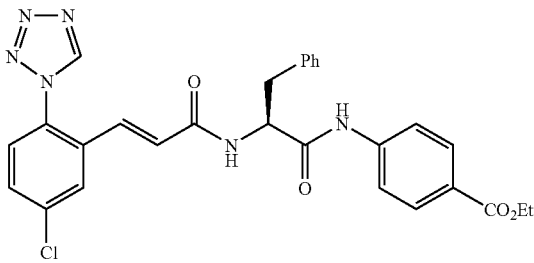 [SMILES: CCOC(=O)c1ccc(NC(=O)[C@H](Cc2ccccc2)NC(=O)/C=C/c2cc(Cl)ccc2-n2cnnn2)cc1]

Example 82 was prepared in a similar manner as described for Example 3 (0.26 g, 84%). LCMS m/z 545.5 [M+H]$^+$. $^1$H NMR (400 MHz, CD$_3$OD) δ: 9.43 (s, 1H), 8.69 (d, J=2.0 Hz, 1H), 8.01-7.97 (m, 3H), 7.83-7.77 (m, 4H), 7.35-7.32 (m, 4H), 7.28-724 (m, 1H), 6.91 (s, 2H), 4.86 (m, 1H), 4.38 (q, 2H), 3.18 (m, 1H), 3.01 (m, 1H), 1.39 (t, 3H) ppm. Analytical HPLC RT: 6.348 min (Method C, 8 min gradient).

Example 83

(S,E)-4-(2-(3-(2-(aminomethyl)-5-chlorophenyl)acrylamido)-3-phenylpropanamido)benzoic acid, TFA salt

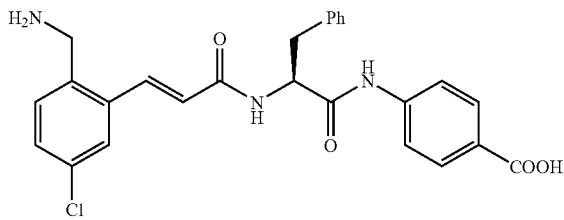 [SMILES: NCc1ccc(Cl)cc1/C=C/C(=O)N[C@@H](Cc1ccccc1)C(=O)Nc1ccc(C(=O)O)cc1]

83A. 4-chloro-2-iodobenzamide: To a stirred solution of 4-chloro-2-iodobenzoic acid (5.0 g, 0.018 mol) in 50 mL of DMF was added HOBT (2.67 g, 0.0198 mol) followed by EDCI (4.13 g, 0.0216 mol). The reaction mixture was cooled to 0° C. and 100 mL of ammonia solution (25%) was added dropwise. The reaction mixture was stirred at rt overnight. Water was added and the solid was filtered, washed with water and dried to afford 83A (4.0 g, 80%). $^1$H NMR (CD$_3$OD, 400 MHz) δ: 7.9 (s, 1H), 7.4 (m, 1H), 7.3 (d, 1H). LCMS m/z 282 [M+H]$^+$.

83B. (4-chloro-2-iodophenyl)methanamine: The solution of 83A (0.5 g, 1.78 mmol) in 10 mL of THF was cooled to 0° C. and added borane dimethylsulphide complex (0.41 g, 5.4 mmol). The reaction was refluxed at 70° C. overnight. The reaction mixture was cooled to rt and quenched with methanol followed by 1.5 N HCl. Methanol was distilled-off and the product was extracted with ethyl acetate. The ethyl acetate layer was washed with brine solution, dried over sodium sulphate and concentrated to afford 83B (0.3 g). $^1$H NMR (CD$_3$OD, 400 MHz) δ: 7.87 (s, 1H), 7.4 (d, 2H), 3.8 (d, 2H). LCMS-[M+H]$^+$ 267.7.

83C. tert-butyl 4-chloro-2-iodobenzylcarbamate: The solution of compound 83B (0.25 g, 0.94 mmol) in 2.5 mL of DCM was cooled to 0° C. and added boc anhydride (0.2451 g, 1.13 mmol). The reaction was stirred at rt overnight. The solvent was distilled off and the residue was purified by silica gel column chromatography using hexane:ethyl acetate as eluent to afford 83C (0.3 g, 94%). $^1$H NMR (CD$_3$OD, 400 MHz) δ: 7.8 (s, 1H), 7.4 (m, 1H), 7.2 (d, 1H), 4.1 (s, 2H). LCMS m/z 367.7 [M+H]$^+$.

83D. (E)-methyl 3-(2-((tert-butoxycarbonylamino)methyl)-5-chlorophenyl)acrylate: To compound 83C (12 g, 0.0326 mol) in acetonitrile (120 mL) was added Pd(OAc)$_2$ (0.74 g, 0.0032 mol) and purged with nitrogen for 1 h. Triethylamine (6.9 mL, 0.049 mol) and methyl acrylate (4.42 mL, 0.049 mol) were added and refluxed overnight. The reaction was cooled and solvent was removed by vacuum. The crude product was purified by silica gel column chromatography using hexane:ethylacetate as eluent to afford 83D (8 g, 75%). $^1$H NMR (CDCl$_3$, 400 MHz) δ: 7.88 (d, 1H), 7.5 (s, 1H), 7.3 (m, 2H), 6.37 (d, 1H), 4.8 (bs, 1H), 4.4 (m, 2H), 3.8 (s, 3H), 1.4 (s, 9H). LCMS m/z 325.6 [M+H]$^+$.

83E. (E)-3-(2-((tert-butoxycarbonylamino)methyl)-5-chlorophenyl)acrylic acid: To a stirred solution compound 83D (20 g, 0.0613 mol) in 300 mL of THF/water mixture (2:1) was added lithium hydroxide monohydrate (3.09 g, 0.0736 mol). The reaction mixture was stirred at rt for 3 h. THF was distilled-off and 250 mL of water was added. The solution was acidified using citric acid and the solid product 83E was filtered, washed with water and dried (8 g, 94%). $^1$H NMR (CD$_3$OD, 400 MHz) δ: 7.93 (d, 1H), 7.6 (s, 1H), 7.35 (m, 2H), 6.4 (d, 1H), 3.67 (m, 1H), 4.3 (s, 2H), 1.4 (s, 9H). LCMS m/z 311.7 [M+H]$^+$.

Example 83 was prepared in a similar manner as described for Example 3, by replacing 1C with 83E. LCMS m/z 478.5 [M+H]$^+$. $^1$H NMR (400 MHz, DMSO-d$_6$) δ: 10.49 (s, 1H), 8.56 (d, J=.1 Hz, 1H), 8.09 (bs, 2H), 7.88 (dd, J=0.6 & 8.8 Hz, 2H), 7.66 (dd, J=0.7 & 8.7 Hz, 2H), 7.59 (m, 1H), 7.52-7.48 (m, 1H), 7.43 (d, J=8.4 Hz, 1H), 7.28-7.21 (m, 4H), 7.16-7.12 (m, 1H), 6.73 (d, J=15.5 Hz, 1H), 4.819 (m, 1H), 4.07 (m, 2H), 3.60 (bs, 2H), 3.10 (m, 1H), 2.91 (m, 1H) ppm. Analytical HPLC RT: 4.385 min (Method C, 8 min gradient).

Example 84

4-((2S)-2-((E)-3-(2-(5-amino-1H-tetrazol-1-yl)-5-chlorophenyl)acrylamido)-3-phenylpropanamido)-3-fluorobenzoic acid, TFA salt

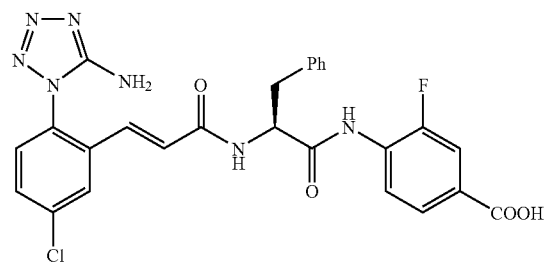 [SMILES: Nc1nnnn1-c1ccc(Cl)cc1/C=C/C(=O)N[C@@H](Cc1ccccc1)C(=O)Nc1ccc(C(=O)O)cc1F]

To the ester precursor for Example 52 (0.1 g, 0.18 mmol) in DMF (5 mL) was added NaOH (0.2 g) and water (1 mL). The reaction was heated at 50° C. overnight. The reaction was quenched with 1N HCl. The organics were extracted with EtOAc (2×100 mL), dried and evaporated to an oil, which was re-dissolved in DMF (1 mL). To this solution was added NH₄Cl (2 g) followed by excess NaN₃ (1 g) and AcOH (2 mL). The reaction mixture was heated at 80° C. for 6 h. The reaction mixture was quenched with water (5 mL) and concentrated. The solids were filtered and re-dissolved in methanol and purified directly via a reverse phase HPLC (methanol/water/TFA gradient). Example 84 was obtained (10 mg, 10%) as white solid. LCMS m/z 550.5 [M+H]$^+$. $^1$H NMR (400 MHz, DMSO-d₆) δ: 7.31-7.27 (t, 1H), 7.14 (d, J=2.7 Hz, 1H), 6.99 (d, J=8.5 Hz, 1H) 6.91-6.88 (dd, J=2.5 & 8.3 Hz, 1H), 6.64 (d, J=8.3 Hz, 1H), 6.45-6.38 (m, 4H), 6.32 (d, J=15.4 Hz, 1H), 5.92 (d, J=15.5 Hz, 1H), 4.14 (m, 1H), 2.42 (m, 1H), 2.26 (m, 1H) ppm. Analytical HPLC RT: 2.355 min (Method C, 4 min gradient).

Example 85

(S,E)-3-(5-chloro-2-(1H-tetrazol-1-yl)phenyl)-N-(1-oxo-1-(4-(5-oxo-4,5-dihydro-1,3,4-oxadiazol-2-yl)phenylamino)-3-phenylpropan-2-yl)acrylamide

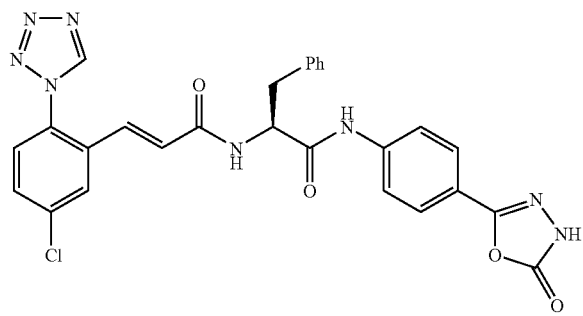 [SMILES: O=C(/C=C/c1cc(Cl)ccc1-n1cnnn1)N[C@@H](Cc1ccccc1)C(=O)Nc1ccc(-c2n[nH]c(=O)o2)cc1]

To Example 8 (0.232 g, 0.45 mmol) in THF (10 mL) was added t-butylcarbazate (0.06 g, 0.45 mmol) and TEA (0.06 mL). The reaction mixture was stirred at rt for 3 h, quenched with water (100 mL). The organics were extracted with EtOAc (2×50 mL), dried and evaporated to a oil, which was re-dissolved in DCM (5 mL). To this solution was added HCl in dioxane (4N, 5 mL). The mixture was stirred for 1 h, concentrated in vacuo followed by the addition of DMF (10 mL), TEA (4 mL) and CDI (0.2 g). The reaction mixture was stirred at rt overnight, quenched with water and acidified with 1N HCl. The organics were extracted with EtOAc (2×50 mL), dried, concentrated and purified via reverse phase HPLC. Pure fractions corresponding to the desired product were collected and lyophilized. Example 85 was obtained (30 mg, 12%) as white solid. LCMS m/z 557.5 [M+H]$^+$. $^1$H NMR (400 MHz, DMSO-d₆) δ: 9.78 (s, 1H), 8.52 (m, 1H), 7.88 (s, 1H), 7.67 (m, 5H), 7.23-7.15 (m, 5H), 6.77 (s, 2H), 4.70 (m, 1H), 3.02 (m, 1H), 2.89 (m, 1H) ppm. Analytical HPLC RT: 5.588 min (Method C, 8 min gradient).

Example 86

(S,E)-N-(1-(4-(5-amino-1,3,4-thiadiazol-2-yl)phenylamino)-1-oxo-3-phenylpropan-2-yl)-3-(5-chloro-2-(1H-tetrazol-1-yl)phenyl)acrylamide, TFA salt

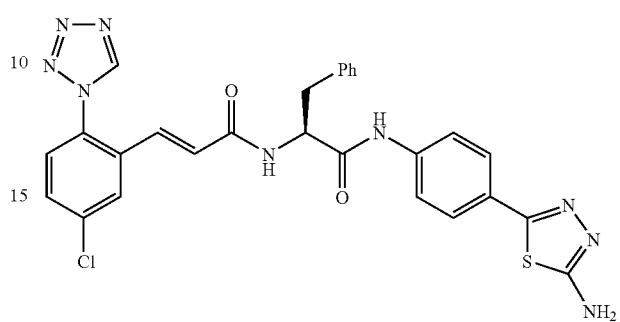

86A. (S)-2-amino-N-(4-(5-amino-1,3,4-thiadiazol-2-yl)phenyl)-3-phenylpropanamide, bis-TFA salt: To TFA (8 mL) was added Example 7 (1.7 g, 4.65 mmol) and hydrazinecarbothioamide (0.42 g, 4.65 mmol). The reaction mixture was heated at 100° C. for 2 h, cooled and quenched with NaOH (1N) solution. Yellow solid was precipitated, filtered and washed with water. The aqueous layer was extracted with EtOAc (2×100 mL), and dried and evaporated to a pale yellow solid 86A. LCMS m/z 340.2 [M+H]$^+$. $^1$H NMR (400 MHz, DMSO-d₆) δ: 7.80 (m, 3H), 7.33-7.17 (m, 6H), 3.62 (t, 1H), 3.04 (m, 1H), 2.78 (m, 1H) ppm.

Example 86: To a DMF (5 mL) of the product from 86A (0.028 g, 0.083 mmol) was added 55E (0.029 g, 0.083 mmol) and TEA (0.1 mL). The reaction reaction mixture was stirred overnight, quenched with water (100 mL) and extracted organics with EtOAc (2×100 mL), dried (MgSO₄) and concentrated. The crude product was purified directly via reverse phase HPLC using methanol/water/TFA gradient. Pure fractions corresponding to the desired product were collected, concentrated and lyophilized to afford Example 86 as a white solid (25 mg, 51%). LCMS m/z 572.5 [M+H]$^+$. $^1$H NMR (400 MHz, DMSO-d₆) δ: 9.78 (s, 1H), 8.55 (d, J=8.0 Hz, 1H), 7.88 (d, J=2.1 Hz, 1H), 7.71-7.59 (m, 5H), 7.44 (bs, 1H), 7.22 (m, 4H), 7.16-7.10 (m, 1H), 6.78 (d(AB), 2H), 4.73 (m, 1H), 3.03 (m, 1H), 2.88 (m, 1H) ppm. Analytical HPLC RT: 5.108 min (Method C, 8 min gradient).

Example 87

(S,E)-methyl 5-(4-(2-(3-(5-chloro-2-(1H-tetrazol-1-yl)phenyl)acrylamido)-3-phenylpropanamido)phenyl)-1,3,4-thiadiazol-2-ylcarbamate

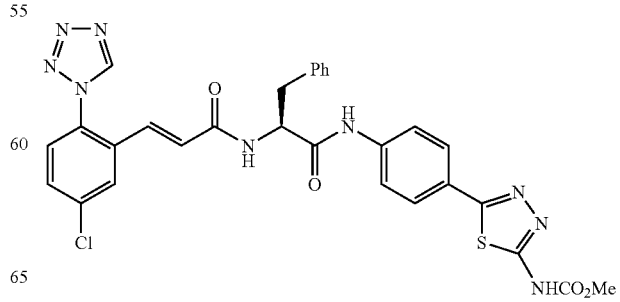

To Example 86 (0.10 g, 0.018 mmol) was added DCM (1 mL), pyridine (1 mL) followed by three drops of methylchloroformate. The reaction mixture was stirred at rt overnight, concentrated and re-dissolved in methanol and directly purified via reverse phase HPLC (water/methol/TFA gradient). Pure fractions corresponding to the desired product were collected and lyophilized to afford Example 87 as a white solid (6 mg, 53%). LCMS m/z 630.0 [M+H]$^+$. $^1$H NMR (400 MHz, DMSO-d$_6$/CDCl$_3$) δ: 9.13 (s, 1H), 8.30 (d, J=8.4 Hz, 1H), 7.83 (t, 3H), 7.71 (d, J=8.8 Hz, 2H), 7.45 (d, J=8.5 Hz, 1H), 7.27 (m, 4H), 7.13 (m, 1H), 7.13 (d, J=15.5 Hz, 1H), 6.83 (d, J=15.5 Hz, 1H), 4.98 (m, 1H), 3.87 (s, 3H), 3.05 (m, 2H) ppm. Analytical HPLC RT: 8.339 min (Method C, 8 min gradient).

Example 88

(S,E)-methyl 4-(2-(3-(3-chloro-2-fluoro-6-(1H-tetrazol-1-yl)phenyl)acrylamido)-3-phenylpropanamido) phenylcarbamate

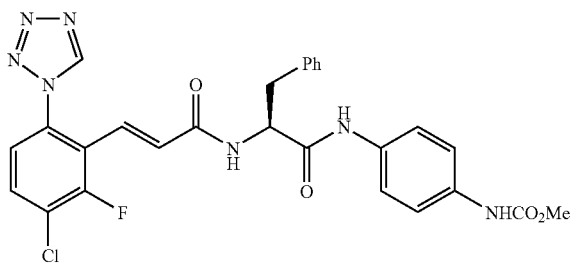

Example 88 was prepared via the coupling of (S)-methyl 4-(2-amino-3-phenylpropanamido)phenylcarbamate and Intermediate 7 according to the procedure described for Example 3 (6 mg, 28%). LCMS m/z 564.1 [M+H]$^+$. $^1$H NMR (400 MHz DMSO-d$_6$/CDCl$_3$) δ: 9.55 (s, 1H), 9.25 (s, 1H), 8.92 (bs, 1H), 8.41 (d, J=8.4 Hz, 1H), 7.45-7.20 (m, 8H), 7.01 (d, J=16.0 Hz, 1H), 6.77 (d, J=16.0 Hz, 1H), 4.88 (m, 1H), 3.73 (s, 3H), 3.10 (m, 2H) ppm. Analytical HPLC RT: 7.829 min (Method C, 8 min gradient).

Example 89

(S,E)-N-(1-(1-aminoisoquinolin-6-ylamino)-1-oxo-3-phenylpropan-2-yl)-3-(5-chloro-2-(1H-tetrazol-1-yl)phenyl)acrylamide

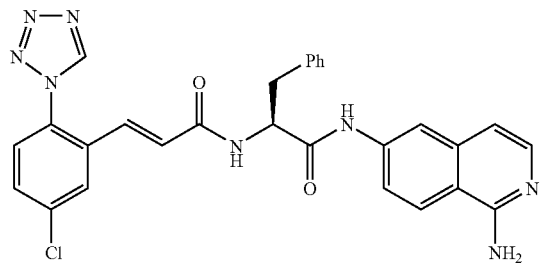 [SMILES: Nc1nccc2cc(NC(=O)[C@H](Cc3ccccc3)NC(=O)/C=C/c3cc(Cl)ccc3-n3cnnn3)ccc12]

89A. (S)-benzyl 1-(1-aminoisoquinolin-bis-tert-butylcarbamate-6-ylamino)-1-oxo-3-phenylpropan-2-ylcarbamate: 89A was prepared according to the procedure described in Example 3A, replacing Boc-L-phenylalanine with (S)-2-(benzyloxycarbonylamino)-3-phenylpropanoic acid and by replacing p-nitroaniline with commercially available bis-tert-butyl-6-aminonaphthalen-1-ylcarbamate. LCMS m/z 641.2 [M+H]$^+$. $^1$H NMR (400 MHz, CDCl$_3$) δ: 8.55 (d, 1H), 8.48 (bs, 1H), 8.29 (d, 1H), 8.25 (bs, 1H), 8.17 (d, 1H), 7.82-7.72 (m, 4H), 7.63-7.47 (m, 2H), 7.20-7.15 (m, 4H), 4.91 (s, 2 h), 4.49 (m, 1H), 3.05 (m, 2H), 1.16 (s, 18H) ppm.

89B. (S)-2-amino-N-(1(bis-tert-butyl-aminoisoquinolin-carbamate)-6-yl)-3-phenylpropanamide: 89A (0.656 g, 1.02 mmol) was dissolved in methanol (50 mL). To this solution was added a spatula tip of 10% Pd/C and the reaction mixture was hydrogenated at 55 psi of hydrogen for 18 h. The reaction mixture was filtered through a Celite® pad and washed with excess methanol. The solvents were evaporated to afford 89B as a foam (0.48 g, 93%). LCMS m/z 507.1 [M+H]$^+$.

Example 89: 89B was converted to the title compound according to the procedures described in Example 3. LCMS m/z 539.0 [M+H]$^+$. $^1$H NMR (400 MHz DMSO-d$_6$) δ: 8.85 (bs, 1H), 8.7 (d, J=8.8 Hz, 1H), 8.49 (d, J=8.6 Hz, 1H), 8.23 (d, J=2.3 Hz, 1H), 7.96 (d, J=2.4 Hz, 1H), 7.80-7.69 (m, 3H), 7.63 (d, J=8.4 Hz, 1H), 7.33-7.18 (m, 4H), 6.85 (s, 2H), 4.80 (m, 1H), 3.11 (m, 1H), 2.95 (m, 1H) ppm. Analytical HPLC RT: 5.358 min (Method C, 8 min gradient).

Example 90 and Example 91

(S,E)-3-(3-(4-carboxyphenylamino)-2-(3-(5-chloro-2-(1H-tetrazol-1-yl)phenyl)acrylamido)-3-oxopropyl)benzoic acid and (S,E)-4-(3-(3-carbamoylphenyl)-2-(3-(5-chloro-2-(1H-tetrazol-1-yl)phenyl)acrylamido) propanamido)benzoic acid Example 90

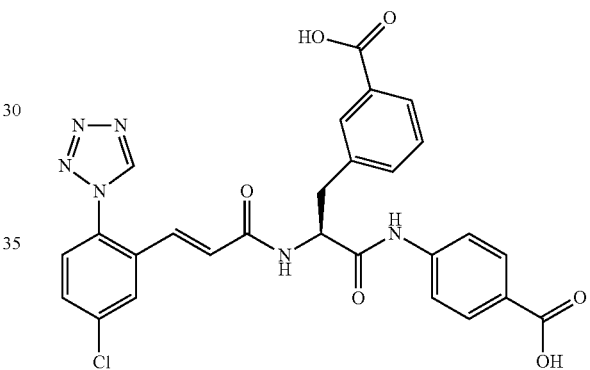

Example 91

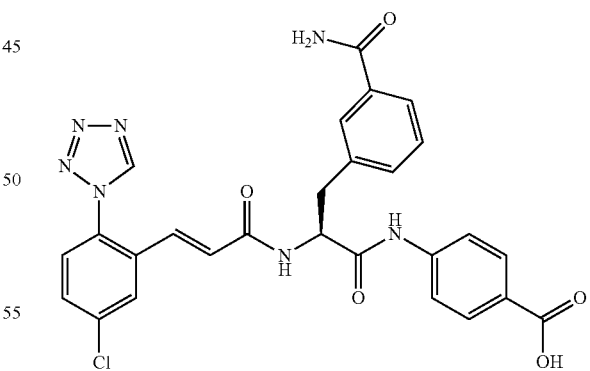

90A. (S)-methyl 3-(3-(4-(tert-butoxycarbonyl)phenylamino)-2-(tert-butoxycarbonylamino)-3-oxopropyl)benzoate: 90A was prepared according to the procedure described in Example 3A, by replacing Boc-L-phenylalaninewith (S)-2-(tert-butoxycarbonylamino)-3-(3-(methoxycarbonyl)phenyl)propanoic acid and by replacing p-nitroaniline with tert-butyl 4-aminobenzoate. LCMS m/z 499.1 [M+H]$^+$. $^1$H NMR (400 MHz, CDCl$_3$) δ: 7.97-7.93 (m, 4H), 7.51-7.29 (m, 4H), 5.10 (bs, 1H), 4.56 (bs, 1H), 3.75 (s, 3H), 3.30 (m, 1H), 3.21 (m, 1H), 1.60 (s, 9H), 1.30 (s, 9H) ppm.

90B. (S)-3-(3-(4-(tert-butoxycarbonyl)phenylamino)-2-(tert-butoxycarbonylamino)-3-oxopropyl)benzoic acid: 90A (0.43 g, 0.86 mmol) was dissolved in a solution consisting of THF (20 mL), methanol (20 mL) and water (10 mL). To this solution was added LiOH (0.17 g, 6.9 mmol). The reaction mixture was stirred at rt for 48 h, quenched with water (100 mL), extracted with EtOAc (2×100 mL), and dried (MgSO$_4$). The aqueous layer was acidified with HCl (1N) and the desired product was extracted with EtOAc (2×100 mL), dried (MgSO$_4$) and evaporated to afford 90B as an oil. LCMS m/z 329.1 [M-Boc]$^+$ and 373.0 [M-t-Bu]$^+$. $^1$H NMR (400 MHz, CDCl$_3$) δ: 9.05 (bs, 1H), 8.02-7.82 (m, 4H), 7.46-7.19 (m, 4H), 5.45 (bs, 1H), 4.80 (bs, 1H), 3.13 (bm, 2H), 1.50 (s, 9H), 1.22 (s, 9H) ppm.

90C. (S)-tert-butyl 4-(2-amino-3-(3-carbamoylphenyl)propanamido)benzoate: Ethylchloroformate (0.02 mL, 0.19 mmol) was added to a cold (−78° C.) THF solution of 90B (0.09 g, 0.19 mmol), followed by TEA (0.26 mmol). The reaction was stirred cold for 0.25 h followed by the addition of ammonia in methanol (2M, 15 mL). The reaction mixture was stirred cold and allowed to warm to rt for 3 h. The reaction was concentrated. The organics were extracted with EtOAc (2×100 mL), dried (MgSO$_4$) and evaporated to a semi-solid mass. The crude mass was treated with HCl in dioxane (4N, 10 mL) and was stirred at rt for 2 h. The solution was concentrated to afford the desired product 90C as an oil (0.15 g, 82%). LCMS m/z 328.1 [M+H]$^+$. The crude LCMS also showed the presence of (S)-3-(2-amino-3-(4-(tert-butoxycarbonyl)phenylamino)-3-oxopropyl)benzoic acid which was carried on to the next coupling step as it was.

Example 90 and Example 91: The title compounds were obtained by coupling 90C with 55E according to the procedure described in Example 3 and separated via reverse phase HPLC. Example 90: LCMS m/z 561.3 [M+H]$^+$. $^1$H NMR (400 MHz DMSO-d$_6$/CD$_3$OD) δ: 8.64 (s, 1H), 7.10 (m, 2H), 7.06-7.04 (d, J=8.6 Hz, 1H), 6.98-6.96 (d, J=7.8 Hz, 1H), 6.78-6.73 (m, 3H), 6.70-6.67 (d, J=8.3 Hz, 1H), 6.64-6.62 (d, J=7.8 Hz, 1H), 6.52-6.48 (t, 1H), 6.16-6.12 (d, J=15.7 Hz, 1H), 5.92-5.88 (d, J=15.7 Hz, 1H), 3.99 (m, 1H), 2.25 (m, 2H) ppm. Analytical HPLC RT: 5.74 min (Method C, 8 min gradient). Example 91: LCMS m/z 560.2 [M+H]$^+$. $^1$H NMR (400 MHz DMSO-d$_6$/CD$_3$OD) δ: 10.24 (s, 1H), 9.37 (d, J=7.8 Hz, 1H), 8.70-8.64 (m, 4H), 8.58 (dd, J=2.1 & 7.8 Hz, 1H), 8.38-8.35 (m, 3H), 8.30-8.28 (d, J=8.6 Hz, 1H), 8.24-8.22 (d, J=7.9 Hz, 1H), 8.13-8.09 (t, 1H), 7.77-7.73 (d, J=15.6 Hz, 1H), 7.53 7.49 (d, J=15.6 Hz, 1H), 5.60-5.56 (m, 1H), 3.96-3.80 (m, 2H) ppm. Analytical HPLC RT: 5.25 min (Method C, 8 min gradient).

Example 92

(S,E)-methyl 2-(2-(3-(5-chloro-2-(1H-tetrazol-1-yl)phenyl)acrylamido)-3-phenylpropanamido)-[1,2,4]triazolo[1,5-a]pyridine-6-carboxylate

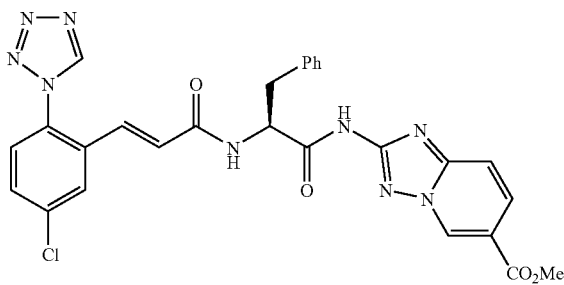 [SMILES: COC(=O)c1ccc2nc(NC(=O)[C@H](Cc3ccccc3)NC(=O)/C=C/c3cc(Cl)ccc3-n3cnnn3)nn2c1]

Example 92 was prepared in a similar manner as described for Example 3, by replacing p-nitroaniline with methyl 2-amino-[1,2,4]triazolo[1,5-a]pyridine-6-carboxylate (Synthesis, 2003, 11, 1649). LCMS m/z 572.0 [M+H]$^+$. $^1$H NMR (400 MHz CD$_3$OD) δ: 9.39 (s, 1H), 9.17 (s, 1H), 8.05-8.03 (dd, J=1.6 & 8.2 Hz, 1H), 7.86 (d, J=2.2 Hz, 1H), 7.58-7.53 (m, 2H), 7.46 (d, J=8.6 Hz, 1H), 7.21-7.14 (m, 5H), 7.00-6.96 (d, J=15.6 Hz, 1H), 6.68-6.64 (d, J=15.6 Hz, 1H, 4.78 (m, 1H), 3.87 (s, 3H), 3.00-2.92 (m, 2H) ppm. Analytical HPLC RT: 6.39 min (Method C, 8 min gradient).

Example 93

(S,E)-methyl 2-(2-(3-(5-chloro-2-(1H-tetrazol-1-yl)phenyl)acrylamido)-3-phenylpropanamido)-[1,2,4]triazolo[1,5-a]pyridine-7-carboxylate

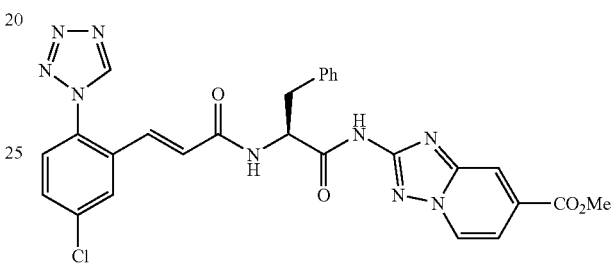

Example 93 was prepared in a similar manner as described for Example 3, by replacing p-nitroaniline with methyl 2-amino-[1,2,4]triazolo[1,5-a]pyridine-7-carboxylate (Synthesis, 2003, 11, 1649). LCMS m/z 572.0 [M+H]$^+$. $^1$H NMR (400 MHz CD$_3$OD) δ: 9.40 (s, 1H), 8.66 (dd, 1H), 8.15 (s, 1H), 7.87 (d, J=2.2 Hz, 1H), 7.56 (m, 1H), 7.47-7.45 (d, J=8.8 Hz, 1H), 7.21-7.15 (m, 9H), 7.00 (d, J=15.6 Hz, 1H), 6.68 (d, J=15.4 Hz, 1H), 4.86 (m, 1H), 3.89 (s, 3H), 3.23 (m, 2H) ppm. Analytical HPLC RT: 6.35 min (Method C, 8 min gradient).

Example 94

(S,E)-2-(2-(3-(5-chloro-2-(1H-tetrazol-1-yl)phenyl)acrylamido)-3-phenylpropanamido)-[1,2,4]triazolo[1,5-a]pyridine-6-carboxylic acid

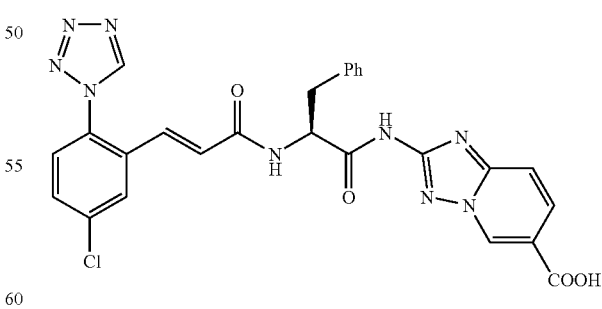

94A. (S)-methyl 2-(2-(tert-butoxycarbonylamino)-3-phenylpropanamido)-[1,2,4]triazolo[1,5-a]pyridine-6-carboxylate: Compound 94A was prepared in a similar manner as described for Example 3A by replacing p-nitroaniline with methyl 2-amino-[1,2,4]triazolo[1,5-a]pyridine-6-carboxylate (Synthesis, 2003, 11, 1649).

Example 94: Saponification of 94A, according to Example 2, followed by Boc-deprotection with 4N HCl/dioxane, and then amide coupling with 55E according to Example 55 gave Example 94. LCMS m/z 558.0 [M+H]$^+$. $^1$H NMR (400 MHz DMSO-d$_6$) δ: 9.78 (s, 1H), 9.22 (s, 1H), 8.52 (d, J=8.9 Hz, 1H), 7.97 (dd, J=1.6 & 9.3 Hz, 1H), 7.89 (d, J=2.1 Hz, 1H), 7.70-7.63 (m, 3H), 7.29-7.11 (m, 5H), 6.80-6.71 (q(AB), 2H), 4.81 (bs, 1H), 3.49 (bs, 1H), 3.31 (m, 1H), 2.83 (m, 1H) ppm. Analytical HPLC RT: 6.098 min (Method C, 8 min gradient).

Example 95

(S,E)-3-(5-chloro-2-(1H-tetrazol-1-yl)phenyl)-N-(1-oxo-3-phenyl-1-(4-(trifluoromethyl)phenylamino)propan-2-yl)acrylamide

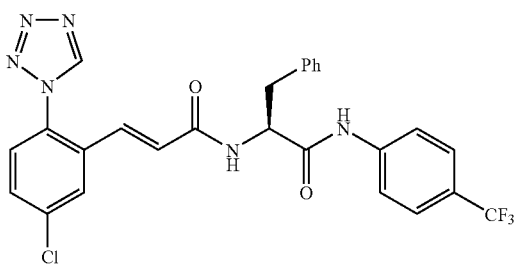 [SMILES: O=C(/C=C/c1cc(Cl)ccc1-n1cnnn1)N[C@@H](Cc1ccccc1)C(=O)Nc1ccc(C(F)(F)F)cc1]

Example 95 was prepared in a similar manner as described for Example 3. LCMS m/z 541.5 [M+H]$^+$. $^1$H NMR (400 MHz DMSO-d$_6$) δ: 9.78 (s, 1H), 8.57 (d, J=8.0 Hz, 1H), 7.88 (d, J=2.1 z, 1H), 7.72-7.59 (m, 6H), 7.21 (m, 4H), 7.13 (m, 1H), 6.78 (s, 2H), 4.70 (m, 1H), 3.01 (m, 1H), 2.87 (m, 1H) ppm. Analytical HPLC RT: 6.74 min (Method C, 8 min gradient).

Example 96

(S,E)-3-(5-chloro-2-(1H-tetrazol-1-yl)phenyl)-N-(1-(5-fluoropyridin-2-ylamino)-1-oxo-3-phenylpropan-2-yl)acrylamide, TFA salt

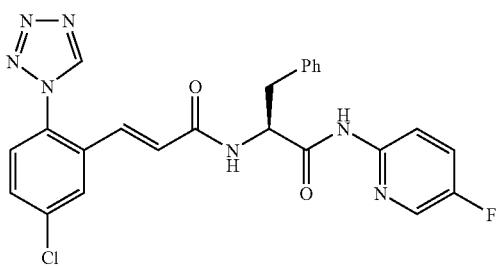 [SMILES: O=C(/C=C/c1cc(Cl)ccc1-n1cnnn1)N[C@@H](Cc1ccccc1)C(=O)Nc1ccc(F)cn1]

Example 96 was prepared in a similar manner as described for Example 3. LCMS m/z 492.4 [M+H]$^+$. $^1$H NMR (400 MHz, DMSO-d$_6$) δ: 9.77 (s, 1H), 8.45 (d, J=8.0 Hz, 1H), 8.29 (d, J=2.0 Hz, 1H), 8.08 (bs, 2H), 8.02 (m, 1H), 7.88 (d, J=2.2 Hz, 1H), 7.70-7.63 (m, 3H), 7.27-7.09 (m, 4H), 6.76 (d(q), 2H), 4.22 (m, 1H), 3.05 (m, 1H), 2.85 (m, 1H). Analytical HPLC RT: 5.756 min (Method C, 8 min gradient).

Example 97

(S,E)-3-(5-chloro-2-(1H-tetrazol-1-yl)phenyl)-N-(1-(6-fluorobenzo[d]thiazol-2-ylamino)-1-oxo-3-phenylpropan-2-yl)acrylamide

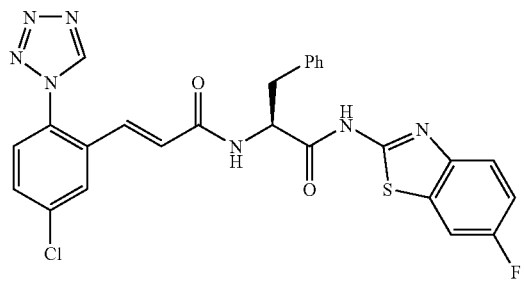 [SMILES: O=C(/C=C/c1cc(Cl)ccc1-n1cnnn1)N[C@@H](Cc1ccccc1)C(=O)Nc1nc2ccc(F)cc2s1]

Example 97 was prepared in a similar manner as described for Example 3. LCMS m/z 548.5 [M+H]$^+$. $^1$H NMR (400 MHz DMSO-d$_6$) δ: 9.77 (s, 1H), 8.62 (d, J=8.1 Hz, 1H), 7.90 (d, J=2.2 Hz, 1H), 7.85 (dd, J=2.2 & 8.2 Hz, 1H), 7.71-7.63 (m, 3H), 7.26-7.21 (m, 5H), 7.15 (m, 1H), 6.76 (s, 2H), 4.84 (m, 1H), 3.10 (m, 1H), 2.90 (m, 1H) ppm. Analytical HPLC RT: 5.756 min (Method C, 8 min gradient).

Example 98

(S,E)-4-(2-(3-(5-chloro-2-(1H-tetrazol-1-yl)phenyl)acrylamido)-3-phenylpropanamido)-N,N-dimethylbenzamide

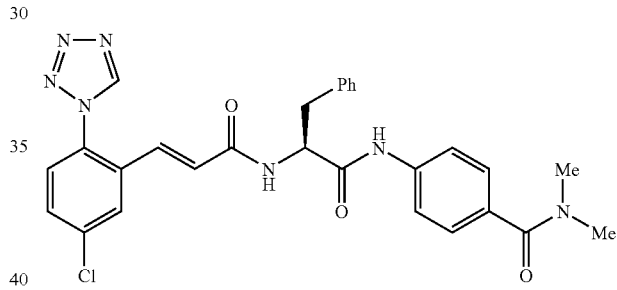

Example 98 was prepared in a similar manner as described for Example 3. LCMS m/z 544.5 [M+H]$^+$. $^1$H NMR (400 MHz CD$_3$OD) δ: 9.40 (s, 1H), 7.86 (d, J=2.2 Hz, 1H), 7.53 (dd, J=2.2 & 8.4 Hz, 1H), 7.49-7.42 (m, 3H), 7.28 (d, 2H), 7.18-7.07 (m, 9H), 6.99 (d, J=15.4 Hz, 1H), 6.68 (d, J=16.0 Hz, 1H), 4.71 (m, 1H), 3.11 (m, 2H), 2.98-2.91 (bd, 6H) ppm. Analytical HPLC RT: 5.323 min (Method C, 8 min gradient).

Example 99

(S,E)-3-(5-chloro-2-(1H-tetrazol-1-yl)phenyl)-N-(1-oxo-3-phenyl-1-(4-thiomorpholinophenylamino)propan-2-yl)acrylamide, TFA salt

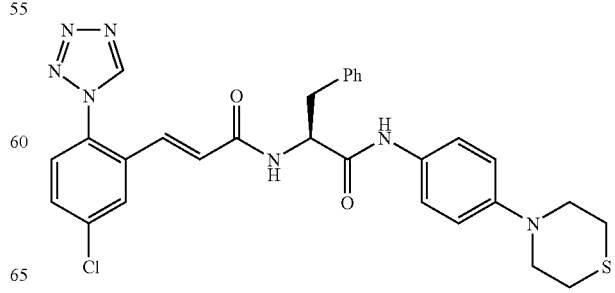

Example 99 was prepared in a similar manner as described for Example 3. LCMS m/z 574.4 [M+H]+. 1H NMR (400 MHz DMSO-d6) δ: 8.54 (bd, 8.4 Hz, 1H), 7.94 (s, 1H), 7.76-7.70 (m, 2H), 7.42 (d, J=8.8 Hz, 2H), 7.27-7.16 (m, 4H), 6.89-6.80 (m 2H), 4.74 (m, 1H), 3.43 (m, 4H), 3.08-3.03 (m, 1H), 2.92-2.89 (m, 1H), 2.68 (m, 4H) ppm. Analytical HPLC RT: 5.388 min (Method C, 8 min gradient).

Example 100

(S,E)-3-(5-chloro-2-(1H-tetrazol-1-yl)phenyl)-N-(1-(4-fluorophenylamino)-1-oxo-3-phenylpropan-2-yl)acrylamide

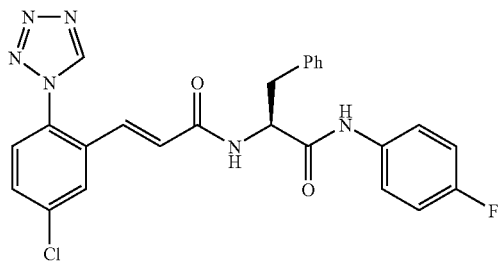 [SMILES: O=C(/C=C/c1cc(Cl)ccc1-n1cnnn1)N[C@@H](Cc1ccccc1)C(=O)Nc1ccc(F)cc1]

Example 100 was prepared in a similar manner as described for Example 3. LCMS m/z 491.4 [M+H]+. 1H NMR (400 MHz DMSO-d6) δ: 9.78 (s, 1H), 8.52 (d, J=8.1 Hz, 1H), 7.87 (d, J=2.2 Hz, 1H), 7.70-7.63 (m, 2H), 7.53-7.48 (m, 2H), 7.23-7.20 (d, 4H), 7.15-7.05 (m, 3H), 7.78 (d(AB), 2H), 4.69 (m, 1H), 3.02 (m, 1H), 2.89 (m, 1H) ppm. Analytical HPLC RT: 6.06 min (Method C, 8 min gradient).

Example 101

(S)—N-(1-(5-chloro-2-(1H-tetrazol-1-yl)phenethylamino)-1-oxo-3-phenylpropan-2-yl)-4-fluorobenzamide

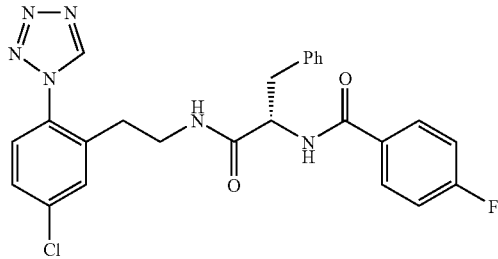 [SMILES: O=C(N[C@@H](Cc1ccccc1)C(=O)NCCc1cc(Cl)ccc1-n1cnnn1)c1ccc(F)cc1]

Example 101 was prepared in a similar manner as described for Example 28. LCMS m/z 493.4 [M+H]+. 1H NMR (400 MHz, CD3OD) δ: 9.42 (s, 1H), 8.25 (d, J=7.9 Hz, 1H), 8.05 (bt, 1H), 7.68 (m, 2H), 7.48 (d, J=2.1 Hz, 1H), 7.48-7.31 (m, 2H), 7.17-7.16 (m, 3H), 7.10-7.02 (m, 2H), 4.58 (m, 1H), 3.20 (m, 2H), 3.05 (m, 1H), 2.91 (m, 1H), 2.50 (m, 2H) ppm. Analytical HPLC RT: 5.861 min (Method C, 8 min gradient).

Example 102

(S)—N-1-(1-(5-chloro-2-(1H-tetrazol-1-yl)phenethylamino)-1-oxo-3-phenylpropan-2-yl)terephthalamide

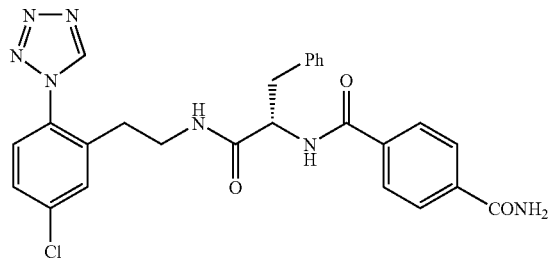 [SMILES: NC(=O)c1ccc(C(=O)N[C@@H](Cc2ccccc2)C(=O)NCCc2cc(Cl)ccc2-n2cnnn2)cc1]

Example 102 was prepared in a similar manner as described for Example 28. LCMS m/z 518.4 [M+H]+. 1H NMR (400 MHz, CD3OD) δ: 9.42 (s, 1H), 8.05 (bt, 1H), 8.08 (d, J=0.8 Hz, 2H), 7.82 (d, J=10.2 Hz, 2H), 7.49 (d, J=2.2 Hz, 1H), 7.39-7.31 (m, 2H), 7.20-7.05 (m, 5H), 4.61 (t, 1H), 3.25 (m, 2H), 3.05 (m, 1H), 2.90 (m, 1H), 2.50 (m, 2H) ppm. Analytical HPLC RT: 4.825 min (Method C, 8 min gradient).

Example 103

(S,E)-methyl 6-(2-(3-(5-chloro-2-(1H-tetrazol-1-yl)phenyl)acrylamido)-3-phenylpropanamido)nicotinate, TFA salt

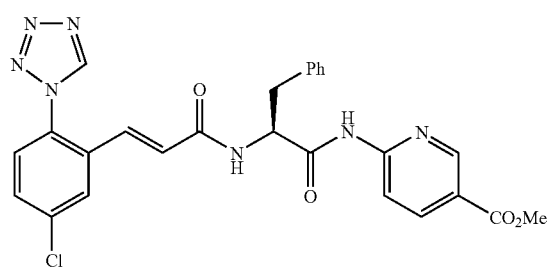

Example 103 was prepared in a similar manner as described for Example 3. LCMS m/z 532.0 [M+H]+. 1H NMR (400 MHz DMSO-d6) δ: 11.2 (s, 1H), 9.77 (s, 1H), 8.80 (d, J=1.5 Hz, 1H), 8.50-8.48 (d, J=7.8 Hz, 1H), 8.25-8.22 (dd, J=2.2 & 8.5 Hz, 1H), 8.13-8.10 (d, J=8.5 Hz, 1H), 7.89-7.88 (d, J=2.3 Hz, 1H), 7.69-7.63 (m, 2H), 7.29-7.11 (m, 5H), 4.85-4.80 (m, 1H), 3.80 (s, 3H), 3.08-3.04 (m, 1H), 2.84-2.67 (m, 1H) ppm. Analytical HPLC RT: 6.685 min (Method C, 8 min gradient).

Example 104

(S,E)-6-(2-(3-(5-chloro-2-(1H-tetrazol-1-yl)phenyl)acrylamido)-3-phenylpropanamido)nicotinic acid, TFA salt

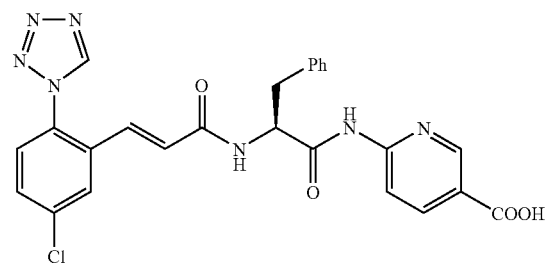 [SMILES: O=C(/C=C/c1cc(Cl)ccc1-n1cnnn1)N[C@@H](Cc1ccccc1)C(=O)Nc1ccc(C(=O)O)cn1]

Example 103 (32 mg, 60 mmol) was hydrolysed with LiOH following the procedured utilized for Example 2 to afford Example 104 as a white solid (5 mg, 15%). LCMS m/z 518.2 [M+H]+. $^1$H NMR (400 MHz, CD$_3$OD) δ: 9.40 (s, 1H), 8.76 (d, J=2.2 Hz, 1H), 8.23-8.20 (dd, J=2.2 & 7.8 Hz, 1H), 8.08-8.06 (d, J=8.8 Hz, 1H), 7.87 (d, J=2.2 Hz, 1H), 7.56-7.54 (dd, J=2.2 & 7.9 Hz, 1H), 7.47-7.45 (d, J=8.7 Hz, 1H), 7.19-7.09 (m, 4H), 7.00-7.69 (d, J=16.0 Hz, 1H), 6.67-6.63 (d, J=16.0 Hz, 1H), 4.82 (m, 1H), 3.18 (m, 1H), 2.98 (m, 1H) ppm. Analytical HPLC RT: 6.218 min (Method C, 8 min gradient).

Example 105

(S,E)-ethyl 1-(4-chloro-2-(3-(1-(4-(methoxycarbonyl)phenylamino)-1-oxo-3-phenylpropan-2-ylamino)-3-oxoprop-1-enyl)phenyl)-1H-1,2,3-triazole-4-carboxylate

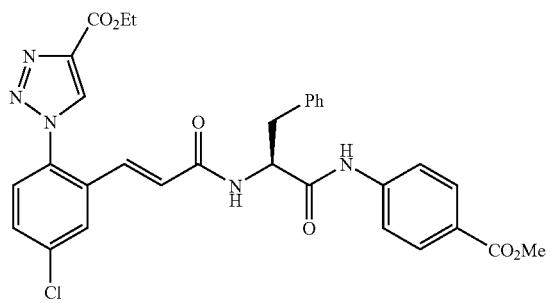 [SMILES: CCOC(=O)c1cn(-c2ccc(Cl)cc2/C=C/C(=O)N[C@@H](Cc2ccccc2)C(=O)Nc2ccc(C(=O)OC)cc2)nn1]

Example 105 was prepared in a similar manner as described for Example 3, by replacing 1C with Intermediate 5 in the amide coupling step. LCMS m/z 602.0 [M+H]+. $^1$H NMR (400 MHz, CD$_3$OD) δ: 8.74 (s, 1H), 7.85-7.82 (m, 2H), 7.54-7.44 (m, 3H), 7.16-7.07 (m, 4H), 7.07 (d, J=15.7 Hz, 1h), 6.67 (d, J=15.7 Hz, 1H), 4.72 (m, 1H), 4.33 (q, 2H), 3.78 (s, 3H), 3.11 (m, 1H), 2.96 (m, 1H), 1.29 (t, 3H) ppm. Analytical HPLC retention time 7.153 min (Method C, 8 min gradient).

Example 106

(S,E)-1-(2-(3-(1-(4-carboxyphenylamino)-1-oxo-3-phenylpropan-2-ylamino)-3-oxoprop-1-enyl)-4-chlorophenyl)-1H-1,2,3-triazole-4-carboxylic acid

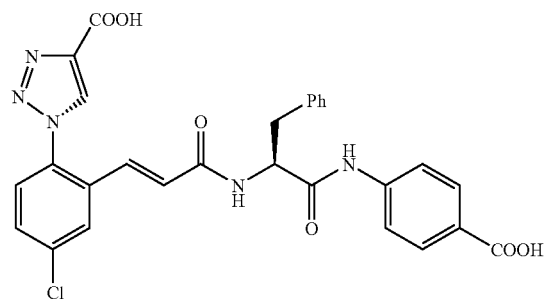

Hydrolysis of Example 105 according to Example 2 provided Example 106 as a white solid (10 mg, 7%). LCMS m/z 560.0 [M+H]+. $^1$H NMR (400 MHz DMSO-d$_6$) δ: 9.10 (s, 1H), 8.61 (d, J=8.0 Hz, 1H), 7.93-7.89 (m, 3H), 7.73-7.66 (m, 4H), 7.29-7.17 (m, 5H), 6.92-6.83 (d(AB), 2H), 4.81-4.75 (m, 1H), 3.12 (m, 1H), 2.94 (m, 1H) ppm. Analytical HPLC RT: 6.325 min (Method C, 8 min gradient).

Example 107

(S,E)-N-(1-(4-(1H-tetrazol-5-yl)phenylamino)-3-(4-fluorophenyl)-1-oxopropan-2-yl)-3-(5-chloro-2-(1H-tetrazol-1-yl)phenyl)acrylamide

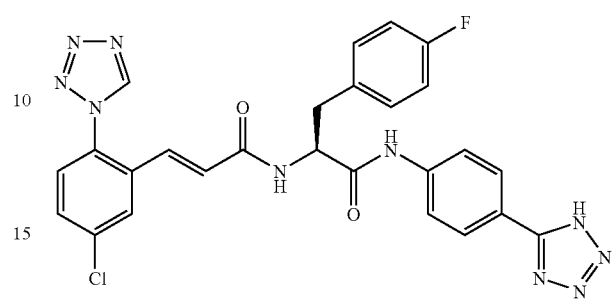

Example 107 was prepared in a similar manner as described for Example 43 LCMS: m/z 559.4 [M+H]+. $^1$H NMR (400 MHz, DMSO-d$_6$) δ 10.51 (1H, s), 9.84 (1H, s), 8.62 (1H, d, J=8.08 Hz), 7.91-8.06 (3H, m), 7.64-7.85 (4H, m), 7.30 (2H, dd, J=8.46, 5.68 Hz), 7.10 (2H, t, J=8.84 Hz), 6.72-6.92 (2H, m), 4.69-4.80 (1H, m), 3.08 (1H, dd, J=14.02, 4.93 Hz), 2.91 (1H, dd, J=13.77, 9.47 Hz) ppm. Analytical HPLC RT: 5.61 min (Method C, 8 min gradient).

Example 108

(E)-N-(1-(4-(1H-tetrazol-5-yl)phenylamino)-1-oxo-3-phenylpropan-2-yl)-3-(5-chloro-2-(1H-tetrazol-1-yl)phenyl)acrylamide

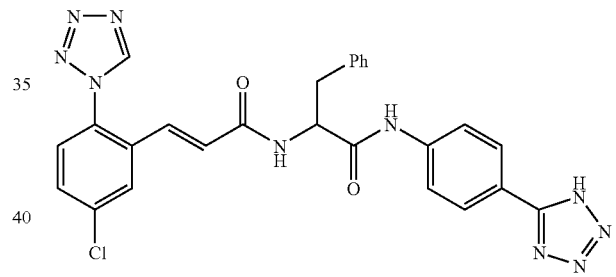

Example 108 was prepared in a similar manner as described for Example 43 starting from Boc-DL-phenylalanine. LCMS: m/z 541 [M+H]+. $^1$H NMR: (400 MHz, DMSO-d$_6$) δ: 10.51 (s, 1H), 9.84 (s, 1H), 8.61 (d, J=7.83 Hz, 1H), 7.92-8.09 (m, 3H), 7.66-7.82 (m, 4H), 7.13-7.33 (m, 6H), 6.71-6.90 (m, 2 H), 4.71-4.85 (m, 1H), 3.09 (dd, J=13.77, 5.18 Hz, 1H), 2.92 (dd, J=13.64, 9.35 Hz, 1H) ppm. Analytical HPLC RT: 5.53 min (Method C, 8 min gradient).

Example 109

4-[(S)-2-[(E)-3-(5-chloro-2-tetrazol-1-yl-phenyl)-acryloylamino]-4-(1,1-dioxo-1λ$^6$-thiomorpholin-4-yl)-4-oxo-butyrylamino]-benzoic acid

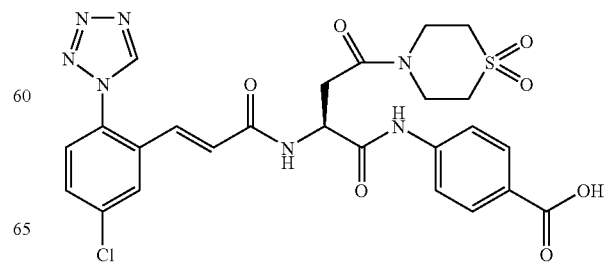

109A. (S)-4-(4-(tert-butoxycarbonyl)phenylamino)-3-(tert-butoxycarbonylamino)-4-oxobutanoic acid: To a solution of (S)-4-(benzyloxy)-2-(tert-butoxycarbonylamino)-4-oxobutanoic acid (1.0 g, 3.09 mmol) and tert-butyl 4-aminobenzoate (0.598 g, 3.09 mmol) in EtOAc (50 mL) was added DCC (0.766 g, 3.71 mmol). After 5 h, the reaction mixture was filtered. Solids were rinsed with EtOAc (2×25 mL). The combined filtrate was washed with 1.0M HCl, water, brine, dried over sodium sulfate, filtered, and concentrated. The residue was dissolved in MeOH (50 mL), 5% Pd/C was added, and slurry was stirred under a hydrogen atmosphere (50 psi) for 14 h. The slurry was filtered through a plug Celite®. The filter-cake was rinsed with MeOH. The combined filtrate was concentrated to give 109A (1.1 g, 87%). MS: m/z 409 [M+H]$^+$.

109B. 4-[(S)-2-tert-Butoxycarbonylamino-4-(1,1-dioxo-1$\lambda^6$-thiomorpholin-4-yl)-4-oxo-butyrylamino]-benzoic acid tert-butyl ester: The title compound was prepared according to Example 48A. LCMS: m/z 526 [M+H]$^+$.

Example 109: Deprotection of 109B with 4.0M HCl/dioxane and then amide coupling with 55E, according to the procedure described in Example 55, gave Example 109 LCMS: m/z 602 [M+H]$^+$. $^1$H NMR (400 MHz, CD$_3$OD) δ: 10.06 (1H, s), 9.45 (1H, s), 7.86-7.94 (3H, m), 7.55-7.66 (3H, m), 7.48-7.53 (1H, m), 7.10 (1H, d, J=15.41 Hz), 6.68 (1H, d, J=15.41 Hz), 4.91-5.03 (1H, m), 3.94 (5H, s), 2.96-3.09 (3H, m), 2.85-2.95 (1H, m), 2.75-2.82 (1H, m) ppm. Analytical HPLC RT: 4.85 min (Method C, 8 min gradient).

Example 110

(S,E)-2-methoxyethyl 4-(2-(3-(5-chloro-2-(1H-tetrazol-1-yl)phenyl)acrylamido)-3-phenylpropanamido)benzylcarbamate

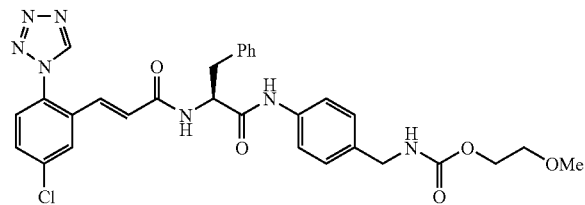 [SMILES: COCCOC(=O)NCc1ccc(NC(=O)[C@H](Cc2ccccc2)NC(=O)/C=C/c2cc(Cl)ccc2-n2cnnn2)cc1]

110A. 2-methoxyethyl 4-aminobenzylcarbamate: 2-Methoxyethyl carbonochloridate (0.075 g, 0.540 mmol) was added dropwise to a solution of tert-butyl 4-(aminomethyl)phenylcarbamate (0.10 g, 0.450 mmol) and pyridine (0.055 mL, 0.675 mmol) in DCM (5 mL) at 0° C. The mixture was allowed to stir at rt for 1 h before concentrating. The residue was taken up in EtOAc (15 mL), washed with 1.0M HCl (3×3 mL), water, brine, dried over sodium sulfate, filtered and concentrated. This material was dissolved in MeOH, and 4.0M HCl (2 mL, in dioxane) was added. The reaction mixture was stirred continuously for 12 h, and evaporated to dryness. The residue was taken up in EtOAc (20 mL) and treated with saturated NaHCO$_3$ solution with stirring. After 10 min, the organic layer was separated, washed with brine, dried over sodium sulfate, filtered, and concentrated to afford 110A. LCMS: m/z 325.4 [M+H]$^+$.

Example 110: 110A was dissolved in EtOAc (10 mL) and (S)-2-(tert-butoxycarbonylamino)-3-phenylpropanoic acid (0.119 g, 0.450 mmol) and DCC (0.111 g, 0.540 mmol) added, respectively. The mixture was stirred overnight. The mixture was washed with 1.0M HCl solution, water, brine, dried over sodium sulfate, filtered, and concentrated. The amine was deprotected by dissolution in MeOH (5 mL) and treatment with 4.0M HCl (2 mL, in dioxane) with stirring. After 2 h, the reaction mixture was evaporated to dryness. The residue was taken up in EtOAc (20 mL) and treated with saturated NaHCO$_3$ solution with stirring. After 10 min, the organic layer was separated, washed with brine, dried over sodium sulfate, filtered, and concentrated. The free base was dissolved in THF (5 mL), 1C (0.113 g, 0.450 mmol), TEA (0.188 mL, 1.350 mmol), and BOP reagent (0.239 g, 0.540 mmol) were added. After 1.5 h, the reaction mixture was partitioned between EtOAc and water. The organic layer was washed with brine, dried over sodium sulfate, filtered, and concentrated. Purification by reverse phase preparatory HPLC (MeOH/water/TFA) afforded Example 110 (32 mg, 11%) as a white solid after lyophilization. LCMS: m/z 605 [M+H]$^+$. $^1$H NMR (400 MHz, DMSO-d$_6$) δ 10.16 (1H, s), 9.84 (1H, s), 8.55 (1H, d, J=8.25 Hz), 7.93 (1H, d, J=2.20 Hz), 7.68-7.78 (3H, m), 7.48 (2H, d, J=8.24 Hz), 7.26 (4H, d, J=4.40 Hz), 7.13-7.20 (3H, m), 6.75-6.93 (2H, m), 4.67-4.84 (1H, m), 4.03-4.15 (4H, m), 3.44-3.52 (2H, m), 3.24 (3H, s), 3.05 (1H, dd, J=13.74, 4.95 Hz), 2.89 (1H, dd, J=13.47, 9.07 Hz) ppm. Analytical HPLC RT: 6.37 min (Method C, 8 min gradient).

Example 111

(S,E)-methyl 4-(2-(3-(5-chloro-2-(1H-tetrazol-1-yl)phenyl)acrylamido)-3-phenylpropanamido)benzylcarbamate

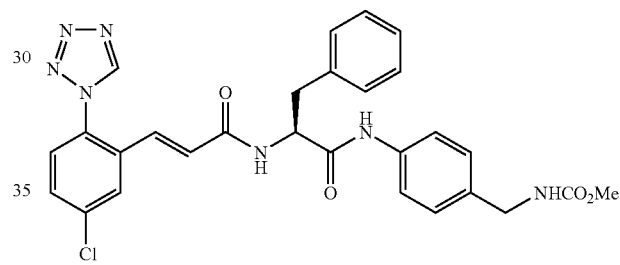

111A. Methyl 4-aminobenzylcarbamate: The title compound was prepared in a similar manner as described for Example 110A. LCMS: m/z 181.2 [M+H]$^+$.

Example 111 was prepared as a white solid in a similar manner as described for Example 3. LCMS: m/z 560 [M+H]$^+$. $^1$H NMR (400 MHz, DMSO-d$_6$) δ: 10.16 (1H, s), 9.84 (1H, s), 8.55 (1H, d, J=8.24 Hz), 7.93 (1H, s), 7.67-7.78 (2H, m), 7.63 (1H, t, J=5.77 Hz), 7.48 (2H, d, J=8.25 Hz), 7.13-7.31 (7H, m), 6.74-7.00 (2H, m), 4.68-4.80 (1H, m, J=4.95 Hz), 4.11 (2H, d, J=6.05 Hz), 3.53 (3H, s), 3.05 (1H, dd, J=13.74, 4.95 Hz), 2.89 (1H, dd, J=13.47, 9.07 Hz) ppm. Analytical HPLC RT: 5.54 min (Method C, 8 min gradient).

Example 112

(S,E)-2-methoxyethyl 4-(2-(3-(5-chloro-2-(1H-tetrazol-1-yl)phenyl)acrylamido)-3-phenylpropanamido)phenylcarbamate

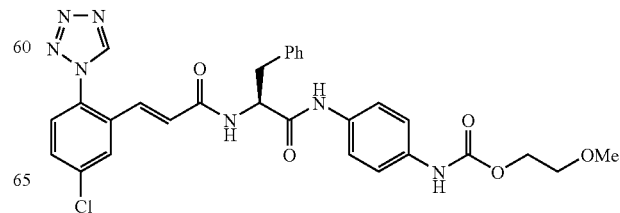

Example 112 was prepared in a similar manner as described for Example 3 LCMS: m/z 560 (M+H, chlorine isotope). $^1$H NMR (400 MHz, DMSO-$d_6$) δ: 10.09 (1H, s), 9.84 (1H, s), 9.66 (1H, s), 8.54 (1H, d, J=8.24 Hz), 7.92 (1H, d, J=2.20 Hz), 7.66-7.78 (2H, m), 7.41-7.49 (2H, m), 7.30-7.40 (2H, m), 7.26 (4H, d, J=4.40 Hz), 7.14-7.20 (1H, m), 6.71-6.97 (2H, m), 4.62-4.80 (1 H, m), 4.11-4.36 (2H, m), 3.50-3.58 (2H, m), 3.27 (3H, s), 3.04 (1H, dd, J=13.74, 5.50 Hz), 2.88 (1H, dd, J=13.74, 9.34 Hz) ppm. Analytical HPLC retention time 6.43 min (Method C, 8 min gradient).

Example 113

(E)-3-(5-chloro-2-tetrazol-1-yl-phenyl)-N-{(S)-1-[4-(1,1-dioxo-1λ$^6$-thiomorpholin-4-yl)-phenylcarbamoyl]-2-phenyl-ethyl}-acrylamide, TFA salt

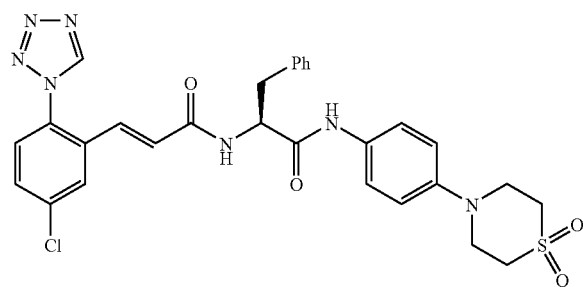 [SMILES: O=C(/C=C/c1cc(Cl)ccc1-n1cnnn1)N[C@@H](Cc1ccccc1)C(=O)Nc1ccc(N2CCS(=O)(=O)CC2)cc1]

Example 113 was prepared via coupling of commercially available 4-(1H-tetrazol-5-yl)aniline with 4-(1,1-dioxo-1δ$^6$-thiomorpholin-4-yl)-phenylamine according to the procedure adopted for Example 3. MS: m/z 606.5 [M+H]$^+$. $^1$H NMR (400 MHz, DMSO-$d_6$) δ 10.02 (1H, s), 9.84 (1H, s), 7.92 (1H, d, J=2.20 Hz), 7.67-7.79 (2H, m), 7.43 (2H, d, J=9.34 Hz), 7.23-7.29 (4H, m), 7.14-7.21 (1H, m), 6.97 (2H, d, J=9.34 Hz), 6.77-6.90 (2H, m), 4.62-4.82 (1H, m), 3.63-3.74 (4H, m), 2.83-3.14 (6H, m) ppm. Analytical HPLC RT: 5.25 min (Method C, 8 min gradient).

Example 114

(S,E)-3-(5-chloro-2-(1H-tetrazol-1-yl)phenyl)-N-(1-oxo-3-phenyl-1-(4-(ureidomethyl)phenylamino)propan-2-yl)acrylamide

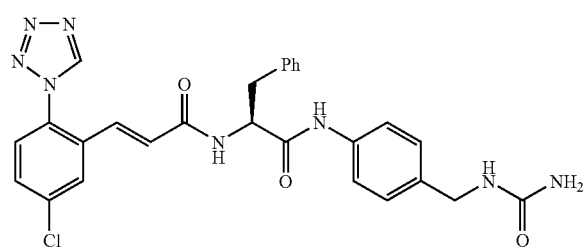 [SMILES: NC(=O)NCc1ccc(NC(=O)[C@H](Cc2ccccc2)NC(=O)/C=C/c2cc(Cl)ccc2-n2cnnn2)cc1]

Example 114 was prepared via coupling of commercially available 4-(1H-tetrazol-5-yl)aniline according to the procedure adopted for Example 3. LCMS: m/z 545 [M+H]$^+$. $^1$H NMR (400 MHz, DMSO-$d_6$) δ 10.13 (1H, s), 9.84 (1H, s), 8.53 (1H, d, J=8.08 Hz), 7.92 (1H, d, J=2.27 Hz), 7.67-7.78 (2H, m), 7.47 (2H, d, J=8.59 Hz), 7.25 (4H, d, J=4.29 Hz), 7.13-7.22 (3H, m), 6.76-6.94 (2H, m), 6.33 (1H, s), 5.48 (2H, s), 4.74 (1H, d, J=4.80 Hz), 4.10 (2H, d, J=5.81 Hz), 3.01-3.15 (1H, m), 2.84-2.97 (1H, m) ppm. Analytical HPLC RT: 5.04 min (Method C, 8 min gradient).

Example 115

(S,E)-3-(4-(2-(3-(5-chloro-2-(1H-tetrazol-1-yl)phenyl)acrylamido)-3-phenylpropanamido)phenylcarbamoyloxy)propanoic acid

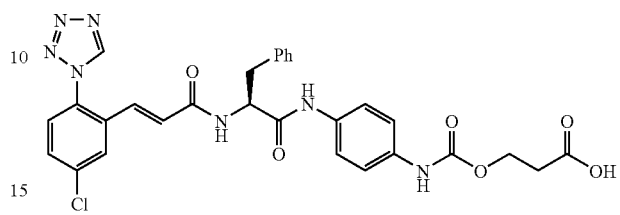

115A. tert-butyl 3-(4-nitrophenylcarbamoyloxy)propanoate: 1-Isocyanato-4-nitrobenzene (0.50 g, 3.05 mmol), tert-butyl 3-hydroxypropanoate (0.534 g, 3.66 mmol), and triethylamine (0.849 mL, 6.09 mmol) were added to THF (30.5 mL) at rt. After stirring for 15 h, the reaction mixture was concentrated onto silica gel and purified by flash chromatography (40 g column, 100% DCM) to afford 115A as an amber solid. LCMS: m/z 311 [M+H]$^+$.

115B. (S)-3-(4-(2-amino-3-phenylpropanamido)phenylcarbamoyloxy)-propanoic acid, TFA salt: A solution of 115A in 5:1 acetone-H$_2$O (16 mL) was treated with zinc (0.996 g, 15.23 mmol) and ammonium chloride (1.630 g, 30.5 mmol) with stirring at rt overnight. The reaction mixture was concentrated, diluted with EtOAc (200 mL), and filtered through a plug of Celite®, and the filter cake was rinsed with EtOAc. The combined filtrate was washed with water (200 mL), brine, dried over sodium sulfate, filtered and concentrated to give crude tert-butyl 3-(4-aminophenylcarbamoyloxy)-propanoate. The residue was dissolved in EtOAc (20 mL) and (S)-2-(tert-butoxycarbonylamino)-3-phenylpropanoic acid (0.808 g, 3.05 mmol) and N,N'-dicyclohexylcarbodiimide were added (0.629 g, 3.05 mmol) according to the procedure described for Example 43A to afford 115B (0.838 g, 57%). LCMS: m/z 372 [M+H]$^+$.

Example 115: Amide coupling of 115B and 55E, according to the procedure described for Example 55, gave Example 115. LCMS: m/z 604 (M+H, chlorine isotope). $^1$H NMR (400 MHz, DMSO-$d_6$) δ 10.08 (1H, s), 9.83 (1H, s), 9.58 (1H, s), 8.52 (1H, d, J=8.08 Hz), 7.92 (1H, d, J=1.77 Hz), 7.65-7.78 (2H, m), 7.41-7.49 (2H, m), 7.31-7.39 (2H, m), 7.25 (4H, d, J=4.29 Hz), 7.13-7.22 (1H, m), 6.72-6.91 (2H, m), 4.62-4.82 (1H, m), 4.24 (2H, t, J=6.06 Hz), 2.99-3.13 (1 H, m), 2.88 (1H, dd, J=13.64, 9.35 Hz), 2.60 (2H, t, J=6.06 Hz) ppm. Analytical HPLC RT: 5.42 min (Method C, 8 min gradient).

Example 116

(S,E)-methyl 3-(3-(4-(2-(3-(5-chloro-2-(1H-tetrazol-1-yl)phenyl)acrylamido)-3-phenylpropanamido)phenyl)ureido)propanoate

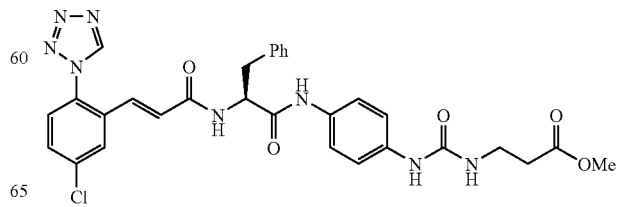

Example 116 was prepared in a similar manner as described for Example 115 LCMS: m/z 617 (M+H, chlorine isotope). $^1$H NMR (400 MHz, CD$_3$OD) δ: 9.49 (1H, s), 7.96 (1H, d, J=1.77 Hz), 7.61-7.66 (1H, m), 7.53-7.58 (1H, m), 7.29-7.36 (2H, m), 7.23-7.29 (6H, m, J=4.80 Hz), 7.15-7.22 (1H, m), 7.08 (1H, d, J=15.66 Hz), 6.75 (1H, d, J=15.41 Hz), 4.73-4.80 (1H, m), 3.68 (3H, s), 3.41-3.50 (3H, m), 3.10-3.20 (2H, m), 2.97-3.06 (1H, m), 2.55 (2H, t, J=6.32 Hz) ppm. Analytical HPLC RT: 5.46 min (Method C, 8 min gradient).

Example 117

(S,E)-pyridin-2-ylmethyl 4-(2-(3-(5-chloro-2-(1H-tetrazol-1-yl)phenyl)acrylamido)-3-phenylpropanamido)phenylcarbamate, TFA salt

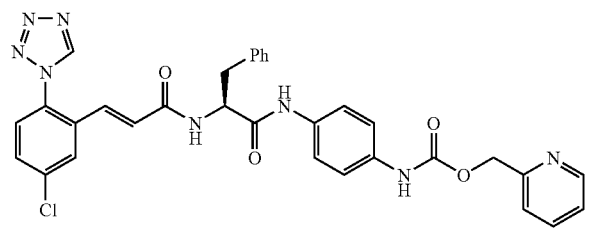 [SMILES: O=C(/C=C/c1cc(Cl)ccc1-n1cnnn1)N[C@@H](Cc1ccccc1)C(=O)Nc1ccc(NC(=O)OCc2ccccn2)cc1]

Example 117 was prepared in a similar manner as described for Example 115 LCMS: m/z 624 [M+H]$^+$. $^1$H NMR (400 MHz, DMSO-d$_6$) δ: 10.11 (1H, s), 9.76-9.89 (2H, m), 8.49-8.62 (2H, m), 7.92 (1H, d, J=2.20 Hz), 7.79-7.88 (1H, m, J=7.70, 7.70 Hz), 7.66-7.77 (2H, m), 7.43-7.49 (3H, m), 7.32-7.41 (3H, m), 7.26 (4H, d, J=4.40 Hz), 7.13-7.21 (1H, m), 6.75-6.90 (2H, m), 5.19 (2 H, s), 4.67-4.78 (1H, m), 3.05 (1H, dd, J=13.74, 4.95 Hz), 2.88 (1H, dd, J=13.74, 9.34 Hz) ppm. Analytical HPLC RT: 6.88 min (Method D, 15 min gradient).

Example 118

((S)-5-oxotetrahydrofuran-2-yl)methyl 4-((S)-2-((E)-3-(5-chloro-2-(1H-tetrazol-1-yl)phenyl)acrylamido)-3-phenylpropanamido)phenylcarbamate

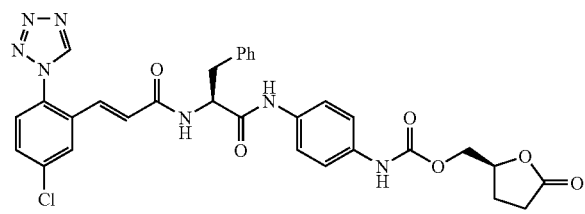 [SMILES: O=C(/C=C/c1cc(Cl)ccc1-n1cnnn1)N[C@@H](Cc1ccccc1)C(=O)Nc1ccc(NC(=O)OC[C@@H]2CCC(=O)O2)cc1]

Example 118 was prepared in a similar manner as described for Example 115 LCMS: m/z 631 [M+H]$^+$. $^1$H NMR (400 MHz, DMSO-d$_6$) δ: 10.11 (1H, s), 9.84 (1H, s), 9.71 (1H, s), 8.55 (1H, d, J=8.25 Hz), 7.92 (1H, d, J=2.20 Hz), 7.68-7.76 (2H, m), 7.43-7.48 (2H, m), 7.37 (2H, d, J=8.25 Hz), 7.26 (4H, d, J=4.40 Hz), 7.14-7.22 (1H, m), 6.77-6.90 (2H, m), 4.67-4.82 (2H, m), 4.23-4.31 (1H, m), 4.11-4.21 (1H, m), 3.05 (1H, dd, J=13.74, 4.95 Hz), 2.88 (1H, dd, J=13.74, 9.34 Hz), 2.51-2.60 (2H, m), 2.20-2.33 (1H, m), 1.88-2.02 (1H, m), 1.44-1.78 (3H, m), 0.96-1.30 (3H, m) ppm. Analytical HPLC RT: 7.67 min (Method D, 15 min gradient).

Example 119

(S,E)-3-(3-(4-(2-(3-(5-chloro-2-(1H-tetrazol-1-yl)phenyl)acrylamido)-3-phenylpropanamido)phenyl)ureido)propanoic acid

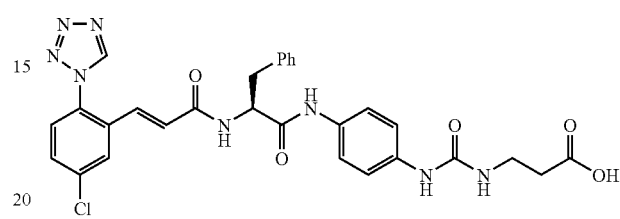

Example 119 was prepared in a similar manner as described for Example 115 LCMS: m/z 604 [M+H]$^+$. $^1$H NMR (400 MHz, DMSO-d$_6$) δ: 12.24 (1H, s), 10.00 (1H, s), 9.84 (1H, s), 8.51 (1H, d, J=8.08 Hz), 8.46 (1H, s), 7.92 (1H, d, J=2.02 Hz), 7.67-7.79 (2H, m), 7.39 (2H, d, J=9.09 Hz), 7.23-7.32 (6H, m), 7.14-7.21 (1H, m), 6.76-6.90 (2H, m), 6.15 (1H, t, J=5.94 Hz), 4.66-4.80 (1H, m, J=5.05 Hz), 3.20-3.30 (2H, m), 3.00-3.11 (1H, m, J=5.31 Hz), 2.82-2.93 (1H, m) ppm. Analytical HPLC RT: 5.18 min (Method C, 8 min gradient).

Example 120

(S,E)-3-(5-chloro-2-(1H-tetrazol-1-yl)phenyl)-N-(1-oxo-3-phenyl-1-(4-(3-(pyridin-2-ylmethyl)ureido)phenylamino)propan-2-yl)acrylamide, TFA salt

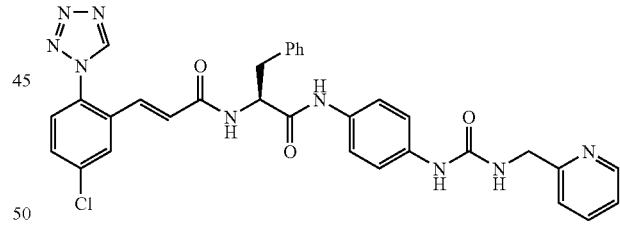

120A. 1-(4-nitrophenyl)-3-(pyridin-2-ylmethyl)urea: The title compound was prepared in a similar manner for 115A using 2-aminomethylpyridine as the urea forming agents. LCMS: m/z 273.3 [M+H]$^+$.

120B. (S)-tert-butyl 1-oxo-3-phenyl-1-(4-(3-(pyridin-2-ylmethyl)ureido)phenylamino)propan-2-ylcarbamate: The title compound was prepared in a similar manner to that adopted for 115B. LCMS: m/z 490 [M+H]$^+$.

Example 120: The title compound was prepared according to the procedures described for Example 3. LCMS: m/z 623 [M+H]$^+$. $^1$H NMR (400 MHz, DMSO-d$_6$) δ: 10.06 (1H, s), 9.85 (1H, s), 8.88 (1H, s), 8.65 (1H, d, J=4.83 Hz), 8.55 (1H, d, J=8.35 Hz), 8.13 (1H, t, J=7.47 Hz), 7.92 (1H, d, J=2.20 Hz), 7.68-7.79 (2H, m), 7.54-7.66 (2H, m), 7.14-7.47 (9H, m), 6.75-6.95 (3H, m), 4.67-4.78 (1H, m), 4.50 (2H, d, J=4.39

Hz), 3.04 (1H, dd, J=13.62, 4.83 Hz), 2.88 (1H, dd, J=13.62, 9.23 Hz) ppm. Analytical HPLC RT: 4.42 min (Method C, 8 min gradient).

Example 121

(S,E)-pyridin-4-ylmethyl 4-(2-(3-(5-chloro-2-(1H-tetrazol-1-yl)phenyl)acrylamido)-3-phenylpropanamido)phenylcarbamate, TFA salt

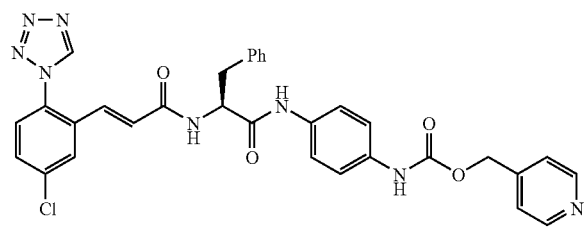 [SMILES: O=C(/C=C/c1cc(Cl)ccc1-n1cnnn1)N[C@@H](Cc1ccccc1)C(=O)Nc1ccc(NC(=O)OCc2ccncc2)cc1]

Example 121 was prepared in a similar manner as described for Example 120 LCMS: m/z 604 [M+H]$^+$. $^1$H NMR (400 MHz, DMSO-d$_6$) δ: 10.12 (1H, s), 9.84 (1H, s), 8.73 (1H, s), 8.64 (1H, d, J=3.95 Hz), 8.56 (1H, d, J=7.91 Hz), 8.04 (1H, d, J=7.91 Hz), 7.92 (1H, d, J=1.76 Hz), 7.68-7.81 (2H, m), 7.60 (1 H, dd, J=7.91, 4.83 Hz), 7.43-7.50 (2H, m), 7.37 (2H, d, J=8.79 Hz), 7.14-7.30 (5H, m), 6.75-6.91 (2H, m), 5.21 (2H, s), 4.66-4.76 (1H, m), 3.04 (1H, dd, J=13.40, 5.05 Hz), 2.88 (1H, dd, J=13.62, 9.23 Hz) ppm. Analytical HPLC RT: 4.57 min (Method C, 8 min gradient).

Example 122

(S,E)-methyl 4-(3-(4-(2-(3-(5-chloro-2-(1H-tetrazol-1-yl)phenyl)acrylamido)-3-phenylpropanamido)phenyl)ureido)butanoate

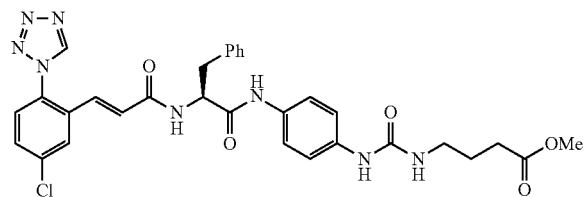 [SMILES: COC(=O)CCCNC(=O)Nc1ccc(NC(=O)[C@H](Cc2ccccc2)NC(=O)/C=C/c2cc(Cl)ccc2-n2cnnn2)cc1]

Example 122 was prepared in a similar manner as described for Example 120 LCMS: m/z 632 [M+H]$^+$. $^1$H NMR (400 MHz, DMSO-d$_6$) δ: 10.03 (1H, s), 9.85 (1H, s), 8.54 (1H, d, J=8.35 Hz), 8.33 (1H, s), 7.92 (1H, d, J=2.20 Hz), 7.66-7.77 (2H, m), 7.35-7.45 (2H, m), 7.12-7.32 (7H, m), 6.76-6.93 (2H, m), 6.12 (1H, t, J=5.93 Hz), 4.66-4.76 (1H, m), 3.58 (3H, s), 3.00-3.14 (3H, m), 2.88 (1H, dd, J=13.62, 9.23 Hz), 2.32 (2H, t, J=7.25 Hz), 1.60-1.74 (2H, m) ppm. Analytical HPLC RT: 5.63 min (Method C, 8 min gradient).

Example 123

(S,E)-pyridin-3-ylmethyl 4-(2-(3-(5-chloro-2-(1H-tetrazol-1-yl)phenyl)acrylamido)-3-phenylpropanamido)phenylcarbamate, TFA salt

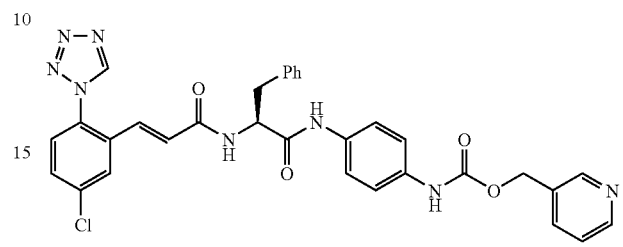

Example 123 was prepared in a similar manner as described for Example 115 and 120. LCMS: m/z 624 [M+H]$^+$. $^1$H NMR (400 MHz, DMSO-d$_6$) δ: 10.12 (1H, s), 9.84 (1H, s), 8.73 (1H, s), 8.64 (1H, d, J=3.95 Hz), 8.56 (1H, d, J=7.91 Hz), 8.04 (1H, d, J=7.91 Hz), 7.92 (1H, d, J=1.76 Hz), 7.68-7.81 (2H, m), 7.60 (1H, dd, J=7.91, 4.83 Hz), 7.43-7.50 (2H, m), 7.37 (2H, d, J=8.79 Hz), 7.14-7.30 (5H, m), 6.75-6.91 (2H, m), 5.21 (2H, s), 4.66-4.76 (1H, m), 3.04 (1H, dd, J=13.40, 5.05 Hz), 2.88 (1H, dd, J=13.62, 9.23 Hz) ppm. Analytical HPLC RT: 4.70 min (Method C, 8 min gradient).

Example 124 ethyl 1-(4-(((S)-2-((E)-3-(5-chloro-2-(1H-tetrazol-1-yl)phenyl)acrylamido)-3-phenylpropanamido)phenylcarbamoyl)piperidine-3-carboxylate

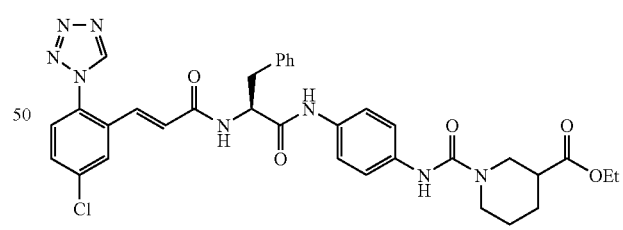

Example 124 was prepared in a similar manner as described for Example 120 LCMS: m/z 672 [M+H]$^+$. $^1$H NMR (400 MHz, DMSO-d$_6$) δ: 10.02 (1H, s), 9.84 (1H, s), 8.52 (1H, d, J=8.34 Hz), 8.46 (1H, s), 7.92 (1H, d, J=2.02 Hz), 7.68-7.77 (2H, m), 7.32-7.43 (4H, m), 7.26 (4H, d, J=4.29 Hz), 7.13-7.22 (1H, m), 6.77-6.93 (2H, m), 4.66-4.78 (1H, m), 4.07 (3H, q, J=7.07 Hz), 3.85 (1H, s), 2.83-3.13 (4H, m), 1.93 (1H, s), 1.61 (2H, d, J=9.09 Hz), 1.43 (1H, s), 1.18 (3H, t, J=7.07 Hz) ppm. Analytical HPLC RT: 5.98 min (Method C, 8 min gradient).

Example 125

1-(4-((S)-2-((E)-3-(5-chloro-2-(1H-tetrazol-1-yl)phenyl)acrylamido)-3-phenylpropanamido)phenylcarbamoyl)piperidine-3-carboxylic acid

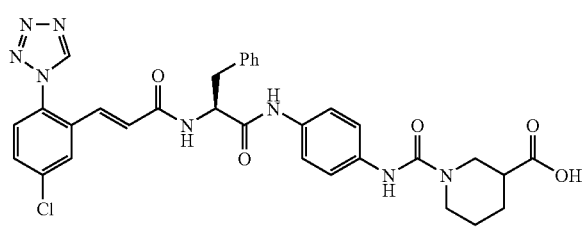 [SMILES: O=C(/C=C/c1cc(Cl)ccc1-n1cnnn1)N[C@@H](Cc1ccccc1)C(=O)Nc1ccc(NC(=O)N2CCCC(C(=O)O)C2)cc1]

Example 124 was hydrolysed as in Example 2 to afford Example 125. LCMS: m/z 644 [M+H]+. 1H NMR (400 MHz, DMSO-d6) δ: 12.39 (1H, br. s.), 10.05 (1H, s), 9.85 (1H, s), 8.55 (1H, d, J=8.35 Hz), 8.47 (1H, s), 7.93 (1H, d, J=2.20 Hz), 7.66-7.78 (2H, m), 7.31-7.42 (4H, m), 7.26 (4H, d, J=3.95 Hz), 7.14-7.21 (1H, m), 6.77-6.89 (2H, m), 4.66-4.77 (1H, m), 4.07-4.15 (1H, m, J=3.08 Hz), 3.86-3.95 (1H, m, J=13.18 Hz), 3.05 (1H, dd, J=13.62, 5.27 Hz), 2.80-2.97 (3H, m), 2.29-2.40 (1H, m), 1.90-2.00 (1H, m, J=12.74 Hz), 1.34-1.69 (3H, m) ppm. Analytical HPLC RT: 5.47 min (Method C, 8 min gradient).

Example 126

(S,E)-methyl 4-(2-(3-(5-chloro-2-(1H-tetrazol-1-yl)phenyl)acrylamido)-3-phenylpropanamido)-2-fluorophenylcarbamate

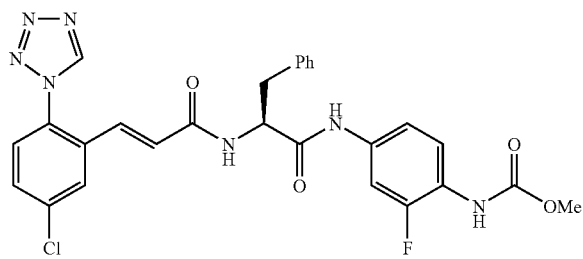 [SMILES: COC(=O)Nc1ccc(NC(=O)[C@H](Cc2ccccc2)NC(=O)/C=C/c2cc(Cl)ccc2-n2cnnn2)cc1F]

126A. methyl 2-fluoro-4-nitrophenylcarbamate: Methyl carbonochloridate (0.121 g, 1.281 mmol) was added dropwise to a solution of 2-fluoro-4-nitroaniline (0.20 g, 1.281 mmol) and pyridine (0.207 mL, 2.56 mmol) in DCM (15 mL) at 0° C. After 1 h, the reaction mixture was concentrated. The resulting oil was dissolved in EtOAc, washed with 1.0M HCl solution (3×50 mL), water, brine, dried over sodium sulfate, filtered, and concentrated to give 126A. LCMS: m/z 213 [M−H]−.

Example 126: Compound 126A was converted to the title compound Example 126 according to Example 3. LCMS: m/z 564 [M+H]+. 1H NMR (400 MHz, DMSO-d6) δ: 10.35 (1H, s), 9.84 (1H, s), 9.19 (1H, s), 8.59 (1H, d, J=7.70 Hz), 7.93 (1H, s), 7.68-7.77 (2H, m), 7.54-7.62 (1H, m), 7.47 (1H, t, J=8.52 Hz), 7.24-7.30 (4H, m), 7.16-7.22 (2H, m), 6.75-6.93 (2H, m), 4.66-4.77 (1H, m), 3.63 (3H, s), 3.05 (1H, dd, J=14.02, 5.22 Hz), 2.89 (1H, dd, J=13.74, 9.34 Hz) ppm. Analytical HPLC RT: 5.57 min (Method C, 8 min gradient).

Example 127

(S,E)-methyl 2-(2-(3-(5-chloro-2-(1H-tetrazol-1-yl)phenyl)acrylamido)-3-phenylpropanoyl)-1,2,3,4-tetrahydroisoquinolin-6-ylcarbamate

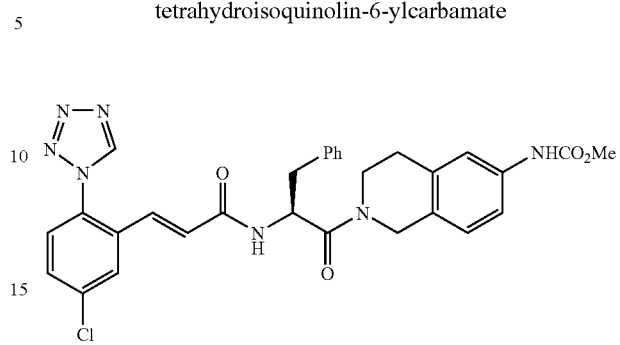

127A. methyl 1,2,3,4-tetrahydroisoquinolin-6-ylcarbamate: tert-Butyl 6-amino-3,4-dihydroisoquinoline-2(1H)-carboxylate (0.58 g, 2.336 mmol) in DCM (10 mL) and pyridine (2 mL) cooled to 0° C. was added methyl chloroformate (0.217 mL, 2.80 mmol). The reaction was warmed to rt and stirred for 24 h, quenched with water (10 mL) and extracted with ethyl acetate (3×30 mL). The combined organic layers were washed with 0.1N HCl (10 mL), sat'd NaHCO3, brine (10 mL) and dried (MgSO4). Purification with silica gel chromatography using hexanes and ethyl acetate as eluents afforded 0.65 g of a yellow solid which was re-dissolved in DCM (10 mL). To this solution was added TFA (3 mL) and stirred for 24 h. The reaction mixture was concentrated and quenched with sat'd NaHCO3 (15 mL) and extracted with ethyl acetate (3×30 mL). The combined organic layers were dried (MgSO4) to afford 127A as yellow solid (0.38 g, 79%). MS m/z 207.2 (M+H)+.

Example 127 was prepared in a similar manner as described for Example 62. 1H NMR (400 MHz, CD3OD) δ: 9.49 (1H, d, J=1.52 Hz), 7.95 (1H, dd, J=11.50, 2.15 Hz), 7.61-7.70 (1H, m), 7.51-7.58 (1H, m), 7.12-7.24 (6H, m), 6.99-7.09 (2H, m), 6.66-6.79 (2H, m), 5.16-5.23 (1H, m), 4.47-4.62 (2H, m), 3.71 (3H, s), 3.52-3.73 (1H, m), 2.94-3.13 (3H, m), 2.70 (2H, br. s.) ppm. LCMS m/z 586.4 [M+H]+. Analytical HPLC RT: 8.90 min. (Method D).

Example 128

(R,E)-methyl 4-(2-(3-(5-chloro-2-(1H-tetrazol-1-yl)phenyl)acrylamido)-3-phenylpropanamido)phenylcarbamate

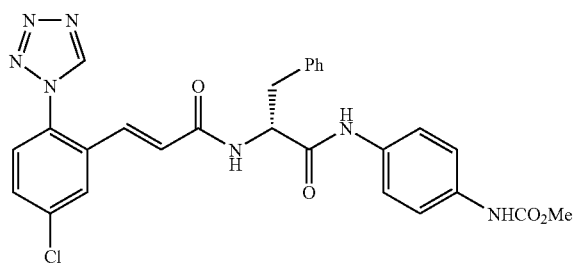

Example 128 was prepared in a similar manner as described for Example 3, by replacing Boc-L-phenylalanine with Boc-D-phenylalanine. LCMS m/z 546.3 [M+H]+. 1H NMR (400 MHz, CD3OD) δ: 9.40 (1H, s), 7.87 (1H, d, J=2.27 Hz), 7.52-7.58 (1H, m), 7.46 (1H, d, J=8.59 Hz), 7.25 (4H, s), 7.14-7.20 (4H, m), 7.06-7.13 (1H, m), 6.98 (1H, d, J=15.66 Hz), 6.66 (1H, d, J=15.66 Hz), 4.66-4.72 (1H, m), 3.62 (3H, s), 3.00-3.13 (1H, m), 2.93 (1H, dd, J=13.52, 7.96 Hz) ppm. Analytical HPLC RT: 8.76 min (Method D).

Example 129

(S,E)-3-(5-chloro-2-(1H-tetrazol-1-yl)phenyl)-N-(1-oxo-1-(3-oxoisoindolin-5-ylamino)-3-phenylpropan-2-yl)acrylamide

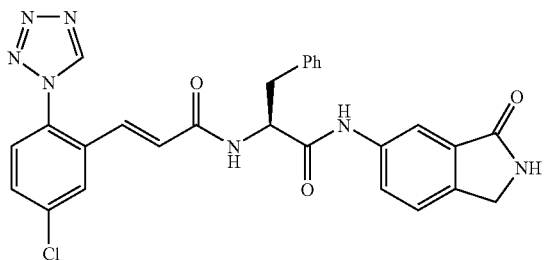 [SMILES: O=C(/C=C/c1cc(Cl)ccc1-n1cnnn1)N[C@@H](Cc1ccccc1)C(=O)Nc1ccc2c(c1)C(=O)NC2]

129A. (S)-2-amino-N-(3-oxoisoindolin-5-yl)-3-phenylpropanamide, TFA salt: To ethyl acetate (10 mL) was added 6-aminoisoindolin-1-one (100 mg, 0.675 mmol), (S)-2-(tert-butoxycarbonylamino)-3-phenylpropanoic acid (179 mg, 0.675 mmol), and DCC (209 mg, 1.012 mmol). The reaction mixture was stirred for 24 h, diluted with ethyl acetate and filtered. The filtrate was washed with 10% citric acid (1×10 mL), brine and dried (MgSO$_4$). The crude product was purified by silica gel chromatography (DCM and 0-10% MeOH as eluents) to afford a white foam (0.192 g). The foam was re-dissolved in DCM (5 mL) and to this solution was added TFA (2 mL). After 1 h, the reaction was concentrated to afford 129A (0.29 g, 105%) as a brown oil. LCMS m/z 296.3 [M+H]$^+$.

Example 129: Compound 129A was coupled with 55E according to the procedure described in Example 55. LCMS m/z 528.4 [M+H]$^+$. $^1$H NMR (400 MHz, DMSO-d$_6$) δ 10.39 (1H, s), 9.85 (1H, s), 8.63 (1H, d, J=8.25 Hz), 8.56 (1H, s), 8.00 (1H, s), 7.94 (1H, d, J=2.20 Hz), 7.69-7.79 (2H, m), 7.64 (1H, dd, J=8.24, 2.20 Hz), 7.49 (1H, d, J=8.25 Hz), 7.23-7.31 (2H, m), 7.15-7.21 (1H, m), 6.77-6.97 (2H, m), 4.76 (1H, d, J=14.29, 8.79 Hz), 4.31 (2H, s), 3.08 (1H, dd, J=13.74, 5.50 Hz), 2.92 (1H, dd, J=13.74, 8.79 Hz) ppm. Analytical HPLC RT: 6.88 min (Method D).

Example 130

(S,E)-3-(5-chloro-2-(1H-tetrazol-1-yl)phenyl)-N-(1-oxo-1-(1-oxo-1,2-dihydroisoquinolin-6-ylamino)-3-phenylpropan-2-yl)acrylamide

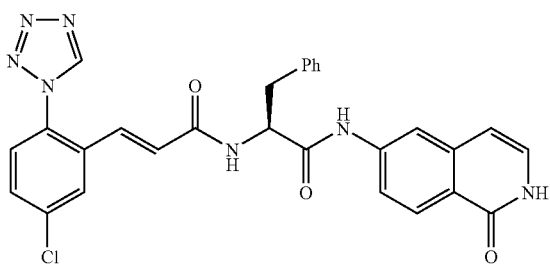 [SMILES: O=C(/C=C/c1cc(Cl)ccc1-n1cnnn1)N[C@@H](Cc1ccccc1)C(=O)Nc1ccc2c(=O)[nH]ccc2c1]

130A. 6-aminoisoquinolin-1(2H)-one: To toluene (4 mL) was added 6-bromoisoquinolin-1(2H)-one (0.5 g, 2.232 mmol), diphenylmethanimine (0.447 mL, 2.68 mmol), BINAP (0.973 g, 1.562 mmol), and sodium t-butoxide (0.643 g, 6.69 mmol). The slurry was degassed for 10 min with N$_2$ followed by the addition of tris(dibenzylideneacetone)dipalladium(0) (0.101 g, 0.111 mmol) and the reaction mixture was heated to 105° C. for 72 h. Hydroxylamine hydrochloride (0.279 g, 4.02 mmol), sodium acetate (0.439 g, 5.36 mmol) and MeOH (20 mL) were subsequently added and the reaction mixture was stirred at rt for 72 h, concentrated and purified by silica gel chromatography (DCM and 0-10% MeOH as eluents) to afford 130A (0.32 g, 90%) as a tan powder. LCMS m/z 161.1 [M+H]$^+$.

Example 130: The title compound was prepared according to the following sequence of the procedures adopted for Example 4. LCMS m/z 540 [M+H]$^+$. $^1$H NMR (400 MHz, DMSO-d$_6$) δ: 11.10 (1H, d, J=5.31 Hz), 10.53 (1H, s), 9.80-9.89 (1H, m), 8.63 (1H, d, J=7.83 Hz), 8.11 (1H, d, J=8.84 Hz), 7.94 (2H, dd, J=7.58, 2.02 Hz), 7.68-7.80 (2H, m), 7.55 (1H, dd, J=8.84, 2.02 Hz), 7.25-7.38 (4H, m), 7.17-7.23 (1H, m), 7.08-7.17 (1H, m), 6.47 (1H, d, J=6.82 Hz), 4.72-4.84 (1H, m), 2.93 (1H, dd, J=13.64, 9.35 Hz) ppm. Analytical HPLC RT: 6.92 min (Method D).

Example 131

(S)—N-(3-amino-1H-indazol-6-yl)-2-(2-(5-chloro-2-(1H-tetrazol-1-yl)phenylthio)acetamido)-3-phenylpropanamide

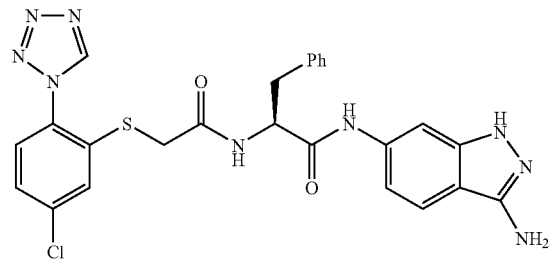 [SMILES: Nc1n[nH]c2cc(NC(=O)[C@H](Cc3ccccc3)NC(=O)CSc3cc(Cl)ccc3-n3cnnn3)ccc12]

131A. methyl 2-(5-chloro-2-(1H-tetrazol-1-yl)phenylthio)acetate: Methyl 2-(trimethylstannylthio)acetate (Dickens et. al, Tet 1991, 47(40), 8621, 3.38 g, 12.56 mmol) and 56A (3.5 g, 11.42 mmol) in toluene (30 mL) was degassed for 10 min, followed by the addition of tetrakis(triphenylphosphine)palladium(0) (0.660 g, 0.571 mmol). The reaction mixture was then heated to 109° C. for 24 h. The reaction mixture was cooled, diluted with EtOAc (50 mL) and quenched with 10% aq. KF (30 mL). The organic layer was washed with brine (30 mL) and dried (MgSO$_4$). The crude material was purified via silica gel chromatography (EtOAc and hexanes as eluents) to afford 131A (0.65 g, 20%) as a dark brown oil. $^1$H NMR (400 MHz, CDCl$_3$) δ 9.14 (1H, s), 7.58-7.67 (1H, m), 7.36-7.52 (2H, m), 3.70 (3H, s), 3.60 (2H, s) ppm.

131B. 2-(5-chloro-2-(1H-tetrazol-1-yl)phenylthio)acetic acid: To 131A (0.114 g, 0.400 mmol) in THF (1 mL), and Water (1.000 mL) was added lithium hydroxide hydrate (0.050 g, 1.201 mmol). After 1.5 h, the reaction was quenched with 1N HCl (10 mL) and extracted with ethyl acetate (3×30 mL). The combined organic layers were washed with brine (10 mL) and dried (MgSO$_4$) and concentrated to afford 131B (0.102 g, 94%) as a tan solid. MS m/z 271.2 (M+H)$^+$.

131C. 2,5-dioxopyrrolidin-1-yl 2-(5-chloro-2-(1H-tetrazol-1-yl)phenylthio)acetate: 131B (0.102 g, 0.377 mmol) and 1-hydroxypyrrolidine-2,5-dione (0.043 g, 0.377 mmol) were combined in THF (2 mL) and DMF (0.1 mL) followed by the addition of DIC (0.059 mL, 0.377 mmol). After 4 h a white solid was filtered off and washed with THF. The desired product remained in the filtrate which was concentrated to afford 0.2 g of 131C as a dark oil which was used in subsequent steps without further purification. MS m/z 368.3 (M+H)$^+$.

Example 131: 131C (70 mg, 0.190 mmol) was coupled with 55D (56.2 mg, 0.190 mmol) as in Example 55 to afford Example 131 (47 mg, 45%) as a tan solid. LCMS m/z 548.4 [M+H]⁺. ¹H NMR (400 MHz, CD₃OD) δ: 9.54 (s, 1H), 8.56 (1H, d, J=7.15 Hz), 8.00 (1H, s), 7.80 (1H, d, J=8.79 Hz), 7.71 (1H, d, J=2.20 Hz), 7.41-7.50 (2H, m), 7.14-7.29 (4H, m), 7.03 (1H, d, J=9.34 Hz), 4.63-4.74 (1H, m), 3.65-3.70 (2H, s), 3.07-3.16 (1H, m), 2.97 (1H, dd, J=13.74, 7.70 Hz) ppm. Analytical HPLC RT: 6.47 min (Method D).

Example 132

(2S)—N-(3-amino-1H-indazol-6-yl)-2-(2-(5-chloro-2-(1H-tetrazol-1-yl)phenylsulfinyl)acetamido)-3-phenylpropanamide, TFA salt, Isomer A

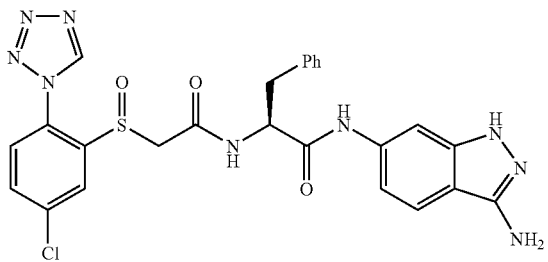 [SMILES: Nc1n[nH]c2cc(NC(=O)[C@H](Cc3ccccc3)NC(=O)CS(=O)c3cc(Cl)ccc3-n3cnnn3)ccc12]

132A. 2,5-dioxopyrrolidin-1-yl 2-(5-chloro-2-(1H-tetrazol-1-yl)phenylsulfinyl)acetate: To a THF (2 mL) and DMF (0.1 mL) solution was added 56E (0.2 g, 0.698 mmol), 1-hydroxypyrrolidine-2,5-dione (0.080 g, 0.698 mmol), and DIC (0.109 mL, 0.698 mmol). After 72 h, white solid was filtered off. The filtrate was concentrated to a dark oil (0.3 g) which was carried on to the next step without further purification. LCMS m/z 348 [M+H]⁺.

Example 132: 132A (90 mg, 0.235 mmol) was coupled with 55E (69.3 mg, 0.235 mmol) as described for Example 55 to afford Example 132 (2 mg, 1.2%). LCMS m/z 564.4 [M+H]⁺. ¹H NMR (400 MHz, CD₃OD) δ: 8.42 (1H, s), 6.71-6.79 (2H, m), 6.42-6.54 (3H, m), 5.91-5.98 (4H, m), 5.82-5.91 (2H, m), 3.39-3.47 (1H, m), 2.95 (1H, d, J=13.64 Hz)) 2.54 (1H, d, J=13.64 Hz), 1.83-1.95 (1H, m), 1.65-1.73 (1H, m) ppm. Analytical HPLC RT: 5.68 min (Method D).

Example 133

(2S)—N-(3-amino-1H-indazol-6-yl)-2-(2-(5-chloro-2-(1H-tetrazol-1-yl)phenylsulfinyl)acetamido)-3-phenylpropanamide, Isomer B

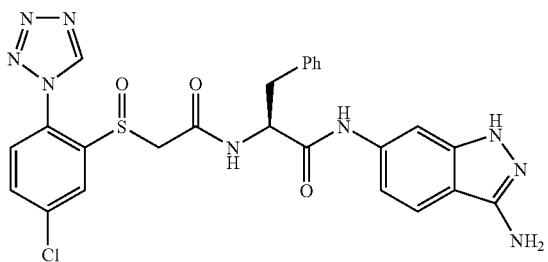 [SMILES: Nc1n[nH]c2cc(NC(=O)[C@H](Cc3ccccc3)NC(=O)CS(=O)c3cc(Cl)ccc3-n3cnnn3)ccc12]

Example 133 was obtained as a white solid (1 mg, 0.6%) along with Example 132. LCMS m/z 564.4 [M+H]⁺. ¹H NMR (400 MHz, CD₃OD) δ: 8.46 (1H, s), 6.86 (1H, d, J=1.52 Hz), 6.72 (1H, s), 6.47-6.58 (3H, m), 5.96-6.01 (4H, m), 5.91 (1H, d, J=5.81 Hz), 5.82 (1H, d, J=9.09 Hz), 3.45-3.58 (1H, m), 2.93 (1H, d, J=13.64 Hz), 2.61 (1H, d, J=13.39 Hz), 1.89-1.95 (1H, m), 1.72-1.81 (1H, m) ppm. Analytical HPLC RT: 5.78 min (Method D).

Example 134

(S)-4-(2-(2-(5-chloro-2-(1H-tetrazol-1-yl)phenylsulfonyl)acetamido)-3-phenyl propanamido)benzoic acid

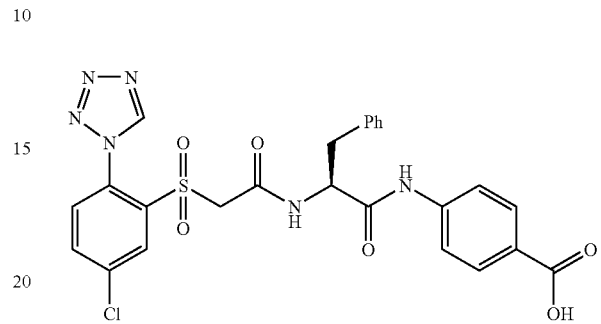

134A. 2-(5-chloro-2-(1H-tetrazol-1-yl)phenylsulfonyl)acetic acid: To 131B (0.42 g, 1.552 mmol) in water (15 mL) was added NaOH (1.552 mL, 1.552 mmol) sodium bicarbonate (1.043 g, 12.41 mmol), followed by Oxone® (1.240 g, 2.017 mmol) in water. An additional equivalent of Oxone® and NaHCO₃ were subsequently added. The reaction mixture was stirred at rt for 5 days, quenched with cold sodium metabisulfite, and acidified with 6N HCl. The organics were extracted with EtOAc (3×100 mL), washed with brine and dried (MgSO₄) to afford 134A (0.45 g, 96%) as a yellow solid. MS m/z 303.3 (M+H)⁺.

Example 134: 134A (70 mg, 0.231 mmol) was coupled with (S)-tert-butyl 4-(2-amino-3-phenylpropanamido)benzoate in a manner similar to Example 4 and deprotected with DCM/TFA to afford Example 134 (16 mg, 11.5%) as a white solid. LCMS m/z 569.4 [M+H]⁺. ¹H NMR (400 MHz, CD₃OD) δ: 8.14 (1H, s), 6.70 (1H, d, J=2.27 Hz), 6.51-6.61 (3H, m), 6.32 (1H, d, J=8.34 Hz), 6.24 (2H, d, J=8.84 Hz), 5.87-5.93 (4H, m), 5.79-5.88 (1H, m), 3.32 (1H, t, J=7.33 Hz), 2.92-3.10 (2H, m), 1.74-1.82 (1H, m), 1.64 (1H, dd, J=13.64, 8.08 Hz) ppm. Analytical HPLC RT: 7.09 min. (Method D).

Example 135

(S,E)-3-(5-chloro-2-(1H-tetrazol-1-yl)phenyl)-N-(1-oxo-1-(2-oxo-1,2-dihydroquinolin-6-ylamino)-3-phenylpropan-2-yl)acrylamide

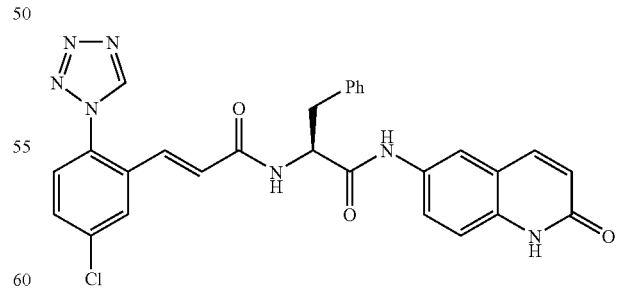

135A. (S)-tert-butyl 1-oxo-1-(2-oxo-1,2,3,4-tetrahydroquinolin-6-ylamino)-3-phenylpropan-2-ylcarbamate: 6-Amino-3,4-dihydroquinolin-2(1H)-one and (S)-2-(tert-butoxycarbonylamino)-3-phenylpropanoic acid were coupled using DCC as described in Example 43A to give 135A. MS m/z 409 (M+H)⁺.

135B. (S)-2-amino-N-(2-oxo-1,2-dihydroquinolin-6-yl)-3-phenylpropanamide: To 135A in toluene (20 mL) was added DDQ (0.560 g, 2.466 mmol) and the mixture was heated to 80° C. for 24 h. The reaction was quenched with water (20 mL) and extracted with ethyl acetate (3×30 mL). The combined organic layers were washed with brine (20 mL) and dried (MgSO$_4$), purified by silica gel chromatography to afford 60 mg of a brown solid, which was deprotected with TFA/DCM, quenched with NaHCO$_3$ (15 mL) and extracted with ethyl acetate (3×25 mL), washed with brine (10 mL) and dried (MgSO$_4$) to afford 135B (40 mg, 10.5%) as a brown solid. MS m/z 308.4 [M+H]$^+$.

Example 135: 135B was coupled with 1C according to Example 4 to afford Example 135. LCMS m/z 540 [M+H]$^+$. $^1$H NMR (400 MHz, DMSO-d$_6$) δ: 11.71 (1H, s), 10.27 (1H, s), 9.85 (1H, s), 8.58 (1H, d, J=8.08 Hz), 7.94 (2H, d, J=4.42, 2.15 Hz), 7.87 (1H, d, J=9.60 Hz), 7.67-7.80 (2H, m), 7.56 (1H, dd, J=8.84, 2.27 Hz), 7.25-7.33 (5H, m), 7.18-7.23 (1H, m), 6.79-6.92 (2H, m), 6.48 (1H, dd, J=9.60, 1.77 Hz), 4.67-4.82 (1H, m), 3.09 (1H, dd, J=13.77, 5.43 Hz), 2.92 (1H, dd, J=13.64, 9.35 Hz) ppm. Analytical HPLC RT: 6.81 min (Method D).

Example 136

(S)-4-(2-(2-(5-chloro-2-(1H-tetrazol-1-yl)phenoxy)acetamido)-3-phenyl propanamido)benzoic acid

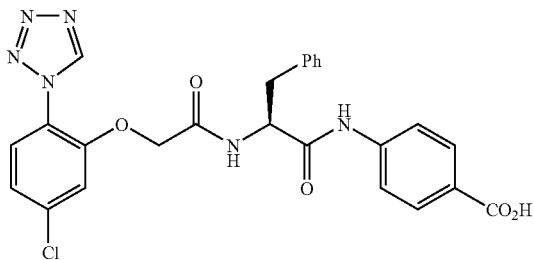 [SMILES: O=C(COc1cc(Cl)ccc1-n1cnnn1)N[C@@H](Cc1ccccc1)C(=O)Nc1ccc(C(=O)O)cc1]

136A. 5-chloro-2-(1H-tetrazol-1-yl)phenol: To 2-amino-5-chlorophenol (1.9 g, 13.23 mmol) was added trimethyl orthoformate (4.39 mL, 39.7 mmol), followed by AcOH (30 mL). The reaction mixture was cooled in an ice bath and to this was added sodium azide (2.58 g, 39.7 mmol) and allowed to gradually warm to rt. After 24 h, the reaction was heated to 75° C. (oil bath) for 3 h. The reaction was cooled and quenched with water to precipitate out 136A (1 g, 38%) as a brown solid. LCMS m/z 197.2 [M+H]$^+$.

136B. tert-butyl 2-(5-chloro-2-(1H-tetrazol-1-yl)phenoxy)acetate: To a cold DMF (5 mL) solution was added 136A (0.5 g, 2.54 mmol) followed by tert-butyl 2-bromoacetate (0.595 g, 3.05 mmol) and 60% NaH (0.073 g, 3.05 mmol). The reaction mixture was stirred at rt for 24 h and quenched with water (10 mL) and extracted with ethyl acetate (3×25 mL). The organic layers were washed with water (10 mL), brine (10 mL), dried (MgSO$_4$) and purified by silica gel chromatography (DCM and 0-10% MeOH as eluents) to afford 136B (0.73 g, 92%) as a brown solid. LCMS m/z 311.3 [M+H]$^+$.

136C. 2-(5-chloro-2-(1H-tetrazol-1-yl)phenoxy)acetic acid: To 136B (0.73 g, 2.349 mmol) was added DCM (5 mL), and TFA (2 mL). The reaction was stirred at rt for 24 h, quenched with water (10 mL) and extracted with DCM (3×20 mL). The combined organic layers were washed with brine (10 mL) and dried (MgSO$_4$), to afford 136C (0.119 g, 19.8%) as a white solid. LCMS m/z 255.2 [M+H]$^+$.

136D. (S)-tert-butyl 4-(2-(benzyloxycarbonylamino)-3-phenylpropanamido)benzoate: Coupling of (S)-2-(benzyloxycarbonylamino)-3-phenylpropanoic acid (2.6 g, 8.69 mmol) with tert-butyl 4-aminobenzoate (1.679 g, 8.69 mmol) according to Example 3A afforded 136D (2.5 g, 61%) as a white foam. LCMS m/z 475.5 [M+H]$^+$.

136E. (S)-tert-butyl 4-(2-amino-3-phenylpropanamido)benzoate: Compound 136D in ethanol (40 mL), was hydrogenated at 50 psi with 10% Pd/C (0.2 g) for 24 h. The reaction was filtered through Celite® to afford 136E (1.45 g, 76%) as a foam. LCMS m/z 341.4 [M+H]$^+$.

Example 136: Amide coupling of 136C and 136E according to Example 4 afforded Example 136. LCMS m/z 521.4 [M+H]$^+$. $^1$H NMR (400 MHz, CD$_3$OD) δ: 9.77 (1H, s), 7.95-8.00 (2H, m), 7.80 (1H, d, J=8.59 Hz), 7.65 (2H, d, J=8.84 Hz), 7.25-7.31 (1H, m), 7.23-7.28 (5H, m), 7.15-7.24 (1H, m), 4.84-4.88 (1H, m), 4.79 (2H, d, J=1.52 Hz), 3.23 (1H, dd, J=13.77, 6.44 Hz), 3.04 (1H, dd, J=13.90, 8.59 Hz) ppm. Analytical HPLC RT: 7.38 min (Method D).

Example 137

(S,E)-N-(1-(1H-pyrazolo[3,4-b]pyridin-3-ylamino)-1-oxo-3-phenylpropan-2-yl)-3-(5-chloro-2-(1H-tetrazol-1-yl)phenyl)acrylamide, TFA salt

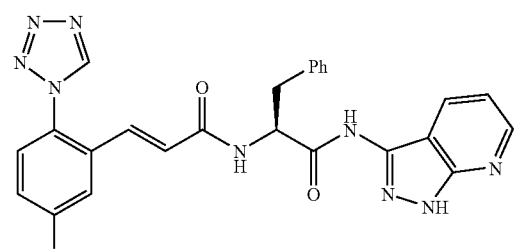

137A. (S)-2-amino-3-phenyl-N-(1H-pyrazolo[3,4-b]pyridin-3-yl)propanamide: Commercially available 1H-pyrazolo[3,4-b]pyridin-3-amine was coupled to (S)-2-(tert-butoxycarbonylamino)-3-phenylpropanoic acid and deprotected in a similar manner as Example 3A to afford a yellow solid which was carried directly to next step. LCMS m/z 182.2 [M+H]$^+$.

Example 137: 137A was coupled to 1C according to Example 4 to afford Example 137. LCMS m/z 514 [M+H]$^+$. $^1$H NMR (400 MHz, DMSO-d$_6$) δ: 13.26 (1H, s), 10.97 (1H, s), 9.86 (1H, s), 8.56 (1H, d, J=7.83 Hz), 8.49 (1H, dd, J=4.42, 1.64 Hz), 8.23 (1H, dd, J=8.21, 1.64 Hz), 7.96 (1H, d, J=2.02 Hz), 7.66-7.80 (2H, m), 7.24-7.42 (4H, m), 7.21 (1H, t, J=7.20 Hz), 7.13 (1 h, dd, J=8.21, 4.42 Hz), 6.71-6.97 (2H, m), 4.83-4.99 (1H, m), 3.18 (1H, dd, J=13.77, 4.93 Hz), 2.99 (1H, dd, J=13.64, 9.35 Hz) ppm. Analytical HPLC RT: 6.9 min (Method D).

Example 138

(S,E)-methyl 6-(2-(3-(5-chloro-2-(1H-tetrazol-1-yl)phenyl)acrylamido)-3-phenyl propanamido)pyridin-3-ylcarbamate

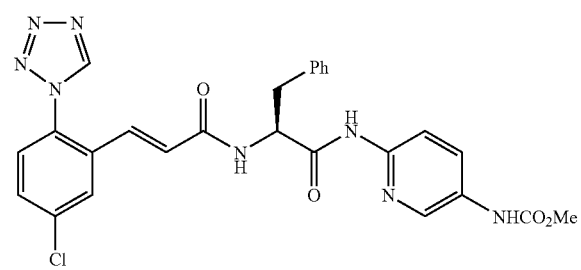

138A. (S)-tert-butyl 1-(5-nitropyridin-2-ylamino)-1-oxo-3-phenylpropan-2-ylcarbamate: 138A was prepared according to the procedure described in Example 3A, by replacing p-nitroaniline with 5-nitropyridin-2-amine LCMS m/z 387.4 [M+H]$^+$.

138B. (S)-tert-butyl 1-(5-aminopyridin-2-ylamino)-1-oxo-3-phenylpropan-2-ylcarbamate: 138A was reacted with zinc (0.123 g, 1.885 mmol) and ammonium chloride (0.202 g, 3.77 mmol) in acetone/water. After 3 h, the reaction was concentrated and extracted with ethyl acetate (2×20 mL), washed with brine (10 mL) and dried (MgSO$_4$). LCMS m/z 357 [M+H]$^+$. The crude product was used directly in the next step.

138C. (S)-methyl 6-(2-amino-3-phenylpropanamido)pyridin-3-ylcarbamate, HCl salt: 138B was converted to the title compound according to the procedures described in Example 3C followed by Boc-deprotection with 4N HCl/dioxane. LCMS m/z 315.4 [M+H]$^+$.

Example 138: 138C was coupled with 1C according to the procedure described in Example 3 to afford Example 138. LCMS m/z 547 [M+H]$^+$. $^1$H NMR (400 MHz, CD$_3$OD) δ: 9.51 (1H, s), 8.40 (1H, s), 7.98 (1H, d, J=2.27 Hz), 7.93 (2H, s), 7.64-7.69 (1H, m), 7.54-7.60 (1H, m), 7.26-7.32 (4H, m), 7.18-7.25 (1H, m), 7.10 (1H, d, J=15.66 Hz), 6.76 (1H, d, J=15.41 Hz), 4.93-4.97 (1H, m), 3.77 (3H, s), 3.26 (1H, dd, J=13.77, 6.19 Hz), 3.05 (1H, dd, J=13.64, 8.59 Hz) ppm. Analytical HPLC RT: 7.21 min (Method D).

Example 139

(S,E)-N-(1-(benzo[d]isoxazol-3-ylamino)-1-oxo-3-phenylpropan-2-yl)-3-(5-chloro-2-(1H-tetrazol-1-yl)phenyl)acrylamide

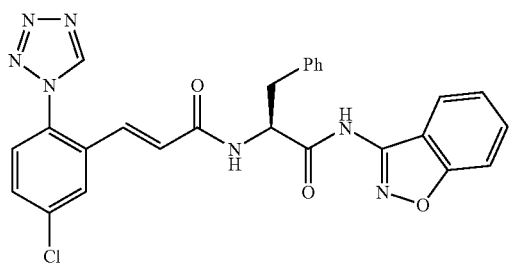 [SMILES: O=C(/C=C/c1cc(Cl)ccc1-n1cnnn1)N[C@@H](Cc1ccccc1)C(=O)Nc1noc2ccccc12]

The title compound was prepared from commercially available benzo[d]isoxazol-3-amine in a similar manner as described for Example 4. LCMS m/z 514.4 [M+H]$^+$. $^1$H NMR (400 MHz, CD$_3$OD) δ: 9.52 (1H, s), 8.00 (1H, d, J=2.27 Hz), 7.89 (1H, d, J=8.08 Hz), 7.61-7.71 (2H, m), 7.56-7.62 (2H, m), 7.26-7.40 (5H, m), 7.18-7.27 (1H, m), 7.13 (1H, d, J=15.41 Hz), 6.79 (1H, d, J=15.41 Hz), 4.90-5.11 (1H, m), 3.23-3.32 (1H, m), 3.09-3.20 (1H, m) ppm. Analytical HPLC RT: 8.31 min (Method D).

Example 140

(S,E)-N-(1-(1H-indazol-3-ylamino)-1-oxo-3-phenylpropan-2-yl)-3-(5-chloro-2-(1H-tetrazol-1-yl)phenyl)acrylamide

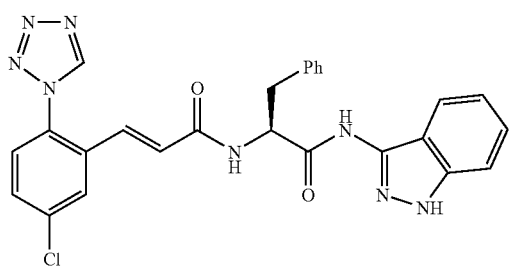 [SMILES: O=C(/C=C/c1cc(Cl)ccc1-n1cnnn1)N[C@@H](Cc1ccccc1)C(=O)Nc1n[nH]c2ccccc12]

140A. 1H-indazol-3-amine: To 2-fluorobenzonitrile (1 mL, 9.08 mmol) in EtOH (10 mL) was added hydrazine (0.855 mL, 27.2 mmol) and the reaction was heated to 160° C. in a microwave for 20 min. LCMS m/z 134.1 (M+H)$^+$. The solvents were removed in vacuo and the residue was quenched with water (10 mL) and ethyl acetate (20 mL). The organic layer was washed with water (10 mL), brine (10 mL), dried (MgSO$_4$) to afford 140A (0.1 g, 8.2%) as an oil which was used directly in the next step.

Example 140: 140A was coupled with 1C according to the procedure described for Example 4. LCMS m/z 513 [M+H]$^+$. $^1$H NMR (400 MHz, CD$_3$OD) δ: 9.53 (1H, s), 7.99 (1H, d, J=2.27 Hz), 7.60-7.70 (2H, m), 7.54-7.62 (1H, m), 7.42-7.51 (1H, m), 7.07-7.42 (8H, m), 6.80 (1H, d, J=15.66 Hz), 4.96-5.09 (1H, m), 3.23-3.33 (1H, m), 3.06-3.20 (m, 1H) ppm. Analytical HPLC RT: 7.6 min (Method D).

Example 141

(S,E)-methyl 3-(2-(3-(5-chloro-2-(1H-tetrazol-1-yl)phenyl)acrylamido)-3-phenyl propanamido)benzo[d]isoxazol-5-ylcarbamate

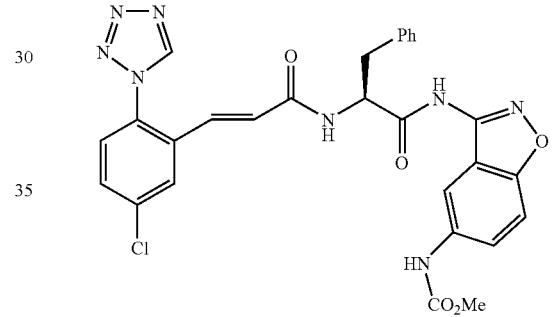

141A. methyl 3-cyano-4-fluorophenylcarbamate: 5-amino-2-fluorobenzonitrile was converted to 141A according to the procedure described in 3C. LCMS m/z 195.3 [M+H]$^+$.

141B. methyl 3-aminobenzo[d]isoxazol-5-ylcarbamate: To 141A (0.29 g, 1.494 mmol) in DMF (3 mL)/water (0.3 mL) was added acetohydroxamic acid (0.112 g, 1.494 mmol) and K$_2$CO$_3$ (0.206 g, 1.494 mmol). The reaction mixture was stirred at rt for 72 h followed by heating in a microwave vial at 140° C. for 20 min. The reaction was quenched with water (10 mL) and extracted with ethyl acetate (3×20 mL). The combined organic layers were washed with water (10 mL), brine (10 mL) and dried (MgSO$_4$). LCMS m/z 208.2 (M+H)$^+$. The crude product was carried onto the next step directly.

Example 141: 141B was coupled sequentially with (S)-2-(tert-butoxycarbonylamino)-3-phenylpropanoic acid, deprotected and coupled with 1C as previously described for Example 4. LCMS m/z 587.4 [M+H]$^+$. $^1$H NMR (400 MHz, CD$_3$OD) δ: 9.50 (1H, s), 8.09 (1H, s), 7.97 (1H, d, J=2.27 Hz), 7.60-7.71 (1H, m), 7.55 (2H, d, J=8.59 Hz), 7.47 (1H, d, J=8.3 Hz), 7.28-7.35 (3H, m), 7.24-7.29 (2H, m), 7.19 (1H, d, J=7.07 Hz), 7.10 (1H, d, J=15.66 Hz), 6.76 (1H, d, J=15.66 Hz), 4.99-5.06 (1H, m), 3.76 (3H, s), 3.24-3.29 (1H, m), 3.09-3.19 (1H, m) ppm. Analytical HPLC RT: 7.48 min. (Method D).

Example 142

(S,E)-3-(5-chloro-2-(1H-tetrazol-1-yl)phenyl)-N-(1-oxo-3-phenyl-1-(3-(trifluoromethyl)-[1,2,4]-triazolo[4,3-a]pyridin-8-ylamino)propan-2-yl)acrylamide

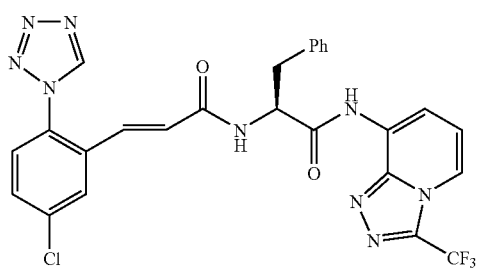 [SMILES: O=C(/C=C/c1cc(Cl)ccc1-n1cnnn1)N[C@@H](Cc1ccccc1)C(=O)Nc1cccn2c(C(F)(F)F)nnc12]

The title compound was prepared according to the procedures described in Example 141, by replacing 141B with commercially available 3-(trifluoromethyl)-[1,2,4]triazolo[4,3-a]pyridin-8-amine LCMS m/z 582.3 [M+H]+. 1H NMR (400 MHz, DMSO-$d_6$) δ: 10.93 (1H, s), 9.76 (1H, s), 8.77 (1H, d, J=6.82 Hz), 8.50 (1H, d, J=8.08 Hz), 8.38 (1H, d, J=7.33 Hz), 7.87 (1H, d, J=2.27 Hz), 7.57-7.72 (2H, m), 7.30-7.39 (3H, m), 7.19-7.24 (2H, m), 7.13 (1H, d, J=7.33 Hz), 6.75 (2H, d, J=2.02 Hz), 5.08-5.16 (1H, m, J=2.53 Hz), 3.03-3.13 (1H, m, J=10.36 Hz), 2.75-2.91 (1H, m) ppm. Analytical HPLC RT: 8.82 min (Method D).

Example 143

(S,E)-methyl 3-(2-(3-(5-chloro-2-(1H-tetrazol-1-yl)phenyl)acrylamido)-3-phenylpropanamido)benzo[d]isoxazol-7-ylcarbamate

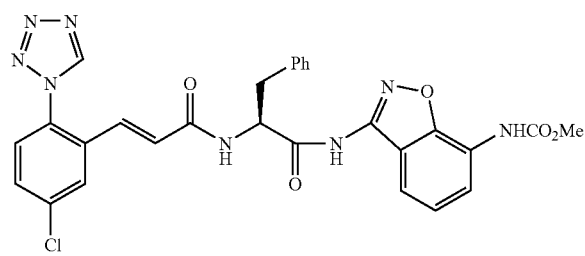

The title compound was prepared following the sequence of reactions described in Example 141, starting with 3-amino-2-fluorobenzonitrile. LCMS m/z 587.3 [M+H]+. 1H NMR (400 MHz, CD3OD) δ: 9.51 (1H, s), 7.98 (2H, d, J=2.27 Hz), 7.66 (1H, dd, J=8.59, 2.27 Hz), 7.53-7.58 (2H, m), 7.25-7.36 (5H, m), 7.18-7.23 (1H, m), 7.12 (1H, d, J=15.41 Hz), 6.78 (1H, d, J=15.41 Hz), 4.95-5.02 (1H, m), 3.80 (3H, s), 3.10-3.26 (2H, m) ppm. Analytical HPLC RT: 7.82 min (Method D).

Example 144

(S,E)-methyl 5-(2-(3-(5-chloro-2-(1H-tetrazol-1-yl)phenyl)acrylamido)-3-phenylpropanamido)-1H-indazole-3-carboxylate

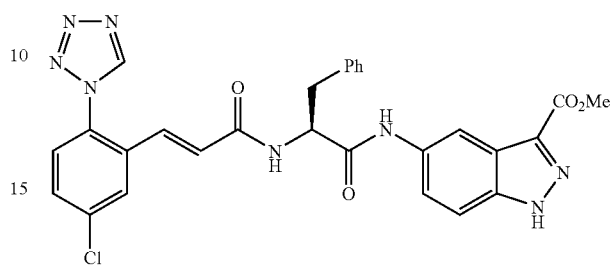

The title compound was prepared according to the procedures described in Example 3 from commercially available methyl 5-amino-1H-indazole-3-carboxylate. LCMS m/z 571.1 [M+H]+. 1H NMR (400 MHz, CD3OD) δ: 9.53 (1H, s), 8.33 (1H, d, J=1.01 Hz), 8.00 (1H, d, J=2.27 Hz), 7.67 (1H, dd, J=8.59, 2.27 Hz), 7.54-7.61 (2H, m), 7.46-7.52 (1H, m), 7.26-7.37 (4H, m), 7.20-7.25 (1H, m), 7.12 (1H, d, J=15.66 Hz), 6.81 (1H, d, J=15.41 Hz), 4.92-4.96 (1H, m), 4.03 (3 H, s), 3.26 (1H, dd, J=13.01, 5.68 Hz), 3.06-3.16 (1H, m) ppm. Analytical HPLC RT: 7.32 min (Method D).

Example 145

(S,E)-N-(1-(7-chloro-1H-indazol-3-ylamino)-1-oxo-3-phenylpropan-2-yl)-3-(5-chloro-2-(1H-tetrazol-1-yl)phenyl)acrylamide

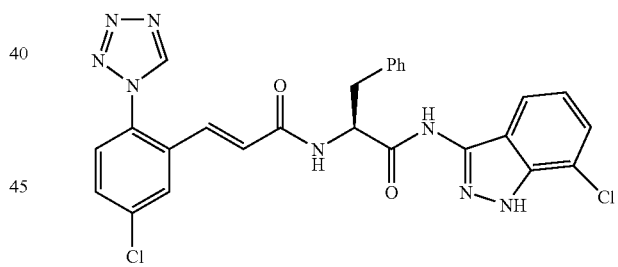

145A. 7-chloro-1H-indazol-3-amine: 145A was prepared following the sequence of reaction described in 140A, using 3-chloro-2-fluorobenzonitrile. LCMS m/z 168.1 [M+H]+.

145B. (S)-tert-butyl 1-(7-chloro-1H-indazol-3-ylamino)-1-oxo-3-phenylpropan-2-ylcarbamate: 145B (0.276 mg, 32%) was prepared according to similar procedures previously described for Example 3 as a bright yellow-green solid. LCMS m/z 415.1 [M+H]+.

Example 145: Deprotection of 145B with 4M HCl/dioxane and then amide coupling with 55E according to the procedure described in Example 55 gave Example 145. 1H NMR (400 MHz, CD3OD) δ: 9.52 (1H, s), 7.97 (1H, d, J=2.02 Hz), 7.64-7.70 (1H, m), 7.52-7.64 (2H, m), 7.39-7.45 (1H, m), 7.27-7.44 (4H, m), 7.24 (1H, d, J=7.33 Hz), 7.02-7.17 (2H, m), 6.79 (1H, d, J=15.66 Hz), 5.02 (1H, dd, J=8.08, 6.57 Hz), 3.30-3.33 (1H, m), 3.13 (1H, dd, J=13.77, 8.21 Hz) ppm. LCMS m/z 547.2 [M+H]+. Analytical HPLC RT: 8.0 min (Method D).

Example 146

(S)-methyl 4-(1-(2-(5-chloro-2-(1H-tetrazol-1-yl)benzoyl)hydrazinyl)-1-oxo-3-phenyl propan-2-ylcarbamoyl)phenylcarbamate

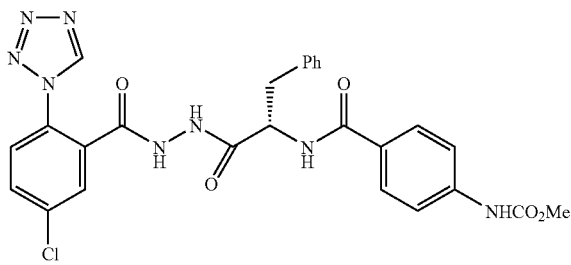

146A. (S)-tert-butyl 1-(2-(5-chloro-2-(1H-tetrazol-1-yl)benzoyl)hydrazinyl)-1-oxo-3-phenylpropan-2-ylcarbamate: To 5-chloro-2-(1H-tetrazol-1-yl)benzoic acid (0.16 g, 0.712 mmol), commercially available (S)-tert-butyl 1-hydrazinyl-1-oxo-3-phenylpropan-2-ylcarbamate (0.199 g, 0.712 mmol), HOBT (0.142 g, 0.926 mmol), EDC (0.178 g, 0.926 mmol) in DMF (1.5 mL) was added Hunig's base (0.373 mL, 2.137 mmol). After 24 h, the reaction was quenched with water (10 mL) and extracted with ethyl acetate (3×20 mL), washed with water (10 mL), brine (10 mL), dried (MgSO$_4$) and purified by silica gel chromatography (DCM/0-10% MeOH as eluents) to afford 146A (0.29 g, 84%) as a white solid. LCMS m/z 486.4 [M+H]$^+$.

Example 146: To 146A (67 mg, 0.138 mmol) was added DCM (4 mL) and TFA (1 mL). After 24 h, the reaction was concentrated and treated with sat'd NaHCO$_3$ (10 mL) and was extracted with ethyl acetate (20 mL), washed with brine (10 mL) and dried (MgSO$_4$). The crude was coupled with 4-(methoxycarbonylamino)benzoic acid (26.9 mg, 0.138 mmol) and Pybop (71.8 mg, 0.138 mmol) as described above and purified by reverse phase HPLC and freeze-dried to afford Example 146 (9.9 mg, 12.7%) as a white solid. $^1$H NMR (400 MHz, DMSO-d$_6$) δ: 10.75 (1H, s), 10.45 (1H, s), 9.91 (1H, s), 9.78 (1H, s), 8.51 (1H, d, J=8.59 Hz), 7.90-7.97 (1H, m), 7.81-7.88 (2H, m), 7.74 (2H, d, J=8.84 Hz), 7.49 (2H, d, J=8.59 Hz), 7.38 (d2H, J=7.07 Hz), 7.20-7.30 (2H, m), 7.11-7.22 (m, 1H), 4.71-4.83 (1H, m, J=3.79 Hz), 3.68 (3H, s), 2.98-3.14 (2H, m) ppm. LCMS m/z 563.5 [M+H]$^+$. Analytical HPLC RT: 6.76 min (Method D).

Example 147

(S)-3-amino-N-(1-(5-chloro-2-(1H-tetrazol-1-yl)phenethylamino)-1-oxo-3-phenylpropan-2-yl)-1H-indazole-6-carboxamide

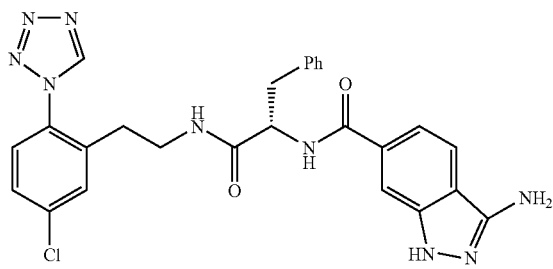 [SMILES: Nc1n[nH]c2cc(C(=O)N[C@@H](Cc3ccccc3)C(=O)NCCc3cc(Cl)ccc3-n3cnnn3)ccc12]

147A. (S)-methyl 2-(4-cyano-3-fluorobenzamido)-3-phenylpropanoate: To 4-cyano-3-fluorobenzoic acid (0.5 g, 3.03 mmol) in DCM (8 mL) was added oxalyl chloride (0.345 mL, 3.94 mmol) and a few drops of DMF. After 3 h the solvent was removed and the acid chloride placed under vacuum for 2 h, re-dissolved in DCM (8 mL), coupled with (S)-methyl 2-amino-3-phenylpropanoate HCl (0.718 g, 3.33 mmol) in the presence of pyridine (0.735 mL, 9.08 mmol). After 24 h, the reaction was quenched with water (10 mL) and extracted with DCM (3×20 mL). The combined organic layers were washed with brine (10 mL) and dried (MgSO$_4$) to afford 147A (0.97 g) as a tan solid. LCMS m/z 327.3 [M+H]$^+$.

147B. (S)-2-(3-amino-1H-indazole-6-carboxamido)-3-phenylpropanoic acid: 147A (0.65 g, 1.99 mmol) was hydrolyzed in THF (10 mL), water (10 mL) and 1N NaOH (2 mL, 1.99 mmol). The reaction was acidified with 1N HCl and extracted with ethyl acetate (3×20 mL). The combined organic layers were washed with brine (10 mL) and dried (MgSO$_4$). The crude material was heated in a microwave oven in EtOH (10 mL) with hydrazine (0.500 mL, 15.94 mmol) at 160° C. for 20 min. The reaction was concentrated and purified by reverse phase HPLC and freeze-dried to afford 147B (0.16 g, 25%). LCMS m/z 325.4 [M+H]$^+$.

Example 147: To 147B (0.16 g, 0.493 mmol), Intermediate 6 (0.110 g, 0.493 mmol) were coupled with BOP as previously described in Example 3 to afford Example 147 (7.7 mg, 2.95%) as a white solid. $^1$H NMR (400 MHz, CD$_3$OD) δ: 9.42 (1H, s), 7.75 (1H, d, J=8.59 Hz), 7.65 (1H, s), 7.49 (1H, d, J=2.02 Hz), 7.28-7.39 (3H, m), 7.13-7.24 (4H, m), 7.05-7.13 (1H, m), 4.61 (1H, dd, J=8.72, 6.44 Hz), 3.24-3.30 (2H, m), 3.00-3.07 (1H, m), 2.86-2.95 (1H, m), 2.41-2.53 (2H, m) ppm. LCMS m/z 530.4 [M+H]$^+$. Analytical HPLC RT: 6.19 min (Method D).

Example 148

(S)-methyl 4-(1-(2-(5-chloro-2-(1H-tetrazol-1-yl)phenyl)-2-oxoethylamino)-1-oxo-3-phenylpropan-2-ylcarbamoyl)phenylcarbamate

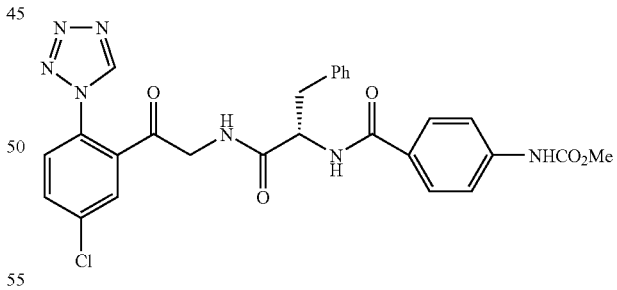

148A. 1-(4-chloro-2-(1-ethoxyvinyl)phenyl)-1H-tetrazole: To 56A (2.48 g, 8.09 mmol) in degassed toluene (15 mL) was added bis(triphenylphosphine) palladium(II) chloride (0.284 g, 0.405 mmol) followed by tributyl(1-ethoxyvinyl)tin (3.01 mL, 8.90 mmol). The reaction was heated to reflux for 24 h. The reaction was cooled, filtered and quenched with water (20 mL) and extracted with ethylacetate (40 mL). The organic layer was washed with aq KF (15 mL), brine (15 mL), dried (MgSO$_4$) and purified by silica gel chromatography (hexanes and ethyl acetate as eluents) to afford 148A (1.48 g, 73%) as a dark oil. LCMS m/z 251.3 [M+H]$^+$.

148B. 2-bromo-1-(5-chloro-2-(1H-tetrazol-1-yl)phenyl) ethanone: To 148A (0.52 g, 2.074 mmol) in DCM (5 mL) was added bromine (0.128 mL, 2.489 mmol) in DCM (2 mL) and stirred at rt for 4 h. The reaction was quenched with water (10 mL) and extracted with DCM (3×20 mL), washed with water (10 mL), brine (10 mL), dried ($Na_2SO_4$) and purified by silica gel chromatography (hexanes and ethyl acetate as eluents) to afford 148B (0.25 g, 40%) as a tan solid. LCMS m/z 303.2 $[M+H]^+$.

148C. 2-amino-1-(5-chloro-2-(1H-tetrazol-1-yl)phenyl) ethanone: To a cold (ice bath) acetonitrile (5 mL) solution of 148B (0.3 g, 0.995 mmol) was added sodium N-formylformamide (0.032 g, 0.332 mmol). The reaction mixture was gradually warmed to rt and stirred for 24 h, filtered, concentrated and treated with MeOH (2 mL) and 1N HCl (3 mL). After 5 days the solvent was removed and resulting brown mass was taken up in $Et_2O$ and filtered to afford 148C (0.23 g, 97%). LCMS m/z 238.2 $[M+H]^+$.

148D. (S)-methyl 2-(4-(methoxycarbonylamino)benzamido)-3-phenylpropanoate: (S)-methyl 2-amino-3-phenylpropanoate HCl (0.35 g, 1.623 mmol) was coupled with 4-(methoxycarbonylamino)benzoic acid (0.317 g, 1.623 mmol) according to Example 4 to afford 148D (0.62 g, 107%) as a yellow solid. LCMS m/z 357.4 $[M+H]^+$.

148E. (S)-2-(4-(methoxycarbonylamino)benzamido)-3-phenylpropanoic acid: To 148D (0.57 g, 1.599 mmol) was added THF (15 mL) and NaOH (3.20 mL, 3.20 mmol). The reaction mixture was stirred for 1 h, quenched with 1N HCl and extracted with ethyl acetate (3×30 mL), washed with brine (10 mL) and dried ($MgSO_4$) to afford 148E as a white foam (0.56 g, 102%). LCMS m/z 343.3 $[M+H]^+$.

Example 148: Compounds 148E and 148C were coupled as previously described in Example 4 to afford Example 148. $^1$H NMR (400 MHz, $CD_3OD$) δ: 9.54 (1H, s), 8.06 (1H, d, J=2.27 Hz), 7.74-7.80 (1H, m), 7.63-7.71 (3H, m), 7.51 (2H, d, J=8.84 Hz), 7.24-7.30 (4H, m), 7.20 (1H, d, J=8.84 Hz), 4.79-4.85 (1H, m), 4.42 (2H, s), 3.77 (3H, s), 3.14-3.24 (1H, m), 3.00 (1H, dd, J=13.89, 9.35 Hz) ppm. LCMS m/z 562 $[M+H]^+$. Analytical HPLC RT: 7.36 min (Method D).

Example 149

(S)—N-(1-(5-chloro-2-(1H-tetrazol-1-yl)phenethylamino)-1-oxo-3-phenylpropan-2-yl)-1H-indazole-3-carboxamide

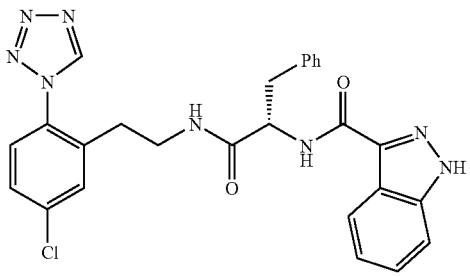 [SMILES: O=C(N[C@@H](Cc1ccccc1)C(=O)NCCc1cc(Cl)ccc1-n1cnnn1)c1n[nH]c2ccccc12]

Example 149 was prepared according to the procedures previously described for Example 147 starting from commercially available 1H-indazole-3-carboxylic acid. $^1$H NMR (400 MHz, $CD_3OD$) δ: 9.54 (1H, s), 8.21 (1H, s), 8.15 (1H, d, J=8.08 Hz), 7.56-7.65 (2H, m), 7.38-7.49 (3H, m), 7.23-7.29 (4H, m), 7.17-7.23 (1H, m), 4.76 (1H, dd, J=7.83, 6.57 Hz), 3.33-3.38 (2H, m), 3.11-3.18 (1H, m), 3.02-3.10 (1H, m), 2.51-2.67 (2H, m) ppm. LCMS m/z 515.2 $[M+H]^+$. Analytical HPLC RT: 7.71 min (Method D).

Example 150

(E)-4-(2-(3-(5-chloro-2-(1H-tetrazol-1-yl)phenyl) acrylamido)-5,5,5-trifluoropentanamido)benzoic acid

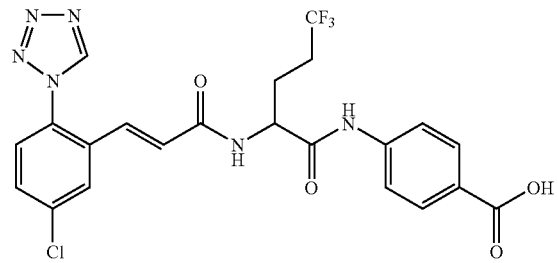 [SMILES: O=C(/C=C/c1cc(Cl)ccc1-n1cnnn1)NC(CCC(F)(F)F)C(=O)Nc1ccc(C(=O)O)cc1]

Example 150 was prepared from the corresponding amino acid via the procedure previously described for Examples 3 and 8. $^1$H NMR (400 MHz, DMSO-$d_6$) δ: 9.87 (s, 1H), 8.67 (d, J=7.8 Hz, 1H), 7.98 (d, J=2.1 Hz, 1H), 7.91 (d, J=8.8 Hz, 2H), 7.78-7.70 (m, 4H), 6.95-6.84 (q(AB), 2H), 4.64-4.58 (m, 1H), 3.32 (bs, 1H), 2.41-2.25 (m, 2H), 2.09-1.84 (m, 2H) ppm. LCMS: m/z 523.3 $[M+H]^+$. Analytical HPLC RT: 6.086 min (Method C, 8 min gradient).

Example 151

(S,E)-3-(5-chloro-2-(1H-tetrazol-1-yl)phenyl)-N-(1-(7-chlorobenzo[d]isoxazol-3-ylamino)-1-oxo-3-phenylpropan-2-yl)acrylamide

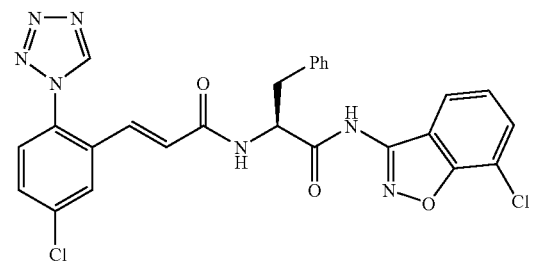 [SMILES: O=C(/C=C/c1cc(Cl)ccc1-n1cnnn1)N[C@@H](Cc1ccccc1)C(=O)Nc1noc2c(Cl)cccc12]

Example 151 was prepared in a similar manner as described for Example 139. $^1$H NMR (400 MHz, $CD_3OD$) δ: 9.52 (1H, s), 8.00 (1H, d, J=2.27 Hz), 7.85 (1H, dd, J=8.08, 1.01 Hz), 7.64-7.74 (2H, m), 7.55-7.60 (1H, m), 7.30-7.39 (5H, m), 7.20-7.25 (1H, m), 7.13 (1H, d, J=15.66 Hz), 6.79 (1H, d, J=15.66 Hz), 4.98-5.06 (1H, m), 3.27-3.31 (1H, m), 3.07-3.16 (1H, m) ppm. LCMS m/z 548.2 $[M+H]^+$. Analytical HPLC RT: 9.58 min (Method D).

Example 152

(S)-4-(2-(3-(5-chloro-2-(1H-tetrazol-1-yl)phenyl) propiolamido)-3-phenylpropanamido)benzamide

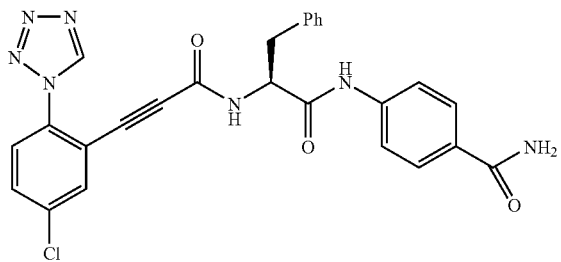 [SMILES: NC(=O)c1ccc(NC(=O)[C@H](Cc2ccccc2)NC(=O)C#Cc2cc(Cl)ccc2-n2cnnn2)cc1]

152A. methyl 3-(5-chloro-2-(1H-tetrazol-1-yl)phenyl) propiolate: To a degassed toluene (40 mL) solution of methyl 3-(tributylstannyl)propiolate (8 g, 21.44 mmol, Logue, M., Teng, K., JOC, 1982, 47, 2549-2553) was added 56A (6 g, 19.58 mmol) and tetrakis(triphenylphosphine) palladium(0) (0.113 g, 0.098 mmol). The reaction mixture was heated to 90° C. for 24 h, quenched with water (30 mL) and extracted with ethyl acetate (100 mL), washed with 10% aq. KF (25 mL), brine (50 mL) and dried (MgSO$_4$), and purified by silica gel chromatography (using DCM and 0-100% ethyl acetate as eluents) to afford 152A (3.9 g, 76%) as a tan solid. LCMS m/z 263.2 [M+H]$^+$.

152B. 3-(5-chloro-2-(1H-tetrazol-1-yl)phenyl)propiolic acid: 152A (1 g, 3.81 mmol) was hydrolysed according to Example 2 to afford 152B (0.8 g, 85%) as a tan solid. LCMS m/z 249.1 (M+H)$^+$.

Example 152: 152B was coupled with (S)-4-(2-amino-3-phenyl propanamido)benzamide (Example 6) as previously described for Example 3 to afford Example 152. $^1$H NMR (400 MHz, DMSO-d$_6$) δ: 10.44 (1H, s), 10.03 (1H, s), 9.39 (1H, d, J=8.08 Hz), 8.05 (1H, d, J=2.02 Hz), 7.81-7.94 (5H, m), 7.64 (2H, d, J=8.59 Hz), 7.31 (4H, d, J=4.29 Hz), 7.18-7.27 (2H, m), 4.70-4.77 (1H, m), 3.05-3.10 (1H, m), 2.91 (1H, dd) ppm. LCMS m/z 514.3 [M+H]$^+$. Analytical HPLC RT: 7.62 min (Method D).

Example 153

(S,E)-methyl 4-(2-(3-(5-chloro-2-(1H-tetrazol-1-yl) phenyl)acrylamido)-4-(piperidin-4-yl)butanamido)-2-fluorophenylcarbamate, TFA salt

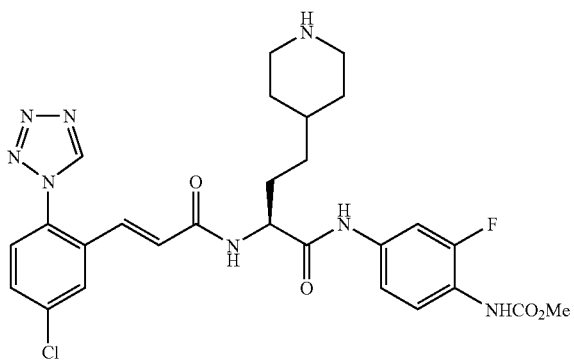

153A. (E)-tert-butyl 4-(3-(benzyloxycarbonylamino)-4-methoxy-4-oxobut-2-enyl)piperidine-1-carboxylate: To a DCM (30 mL) solution of tert-butyl 4-(2-oxoethyl)piperidine-1-carboxylate (3 g, 13.20 mmol) and methyl 2-(benzyloxycarbonyl amino)-2-(dimethoxy phosphoryl)acetate (4.81 g, 14.52 mmol) was added DBU (2.59 mL, 17.16 mmol). The reaction mixture was stirred at rt, quenched with water (10 mL) and extracted with DCM (3×20 mL) and washed with dilute HCl (10 mL), brine (10 mL), dried (MgSO$_4$) and purified by silica gel chromatography (using hexanes and ethyl acetate as eluents) to afford 153A (4.78 g, 84%) as a yellow oil. LCMS m/z 377.1 [M+H-tbutyl]$^+$.

153B. (S)-tert-butyl 4-(3-(benzyloxycarbonylamino)-4-methoxy-4-oxobutyl)piperidine-1-carboxylate: 153A (4.78 g, 11.05 mmol) in MeOH (65 mL) was hydrogenated at 50 psi in the presence of (+)-1,2-Bis((2S,5S)-2,5-diethylphospholano)benzene(cyclooctadiene)rhodium (I) tetrafluoroborate (0.219 g, 0.332 mmol), filtered through Celite®. The filtrate was concentrated to afford 153B (5 g, 104%) of as a yellow oil. $^1$H NMR (400 MHz, CDCl$_3$) δ: 7.29-7.40 (5H, m), 5.26 (1H, d, J=8.08 Hz), 5.13 (2H, s), 4.30-4.44 (1H, m), 4.06 (2H, br. s.), 3.74 (3H, s), 2.65 (2H, br. s.), 1.80-1.95 (1H, m), 1.56-1.72 (3H, m), 1.45 (9H, s), 1.18-1.35 (3H, m), 1.05 (2H, q) ppm. LCMS m/z 379.1 [M+H-tbutyl]$^+$.

153C. (S)-2-(benzyloxycarbonylamino)-4-(1-(tert-butoxycarbonyl)piperidin-4-yl)butanoic acid: 153B (3 g, 6.90 mmol) was hydrolysed according to Example 2 to afford 153C (0.29 g, 100%) as an orange solid. LCMS m/z 421.3 [M+H]$^+$.

153D. methyl 4-amino-2-fluorophenylcarbamate: 2-fluoro-4-nitroaniline was converted to 153D by following the procedure described in Example 3C and then reduced with zinc/NH$_4$Cl according to Example 115B to afford 153D. LCMS m/z 185.2 [M+H]$^+$.

153E. (S)-tert-butyl 4-(3-amino-4-(3-fluoro-4-(methoxycarbonyl amino)phenyl amino)-4-oxobutyl)piperidine-1-carboxylate: Coupling of 153C and 153D according to the procedure described previously in Example 3 followed by deprotection of the Cbz group as in Example 3B afforded 153E. LCMS m/z 353.3 [M+H]$^+$.

Example 153: Treatment of 153E with 55E according to the procedure described in Example 55, followed by deprotection with 4M HCl/dioxane, afforded Example 153. $^1$H NMR (400 MHz, CD$_3$OD) δ: 9.55 (1H, s), 8.00 (1H, d, J=2.27 Hz), 7.59-7.77 (4H, m), 7.21 (1H, dd, J=8.84, 1.01 Hz), 7.15 (1H, d, J=15.66 Hz), 6.81 (1H, d, J=15.66 Hz), 4.50-4.60 (1H, m), 3.76 (3H, s), 3.38 (2H, d, J=1.26 Hz), 2.97 (2H, t, J=12.63 Hz), 1.93-2.03 (3H, m), 1.77-1.87 (1H, m), 1.64 (1H, ddd, J=7.20, 3.79, 3.66 Hz), 1.29-1.53 (4H, m) ppm. LCMS m/z 585.3 [M+H]$^+$. Analytical HPLC RT: 5.43 min (Method D).

Example 154

(S)-methyl 4-(2-(3-(5-chloro-2-(1H-tetrazol-1-yl) phenyl)propiolamido)-4-(piperidin-4-yl)butanamido)-2-fluorophenylcarbamate, TFA salt

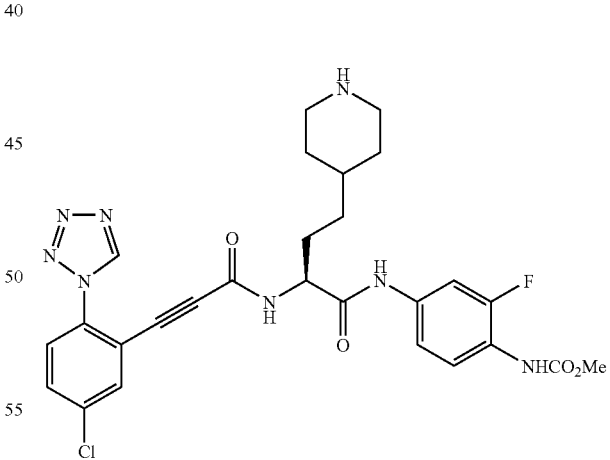

Example 154 was prepared from 152B according to the procedure as previously described for Example 153. $^1$H NMR (400 MHz, CD$_3$OD) δ: 9.78 (1H, s), 7.96 (1H, d, J=1.01 Hz), 7.80-7.86 (2H, m), 7.73 (1H, br. s.), 7.63 (1H, dd, J=12.88, 2.27 Hz), 7.18-7.27 (1H, m), 4.51 (1H, dd, J=8.46, 5.68 Hz), 3.78 (3H, s), 3.39-3.45 (2H, m), 2.94-3.07 (2H, m), 1.90-2.03 (3H, m), 1.74-1.88 (1H, m), 1.64 (1H, dt, J=7.14, 3.63 Hz), 1.33-1.49 (4H, m) ppm. LCMS m/z 583.3 [M+H]$^+$. Analytical HPLC RT: 5.58 min (Method D).

Example 155

(S,E)-methyl 4-(2-(3-(5-chloro-2-(1H-tetrazol-1-yl)phenyl)acrylamido)-3-phenylpropanamido)-2-fluorobenzoate

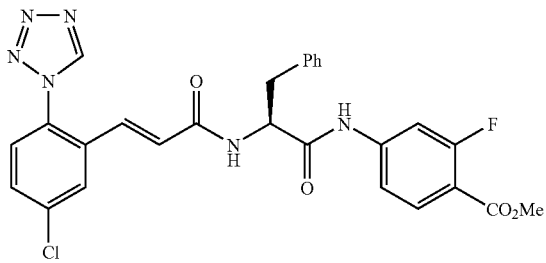 [SMILES: COC(=O)c1ccc(NC(=O)[C@H](Cc2ccccc2)NC(=O)/C=C/c2cc(Cl)ccc2-n2cnnn2)cc1F]

Example 155 was prepared in a similar fashion as described for Example 3. $^1$H NMR (400 MHz, CD$_3$OD) δ: 9.36-9.43 (1H, m), 7.86 (1H, d, J=2.27 Hz), 7.74 (1H, t, J=8.34 Hz), 7.51-7.56 (1H, m), 7.43-7.50 (2H, m), 7.08-7.19 (6H, m), 6.98 (1H, d, J=15.66 Hz), 6.65 (1H, d, J=15.66 Hz), 4.66-4.71 (1H, m), 3.77 (3H, s), 3.04-3.10 (1H, m), 2.91-2.98 (1H, m). LCMS m/z 549.3 [M+H]$^+$. Analytical HPLC RT: 9.12 min (Method D).

Example 156

(S,E)-4-(2-(3-(5-chloro-2-(1H-tetrazol-1-yl)phenyl)acrylamido)-3-phenyl propanamido)-2-fluorobenzoic acid

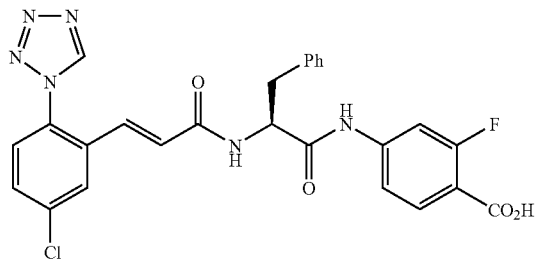 [SMILES: O=C(/C=C/c1cc(Cl)ccc1-n1cnnn1)N[C@@H](Cc1ccccc1)C(=O)Nc1ccc(C(=O)O)c(F)c1]

Example 155 was hydrolysed according to the procedure previously employed for Example 2 to afford Example 156. $^1$H NMR (400 MHz, DMSO-d$_6$) δ:12.99 (1H, br. s.), 10.68 (1H, s), 9.85 (1H, s), 8.65 (1H, d, J=7.83 Hz), 7.95 (1H, d, J=2.02 Hz), 7.84 (1H, t, J=8.59 Hz), 7.70-7.83 (2H, m), 7.64 (1H, dd, J=13.39, 1.77 Hz), 7.35 (1H, dd, J=8.59, 1.77 Hz), 7.26-7.31 (4H, m), 7.17-7.23 (1H, m, J=8.75, 4.28, 4.28, 3.92 Hz), 6.84 (2H, s), 4.64-4.80 (1H, m), 3.08 (1H, dd, J=13.90, 5.31 Hz), 2.91 (1H, dd) ppm. LCMS m/z 535.3 [M+H]$^+$. Analytical HPLC RT: 6.34 min (Method C).

Example 157

(S,E)-2-(4-(2-(3-(5-chloro-2-(1H-tetrazol-1-yl)phenyl)acrylamido)-3-phenylpropanamido)-2-fluorobenzamido)acetic acid

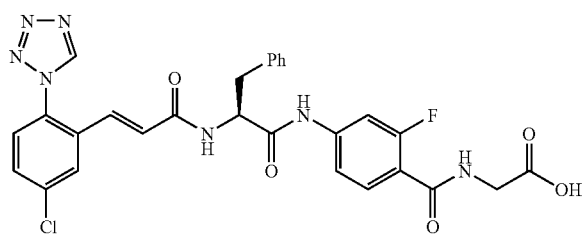 [SMILES: O=C(O)CNC(=O)c1ccc(NC(=O)[C@H](Cc2ccccc2)NC(=O)/C=C/c2cc(Cl)ccc2-n2cnnn2)cc1F]

Example 156 (67 mg, 0.125 mmol) was coupled with tert-butyl 2-aminoacetate, HCl (21.00 mg, 0.125 mmol) and BOP (55.4 mg, 0.125 mmol) in DMF (1 mL) and Hunig's base (88 mL, 0.501 mmol), followed by TFA deprotection afforded Example 157 (23 mg, 31%) as a white solid. $^1$H NMR (400 MHz, CD$_3$OD) δ: 9.51 (1H, s), 7.96 (1H, d, J=2.27 Hz), 7.74-7.83 (1H, m), 7.64-7.71 (2H, m), 7.54-7.57 (1H, m), 7.17-7.33 (6H, m), 7.10 (1H, d, J=15.66 Hz), 6.77 (1H, d, J=15.41 Hz), 4.79-4.86 (1H, m), 4.12 (2H, s), 3.17-3.26 (1H, m), 3.06 (1H, dd) ppm. LCMS m/z 592.3 [M+H]$^+$. Analytical HPLC RT: 6.07 min (Method C).

Example 158

(S,E)-4-(2-(3-(5-chloro-2-(1H-tetrazol-1-yl)phenyl)acrylamido)-3-phenylpropanamido)-2-fluorobenzamide

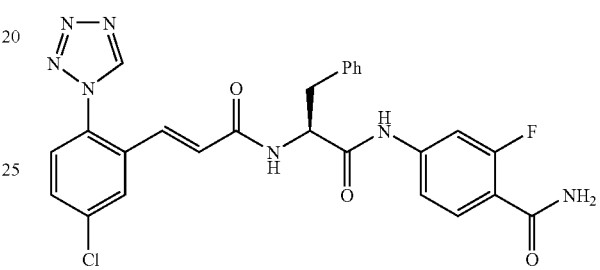

Example 158 was prepared according to Example 157, by replacing tert-butyl 2-aminoacetate with ammonium chloride. $^1$H NMR (400 MHz, CD$_3$OD) δ: 9.52 (1H, s), 7.99 (1H, d, J=2.27 Hz), 7.79 (1H, t, J=8.59 Hz), 7.61-7.70 (2H, m), 7.55-7.61 (1H, m), 7.19-7.33 (6H, m), 7.11 (1H, d, J=15.66 Hz), 6.77 (1H, d, J=15.66 Hz), 4.78-4.83 (1H, m), 3.16-3.24 (1H, m), 3.06 (1H, dd) ppm. LCMS m/z 534.2 [M+H]$^+$. Analytical HPLC RT: 6.09 min (Method C).

Example 159

(E)-3-(5-chloro-2-(1H-tetrazol-1-yl)phenyl)-N—((S)-1-(3-fluoro-4-((R)-3-hydroxypyrrolidine-1-carbonyl)phenylamino)-1-oxo-3-phenylpropan-2-yl)acrylamide

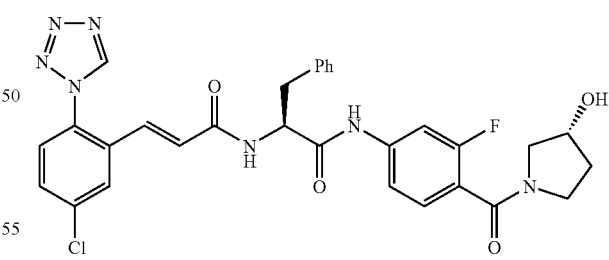

Example 159 was prepared according to Example 157, by replacing tert-butyl 2-aminoacetate with (R)-pyrrolidin-3-ol. $^1$H NMR (400 MHz, CD$_3$OD) δ: 9.51 (1H, s), 7.97 (1H, d, J=2.02 Hz), 7.62-7.69 (2H, m), 7.55-7.60 (1H, m), 7.34-7.42 (1H, m), 7.26-7.29 (5H, m), 7.20-7.27 (1H, m), 7.10 (1H, d, J=15.66 Hz), 6.77 (1H, d, J=15.66 Hz), 4.82 (1H, t, J=7.58 Hz), 4.34-4.57 (1H, m), 3.67-3.76 (1H, m), 3.50-3.60 (2H, m), 3.36-3.42 (1H, m), 3.21 (2H, dt, J=13.71, 6.92 Hz), 3.02-3.09 (1H, m), 1.90-2.15 (2H, m) ppm. LCMS m/z 604.3 [M+H]$^+$. Analytical HPLC RT: 5.98 min (Method C).

Example 160

(S)-methyl 3-(2-(3-(5-chloro-2-(1H-tetrazol-1-yl)phenyl)propiolamido)-3-phenylpropanamido)benzo[d]isoxazol-7-ylcarbamate

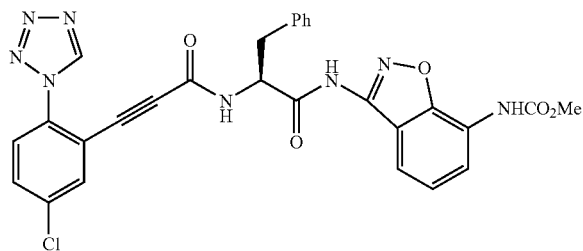

Example 160 was prepared via the amide coupling of 152B and the corresponding amine from Example 141 according to Example 3. $^1$H NMR (400 MHz, CD$_3$OD) δ: 9.75 (1H, s), 7.99 (1H, d, J=7.33 Hz), 7.94 (1H, t, J=1.39 Hz), 7.78 (2H, d, J=1.26 Hz), 7.56 (1H, d, J=7.33 Hz), 7.27-7.36 (5H, m), 7.24 (1H, ddd, J=6.19, 3.03, 2.91 Hz), 4.97-5.04 (1H, m), 3.82 (3H, s), 3.27 (1H, dd, J=13.64, 6.82 Hz), 3.10 (1H, dd) ppm. LCMS m/z 585.3 [M+H]$^+$. Analytical HPLC RT: 6.54 min (Method C).

Example 161

(S)—N-(1-(7-chloro-1H-indazol-3-ylamino)-1-oxo-3-phenylpropan-2-yl)-3-(5-chloro-2-(1H-tetrazol-1-yl)phenyl)propiolamide

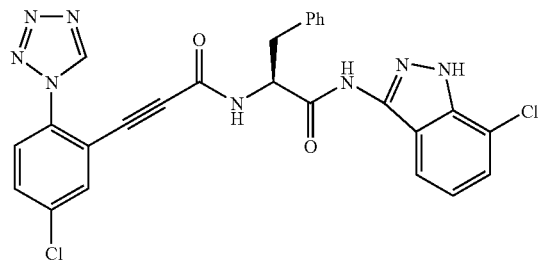 [SMILES: O=C(C#Cc1cc(Cl)ccc1-n1cnnn1)N[C@@H](Cc1ccccc1)C(=O)Nc1n[nH]c2c(Cl)cccc12]

Example 161 was prepared via the deprotection of 145B with 4M HCl/dioxane followed by coupling with 152B according to Example 3. $^1$H NMR (400 MHz, CD$_3$OD) δ: 9.75 (1H, s), 7.92 (1H, s), 7.77 (2H, d, J=1.52 Hz), 7.62 (1H, d, J=7.58 Hz), 7.40 (1H, d, J=7.07 Hz), 7.31-7.37 (4H, m), 7.22-7.29 (1H, m), 7.08 (1H, t, J=7.83 Hz), 4.94-5.00 (1H, m), 3.28-3.32 (1H, m), 3.10 (1H, dd) ppm. LCMS m/z 545.2 [M+H]$^+$. Analytical HPLC RT: 6.8 min (Method C).

Example 162

(S,E)-3-(5-chloro-2-(1H-tetrazol-1-yl)phenyl)-N-(1-oxo-1-(1-oxo-1,2,3,4-tetrahydroisoquinolin-6-ylamino)-3-phenylpropan-2-yl)acrylamide

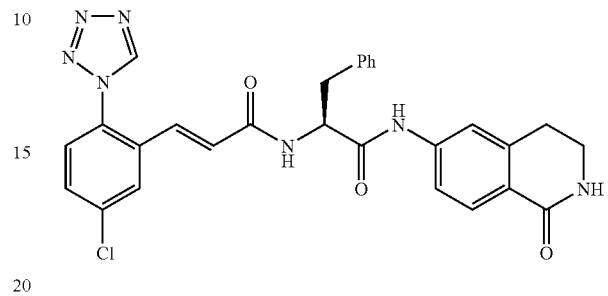

Example 162 was prepared in a similar manner as described for Example 65. $^1$H NMR (400 MHz, CD$_3$OD) δ: 9.51 (1H, s), 7.96 (1H, d, J=2.27 Hz), 7.85 (1H, d, J=8.59 Hz), 7.61-7.70 (1H, m), 7.51-7.58 (2H, m), 7.42 (1H, dd, J=8.34, 2.02 Hz), 7.25-7.33 (4H, m), 7.19-7.25 (1H, m), 7.10 (1H, d, J=15.66 Hz), 6.78 (1H, d, J=15.41 Hz), 4.81-4.85 (1H, m), 3.44-3.54 (2H, m), 3.18-3.23 (1H, m), 2.99-3.09 (1H, m), 2.95 (2H, t, J=6.57 Hz) ppm. MS m/z 542.4 [M+H]$^+$. Analytical HPLC RT: 6.94 min (Method D).

Example 163

(S,E)-ethyl 3-(4-(2-(3-(5-chloro-2-(1H-tetrazol-1-yl)phenyl)acrylamido)-3-phenylpropanamido)phenylcarbamoyloxy)propanoate

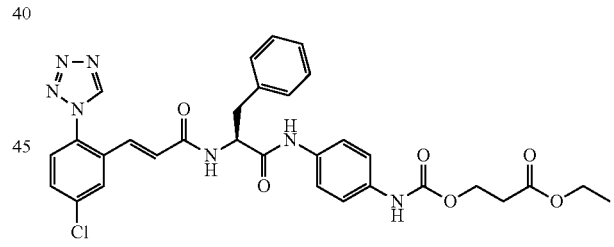

163A. (S)-ethyl 3-(4-(2-amino-3-phenylpropanamido)phenylcarbamoyloxy)propanoate: Esterification of 115B (0.100 g, 0.27 mmol) by treatment with 4.0M HCl/dioxane (0.337 mL, 1.35 mmol) in the presence of EtOH (10 mL) afforded 163A. MS: m/z 400 [M+H]$^+$.

Example 163: 163A was coupled with 1C according to Example 3 to give Example 163. LCMS: m/z 633 [M+H]$^+$. $^1$H NMR (400 MHz, DMSO-d$_6$) δ: 10.08 (1H, s), 9.83 (1H, s), 9.59 (1H, s), 8.52 (1H, d, J=8.34 Hz), 7.92 (1H, d, J=2.02 Hz), 7.66-7.78 (2H, m), 7.41-7.48 (2H, m), 7.35 (2H, d, J=8.59 Hz), 7.23-7.28 (4H, m), 7.15-7.21 (1H, m), 6.75-6.95 (2H, m), 4.67-4.77 (1H, m), 4.26 (2H, t, J=6.06 Hz), 4.08 (2H, q, J=7.24 Hz), 3.05 (1H, dd, J=13.64, 5.31 Hz), 2.88 (1H, dd, J=13.77, 9.22 Hz), 2.68 (2H, t, J=5.94 Hz), 1.18 (3H, t, J=7.07 Hz) ppm. Analytical HPLC RT: 5.85 min (Method C, 8 min gradient).

Example 164

(S,E)-3-(4-(2-(3-(5-chloro-2-(1H-tetrazol-1-yl)phenyl)acrylamido)-3-phenyl-propanamido)benzamido)propanoic acid

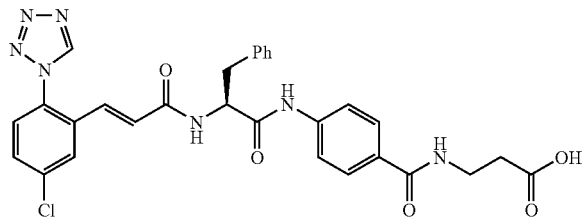 [SMILES: O=C(O)CCNC(=O)c1ccc(NC(=O)[C@H](Cc2ccccc2)NC(=O)/C=C/c2cc(Cl)ccc2-n2cnnn2)cc1]

164A. (S)-tert-butyl 3-(4-(2-(tert-butoxycarbonylamino)-3-phenylpropanamido)-benzamido)propanoate: 4-Nitrobenzoyl chloride (0.5 g, 2.69 mmol) was added to a stirring solution of β-alanine t-butyl ester hydrochloride (0.489 g, 2.69 mmol) and DIPEA (1.412 mL, 8.08 mmol) in DCM (26.9 mL) at rt. After 4 h, the reaction mixture was diluted with EtOAc, washed with 1.0M HCl solution, water, and brine, dried over sodium sulfate, filtered and concentrated to give a residue, which was reduced with zinc/NH$_4$Cl. The resulting amine was coupled with (S)-2-(tert-butoxycarbonylamino)-3-phenylpropanoic acid using DCC as described in 115B to give 164A. LCMS: m/z 512 [M+H]$^+$.

Example 164: Deprotection of 164A with TFA/DCM followed by amide coupling with 1C according to Example 4 gave Example 164. LCMS: m/z 589 [M+H]$^+$. $^1$H NMR (400 MHz, CD$_3$OD) δ: 10.05 (1H, s), 9.49 (1H, s), 8.61 (1H, d, J=7.58 Hz), 7.92-7.99 (1H, m), 7.61-7.67 (1H, m), 7.56 (3H, t, J=7.83 Hz), 7.15-7.30 (6H, m), 7.08 (1H, d, J=15.66 Hz), 6.71-6.79 (1H, m), 4.76-4.83 (1H, m), 3.60 (2H, t, J=6.82 Hz), 3.18 (1H, dd, J=13.52, 6.95 Hz), 3.03 (1H, dd, J=13.77, 7.96 Hz), 2.62 (2H, t, J=6.95 Hz) ppm. Analytical HPLC RT: 5.10 min (Method C, 8 min gradient).

Example 165

(S,E)-2-(1H-tetrazol-5-yl)ethyl 4-(2-(3-(5-chloro-2-(1H-tetrazol-1-yl)phenyl)-acrylamido)-3-phenylpropanamido)phenylcarbamate

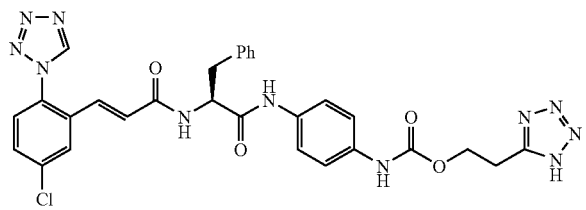 [SMILES: O=C(/C=C/c1cc(Cl)ccc1-n1cnnn1)N[C@@H](Cc1ccccc1)C(=O)Nc1ccc(NC(=O)OCCc2nnn[nH]2)cc1]

Example 165: TEA (0.135 mL, 0.967 mmol) was added to a solution of Example 8 (0.10 g, 0.193 mmol) in THF (1.934 mL) at 0° C. After 20 min, ethyl carbonochloridate (0.021 g, 0.193 mmol) was added dropwise and stirred for an additional 20 min before treating with sodium azide (0.015 g, 0.232 mmol) in water (0.5 mL) dropwise. After an additional hour, the mixture was partitioned between EtOAc and water. The organic layer was washed with brine, dried over sodium sulfate, filtered, and concentrated. The acyl azide intermediate was dissolved and stirred in toluene (5 mL) at 90° C. for 30 min before adding 2-(1H-tetrazol-5-yl)ethanol (0.022 g, 0.193 mmol) in CH$_3$CN (5 mL). The reaction mixture was stirred at 85° C. for 3 h. Then, the reaction mixture was cooled to rt, concentrated, and purified by reverse phase prep HPLC (MeOH/H$_2$O/TFA). The product fractions were liberated of organics and freeze dried to afford Example 165 (30 mg, 25%) as a white solid. LCMS: m/z 628.4 [M+H]$^+$. $^1$H NMR (400 MHz, DMSO-d$_6$) δ: 10.10 (1H, s), 9.84 (1H, s), 9.56 (1H, s), 8.54 (1H, d, J=8.25 Hz), 7.92 (1H, d, J=2.20 Hz), 7.67-7.77 (2H, m), 7.41-7.47 (2H, m), 7.30-7.39 (2H, m), 7.24-7.29 (4H, m), 7.13-7.23 (1H, m), 6.76-6.91 (2H, m), 4.67-4.77 (1H, m), 4.44 (2H, t, J=6.32 Hz), 3.28 (2H, t, J=6.32 Hz), 3.04 (1H, dd, J=13.74, 4.95 Hz), 2.83-2.92 (1H, m) ppm. Analytical HPLC RT: 6.06 min (Method C, 8 min gradient).

Example 166

(R)-5-oxotetrahydrofuran-2-yl)methyl 4-((S)-2-((E)-3-(5-chloro-2-(1H-tetrazol-1-yl)phenyl)acrylamido)-3-phenylpropanamido)phenylcarbamate

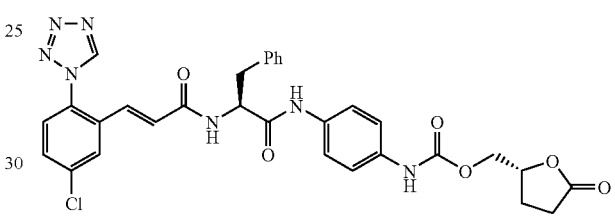

Example 166 was prepared in a similar manner as described for Example 118 LCMS: m/z 630.4 [M+H]$^+$. $^1$H NMR (400 MHz, DMSO-d$_6$) δ: 10.04 (1H, s), 9.78 (1H, s), 9.64 (1H, s), 8.47 (1H, d, J=7.83 Hz), 7.86 (1H, d, J=1.77 Hz), 7.60-7.71 (2H, m), 7.26-7.45 (4H, m), 7.20 (4H, d, J=4.29 Hz), 7.08-7.16 (1H, m), 6.71-6.84 (2H, m), 4.62-4.77 (2H, m), 4.18-4.26 (1H, m), 4.07-4.15 (1H, m), 2.95-3.04 (1H, m), 2.78-2.87 (1H, m), 2.46-2.52 (2H, m), 2.21 (1 H, d, J=7.33 Hz), 1.90 (1H, s) ppm. Analytical HPLC RT: 6.13 min (Method C, 8 min gradient).

Example 167

(S,E)-ethyl 4-(4-(2-(3-(5-chloro-2-(1H-tetrazol-1-yl)phenyl)acrylamido)-3-phenylpropanamido)benzamido)butanoate

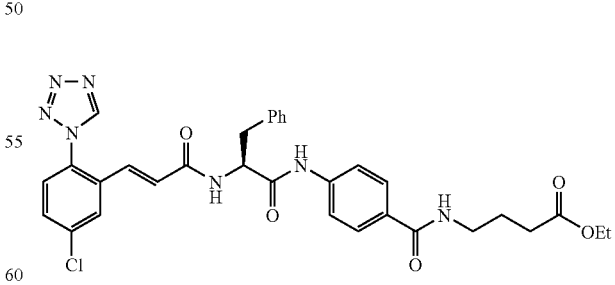

167A. (S)-ethyl 4-(2-(tert-butoxycarbonylamino)-3-phenylpropanamido)-benzoate: The title compound was prepared in a similar manner to that adopted for Example 3A. LCMS: m/z 413.5 [M+H]$^+$.

167B. (S)-4-(2-(tert-butoxycarbonylamino)-3-phenylpropanamido)benzoic acid: NaOH (56.5 mL, 56.5 mmol) was added to 167A in THF/EtOH (2:1; 150 mL) and heated at 60° C. for 2 h. The reaction mixture was cooled to rt, organics were evaporated, and the remaining aqueous phase acidified with 1.0M HCl solution. The remaining aqueous phase was extracted with EtOAc (3×). The combined organic extracts were washed with water, brine, dried over sodium sulfate, filtered, and concentrated to a afford 167B (4.3 g, 59%) as an amber solid. LCMS: m/z 385.5 [M+H]$^+$.

Example 167: 167B was coupled to ethyl 4-aminobutyrate hydrochloride according to Example 3 removal of the Boc group with 4.0M HCl (in dioxane, 10 mL). Subsequent coupling with 1C (0.13 g, 0.52 mmol) according to Example 3 provided Example 167 (28 mg, 17%) as a white solid. LCMS: m/z 632.4 [M+H]$^+$. $^1$H NMR (400 MHz, DMSO-d$_6$) δ: 10.39 (1H, s), 9.84 (1H, s), 8.58 (1H, d, J=8.08 Hz), 8.35 (1H, t, J=5.56 Hz), 7.93 (1H, d, J=2.27 Hz), 7.67-7.83 (4H, m), 7.62 (2H, d, J=8.59 Hz), 7.22-7.30 (4H, m), 7.15-7.22 (1H, m), 6.76-6.93 (2H, m), 4.69-4.82 (1H, m), 4.03 (2H, q, J=7.07 Hz), 3.25 (2H, q, J=6.65 Hz), 3.07 (1H, dd, J=13.64, 5.31 Hz), 2.90 (1H, dd, J=13.77, 9.22 Hz), 2.33 (2H, t, J=7.45 Hz), 1.68-1.83 (2H, m), 1.16 (3H, t, J=7.07 Hz) ppm. Analytical HPLC RT: 6.63 min (Method C, 8 min gradient).

Example 168

(S,E)-4-(4-(2-(3-(5-chloro-2-(1H-tetrazol-1-yl)phenyl)acrylamido)-3-phenylpropanamido)benzamido)butanoic acid

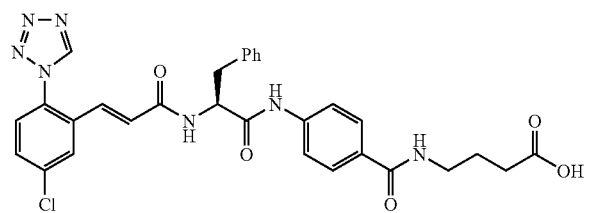 [SMILES: O=C(O)CCCNC(=O)c1ccc(NC(=O)[C@H](Cc2ccccc2)NC(=O)/C=C/c2cc(Cl)ccc2-n2cnnn2)cc1]

Example 168 was prepared via the saponification of Example 167 according to the procedure described in Example 2. LCMS: m/z 602.3 [M+H]$^+$. $^1$H NMR (400 MHz, DMSO-d$_6$) δ: 10.39 (1H, s), 9.84 (1H, s), 8.58 (1H, d, J=7.83 Hz), 8.35 (1H, t, J=5.68 Hz), 7.93 (1H, d, J=2.02 Hz), 7.68-7.84 (4H, m), 7.62 (2 H, d, J=8.84 Hz), 7.22-7.34 (4H, m), 7.13-7.23 (1H, m), 6.75-6.92 (2H, m), 4.70-4.82 (1H, m), 3.24 (2H, q, J=6.74 Hz), 3.04-3.11 (1H, m), 2.90 (1H, dd, J=13.77, 9.22 Hz), 2.26 (2H, t, J=7.33 Hz), 1.65-1.78 (2H, m) ppm. Analytical HPLC RT: 5.23 min (Method C, 8 min gradient).

Example 169

(S,E)-3-(5-chloro-2-(1H-tetrazol-1-yl)phenyl)-N-(1-(4-(3-methyl-3-(pyridin-3-ylmethyl)ureido)phenylamino)-1-oxo-3-phenylpropan-2-yl)acrylamide, TFA salt

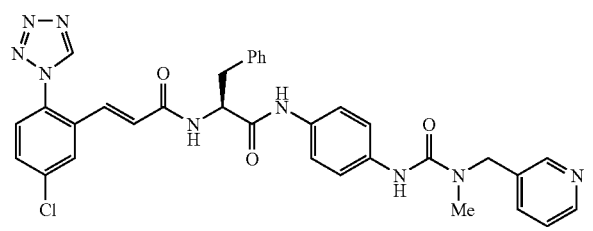 [SMILES: CN(Cc1cccnc1)C(=O)Nc1ccc(NC(=O)[C@H](Cc2ccccc2)NC(=O)/C=C/c2cc(Cl)ccc2-n2cnnn2)cc1]

Example 169 was prepared in a similar manner as described for Example 115 LCMS: m/z 636.5 [M+H]$^+$. $^1$H NMR (400 MHz, DMSO-d$_6$) δ: 10.05 (1H, s), 9.83 (1H, s), 8.65 (2H, s), 8.54 (1H, d, J=8.25 Hz), 8.42 (1H, s), 8.05 (1H, d, J=8.24 Hz), 7.92 (1H, d, J=2.20 Hz), 7.67-7.75 (2H, m), 7.36-7.45 (4H, m), 6.75-6.91 (2H, m), 4.67-4.78 (1H, m), 4.60 (2H, s), 3.04 (1H, dd, J=13.47, 5.22 Hz), 2.97 (3H, s), 2.84-2.92 (1H, m) ppm. Analytical HPLC RT: 5.28 min (Method C, 8 min gradient).

Example 170

(S,E)-N-(1-(4-(3-1H-indazol-5-ylureido)phenylamino)-1-oxo-3-phenylpropan-2-yl)-3-(5-chloro-2-(1H-tetrazol-1-yl)phenyl)acrylamide

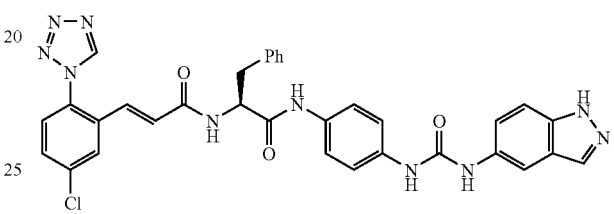

Example 170 was prepared in a similar manner as described for Example 115 LCMS: m/z 647.2 [M+H]$^+$. $^1$H NMR (400 MHz, CD$_3$OD) δ 10.03 (1H, s), 9.51 (1H, s), 8.50 (1H, d, J=9.34 Hz), 8.35 (1H, s), 7.97 (1H, d, J=2.20 Hz), 7.82 (1H, s), 7.60-7.67 (3H, m), 7.46-7.58 (4H, m), 7.17-7.32 (5H, m), 7.09 (1H, d, J=15.39 Hz), 6.78 (1H, d, J=15.39 Hz), 4.81 (1H, t, J=7.42 Hz), 3.20 (1H, dd, J=13.47, 6.87 Hz), 3.01-3.09 (1H, m) ppm. Analytical HPLC RT: 4.89 min (Method C, 8 min gradient).

Example 171

(S,E)-2-(dimethoxyphosphoryl)ethyl 4-(2-(3-(5-chloro-2-(1H-tetrazol-1-yl)phenyl)-acrylamido)-3-phenylpropanamido)phenylcarbamate

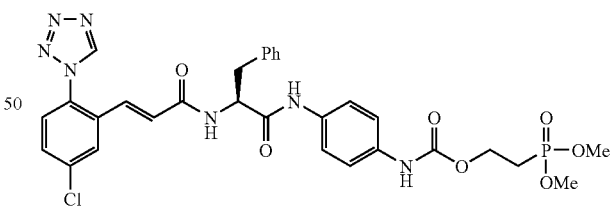

Example 171 was prepared in a similar manner as described for Example 115, by replacing tert-butyl 3-hydroxypropanoate with commercially available dimethyl 2-hydroxyethylphosphonate. LCMS: m/z 670.4 [M+H]$^+$. $^1$H NMR (400 MHz, DMSO-d$_6$) δ: 10.12 (1H, s), 9.85 (1H, s), 9.64 (1H, s), 8.57 (1H, d, J=8.35 Hz), 7.93 (1H, d, J=2.20 Hz), 7.67-7.78 (2H, m), 7.43-7.50 (2H, m), 7.37 (2H, d, J=8.79 Hz), 7.26 (4H, d, J=3.95 Hz), 7.13-7.21 (1H, m), 6.66-6.98 (2H, m), 4.65-4.78 (1H, m), 4.13-4.28 (2H, m), 3.65 (3H, s), 3.63 (3H, s), 2.98-3.14 (3H, m), 2.87 (1H, dd, J=13.40, 9.45 Hz) ppm. Analytical HPLC RT: 6.15 min (Method C, 8 min gradient).

Example 172

(S,E)-2-(4-(2-(3-(5-chloro-2-(1H-tetrazol-1-yl)phenyl)acrylamido)-3-phenylpropanamido)phenylcarbamoyloxy)ethylphosphonic acid

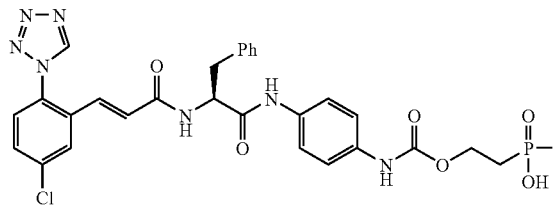

Example 171 (0.234 g, 0.359 mmol) in DCM (15 mL) was treated dropwise with bromotrimethylsilane (0.209 mL, 1.582 mmol) followed by 2,6-lutidine (0.084 mL, 0.719 mmol) at rt for 5 h. The reaction was quenched with addition of MeOH (5 mL), stirred for 1 h, and concentrated. Purification by reverse phase HPLC gave Example 172 (32 mg, 14%) as a white solid after lyophilization. LCMS: m/z 640 [M+H]$^+$. $^1$H NMR (400 MHz, DMSO-d$_6$) δ: 10.11 (1H, s), 9.85 (1H, s), 9.59 (1H, br. s.), 8.55 (1H, d, J=7.70 Hz), 7.93 (1H, s), 7.69-7.77 (2H, m), 7.42-7.49 (2H, m), 7.37 (2H, d, J=8.79 Hz), 7.27 (4H, d, J=4.40 Hz), 7.15-7.22 (1H, m), 6.77-6.91 (2H, m), 4.68-4.77 (1H, m), 4.21 (2H, q, J=7.70 Hz), 3.02-3.11 (1H, m), 2.89 (1H, dd, J=13.47, 9.62 Hz), 1.92-2.04 (2H, m). Analytical HPLC RT: 5.83 min (Method C, 8 min gradient).

Example 173

(S,E)-diethyl 2-(4-(2-(3-(5-chloro-2-(1H-tetrazol-1-yl)phenyl)acrylamido)-3-phenylpropanamido)benzamido)ethylphosphonate

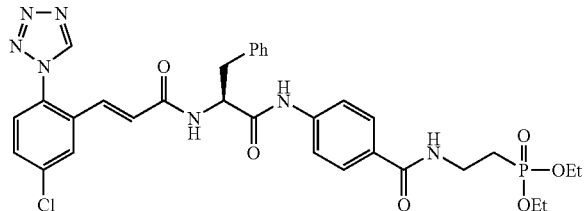 [SMILES: CCOP(=O)(CCNC(=O)c1ccc(NC(=O)[C@H](Cc2ccccc2)NC(=O)/C=C/c2cc(Cl)ccc2-n2cnnn2)cc1)OCC]

Example 173 was prepared in a similar manner as described for Example 167, with commercially available diethyl 2-aminoethylphosphonate. LCMS: m/z 682.4 [M+H]$^+$. $^1$H NMR (400 MHz, DMSO-d$_6$) δ: 10.36-10.47 (1H, m), 9.84 (1H, s), 8.59 (1H, d, J=8.08 Hz), 8.46 (1H, t, J=5.56 Hz), 7.93 (1H, d, J=1.52 Hz), 7.68-7.83 (4H, m), 7.63 (2H, d, J=8.59 Hz), 7.22-7.33 (4H, m, J=3.54 Hz), 7.19 (1H, d, J=7.83 Hz), 6.77-6.91 (2H, m), 4.75 (1H, d, J=5.05 Hz), 3.90-4.06 (4H, m), 3.36-3.50 (2H, m, J=15.79, 15.79 Hz), 3.07 (1H, dd, J=13.89, 5.05 Hz), 2.83-2.96 (1H, m), 1.95-2.12 (2H, m), 1.22 (6H, t, J=6.95 Hz) ppm. Analytical HPLC RT: 6.47 min (Method C, 8 min gradient).

Example 174

(S,E)-2-(4-(2-(3-(5-chloro-2-(1H-tetrazol-1-yl)phenyl)acrylamido)-3-phenylpropanamido)benzamido)ethylphosphonic acid

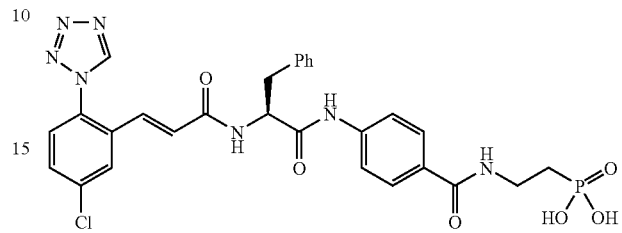

Example 174 was prepared in a similar manner as described for Example 172 LCMS: m/z 681.2 [M+H]$^+$. $^1$H NMR (400 MHz, DMSO-d$_6$) δ: 10.43 (1H, s), 9.85 (1H, s), 8.61 (1H, d, J=8.25 Hz), 8.41 (1H, t, J=5.50 Hz), 7.94 (1H, d, J=2.20 Hz), 7.69-7.80 (4H, m), 7.63 (2H, d, J=8.79 Hz), 7.24-7.31 (4H, m), 7.15-7.22 (1H, m), 6.78-6.90 (2H, m), 4.70-4.80 (1H, m), 3.36-3.47 (2H, m), 3.08 (1H, dd, J=13.74, 4.95 Hz), 2.91 (1H, dd, J=13.74, 9.34 Hz), 1.77-1.89 (2H, m) ppm. Analytical HPLC RT: 5.71 min (Method C, 8 min gradient).

Example 175

(S,E)-N-(3-(1H-tetrazol-5-yl)propyl)-4-(2-(3-(5-chloro-2-(1H-tetrazol-1-yl)phenyl)acrylamido)-3-phenylpropanamido)benzamide

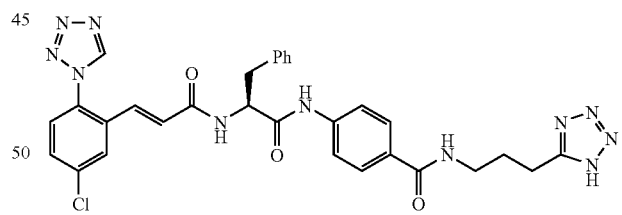

Example 175 was prepared in a similar manner as described for Example 167 replacing ethyl 4-aminobutyrate hydrochloride with 3-(1H-tetrazol-5-yl)propan-1-amine hydrochloride. LCMS: m/z 627.4 [M+H]$^+$. $^1$H NMR (400 MHz, DMSO-d$_6$) δ: 15.93 (1H, s), 10.39 (1H, s), 9.84 (1H, s), 8.58 (1H, d, J=7.83 Hz), 8.44 (1H, t, J=5.56 Hz), 7.93 (1H, d, J=2.02 Hz), 7.68-7.82 (4H, m), 7.62 (2H, d, J=8.84 Hz), 7.22-7.31 (4H, m), 7.12-7.23 (1H, m), 6.78-6.91 (2H, m, J=1.26 Hz), 4.70-4.80 (1H, m), 3.25-3.31 (2H, m), 3.07 (1H, dd, J=13.64, 5.05 Hz), 2.85-2.98 (3H, m), 1.90-2.00 (2H, m) ppm. Analytical HPLC RT: 5.95 min (Method C, 8 min gradient).

Example 176

(S,E)-methyl 3-(4-(2-(3-(5-chloro-2-(1H-tetrazol-1-yl)phenyl)acrylamido)-3-(3,5-difluorophenyl)propanamido)phenylcarbamoyloxy)propanoate

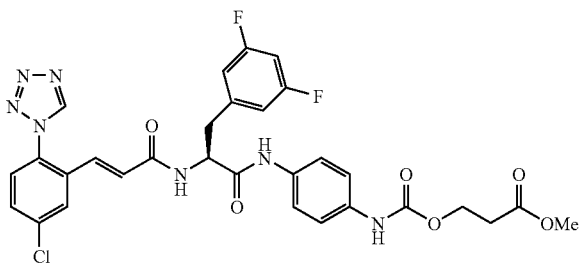 [SMILES: COC(=O)CCOC(=O)Nc1ccc(NC(=O)[C@H](Cc2cc(F)cc(F)c2)NC(=O)/C=C/c2cc(Cl)ccc2-n2cnnn2)cc1]

Example 176 was prepared in a similar manner as described for Example 163 LCMS: m/z 655 [M+H]$^+$. $^1$H NMR (400 MHz, DMSO-d$_6$) δ: 10.11 (1H, s), 9.85 (1H, s), 9.64 (1H, br. s.), 8.62 (1H, d, J=8.24 Hz), 7.96 (1H, d, J=2.20 Hz), 7.69-7.81 (2H, m), 7.35-7.48 (4H, m), 6.96-7.11 (3H, m), 6.77-6.91 (1H, m), 4.69-4.80 (1H, m), 4.28 (2H, t, J=6.05 Hz), 3.64 (3H, s), 3.09 (1H, dd, J=13.74, 4.95 Hz), 2.93 (1H, dd, J=13.74, 9.89 Hz), 2.72 (2H, t, J=6.05 Hz) ppm. Analytical HPLC RT: 6.17 min (Method C, 8 min gradient).

Example 177

(S,E)-methyl 3-(4-(2-(3-(5-chloro-2-(1H-tetrazol-1-yl)phenyl)acrylamido)-propanamido)phenylcarbamoyloxy)propanoate

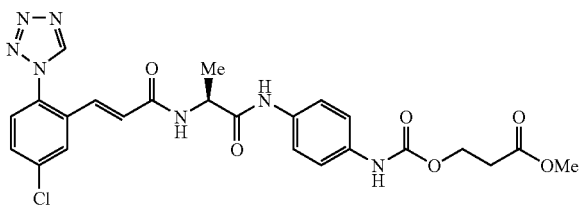 [SMILES: COC(=O)CCOC(=O)Nc1ccc(NC(=O)[C@H](C)NC(=O)/C=C/c2cc(Cl)ccc2-n2cnnn2)cc1]

Example 177 was prepared in a similar manner as described for Example 163 LCMS: m/z 542.3 [M+H]$^+$. $^1$H NMR (400 MHz, DMSO-d$_6$) δ: 10.01 (1H, s), 9.87 (1H, s), 9.61 (1H, br. s.), 8.47 (1H, d, J=7.15 Hz), 7.94 (1H, d, J=2.20 Hz), 7.70-7.79 (2H, m), 7.45-7.51 (2H, m), 7.37 (2H, d, J=8.79 Hz), 6.82-6.97 (2H, m), 4.50 (1H, quin, J=7.15 Hz), 4.27 (2H, t, J=6.05 Hz), 3.63 (3H, s), 2.71 (2H, t, J=6.05 Hz), 1.31 (3H, d, J=7.15 Hz) ppm. Analytical HPLC RT: 6.45 min (Method C, 8 min gradient).

Example 178

(S,E)-3-(4-(2-(3-(5-chloro-2-(1H-tetrazol-1-yl)phenyl)acrylamido)propanamido)-phenylcarbamoyloxy)propanoic acid

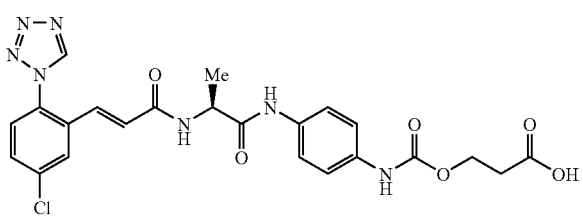 [SMILES: C[C@H](NC(=O)/C=C/c1cc(Cl)ccc1-n1cnnn1)C(=O)Nc1ccc(NC(=O)OCCC(=O)O)cc1]

Example 178 was prepared in a similar manner as described for Examples 163 and 164. LCMS: m/z 528.3 [M+H]$^+$. $^1$H NMR (400 MHz, DMSO-d$_6$) δ 10.00 (1H, s), 9.85-9.88 (1H, m), 9.60 (1H, br. s.), 8.46 (1H, d, J=7.15 Hz), 7.93 (1H, d, J=2.20 Hz), 7.70-7.78 (2H, m), 7.47 (2H, d, J=9.34 Hz), 7.36 (2H, d, J=8.25 Hz), 6.82-6.94 (2H, m), 4.45-4.55 (1H, m), 4.23 (2H, t, J=6.05 Hz), 2.60 (2H, t, J=6.05 Hz), 1.30 (3H, d, J=6.60 Hz) ppm. Analytical HPLC RT: 4.99 min (Method C, 8 min gradient).

Example 179

(S,E)-diethyl 4-(2-(3-(5-chloro-2-(1H-tetrazol-1-yl)phenyl)acrylamido)-3-phenylpropanamido)benzylphosphonate

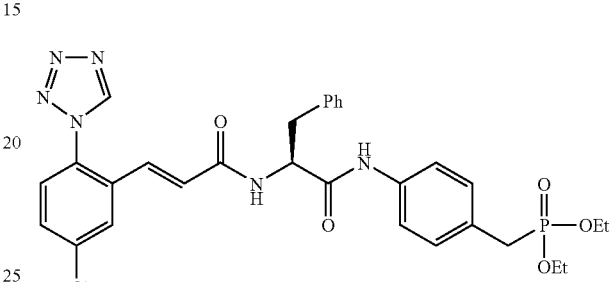

179A. (S)-diethyl 4-(2-amino-3-phenylpropanamido)benzylphosphonate hydrochloride salt: 179A was prepared according to the procedures described for Example 43A, by replacing 6-aminoisoindolin-1-one with diethyl 4-aminobenzylphosphonate and by subsequent deprotection with 4M HCl/dioxane. LCMS: m/z 391.3 [M+H]$^+$.

Example 179: Amide coupling of 179A and 1C according to the procedure described in Example 3 gave Example 179. LCMS: m/z 623.3 [M+H]$^+$. $^1$H NMR (400 MHz, CD$_3$OD) δ: 9.85 (1H, s), 9.49 (1H, s), 8.57 (1H, d, J=7.58 Hz), 7.96 (1H, d, J=2.02 Hz), 7.61-7.67 (1H, m), 7.53-7.58 (1H, m), 7.41 (2H, d, J=8.08 Hz), 7.15-7.29 (7H, m), 7.07 (1H, d, J=15.66 Hz), 6.75 (1H, d, J=15.66 Hz), 4.74-4.83 (1H, m), 3.96-4.09 (4H, m), 3.12-3.23 (3H, m), 2.98-3.07 (1H, m), 1.24 (6H, t, J=7.07 Hz) ppm. Analytical HPLC RT: 6.73 min (Method C, 8 min gradient).

Example 180

(S,E)-4-(2-(3-(5-chloro-2-(1H-tetrazol-1-yl)phenyl)acrylamido)-3-phenylpropanamido)benzylphosphonic acid

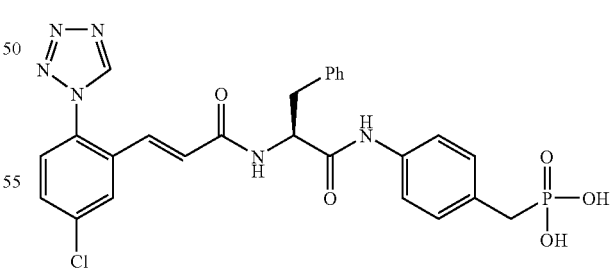

Example 180 was prepared from Example 179 in a similar manner as described for Example 172. LCMS: m/z 566 [M+H]$^+$. $^1$H NMR (400 MHz, DMSO-d$_6$) δ: 10.13 (1H, s), 9.86 (1H, s), 8.56 (1H, d, J=7.70 Hz), 7.94 (1H, d, J=2.20 Hz), 7.69-7.78 (2H, m), 7.44 (2H, d, J=8.25 Hz), 7.23-7.31 (4H, m), 7.14-7.23 (3H, m), 6.79-6.91 (2H, m), 4.71-4.79 (1H, m), 3.06 (1H, dd, J=13.47, 5.22 Hz), 2.84-2.96 (3H, m) ppm. Analytical HPLC RT: 5.82 min (Method C, 8 min gradient).

Example 181

(S,E)-diethyl 4-(2-(3-(5-chloro-2-(1H-tetrazol-1-yl)phenyl)acrylamido)-3-phenylpropanamido)phenylphosphonate

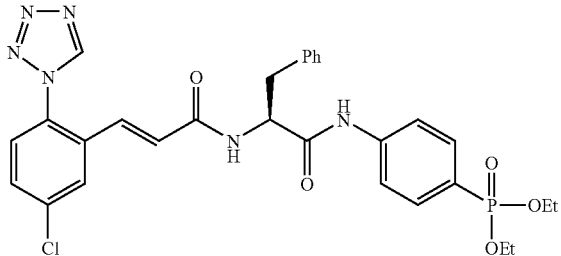 [SMILES: CCOP(=O)(OCC)c1ccc(NC(=O)[C@H](Cc2ccccc2)NC(=O)/C=C/c2cc(Cl)ccc2-n2cnnn2)cc1]

181A. diethyl 4-aminophenylphosphonate: (Reference: Y. Kim et al., J. Med. Chem., 44, 2001, pp. 340-349). A mixture of tert-butyl 4-iodophenylcarbamate (1.277 g, 4.0 mmol), diethyl phosphite (0.567 mL, 4.4 mmol), triethylamine (0.613 mL, 4.4 mmol), and tetrakis(triphenylphosphine) palladium(0) (0.231 g, 0.2 mmol) in dry toluene (10 mL) were heated at 90° C. in a sealed vial (20 mL) under a blanket of nitrogen for 15 h. After cooling to rt, the reaction mixture was diluted with EtOAc, filtered through a plug of Celite®), and filtrate concentrated. Purification by flash chromatography (hexane/EtOAc as eluants) gave an oil. The Boc group was removed by treatment with 4.0M HCl in dioxane (15 mL) with stirring at rt for 2 h. The reaction mixture was evaporated to dryness. The residue was dissolved in EtOAc and washed with a 20% NaHCO$_3$ solution, brine, dried over sodium sulfate, filtered, and concentrated to afford crude 181A (0.36 g, 39%). LCMS: m/z 230.2 [M+H]$^+$.

Example 181: 181A was converted to Example 181 according to the procedures described in Example 179. LCMS: m/z 609.3 [M+H]$^+$. $^1$H NMR (400 MHz, DMSO-d$_6$) δ: 10.46 (1H, s), 9.86 (1H, s), 8.64 (1H, d, J=7.91 Hz), 8.51 (1H, t, J=5.49 Hz), 7.95 (1H, d, J=1.76 Hz), 7.69-7.82 (4H, m), 7.64 (2H, d, J=8.79 Hz), 7.24-7.32 (4H, m), 7.15-7.23 (1H, m), 6.77-6.90 (2H, m), 4.69-4.81 (1H, m), 3.92-4.07 (4H, m), 3.38-3.47 (2H, m), 3.03-3.16 (1H, m), 2.90 (1H, dd, J=13.40, 9.45 Hz), 1.98-2.11 (2H, m), 1.22 (6H, t, J=7.03 Hz) ppm. Analytical HPLC RT: 6.73 min (Method C, 8 min gradient).

Example 182

(S,E)-4-(2-(3-(5-chloro-2-(1H-tetrazol-1-yl)phenyl)acrylamido)-3-phenyl-propanamido)phenylphosphonic acid

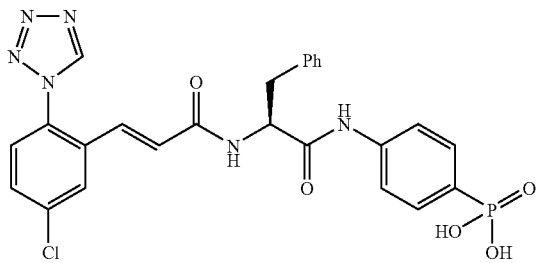 [SMILES: O=C(/C=C/c1cc(Cl)ccc1-n1cnnn1)N[C@@H](Cc1ccccc1)C(=O)Nc1ccc(P(=O)(O)O)cc1]

Example 182 was prepared from Example 171 in a similar manner as described for Example 172. LCMS: m/z 553.2 [M+H]$^+$. $^1$H NMR (400 MHz, DMSO-d$_6$) δ: 10.38 (1H, s), 9.85 (1H, s), 8.59 (1H, d, J=7.83 Hz), 7.94 (1H, d, J=2.02 Hz), 7.69-7.78 (2H, m), 7.56-7.68 (4H, m), 7.23-7.34 (4H, m), 7.15-7.23 (1H, m), 6.78-6.93 (2H, m), 4.71-4.82 (1H, m), 3.08 (1H, dd, J=13.77, 5.18 Hz), 2.92 (1H, dd, J=13.64, 9.09 Hz) ppm. Analytical HPLC RT: 5.62 min (Method C, 8 min gradient).

Example 183

(S,E)-ethyl 4-(4-(2-(3-(5-chloro-2-(1H-tetrazol-1-yl)phenyl)acrylamido)-3-phenylpropanamido)-2-fluorobenzamido)butanoate

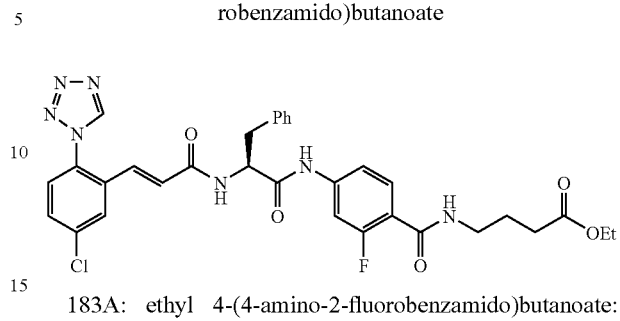

183A: ethyl 4-(4-amino-2-fluorobenzamido)butanoate: Triethylamine (1.13 mL, 8.10 mmol) was added to a suspension of 2-fluoro-4-nitrobenzoic acid (0.50 g, 2.70 mmol), ethyl 4-aminobutyrate hydrochloride (0.68 g, 4.05 mmol), and BOP reagent (1.31 g, 2.97 mmol) in THF (30 mL) at rt and stirred for 14 h. The reaction mixture was poured into EtOAc, washed with 1.0M HCl solution, water, brine, dried over sodium sulfate, filtered, and concentrated. The oil was dissolved in acetone (40 mL) and zinc (0.88 g, 13.51 mmol) and ammonium chloride (1.45 g, 27.0 mmol) dissolved in water (10 mL) added, respectively. The reaction mixture was stirred overnight, diluted with acetone and filtered through a plug of Celite®. The filtrate was concentrated under vacuum. The resulting suspension was diluted with water and extracted with EtOAc (3×30 mL). The combined organic layers were washed with brine, dried over sodium sulfate, filtered, and concentrated to afford crude 183A (0.620 g, 2.311 mmol, 86% yield) as an amber oil, which was carried forward to next reaction without purification. LCMS: m/z 269 [M+H]$^+$.

Example 183. 183A was converted to Example 183 according to the procedures described for Example 3. LCMS: m/z 649.4 [M+H]$^+$. $^1$H NMR (400 MHz, DMSO-d$_6$) δ: 10.55 (1H, s), 9.84 (1H, s), 8.62 (1H, d, J=7.83 Hz), 8.12-8.20 (1H, m), 7.94 (1H, d, J=2.02 Hz), 7.67-7.78 (2H, m), 7.54-7.64 (2H, m), 7.15-7.35 (7H, m), 6.74-7.00 (2H, m), 4.69-4.80 (1H, m), 4.04 (2H, q, J=7.24 Hz), 3.24 (2H, q, J=6.57 Hz), 3.03-3.11 (1H, m), 2.91 (1H, dd, J=13.52, 9.22 Hz), 2.34 (2H, t, J=7.45 Hz), 1.75 (2H, quin, J=7.14 Hz), 1.17 (3H, t, J=7.07 Hz) ppm. Analytical HPLC RT: 6.73 min (Method C, 8 min gradient).

Example 184

(S,E)-2-(dimethoxyphosphoryl)ethyl 4-(2-(3-(5-chloro-2-(1H-tetrazol-1-yl)phenyl)acrylamido)-3-phenylpropanamido)benzoate

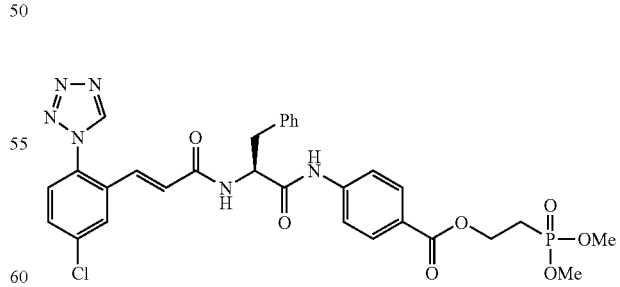

184A. 2-(dimethoxyphosphoryl)ethyl 4-aminobenzoate: To a stirred solution of 4-nitrobenzoyl chloride (0.36 g, 1.95 mmol) in DCM (2 mL) was sequentially added a solution of dimethyl 2-hydroxyethylphosphonate (0.30 g, 1.95 mmol) in DCM (5 mL), pyridine (0.39 mL, 4.87 mmol), and DMAP (0.024 g, 0.195 mmol) at 0° C. The reaction was allowed to warm to rt and stirred for 6 h, and then concentrated. The residue was dissolved in EtOAc, washed with 1.0M HCl solution, water, brine, dried over sodium sulfate, filtered, and concentrated. The residue was re-dissolved in acetone (12 mL) and treated with zinc (0.64 g, 9.73 mmol) and ammonium chloride (1.04 g, 19.5 mmol) in water (3 mL), respectively. The reaction mixture was filtered through a plug of Celite®. The filter-cake was rinsed with acetone, and the filtrate was concentrated. The resulting residue was diluted with water and extracted with EtOAc (3×). The combined organic extracts were washed with brine, dried over sodium sulfate, filtered, and concentrated to give 184A. LCMS: m/z 274.2 [M+H]$^+$.

Example 184: Amide coupling of Boc-L-phenylalanie and 184A in a similar manner as Example 3A, followed by deprotection with 4M HCl/dioxane, and final coupling according to Example 55 afforded Example 184 (181 mg, 29%) as a white solid. LCMS: m/z 653.3 [M+H]$^+$. $^1$H NMR (400 MHz, DMSO-d$_6$) δ: 10.57 (1H, s), 9.85 (1H, s), 8.64 (1H, d, J=7.70 Hz), 7.90-7.96 (2H, m), 7.69-7.78 (4H, m), 6.79-6.89 (2H, m), 4.73-4.81 (1H, m), 4.35-4.46 (2H, m), 3.66 (3H, s), 3.63 (3H, s), 3.09 (1H, dd, J=13.74, 4.95 Hz), 2.91 (1H, dd, J=13.74, 9.34 Hz), 2.34 (2H, dt, J=18.14, 7.15 Hz). Analytical HPLC RT: 6.57 min (Method C, 8 min gradient).

Example 185

(S)-2-methoxyethyl 4-(1-(5-chloro-2-(1H-tetrazol-1-yl)phenethylamino)-1-oxo-3-phenylpropan-2-ylcarbamoyl)phenylcarbamate

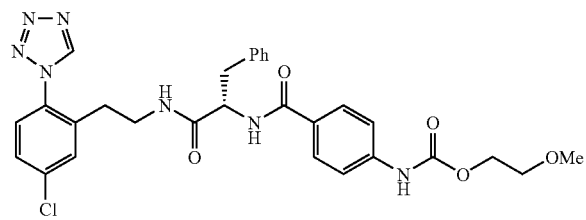 [SMILES: COCCOC(=O)Nc1ccc(C(=O)N[C@@H](Cc2ccccc2)C(=O)NCCc2cc(Cl)ccc2-n2cnnn2)cc1]

Example 185 was prepared according to the procedures described in Examples 28A and 28B, by replacing 4-(methoxycarbonyl)benzoic acid with 4-((2-methoxyethoxy)carbonylamino)benzoic acid. LCMS: m/z 592.3 [M+H]$^+$. $^1$H NMR (400 MHz, DMSO-d$_6$) δ: 9.98 (1H, s), 9.79 (1H, s), 8.36 (1H, d, J=8.34 Hz), 8.14 (1H, t, J=5.56 Hz), 7.45-7.76 (7H, m), 7.09-7.31 (5H, m), 4.47-4.58 (1H, m), 4.17-4.29 (2H, m), 3.52-3.60 (2H, m), 3.12-3.32 (5H, m), 2.85-2.98 (2H, m), 2.51-2.56 (2H, m) ppm. Analytical HPLC RT: 7.40 min (Method D, 15 min gradient).

Example 186

(S)—N-(1-(5-chloro-2-(1H-tetrazol-1-yl)phenethylamino)-1-oxo-3-phenylpropan-2-yl)-4-(1H-tetrazol-5-yl)benzamide

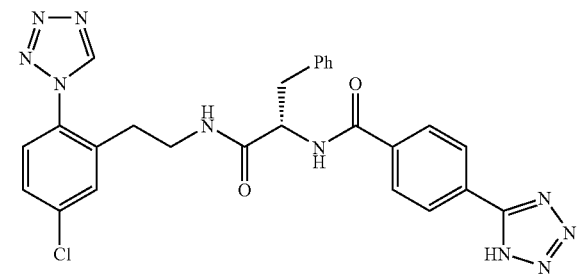 [SMILES: O=C(N[C@@H](Cc1ccccc1)C(=O)NCCc1cc(Cl)ccc1-n1cnnn1)c1ccc(-c2nnn[nH]2)cc1]

Example 186 was prepared in a similar manner as described for Example 28 LCMS: m/z 543.4 [M+H]$^+$. $^1$H NMR (400 MHz, DMSO-d$_6$) δ: 9.80 (1H, s), 8.74 (1H, d, J=8.34 Hz), 8.22 (1H, t, J=5.68 Hz), 8.08 (2H, d, J=8.34 Hz), 7.98 (2H, d, J=8.34 Hz), 7.64 (1H, d, J=2.02 Hz), 7.53-7.61 (2H, m), 7.27-7.33 (2H, m), 7.23 (2H, t, J=7.58 Hz), 7.14 (1H, t, J=7.33 Hz), 4.55-4.66 (1H, m), 3.14-3.28 (2H, m), 2.87-3.02 (2H, m), 2.51-2.58 (2H, m) ppm. Analytical HPLC RT: 6.93 min (Method D, 15 min gradient).

Example 187

(S)—N-(1-(5-chloro-2-(1H-tetrazol-1-yl)phenethylamino)-1-oxo-3-phenylpropan-2-yl)-2,5-dioxo-2,3,4,5-tetrahydro-1H-benzo[e][1,4]diazepine-8-carboxamide

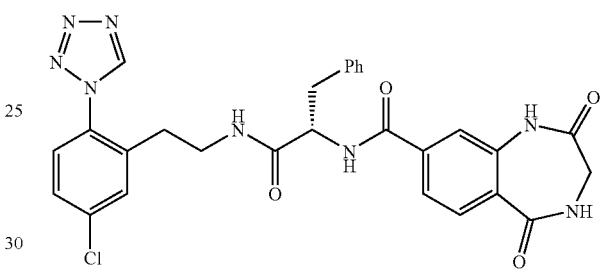

Example 187 was prepared in a similar manner as described for Example 28 LCMS: m/z 573.3 [M+H]$^+$. $^1$H NMR (400 MHz, DMSO-d$_6$) δ: 10.43 (1H, s), 9.77-9.82 (1H, m), 8.69 (1H, d, J=8.59 Hz), 8.63 (1H, s), 8.19 (1H, s), 7.78 (1H, d, J=8.34 Hz), 7.53-7.66 (4H, m), 7.48 (1H, d, J=1.26 Hz), 7.19-7.29 (4 H, m), 7.14 (1H, t, J=7.20 Hz), 4.57 (1H, s), 3.52-3.64 (2H, m), 3.21 (2H, d, J=25.01 Hz), 2.86-2.99 (2H, m), 2.53-2.57 (2H, m) ppm. Analytical HPLC RT: 6.13 min (Method D, 15 min gradient).

Example 188

(S,E)-3-(4-(2-(3-(5-chloro-2-(1H-tetrazol-1-yl)phenyl)acrylamido)-3-phenylpropanamido)-2-fluorophenylcarbamoyloxy)propanoic acid

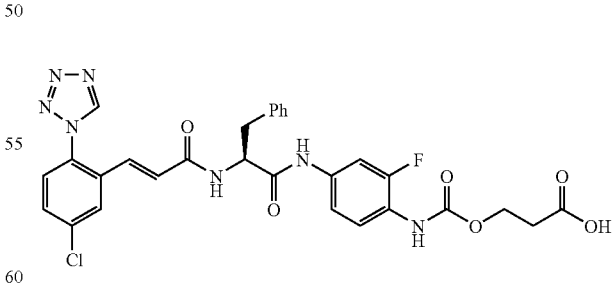

188A. (S)-tert-butyl 1-(4-amino-3-fluorophenylamino)-1-oxo-3-phenylpropan-2-ylcarbamate: 188A was prepared according to the procedures described in Example 3A, by replacing p-nitroaniline with 3-fluoro-4-nitroaniline, followed by the reduction of the nitro group with zinc/NH$_4$Cl as described in Example 115B. LCMS: m/z 374.3 [M+H]$^+$.

188B. (S)-3-(4-(2-amino-3-phenylpropanamido)-2-fluorophenyl-carbamoyloxy)-propanoic acid: To a stirred solution of triphosgene (0.148 g, 0.500 mmol) in dry Et₂O (10 mL), activated charcoal was added. The reaction mixture was stirred at rt for 1 h. The suspension was cooled to 0° C. and tert-butyl 3-hydroxypropanoate (0.146 g, 1.0 mmol) in Et₂O (5 mL) were added dropwise and stirring continued overnight at rt. The reaction mixture was filtered, concentrated, dissolved in DCM (5 mL), and then added to 188A (0.373 g, 1.000 mmol) and pyridine (0.243 mL, 3.00 mmol) in DCM (10 mL) at 0° C. The reaction mixture was stirred at rt. After 1 h, the reaction mixture was concentrated. The resulting oil was diluted with EtOAc, washed several times with 1.0M HCl, water, brine, dried over sodium sulfate, filtered, and concentrated to afford a solid. The Boc group was removed by treatment with HCl in dioxane (4.0 M, 3.0 mL, 12.0 mmol) for 1 h, and concentrating to dryness to afford 188B that was used in subsequent reaction without further purification. LCMS: m/z 390.2 [M+H]⁺.

Example 188 was prepared by coupling 188B with 55E according to Example 55 LCMS: m/z 622.3 [M+H]⁺. ¹H NMR (400 MHz, DMSO-d₆) δ: 10.34 (1H, s), 9.85 (1H, s), 9.21 (1H, br. s.), 8.58 (1H, d, J=8.08 Hz), 7.94 (1H, d, J=2.27 Hz), 7.69-7.79 (2H, m), 7.57 (1H, dd, J=12.88, 2.02 Hz), 7.40-7.49 (1H, m), 7.24-7.29 (4H, m), 7.15-7.23 (2H, m), 6.79-6.90 (2H, m), 4.68-4.76 (1H, m), 4.23 (2H, t, J=6.19 Hz), 3.06 (1H, dd, J=13.77, 5.43 Hz), 2.90 (1H, dd, J=13.77, 9.22 Hz), 2.60 (2H, t, J=6.06 Hz) ppm. Analytical HPLC RT: 7.81 min (Method D, 15 min gradient).

Example 189

(S,E)-ethyl 3-(4-(2-(3-(5-chloro-2-(1H-tetrazol-1-yl)phenyl)acrylamido)-3-phenylpropanamido)-2-fluorophenylcarbamoyloxy)propanoate

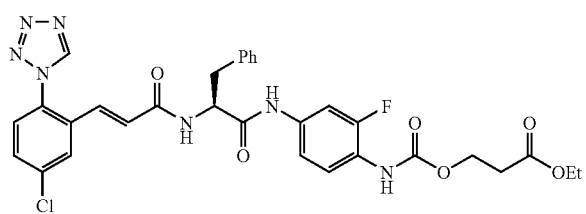 [SMILES: CCOC(=O)CCOC(=O)Nc1ccc(NC(=O)[C@H](Cc2ccccc2)NC(=O)/C=C/c2cc(Cl)ccc2-n2cnnn2)cc1F]

Example 189 was prepared as a white solid (22 mg, 11%), by the esterification of 188B (0.117 g, 0.30 mmol) by treatment with HCl in dioxane (4.0 M, 3.0 mL, 12.0 mmol) in the presence of EtOH (1 mL) at rt. followed by the coupling of the amine and 55E according to the procedure described in Example 55. LCMS: m/z 650.3 [M+H]⁺. ¹H NMR (400 MHz, DMSO-d₆) δ: 10.35 (1H, s), 9.85 (1H, s), 9.23 (1H, br. s.), 8.59 (1H, d, J=8.08 Hz), 7.95 (1H, d, J=2.27 Hz), 7.70-7.78 (2H, m), 7.58 (1H, dd, J=13.01, 2.15 Hz), 7.40-7.49 (1H, m), 7.25-7.31 (4H, m), 7.18-7.24 (2H, m), 6.80-6.93 (2H, m), 4.69-4.77 (1H, m), 4.27 (2H, t, J=6.06 Hz), 4.10 (2H, q, J=7.16 Hz), 3.07 (1H, dd, J=13.64, 5.31 Hz), 2.88-2.95 (1H, m), 2.68 (2H, t, J=6.06 Hz), 1.20 (3H, t, J=7.07 Hz) ppm. Analytical HPLC RT: 8.91 min (Method D, 15 min gradient).

Example 190

(S,E)-4-(4-(2-(3-(5-chloro-2-(1H-tetrazol-1-yl)phenyl)acrylamido)-3-phenylpropanamido)-2-fluorobenzamido)butanoic acid

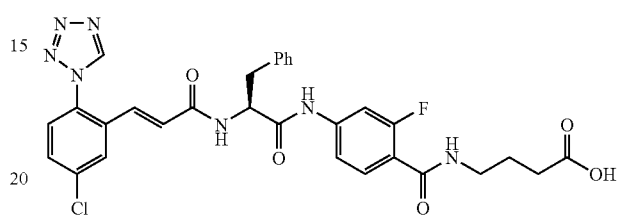

Example 190 was prepared according to the procedures described in Examples 167/168 and Example 55. LCMS: m/z 621.4 [M+H]⁺. ¹H NMR (400 MHz, DMSO-d₆) δ: 12.05 (1H, br. s.), 10.56 (1H, s), 9.85 (1H, s), 8.63 (1H, d, J=7.83 Hz), 8.13-8.23 (1H, m), 7.95 (1H, d, J=2.27 Hz), 7.68-7.79 (2H, m), 7.55-7.65 (2H, m), 7.15-7.34 (6H, m), 6.73-6.92 (1H, m), 4.69-4.80 (1H, m), 3.20-3.30 (2H, m), 3.08 (1H, dd, J=13.77, 5.18 Hz), 2.92 (1H, dd, J=13.64, 9.09 Hz), 2.27 (2H, t, J=7.45 Hz), 1.73 (2H, quin, J=7.14 Hz) ppm. Analytical HPLC RT: 7.54 min (Method D, 15 min gradient).

Example 191

(S,E)-2-(dimethoxyphosphoryl)ethyl 4-(2-(3-(5-chloro-2-(1H-tetrazol-1-yl)phenyl)acrylamido)-3-phenylpropanamido)-2-fluorophenylcarbamate

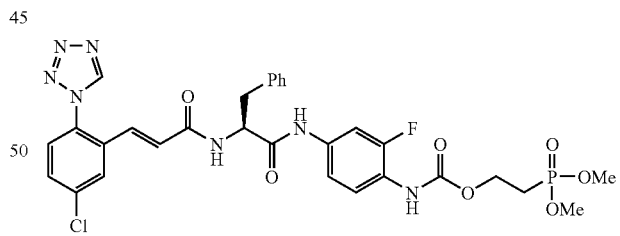

Example 191 was prepared in a similar manner as described for Example 189 LCMS: m/z 686.3 [M+H]⁺. ¹H NMR (400 MHz, DMSO-d₆) δ: 10.37 (1H, s), 9.86 (1H, s), 9.26 (1H, br. s.), 8.61 (1H, d, J=7.70 Hz), 7.91-7.98 (1H, m), 7.94 (1H, d, J=2.20 Hz), 7.70-7.79 (2H, m), 7.59 (1H, dd, J=12.64, 2.20 Hz), 7.46 (1H, t, J=8.52 Hz), 7.25-7.31 (4H, m), 7.16-7.25 (2H, m), 6.76-6.91 (2H, m), 4.68-4.78 (1H, m), 4.16-4.27 (1H, m), 3.66 (3H, s), 3.63 (3H, s), 3.07 (1H, dd, J=13.74, 4.95 Hz), 2.91 (1H, dd, J=13.74, 9.34 Hz), 2.17-2.29 (1H, m) ppm. Analytical HPLC RT: 7.23 min (Method D, 15 min gradient).

Example 192

(S,E)-ethyl 2-(5-(2-(3-(5-chloro-2-(1H-tetrazol-1-yl)phenyl)acrylamido)-3-phenylpropanamido)-1H-indol-3-yl)acetate

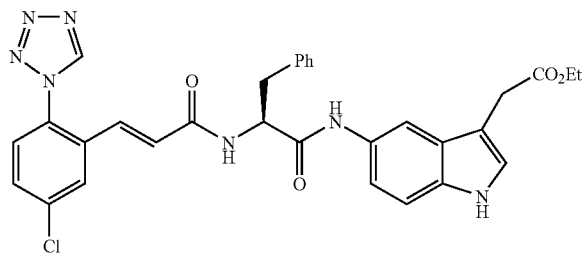 [SMILES: CCOC(=O)Cc1c[nH]c2ccc(NC(=O)[C@H](Cc3ccccc3)NC(=O)/C=C/c3cc(Cl)ccc3-n3cnnn3)cc12]

192A. tert-butyl 2-iodo-4-nitrophenylcarbamate: A solution of 2-iodo-4-nitroaniline (2.75 g, 10.4 mmol), di-tert-butyl dicarbonate (5.45 g, 24.96 mmol), and DMAP (0.127 g, 1.04 mmol) in THF (50 mL) stirred at rt overnight. The sample was dry loaded on silica gel and purified (80 g column, 100% DCM) to afford the corresponding N,N-diBOC substituted aniline. This material was dissolved in DCM (50 mL) and TFA (1.202 mL, 15.60 mmol) at rt for 15 h. The reaction was quenched with triethylamine (5 mL). The reaction mixture was washed with 1.0M HCl, water, brine, dried over sodium sulfate, filtered, and concentrated. The crude monoboc desired product was purified by normal phase column chromatography (hexane/EtOAc solvent system) to afford 192A (2.01 g, 53%) as a yellow solid. LCMS: m/z 365 [M+H]$^+$.

192B: tert-butyl 5-amino-3-(2-ethoxy-2-oxoethyl)-1H-indole-1-carboxylate: (E)-ethyl 4-bromobut-2-enoate (1.59 g, 8.24 mmol) was added to a stirring suspension of 192A (2.0 g, 5.49 mmol) and potassium carbonate (3.04 g, 22.0 mmol) in DMF (36.6 mL) at rt. After stirring for 3 h, triphenylphosphine (0.144 g, 0.549 mmol) and palladium(II) acetate (0.062 g, 0.28 mmol) were added at rt under a nitrogen atmosphere. After 30 min, the reaction mixture was heated at 65° C. overnight. The reaction mixture was cooled to rt and extracted with Et$_2$O (100 mL), washed with water, brine, dried over sodium sulfate, filtered, and concentrated. The crude product was purified by flash chromatography (hexane/DCM as eluants) to afford an amber oil. The material was dissolved in acetone (50 mL) and treated with zinc (1.796 g, 27.5 mmol) followed by ammonium chloride (2.94 g, 54.9 mmol) in water (10 mL) at rt. After stirring for 18 h, the reaction mixture was filtered through a plug of Celite®. The filter cake was rinsed with acetone, and the organics were evaporated. The resulting residue was dissolved in EtOAc, washed with water, brine, dried over sodium sulfate, filtered, and concentrated to afford 192B, which was carried forward to next reaction without further purification. LCMS: m/z 319 [M+H]$^+$.

Example 192: the title compound was subsequently prepared according to the procedure described in Example 55. LCMS: m/z 598.3 [M+H]$^+$. $^1$H NMR (400 MHz, DMSO-d$_6$) δ: 10.90 (1H, s), 10.00 (1H, s), 9.85 (1H, s), 8.53 (1H, d, J=8.25 Hz), 7.93-7.95 (1H, m), 7.69-7.78 (3H, m), 7.15-7.31 (9H, m), 6.78-6.93 (2H, m), 4.73-4.82 (1H, m), 4.07 (2H, q, J=7.15 Hz), 3.67 (2H, s), 3.09 (1H, dd, J=13.74, 4.95 Hz), 2.87-2.96 (1H, m), 1.18 (3H, t, J=7.15 Hz) ppm. Analytical HPLC RT: 6.60 min (Method C, 8 min gradient).

Example 193

(S,E)-2-(5-(2-(3-(5-chloro-2-(1H-tetrazol-1-yl)phenyl)acrylamido)-3-phenylpropanamido)-1H-indol-3-yl)acetic acid

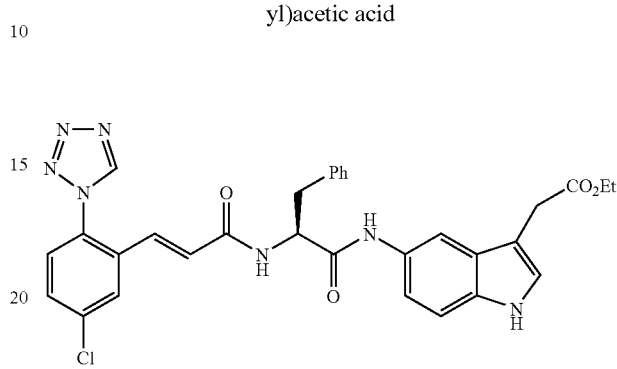

Example 193 was prepared by saponification of 192C according to Example 2, Boc-deprotection with 4M HCl/dioxane, and then amide coupling with 55E according to Example 55. LCMS: m/z 570.3 [M+H]$^+$. $^1$H NMR (400 MHz, DMSO-d$_6$) δ: 10.84 (1H, s), 9.99 (1H, s), 9.85 (1H, s), 8.50 (1H, d, J=8.34 Hz), 7.94 (1H, d, J=2.27 Hz), 7.65-7.75 (2H, m), 7.15-7.31 (9H, m), 6.78-6.95 (2H, m), 4.73-4.82 (1H, m), 3.58 (2H, s), 3.06-3.14 (1H, m), 2.92 (1H, s) ppm. Analytical HPLC RT: 6.00 min (Method C, 8 min gradient).

Examples 195-196

195A. (S,E)-2-(3-(5-chloro-2-(1H-tetrazol-1-yl)phenyl)acrylamido)-3-phenylpropanoic acid: 4-Methylmorpholine (4.22 g, 41.7 mmol) was added to a solution of (S)-methyl 2-amino-3-phenylpropanoate hydrochloride (3.0 g, 13.9 mmol), 1C (3.49 g, 13.9 mmol), EDC (4.8 g, 25.0 mmol), and 1-hydroxybenzotriazole hydrate (2.13 g, 13.9 mmol) in DMF (25 mL). After stirring for 14 h, the reaction mixture was partitioned between water/brine (1:1) and EtOAc. The organic layer was washed with brine, dried over sodium sulfate, filtered, and concentrated. The ester intermediate was dissolved in THF (69.5 mL) at rt and lithium hydroxide monohydrate (1.28 g, 30.6 mmol) in water (69.5 mL) slowly added with stirring. After 1 h, the mixture was acidified with 1.0N HCl solution and extracted several times with EtOAc. The combined organic extracts were washed with brine, dried over sodium sulfate, filtered, and concentrated to give 195A (4.5 g, 81%) as an off-white solid LCMS: m/z 398 [M+H]$^+$.

General Procedure: 195A (0.08 mmol) in DMF (0.30 mL) was added into Wheaton tubes (16×100 mm) containing the appropriate amine (0.08 mmol) at rt. A solution of HOBt (0.094 mmol, 1.25 eq), EDC (0.094 mmol, 1.25 eq), and DIPEA (0.375 mmol, 4.7 eq) in DMF (0.375 mL) was added to the reaction mixtures, the tubes placed on Bohdan Miniblock XT, and the mixtures agitated at 400 rpm on an Innova platform shaker for 15 h. The samples were diluted with MeOH (0.250 mL), purified by reversed phase preparative HPLC (ACN/H$_2$O/TFA). Concentration of the product fractions gave Examples 195-196.

| Example # | Structure | Analytical HPLC RT (Method C, 4 min Run) | [M + H]+ |
|---|---|---|---|
| 195 | 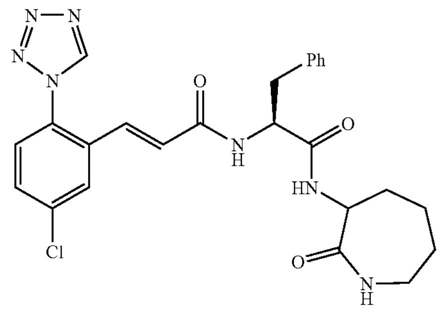 [SMILES: O=C(/C=C/c1cc(Cl)ccc1-n1cnnn1)N[C@@H](Cc1ccccc1)C(=O)NC1CCCCNC1=O] | 1.82 | 508.19 |
| 196 | 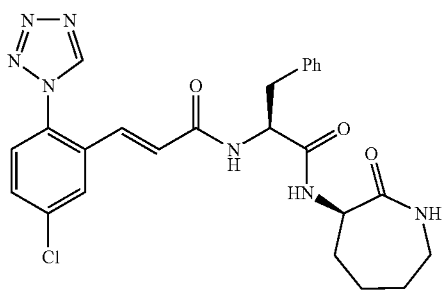 [SMILES: O=C(/C=C/c1cc(Cl)ccc1-n1cnnn1)N[C@@H](Cc1ccccc1)C(=O)N[C@@H]1CCCCNC1=O] | 2.02 | 508.36 |

Example 197

(S,E)-ethyl 2-(4-(2-(3-(5-chloro-2-(1H-tetrazol-1-yl)phenyl)acrylamido)-3-phenylpropanamido)phenyl)acetate Example 198

(S,E)-2-(4-(2-(3-(5-Chloro-2-(1H-tetrazol-1-yl)phenyl)acrylamido)-3-phenylpropanamido)phenyl)aceticacid

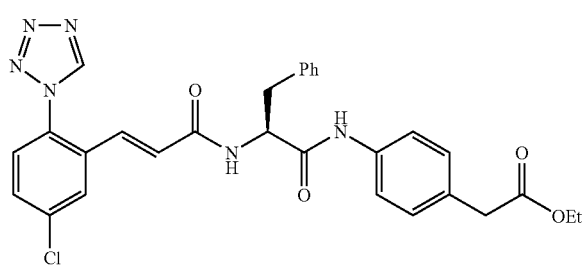 [SMILES: CCOC(=O)Cc1ccc(NC(=O)[C@H](Cc2ccccc2)NC(=O)/C=C/c2cc(Cl)ccc2-n2cnnn2)cc1]

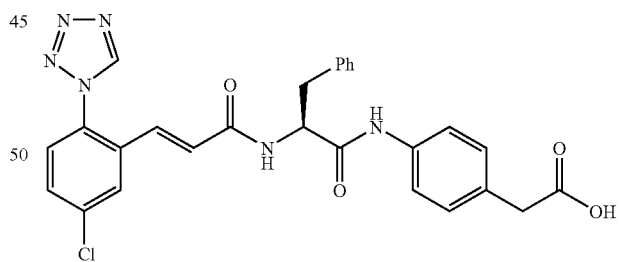

Example 197 was prepared according to Example 1, by replacing 1D with 1C. LCMS: m/z 559.1 (M+H)+. $^1$H NMR (500 MHz, DMSO-d$_6$) δ: 10.18 (s, 1H) 9.84 (s, 1H) 8.56 (d, J=8.25 Hz, 1H) 7.93 (d, J=2.20 Hz, 1H) 7.68-7.76 (m, 2H) 7.49 (d, J=8.25 Hz, 2H) 7.25-7.29 (m, 4H) 7.15-7.21 (m, 3H) 6.79-6.89 (m, 2H) 4.68-4.80 (m, 1H) 4.05 (q, J=7.15 Hz, 2H) 3.54-3.63 (m, 2H) 3.06 (dd, J=13.75, 5.50 Hz, 1H) 2.84-2.97 (m, 1H) 1.09-1.23 (t, J=7.15 Hz, 3H) ppm. Analytical HPLC RT: 3.98 min (Method A, 4 min gradient).

Example 198 was prepared according to Example 2, by replacing Example 1 with Example 197. LCMS: m/z 531.3 (M+H).+ $^1$H NMR (500 MHz, CD$_3$OD) δ: 9.39 (s, 1H) 7.86 (s, 1H) 7.40-7.59 (m, 2H) 7.30 (d, J=8.25 Hz, 2H) 7.05-7.22 (m, 7H) 6.97 (d, J=15.95 Hz, 1H) 6.66 (d, J=15.95 Hz, 1H) 4.69 (t, J=7.42 Hz, 1H) 3.44 (s, 2H) 3.20 (m, 3H) 3.07 (dd, J=13.75, 6.60 Hz, 1H) 2.88-2.98 (m, 1H) ppm. Analytical HPLC RT: 3.99 min (Method A, 4 min gradient).

Example 199

(S,E)-4-(2-(3-(5-chloro-2-(1H-tetrazol-1-yl)phenyl)acrylamido)-3-(1-ethyl-1H-pyrazol-3-yl)propanamido)benzoic acid

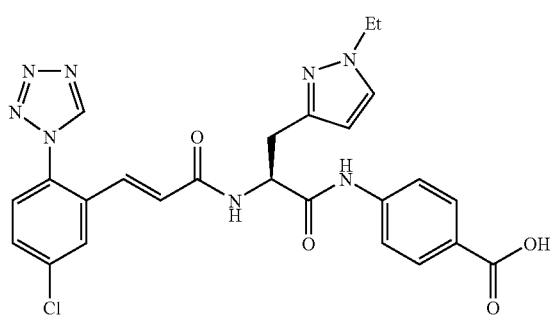 [SMILES: CCn1ccc(C[C@H](NC(=O)/C=C/c2cc(Cl)ccc2-n2cnnn2)C(=O)Nc2ccc(C(=O)O)cc2)n1]

Example 199 was prepared according to the procedures described for Example 55 from Intermediate 2. LC/MS m/z 535.3 (M+H)$^+$. $^1$H NMR (500 MHz, DMSO-$d_6$) δ: 10.47 (1H, s), 9.86 (1H, s), 8.55 (1H, d, J=7.70 Hz), 7.94 (1H, d, J=2.20 Hz), 7.87 (2H, d, J=8.80 Hz), 7.67-7.76 (4H, m), 7.55 (1H, d, J=2.20 Hz), 6.85-6.92 (2H, m), 6.05 (1H, d, J=2.20 Hz), 4.72-4.77 (1H, m), 4.00 (2H, q, J=7.15 Hz), 2.99-3.04 (1H, m), 2.89 (1H, dd, J=14.30, 8.80 Hz), 1.26 (3H, t, J=7.42 Hz) ppm. Analytical HPLC RT: 3.89 min (Method A, 4 min gradient, 4.6×50 mm column)

Example 200

(R)—N-(1-(5-chloro-2-(1H-tetrazol-1-yl)phenethylamino)-1-oxo-3-phenylpropan-2-yl)-4-hydroxy-2-oxo-1,2-dihydroquinoline-6-carboxamide

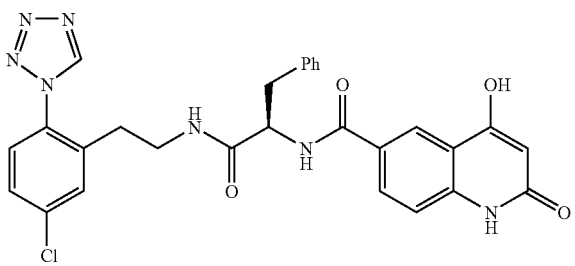 [SMILES: O=C(N[C@H](Cc1ccccc1)C(=O)NCCc1cc(Cl)ccc1-n1cnnn1)c1ccc2[nH]c(=O)cc(O)c2c1]

Example 200 was prepared following the procedures described in Example 66 by replacing (S)-2-(tert-butoxycarbonylamino)-3-phenylpropanoic acid with (R)-2-(tert-butoxycarbonylamino)-3-phenylpropanoic acid. $^1$H NMR (500 MHz, DMSO-$d_6$) δ: 2.52 (t, J=7.42 Hz, 2H) 2.94 (d, J=7.70 Hz, 2H) 3.12-3.29 (m, 2H) 4.54-4.62 (m, 1H) 5.75 (s, 1H) 7.12 (t, J=7.15 Hz, 1H) 7.18-7.24 (m, 3H) 7.25-7.30 (m, 2H) 7.55 (dd, J=8.25, 1.65 Hz, 1H) 7.58 (d, J=8.25 Hz, 1H) 7.63 (d, J=2.20 Hz, 1H) 7.89 (dd, J=8.52, 1.92 Hz, 1H) 8.18 (t, J=5.77 Hz, 1H) 8.30 (d, J=1.65 Hz, 1H) 8.62-8.67 (m, 1H) 9.80 (s, 1H) 11.39 (s, br, 1H) 11.55 (s, br, 1H). LCMS (ESI) m/z: 558.3 (M+H)$^+$. Analytical HPLC RT: 9.2 min (Method D).

Example 201

(S)—N-(1-(5-chloro-2-(1H-tetrazol-1-yl)phenethylamino)-1-oxo-3-phenylpropan-2-yl)-2-fluoroisonicotinamide

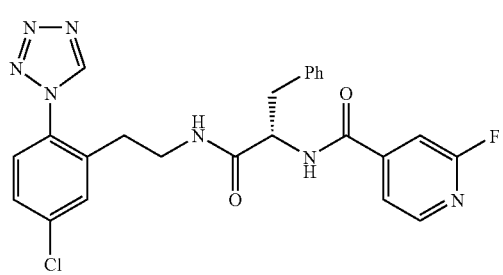 [SMILES: O=C(N[C@@H](Cc1ccccc1)C(=O)NCCc1cc(Cl)ccc1-n1cnnn1)c1ccnc(F)c1]

Example 201 was prepared following the procedures described in Example 66. $^1$H NMR (400 MHz, CD$_3$OD) δ: 2.51-2.63 (m, 2H) 2.96 (dd, J=13.69, 8.80 Hz, 1H) 3.13 (dd, J=13.69, 6.36 Hz, 1H) 3.25-3.29 (m, 2H) 4.64-4.72 (m, 1H) 7.16-7.28 (m, 5H) 7.31 (s, 1H) 7.43 (d, J=8.31 Hz, 1H) 7.47 (dd, J=8.80, 2.45 Hz, 1H) 7.55 (td, J=3.30, 1.71 Hz, 1H) 7.58 (d, J=1.96 Hz, 1H) 8.23 (t, J=5.62 Hz, 1H) 8.30 (d, J=5.38 Hz, 1H) 8.78 (d, J=7.83 Hz, 1H) 9.52 (s, 1H). LCMS (ESI) m/z: 494.0 (M+H)$^+$. Analytical HPLC RT: 7.91 min (Method D).

Example 202

(S)—N-(1-(5-chloro-2-(1H-tetrazol-1-yl)phenethylamino)-1-oxo-3-phenylpropan-2-yl)-2-hydroxyisonicotinamide

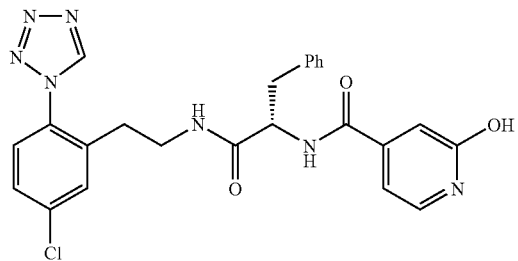 [SMILES: O=C(N[C@@H](Cc1ccccc1)C(=O)NCCc1cc(Cl)ccc1-n1cnnn1)c1ccnc(O)c1]

Example 202 was prepared following the procedures described in Example 66. $^1$H NMR (400 MHz, CD$_3$OD) δ: 2.50-2.64 (m, 2H) 2.93 (dd, J=13.69, 9.29 Hz, 1H) 3.11 (dd, J=13.69, 6.36 Hz, 1H) 3.22-3.29 (m, 2H) 4.62 (dd, J=9.29, 6.36 Hz, 1H) 6.55 (d, J=6.36 Hz, 1H) 6.74 (s, 1H) 7.13-7.29 (m, 5H) 7.43 (d, J=8.80 Hz, 1H) 7.45-7.50 (m, 2H) 7.58 (d, J=1.96 Hz, 1H) 8.19 (t, br, J=5.87 Hz, 1H) 8.66 (d, br, J=8.31 Hz, 1H) 9.52 (s, 1H). LCMS (ESI) m/z: 492.0 (M+H)$^+$. Analytical HPLC RT: 6.05 min (Method D).

Example 203

(S)-methyl 5-(1-(5-chloro-2-(1H-tetrazol-1-yl)phen-ethylamino)-1-oxo-3-phenylpropan-2-ylcarbamoyl)thiophene-2-carboxylate

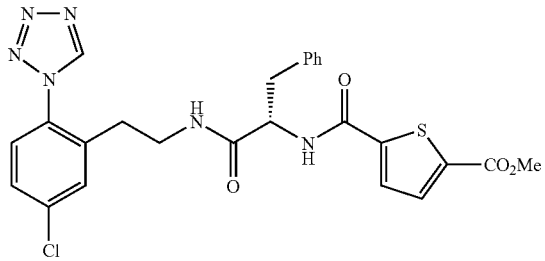 [SMILES: COC(=O)c1ccc(C(=O)N[C@@H](Cc2ccccc2)C(=O)NCCc2cc(Cl)ccc2-n2cnnn2)s1]

Example 203 was prepared following the procedures described in Example 66. $^1$H NMR (400 MHz, CD$_3$OD) δ: 2.47-2.63 (m, 2H) 2.96 (dd, J=13.69, 9.29 Hz, 1H) 3.11 (dd, J=13.69, 6.85 Hz, 1H) 3.22-3.36 (m, 2H) 3.88 (s, 3H) 4.62 (dd, J=8.80, 6.36 Hz, 1H) 7.13-7.19 (m, 1H) 7.19-7.28 (m, 4H) 7.41 (d, J=8.31 Hz, 1H) 7.46 (dd, J=8.31, 2.45 Hz, 1H) 7.57 (d, J=2.45 Hz, 1H) 7.66 (d, J=3.91 Hz, 1H) 7.73 (d, J=3.91 Hz, 1H) 9.52 (s, 1H). LCMS (ESI) m/z: 539.1.0 (M+H)$^+$. Analytical HPLC RT: 8.07 min (Method D).

Example 204

(S)-2-amino-N-(1-(5-chloro-2-(1H-tetrazol-1-yl)phenethylamino)-1-oxo-3-phenylpropan-2-yl)benzo[d]thiazole-6-carboxamide, TFA salt

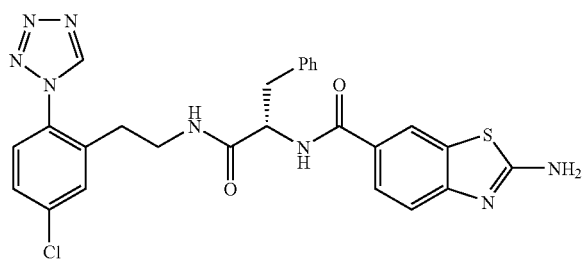 [SMILES: Nc1nc2ccc(C(=O)N[C@@H](Cc3ccccc3)C(=O)NCCc3cc(Cl)ccc3-n3cnnn3)cc2s1]

Example 204 was prepared following the procedures described in Example 66. $^1$H NMR (400 MHz, CD$_3$OD) δ: 2.48-2.63 (m, 2H) 2.98 (dd, J=13.69, 8.80 Hz, 1H) 3.12 (dd, J=13.69, 6.36 Hz, 1H) 3.22-3.37 (m, 2H) 4.68 (dd, J=8.80, 6.85 Hz, 1H) 7.14-7.20 (m, 1H) 7.20-7.25 (m, 4H) 7.42 (d, J=8.80 Hz, 1H) 7.46 (dd, J=8.80, 1.96 Hz, 1H) 7.47 (d, J=8.80 Hz, 1H) 7.58 (d, J=1.96 Hz, 1H) 7.81 (dd, J=8.31, 1.47 Hz, 1H) 8.12 (d, J=1.47 Hz, 1H) 8.20 (t, J=5.62 Hz, 1H) 9.52 (s, 1H). LCMS (ESI) m/z: 547.1 (M+H)$^+$. Analytical HPLC RT: 5.78 min (Method D).

Example 205

(S)—N$^2$-(1-(5-chloro-2-(1H-tetrazol-1-yl)phenethylamino)-1-oxo-3-phenylpropan-2-yl)thiophene-2,5-dicarboxamide

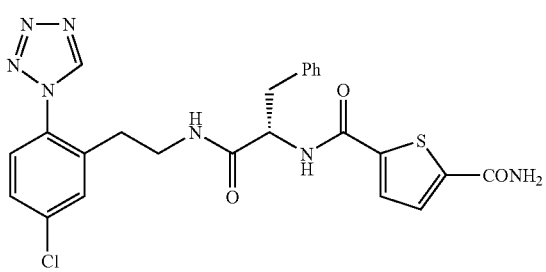 [SMILES: NC(=O)c1ccc(C(=O)N[C@@H](Cc2ccccc2)C(=O)NCCc2cc(Cl)ccc2-n2cnnn2)s1]

A solution of Example 203 (10 mg, 0.019 mmol) in NH$_3$ (7M in MeOH, 3 mL) was stirred at rt. for 72 h. Solvent was removed. Purification by reverse phase chromatography gave Example 205 (6.1 mg, 62.7% yield) as a white solid. $^1$H NMR (500 MHz, CD$_3$OD) δ: 2.48-2.62 (m, 2H) 2.97 (dd, J=13.75, 8.80 Hz, 1H) 3.11 (dd, J=13.75, 6.60 Hz, 1H) 3.25-3.35 (m, 2H, overlapped with solvent, COSY) 4.58-4.68 (m, 1H) 7.14-7.19 (m, 1H) 7.19-7.26 (m, 4H) 7.41 (d, J=8.80 Hz, 1H) 7.45 (dd, J=8.80, 2.20 Hz, 1H) 7.57 (d, J=2.20 Hz, 1H) 7.63 (s, 2 H) 8.16 (t, J=5.77 Hz, 1H, br) 8.48 (d, J=7.70 Hz, 1H, br) 9.52 (s, 1H). LCMS (ESI) m/z: 524.0 (M+H)$^+$. Analytical HPLC RT: 6.79 min (Method D).

Example 206

(S)—N-(1-(5-chloro-2-(1H-tetrazol-1-yl)phenethylamino)-1-oxo-3-phenylpropan-2-yl)-3-oxo-3,4-dihydro-2H-benzo[b][1,4]thiazine-7-carboxamide

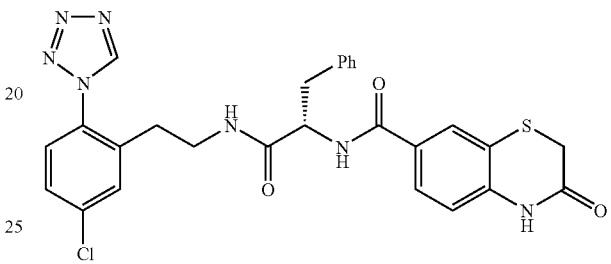

206A. 3-oxo-3,4-dihydro-2H-benzo[b][1,4]thiazine-7-carbonitrile: To a solution of 7-bromo-2H-benzo[b][1,4]thiazin-3(4H)-one (0.50 g, 2.048 mmol) in DMF (10 mL) were added zinc cyanide (0.390 mL, 6.14 mmol), TEA (0.571 mL, 4.10 mmol) and [1,1'-bis(diphenylphosphino)ferrocene]dichloropalladium(II) (0.084 g, 0.102 mmol). The reaction mixture was heated in a microwave at 150° C. for 15 min. The reaction mixture was diluted with EtOAc, filtered through a pad of Celite®, washed with sat NaHCO$_3$, 1M HCl and saturated NaCl. The organic phase was dried over MgSO$_4$, filtered and concentrated. Purification by normal phase chromatography gave 206A (275 mg, 70.6% yield) as a pale solid. LCMS (ESI) m/z: 191.1 (M+H)$^+$.

206B. 3-oxo-3,4-dihydro-2H-benzo[b][1,4]thiazine-7-carboxylic acid: A solution of 206A (175 mg, 0.920 mmol) in 6N HCl (5 mL, 30.0 mmol) was stirred at 100° C. for 3 days. Solvent was removed under reduced pressure to give 206B (192 mg, 100% yield) as a brown solid. MS (ESI) m/z: 210.0 (M+H)$^+$.

Example 206: The title compound was prepared following the procedures described in Example 66 by replacing 66C with 225B. $^1$H NMR (400 MHz, CD$_3$OD) δ: 2.49-2.62 (m, 2H) 2.92-3.01 (m, 1H) 3.07-3.14 (m, 1H) 3.19-3.41 (m, 2H) 3.46 (s, 2H) 4.64 (dd, J=8.80, 6.85 Hz, 1H) 6.97 (d, J=8.31 Hz, 1H) 7.11-7.29 (m, 5H) 7.42 (d, J=8.31 Hz, 1H) 7.44-7.49 (m, 1H) 7.53-7.60 (m, 1H) 7.72 (d, J=1.96 Hz, 1H) 8.15 (t, br, J=5.87 Hz, 1H) 9.52 (s, 1H). LCMS (ESI) m/z: 562.1 (M+H)$^+$. Analytical HPLC RT: 10.84 min (Method D).

Example 207

(S,E)-2-(4-(2-(3-(5-chloro-2-(1H-tetrazol-1-yl)phenyl)acrylamido)-3-phenylpropanamido)-2-fluoro-N-methylbenzamido)acetic acid

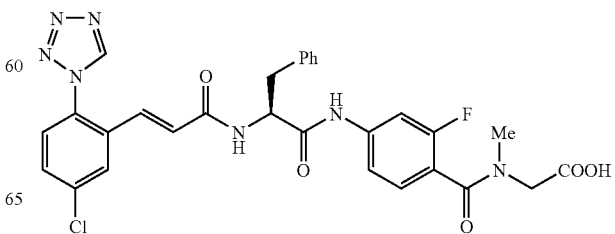

Example 207 was prepared according to Example 157, by replacing tert-butyl 2-aminoacetate, HCl with tert-butyl 2-(methylamino)acetate. $^1$H NMR (400 MHz, CD$_3$OD) δ: 9.51 (1H, s), 7.98 (1H, d, J=2.27 Hz), 7.61-7.68 (2H, m), 7.55-7.60 (1H, m), 7.32-7.42 (1H, m), 7.28 (5H, t, J=3.79 Hz), 7.18-7.26 (1H, m), 7.05-7.16 (1H, m), 6.70-6.85 (1H, m), 4.76-4.87 (1H, m), 3.95-4.31 (2H, m), 3.17-3.25 (1H, m), 2.96-3.16 (4H, m) ppm. LCMS m/z 606.3 [M+H]$^+$. Analytical HPLC RT: 7.45 min (Method D).

Example 208

(S,E)-3-(4-(2-(3-(5-chloro-2-(1H-tetrazol-1-yl)phenyl)acrylamido)-3-phenylpropanamido)-2-fluorobenzamido)propanoic acid

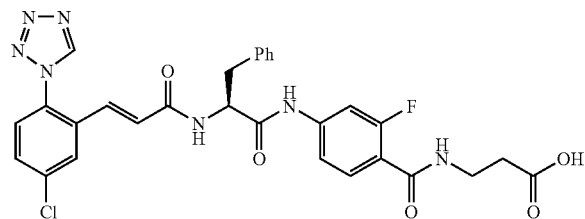 [SMILES: O=C(O)CCNC(=O)c1ccc(NC(=O)[C@H](Cc2ccccc2)NC(=O)/C=C/c2cc(Cl)ccc2-n2cnnn2)cc1F]

Example 208 was prepared according to Example 157, by replacing tert-butyl 2-aminoacetate, HCl with tert-butyl 3-aminopropanoate. $^1$H NMR (400 MHz, CD$_3$OD) δ: 9.51 (1H, s), 7.97 (1H, d, J=2.27 Hz), 7.71 (1H, t, J=8.46 Hz), 7.62-7.68 (2H, m), 7.53-7.58 (1H, m), 7.24-7.34 (5H, m), 7.17-7.24 (1H, m), 7.10 (1H, d, J=15.66 Hz), 6.77 (1H, d, J=15.41 Hz), 4.81 (1H, t, J=7.45 Hz), 3.65 (2H, t, J=6.69 Hz), 3.20 (1H, dd, J=13.64, 7.07 Hz), 3.02-3.10 (1H, m), 2.64 (2H, t, J=6.82 Hz) ppm. LCMS m/z 606.3 [M+H]$^+$. Analytical HPLC RT: 7.36 min (Method D).

Example 209

(S,E)-4-(2-(3-(5-chloro-2-(1H-tetrazol-1-yl)phenyl)acrylamido)-3-phenylpropanamido)-2-fluoro-N-(methylsulfonyl)benzamide

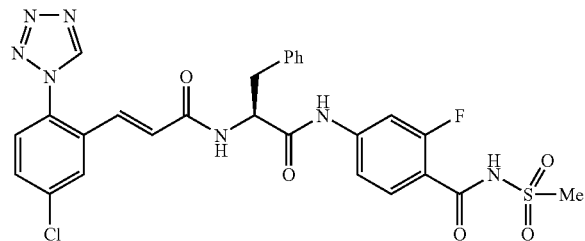 [SMILES: CS(=O)(=O)NC(=O)c1ccc(NC(=O)[C@H](Cc2ccccc2)NC(=O)/C=C/c2cc(Cl)ccc2-n2cnnn2)cc1F]

Example 209 was prepared according to Example 157, by replacing tert-butyl 2-aminoacetate, HCl with methanesulfonamide. $^1$H NMR (400 MHz, CD$_3$OD) δ: 9.51 (1H, s), 7.98 (1H, d, J=2.02 Hz), 7.65-7.73 (3H, m), 7.53-7.62 (1H, m), 7.27-7.37 (5H, m), 7.19-7.25 (1H, m), 7.10 (1H, d, J=15.66 Hz), 6.77 (1H, d, J=15.41 Hz), 4.77-4.86 (1H, m), 3.37 (3H, s), 3.15-3.22 (1H, m), 3.01-3.10 (1H, m) ppm. LCMS m/z 612.3 [M+H]$^+$. Analytical HPLC RT: 6.99 min (Method D).

Example 210

(S,E)-4-(2-(3-(5-chloro-2-(1H-tetrazol-1-yl)phenyl)acrylamido)-4-(piperidin-4-yl)butanamido)benzoic acid, TFA salt

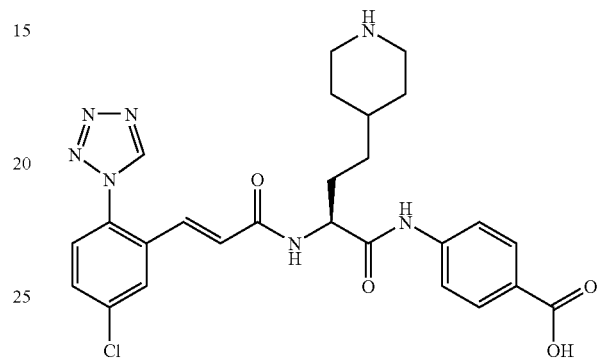

Example 210 was prepared according to the procedure previously described in Example 153. LCMS m/z 538.3 [M+H]$^+$. $^1$H NMR (400 MHz, CD$_3$OD) δ: 9.55 (1H, s), 7.94-8.04 (3H, m), 7.65-7.75 (3H, m), 7.55-7.62 (1H, m), 7.16 (1H, d, J=15.66 Hz), 6.82 (1H, d, J=15.66 Hz), 4.59 (1H, dd, J=8.21, 5.68 Hz), 3.34-3.47 (2H, m), 2.97 (2H, t, J=12.88 Hz), 1.90-2.06 (3H, m), 1.78-1.86 (1H, m), 1.65 (1H, td, J=7.07, 3.54 Hz), 1.34-1.51 (4H, m) ppm. Analytical HPLC RT: 4.98 min (Method D).

Example 211

(S,E)-4-(2-(3-(5-chloro-2-(1H-tetrazol-1-yl)phenyl)acrylamido)-3-(1,3-dimethyl-1H-pyrazol-5-yl)propanamido)benzoic acid

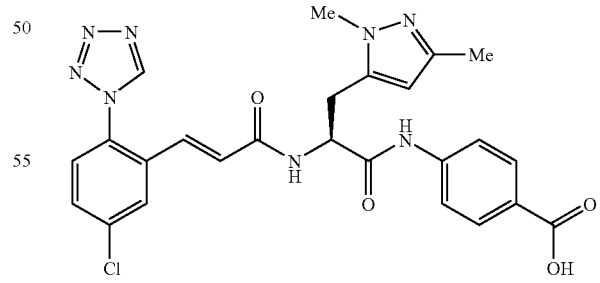

Example 211 was prepared according to the procedure previously described in Example 199 from Intermediate 4. LCMS m/z 535.3 [M+H]$^+$. $^1$H NMR (400 MHz, CD$_3$OD) δ: 9.54 (1H, s), 7.99 (3H, dd, J=5.43, 3.16 Hz), 7.65-7.72 (3H, m), 7.56-7.62 (1H, m), 7.15 (1H, d, J=15.66 Hz), 6.76 (1H, d, J=15.66 Hz), 6.14 (1H, s), 4.89-5.04 (1H, m), 3.87 (3H, s), 3.28-3.37 (1H, m), 3.14-3.22 (1H, m), 2.25 (3H, s) ppm. Analytical HPLC RT: 5.11 min (Method D).

Example 212

(S,E)-methyl 6-(2-(3-(3-chloro-2-fluoro-6-(1H-tetrazol-1-yl)phenyl)acrylamido)-3-(1-ethyl-1H-pyrazol-3-yl)propanamido)nicotinate, TFA salt

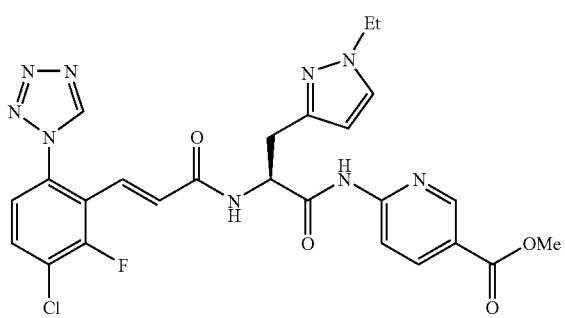 [SMILES: CCn1ccc(C[C@H](NC(=O)/C=C/c2c(-n3cnnn3)ccc(Cl)c2F)C(=O)Nc2ccc(C(=O)OC)cn2)n1]

Amide coupling of Intermediate 2 and methyl 6-aminonicotinate in similar manner as Example 3A, followed by deprotection with 4M HCl/dioxane, and final coupling with Intermediate 7 according to the procedure describe in Example 3 gave the title compound (17 mg, 30%) as white solid. LCMS: m/z 568.3 [M+H]+. 1H NMR (400 MHz, DMSO-d6) δ 11.06 (1H, s), 9.85 (1H, s), 8.84-8.86 (1H, m), 8.76 (1H, d, J=7.33 Hz), 8.29 (1H, dd, J=8.59, 2.27 Hz), 8.17 (1H, d, J=8.84 Hz), 7.90-7.97 (1H, m), 7.63 (1H, dd, J=8.59, 1.26 Hz), 7.57 (1H, d, J=2.27 Hz), 6.74-6.87 (2H, m), 6.10 (1H, d, J=2.27 Hz), 4.86-4.94 (1H, m), 3.98-4.06 (2H, m), 3.87 (3H, s), 3.01-3.08 (1H, m), 2.88-2.96 (1H, m), 1.25-1.30 (3H, m) ppm. Analytical HPLC RT: 6.11 min (Method C, 8 min gradient).

Example 213

(S,E)-methyl 6-(2-(3-(5-chloro-2-(1H-tetrazol-1-yl)phenyl)acrylamido)-3-(1-ethyl-1H-pyrazol-3-yl)propanamido)nicotinate, TFA salt

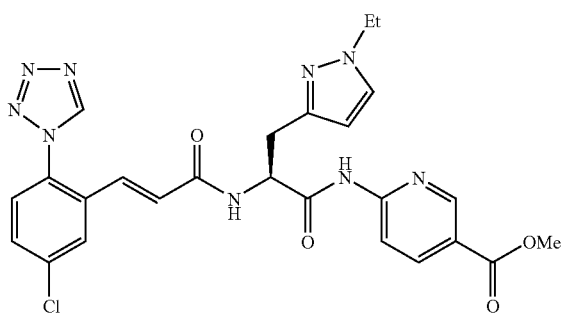 [SMILES: CCn1ccc(C[C@H](NC(=O)/C=C/c2cc(Cl)ccc2-n2cnnn2)C(=O)Nc2ccc(C(=O)OC)cn2)n1]

The title compound (7 mg, 25%) was prepared in a similar manner to Example 212 as a white solid. LCMS: m/z 550.3 [M+H]+. 1H NMR (400 MHz, DMSO-d6) δ: 11.06 (1H, s), 9.86 (1H, s), 8.85 (1H, d, J=3.30 Hz), 8.46 (1H, d, J=7.70 Hz), 8.28 (1H, dd, J=8.79, 2.20 Hz), 8.16 (1H, d, J=8.79 Hz), 7.95-7.98 (1 H, m), 7.70-7.78 (2H, m), 7.56 (1H, d, J=2.20 Hz), 6.81-6.96 (2H, m), 6.09 (1H, d, J=2.20 Hz), 4.84-4.93 (1H, m), 4.01 (2H, q, J=7.51 Hz), 3.86 (3H, s), 3.00-3.07 (1H, m), 2.88-2.97 (1H, m), 1.27 (3H, t, J=7.15 Hz) ppm. Analytical HPLC RT: 5.94 min (Method C, 8 min gradient).

Example 214

(S,E)-3-(4-(2-(3-(3-chloro-2-fluoro-6-(1H-tetrazol-1-yl)phenyl)acrylamido)-3-(1-ethyl-1H-pyrazol-3-yl)propanamido)phenylcarbamoyloxy)propanoic acid

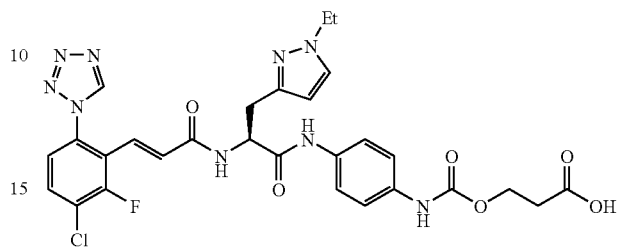

214A. (S)-3-(4-(2-amino-3-(1-ethyl-1H-pyrazol-3-yl)propanamido)phenylcarbamoyloxy)propanoic acid: 214A was prepared according to the procedure described in Example 43A via coupling of Intermediate 2 with tert-butyl 3-(4-aminophenylcarbamoyloxy)propanoate from Example 115B. LCMS: m/z 546.4 [M+H]+.

214B. (E)-2,5-dioxopyrrolidin-1-yl 3-(3-chloro-2-fluoro-6-(1H-tetrazol-1-yl)phenyl)acrylate: To a solution of Intermediate 7 (0.10 g, 0.37 mmol) in THF (1.870 mL) and DMF (0.187 mL), 1-hydroxypyrrolidine-2,5-dione (0.047 g, 0.409 mmol) and DIC (0.064 mL, 0.409 mmol) were added, respectively. After stirring for 15 h, the resulting precipitate was collected by filtration, washed with MeOH, water, and dried under vacuum. Additional product was obtained from the filtrate by dry-loading the crude material onto silica gel and purification by flash chromatography (12 g column; DCM eluant). Combining of both aliquots gave 214B (0.099 g, 0.27 mmol, 73% yield) as a white solid. LCMS: m/z 366.2 [M+H]+.

Example 214: The title compound was prepared by coupling 214A with 214B according to Example 55. LCMS: m/z 640.4 [M+H]+. 1H NMR (400 MHz, DMSO-d6) δ: 12.37 (1H, br. s.), 10.04 (1H, s), 9.85 (1H, s), 9.57 (1H, br. s.), 8.75 (1H, d, J=8.08 Hz), 7.87-7.97 (1H, m), 7.62 (1H, dd, J=8.72, 1.39 Hz), 7.55 (1H, d, J=2.27 Hz), 7.43-7.48 (2H, m), 7.31-7.39 (2H, m), 6.72-6.85 (2H, m), 6.03 (1H, d, J=2.27 Hz), 4.67-4.76 (1H, m), 4.24 (2H, t, J=6.06 Hz), 4.02 (2H, q, J=7.16 Hz), 2.96-3.04 (1H, m), 2.81-2.89 (1H, m), 2.61 (2H, t, J=6.19 Hz), 1.29 (3H, t, J=7.33 Hz) ppm. Analytical HPLC RT: 5.48 min (Method C, 8 min gradient).

Example 215

(S,E)-3-(4-(2-(3-(5-chloro-2-(1H-tetrazol-1-yl)phenyl)acrylamido)-3-(1-ethyl-1H-pyrazol-3-yl)propanamido)phenylcarbamoyloxy)propanoic acid

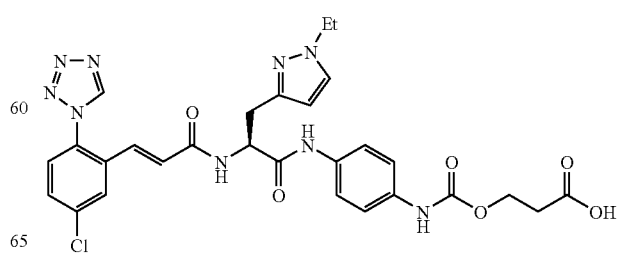

Example 215 was prepared in a similar manner to Example 214. $^1$H NMR (400 MHz, DMSO-$d_6$) δ: 12.40 (1H, br. s.), 10.06 (1H, s), 9.87 (1H, s), 9.60 (1H, br. s.), 8.47 (1H, d, J=8.25 Hz), 7.91-7.96 (1H, m), 7.70-7.78 (2H, m), 7.56 (1H, d, J=2.20 Hz), 7.47 (2H, d, J=8.79 Hz), 7.36 (2H, d, J=8.79 Hz), 6.81-6.98 (2H, m), 6.04 (1H, d, J=2.20 Hz), 4.67-4.76 (1H, m), 4.24 (2H, t, J=6.05 Hz), 4.02 (2H, q, J=7.15 Hz), 2.97-3.04 (1H, m), 2.84-2.92 (1H, m), 2.61 (2H, t, J=6.05 Hz), 1.29 (3H, t, J=7.42 Hz) ppm. LCMS: m/z 622.2 [M+H]$^+$. Analytical HPLC RT: 5.34 min (Method C, 8 min gradient).

Example 216

(S,E)-methyl 6-(2-(3-(3-chloro-2-fluoro-6-(1H-tetrazol-1-yl)phenyl)acrylamido)-3-(1,5-dimethyl-1H-pyrazol-3-yl)propanamido)nicotinate, TFA salt

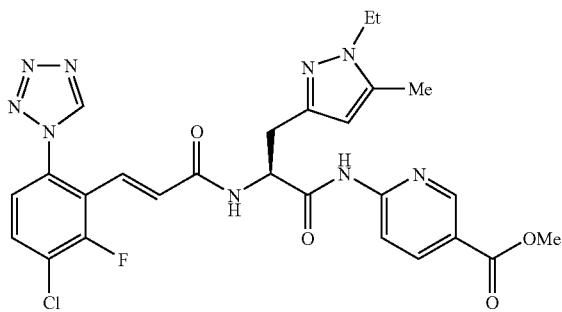 [SMILES: CCn1nc(C[C@H](NC(=O)/C=C/c2c(-n3cnnn3)ccc(Cl)c2F)C(=O)Nc2ccc(C(=O)OC)cn2)cc1C]

Example 216 was prepared from Intermediate 3 according to the procedure described in Example 212. LCMS: m/z 568.3 [M+H]$^+$. $^1$H NMR (400 MHz, DMSO-$d_6$) δ: 11.27 (1H, s), 9.86 (1H, s), 8.85-8.89 (2H, m), 8.31 (1H, dd, J=8.79, 2.20 Hz), 8.19 (1H, d, J=8.79 Hz), 7.91-7.96 (1H, m), 7.61-7.65 (1H, m), 6.76-6.83 (2H, m), 5.84 (1H, s), 4.86-4.95 (1H, m), 3.87 (3H, s), 3.68 (3H, s), 3.04-3.13 (1H, m), 2.90-2.99 (1H, m), 2.03 (3H, s) ppm. Analytical HPLC RT: 5.99 min (Method C, 8 min gradient).

Example 217

(S,E)-methyl 6-(2-(3-(3-chloro-2-fluoro-6-(1H-tetrazol-1-yl)phenyl)acrylamido)-3-phenylpropanamido)nicotinate, TFA salt

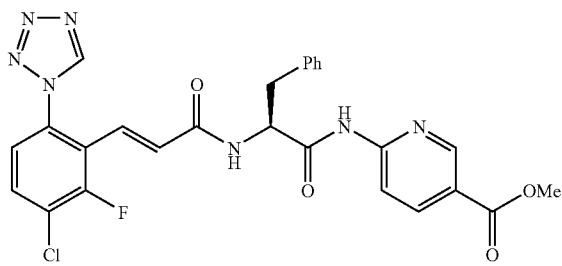 [SMILES: COC(=O)c1ccc(NC(=O)[C@H](Cc2ccccc2)NC(=O)/C=C/c2c(-n3cnnn3)ccc(Cl)c2F)nc1]

Example 217 was prepared according to the procedure described in Example 103 and Example 212. LCMS: m/z 550.3 [M+H]$^+$. $^1$H NMR (400 MHz, DMSO-$d_6$) δ: 11.27 (1H, s), 9.82 (1H, s), 8.86 (1H, d, J=1.77 Hz), 8.79 (1H, d, J=7.58 Hz), 8.29 (1H, dd, J=8.84, 2.27 Hz), 8.18 (1H, d, J=8.59 Hz), 7.91 (1H, t, J=8.21 Hz), 7.61 (1H, dd, J=8.72, 1.39 Hz), 7.32-7.36 (2H, m), 7.23-7.30 (2H, m), 7.14-7.20 (1H, m), 6.67-6.79 (2H, m), 4.84-4.92 (1H, m), 3.86 (3H, s), 3.07-3.15 (1H, m), 2.85 (1H, dd, J=13.64, 10.36 Hz) ppm. Analytical HPLC RT: 6.81 min (Method C, 8 min gradient).

Example 218

(S,E)-4-(2-(3-(5-chloro-2-(1H-tetrazol-1-yl)phenyl)acrylamido)-3-(3-(dimethylcarbamoyl)phenyl)propanamido)benzoic acid

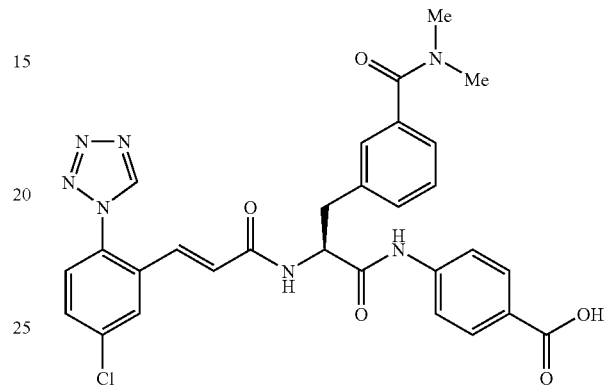

Example 218 was prepared according to the procedure used for Example 90 by replacing ammonia with dimethylamine $^1$H NMR (CD$_3$OD) δ: 9.40 (s, 1H), 8.01 (d, J=8.7 Hz, 3H), 7.58-7.41 (m, 4H), 7.30-7.15 (m, 4H), 6.99 (d, J=15.6 Hz, 1H), 6.67 (d, J=15.6 Hz, 1H), 4.80 (m, 1H), 3/20 (m, 1H), 3.02 (m, 1H), 2.80 (s, 3H), 2.74 (s, 3H) ppm. Analytical HPLC RT: 5.565 min (Method C, 8 min gradient). LCMS: m/z 588.0 [M+H]$^+$.

Example 219

(S,E)-ethyl 2-(2-(3-(5-chloro-2-(1H-tetrazol-1-yl)phenyl)acrylamido)-3-phenylpropanamido)-4-hydroxypyrimidine-5-carboxylate

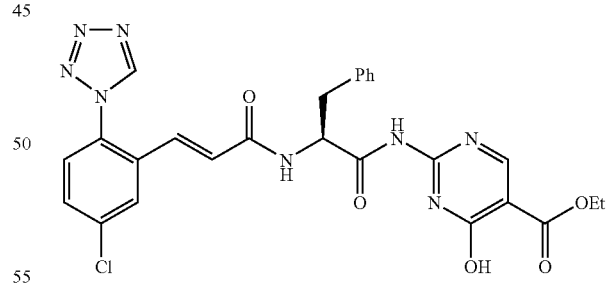

Example 219 was prepared via the coupling of ethyl 2-amino-4-hydroxypyrimidine-5-carboxylate to N-Boc-L-phenylalanine with HATU and Hunig's base and TEA in a THF/DMF solution followed by the procedure described in Example 3. $^1$H NMR (400 MHz, DMSO-$d_6$) δ: 9.88 (s, 1H), 8.70 (d, J=7.4 Hz, 1H), 8.49 (bs, 1H), 7.97 (d, J=2.2 Hz, 1H), 7.77-7.71 (m, 2H), 7.36-7.20 (m, 5H), 6.86-6.77 (dq(AB), 2H), 4.83-4.77 (m, 1H), 4.24-4.14 (q, 2H), 3.17-3.12 (m, 1H), 2.90-2.84 (m, 1H), 1.28-1.20 (t, 3H) ppm. Analytical HPLC RT: 6.25 min (Method C, 8 min gradient). LCMS: m/z 563.3 [M+H]$^+$.

Example 220

(S,E)-3-(5-chloro-2-(1H-tetrazol-1-yl)phenyl)-N-(1-oxo-3-phenyl-1-(4-(trifluoromethoxy)phenylamino)propan-2-yl)acrylamide

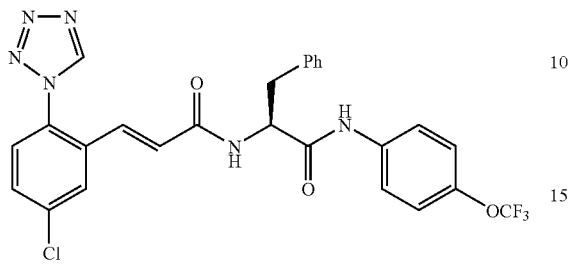

Example 220 was prepared in a manner similar to that described for Example 3. $^1$H NMR (400 MHz, DMSO-$d_6$) δ: 9.782 (s, 1H), 8.55 (d, J=8.2 Hz, 1H), 7.87 (d, J=2.1 Hz, 1H), 7.62-7.59 (m, 4H), 7.26-7.19 (m, 6H), 6.77 (d(AB), 2H), 4.80 (m, 1H), 3.03 (m, 1H), 2.85 (m, 1H) ppm. Analytical HPLC RT: 7.14 min (Method C, 8 min gradient). LCMS: m/z 577.0 [M+H]$^+$.

Example 221

(E)-4-(2-(3-(5-chloro-2-(1H-tetrazol-1-yl)phenyl)acrylamido)-4,4,4-trifluorobutanamido)benzoic acid

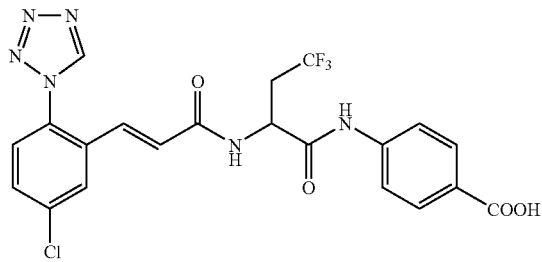 [SMILES: O=C(/C=C/c1cc(Cl)ccc1-n1cnnn1)NC(CC(F)(F)F)C(=O)Nc1ccc(C(=O)O)cc1]

Example 221 was prepared in a manner similar to that described for Example 8. $^1$H NMR (400 MHz, DMSO-$d_6$) δ: 12.76 (bs, 1H), 10.67 (s, 1H), 10.45 (s, 1H), 8.83 (d, J=8.1 Hz, 1H), 7.98 (s, 1H), 7.92 (d, J=8.7 Hz, 2H), 7.73-7.62 (m, 4H), 6.98-6.81 (q, 2H), 4.94 (m, 1H), 2.95 (m, 1H), 2.73 (m, 1H) ppm. Analytical HPLC RT: 7.24 min (Method C, 8 min gradient). LCMS: m/z 507.1 [M+H]$^+$.

Example 222

(S,E)-5-(2-(3-(5-chloro-2-(1H-tetrazol-1-yl)phenyl)acrylamido)-3-phenylpropanamido)-1H-indazole-3-carboxylic acid

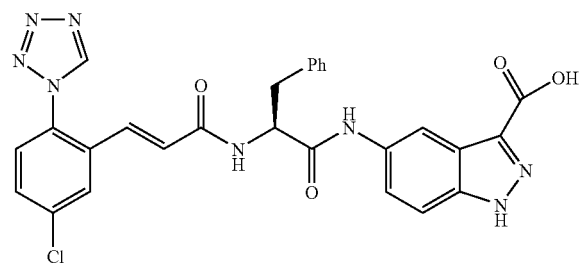 [SMILES: O=C(/C=C/c1cc(Cl)ccc1-n1cnnn1)N[C@@H](Cc1ccccc1)C(=O)Nc1ccc2[nH]nc(C(=O)O)c2c1]

222A. (S)-5-(2-amino-3-phenylpropanamido)-1H-indazole-3-carboxylic acid: 144A (0.1 g, 0.228 mmol) was hydrolysed via LiOH as previously described to afford 222A (17 mg, 17%) as a white solid. LCMS m/z 325.3 [M+H]$^+$.

Example 222: The title compound was prepared from 222A following the procedures described in Example 55 to afford (4 mg, 17.8%) as a white solid. LCMS m/z 557 [M+H]$^+$. $^1$H NMR (400 MHz, CD$_3$OD) δ: 9.52 (1H, s), 8.29-8.37 (1H, m), 7.99 (1H, d, J=2.27 Hz), 7.63-7.71 (1H, m), 7.54-7.61 (2H, m), 7.47-7.51 (1H, m), 7.25-7.36 (4H, m), 7.20-7.25 (1H, m), 7.12 (1H, d, J=15.66 Hz), 6.80 (1H, d, J=15.41 Hz), 4.91-4.97 (1H, m), 3.18-3.28 (1H, m), 3.04-3.17 (1H, m) ppm. Analytical HPLC RT: 6.00 min (Method C, 8 min gradient).

Example 223

(S,E)-4-(4-(1-acetylpiperidin-4-yl)-2-(3-(5-chloro-2-(1H-tetrazol-1-yl)phenyl)acrylamido)butanamido)benzoic acid

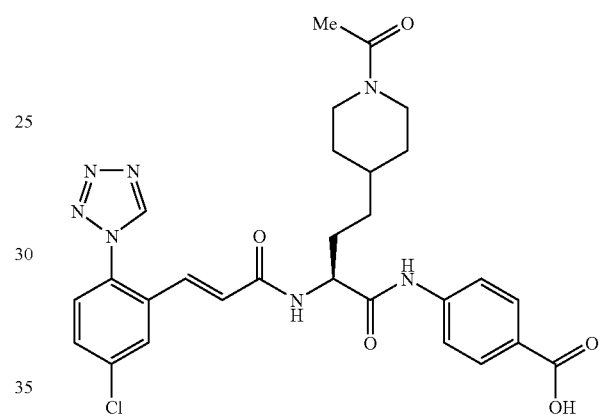

To Example 210 (10 mg, 0.015 mmol) in DMF (0.5 mL) was added acetyl chloride (1.204 mg, 0.015 mmol) and Hunig's base (8.04 μL, 0.046 mmol). After 18 h, the reaction was diluted with MeOH (4 mL) and purified by reverse phase HPLC to afford Example 223 (3 mg, 33%) as a white solid. LCMS m/z 580.3 [M+H]$^+$. $^1$H NMR (400 MHz, CD$_3$OD) δ: 9.54 (1H, s), 7.94-8.09 (3H, m), 7.65-7.78 (3H, m), 7.56-7.62 (1H, m), 7.16 (1H, d, J=15.66 Hz), 6.82 (1H, d, J=15.41 Hz), 4.57 (1H, dd, J=8.08, 6.06 Hz), 4.44-4.53 (1H, m), 3.91 (1H, d, J=11.12 Hz), 2.99-3.17 (2H, m), 2.57-2.68 (1H, m), 2.09 (3H, s), 1.91-2.00 (1H, m), 1.74-1.89 (3H, m), 1.59 (1H, br. s.), 1.15-1.48 (2H, m) ppm. Analytical HPLC RT: 5.53 min (Method C, 8 min gradient).

Example 224

(S,E)-6-(2-(3-(3-chloro-2-fluoro-6-(1H-tetrazol-1-yl)phenyl)acrylamido)-3-(1-ethyl-1H-pyrazol-3-yl)propanamido)nicotinic acid, TFA salt

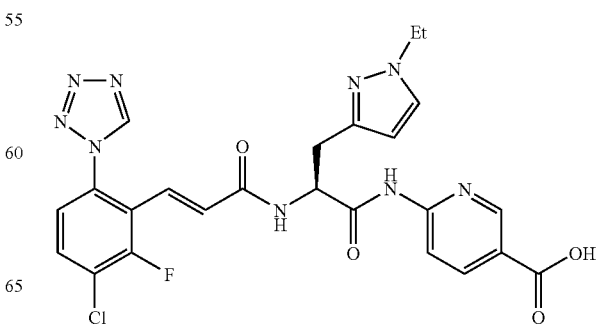

Example 212 was hydrolysed as previously described in Example 2 to yield Example 224. LCMS: m/z 554.3 [M+H]$^+$. $^1$H NMR (400 MHz, DMSO-d$_6$) δ: 11.01 (1H, s), 9.84 (1H, s), 8.81 (1H, d, J=2.20 Hz), 8.76 (1H, d, J=7.70 Hz), 8.24 (1H, dd, J=8.79, 2.20 Hz), 8.13 (1H, d, J=8.79 Hz), 7.92 (1H, t, J=7.97 Hz), 7.62 (1H, d, J=8.25 Hz), 7.55 (1H, d, J=2.20 Hz), 6.72-6.85 (2H, m), 6.08 (1H, d, J=2.20 Hz), 4.84-4.92 (1H, m), 4.00 (2H, q, J=7.15 Hz), 2.98-3.05 (1H, m), 2.86-2.94 (1H, m), 1.26 (3H, t, J=7.15 Hz) ppm. Analytical HPLC RT: 6.54 min (Method D, 8 min gradient).

Example 225

(S,E)-6-(2-(3-(3-chloro-2-fluoro-6-(1H-tetrazol-1-yl)phenyl)acrylamido)-3-(1,5-dimethyl-1H-pyrazol-3-yl)propanamido)nicotinic acid, TFA salt

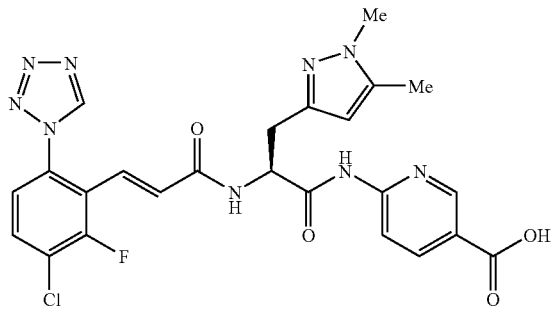 [SMILES: Cc1cc(C[C@H](NC(=O)/C=C/c2c(-n3cnnn3)ccc(Cl)c2F)C(=O)Nc2ccc(C(=O)O)cn2)nn1C]

Example 216 was hydrolysed as previously described in Example 2 to yield Example 225. MS: m/z 554.3 [M+H]$^+$. $^1$H NMR (400 MHz, DMSO-d$_6$) δ: 11.20 (1H, s), 9.85 (1H, s), 8.81-8.88 (2H, m), 8.27 (1H, dd, J=8.79, 2.75 Hz), 8.16 (1H, d, J=8.79 Hz), 7.91-7.98 (1H, m), 7.61-7.65 (1H, m), 6.74-6.84 (2H, m), 5.83 (1H, s), 4.85-4.96 (1H, m), 3.67 (3H, s), 3.08 (1H, dd, J=15.12, 5.22 Hz), 2.88-2.99 (1H, m), 2.03 (3H, s) ppm. Analytical HPLC RT: 5.90 min (Method D, 8 min gradient).

Example 226

(S,E)-6-(2-(3-(3-chloro-2-fluoro-6-(1H-tetrazol-1-yl)phenyl)acrylamido)-3-phenylpropanamido)nicotinic acid, TFA salt

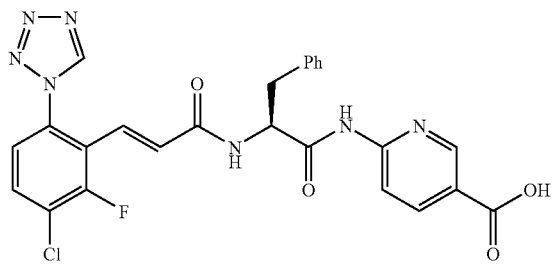

Example 217 was hydrolysed as previously described in Example 2 to yield Example 226. MS: m/z 536.3 [M+H]$^+$. $^1$H NMR (400 MHz, DMSO-d$_6$) δ: 11.24 (1H, s), 9.82 (1H, s), 8.78-8.86 (2H, m), 8.27 (1H, dd, J=8.79, 2.20 Hz), 8.16 (1H, d, J=8.79 Hz), 7.89-7.95 (1H, m), 7.60-7.64 (1H, m), 7.32-7.36 (2H, m), 7.27 (2H, t, J=7.42 Hz), 7.16-7.21 (1H, m), 6.66-6.81 (2H, m), 4.85-4.93 (1H, m), 3.12 (1H, dd, J=13.74, 4.40 Hz), 2.85 (1H, dd, J=13.19, 10.44 Hz) ppm. Analytical HPLC RT: 7.49 min (Method D, 8 min gradient).

Example 227

(S,E)-4-(2-(3-(3-chloro-2-fluoro-6-(1H-tetrazol-1-yl)phenyl)acrylamido)-3-(1-ethyl-1H-pyrazol-3-yl)propanamido)benzoic acid

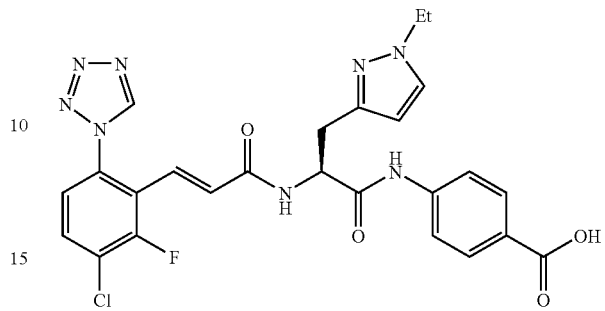

227A: (S)-4-(2-amino-3-(1-ethyl-1H-pyrazol-3-yl)propanamido)benzoic acid, HCl salt: 227A was made as previously described in Example 212 substituting tert-butyl 2-aminoacetate for methyl 6-aminonicotinate followed by deprotection with 4N HCl in dioxane to afford 227A (0.28 g, 75%) of a brown solid. LCMS m/z 303.3 [M+H]$^+$.

Example 227: To Intermediate 7 (40 mg, 0.149 mmol) and N-hydroxysuccinimide (18.85 mg, 0.164 mmol) in DMF (0.5 mL) was added DIC (25.5 mL, 0.164 mmol) in DMF (1 mL). After 2 h, 227A (50.4 mg, 0.149 mmol) and Hunig's base (0.078 mL, 0.447 mmol) were added. After 2 h, the reaction mixture was concentrated and purified by reverse phase HPLC and freeze-dried to afford Example 227 (10.3 mg, 11.8%) as a white solid. $^1$H NMR (400 MHz, MeOD) δ: 9.54 (1H, s), 7.93-8.01 (2H, m), 7.75-7.84 (1H, m), 7.67 (2H, d, J=8.84 Hz), 7.56 (1H, d, J=2.53 Hz), 7.47 (1H, dd, J=8.72, 1.39 Hz), 7.01 (1H, d, J=15.92 Hz), 6.79 (1H, d, J=15.92 Hz), 6.19 (1H, d, J=2.27 Hz), 5.01-5.05 (1H, m), 4.05-4.22 (2H, m), 3.22 (1H, dd, J=14.40, 6.82 Hz), 3.06-3.16 (1H, m), 1.38 (3H, t, J=7.33 Hz) ppm. LCMS m/z 553.3 [M+H]$^+$. Analytical HPLC RT: 6.81 min (Method D).

Example 228

4-((2S)-2-((E)-3-(5-chloro-2-(1H-tetrazol-1-yl)phenyl)acrylamido)-3-(piperidin-3-yl)propanamido)benzoic acid, TFA salt

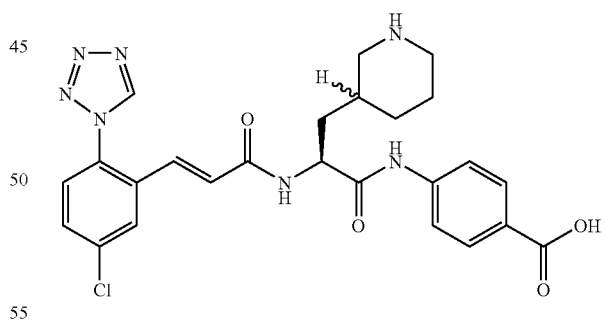

Example 228 was prepared as previously described in Examples 153 and 210, substituting tert-butyl 3-formylpiperidine-1-carboxylate for tert-butyl 4-(2-oxoethyl)piperidine-1-carboxylate and substituting 50% 1-propanephosphoric acid cyclic anhydride in EtOAc as coupling agent. $^1$H NMR (400 MHz, MeOD) δ: 9.45 (1H, s), 7.79-8.00 (3H, m), 7.56-7.67 (3H, m), 7.46-7.51 (1H, m), 7.08 (1H, d, J=15.66 Hz), 6.69 (1H, t, J=15.41 Hz), 4.62-4.72 (1H, m), 3.39 (1H, ddd, J=3.16, 1.77, 1.64 Hz), 2.75-2.87 (1H, m), 2.63 (1H, td, J=11.62, 8.08 Hz), 1.96-2.15 (1H, m), 1.86 (2H, d, J=11.87 Hz), 1.55-1.81 (4H, m), 1.10-1.35 (1H, m) ppm. LCMS (ESI) m/z: 524.3 [M+H]$^+$. Analytical HPLC RT: 5.03 and 5.19 min for diastereomers (Method D).

Example 229

(S,E)-4-(3-(azetidin-3-yl)-2-(3-(5-chloro-2-(1H-tet-razol-1-yl)phenyl)acrylamido)propanamido)benzoic acid, TFA salt

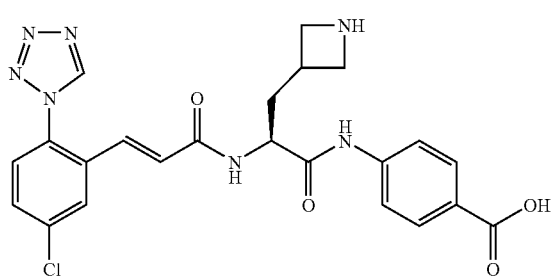 [SMILES: O=C(/C=C/c1cc(Cl)ccc1-n1cnnn1)N[C@@H](CC1CNC1)C(=O)Nc1ccc(C(=O)O)cc1]

Example 229 was prepared as previously described in Examples 153 and 210, substituting tert-butyl 3-formylazetidine-1-carboxylate for tert-butyl 4-(2-oxoethyl)piperidine-1-carboxylate and substituting 50% 1-propanephosphoric acid cyclic anhydride in EtOAc as coupling agent. $^1$H NMR (400 MHz, MeOD) δ: 9.44 (1H, s), 7.87-7.92 (3H, m), 7.56-7.65 (3H, m), 7.46-7.52 (1H, m), 7.06 (1H, d, J=15.66 Hz), 6.68 (1H, d, J=15.66 Hz), 4.49-4.58 (1H, m), 3.92-4.04 (2H, m), 3.78 (2H, ddd, J=13.20, 11.05, 8.34 Hz), 2.93-3.06 (1H, m), 2.17 (1H, ddd, J=13.90, 8.21, 5.68 Hz), 1.95-2.06 (1H, m) ppm. LCMS (ESI) m/z: 496.3 [M+H]$^+$. Analytical HPLC RT: 4.94 min (Method D).

Example 230

(S,E)-4-(2-(3-(5-chloro-2-(1H-tetrazol-1-yl)phenyl)acrylamido)-3-(piperidin-4-yl)propanamido)benzoic acid, TFA salt

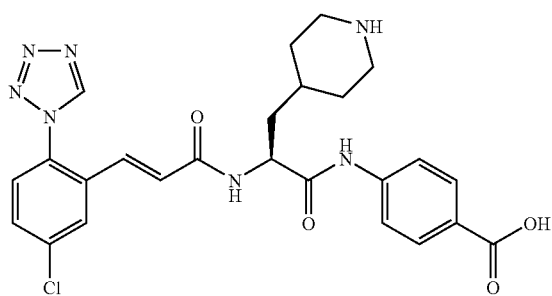 [SMILES: O=C(/C=C/c1cc(Cl)ccc1-n1cnnn1)N[C@@H](CC1CCNCC1)C(=O)Nc1ccc(C(=O)O)cc1]

Example 230 was prepared as previously described in Examples 153 and 210, substituting tert-butyl 4-formylpiperidine-1-carboxylate for tert-butyl 4-(2-oxoethyl)piperidine-1-carboxylate and substituting 50% 1-propanephosphoric acid cyclic anhydride in EtOAc as coupling agent. $^1$H NMR (400 MHz, MeOD) δ: 9.44 (1 H, s), 7.81-7.94 (3H, m), 7.54-7.65 (3H, m), 7.45-7.54 (1H, m), 7.05 (1H, d, J=15.66 Hz), 6.67 (1H, d, J=15.66 Hz), 4.64 (1H, dd, J=9.35, 5.56 Hz), 2.75-2.99 (3H, m), 1.96-2.07 (1H, m), 1.83-1.92 (1H, m), 1.56-1.81 (3H, m), 1.28-1.49 (3H, m). LCMS (ESI) m/z: 524.3 [M+H]$^+$. Analytical HPLC RT: 4.69 min (Method D).

Example 231

(S,E)-4-(2-(3-(5-chloro-2-(1H-tetrazol-1-yl)phenyl)acrylamido)-4-(methylsulfonyl)butanamido)benzoic acid

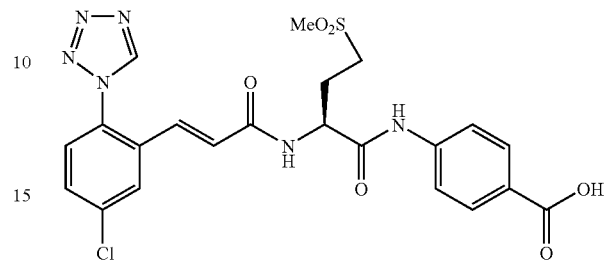

Example 231 was prepared according to the procedures previously described for Examples 3 and 8 from the corresponding commercially available amino acid. $^1$H NMR (400 MHz, DMSO-d$_6$) δ: 9.85 (s, 1H), 8.67 (d, J=8.5 Hz, 1H), 7.97 (s, 1H), 7.92 (d, J=8.8 Hz, 2H), 7.78-7.71 (m, 4H), 6.95-6.86 (dq, 2H), 4.65 (m, 1H), 3.38 (bs, 2H), 3.18 (t, 2H), 3.04 (s, 3H), 2.25 (m, 1H), 2.10 (m, 1H) ppm. LCMS (ESI) m/z: 532.9 [M+H]$^+$. Analytical HPLC RT: 6.61 min (Method C).

Example 232

(S,E)-2-(2-(3-(5-chloro-2-(1H-tetrazol-1-yl)phenyl)acrylamido)-3-phenylpropanamido)pyrimidine-5-carboxylic acid

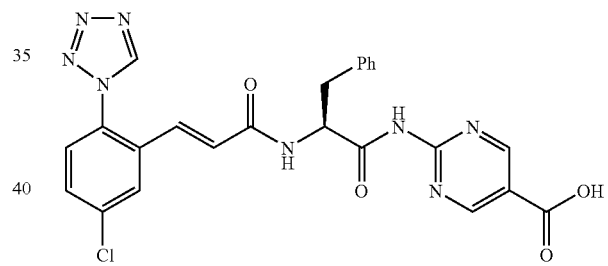

Example 232 was prepared in a similar manner to that was previously described for Example 3. $^1$H NMR (400 MHz, DMSO-d$_6$) δ: 9.85 (s, 1H), 9.07 (s, 2H), 8.66 (d, J=8.0 Hz, 1H), 7.96 (s, 1H), 7.95-7.69 (m, 2H), 7.40-7.20 (m, 5H), 6.83-6.77 (dq(AB, 2H), 5.09 (m, 1H), 3.15 (m, 1H), 2.89 (m, 1H) ppm. LCMS (ESI) m/z: 519.0 [M+H]$^+$. Analytical HPLC RT: 5.89 min (Method C).

Example 233

(S,E)-4-(2-(3-(5-chloro-2-(1H-tetrazol-1-yl)phenyl)acrylamido)-4,4-dimethylpentanamido)benzoic acid

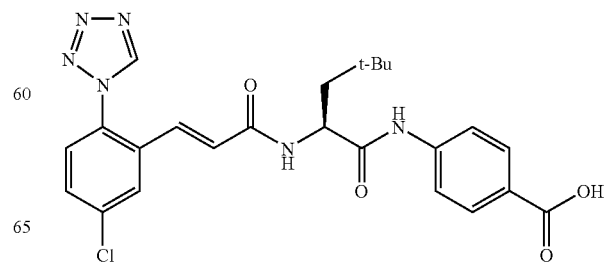

Example 233 was prepared in a similar manner to that was previously described for Example 3. ¹H NMR (400 MHz, DMSO-d$_6$) δ: 9.85 (s, 1H), 8.52 (d, J=8.2 Hz, 1H), 7.94-7.88 (m, 2H), 7.77-7.71 (m, 4H), 6.92 (dq2H), 4.63 (m, 1H), 1.74 (m, 1H), 1.59 (m, 1H), 0.93 (s, 9H) ppm. LCMS (ESI) m/z: 497.0 [M+H]$^+$. Analytical HPLC RT: 4.776 min (Method C).

Example 234

(S,E)-4-(2-(3-(5-chloro-2-(1H-tetrazol-1-yl)phenyl)acrylamido)-3-(1-methyl-1H-imidazol-4-yl)propanamido)benzoic acid, TFA salt

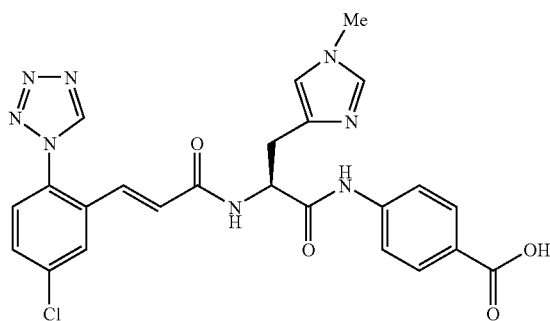 [SMILES: Cn1cnc(C[C@H](NC(=O)/C=C/c2cc(Cl)ccc2-n2cnnn2)C(=O)Nc2ccc(C(=O)O)cc2)c1]

Example 234 was prepared according to the procedures described for Example 55 starting from commercially available (S)-2-(tert-butoxycarbonylamino)-3-(1-methyl-1H-imidazol-4-yl)propanoic acid. LCMS m/z 521.4 [M+H]$^+$. ¹H NMR (400 MHz, DMSO-d$_6$) δ: 10.50 (1H, s), 9.88 (1H, s), 8.91 (1H, br. s.), 8.69-8.75 (1H, m), 7.96 (1H, d, J=2.20 Hz), 7.91 (2H, d, J=8.79 Hz), 7.67-7.80 (4H, m), 7.39 (1H, s), 6.80-6.95 (2H, m), 4.78-4.88 (1H, m), 3.81 (3H, s), 3.14-3.22 (1H, m), 3.00-3.10 (1H, m) ppm. Analytical HPLC RT: 4.17 min (Method D).

Example 235

(S,E)-4-(2-(3-(5-chloro-2-(1H-tetrazol-1-yl)phenyl)acrylamido)-3-(1H-imidazol-4-yl)propanamido)benzoic acid, TFA salt

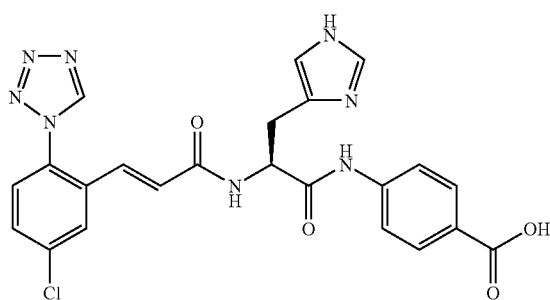 [SMILES: O=C(/C=C/c1cc(Cl)ccc1-n1cnnn1)N[C@@H](Cc1c[nH]cn1)C(=O)Nc1ccc(C(=O)O)cc1]

Example 235 was prepared according to the procedures described for Example 55 starting from commercially available (S)-3-(1-(tert-butoxycarbonyl)-1H-imidazol-4-yl)-2-(tert-butoxycarbonylamino)propanoic acid. LCMS m/z 507.4 [M+H]$^+$. ¹H NMR (400 MHz, DMSO-d$_6$) δ: 14.17 (1H, br. s.), 10.50 (1H, s), 9.87 (1H, s), 8.94 (1H, s), 8.72 (1H, d, J=7.70 Hz), 7.94-7.98 (1H, m), 7.90 (2H, d, J=8.79 Hz), 7.66-7.81 (4H, m), 7.37 (1H, s), 6.79-6.97 (2H, m), 4.80-4.92 (1H, m), 3.14-3.25 (1H, m), 3.02-3.12 (1H, m) ppm. Analytical HPLC RT: 4.17 min (Method D).

Example 236

(S,E)-4-(2-(3-(5-chloro-2-(1H-tetrazol-1-yl)phenyl)acrylamido)-3-(thiazol-4-yl)propanamido)benzoic acid

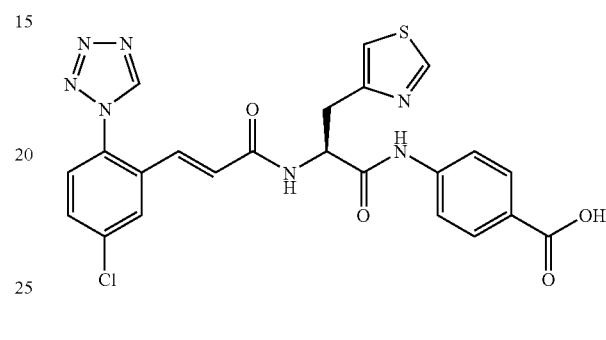

Example 236 was prepared according to the procedures described for Example 55 starting from commercially available ((S)-2-(tert-butoxycarbonylamino)-3-(thiazol-4-yl)propanoic acid. LCMS m/z 524.5 [M+H]$^+$. ¹H NMR (400 MHz, DMSO-d$_6$) δ: 10.50 (1H, s), 9.85 (1H, s), 9.01 (1H, d, J=1.77 Hz), 8.56 (1H, d, J=7.83 Hz), 7.95 (1H, d, J=1.77 Hz), 7.87 (2H, d, J=8.84 Hz), 7.65-7.78 (4H, m), 7.38 (1H, d, J=1.77 Hz), 6.79-6.91 (2H, m), 4.85-4.96 (1H, m), 3.23-3.32 (1H, m), 3.09-3.19 (1H, m) ppm. Analytical HPLC RT: 5.28 min (Method D).

Example 237

(S,E)-4-(3-carboxy-2-(3-(5-chloro-2-(1H-tetrazol-1-yl)phenyl)acrylamido)-propanamido)benzoic acid

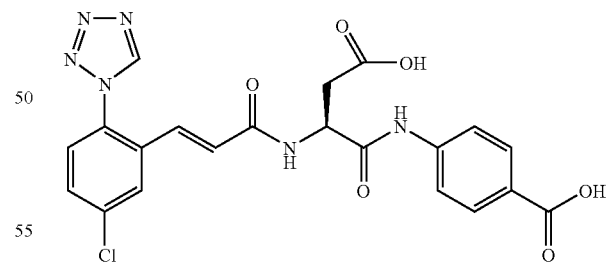

Example 237 was prepared according to the procedures described for Example 55 starting from commercially available (S)-4-tert-butoxy-2-(tert-butoxycarbonylamino)-4-oxobutanoic acid. LCMS m/z 485.3 [M+H]$^+$. ¹H NMR (400 MHz, DMSO-d$_6$) δ: 10.45 (1H, s), 9.87 (1H, s), 8.64 (1H, d, J=7.83 Hz), 7.96 (1H, d, J=2.02 Hz), 7.88 (2H, d, J=8.59 Hz), 7.69-7.79 (4H, m), 6.79-6.96 (2H, m), 4.77-4.89 (1H, m), 2.78 (1H, dd, J=16.55, 5.94 Hz), 2.58-2.67 (1H, m) ppm. Analytical HPLC RT: 4.70 min (Method D).

Example 238

(S,E)-4-(2-(3-(5-chloro-2-(1H-tetrazol-1-yl)phenyl)acrylamido)-3-(1H-indol-3-yl)propanamido)benzoic acid, TFA salt

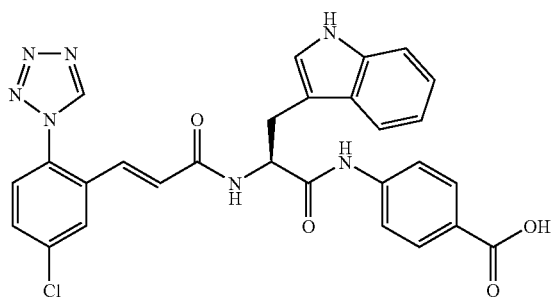 [SMILES: O=C(/C=C/c1cc(Cl)ccc1-n1cnnn1)N[C@@H](Cc1c[nH]c2ccccc12)C(=O)Nc1ccc(C(=O)O)cc1]

Example 238: (S)-tert-butyl 4-(2-(tert-butoxycarbonylamino)-3-(1H-indol-3-yl)propanamido)benzoate: 1-Propanephosphonic acid cyclic anhydride (TP3) (0.38 mL, 0.66 mmol) was added to a solution of (S)-2-(tert-butoxycarbonylamino)-3-(1H-indol-3-yl)propanoic acid (0.10 g, 0.33 mmol), tert-butyl 4-aminobenzoate (0.063 g, 0.33 mmol), and DIPEA (0.17 mL, 0.99 mmol) in EtOAc (5 mL) at 0° C. for 1 h. The reaction mixture was washed with 1.0M HCl solution, water, dried over sodium sulfate, filtered, and concentrated. The resulting oil was treated with 4.0M HCl solution (2 mL) for 2 h and concentrated to dryness. The residue was diluted with DMF (3 mL) and treated with 55E (E)-2,5-dioxopyrrolidin-1-yl 3-(5-chloro-2-(1H-tetrazol-1-yl)phenyl)acrylate (0.114 g, 0.329 mmol) and DIPEA (0.172 mL, 0.986 mmol), respectively. After stirring for 1.5 h, the reaction mixture was purified by reverse phase prep. HPLC (MeOH/H$_2$O/TFA) to give the title compound Example 238 (52 mg, 22%) as a white solid. LCMS m/z 556.5 [M+H]$^+$. $^1$H NMR (400 MHz, DMSO-d$_6$) δ: 10.83 (1H, s), 10.53 (1H, s), 9.85 (1H, s), 8.55 (1H, d, J=7.70 Hz), 7.85-7.94 (3H, m), 7.60-7.78 (5H, m), 7.30 (1H, d, J=8.24 Hz), 7.15 (1H, d, J=2.20 Hz), 7.04 (1H, t, J=7.15 Hz), 6.91-6.99 (1H, m), 6.79-6.90 (2H, m), 4.77-4.87 (1H, m), 3.21 (1H, dd, J=14.84, 5.50 Hz), 3.02-3.11 (1H, m) ppm. Analytical HPLC RT: 6.02 min (Method D).

Example 239

(S,E)-4-(2-(3-(5-chloro-2-(1H-tetrazol-1-yl)phenyl)acrylamido)-3-(1-methyl-1H-imidazol-5-yl)propanamido)benzoic acid, TFA salt

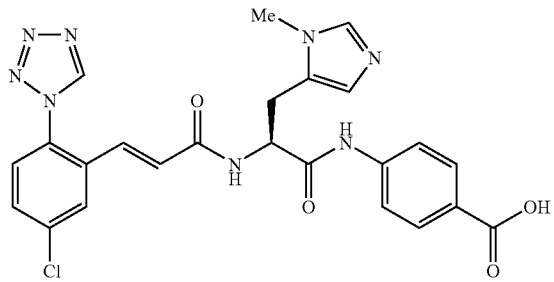 [SMILES: Cn1cncc1C[C@H](NC(=O)/C=C/c1cc(Cl)ccc1-n1cnnn1)C(=O)Nc1ccc(C(=O)O)cc1]

Example 239 was prepared according to the procedures described for Example 55 starting from commercially available (S)-2-(tert-butoxycarbonylamino)-3-(1-methyl-1H-imidazol-5-yl)propanoic acid. LCMS m/z 521.3 [M+H]$^+$. $^1$H NMR (400 MHz, DMSO-d$_6$) δ: 10.57 (1H, s), 9.86 (1H, s), 8.97 (1H, s), 8.78 (1H, d, J=7.70 Hz), 7.88-7.97 (3H, m), 7.66-7.79 (4H, m), 7.37 (1H, s), 6.80-6.93 (2H, m), 4.81-4.97 (1H, m), 3.84 (3H, s), 3.22 (1H, dd, J=15.39, 6.05 Hz), 3.01-3.10 (1H, m) ppm. Analytical HPLC RT: 4.23 min (Method D).

Example 240

(S,E)-4-(2-(3-(5-chloro-2-(1H-tetrazol-1-yl)phenyl)acrylamido)-4-(methylthio)butanamido)benzoic acid

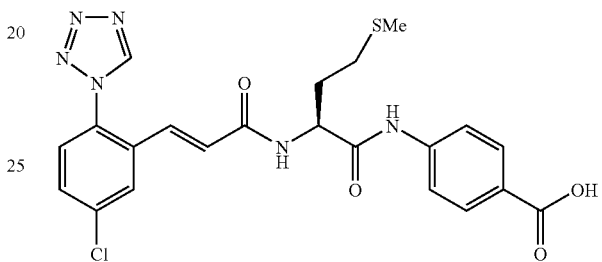

Example 240 was prepared according to the procedures described for Example 55 starting from commercially available (S)-2-(tert-butoxycarbonylamino)-4-(methylthio)butanoic acid. LCMS m/z 501.2 [M+H]$^+$. $^1$H NMR 77142-032-03 (400 MHz, DMSO-d$_6$) δ: 10.47 (1H, s), 9.85-9.90 (1H, m), 8.58 (1H, d, J=7.58 Hz), 7.97 (1H, d, J=2.02 Hz), 7.90 (2H, d, J=8.84 Hz), 7.69-7.79 (4H, m), 6.83-6.96 (2H, m), 4.54-4.66 (1H, m), 1.98-2.10 (4H, m), 1.86-1.98 (1H, m) ppm. Analytical HPLC RT: 5.79 min (Method D).

Example 241

4-((2S)-2-((E)-3-(5-chloro-2-(1H-tetrazol-1-yl)phenyl)acrylamido)-4-(methylsulfinyl)butanamido)benzoic acid

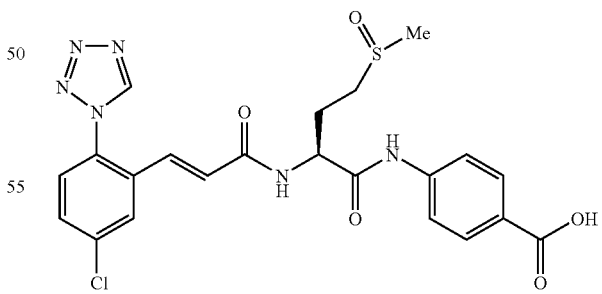

Example 241 was prepared according to the procedures described for Example 55 starting from commercially available (2S)-2-(tert-butoxycarbonylamino)-4-(methylsulfinyl)butanoic acid. LCMS m/z 517.2 [M+H]$^+$. $^1$H NMR (400 MHz, DMSO-d$_6$) δ: 10.53 (1H, s), 9.88 (1H, s), 8.65 (1H, d, J=7.83 Hz), 7.97 (1H, d, J=2.02 Hz), 7.91 (2H, d, J=8.84 Hz), 7.70-7.79 (4H, m), 6.85-6.98 (2H, m), 4.61-4.71 (1H, m), 2.77-2.89 (1H, m), 2.63-2.76 (1H, m), 2.54-2.58 (3H, m), 1.97-2.22 (2H, m) ppm. Analytical HPLC RT: 5.76 min (Method D).

Example 242

(S,E)-4-(2-(3-(5-chloro-2-(1H-tetrazol-1-yl)phenyl)acrylamido)-6-(dimethylamino)hexanamido)benzoic acid, TFA salt

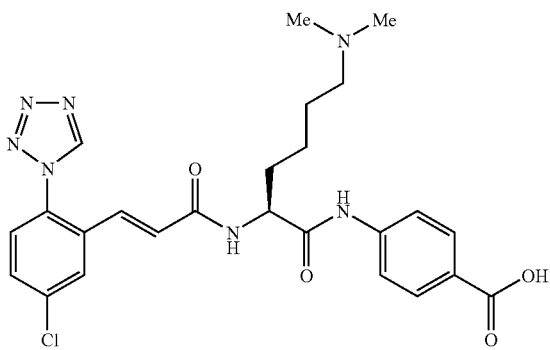 [SMILES: CN(C)CCCC[C@H](NC(=O)/C=C/c1cc(Cl)ccc1-n1cnnn1)C(=O)Nc1ccc(C(=O)O)cc1]

Example 242 was prepared according to the procedures described for Example 238 starting from commercially available (S)-2-(tert-butoxycarbonylamino)-6-(dimethylamino)hexanoic acid. LCMS m/z 526 [M+H]⁺. ¹H NMR (400 MHz, DMSO-d₆) δ: 10.49 (1H, s), 9.88 (1H, d, J=1.52 Hz), 9.34 (1H, br. s.), 8.55 (1H, d, J=8.08 Hz), 7.86-7.99 (3H, m), 7.68-7.79 (4H, m), 6.85-6.97 (2H, m), 4.48-4.61 (1H, m), 2.92-3.08 (2H, m), 2.74 (6H, d, J=3.28 Hz), 1.57-1.86 (4H, m), 1.18-1.43 (2H, m) ppm. Analytical HPLC RT: 4.13 min (Method D).

Example 243

4-((2S)-2-((E)-3-(5-chloro-2-(1H-tetrazol-1-yl)phenyl)acrylamido)-4-(3-(2-ethoxyethoxy)pyrrolidin-1-yl)-4-oxobutanamido)benzoic acid

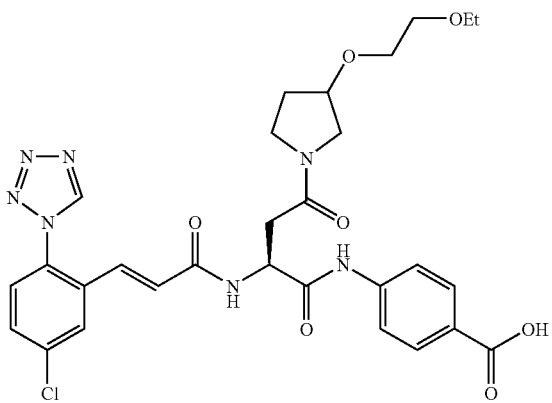 [SMILES: CCOCCOC1CCN(C(=O)C[C@H](NC(=O)/C=C/c2cc(Cl)ccc2-n2cnnn2)C(=O)Nc2ccc(C(=O)O)cc2)C1]

243A. (2S)-2-(tert-butoxycarbonylamino)-4-(3-(2-ethoxyethoxy)pyrrolidin-1-yl)-4-oxobutanoic acid: 1-Propanephosphonic acid cyclic anhydride (0.37 mL, 1.24 mmol) was added to a stirring solution of 3-(2-ethoxyethoxy)pyrrolidine hydrogen chloride salt (0.121 g, 0.62 mmol), (S)-4-(benzyloxy)-3-(tert-butoxycarbonylamino)-4-oxobutanoic acid (0.20 g, 0.62 mmol), and DIPEA (0.54 mL, 3.09 mmol) at 0° C. The mixture was allowed to gradually come to rt overnight. The reaction mixture was washed with 1.0M HCl solution, water, brine, dried over sodium sulfate, filtered, and concentrated. The benzyl group was removed by adding NaOH (2.47 mL, 2.47 mmol) to the ester in MeOH (20 mL) for 1 h. Afterwards, the solution was acidified with citric acid and extracted with EtOAc (3×25 mL). The combined organic layer was dried over sodium sulfate, filtered, and concentrated to give the crude 243A which was carried out in the next reaction. LCMS m/z 375.4 [M+H]⁺.

Example 243. 1-Propanephosphonic acid cyclic anhydride (0.37 mL, 1.237 mmol) was added to a stirring solution of the acid, tert-butyl 4-aminobenzoate (0.12 g, 0.62 mmol), and DIPEA (0.54 mL, 3.09 mmol) in EtOAc (10 mL) at 0° C. After 2 h, the mixture was washed with 1.0M HCl solution, water, brine, dried over sodium sulfate, filtered, and concentrated. The Boc group was removed by treatment with 4.0M HCl solution (in dioxane, 3 mL) for 2 h and concentrated to dryness. DIPEA (0.54 mL, 3.09 mmol) was added to a stirring solution of the amine hydrochloride salt and 55E (E)-2,5-dioxopyrrolidin-1-yl-3-(5-chloro-2-(1H-tetrazol-1-yl)phenyl)acrylate (0.22 g, 0.62 mmol) in DMF (3 mL). After 3 h, the crude product was purified by reverse phase HPLC (MeOH/H₂O/TFA). The product fractions were liberated of organics and freeze dried to give Example 243 (52 mg, 13%) as a white solid. LCMS m/z 626.4 [M+H]⁺. ¹H NMR (400 MHz, DMSO-d₆) δ: 12.71 (1H, br. s.), 10.43 (1H, d, J=2.75 Hz), 9.87 (1H, s), 8.48-8.59 (1H, m), 7.96 (1H, s), 7.84-7.90 (2H, m), 7.70-7.78 (4H, m), 6.78-7.04 (2H, m), 4.77-4.94 (1H, m), 3.99-4.21 (1H, m), 3.13-3.62 (11H, m), 2.62-2.89 (2H, m), 1.76-2.05 (2H, m), 1.03-1.15 (3H, m) ppm. Analytical HPLC RT: 5.54 min (Method D).

Example 244

(S,E)-4-(2-(3-(5-chloro-2-(1H-tetrazol-1-yl)phenyl)acrylamido)-4-(dimethylamino)-4-oxobutanamido)benzoic acid

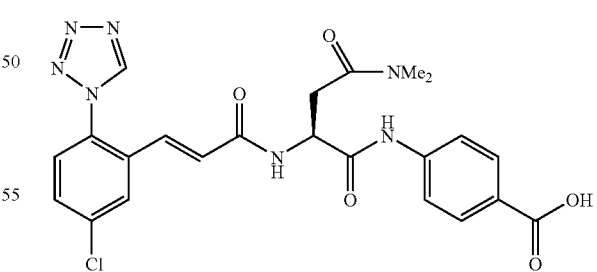

Example 244 was prepared according to the procedures described for Example 243 starting from commercially available dimethylamine (2.0M in MeOH). LCMS m/z 512.2 [M+H]⁺. ¹H NMR (400 MHz, DMSO-d₆) δ: 10.40 (1H, s), 9.87 (1H, s), 8.52 (1H, d, J=7.15 Hz), 7.96 (1H, d, J=2.20 Hz), 7.88 (2H, d, J=8.24 Hz), 7.70-7.78 (4H, m), 6.78-6.93 (2H, m), 4.79-4.91 (1H, m), 2.96 (3H, s), 2.73-2.85 (5H, m) ppm. Analytical HPLC RT: 4.89 min (Method D).

Example 245

(S,E)-3-(dibutylamino)propyl 4-(2-(3-(5-chloro-2-(1H-tetrazol-1-yl)phenyl)acrylamido)-3-phenylpropanamido)benzoate, TFA salt

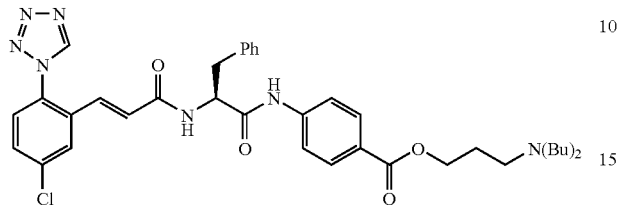

Example 245 was prepared according to the procedures described for Example 3 starting from commercially available Butacaine. LCMS m/z 687.4 [M+H]⁺. ¹H NMR (400 MHz, DMSO-d₆) δ: 10.57 (1H, s), 9.85 (1H, s), 8.63 (1H, d, J=7.83 Hz), 7.92-7.99 (3H, m), 7.68-7.79 (4H, m), 7.16-7.32 (5H, m), 6.79-6.92 (2H, m), 4.70-4.82 (1H, m), 4.31 (2H, t, J=5.94 Hz), 3.20-3.29 (2H, m), 3.05-3.14 (4H, m), 2.88-2.97 (1H, m), 2.05-2.17 (2H, m), 1.53-1.66 (4H, m), 1.26-1.39 (4H, m), 1.13-1.23 (1H, m), 0.91 (6H, t, J=7.33 Hz) ppm. Analytical HPLC RT: 6.06 min (Method D).

Example 246

(S,E)-4-(2-(3-(5-methyl-2-(1H-tetrazol-1-yl)phenyl)acrylamido)-3-phenylpropanamido)benzoic acid

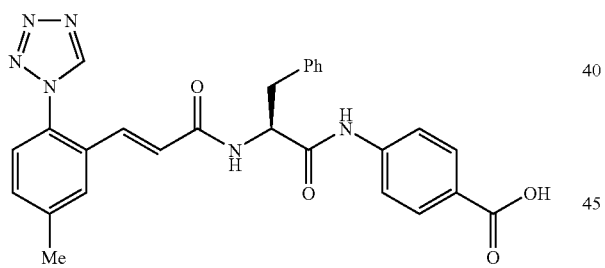

246A. (E)-2,5-dioxopyrrolidin-1-yl-3-(5-methyl-2-(1H-tetrazol-1-yl)phenyl)acrylate: To (E)-3-(5-methyl-2-(1H-tetrazol-1-yl)phenyl)acrylic acid (1.0 g, 4.34 mmol) was added THF (21.8 mL) and DMF (2.18 mL). Next, 1-hydroxypyrrolidine-2,5-dione (0.55 g, 4.78 mmol) and DIC (0.74 mL, 4.78 mmol) were added and the reaction was stirred at rt for 18 h. The resulting solid was collected by filtration and washed with MeOH, water, MeOH, air-dried, and dried under vacuum to give 246A (1.10 g, 77% yield) as a white solid. ¹H NMR (400 MHz, DMSO-d₆) δ: 9.89 (1H, s), 8.15 (1H, s), 7.57-7.65 (2H, m), 7.42 (1H, d, J=15.94 Hz), 7.08 (1H, d, J=15.39 Hz), 2.83 (4H, m), 2.48 (3H, s) ppm.

Example 246 was prepared according to the procedures described for Example 55 replacing 55E with 246A. LCMS m/z 687.4 [M+H]⁺.]⁺. ¹H NMR (400 MHz, DMSO-d₆) δ: 10.52 (1H, s), 9.81 (1H, s), 8.65 (1H, d, J=8.24 Hz), 7.89 (2H, d, J=8.79 Hz), 7.66-7.71 (3H, m), 7.50-7.55 (1H, m), 7.44-7.48 (1H, m), 7.24-7.31 (4H, m), 7.15-7.23 (1H, m), 6.74-6.90 (2H, m), 4.70-4.81 (1H, m), 3.08 (1H, dd, J=13.74, 4.95 Hz), 2.86-2.97 (1H, m), 2.46 (3H, s) ppm. Analytical HPLC RT: 6.06 min (Method D).

Example 247

(S,E)-4-(2-(3-(5-chloro-2-(1H-tetrazol-1-yl)phenyl)acrylamido)-3-(pyridin-4-yl)propanamido)benzoic acid

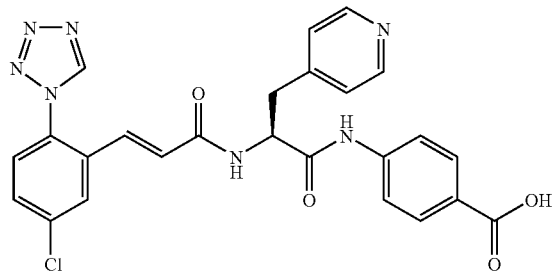 [SMILES: O=C(/C=C/c1cc(Cl)ccc1-n1cnnn1)N[C@@H](Cc1ccncc1)C(=O)Nc1ccc(C(=O)O)cc1]

Example 247 was prepared as previously described for Example 2. ¹H NMR (400 MHz, MeOD) δ: 9.52 (s, 1H), 8.73 (d, J=6.53 Hz, 2H), 7.99-7.95 (m, 3H), 7.92 (d, J=6.53 Hz, 2H), 7.69-7.57 (m, 4H), 7.08 (d, J=15.56 Hz, 1H), 6.70 (d, J=15.81 Hz, 1H), 5.10-5.07 (dd, J=8.78 Hz, J=5.52 Hz, 1H), 3.58-3.54 (m, 1H), 3.29-3.27 (m, 1H) ppm. LCMS (ESI) m/z: 518.3 (M+H).⁺ Analytical HPLC RT: 4.68 min (Method D).

Example 248

(S,E)-4-(2-(3-(5-chloro-2-(1H-tetrazol-1-yl)phenyl)acrylamido)-3-(thiophen-2-yl)propanamido)benzoic acid

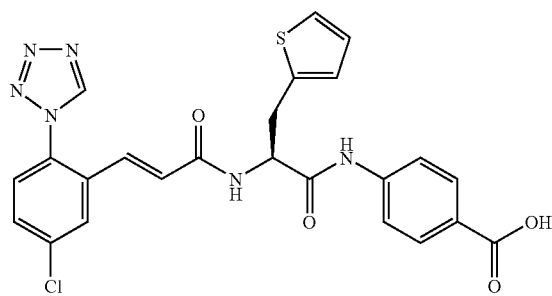 [SMILES: O=C(/C=C/c1cc(Cl)ccc1-n1cnnn1)N[C@@H](Cc1cccs1)C(=O)Nc1ccc(C(=O)O)cc1]

Example 228 was prepared as previously described for Example 2. ¹H NMR (400 MHz, MeOD) δ: 10.23 (s, 1H), 9.51 (s, 1H), 8.71 (d, J=7.53 Hz, 1H), 7.98-7.94 (m, 3H), 7.66-7.55 (m, 4), 7.23 (dd, J=4.52 HZ, J=1.76 Hz, 1H), 7.13 (d, J=15.56 Hz, 1H), 6.92 (m, 2H), 6.80 (d, J=15.56 Hz, 1H), 4.93-4.83 (m, 1H), 3.44-3.26 (m, 2H) ppm. LCMS (ESI) m/z: 523.3 (M+H).⁺ Analytical HPLC RT: 7.61 min (Method D).

Example 249

(S,E)-4-(2-(3-(5-chloro-2-(1H-tetrazol-1-yl)phenyl)acrylamido)-3-(pyridin-3-yl)propanamido)benzoic acid

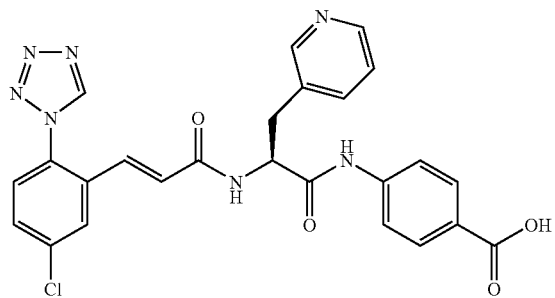 [SMILES: O=C(/C=C/c1cc(Cl)ccc1-n1cnnn1)N[C@@H](Cc1cccnc1)C(=O)Nc1ccc(C(=O)O)cc1]

Example 249 was prepared as previously described for Example 2. $^1$H NMR (400 MHz, MeOD) δ: 9.52 (s, 1H), 8.72 (s, 1H), 8.69 (d, J=5.02 Hz, 1H), 8.39 (d, J=8.03, 1H), 7.96-7.98 (m, 3H), 7.90 (dd, J=8.03 Hz, J=5.77 Hz, 1H), 7.56-7.68 (m, 4H), 7.07 (d, J=15.56 Hz, 1H), 6.73 (d, J=15.56 Hz, 1H), 5.01-4.99 (m, 1H), 3.50-3.46 (dd, J=14.05 Hz, J=6.02 Hz, 1H), 3.26-3.20 (dd, J=14.05 Hz, J=8.53 Hz, 1H) ppm. LCMS (ESI) m/z: 518.3 (M+H).$^+$ Analytical HPLC RT: 4.70 min (Method D).

Example 250

(S,E)-4-(2-(3-(5-chloro-2-(1H-tetrazol-1-yl)phenyl)acrylamido)-3-(pyridin-2-yl)propanamido)benzoic acid

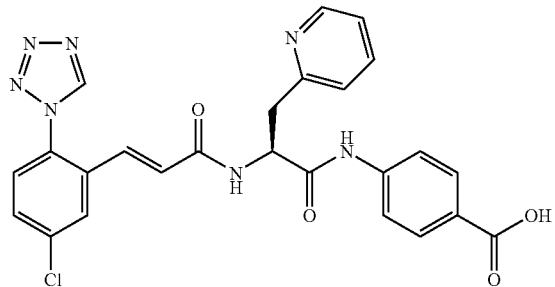 [SMILES: O=C(/C=C/c1cc(Cl)ccc1-n1cnnn1)N[C@@H](Cc1ccccn1)C(=O)Nc1ccc(C(=O)O)cc1]

Example 250 was prepared as previously described for Example 2. $^1$H NMR (400 MHz, MeOD) δ: 9.52 (s, 1H), 8.71 (d, J=5.77 Hz, 1H), 8.36 (m, 1H), 7.8-7.962 (m, 3H), 7.83 (m, 2H), 7.69-7.57 (m, 4H), 7.08 (d, J=15.81 Hz, 1H), 6.72 (d, J=15.56 Hz, 1H), 5.11 (t, J=7.03 Hz, 1H), 3.65-3.60 (m, 1H), 3.39-3.31 (m, 1H) ppm. LCMS (ESI) m/z: 518.3 (M+H).$^+$ Analytical HPLC RT: 4.89 min (Method D).

Example 251

(E)-4-(2-(3-(5-chloro-2-(1H-tetrazol-1-yl)phenyl)acrylamido)-3-(quinoxalin-2-yl)propanamido)benzoic acid

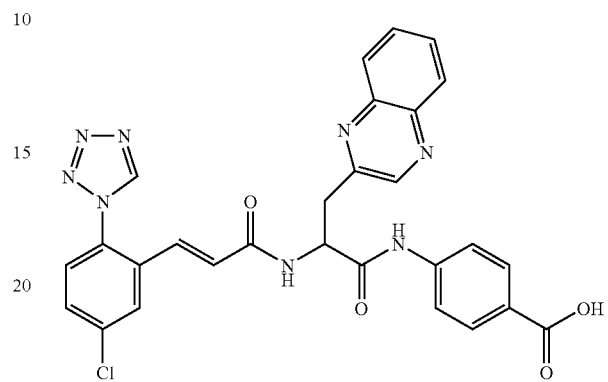

Example 251 was prepared as previously described for Example 2. $^1$H NMR (400 MHz, MeOD) δ: 10.32 (br, 1H), 9.48 (s, 1H), 8.84 (s, 1H), 8.36 (m, 1H), 8.06-7.94 (m, 5H), 7.79 (m, 2H), 7.66-7.60 (m, 3H), 7.55 (m, 1H), 7.09 (d, J=15.56 Hz, 1H), 6.77 (d, J=15.56 Hz, 1H), 5.25 (m, 1H), 3.69-3.66 (dd, J=14.68 Hz, J=6.15 Hz, 1H), 3.47-3.53 (m, 1H) ppm. LCMS (ESI) m/z: 569.3 (M+H).$^+$ Analytical HPLC RT: 7.17 min (Method D).

Example 252

(S,E)-4-(2-(3-(5-chloro-2-(1H-tetrazol-1-yl)phenyl)acrylamido)-4-oxo-4-(pyrazin-2-ylmethylamino)butanamido)benzoic acid

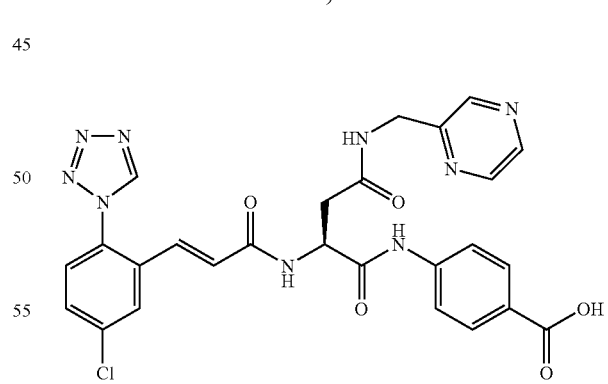

Example 252 was prepared as previously described for Example 45. $^1$H NMR (400 MHz, MeOD) δ: 10.36 (s, 1H), 9.75 (s, 1H), 8.57 (m, 1H), 8.52 (s, 1H), 8.37 (dd, J=11.42 HZ, J=1.88 Hz, 2H), 7.95-7.81 (m, 3H), 7.67-7.65 (m, 4H), 6.90 (d, J=4.52 Hz, 2H), 4.87 (t, J=5.4 Hz, 1H), 4.38 (s, 2H), 2.85-2.68 (m, 2H) ppm. LCMS (ESI) m/z: 576.3 (M+H).$^+$ Analytical HPLC RT: 5.78 min (Method D).

Example 253

4-((S)-2-((E)-3-(5-chloro-2-(1H-tetrazol-1-yl)phenyl)acrylamido)-5-((Z)-2-nitroguanidino)pentanamido)benzoic acid

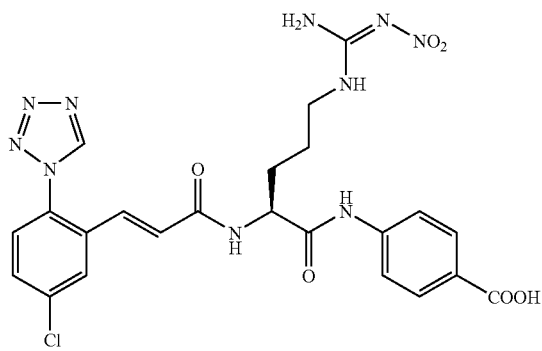 [SMILES: N/C(=N/[N+](=O)[O-])NCCC[C@H](NC(=O)/C=C/c1cc(Cl)ccc1-n1cnnn1)C(=O)Nc1ccc(C(=O)O)cc1]

Example 253 was prepared as previously described for Example 2. $^1$H NMR (400 MHz, DMSO-d$_6$) δ: 10.48 (s, 1H), 9.87 (s, 1H), 8.56 (d, J=J=8.2 Hz, 1H), 7.96 (d, J=2.2 Hz, 1H), 7.91 (d, J=8.8 Hz, 1H), 7.74-7.70 (m, 4H), 6.90 (s, 2H), 4.56 (m, 1H), 3.19 (m, 2H), 1.99-1.51 (m, 4H) ppm. LCMS (ESI) m/z: 471.0 (M+H).$^+$ Analytical HPLC RT: 4.833 min (Method C).

Example 254

(S,E)-4-(2-(3-(5-chloro-2-(1H-tetrazol-1-yl)phenyl)acrylamido)-3-methoxypropanamido)benzoic acid

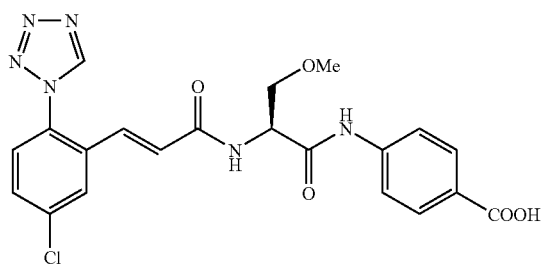

Example 254 was prepared as previously described for Example 2. $^1$H NMR (400 MHz, DMSO-d$_6$) δ: 9.87 (s, 1H), 8.55 (d, J=7.7 Hz, 1H), 7.95 (d, J=2.1 Hz, 1H), 7.87 (d, J=8.8 Hz, 2H), 7.78-7.70 (m, 4H), 7.00-6.87 (q, 2H), 4.76 (m, 1H), 3.62 (d, 2H), 3.28 (s, 3H) ppm. LCMS (ESI) m/z: 471.1 (M+H).$^+$ Analytical HPLC RT: 3.328 min (Method B).

Example 255

(S,E)-4-(2-(3-(5-chloro-2-(1H-tetrazol-1-yl)phenyl)acrylamido)-4-((2-(dimethylamino)ethyl)(methyl)amino)-4-oxobutanamido)benzoic acid, TFA salt

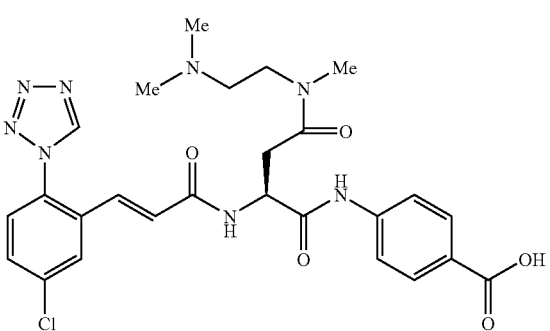 [SMILES: CN(C)CCN(C)C(=O)C[C@H](NC(=O)/C=C/c1cc(Cl)ccc1-n1cnnn1)C(=O)Nc1ccc(C(=O)O)cc1]

Example 255 was prepared according to the procedures described for Example 243 starting from commercially available N,N,N'-Trimethylethylenediamine. $^1$H NMR (400 MHz, DMSO-d$_6$) δ: 10.38 (1H, s), 9.88 (1H, s), 8.72 (1H, d, J=7.70 Hz), 7.94 (1H, s), 7.89 (2H, d, J=8.79 Hz), 7.71-7.78 (2 H, m), 7.66 (2H, d, J=8.79 Hz), 6.87-6.99 (1H, m), 6.75-6.83 (1H, m), 5.06-5.22 (1H, m), 3.65-3.78 (1H, m), 3.52-3.63 (1H, m), 3.16-3.25 (2H, m), 3.09-3.14 (2H, m), 2.93-3.02 (1H, m), 2.77-2.89 (7H, m), 2.64-2.75 (1H, m) ppm. LCMS (ESI) m/z: 570.4 (M+H).$^+$ Analytical HPLC RT: 4.19 min (Method C).

Example 256

(S,E)-tert-butyl 4-(2-(3-(5-chloro-2-(1H-tetrazol-1-yl)phenyl)acrylamido)-4-(2-methoxyethylamino)-4-oxobutanamido)benzoate

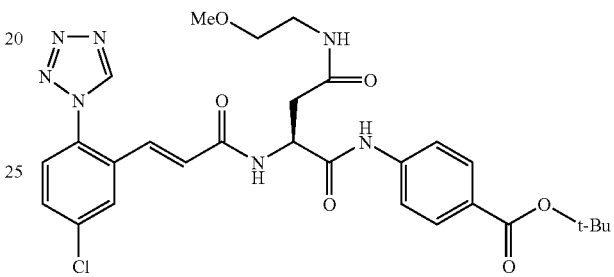

Example 256 was prepared according to the procedures described for Example 243 starting from commercially available 2-methoxyethanamine. $^1$H NMR (400 MHz, DMSO-d$_6$) δ: 10.27 (1H, s), 9.87 (1H, s), 8.44 (1H, d, J=8.25 Hz), 7.93-8.02 (1H, m), 7.79-7.87 (2H, m), 7.62-7.76 (4H, m), 6.80-6.95 (2H, m), 4.67-4.77 (1H, m), 3.26-3.35 (2H, m), 3.17-3.24 (5H, m), 2.64-2.87 (2H, m), 1.53 (9H, s) ppm. LCMS (ESI) m/z: 542.3 [M+H]$^+$. Analytical HPLC RT: 6.71 min (Method D).

Example 257

(S,E)-4-(2-(3-(3-chloro-2-fluoro-6-(1H-tetrazol-1-yl)phenyl)acrylamido)-3-phenylpropanamido)benzoic acid

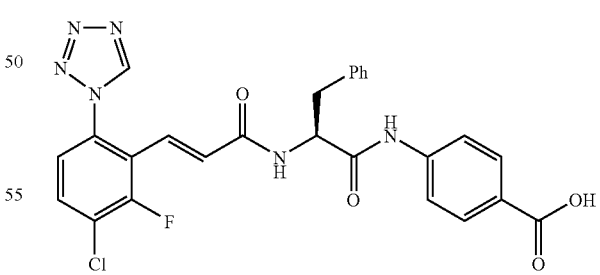

Example 257 was prepared according to the procedures described for Example 55 replacing 55E with Intermediate 7 in the final amide coupling. $^1$H NMR (400 MHz, DMSO-d$_6$) δ: 12.75 (1H, br. s.), 10.54 (1H, s), 9.84 (1H, s), 8.90 (1H, d, J=7.91 Hz), 7.85-8.00 (3H, m), 7.58-7.75 (3H, m), 7.14-7.34 (5H, m), 6.67-6.84 (2H, m), 4.71-4.79 (1H, m), 3.08 (1H, dd, J=13.84, 5.05 Hz), 2.89 (1H, dd) ppm. LCMS (ESI) m/z: 535.3 [M+H]$^+$. Analytical HPLC RT: 6.38 min (Method D).

Example 258

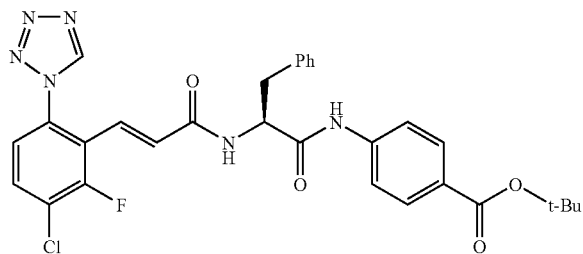 [SMILES: CC(C)(C)OC(=O)c1ccc(NC(=O)[C@H](Cc2ccccc2)NC(=O)/C=C/c2c(-n3cnnn3)ccc(Cl)c2F)cc1]

Example 258 was isolated as a by-product from Example 257. ¹H NMR (400 MHz, DMSO-d$_6$) δ 10.55 (1H, s), 9.84 (1H, s), 8.89 (1H, d, J=7.91 Hz), 7.93 (1H, t, J=8.13 Hz), 7.85 (2H, d, J=8.79 Hz), 7.59-7.72 (3H, m), 7.24-7.32 (4H, m), 7.13-7.23 (1H, m), 6.68-6.83 (2H, m), 4.70-4.81 (1H, m), 3.07 (1H, dd, J=13.84, 4.61 Hz), 2.88 (1H, dd, J=13.62, 9.67 Hz), 1.53 (9H, s) ppm. LCMS (ESI) m/z: 592 [M+H]⁺. Analytical HPLC RT: 7.63 min (Method D).

Example 259

4-[(S)-2-[(E)-3-(5-chloro-2-tetrazol-1-yl-phenyl)-acryloylamino]-3-(1,1-dioxo-hexahydro-1λ⁶-thiopyran-4-yl)-propionylamino]-benzoic acid

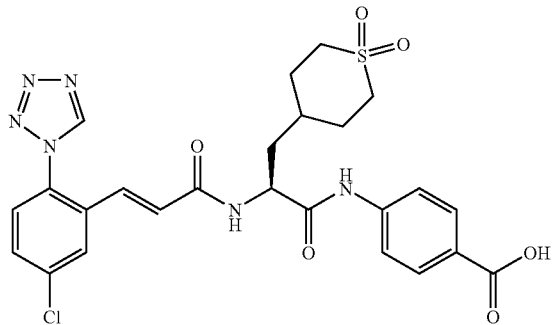 [SMILES: O=C(/C=C/c1cc(Cl)ccc1-n1cnnn1)N[C@@H](CC1CCS(=O)(=O)CC1)C(=O)Nc1ccc(C(=O)O)cc1]

Example 259 was readily prepared from (S)-2-Benzyloxycarbonylamino-3-(1,1-dioxo-hexahydro-1λ⁶-thiopyran-4-yl)-propionic acid methyl ester (prepared according to Example 153. In this case tetrahydro-2H-thiopyran-4-carbaldehyde was used. The resulting thiono derivative was oxidized with MCPBA to afford desired intermediate). ¹H NMR (400 MHz, MeOD) δ: 9.54 (1H, s), 7.95-8.06 (3H, m), 7.65-7.77 (3H, m), 7.57-7.62 (1H, m), 7.17 (1H, d, J=15.66 Hz), 6.79 (1H, d, J=15.66 Hz), 4.72 (1H, dd, J=9.47, 5.18 Hz), 2.98-3.20 (5H, m), 2.28 (1H, d, J=12.88 Hz), 2.13 (1H, br. s.), 1.71-1.96 (4H, m) ppm. LCMS (ESI) m/z: 573.3 [M+H]⁺. Analytical HPLC RT: 7.63 min (Method C).

Example 260

4-((S)-2-((E)-3-(5-chloro-2-(1H-tetrazol-1-yl)phenyl)acrylamido)-3-((R)-pyrrolidin-2-yl)propanamido)benzoic acid

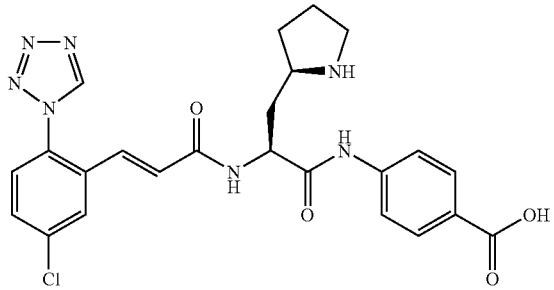 [SMILES: O=C(/C=C/c1cc(Cl)ccc1-n1cnnn1)N[C@@H](C[C@H]1CCCN1)C(=O)Nc1ccc(C(=O)O)cc1]

Example 260 was prepared following the procedure used to prepare Example 225/153 ((R)-tert-butyl 2-formylpyrrolidine-1-carboxylate was used in the preparation of the desire amino acid derivative). ¹H NMR (400 MHz, MeOD) δ: 9.44 (1H, s), 7.84-7.94 (3H, m), 7.54-7.67 (3H, m), 7.46-7.53 (1H, m), 7.11 (1H, d, J=15.66 Hz), 6.68 (1H, d, J=15.41 Hz), 4.66 (1H, dd, J=8.21, 5.94 Hz), 3.42-3.51 (1H, m), 2.32 (1H, ddd, J=14.27, 7.96, 6.06 Hz), 2.19 (1H, dddd, J=16.61, 7.33, 3.92, 3.73 Hz), 1.85-2.04 (4H, m), 1.59-1.73 (2H, m, J=13.11, 8.92, 8.92, 8.72 Hz) ppm. LCMS (ESI) m/z: 510.3 [M+H]⁺. Analytical HPLC RT: 4.19 min (Method C).

Example 261

(S,E)-4-(2-(3-(5-chloro-2-(1H-tetrazol-1-yl)phenyl)acrylamido)-3-(6,7-dihydro-4H-pyrazolo[5,1-c][1,4]oxazin-2-yl)propanamido)benzoic acid

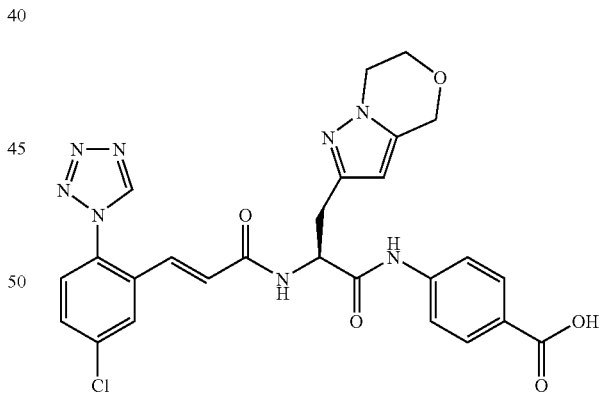

Example 261 was readily prepared following the procedure outlined for Examples 225/153 (Intermediate 6,7-dihydro-4H-pyrazolo[5,1-c][1,4]oxazine-2-carbaldehyde was prepared following similar procedure of A. M. Vendatesan et. al, J. Med. Chem. 2006, 49, 4623). ¹H NMR (400 MHz, DMSO-d$_6$) δ: 12.71 (1H, br. s.), 10.48 (1H, s), 9.85 (1H, s), 8.53 (1H, d, J=7.70 Hz), 7.94 (1H, s), 7.87 (2H, d, J=8.79 Hz), 7.59-7.79 (4H, m), 6.75-6.99 (2H, m), 5.88 (1H, s), 4.72-4.83 (1H, m), 4.70 (2H, s), 3.98 (4H, s), 3.01 (1H, dd, J=14.57, 5.22 Hz), 2.88 (1H, dd) ppm. LCMS (ESI) m/z: 619.3 [M+H]⁺. Analytical HPLC RT: 6.39 min (Method D).

Example 262

4-((S)-2-((E)-3-(5-chloro-2-(1H-tetrazol-1-yl)phenyl)acrylamido)-2-((R)-piperidin-3-yl)acetamido)benzoic acid

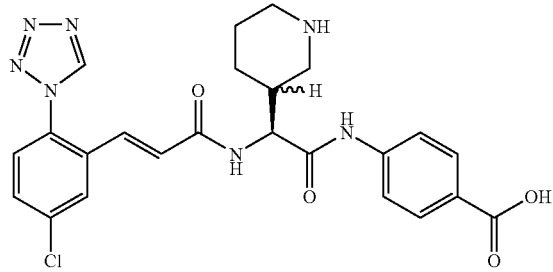 [SMILES: O=C(/C=C/c1cc(Cl)ccc1-n1cnnn1)N[C@H](C(=O)Nc1ccc(C(=O)O)cc1)C1CCCNC1]

Example 262 was readily prepared as a mixture of diastereomers following the procedure outlined for Examples 225/153 (by utilizing intermediate N-Boc-3-piperidinyl-carboxaldehyde as the precursor to the amino acid synthesis). $^1$H NMR (400 MHz, MeOD) δ: 9.55 (1H, s), 8.01 (3H, dd, J=5.68, 3.16 Hz), 7.68-7.80 (3H, m), 7.56-7.65 (1H, m), 7.20 (1H, d, J=15.66 Hz), 6.79-6.90 (1H, m), 2.84-2.97 (4H, m), 2.28-2.48 (1H, m), 2.05 (1H, s), 1.95 (1H, br. s.), 1.74 (1H, br. s.), 1.48 (1H, br. s.), 1.35 (1H, t, J=7.33 Hz) ppm. LCMS (ESI) m/z: 510.1 [M+H]$^+$. Analytical HPLC RT: 6.39 min (Method D).

Example 263

4-((S)-2-((E)-3-(5-chloro-2-(1H-tetrazol-1-yl)phenyl)acrylamido)-3-((S)-pyrrolidin-2-yl)propanamido)benzoic acid

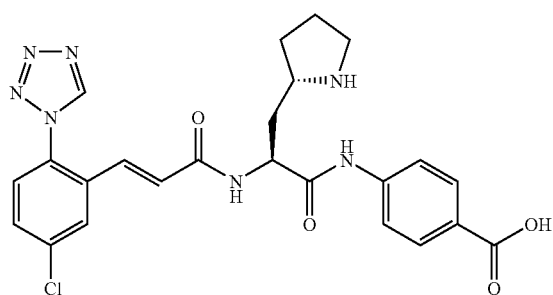 [SMILES: O=C(/C=C/c1cc(Cl)ccc1-n1cnnn1)N[C@@H](C[C@@H]1CCCN1)C(=O)Nc1ccc(C(=O)O)cc1]

Example 263 was readily prepared following the procedure outlined for Examples 225/153/260. $^1$H NMR (400 MHz, MeOD) δ: 9.54 (1H, s), 7.91-8.04 (3H, m), 7.70-7.77 (2H, m), 7.63-7.68 (1H, m), 7.54-7.62 (1H, m), 7.18 (1H, d, J=15.41 Hz), 6.82 (1H, d, J=15.66 Hz), 4.74-4.81 (1H, m), 3.67 (1H, dq, J=7.33, 7.16 Hz), 2.24-2.42 (4H, m), 1.95-2.16 (2H, m), 1.65-1.88 (2H, m) ppm. LCMS (ESI) m/z: 510.1 [M+H]$^+$. Analytical HPLC RT: 4.83 min (Method D).

Example 264

(S,E)-4-(2-(3-(5-chloro-2-(1H-tetrazol-1-yl)phenyl)acrylamido)-3-(tetrahydro-2H-pyran-4-yl)propanamido)benzoic acid

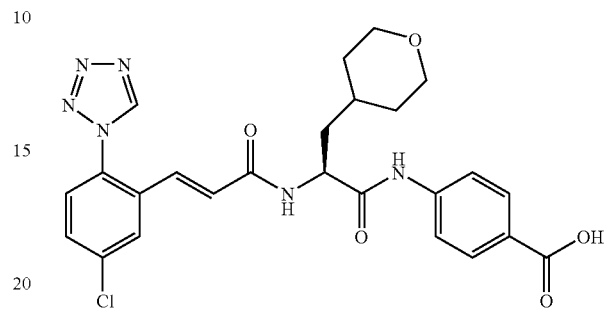

Example 264 was readily prepared following the procedure outlined for Examples 225/153/259 (commercially available tetrahydro-2H-pyran-4-carbaldehyde was utilized for the requisite amino acid synthesis). $^1$H NMR (400 MHz, MeOD) δ: 9.54 (1H, s), 7.94-8.09 (3H, m), 7.64-7.76 (3H, m), 7.53-7.62 (1H, m), 7.16 (1H, d, J=15.66 Hz), 6.81 (1H, d, J=15.66 Hz), 4.71 (1H, t, J=7.45 Hz), 3.95 (1H, dt, J=11.37, 2.02 Hz), 3.33-3.44 (2H, m), 1.63-1.84 (6H, m), 1.30-1.44 (2H, m) ppm. LCMS (ESI) m/z: 525.3 [M+H]$^+$. Analytical HPLC RT: 6.73 min (Method D).

Example 265

(S,E)-3-(3-(4-carboxyphenylamino)-2-(3-(5-chloro-2-(1H-tetrazol-1-yl)phenyl)acrylamido)-3-oxopropyl)pyridine 1-oxide

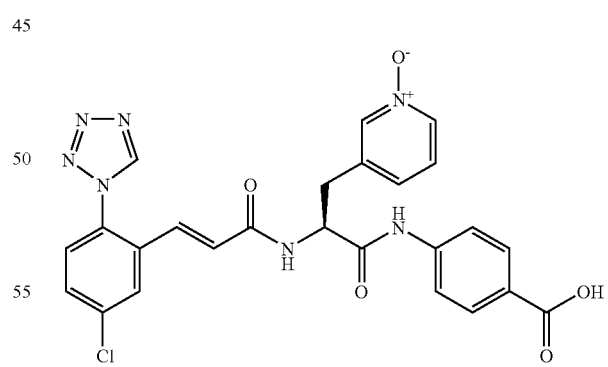

Example 265 was prepared via the MCPBA oxidation of Example 249. $^1$H NMR (400 MHz, MeOD) δ: 9.54 (s, 1H), 8.32 (m, 1H), 8.23 (m, 1H), 8.00-7.98 (m, 3H), 7.70-7.68 (m, 3H), 7.59-7.51 (m, 2H), 7.49 (m, 1H), 7.08 (d, J=15.67 Hz, 1H), 6.78 (d, J=15.31 Hz, 1H), 5.00 (m, 1H), 3.14-3.28 (m, 2H) ppm. LCMS (ESI) m/z: 534.3 (M+H).$^+$ Analytical HPLC retention time 5.54 min. (Method D).

Example 266

(S,E)-4-(3-(4-carboxyphenylamino)-2-(3-(5-chloro-2-(1H-tetrazol-1-yl)phenyl)acrylamido)-3-oxopropyl)pyridine 1-oxide

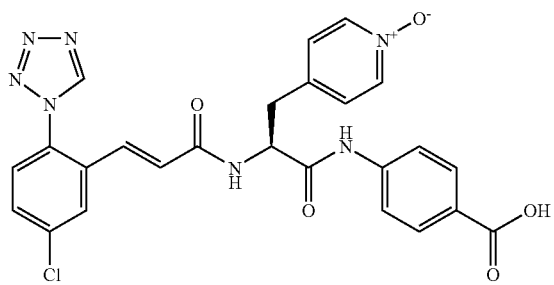 [SMILES: O=C(/C=C/c1cc(Cl)ccc1-n1cnnn1)N[C@@H](Cc1cc[n+]([O-])cc1)C(=O)Nc1ccc(C(=O)O)cc1]

Example 266 was prepared via the MCPBA oxidation of Example 247. ¹H NMR (400 MHz, MeOD) δ: 9.52 (s, 1H), 8.28 (d, J=6.78 Hz, 2H), 7.98 (d, J=8.03 Hz, 3H), 7.67 (m, 3H), 7.58 (m, 1H), 7.49 (d, J=6.52 Hz, 2H), 7.13 (d, J=15.56 Hz, 1H), 6.74 (d, J=15.81 Hz, 1H), 4.93 (m, 1H), 3.14-3.28 (m, 2H) ppm. LCMS (ESI) m/z: 534.3 (M+H)⁺. Analytical HPLC RT: 5.46 min (Method D).

Example 267

(S,E)-4-(2-(3-(3-chloro-2-fluoro-6-(1H-tetrazol-1-yl)phenyl)acrylamido)-3-(pyridin-4-yl)propanamido)benzoic acid

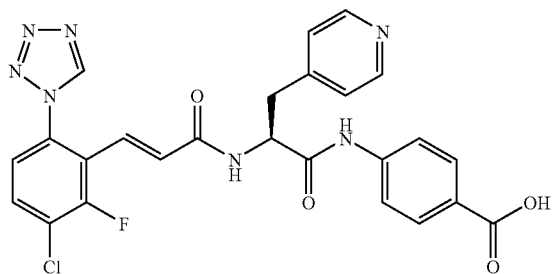 [SMILES: O=C(/C=C/c1c(-n2cnnn2)ccc(Cl)c1F)N[C@@H](Cc1ccncc1)C(=O)Nc1ccc(C(=O)O)cc1]

Example 267 was prepared via the procedure adopted for Example 2/247. ¹H NMR (400 MHz, MeOD) δ: 9.52 (s, 1H), 8.69 (d, J=6.02 Hz, 2H), 7.99 (d, J=8.78 Hz, 2H), 7.82-7.75 (m, 3H), 7.68 (d, J=8.53 Hz, 2H), 7.48 (d, J=8.53 Hz, 1H), 6.98 (d, J=16.06 Hz, 1H), 6.67 (d, J=15.81 Hz, 1H), 5.05-5.02 (m, 1H), 3.48 (m, 1H), 3.22 (m, 1H) ppm. LCMS (ESI) m/z: 536.2 (M+H)⁺ Analytical HPLC RT: 5.53 min (Method D).

Example 268

(S,E)-4-(2-(3-(3-chloro-2-fluoro-6-(1H-tetrazol-1-yl)phenyl)acrylamido)-3-(pyridin-3-yl)propanamido)benzoic acid

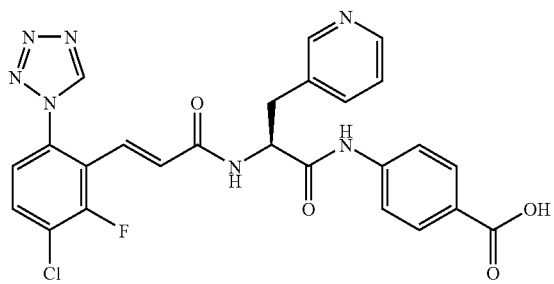 [SMILES: O=C(/C=C/c1c(-n2cnnn2)ccc(Cl)c1F)N[C@@H](Cc1cccnc1)C(=O)Nc1ccc(C(=O)O)cc1]

Example 268 was prepared via the procedure adopted for Example 2/249. ¹H NMR (400 MHz, MeOD) δ: 9.52 (s, 1H), 8.70-8.67 (m, 2H), 8.33 (d, J=7.53 Hz, 1H), 7.98 (d, J=8.78 Hz, 2H), 7.88 (dd, J=7.65 Hz, J=5.65 Hz, 1H), 7.78 (t, J=8.03 Hz, 1H), 7.68 (d, J=8.78 Hz, 2H), 7.48 (d, J=8.78 Hz, 1H), 6.96 (d, J=15.81 Hz, 1H), 6.72 (d, J=16.06 Hz, 1H), 4.99-4.93 (m, 1H), 3.47-3.41 (m, 1H), 3.23-3.17 (m, 1H) ppm. LCMS (ESI) m/z: 536.2 (M+H).⁺ Analytical HPLC RT: 5.63 min (Method D).

Example 269

(S,E)-4-(2-(3-(5-chloro-2-(1H-tetrazol-1-yl)phenyl)acrylamido)-3-(6-hydroxypyridin-3-yl)propanamido)benzoic acid

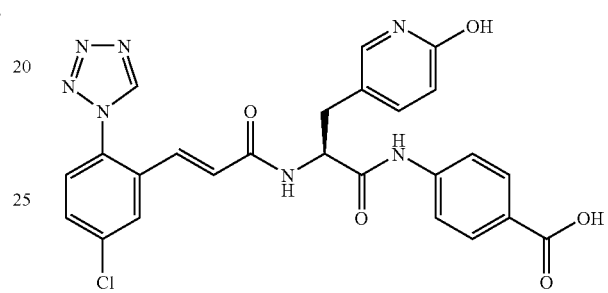

Example 269 was prepared in a similar manner to that was described for Example 3 from commercially available starting materials. ¹H NMR (400 MHz, MeOD) δ: 9.52 (s, 1H), 7.98 (m, 3H), 7.67-7.56 (m, 5H), 7.32 (s, 1H), 7.11 (d, J=15.56 Hz, 1H), 6.79 (d, J=15.56 Hz, 1H), 6.52 (d, J=9.54 Hz, 1H), 4.77 (m, 1H), 3.02 (m, 1H), 3.90 (m, 1H) ppm. LCMS (ESI) m/z: 534.2 [M+H]⁺. Analytical HPLC RT: 5.63 min (Method D).

Example 270

(S,E)-4-(2-(3-(3-chloro-2-fluoro-6-(1H-tetrazol-1-yl)phenyl)acrylamido)-3-(6-hydroxypyridin-3-yl)propanamido)benzoic acid

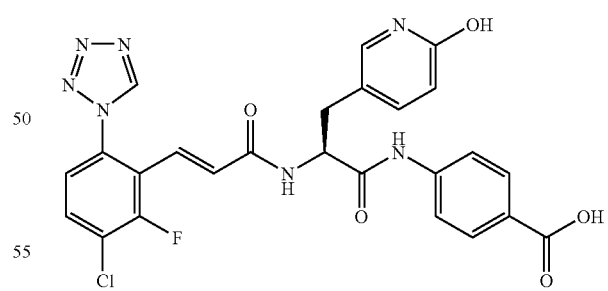

Example 270 was prepared in a similar manner to that was described for Example 269. ¹H NMR (400 MHz, MeOD) δ: 10.21 (s, 1H), 9.52 (s, 1H), 8.81 (d, J=7.78 Hz, 1H), 7.97 (d, J=8.78 Hz, 2H), 7.77 (m, 1H), 7.65 (d, J=8.78 Hz, 2H), 7.58 (dd, J=9.29 Hz, J=2.51 Hz, 1H), 7.47 (dd, J=8.66 Hz, J=1.38 Hz, 1H), 7.31 (s, 1H), 6.99 (d, J=16.06 Hz, 1H), 6.78 (d, J=16.06 Hz, 1H), 4.73-4.77 (m, 1H), 2.99 (dd, J=14.05 Hz, J=6.78 Hz, 1H), 2.88 (dd, J=14.05 Hz, J=7.78 Hz, 1H) ppm. LCMS (ESI) m/z: 552.3 [M+H]⁺. Analytical HPLC RT: 5.78 min (Method D).

Example 271

(E)-4-(2-(3-(5-chloro-2-(1H-tetrazol-1-yl)phenyl)acrylamido)-3-(thiazol-2-yl)propanamido)benzoic acid

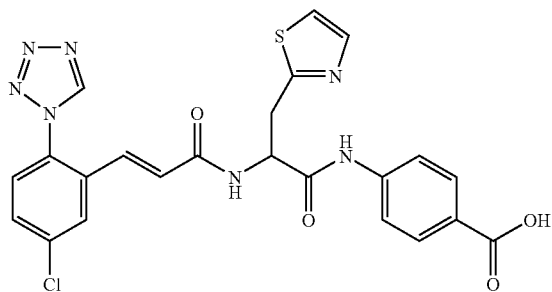 [SMILES: O=C(/C=C/c1cc(Cl)ccc1-n1cnnn1)NC(Cc1nccs1)C(=O)Nc1ccc(C(=O)O)cc1]

Example 271 was prepared in a similar manner to that was described for Example 3 from commercially available starting materials. $^1$H NMR (400 MHz, MeOD) δ: 9.52 (s, 1H), 7.99-7.95 (m, 3H), 7.75 (d, J=3.51 Hz, 1H), 7.68-7.53 (m, 5H), 7.13 (d, J=15.56 Hz, 1H), 6.79 (d, J=15.56 Hz, 1H), 5.05-5.04 (dd, J=7.78 Hz, J=5.77 Hz, 1H), 3.65 (dd, J=14.93 Hz, J=5.9 Hz, 1H), 3.52 (m, 1H) ppm. LCMS (ESI) m/z: 524.2 (M+H)$^+$. Analytical HPLC RT: 6.73 min (Method D).

Example 272

(S,E)-4-(2-(3-(5-chloro-2-(1H-tetrazol-1-yl)phenyl)acrylamido)-3-(1-methyl-5-(methylsulfinyl)-1H-pyrazol-3-yl)propanamido)benzoic acid

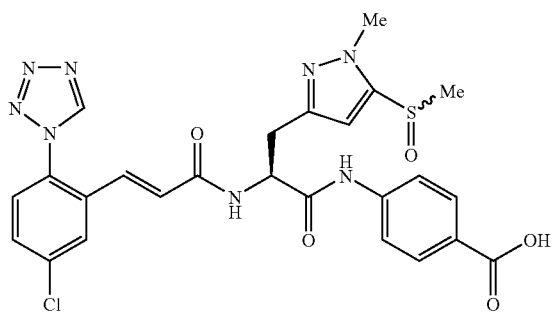 [SMILES: Cn1nc(C[C@H](NC(=O)/C=C/c2cc(Cl)ccc2-n2cnnn2)C(=O)Nc2ccc(C(=O)O)cc2)cc1S(C)=O]

272A. 3-(dimethoxymethyl)-1-methyl-5-(methylthio)-1H-pyrazole: To a solution of 1,1-dimethoxy-4,4-bis(methylthio)but-3-en-2-one (2.6 g, 11.69 mmol), which was prepared according to the procedure described by P. K. Mahata, et al., (*Tetrahedron*, 2003, 2631-2639) in EtOH (25 mL), was added methylhydrazine (0.616 mL, 11.69 mmol) at rt. The reaction mixture was stirred under argon at 80° C. for 4 h. Removing solvent afforded 272A as a red oil (2.36, 100% yield). LCMS (ESI) m/z: 170.9 (M-MeO)$^+$.

272B. 3-(dimethoxymethyl)-1-methyl-5-(methylsulfinyl)-1H-pyrazole: To a solution of 272A (2.36 g, 11.67 mmol) in Acetone (50 mL) was added Oxone (14.35 g, 23.33 mmol) at rt. The reaction mixture was stirred under argon at rt over night. The solid was filtered through a pad of silica gel, and washed with acetone. Removing solvent afforded 272B as a tan oil (1.89 g, yield 74.2%). LCMS (ESI) m/z: 187.2 (M-MeO)$^+$.

272C. 1-methyl-5-(methylsulfinyl)-1H-pyrazole-3-carbaldehyde: A solution of 272B (1.89 g, 8.66 mmol) in water (20.00 mL) and acetic acid (20 mL) was stirred under argon at 60° C. for 2 h. Removing solvent in vacuo afforded a tan oil. Purification by normal phase chromatography gave 272C as a white solid (1.18 g, 6.85 mmol, 79% yield). LCMS (ESI) m/z: 173.1 (M+H)$^+$.

272D. methyl 2-(tert-butoxycarbonylamino)-3-(1-methyl-5-(methylsulfinyl)-1H-pyrazol-3-yl)acrylate: 272D was synthesized following the procedure described in Intermediate 1A by replacing 1-methyl-1H-pyrazole-3-carbaldehyde with 272C. The title compound 272D was obtained as a white solid (2.22 g, 6.46 mmol, 94% yield). LC-MS (ESI) m/z: 344.0 (M+H)$^+$.

272 E. (S)-methyl 2-(tert-butoxycarbonylamino)-3-(1-methyl-5-(methylsulfinyl)-1H-pyrazol-3-yl)propanoate: 272E was synthesized following the procedure described in Intermediate 1B by replacing Intermediate 1A with 272D (1.0 g, 2.91 mmol). The title compound 272E was obtained as a white solid (887 mg, 88% yield). LC-MS (ESI) m/z: 346.1 (M+H)$^+$. $^1$H NMR (400 MHz, CHLOROFORM-d) δ ppm 6.40 (d, 1H) 5.33 (t, J=6.90 Hz, 1H) 4.51-4.69 (m, 1H) 4.05 (s, 3H) 3.73 (s, 3 H) 3.13 (d, J=4.27 Hz, 2H) 2.95 (d, 3H) 1.44 (s, 9H) ppm.

272F. (S)-2-(tert-butoxycarbonylamino)-3-(1-methyl-5-(methylsulfinyl)-1H-pyrazol-3-yl)propanoic acid: 272F was synthesized following the procedure described in Intermediate 1 by replacing Intermediate 1B with 272E (160 mg, 0.463 mmol). The title compound 272F was obtained as a white solid (154 mg, 100% yield). LCMS (ESI) m/z: 232.1 (M-Boc)$^+$.

Example 272: The title compound was synthesized following the procedure described in Example 3. $^1$H NMR (400 MHz, MeOD) δ: 9.52 (s, 1H) 7.99 (br. s., 1H) 7.96 (d, J=8.53 Hz, 2H) 7.65 (d, J=8.78 Hz, 3H) 7.57 (d, J=8.53 Hz, 1H) 7.11 (dd, J=15.69, 2.64 Hz, 1H) 6.77 (dd, J=15.56, 3.76 Hz, 1H) 6.67 (d, J=11.04 Hz, 1H) 4.8-5.0 (m, 1H, overlapped with CD$_3$OD, COSY) 3.98 (d, 3H) 3.22 (ddd, J=14.81, 6.15, 2.64 Hz, 1H) 3.05-3.15 (m, 1H) 2.96 (d, 3H) ppm. LCMS (ESI) m/z: 583.2 [M+H]$^+$. Analytical HPLC RT: 5.853 min (Method D).

Example 273

(S,E)-4-(2-(3-(5-chloro-2-(1H-tetrazol-1-yl)phenyl)acrylamido)-3-(1-methyl-5-(methylsulfonyl)-1H-pyrazol-3-yl)propanamido)benzoic acid

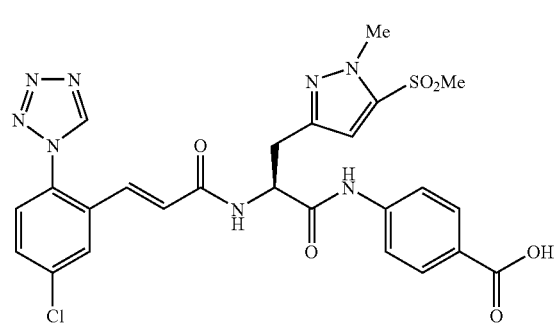 [SMILES: Cn1nc(C[C@H](NC(=O)/C=C/c2cc(Cl)ccc2-n2cnnn2)C(=O)Nc2ccc(C(=O)O)cc2)cc1S(C)(=O)=O]

To a solution of Example 272 (34 mg, 0.058 mmol) in acetonitrile (2 mL) and MeOH (2 mL) was added mCPBA (13.07 mg, 0.058 mmol) at rt. The reaction mixture was stirred under argon at rt for 2 h. Purification by reverse phase chromatography gave Example 273 as a white solid (20.5 mg, 0.034 mmol, 58.7% yield.) $^1$H NMR (400 MHz, METHANOL-$d_4$) δ: 9.52 (s, 1H) 7.92-8.03 (m, 3H) 7.66 (d, J=8.28 Hz, 3H) 7.53-7.61 (m, J=8.53 Hz, 1H) 7.12 (d, J=15.56 Hz, 1H) 6.73-6.82 (m, 2H) 4.86-4.90 (m, 1H) 4.04 (s, 3H) 3.20-3.25 (m, 1H) 3.18 (s, 3H) 3.05-3.14 (m, 1H) ppm. LCMS (ESI) m/z: 599.2 [M+H]$^+$. Analytical HPLC RT: 6.81 min (Method D).

Example 274

(S,E)-4-(2-(3-(5-chloro-2-(1H-tetrazol-1-yl)phenyl)acrylamido)-3-(6,7-dihydro-5H-pyrazolo[5,1-b][1,3]oxazin-2-yl)propanamido)benzoic acid

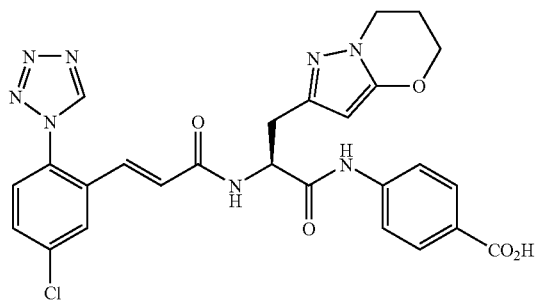 [SMILES: O=C(/C=C/c1cc(Cl)ccc1-n1cnnn1)N[C@@H](Cc1cc2n(n1)CCCO2)C(=O)Nc1ccc(C(=O)O)cc1]

274A. (S)-2-(tert-butoxycarbonylamino)-3-(6,7-dihydro-5H-pyrazolo[5,1-b][1,3]oxazin-2-yl)propanoic acid: The title compound was prepared according the procedures described in 272E, by replacing 272C with 6,7-dihydro-5H-pyrazolo[5,1-b][1,3]oxazine-2-carbaldehyde, which was prepared according to a literature procedure (A. M. Venkatesan, et al., *J. Med. Chem.*, 2006, 49, 4623-4637), in 272D. LC-MS (ESI) m/z: 312.2 (M+H)$^+$.

Example 274: The title compound was synthesized following the procedure described in Example 3. $^1$H NMR (400 MHz, MeOD/CD$_3$CN) δ: 9.35 (s, 1H) 7.99 (s, 1H) 7.94-7.98 (m, 2H) 7.61-7.69 (m, 3H) 7.52-7.57 (m, 1H) 7.09 (d, J=15.56 Hz, 1H) 6.73 (d, J=15.56 Hz, 1H) 5.47 (s, 1H) 4.70-4.84 (m, 1H) 4.24-4.32 (m, 2H) 4.01-4.08 (m, 2H) 3.03-3.13 (m, 1H) 2.90-3.00 (m, 1H) 2.14-2.26 (m, 2H) ppm. LCMS (ESI) m/z: 563.3 (M+H)$^+$. Analytical HPLC RT: 6.321 min (Method D).

Example 275

(S,E)-4-(2-(3-(5-chloro-2-(1H-tetrazol-1-yl)phenyl)acrylamido)-3-(1-(methoxycarbonyl)azetidin-3-yl)propanamido)benzoic acid

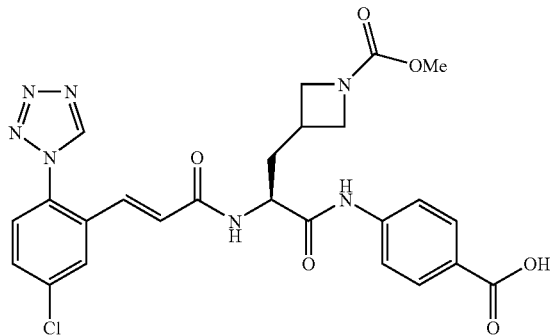 [SMILES: COC(=O)N1CC(C[C@H](NC(=O)/C=C/c2cc(Cl)ccc2-n2cnnn2)C(=O)Nc2ccc(C(=O)O)cc2)C1]

Example 275 was prepared from Example 229 as previously described for Example 223, but substituting methyl chloroformate for acetyl chloride. $^1$H NMR (400 MHz, MeOD) δ: 9.42 (1H, s), 7.83-7.96 (3H, m), 7.54-7.68 (3H, m), 7.47 (1H, d, J=8.59 Hz), 7.05 (1H, d, J=15.66 Hz), 6.69 (1H, d, J=15.41 Hz), 4.44-4.58 (1H, m), 3.91-4.03 (2H, m), 3.55-3.68 (2H, m), 3.52 (3H, s), 2.67 (1H, br. s.), 2.06-2.15 (1H, m), 1.93-2.02 (1H, m) ppm. LCMS m/z 554.4 [M+H]$^+$. Analytical HPLC RT: 6.45 min (Method D).

Example 276

(S,E)-4-(2-(3-(5-chloro-2-(1H-tetrazol-1-yl)phenyl)acrylamido)-3-(1-(methoxycarbonyl)piperidin-4-yl)propanamido)benzoic acid

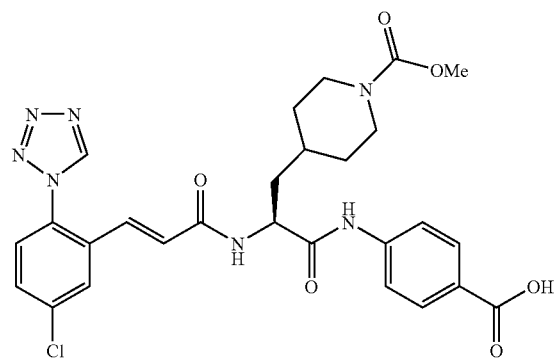 [SMILES: COC(=O)N1CCC(C[C@H](NC(=O)/C=C/c2cc(Cl)ccc2-n2cnnn2)C(=O)Nc2ccc(C(=O)O)cc2)CC1]

Example 276 was prepared from Example 230 in a similar manner as described in Example 275. $^1$H NMR (400 MHz, MeOD) δ: 9.42 (1H, s), 7.82-7.96 (3H, m), 7.55-7.66 (3H, m), 7.44-7.51 (1H, m), 7.04 (1H, d, J=15.66 Hz), 6.69 (1H, d, J=15.66 Hz), 4.56-4.64 (1H, m), 3.93-4.07 (3H, m), 3.57 (3H, s), 2.71 (2H, br. s.), 1.66 (3H, t, J=7.07 Hz), 1.52 (1H, br. s.), 0.83-1.19 (2H, m) ppm. LCMS m/z 582.4 [M+H]$^+$. Analytical HPLC RT: 6.93 min (Method D).

Example 277

(S,E)-4-(3-(1-acetylazetidin-3-yl)-2-(3-(5-chloro-2-(1H-tetrazol-1-yl)phenyl)acrylamido)propanamido)benzoic acid

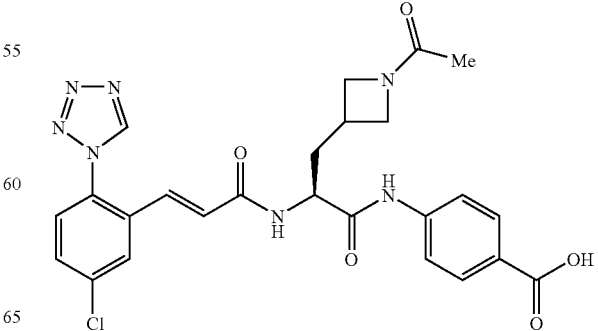

Example 277 was prepared from Example 229 in a similar manner as described for Example 223. ¹H NMR (400 MHz, MeOD) δ: 9.54 (1H, s), 7.98-8.04 (3H, m), 7.65-7.77 (3H, m), 7.56-7.61 (1H, m), 7.17 (1H, d, J=15.66 Hz), 6.81 (1H, dd, J=15.54, 6.69 Hz), 4.62-4.69 (1H, m), 4.30 (1H, ddd, J=16.55, 8.46, 8.34 Hz), 4.03-4.13 (1H, m), 3.88-3.97 (1H, m), 3.70 (1H, ddd, J=18.82, 9.98, 6.06 Hz), 2.75-2.85 (1H, m), 2.23 (1H, ddd, J=14.02, 8.34, 5.68 Hz), 2.06-2.17 (1H, m), 1.85 (3H, s) ppm. LCMS m/z 538.4 [M+H]⁺. Analytical HPLC RT: 8.05 min (Method D).

Example 278

(S,E)-4-(3-(1-acetylpiperidin-4-yl)-2-(3-(5-chloro-2-(1H-tetrazol-1-yl)phenyl)acrylamido)propanamido)benzoic acid

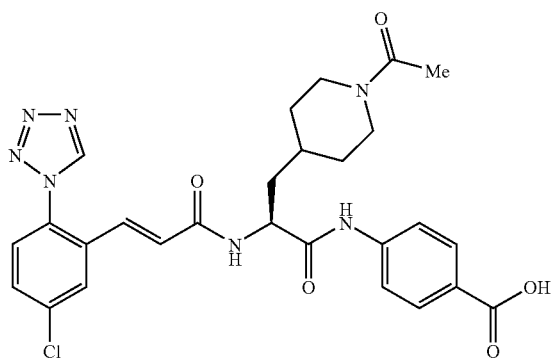 [SMILES: CC(=O)N1CCC(C[C@H](NC(=O)/C=C/c2cc(Cl)ccc2-n2cnnn2)C(=O)Nc2ccc(C(=O)O)cc2)CC1]

Example 278 was prepared from Example 230 in a similar manner as described for Example 223. ¹H NMR (400 MHz, MeOD) δ: 9.54 (1H, s), 7.98 (3H, d, J=8.59 Hz), 7.66-7.74 (3H, m), 7.53-7.65 (1H, m), 7.16 (1H, d, J=15.41 Hz), 6.80 (1H, dd, J=15.66, 3.54 Hz), 4.72 (1H, t, J=7.33 Hz), 4.52 (1H, d, J=11.87 Hz), 3.93 (1H, d, J=13.64 Hz), 3.02-3.18 (1H, m), 2.54-2.69 (1H, m), 2.10 (3H, s), 1.62-1.93 (5H, m), 1.08-1.38 (2H, m) ppm. LCMS m/z 566.3 [M+H]⁺. Analytical HPLC RT: 8.39 min (Method D).

Example 279

4-((2S)-2-((E)-3-(5-chloro-2-(1H-tetrazol-1-yl)phenyl)acrylamido)-3-(piperidin-3-yl)propanamido)benzoic acid, Diastereomer A

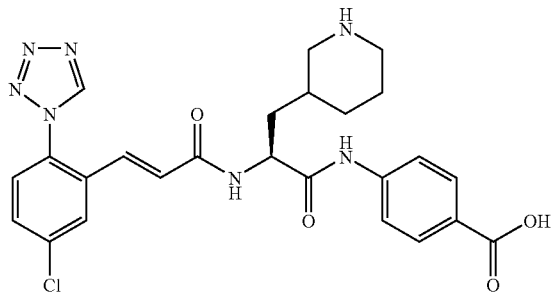 [SMILES: O=C(/C=C/c1cc(Cl)ccc1-n1cnnn1)N[C@@H](CC1CCCNC1)C(=O)Nc1ccc(C(=O)O)cc1]

Example 279 was isolated from Example 228 by chiral preparative separation using Regis Whelk-01, 250×30 mm ID; mobile phase: 30% Ethanol/70% Heptane/0.1% DEA/ 0.1% TFA. ¹H NMR (400 MHz, MeOD) δ: 9.44 (1H, s), 7.82-7.93 (3H, m), 7.55-7.65 (3H, m), 7.46-7.53 (1H, m), 7.07 (1H, d, J=15.66 Hz), 6.67 (1H, d, J=15.41 Hz), 4.64-4.71 (1H, m), 3.27-3.33 (1H, m), 2.76-2.86 (1H, m), 2.57-2.66 (1H, m), 1.95-2.09 (1H, m), 1.71-1.89 (3H, m), 1.25 (2H, m), 0.85 (2H, m) ppm. LCMS m/z 524.4 [M+H]⁺. Analytical HPLC RT: 4.27 min (Method C). Chiral analytical HPLC (RegisWhelk-01(R,R), 250×4.6 mm ID; mobile phase: 30% EtOH, 70% Heptane, 0.1% DEA, 0.1% TFA; Flow 1 mL/min) RT: 18.73 min. % de=95.6.

Example 280

4-((2S)-2-((E)-3-(5-chloro-2-(1H-tetrazol-1-yl)phenyl)acrylamido)-3-(piperidin-3-yl)propanamido)benzoic acid, Diastereomer B

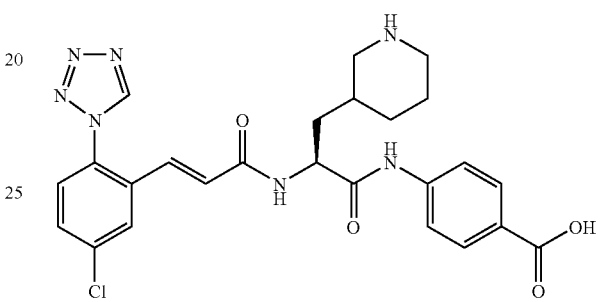

Example 280 was isolated from Example 228 by chiral preparative separation using Regis Whelk-01, 250×30 mm ID; mobile phase: 30% Ethanol/70% Heptane/0.1% DEA/ 0.1% TFA. ¹H NMR (400 MHz, MeOD) δ: 9.44 (1H, s), 7.82-7.93 (3H, m), 7.55-7.65 (3H, m), 7.46-7.53 (1H, m), 7.07 (1H, d, J=15.66 Hz), 6.67 (1H, d, J=15.41 Hz), 4.64-4.71 (1H, m), 3.27-3.33 (1H, m), 2.76-2.86 (1H, m), 2.57-2.66 (1H, m), 1.95-2.09 (1H, m), 1.81-1.89 (1H, m), 1.71-1.79 (2H, m), 1.55-1.71 (2H, m), 1.21 (2H, dt, J=11.87, 7.33 Hz) ppm. LCMS m/z 524.4 [M+H]⁺. Analytical HPLC RT: 4.17 min (Method C). Chiral analytical HPLC (RegisWhelk-01(R, R), 250×4.6 mm ID; mobile phase: 30% EtOH, 70% Heptane, 0.1% DEA, 0.1% TFA; Flow 1 mL/min) RT: 23.74 min. % de=96.6.

Example 281

(E)-4-(2-(3-(5-chloro-2-(1H-tetrazol-1-yl)phenyl)acrylamido)-3-(3-(morpholine-4-carbonyl)phenyl)propanamido)benzoic acid

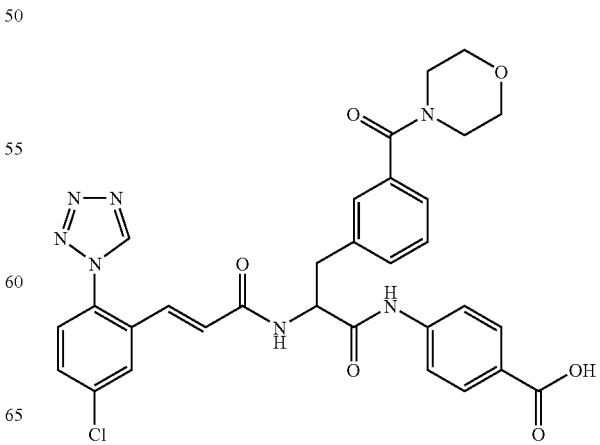

Example 281 was prepared according to the procedure employed for Example 3. ¹H NMR (400 MHz, DMSO-d₆) δ: 10.529 (s, 1H), 9.84 (s, 1H), 8.67 (d, J=7.7 Hz, 1H), 7.93 (d, J=3.3 Hz, 1H), 7.90 (d, J=8.2 Hz, 2H), 7.72-7.66 (m, 4H), 7.36 (d, J=4.6 Hz, 2H), 7.29 (s, 1H), 7.23 (m, 1H), 6.833 (s, 2H), 4.82 (m, 1H), 3.57 (bs, 2H), 3.13 (bm, 1H), 2.95 (m, 1H) ppm. LCMS m/z: 630.3 [M+H].⁺ Analytical HPLC RT: 5.588 (Method C, 8 min gradient).

Example 282

(R,E)-4-(3-(tert-butylthio)-2-(3-(5-chloro-2-(1H-tetrazol-1-yl)phenyl)acrylamido)propanamido)benzoic acid

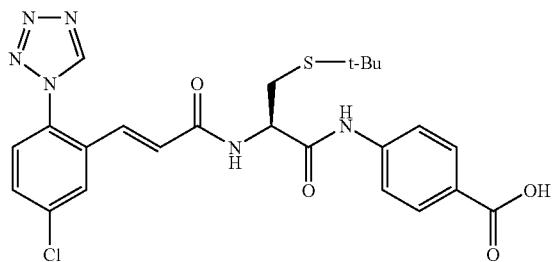 [SMILES: CC(C)(C)SC[C@H](NC(=O)/C=C/c1cc(Cl)ccc1-n1cnnn1)C(=O)Nc1ccc(C(=O)O)cc1]

Example 282 was prepared from commercially available starting materials according to the procedure of Example 3. ¹H NMR (400 MHz, DMSO-d₆) δ: 9.87 (s, 1H), 7.95-7.88 (m, 3H), 7.74-7.72 (m, 4H), 6.91 (s, 2H), 4.69 (m, 1H), 2.95 (m, 1H), 2.85 (m, 1H), 1.27 (s, 9H) ppm. LCMS m/z: 529.3 [M+H].⁺ Analytical HPLC RT: 6.571 min (Method C, 8 min gradient).

Example 283

4-((2S)-2-((E)-3-(5-chloro-2-(1H-tetrazol-1-yl)phenyl)acrylamido)-3-(pyrrolidin-3-yl)propanamido)benzoic acid

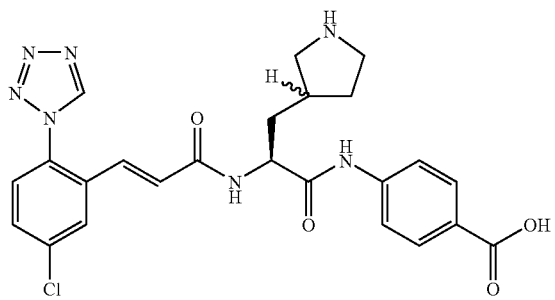 [SMILES: O=C(/C=C/c1cc(Cl)ccc1-n1cnnn1)N[C@@H](CC1CCNC1)C(=O)Nc1ccc(C(=O)O)cc1]

Example 283 was prepared from commercially available starting materials according to the procedure of Example 228. ¹H NMR (400 MHz, DMSO-d₆) δ: 10.57 (d, J=8.2 Hz, 1H), 9.88 (s, 1H), 8.70-8.51 (bm, 2H), 7.95-7.90 (m, 3H), 7.80-7.66 (m, 4H), 6.92 (s, 1H), 4.59 (m, 1H), 3.40-2.59 (m, 3H), 2.80 (m, 1H), 2.22-1.87 (m, 2H), 1.85 (m, 1H), 1.81 (m, 1H) ppm. LCMS m/z: 510.2 [M+H]⁺. Analytical HPLC RT: 4.220 min (Method C, 8 min gradient).

Example 284

(E)-4-(2-(3-(5-chloro-2-(1H-tetrazol-1-yl)phenyl)acrylamido)-3-(1H-pyrrolo[2,3-b]pyridin-3-yl)propanamido)benzoic acid, TFA salt

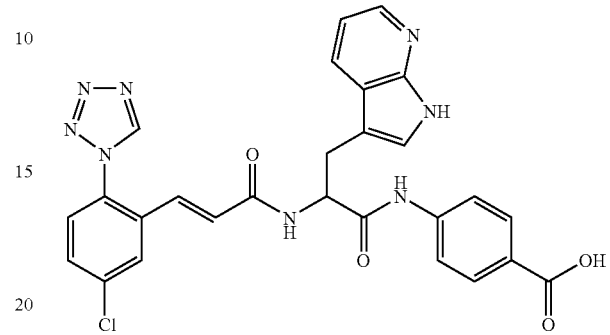

Example 284 was prepared according to the procedure described for Example 238 starting from commercially available Boc-DL-7-Azatrytophan. LCMS m/z: 557.3 [M+H]⁺. ¹H NMR (400 MHz, DMSO-d₆) δ: 11.45 (1H, br. s.), 10.51 (1 H, s), 9.85 (1H, s), 8.59 (1H, d, J=7.83 Hz), 8.17 (1H, dd, J=4.67, 1.39 Hz), 8.07 (1H, d, J=7.07 Hz), 7.93 (1H, d, J=2.02 Hz), 7.88 (2H, d, J=8.59 Hz), 7.65-7.78 (4H, m), 7.28 (1H, d, J=2.27 Hz), 7.03 (1H, dd, J=7.83, 4.55 Hz), 6.82-6.95 (2H, m), 4.82 (1H, d, J=5.81 Hz), 3.22 (1H, dd, J=14.53, 5.94 Hz), 3.02-3.13 (1H, m) ppm. Analytical HPLC RT: 4.70 min (Method C, 8 min gradient).

Example 285

(E)-4-(2-(3-(5-chloro-2-(1H-tetrazol-1-yl)phenyl)acrylamido)-3-(1-methyl-1H-indol-3-yl)propanamido)benzoic acid

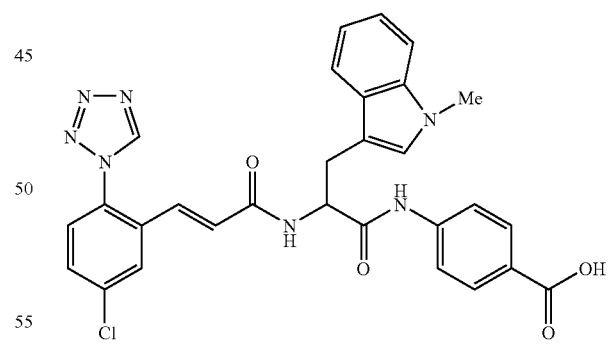

Example 285 was prepared according to the procedure described for Example 238 starting from commercially available Boc-1-Methyl-DL-tryptophan. LCMS m/z: 570.3 [M+H]⁺. ¹H NMR (400 MHz, DMSO-d₆) δ: 9.85 (1H, s), 8.55 (1H, d, J=7.83 Hz), 7.92-7.95 (1H, m), 7.88 (2H, d, J=8.84 Hz), 7.63-7.79 (5H, m), 7.35 (1H, d, J=8.08 Hz), 7.08-7.17 (2H, m), 6.99 (1H, t, J=7.07 Hz), 6.82-6.94 (2H, m), 4.76-4.85 (1H, m), 3.72 (3H, s), 3.21 (1H, d, J=15.16 Hz), 3.02-3.12 (1H, m) ppm. Analytical HPLC RT: 6.62 min (Method C, 8 min gradient).

Example 286

(S,E)-4-(2-(3-(5-chloro-2-(1H-tetrazol-1-yl)phenyl)acrylamido)-4-(2-morpholinoethylamino)-4-oxobutanamido)benzoic acid, Trifluoroacetic acid salt

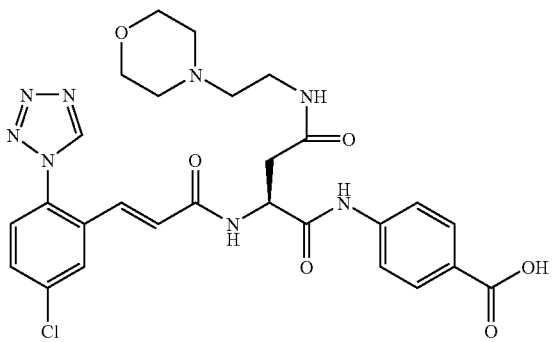 [SMILES: O=C(/C=C/c1cc(Cl)ccc1-n1cnnn1)N[C@@H](CC(=O)NCCN1CCOCC1)C(=O)Nc1ccc(C(=O)O)cc1]

Example 286 was prepared according to the procedures described for Example 243 starting from commercially available 2-morpholinoethanamine LCMS m/z: 598.4 [M+H]+. 1H NMR (400 MHz, METHANOL-d3) δ: 9.57 (1H, s), 7.97-8.03 (3H, m), 7.65-7.72 (3H, m), 7.59-7.64 (1H, m), 7.12-7.20 (1H, m), 6.80-6.87 (1H, m), 4.72 (1H, t, J=6.37 Hz), 3.99-4.11 (2H, m), 3.57-3.80 (6H, m), 3.35-3.41 (1H, m), 3.13-3.26 (3H, m), 2.96-3.08 (2H, m) ppm. Analytical HPLC RT: 4.15 min (Method C, 8 min gradient).

Example 287

(S,E)-4-(2-(3-(5-chloro-2-(1H-tetrazol-1-yl)phenyl)acrylamido)-4-oxo-4-(phenylamino)butanamido)benzoic acid

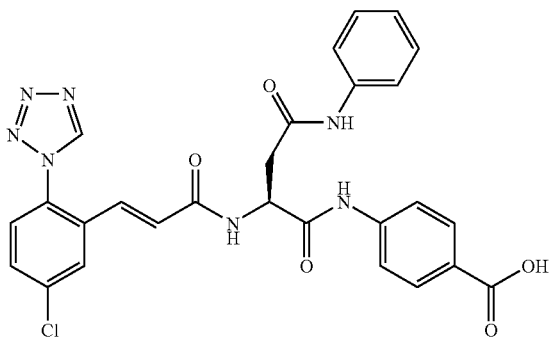 [SMILES: O=C(/C=C/c1cc(Cl)ccc1-n1cnnn1)N[C@@H](CC(=O)Nc1ccccc1)C(=O)Nc1ccc(C(=O)O)cc1]

Example 287 was prepared according to the procedures described for Example 243 starting from commercially available aniline. LCMS m/z: 560.4 [M+H]+. 1H NMR (400 MHz, DMSO-d6) δ: 12.72 (1H, br. s.), 10.48 (1H, s), 10.02 (1H, s), 9.87 (1H, s), 8.64 (1H, d, J=7.47 Hz), 7.95-8.00 (1H, m), 7.88 (2H, d, J=8.35 Hz), 7.70-7.78 (4H, m), 7.56 (2H, d, J=7.91 Hz), 7.28 (2H, t, J=7.69 Hz), 7.03 (1H, t, J=7.25 Hz), 6.84-6.94 (2H, m), 4.86-4.96 (1H, m), 2.85-2.95 (1H, m), 2.74-2.84 (1H, m) ppm. Analytical HPLC RT: 5.80 min (Method C, 8 min gradient).

Examples 288 to 301

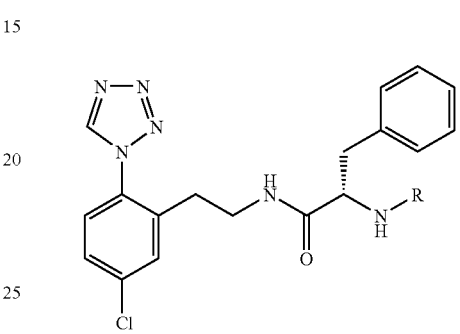

General Procedure (Coupling with carboxylic acids): A solution of amine 66B (27.8 mg, 0.068 mmol) and DIPEA (0.057 mL, 0.34 mmol, 5 eq.) in DMF (0.750 mL) was added to a Wheaton vial (16×100) containing the appropriate carboxylic acid (1.25 eq.), EDC (16 mg, 0.085 mmol, 1.25 eq.), and HOBt hydrate (11.5 mg, 0.085 mmol, 1.25 eq.) in DMF (0.375 mL). The tubes were placed on Bohdan Miniblock XT and agitated at 400 rpm on an Innova platform shaker overnight. The samples were diluted with MeOH (0.250 mL), purified by reversed phase preparative HPLC (ACN/H2O/TFA), and product fractions were concentrated.

General Procedure (Coupling with acid chlorides): A solution of amine 66B (27.8 mg, 0.068 mmol) and DIPEA (0.071 mL, 0.41 mmol, 6 eq.) in THF (0.60 mL) was added to a Wheaton vial (16×100) containing the appropriate acid chloride (0.12 mmol) in THF (0.40 mL). The tubes were placed on Bohdan Miniblock XT and agitated at 400 rpm on an Innova platform shaker overnight. The samples were diluted with MeOH (0.250 mL), purified by reversed phase preparative HPLC (ACN/H2O/TFA), and product fractions were concentrated.

| Example # | Structure | HPLC (Method C, 4 min Run) | [M + H]+ |
|---|---|---|---|
| 288 | ![structure] | 2.17 | 558.8 |

-continued

| Example # | Structure | HPLC (Method C, 4 min Run) | [M + H]+ |
|---|---|---|---|
| 289 | 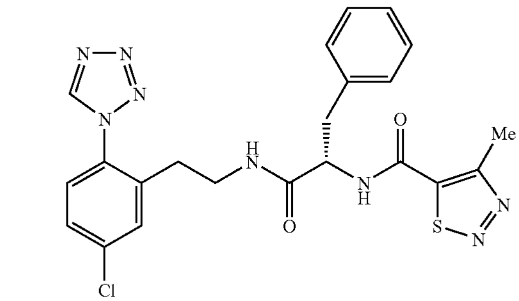 [SMILES: Cc1nnsc1C(=O)N[C@@H](Cc1ccccc1)C(=O)NCCc1cc(Cl)ccc1-n1cnnn1] | 2.13 | 496.8 |
| 290 | 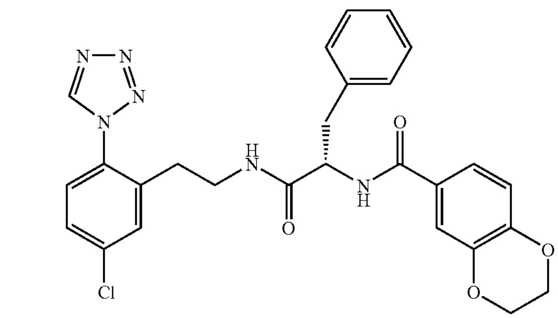 [SMILES: O=C(N[C@@H](Cc1ccccc1)C(=O)NCCc1cc(Cl)ccc1-n1cnnn1)c1ccc2c(c1)OCCO2] | 2.25 | 532.8 |
| 291 | 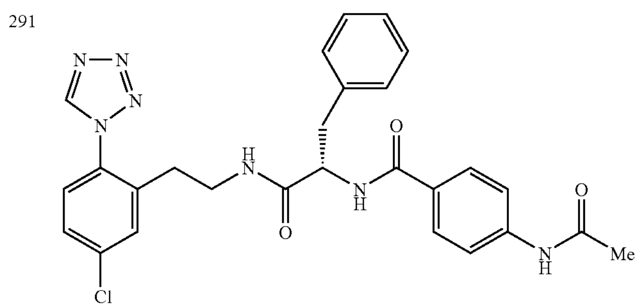 | 1.92 | 531.85 |
| 292 | 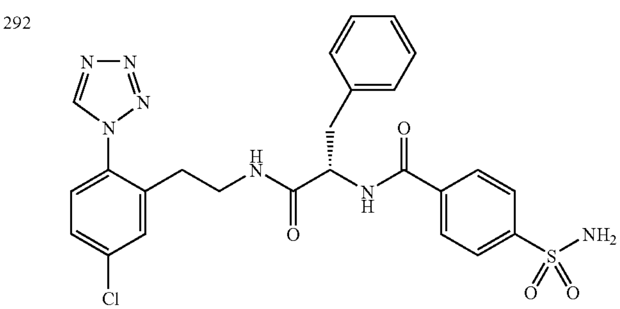 | 1.91 | 553.8 |
| 293 | 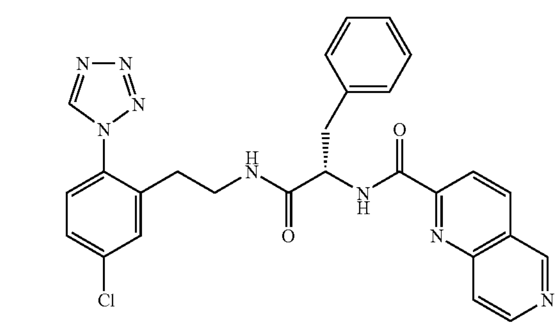 [SMILES: O=C(N[C@@H](Cc1ccccc1)C(=O)NCCc1cc(Cl)ccc1-n1cnnn1)c1ccc2cnccc2n1] | 2.13 | 526.8 |

-continued

| Example # | Structure | HPLC (Method C, 4 min Run) | [M + H]+ |
|---|---|---|---|
| 294 | 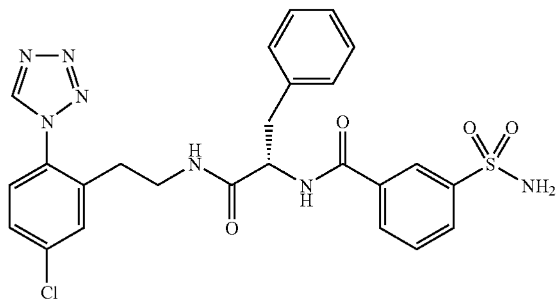 [SMILES: NS(=O)(=O)c1cccc(C(=O)N[C@@H](Cc2ccccc2)C(=O)NCCc2cc(Cl)ccc2-n2cnnn2)c1] | 1.92 | 553.8 |
| 295 | 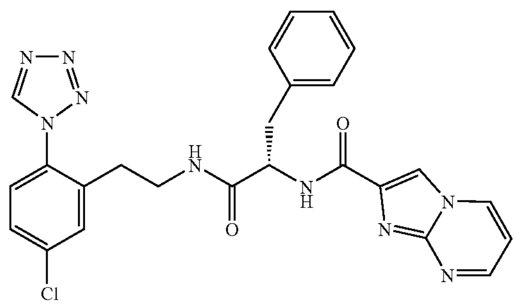 [SMILES: O=C(N[C@@H](Cc1ccccc1)C(=O)NCCc1cc(Cl)ccc1-n1cnnn1)c1cn2cccnc2n1] | 1.81 | 515.8 |
| 296 | 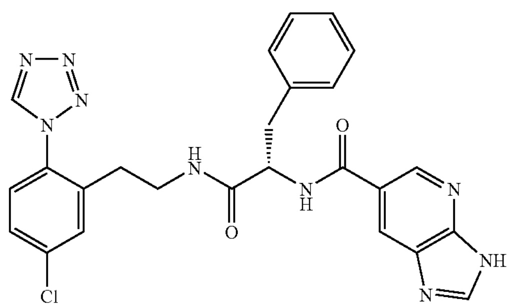 [SMILES: O=C(N[C@@H](Cc1ccccc1)C(=O)NCCc1cc(Cl)ccc1-n1cnnn1)c1cnc2[nH]cnc2c1] | 1.65 | 515.8 |
| 297 | 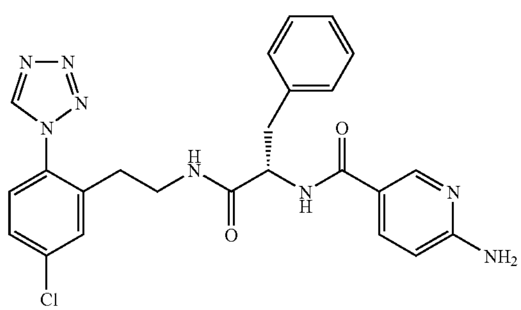 [SMILES: Nc1ccc(C(=O)N[C@@H](Cc2ccccc2)C(=O)NCCc2cc(Cl)ccc2-n2cnnn2)cn1] | 1.76 | 490.8 |
| 298 | 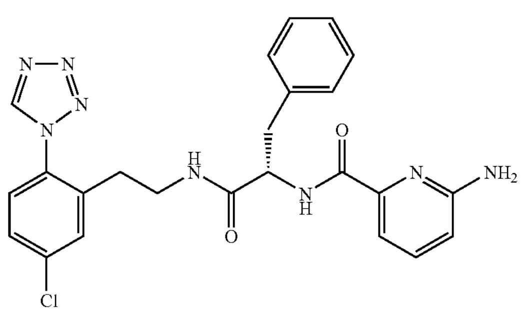 [SMILES: Nc1cccc(C(=O)N[C@@H](Cc2ccccc2)C(=O)NCCc2cc(Cl)ccc2-n2cnnn2)n1] | 2.03 | 490.8 |

-continued

| Example # | Structure | HPLC (Method C, 4 min Run) | [M + H]+ |
|---|---|---|---|
| 299 | 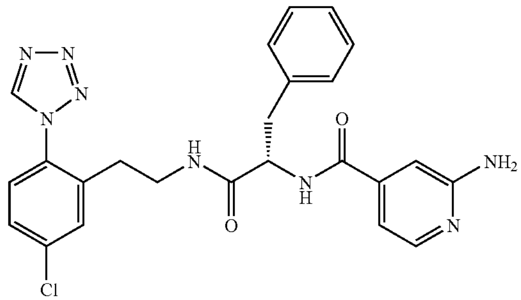 [SMILES: Nc1cc(C(=O)N[C@@H](Cc2ccccc2)C(=O)NCCc2cc(Cl)ccc2-n2cnnn2)ccn1] | 1.95 | 490.8 |
| 300 | 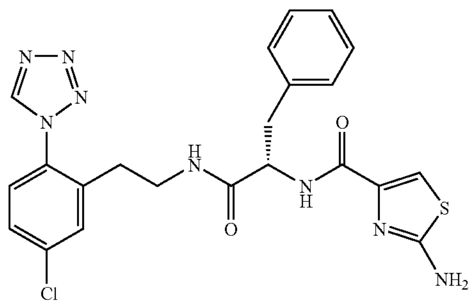 [SMILES: Nc1nc(C(=O)N[C@@H](Cc2ccccc2)C(=O)NCCc2cc(Cl)ccc2-n2cnnn2)cs1] | 2.01 | 496.88 |
| 301 | 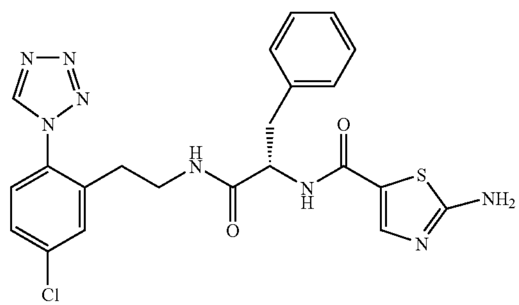 [SMILES: Nc1ncc(C(=O)N[C@@H](Cc2ccccc2)C(=O)NCCc2cc(Cl)ccc2-n2cnnn2)s1] | 1.88 | 496.88 |

Example 302

(S,E)-4-(2-(3-(5-chloro-2-(1H-tetrazol-1-yl)phenyl)acrylamido)-3-(1-methyl-1H-indazol-3-yl)propanamido)benzoic acid

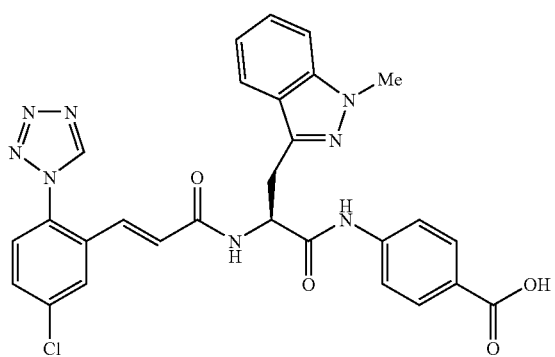 [SMILES: Cn1nc(C[C@H](NC(=O)/C=C/c2cc(Cl)ccc2-n2cnnn2)C(=O)Nc2ccc(C(=O)O)cc2)c2ccccc21]

302A: (S)-2-(benzyloxycarbonylamino)-3-(1-methyl-1H-indazol-3-yl)propanoic acid: To a of solution (±)-Methyl 2-benzyloxycarbonylamino-2-(dimethoxyphosphinyl)acetate (1.24 g, 3.75 mmol) was dissolved in DCM (30 mL) under nitrogen at −15° C. added DBU (0.52 mL, 3.43 mmol) was added. After 10 min, 1-methyl-1H-indazole-3-carbaldehyde (0.500 g, 3.12 mmol) in DCM (30 mL) was added drop wise and the complete mixture stirred overnight at rt. The mixture was diluted with EtOAc and washed with 5% aq. citric acid, and brine, then dried over anhydrous $Na_2SO_4$, filtered, and concentrated. Purification by flash chromatography (Isco; 40 g cartridge; 0-100% EtOAc in hexane gradient) gave a clear, colorless oil. This material was diluted with MeOH (50 mL), treated with (+)-1,2-Bis((2S,5S)-2,5-diethylphospholano)-benzene(cyclooctadiene)rhodium(1)tetrafluoroborate (0.082 g, 0.125 mmol), and subjected with a hydrogen atmosphere (55 psi pressure) for 48 h. The reaction mixture was filtered through a plug of Celite® and the filtrate concentrated. The ester was hydrolyzed by dissolution in THF/water (40 mL, 1:1) and treatment with lithium hydroxide monohydrate (0.39 g, 9.36 mmol). After 3 h, the organics were concentrated. The remaining aqueous layer was acidified with 1.0N HCl solution and extracted with EtOAc (3×40 mL). The combined organic extract was washed with water, brine, dried over sodium sulfate, filtered, and concentrated to give (S)-2-(benzyloxycarbonylamino)-3-(1-methyl-1H-indazol-3-yl)propanoic acid 302A (0.916 g, 83%) as an off-white solid. LCMS m/z 354.3 [M+H]+. 1H NMR (400 MHz, DMSO-d$_6$) δ: 12.76 (1H, br. s.), 7.76 (1H, d, J=8.35 Hz), 7.64 (1H, d, J=8.35 Hz), 7.56 (1H, d, J=8.79 Hz), 7.22-7.40 (6H, m), 7.09 (1H, t, J=7.25 Hz), 4.91-5.01 (2H, m), 4.41 (1H, td, J=8.68, 5.05 Hz), 3.97 (3H, s), 3.20-3.41 (2H, m) ppm.

Example 302: 1-propanephosphonic acid cyclic anhydride (0.124 mL, 0.42 mmol) was added to 302A (0.100 g, 0.28 mmol), tert-butyl 4-aminobenzoate (0.055 g, 0.28 mmol), and DIPEA (0.148 mL, 0.85 mmol) in EtOAc (5 mL) at 0° C. The mixture stirred at rt overnight. The reaction was washed with 1.0M HCl solution, water, brine, organics separated, dried over sodium sulfate, filtered and concentrated. The crude material was purified by flash chromatography (ISCO; 4 g column; (100% hexane/0% EtOAC to 0% hexane over 16 min) to give an oil (87 mg, 58%). This material was dissolved in MeOH, treated with 10% Pd/C, and placed under a hydrogen atmosphere (55 psi) for 2 h. The suspension was filtered through a plug of Celite® and filtrate concentrated. The amine, (E)-3-(5-chloro-2-(1H-tetrazol-1-yl)phenyl)acrylic acid (0.071 g, 0.28 mmol), and DIPEA (0.148 mL, 0.85 mmol) in EtOAc (5 mL) were treated with 1-propanephosphonic acid cyclic anhydride (0.124 mL, 0.42 mmol) at 0° C. After 2 h, the mixture was washed with 1.0M HCl solution, water, brine, organics separated, dried over sodium sulfate, filtered and concentrated. The crude material was purified by flash chromatography (ISCO; 4 g column; 100% hexane/0% EtOAc to 0% hexane over 16 min) The residue was treated with 50% TFA/DCM for 2 h and then purified by prep HPLC to give 302 (22 mg, 13%) as a white solid. LCMS m/z: 571.4 [M+H]$^+$. $^1$H NMR (400 MHz, DMSO-d$_6$) δ 12.71 (1H, br. s.), 10.52 (2H, s), 9.85 (2H, s), 8.58 (2H, d, J=7.83 Hz), 7.85-7.94 (3H, m), 7.64-7.82 (5H, m), 7.54 (1H, d, J=8.59 Hz), 7.34 (1H, t, J=7.20 Hz), 7.07 (1H, t, J=7.20 Hz), 6.80-6.95 (2H, m), 4.95-5.05 (1H, m), 3.95 (3H, s), 3.41 (1H, dd, J=14.53, 5.94 Hz), 3.26-3.34 (1H, m) ppm. Analytical HPLC RT: 6.21 min (Method C, 8 min gradient).

Example 303

(S,E)-4-(2-(3-(5-chloro-2-(1H-tetrazol-1-yl)phenyl)acrylamido)-4-phenylbutanamido)benzoic acid

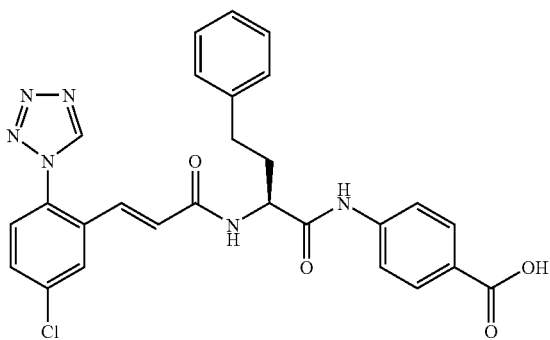 [SMILES: O=C(/C=C/c1cc(Cl)ccc1-n1cnnn1)N[C@@H](CCc1ccccc1)C(=O)Nc1ccc(C(=O)O)cc1]

Example 303 was prepared according to the procedures described for Example 238 starting from commercially available (S)-2-(tert-butoxycarbonylamino)-4-phenylbutanoic acid. LCMS m/z 531.4 [M+H]$^+$. $^1$H NMR (400 MHz, DMSO-d$_6$) δ: 12.71 (1H, br. s.), 10.46 (1H, s), 9.87 (1H, s), 8.63 (1H, d, J=7.70 Hz), 7.96-8.00 (1H, m), 7.88 (2H, d, J=8.79 Hz), 7.68-7.79 (4H, m), 7.24-7.30 (2H, m), 7.14-7.22 (3H, m), 6.86-6.97 (2H, m), 4.51-4.59 (1H, m), 2.55-2.75 (2H, m), 2.00-2.11 (1H, m), 1.87-2.00 (1H, m) ppm. Analytical HPLC RT: 6.62 min (Method C, 8 min gradient).

Example 304

4-((2S)-2-((E)-3-(5-chloro-2-(1H-tetrazol-1-yl)phenyl)acrylamido)-3-(1-(methoxycarbonyl)piperidin-3-yl)propanamido)benzoic acid

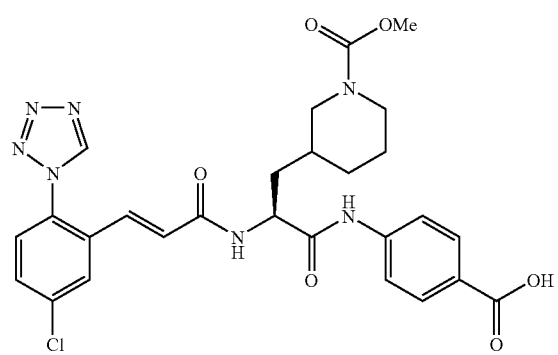 [SMILES: COC(=O)N1CCCC(C[C@H](NC(=O)/C=C/c2cc(Cl)ccc2-n2cnnn2)C(=O)Nc2ccc(C(=O)O)cc2)C1]

304A. (2S)-methyl 2-(benzyloxycarbonylamino)-3-(piperidin-3-yl)propanoate, HCl: The title compound was prepared in Example 228 as previously described in Examples 153 and 210, substituting tert-butyl 3-formylpiperidine-1-carboxylate for tert-butyl 4-(2-oxoethyl)piperidine-1-carboxylate and substituting 50% 1-propanephosphoric acidcyclic anhydride in EtOAc as coupling agent. Deprotection with excess 4N HCl in dioxane and DCM afforded the title compound (1.3 g, 117%) as a yellow foam; LCMS m/z 321.3 [M+H]$^+$.

304B. (2S)-2-(benzyloxycarbonylamino)-3-(1-(methoxycarbonyl)piperidin-3-yl)propanoic acid: To 304A (0.135 g, 0.421 mmol) in DCM (1 mL), cooled in ice bath, was added Hunig'sBase (0.221 mL, 1.264 mmol), followed by methyl chloroformate (0.065 mL, 0.843 mmol) and the reaction was stirred for 18 h. The solvent was removed and the residue was dissolved in THF (3 mL) and water (3 mL), cooled in ice bath, and lithium hydroxide hydrate (0.053 g, 1.264 mmol) was added. After 3 h, the reaction was partitioned with EtOAc (50 mL) and 1N HCl (5 mL). The organic layer was washed with brine (10 mL) and dried (MgSO$_4$) to afford 0.145 g (91%) yellow oil. LCMS m/z 365.3 [M+H]$^+$.

304C. methyl 3-((S)-2-(benzyloxycarbonylamino)-3-(4-(tert-butoxycarbonyl)phenylamino)-3-oxopropyl)piperidine-1-carboxylate: To 304B (0.145 g, 0.39 mmol) and tert-butyl 4-aminobenzoate (0.081 g, 0.421 mmol) in EtOAc (4 mL), cooled in ice bath, was added Hunig'sBase (0.221 mL, 1.264 mmol) and 50% 1-propanephosphoric acid cyclic anhydride in EtOAc (0.179 mL, 0.632 mmol). After 2 h, the reaction was concentrated and purified by silica gel chromatography to afford still impure 304C (0.132 g, 50%) as a yellow solid. LCMS (ESI) m/z: 340.5 [M+H]$^+$.

304D. methyl 3-((S)-2-amino-3-(4-(tert-butoxycarbonyl)phenylamino)-3-oxopropyl)piperidine-1-carboxylate: 304C (0.1 g, 0.185 mmol) was hydrogenated in the presence of 10% Pd/C at 50 psi for 1 h. Filtered through Celite® and concentrated to 0.11 g crude white foam. LCMS (ESI) m/z: 406.4 [M+H]$^+$.

Example 304: The title compound was prepared from 304D as previously described in Example 223, substituting 50% 1-propanephosphoric acid cyclic anhydride in EtOAc as coupling agent. $^1$H NMR (400 MHz, MeOD) δ: 7.78 (1H, d, J=2.27 Hz), 6.14-6.30 (3H, m), 5.95 (2H, d, J=8.84 Hz), 5.88-5.93 (1H, m), 5.80-5.86 (1H, m), 5.37-5.45 (1H, m), 5.04 (1H, d, J=15.66 Hz), 2.88-3.02 (1H, m), 2.12-2.34 (2H, m), 1.89 (3H, br. s.), 1.13 (1H, br. s.), 0.94 (1H, br. s.), 0.20 (1H, d, J=13.64 Hz), −0.16-0.06 (4H, m), −0.37-1-0.26 (1H, m), −0.58-1-0.45 (1H, m) ppm. LCMS (ESI) m/z: 582.4 [M+H]$^+$. Analytical HPLC: RT=6.85 and 6.95 min for diastereomers (Method D).

Example 305

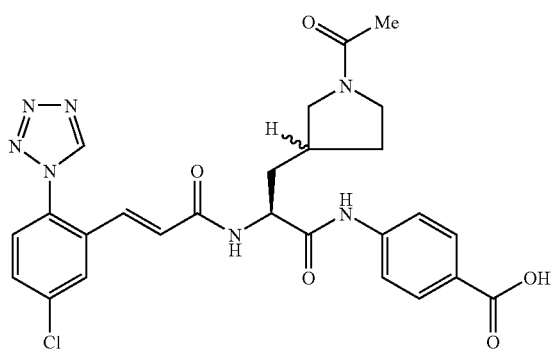 [SMILES: CC(=O)N1CCC(C[C@H](NC(=O)/C=C/c2cc(Cl)ccc2-n2cnnn2)C(=O)Nc2ccc(C(=O)O)cc2)C1]

Example 305 was prepared from Example 283 by treatment with acetyl chloride in pyridine. $^1$H NMR (400 MHz, DMSO-d$_6$) δ: 10.54 (d, 1H), 9.87 (s, 1H), 8.59 (m, 1H), 7.99-7.88 (m, 3H), 7.74 (m, 3H), 6.91 (d, 2H), 6.00 (m, 1H), 5.40 (m, 1H), 4.62-4.54 (bm, 1H), 3.86-3.30 (m, 3H), 3.41-3.33 (m, 1H), 2.95-2.60 (m, 2H), 1.90 (s, 3H), 1.83-1.77 (m, 2H) ppm. LCMS m/z: 552.3 [M+H]$^+$. Analytical HPLC RT: 5.126 min (Method C, 8 min gradient).

Example 306

4-((2S)-2-((E)-3-(5-chloro-2-(1H-tetrazol-1-yl)phenyl)acrylamido)-3-(1-(methoxycarbonyl)pyrrolidin-3-yl)propanamido)benzoic acid

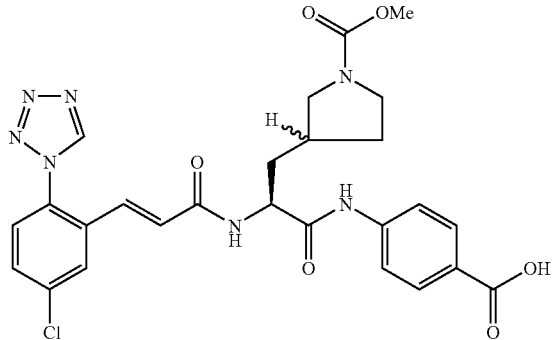 [SMILES: COC(=O)N1CCC(C[C@H](NC(=O)/C=C/c2cc(Cl)ccc2-n2cnnn2)C(=O)Nc2ccc(C(=O)O)cc2)C1]

Example 306 was prepared from Example 283 by treatment with methylchloroformate in pyridine. $^1$H NMR (400 MHz, DMSO-d$_6$) δ: 10.53 (d, 1H), 9.87 (s, 1H), 8.60 (d, J=7.6 Hz, 1H), 7.96 (m, 1H), 7.91-7.69 (m, 2H0, 7.78-7.69 (m, 3H), 6.92 (s, 2H), 4.57 (m, 1H), 3.56 (ss, 3H), 3.47-3.17 (m, 2H), 3.35 (m, 1H), 3.01-2.76 (m, 1H), 2.25 (m, 1H), 1.96 (m, 1H), 1.80 (m, 2H), 1.58 (m, 1H) ppm. LCMS m/z: 568.3 [M+H].$^+$ Analytical HPLC RT: 5.716 min (Method C, 8 min gradient).

Example 307

4-((2S)-3-(1-benzoylpyrrolidin-3-yl)-2-((E)-3-(5-chloro-2-(1H-tetrazol-1-yl)phenyl)acrylamido)propanamido)benzoic acid

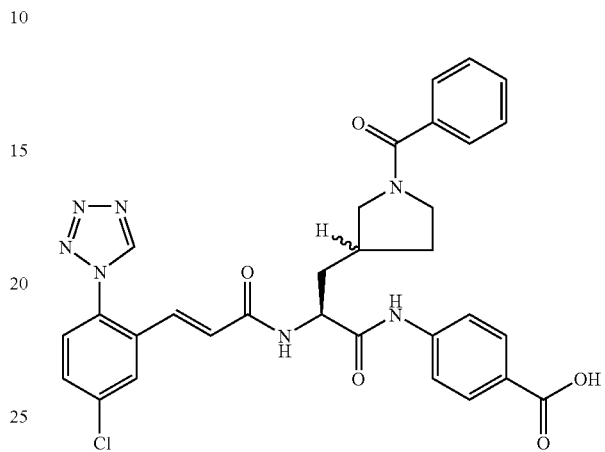

Example 307 was prepared from Example 283 by treatment with benzoylchloride in pyridine. $^1$H NMR (400 MHz, DMSO-d$_6$) δ: 10.59 (m, 1H), 9.86 (s, 1H), 8.64-8.51 (m, 1H), 7.96-7.88 (m, 5H), 7.75-7.70 (m, 5H), 7.60-7.37 (m, 2H), 6.92 (m, 2H), 4.62 (m, 1H), 3.86-3.11 (m, 4H), 2.33-2.18 (m, 1H), 2.20-1.57 (m, 3H) ppm. LCMS m/z: 614.3 [M+H].$^+$ Analytical HPLC RT: 5.880 min (Method C, 8 min gradient).

Example 308

(E)-4-(2-(3-(5-chloro-2-(1H-tetrazol-1-yl)phenyl)acrylamido)-3-(1-(2-hydroxyethyl)-5-methyl-1H-pyrazol-3-yl)propanamido)benzoic acid

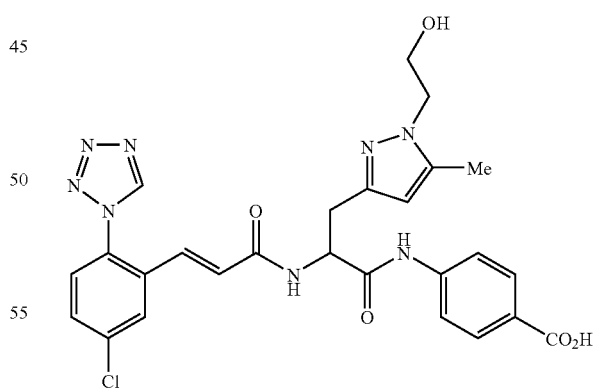

308A. 1-(2-(tert-butyldimethylsilyloxy)ethyl)-5-methyl-1H-pyrazole-3-carbaldehyde: To a solution of NaH (0.40 g, 9.99 mmol) in DMF (15 mL) at 0° C. was added 5-methyl-1H-pyrazole-3-carbaldehyde (1.0 g, 9.08 mmol) in DMF (5 mL) dropwise. The solution was stirred for 15-20 min, then (2-bromoethoxy)-tert-butyldimethylsilane (2.34 mL, 10.90 mmol) was added dropwise. The reaction was stirred overnight allowing the temperature to slowly rise to room temperature. The reaction was quenched with water and extracted with EtOAc (3×), then the combined organic layers were washed with brine, dried over sodium sulfate, filtered, and condensed to a brown oil which was purified by silica gel column chromatography (0-10% EtOAc in hexane) to provide 308A (1.55 g, 63.5%). LCMS m/z: 269.3 (M+H)+.

308B. (E)-methyl 2-(tert-butoxycarbonylamino)-3-(1-(2-(tert-butyldimethylsilyloxy)ethyl)-5-methyl-1H-pyrazol-3-yl)acrylate: Boc-alpha-phosphonoglycine trimethyl ester (2.06 g, 6.92 mmol) was dissolved in DCM (15 mL), and DBU (0.96 mL, 6.34 mmol) was added. The mixture was stirred for 10 min, followed by dropwise addition of a solution of 308A (1.55 g, 5.77 mmol) in DCM (15 mL) over 15-20 min. Stirring was continued at room temperature overnight. The reaction was diluted EtOAc, washed with 5% citric acid and brine, then dried over sodium sulfate, filtered, and condensed to a clear oil which was purified by silica gel column chromatography (0-25% EtOAc in hexane) to provide the olefin product (2.4 g, 95%). LCMS m/z: 440.3 (M+H)+.

308C. methyl 2-(tert-butoxycarbonylamino)-3-(1-(2-(tert-butyldimethylsilyloxy)ethyl)-5-methyl-1H-pyrazol-3-yl) propanoate: 308B (2.405 g, 5.47 mmol) was added to 10% Pd/C (0.240 g, 0.226 mmol) in methanol (30 mL). The solution was purged via vacuum and flushed with nitrogen three times, then stirred under 30 psi $H_2$ over the weekend. Catalyst was removed by filtration though a pad of Celite®, and washed with MeOH. The filtrate was evaporated to yield an oil, which was a 1:1 mixture of the desilylated alcohol and the desired product. This mixture was treated with TBDMS-Cl (0.495 g, 3.29 mmol) and imidazole (0.224 g, 3.29 mmol) in DMF (15 mL), and the resulting mixture was stirred at room temperature overnight followed by addition of a second aliquot of imidazole (0.224 g, 3.29 mmol). Stirring was continued for another 1.5-2 hours at room temperature then at 40° C. for 2 h. Additional TBDMS-Cl (0.495 g, 3.29 mmol) was added along with another equivalent of imidazole (0.448 g), and the reaction was allowed to stir at room temperature over 2 days. The reaction mixture was diluted with EtOAc, washed with water (3×) and brine, dried over anhydrous $Na_2SO_4$, filtered, and concentrated to a clear oil which was purified by silica gel column chromatography (0-100% EtOAc in hexane) to provide 308C (2.036 g, 4.61 mmols, 72.9%). LCMS m/z: 442.3 (M+H)+.

308D. 2-(tert-butoxycarbonylamino)-3-(1-(2-(tert-butyldimethylsilyloxy)ethyl)-5-methyl-1H-pyrazol-3-yl)propanoic acid: 308C (2.036 g, 4.61 mmol) was dissolved in THF (28 mL), and 1M lithium hydroxide (6.92 mL, 6.92 mmol) was added. The resulting mixture was stirred at room temperature for 1 hour, then neutralized by addition of 5% citric acid solution. Most of the THF was removed by rotovap, and the aqueous solution was extracted with EtOAc (3×). The combined extracts were washed with brine, dried over $Na_2SO_4$, filtered, and evaporated to provide 308D as a white solid (2.02 g). LCMS m/z: 428.3 (M+H)+.

308E. tert-butyl 4-(2-(tert-butoxycarbonylamino)-3-(1-(2-(tert-butyldimethylsilyloxy)ethyl)-5-methyl-1H-pyrazol-3-yl)propanamido)benzoate: To a 0° C. solution of 308D (0.181 g, 0.935 mmol) and tert-butyl 4-aminobenzoate (0.181 g, 0.935 mmol) in ethyl acetate (5 mL) was added Hunig'sBase (0.490 mL, 2.81 mmol) and a 50% w/w solution of T3P in EtOAc (0.397 mL, 1.403 mmol). The reaction was allowed to slowly assume room temperature and stirred overnight. Solvent was removed by evaporation and the crude product purified by silica gel column chromatography (0-100% EtOAc in hexane) to provide 309E (0.225 g, 39.9%). LCMS m/z: 603.5 (M+H)+.

308F. tert-butyl 4-(2-amino-3-(1-(2-hydroxyethyl)-5-methyl-1H-pyrazol-3-yl)propanamido)benzoate, HCl: To a solution of 308E (0.114 g, 0.189 mmol) in dioxane (1 mL) was added 4 N HCl in dioxane (1 mL). A white precipitate separated out of the initially clear solution within 30 min. The reaction mixture was stirred at room temperature overnight. Excess ether was added, and the white precipitate was collected by filtration and washed with ether to provide 308F (0.051 g, 0.120 mmol, 63.5%). Additional product was obtained by addition of a few drops of MeOH to the filtrate and evaporation to leave a clear oil. This oil was triturated with ether to provide additional product 308F (0.013 g, 16.2%) for a total of 79.7%. LCMS m/z: 389.3 (M+H)+.

308G. (E)-tert-butyl 4-(2-(3-(5-chloro-2-(1H-tetrazol-1-yl)phenyl)acrylamido)-3-(1-(2-hydroxyethyl)-5-methyl-1H-pyrazol-3-yl)propanamido)benzoate: 308F (0.063 g, 0.148 mmol) and (E)-2,5-dioxopyrrolidin-1-yl-3-(5-chloro-2-(1H-tetrazol-1-yl)phenyl)acrylate (0.052 g, 0.148 mmol) were dissolved in DMF (2 mL), and then DIPEA (0.129 mL, 0.741 mmol) was added. The mixture was stirred at room temperature overnight then diluted with EtOAc, washed with water (2×), 5% citric acid, and brine, dried over anhydrous $Na_2SO_4$, filtered and evaporated to provide 308G as a white solid, (0.079 g, 86%). LCMS m/z: 621.5 (M+H)+.

Example 308: 308G (0.040 g, 0.064 mmol) was taken up in DCM (0.5 mL) and TFA (0.500 mL) and stirred at room temperature for 1 hour. A drop of MeOH was added, and the solution was stripped via rotovap, then triturated with ether twice to yield a white solid. Purification by reverse phase HPLC (Method D) provided the title compound as a white solid (0.020 g, 53.9%). LCMS m/z: 565 (M+H)+. $^1$H NMR (500 MHz, DMSO-$d_6$) δ: 10.46 (1H, s) 9.86 (1H, s) 8.51 (1H, d, J=7.70 Hz) 7.95 (1H, s) 7.88 (2H, d, J=8.25 Hz) 7.66-7.78 (4H, m) 6.88 (2H, dd) 5.85 (1H, s) 4.72 (1H, dd) 3.95 (2H, t, J=5.77 Hz) 3.62 (2H, t, J=6.05 Hz) 2.93-3.00 (1H, m) 2.80-2.87 (1H, m) 2.19 (3H, s) ppm. Anal HPLC: RT: 3.066 min (Method A, 4 min gradient).

Table 1 below lists Factor XIa Ki values for representative examples of this invention measured in the Factor XIa assay described above.

TABLE 1

| Example Number | Factor XIa Ki (nM) |
| --- | --- |
| 1 | 139.7 |
| 3 | 40.52 |
| 5 | 67.85 |
| 8 | 1.98 |
| 9 | 45.56 |
| 11 | 4444 |
| 14 | 2961 |
| 15 | 291.5 |
| 21 | 104.9 |
| 30 | 12.65 |
| 31 | 1.38 |
| 36 | 33.91 |
| 43 | 1.61 |
| 45 | 33.41 |
| 50 | 1121 |
| 51 | 316.9 |
| 53 | 244.2 |
| 57 | 3567 |
| 66 | 1.56 |
| 83 | 63.85 |
| 92 | 53.91 |
| 97 | 532.9 |
| 99 | 1480 |
| 103 | 112 |
| 127 | 7797 |
| 129 | 67.88 |
| 133 | 671.5 |

TABLE 1-continued

| Example Number | Factor XIa Ki (nM) |
|---|---|
| 137 | 53.90 |
| 142 | 3855 |
| 149 | 6499 |
| 171 | 38.11 |
| 187 | 9369 |
| 196 | 8315 |
| 200 | 1317 |
| 204 | 27.65 |
| 206 | 19.51 |
| 216 | 65.93 |
| 231 | 44.42 |
| 238 | 4.66 |
| 248 | 2.41 |
| 249 | 6.09 |
| 251 | 16.23 |
| 252 | 16.15 |
| 253 | 19.30 |
| 254 | 3626 |
| 262 | 2328 |
| 282 | 32.54 |
| 286 | 481.5 |
| 295 | 9260 |
| 307 | 12.4 |

While the foregoing specification teaches the principles of the present invention, which examples provided for the purpose of illustration, it will be understood that thr practice of the invention encompasses all of the usual variations, adaptations and/or modifications as come within the scope of the following claims and their equivalents.

What is claimed is:

1. A compound of Formula (Ib) or (IIb):

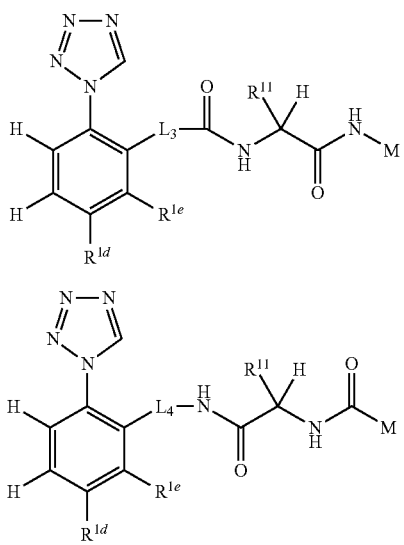

or a stereoisomer, a tautomer, or a pharmaceutically acceptable salt thereof, wherein:

$L_3$ is —$CH_2CH_2$—, —CH═CH—, —C≡C— or —S(O)$CH_2$—;

$L_4$ is —$CH_2CH_2$—, —CH═CH—, —C≡C—, —CONH—, or —COCH$_2$—;

M is —(CH$_2$)$_r$—C$_{3-10}$ carbocycle substituted with 0-3 $R^3$ or a —(CH$_2$)$_r$-5- to 12-membered heterocycle comprising: carbon atoms and 1-4 heteroatoms selected from the group consisting of N, NR$^{13}$, O, and S(O)$_p$, wherein said heterocycle is substituted with 0-3 $R^3$;

$R^{1d}$ is, independently at each occurrence, Cl or Me;

$R^{1e}$ is, independently at each occurrence, H or F;

$R^3$ is, independently at each occurrence, ═O, F, Cl, Br, I, OCF$_3$, CF$_3$, —(CH$_2$)$_r$CN, NO$_2$, —(CH$_2$)$_r$OR$^{3b}$, —(CH$_2$)$_r$SR$^{3b}$, —(CH$_2$)$_r$NR$^7$R$^8$, —(CH$_2$)$_r$NHC(O)NR$^8$R$^9$, —C(═NR$^8$)NR$^8$R$^9$, —(C═NH)NHOR$^{3b}$, —(CH$_2$)$_r$C(O)OR$^{3b}$, —C(O)C$_{1-4}$ alkyl, —SO$_2$NHR$^{3b}$, —SO$_2$NHCOR$^{3c}$, —SO$_2$NHCO$_2$R$^{3c}$, —CONHSO$_2$R$^{3c}$, —(CH$_2$)$_r$NR$^8$C(O)R$^{3b}$, —(CH$_2$)$_r$NR$^8$CO$_2$R$^{3c}$, —(CH$_2$)$_r$S(O)$_p$NR$^8$R$^9$, —(CH$_2$)$_r$NR$^8$S(O)$_p$R$^{3c}$, —NHSO$_2$CF$_3$, —S(O)R$^{3c}$, —S(O)$_2$R$^{3c}$, —(CH$_2$)$_r$OC(O)R$^{3b}$, —(CH$_2$)$_r$C(O)(CH$_2$)$_r$NR$^8$R$^9$, —(CH$_2$)$_r$OC(O)NR$^8$R$^9$, —NHCOCF$_3$, —CONHOR$^{3b}$, —(CH$_2$)$_r$P(O)(OH)$_2$, —(CH$_2$)$_r$P(O)(OC$_{1-4}$ alkyl)$_2$, C$_{1-4}$ haloalkyl, C$_{1-4}$ haloalkyloxy-, C$_{1-6}$ alkyl substituted by $R^{3e}$, C$_{2-6}$ alkenyl substituted by $R^{3e}$, C$_{1-6}$ alkynyl substituted by $R^{3e}$, C$_{3-6}$ cycloalkyl substituted by 0-1 $R^{3d}$, —(CH$_2$)$_r$—C$_{3-10}$ carbocycle substituted by 0-3 $R^{3d}$ or —(CH$_2$)$_r$-5- to 10-membered heterocycle comprising: carbon atoms and 1-4 heteroatoms selected from the group consisting of N, O, and S(O)$_p$, wherein said heterocycle is substituted with 0-3 $R^{3d}$;

alternately, when two $R^3$ groups are substituted on adjacent atoms, they can be taken together with the atoms to which they are attached to form a C$_{3-10}$ carbocycle substituted with 0-2 $R^{3d}$, or a 5- to 10-membered heterocycle comprising: carbon atoms and 1-4 heteroatoms selected from the group consisting of N, O, and S(O)$_p$, wherein said heterocycle is substituted with 0-2 $R^{3d}$;

$R^{3b}$ is, independently at each occurrence, H, C$_{1-6}$ alkyl substituted with 0-2 $R^{3d}$, C$_{2-6}$ alkenyl substituted with 0-2 $R^{3d}$, C$_{2-6}$ alkynyl substituted with 0-2 $R^{3d}$, —(CH$_2$)$_r$—C$_{3-10}$ carbocycle substituted with 0-3 $R^{3d}$, or —(CH$_2$)$_r$-5- to 10-membered heterocycle comprising: carbon atoms and 1-4 heteroatoms selected from the group consisting of N, O, and S(O)$_p$, wherein said heterocycle is substituted with 0-3 $R^{3d}$;

$R^{3c}$ is, independently at each occurrence, C$_{1-6}$ alkyl substituted with 0-2 $R^{3d}$, C$_{2-6}$ alkenyl substituted with 0-2 $R^{3d}$, C$_{2-6}$ alkynyl substituted with 0-2 $R^{3d}$, —(CH$_2$)$_r$C$_{3-10}$ carbocycle substituted with 0-3 $R^{3d}$, or —(CH$_2$)$_r$5- to 10-membered heterocycle comprising: carbon atoms and 1-4 heteroatoms selected from the group consisting of N, O, and S(O)$_p$, wherein said heterocycle is substituted with 0-3 $R^{3d}$;

$R^{3d}$ is, independently at each occurrence, ═O, F, Cl, Br, CN, NO$_2$, —(CH$_2$)$_r$NR$^7$R$^8$, —(CH$_2$)$_r$OR$^a$, —C(O)R$^a$, —C(O)OR$^a$, —OC(O)R$^a$, —NR$^8$C(O)R$^c$, —C(O)NR$^8$R$^9$, —S(O)$_2$NR$^8$R$^9$, —NR$^8$S(O)$_2$NR$^8$R$^9$, —NR$^8$S(O)$_2$R$^c$, —S(O)$_p$R$^c$, —(CF$_2$)$_r$CF$_3$, —(CH$_2$)$_r$P(O)(OH)$_2$, —(CH$_2$)$_r$P(O)(OC$_{1-4}$ alkyl)$_2$, C$_{1-6}$ alkyl substituted with 0-2 $R^e$, C$_{2-6}$ alkenyl substituted with 0-2 $R^e$, C$_{2-6}$ alkynyl substituted with 0-2 $R^e$, —(CH$_2$)$_r$—C$_{3-10}$ carbocycle substituted with 0-3 $R^d$, or —(CH$_2$)$_r$-5- to 10-membered heterocycle comprising: carbon atoms and 1-4 heteroatoms selected from the group consisting of N, O, and S(O)$_p$, wherein said heterocycle is substituted with 0-3 $R^d$;

$R^{3e}$ is, independently at each occurrence, —(CH$_2$)$_r$OR$^a$, F, ═O, CN, NO$_2$, —(CH$_2$)$_r$NR$^7$R$^8$, —C(O)R$^a$, —C(O)OR$^a$, —OC(O)R$^a$, —NR$^8$C(O)R$^c$, —C(O)NR$^8$R$^9$, —S(O)$_2$NR$^8$R$^9$, —NR$^8$S(O)$_2$NR$^8$R$^9$, —NR$^8$S(O)$_2$R$^c$, —S(O)$_p$R$^c$, —(CF$_2$)$_r$CF$_3$, —(CH$_2$)$_r$—C$_{3-10}$ carbocycle substituted with 0-3 $R^d$, or —(CH$_2$)$_r$-5- to 10-membered heterocycle comprising: carbon atoms and 1-4 heteroatoms selected from the group consisting of N, O, and S(O)$_p$, wherein said heterocycle is substituted with 0-3 R$^d$;

R$^7$ is, independently at each occurrence, H, C$_{1-6}$ alkyl, —(CH$_2$)$_n$—C$_{3-10}$ carbocycle, —(CH$_2$)$_n$-(5- to 10-membered heteroaryl), —C(O)R$^c$, —CHO, —C(O)$_2$R$^c$, —S(O)$_2$R$^c$, —CONR$^{81}$R$^c$, —OCONHR$^c$, —C(O)O—(C$_{1-4}$ alkyl)OC(O)—(C$_{1-4}$ alkyl), or —C(O)O—(C$_{1-4}$ alkyl)OC(O)—(C$_{6-10}$ aryl); wherein said alkyl, carbocycle, heteroaryl, and aryl are substituted with 0-2 R$^f$; wherein said heteroaryl comprises: carbon atoms and 1-4 heteroatoms selected from the group consisting of N, O, and S(O)$_p$;

R$^8$ is, independently at each occurrence, H, C$_{1-6}$ alkyl, —(CH$_2$)$_n$-phenyl, or —(CH$_2$)$_n$-5- to 10-membered heterocycle comprising: carbon atoms and 1-4 heteroatoms selected from the group consisting of N, O, and S(O)$_p$; wherein said alkyl, phenyl and heterocycle are optionally substituted with 0-2 R$^f$;

alternatively, R$^7$ and R$^8$, when attached to the same nitrogen, combine to form a 5- to 10-membered heterocycle comprising: carbon atoms and 0-3 additional heteroatoms selected from the group consisting of N, O, and S(O)$_p$, wherein said heterocycle is substituted with 0-2 R$^f$;

R$^9$ is, independently at each occurrence, H, C$_{1-6}$ alkyl, or —(CH$_2$)$_n$-phenyl; wherein said alkyl and phenyl are optionally substituted with 0-2 R$^f$;

alternatively, R$^8$ and R$^9$, when attached to the same nitrogen, combine to form a 5- to 12-membered heterocycle comprising: carbon atoms and 0-2 additional heteroatoms selected from the group consisting of N, O, and S(O)$_p$, wherein said heterocycle is substituted with 0-2 R$^d$;

R$^{11}$ is C$_{1-4}$ haloalkyl, —C(O)NR$^8$R$^9$, —CH$_2$C(O)NR$^8$R$^9$, —CH$_2$CH$_2$C(O)NR$^8$R$^9$, —C(O)R$^a$, —CH$_2$C(O)R$^a$, —CH$_2$CH$_2$C(O)R$^a$, —C(O)OR$^a$, —CH$_2$C(O)OR$^a$, —CH$_2$CH$_2$C(O)OR$^a$, C$_{1-6}$ alkyl substituted with 0-3 R$^{11c}$, C$_{2-6}$ alkenyl substituted with 0-3 R$^{11a}$, C$_{2-6}$ alkynyl substituted with 0-3 R$^{11a}$, —(CH$_2$)$_r$—C$_{3-10}$ carbocycle substituted with 0-3 R$^{11b}$, or —(CH$_2$)$_r$-5- to 10-membered heterocycle comprising: carbon atoms and 1-4 heteroatoms selected from the group consisting of N, O, and S(O)$_p$, wherein said heterocycle is substituted with 0-3 R$^{11b}$;

R$^{11a}$ is, independently at each occurrence =O, OR$^a$, SR$^a$, F, CF$_3$, CN, NO$_2$, —C(O)R$^a$, —C(O)OR$^a$, —NR$^7$R$^8$, —C(O)NR$^8$R$^9$, —NR$^8$C(O)R$^d$, —NR$^8$C(O)OR$^d$, —NR$^8$CHO, —S(O)$_p$NR$^8$R$^9$, —NR$^8$S(O)$_p$R$^d$, —S(O)$_p$R$^d$, C$_{1-4}$ alkyl, C$_{3-6}$ cycloalkyl, C$_{1-4}$ haloalkyl, C$_{1-4}$ haloalkyloxy-, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from the group consisting of N, O, and S(O)$_p$, and substituted with 0-3 R$^d$;

R$^{11b}$ is, independently at each occurrence, =O, =NR$^8$, ORE, —CH$_2$OR$^a$, F, Cl, Br, CN, NO$_2$, CF$_3$, OCF$_3$, OCHF$_2$, —C(CH$_3$)$_2$OR$^a$, —C(O)R$^a$, —C(O)OR$^a$, —NR$^7$R$^8$, —C(O)NR$^8$R$^9$, —NR$^7$C(O)R$^b$, —NR$^8$C(O)$_2$R$^c$, —S(O)$_p$NR$^8$R$^9$, —NR$^8$S(O)$_p$R$^d$, —S(O)$_p$R$^d$, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyloxy-, —(CH$_2$)$_r$C$_{3-10}$ carbocycle substituted with 0-3 R$^d$, or —(CH$_2$)$_r$5- to 10-membered heterocycle comprising carbon atoms and 1-4 heteroatoms selected from the group consisting of N, O, and S(O)$_p$, and substituted with 0-3 R$^d$;

alternately, when two R$^{11b}$ groups are substituents on adjacent atoms they may be taken together with the atoms to which they are attached to form a 5- to 7-membered heterocycle comprising carbon atoms and 1-4 heteroatoms selected from the group consisting of N, O, and S(O)$_p$ and substituted with 0-2 R$^g$;

R$^{11c}$ is, independently at each occurrence =O, OR$^a$, SR$^a$, F, CF$_3$, CN, NO$_2$, —NR$^7$R$^8$, —NR$^8$C(O)R$^d$, —NR$^8$C(O)OR$^d$, —NR$^8$CHO, —NHC(NH$_2$)=N(NO$_2$), —C(=NR$^8$)NR$^8$R$^9$, —S(O)$_p$NR$^8$R$^9$, —NR$^8$S(O)$_p$R$^d$, —S(O)$_p$R$^d$, C$_{1-4}$ alkyl, C$_{3-6}$ cycloalkyl, C$_{1-4}$ haloalkyl, C$_{1-4}$ haloalkyloxy-, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from the group consisting of N, O, and S(O)$_p$, and substituted with 0-3 R$^d$;

R$^{13}$ is, independently at each occurrence, H, C$_{1-4}$ alkyl, CO$_2$R$^a$, or benzyl;

R$^a$ is, independently at each occurrence, H, CF$_3$, C$_{1-6}$ alkyl, —(CH$_2$)$_r$C$_{3-7}$ cycloalkyl, —(CH$_2$)$_r$—C$_{6-10}$ aryl, or —(CH$_2$)$_r$-5- to 10-membered heterocycle comprising carbon atoms and 1-4 heteroatoms selected from the group consisting of N, O, and S(O)$_p$, wherein said cycloalkyl, aryl or heterocycle groups are optionally substituted with 0-2 R$^f$;

R$^b$ is, independently at each occurrence, CF$_3$, OH, C$_{1-4}$ alkoxy, C$_{1-6}$ alkyl, —(CH$_2$)$_r$—C$_{3-10}$ carbocycle substituted with 0-2 R$^d$, or —(CH$_2$)$_r$5- to 10-membered heterocycle comprising: carbon atoms and 1-4 heteroatoms selected from the group consisting of N, O, and S(O)$_p$ and substituted with 0-3 R$^d$;

R$^c$ is, independently at each occurrence, CF$_3$, C$_{1-6}$ alkyl substituted with 0-2 R$^f$, C$_{3-6}$ cycloalkyl substituted with 0-2 R$^f$, C$_{6-10}$ aryl, 5- to 10-membered heteroaryl, (C$_{6-10}$ aryl)-C$_{1-4}$ alkyl, or (5- to 10-membered heteroaryl)-C$_{1-4}$ alkyl, wherein said aryl is substituted with 0-3 R$^f$ and said heteroaryl comprises: carbon atoms and 1-4 heteroatoms selected from the group consisting of N, O, and S(O)$_p$ and substituted with 0-3 R$^f$;

R$^d$ is, independently at each occurrence, H, =O, =NR$^8$, OR$^a$, F, Cl, Br, I, CN, NO$_2$, —NR$^7$R$^8$, —C(O)R$^a$, —C(O)OR$^a$, —OC(O)R$^a$, —NR$^8$C(O)R$^c$, —C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl substituted with 0-2 R$^e$, C$_{2-6}$ alkenyl substituted with 0-2 R$^e$, or C$_{2-6}$ alkynyl substituted with 0-2 R$^e$;

R$^e$ is, independently at each occurrence, =O, OR$^a$, F, Cl, Br, I, CN, NO$_2$, —NR$^7$R$^8$, —C(O)R$^a$, —C(O)OR$^a$, —NR$^8$C(O)R$^c$, —C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

R$^f$ is, independently at each occurrence, H, =O, —(CH$_2$)$_r$OR$^g$, F, Cl, Br, I, CN, NO$_2$, —NR$^g$R$^g$, —C(O)R$^g$, —C(O)OR$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, —(CH$_2$)$_n$-phenyl, or —(CH$_2$)$_n$-5- to 10-membered heterocycle comprising carbon atoms and 1-4 heteroatoms selected from the group consisting of N, O, and S(O)$_p$;

R$^g$ is, independently at each occurrence, H, C$_{1-6}$ alkyl, or —(CH$_2$)$_n$-phenyl;

n, at each occurrence, is selected from the group consisting of 0, 1, 2, 3, and 4;

p, at each occurrence, is selected from the group consisting of 0, 1, and 2; and r, at each occurrence, is selected from the group consisting of 0, 1, 2, 3, and 4.

2. A compound according to claim 1, wherein:

M is substituted with 0-3 $R^3$ and selected from the group consisting of: cyclohexyl, phenyl, benzyl, pyridyl, pyrimidinyl, pyrazinyl, furanyl, thienyl, pyrrolyl, pyrazolyl, imidazolyl, oxazolyl, thiazolyl, thiadiazolyl, indolyl, indolinyl, isoindolyl, indazolyl, benzofuranyl, benzothienyl, benzimidazolyl, benzothiazolyl, benzoisothiazolyl, benzoxazolyl, benzisoxazolyl, tetrahydroisoquinolinyl, dihydroisoquinolinyl, isoquinolinyl, tetrahydroquinolinyl, dihydroquinolinyl, quinolinyl,

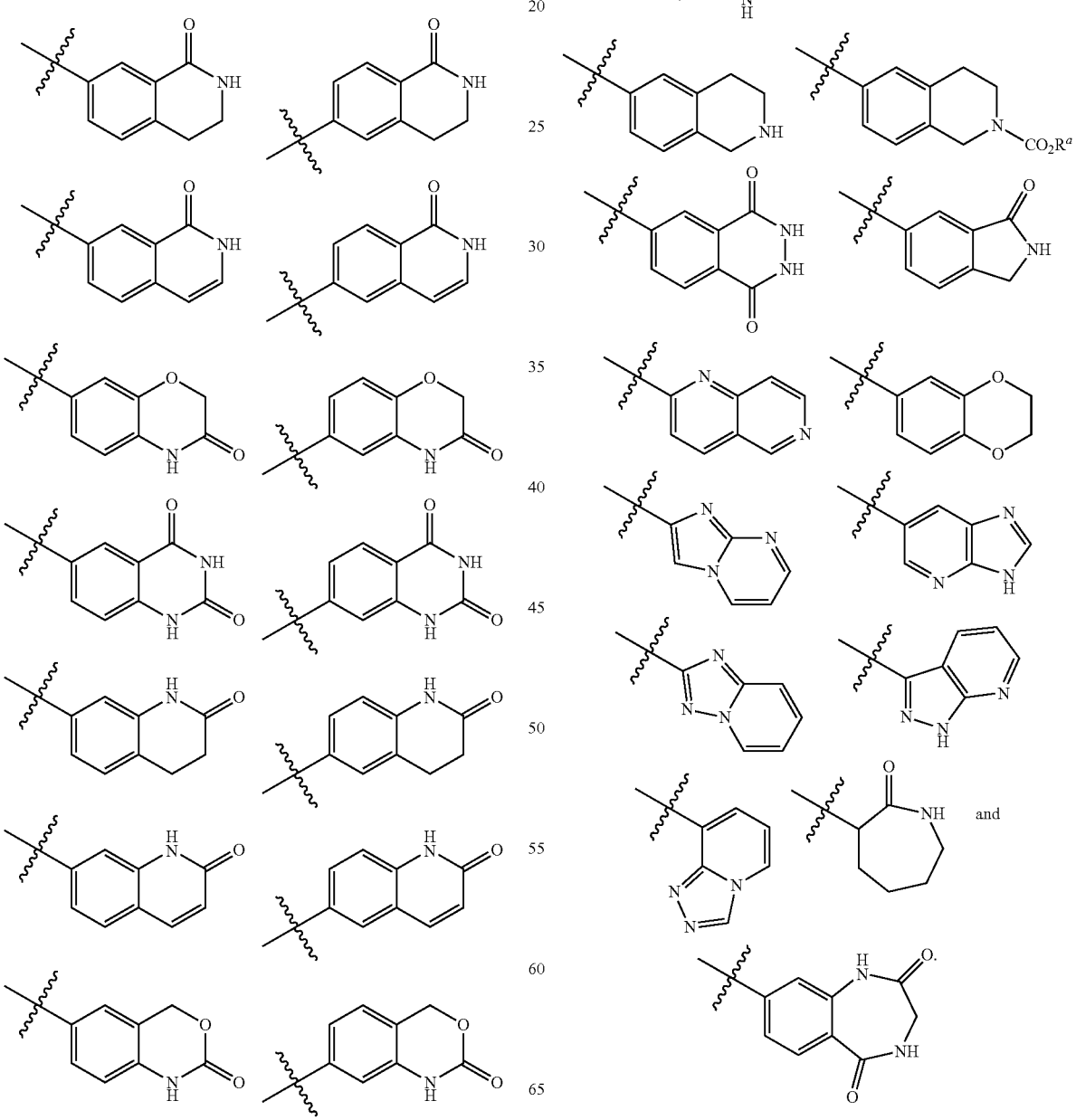

3. A compound according to claim 1, wherein:

R$^{11}$ is C$_{1-4}$ haloalkyl, —CH$_2$C(O)NR$^8$R$^9$, —CH$_2$CH$_2$C(O)NR$^8$R$^9$, —CH$_2$C(O)R$^a$, —CH$_2$CH$_2$C(O)R$^a$, —CH$_2$C(O)OR$^a$, —CH$_2$CH$_2$C(O)OR$^a$, C$_{1-6}$ alkyl substituted with 0-2 R$^{11c}$, —(CH$_2$)$_r$—C$_{3-7}$ cycloalkyl substituted with 0-2 R$^{11b}$, —(CH$_2$)$_r$-indanyl substituted with 0-2 R$^{11b}$, —(CH$_2$)$_r$-indenyl substituted with 0-2 R$^{11b}$, —(CH$_2$)$_r$-phenyl substituted with 0-2 R$^{11b}$, —(CH$_2$)$_r$-naphthyl substituted with 0-2 R$^{11b}$, or —(CH$_2$)$_r$-5- to 10-membered heterocycle comprising carbon atoms and 1-4 heteroatoms selected from the group consisting of N, O, and S(O)$_p$, wherein said heterocycle is substituted with 0-2 R$^{11b}$.

4. A compound according to claim 2, wherein:

M is substituted with 0-2 R$^3$ and is selected from the group consisting of: cyclohexyl, phenyl, pyridyl, pyrimidinyl, thienyl, thiazolyl,

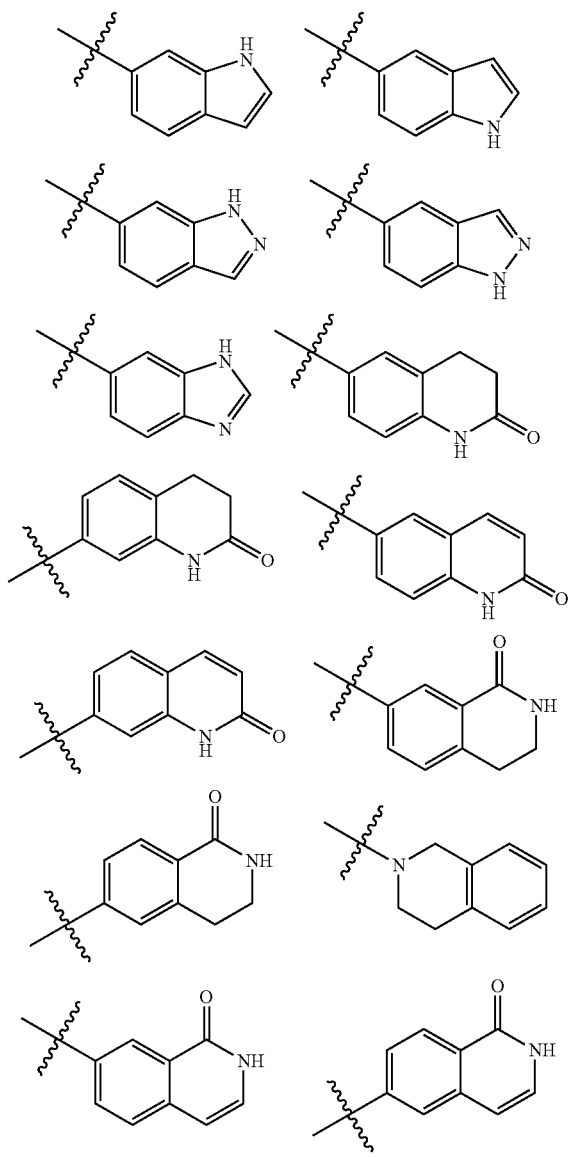

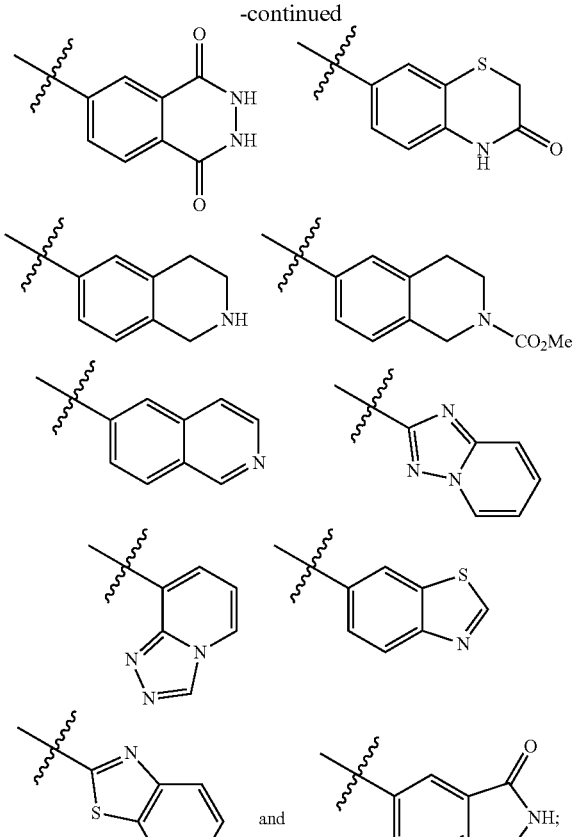

and

R$^3$ is, independently at each occurrence, =O, F, Cl, Br, OCF$_3$, CF$_3$, CN, —CH$_2$CN, OR$^{3b}$, —CH$_2$OR$^{3b}$, SR$^{3b}$, —CH$_2$SR$^{3b}$, —C(O)C$_{1-4}$ alkyl, —OC(O)(C$_{1-4}$ alkyl), —(CH$_2$)$_r$C(O)OR$^{3b}$, —(CH$_2$)$_r$NR$^7$R$^8$, C(O)NR$^8$R$^9$, —CH$_2$C(O)NR$^8$R$^9$, —NR$^8$C(O)R$^{3b}$, —CH$_2$NR$^8$C(O)R$^{3b}$, —NR$^8$CO$_2$R$^{3c}$, —CH$_2$NR$^8$CO$_2$R$^{3c}$, —(C=NH)NH$_2$, —(C=NH)NHOH, —NHC(O)NR$^8$R$^9$, —CH$_2$NHC(O)NR$^8$R$^9$, —SO$_2$NR$^8$R$^9$, —NHSO$_2$R$^{3c}$, —CONHSO$_2$R$^{3c}$, P(O)(OH)$_2$, P(O)(OC$_{1-4}$ alkyl)$_2$, —CH$_2$P(O)(OH)$_2$, —CH$_2$P(O)(OC$_{1-4}$ alkyl)$_2$, C$_{1-4}$ alkyl, or —(CH$_2$)$_r$-5- to 6-membered heterocycle comprising: carbon atoms and 1-4 heteroatoms selected from the group consisting of N, O, and S(O)$_p$, wherein said heterocycle is substituted with 0-1 R$^{3d}$.

5. A compound according to claim 1, wherein:

R$^3$ is, independently at each occurrence, F, Cl, Me, CF$_3$, OCF$_3$, OH, CN, NH$_2$, CO$_2$H, CO$_2$Me, CO$_2$Et, CO$_2$(t-Bu), —CH$_2$CO$_2$H, —CH$_2$CO$_2$Me, —CH$_2$CO$_2$Et, —CONH$_2$, —CON(Me)$_2$, —NHCOMe, —NHCO$_2$Me, —NHCO$_2$(t-Bu), —(C=NH)NH$_2$, —(C=NH)NHOH, —CONHCH$_2$CO$_2$H, —CON(Me)CH$_2$CO$_2$H, —CONH(CH$_2$)$_2$CO$_2$H, —CONH(CH$_2$)$_2$CO$_2$Et, —CONH(CH$_2$)$_3$CO$_2$H, —CONH(CH$_2$)$_3$CO$_2$Et, —CO$_2$(CH$_2$)$_2$NEt$_2$, —CO$_2$(CH$_2$)$_3$N(Bu)$_2$, —CH$_2$NHCO$_2$Me, —NHCO$_2$(CH$_2$)$_2$OMe, —CH$_2$NHCO$_2$(CH$_2$)$_2$OMe, —NHCO$_2$(CH$_2$)$_2$CO$_2$H, —NHCO$_2$(CH$_2$)$_2$CO$_2$Me, —NHCO$_2$(CH$_2$)$_2$CO$_2$Et, —NHCO$_2$(CH$_2$)$_2$N(Me)$_2$, —CH$_2$NHCONH$_2$, —NHCONH(CH$_2$)$_2$CO$_2$H, —NHCONH(CH$_2$)$_2$CO$_2$Me, —NHCONH(CH$_2$)$_3$CO$_2$Me, —CONHSO$_2$Me, —SO$_2$NH$_2$, P(O)(OH)$_2$, P(O)(OEt)$_2$, —CH$_2$P(O)(OH)$_2$, —CH$_2$P(O)(OEt)$_2$, 2-(N,N-dimethylaminomethyl)-phenyl, pyridin-4-yl-, tetrahydrofuran-2-yl-methoxy-, 2-oxo-piperidin-1-yl, 2-oxo-2H-pyridin-1-yl, imidazol-1-yl, 2-(N,N-dimethylaminomethyl)-imidazol-1-yl, 1,2,4-triazol-1-yl, tetrazol-1-yl, tetrazol-5-yl,
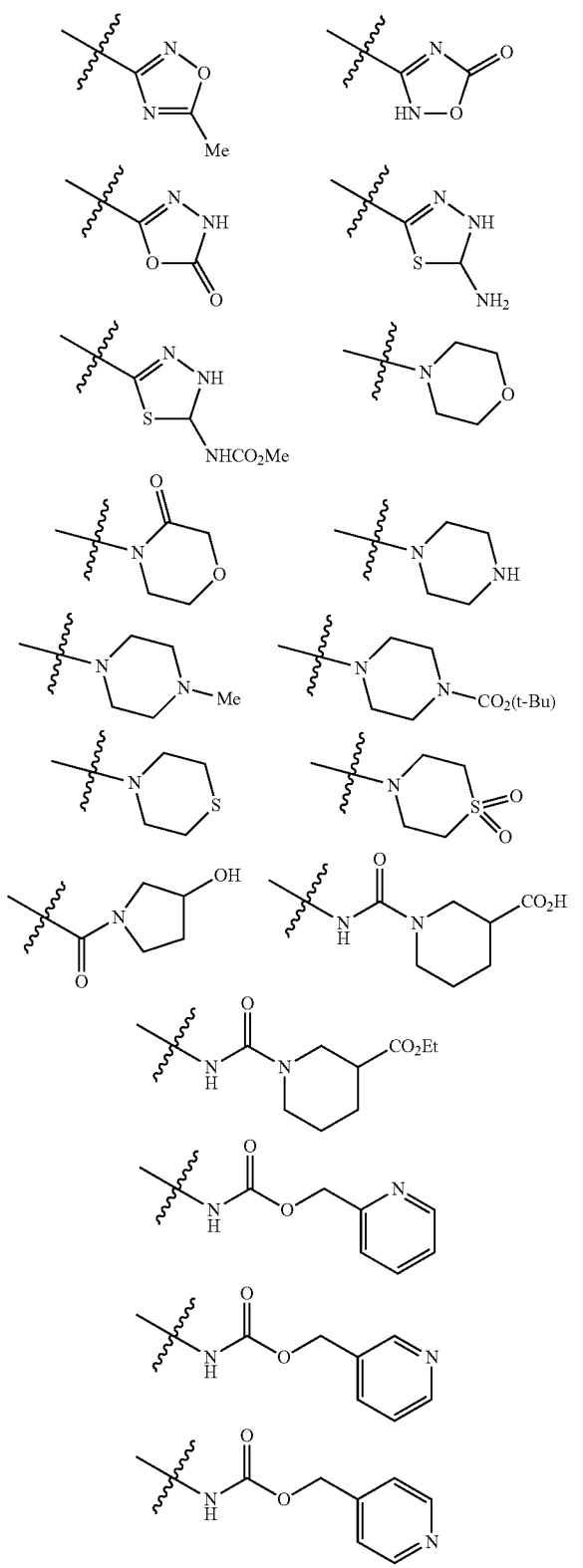
-continued
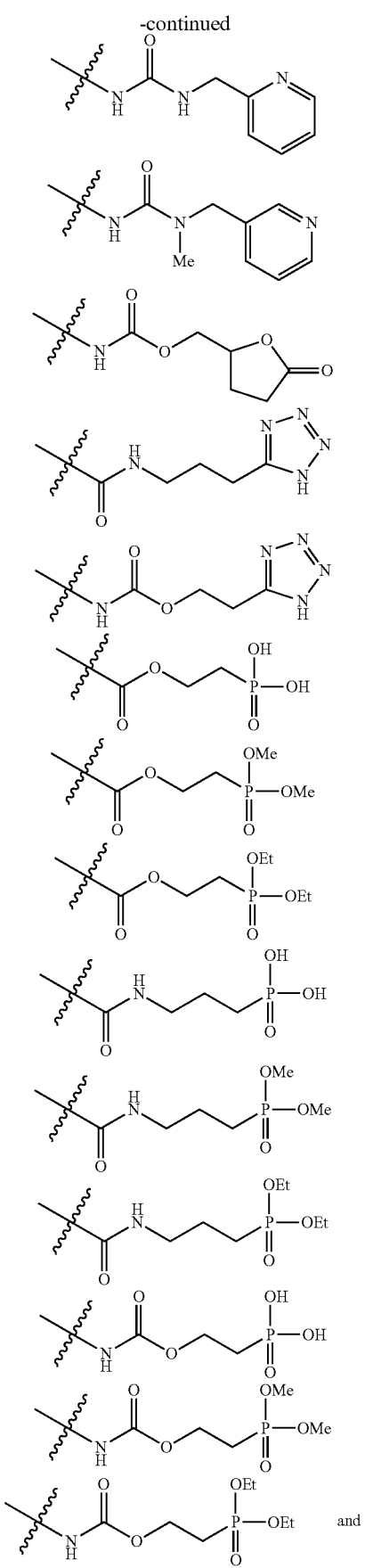
and -continued

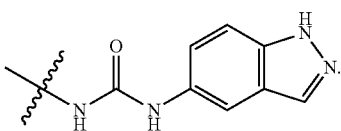

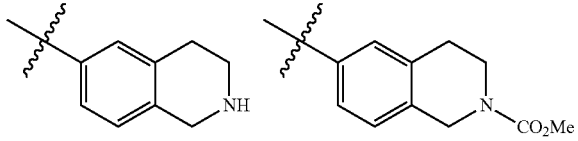

6. A compound according to claim 1, wherein:

M is substituted with 0-2 $R^3$ and is selected from the group consisting of: cyclohexyl, phenyl, pyridyl, pyrimidinyl, thienyl, and thiazolyl,

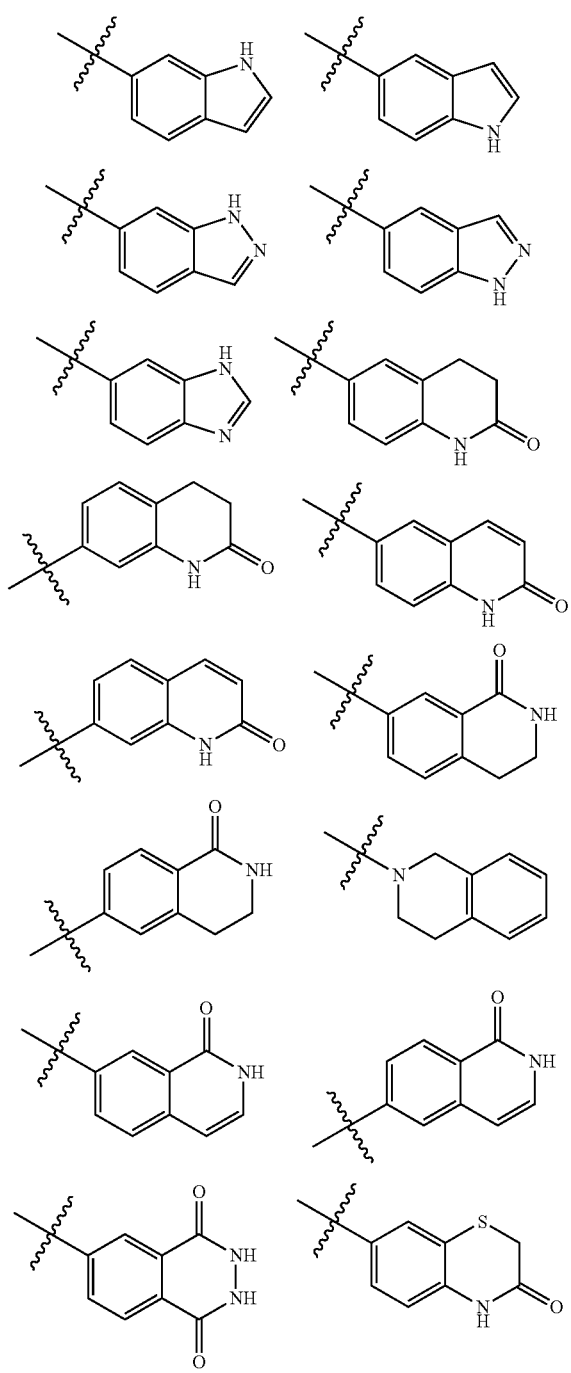

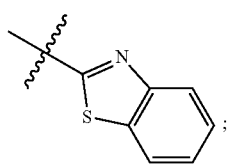

$R^3$ is, independently at each occurrence, F, Cl, Me, $CF_3$, $OCF_3$, OH, CN, $NH_2$, $CO_2H$, $CO_2Me$, $CO_2Et$, $CO_2(t\text{-}Bu)$, —$CH_2CO_2H$, —$CH_2CO_2Me$, —$CH_2CO_2Et$, —$CONH_2$, —$CON(Me)_2$, —NHCOMe, —$NHCO_2Me$, —$NHCO_2(t\text{-}Bu)$, —(C=NH)$NH_2$, —(C=NH)NHOH, —$CONHCH_2CO_2H$, —$CON(Me)CH_2CO_2H$, —$CONH(CH_2)_2CO_2H$, —$CONH(CH_2)_2CO_2Et$, —$CONH(CH_2)_3CO_2H$, —$CONH(CH_2)_3CO_2Et$, —$CO_2(CH_2)_2NEt_2$, —$CO_2(CH_2)_3N(Bu)_2$, —$CH_2NHCO_2Me$, —$NHCO_2(CH_2)_2OMe$, —$CH_2NHCO_2(CH_2)_2OMe$, —$NHCO_2(CH_2)_2CO_2H$, —$NHCO_2(CH_2)_2CO_2Me$, —$NHCO_2(CH_2)_2CO_2Et$, —$NHCO_2(CH_2)_2N(Me)_2$, —$CH_2NHCONH_2$, —$NHCONH(CH_2)_2CO_2H$, —$NHCONH(CH_2)_2CO_2Me$, —$NHCONH(CH_2)_3CO_2Me$, —$CONHSO_2Me$, —$SO_2NH_2$, $P(O)(OH)_2$, $P(O)(OEt)_2$, —$CH_2P(O)(OH)_2$, —$CH_2P(O)(OEt)_2$, 2-(N,N-dimethylaminomethyl)-phenyl, pyridin-4-yl-, tetrahydrofuran-2-ylmethoxy-, 2-oxo-piperidin-1-yl, 2-oxo-2H-pyridin-1-yl, imidazol-1-yl, 2-(N,N-dimethylaminomethyl)-imidazol-1-yl, 1,2,4-triazol-1-yl, tetrazol-1-yl, tetrazol-5-yl, 265
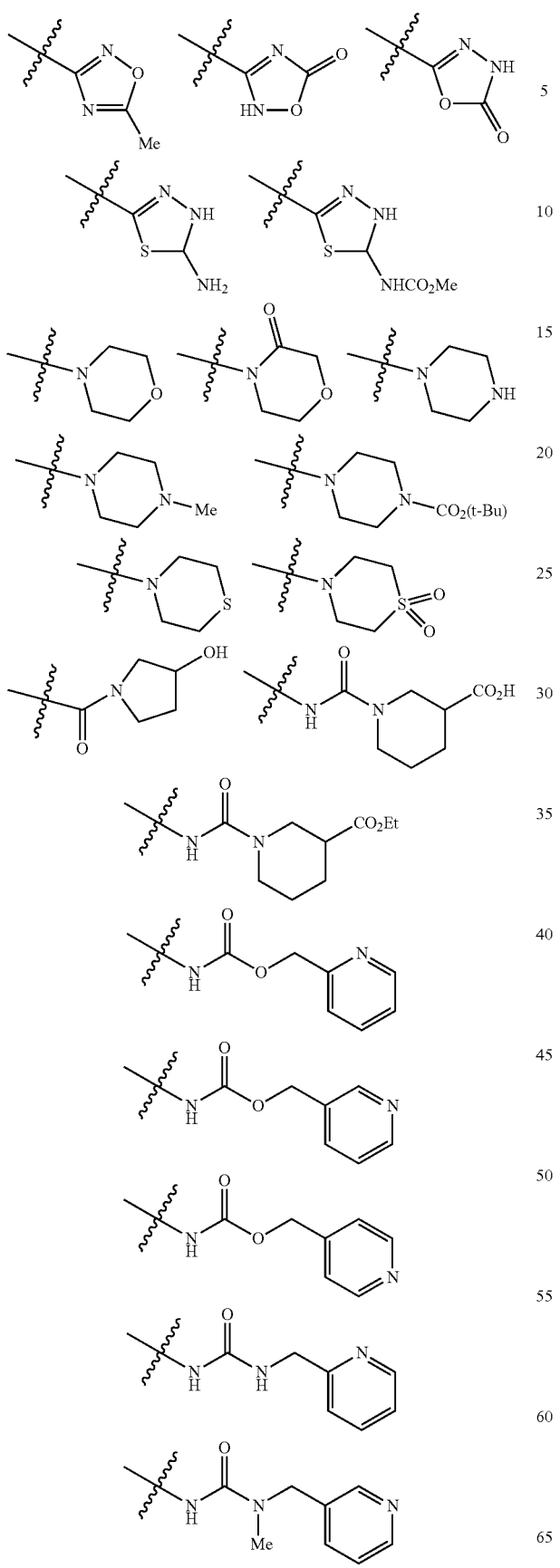
266
-continued
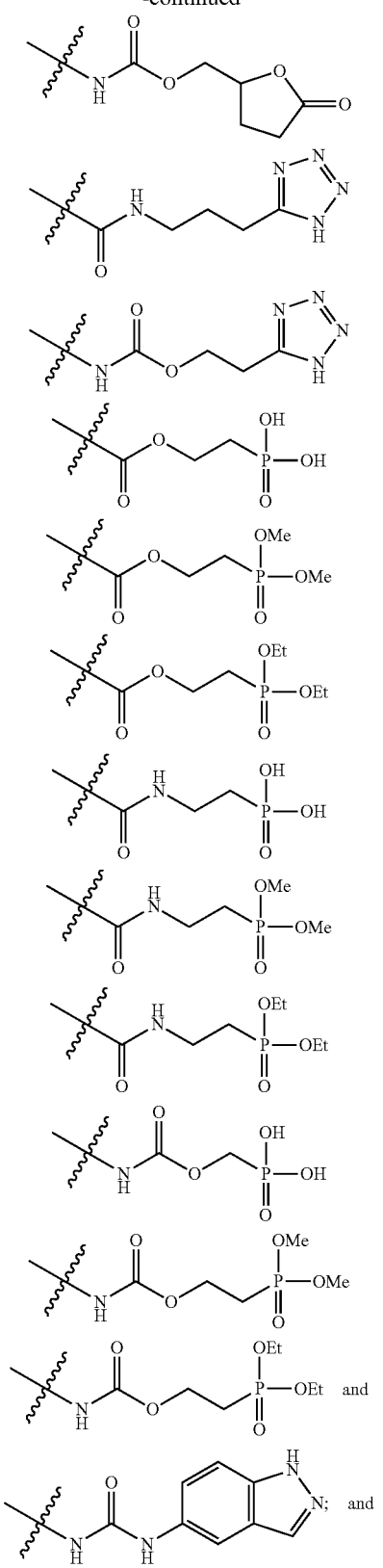
R[11] is methyl, ethyl, neopentyl, —CH$_2$CO$_2$H, —CH$_2$CO$_2$Me, —CH$_2$CONMe, —CH$_2$CF$_3$, —CH$_2$CH$_2$CF$_3$, —CH$_2$CH$_2$SMe, —CH$_2$S(t-Bu), —CH$_2$CH$_2$S(O)Me, —CH$_2$CH$_2$S(O)$_2$Me, —(CH$_2$)$_4$N(Me)$_2$, —CH$_2$C(O)N(Me)(CH$_2$)$_2$N(Me)$_2$, —(CH$_2$)$_3$NHC(NH$_2$)=N(NO$_2$), (2-morpholinoethyl)carbamoylmethyl, phenylcarbamoylmethyl, benzyl, 2-fluorobenzyl, 3-fluorobenzyl, 4-fluorobenzyl, 3,5-difluorobenzyl, 3-carboxybenzyl, 3-carbamoyl benzyl, 3-(N-methylcarbamoyl)-benzyl, 3-methoxycarbonylbenzyl, 3-methylcarbonylamino-benzyl, 3-(isopropyl-methyl-carbamoyl)-benzyl, 3-(methyl-phenyl-carbamoyl)-benzyl, 3-(N,N-dimethylcarbamoyl)-benzyl, 3-(morpholin-4-ylcarbonyl)benzyl, phenethyl, thien-2-ylmethyl, (dimethylamino)-carbonylmethyl, benzyloxymethyl, benzylthiomethyl, 1-naphthylmethyl, 2-naphthylmethyl, thiazol-2-ylmethyl, thiazol-4-ylmethyl, pyrid-2-ylmethyl, pyrid-3-ylmethyl, pyrid-4-ylmethyl, N-oxide-pyrid-2-ylmethyl, N-oxide-pyrid-3-ylmethyl, N-oxide-pyrid-4-ylmethyl, (2-hydroxy-pyrid-5-yl)methyl, (benzyloxycarbonyl)methyl, (1-methylpyrazol-3-yl)methyl, (1-methylpyrazol-5-yl)methyl, (3-methylpyrazol-5-yl)methyl, (1-ethylpyrazol-3-yl)methyl, 3-pyrazolylmethyl, [1-(4-methoxybenzyl)-pyrazol-3-yl]methyl, (1,5-dimethylpyrazol-3-yl)methyl, (1,3-dimethylpyrazol-5-yl)methyl, [1-(4-methoxybenzyl)-5-methyl-pyrazol-3-yl]methyl, (3-trifluoromethylpyrazol-5-yl)methyl, [1-(4-methoxybenzyl)-3-trifluoromethylpyrazol-5-yl]methyl, (1-(2-hydroxyethyl)-5-methyl-1H-pyrazol-3-yl)methyl, (1-methyl-5-(methylsulfinyl)-1H-pyrazol-3-yl)methyl, (1-methyl-5-(methylsulfonyl)-1H-pyrazol-3-yl)methyl, 1H-imidazol-4-ylmethyl, 1-methyl-1H-imidazol-4-ylmethyl, 1-methyl-1H-imidazol-5-ylmethyl, azetidin-3-ylmethyl, (1-acetyl-azetidin-3-yl)methyl, (1-CO$_2$Me-azetidin-3-yl)methyl, pyrrolidin-2-ylmethyl, pyrrolidin-3-ylmethyl, (1-acetyl-pyrrolidin-3-yl)methyl, (1-CO$_2$Me-pyrrolidin-3-yl)methyl, (3-(2-ethoxyethoxy)pyrrolidin-1-yl)carbonylmethyl, (1-benzoylpyrrolidin-3-yl)methyl, pyrrolidin-1-ylcarbonylmethyl, 2-methoxypyrrolidin-1-ylcarbonylmethyl, piperidin-3-ylmethyl, piperidin-4-ylmethyl, piperidin-4-ylethyl, (1-acetyl-piperidin-4-yl)ethyl, (1-CO$_2$Me-piperidin-3-yl)methyl, (1-CO$_2$Me-piperidin-4-yl)methyl, (2-methoxypyridin-3-yl)methyl, (2-methoxypyridin-5-yl)methyl, (4-(methoxycarbonyl)-oxazol-2-yl)methyl, morpholin-4-ylcarbonylmethyl, (2,6-dimethyl-morpholin-4-yl)carbonylmethyl, N-((5-methylpyrazin-2-yl)methyl)-aminocarbonylmethyl, 4-methylpiperazin-1-ylcarbonylmethyl, piperazin-1-ylcarbonylmethyl, 4-methylcarbonylpiperazin-1-ylcarbonylmethyl, tetrahydro-2H-pyran-4-ylmethyl, (1,1-dioxo-1λ$^6$-thiomorpholin-4-yl)methyl, (1,1-dioxo-1λ$^6$-thiomorpholin-4-yl)carbonylmethyl, N-(pyrazin-2-ylmethyl)aminocarbonylmethyl, 1H-indol-3-yl, quinoxalin-2-ylmethyl,

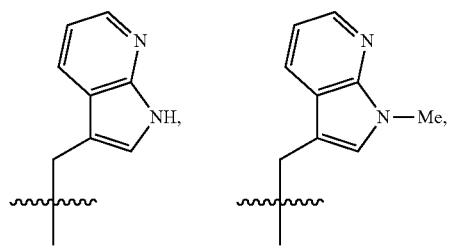

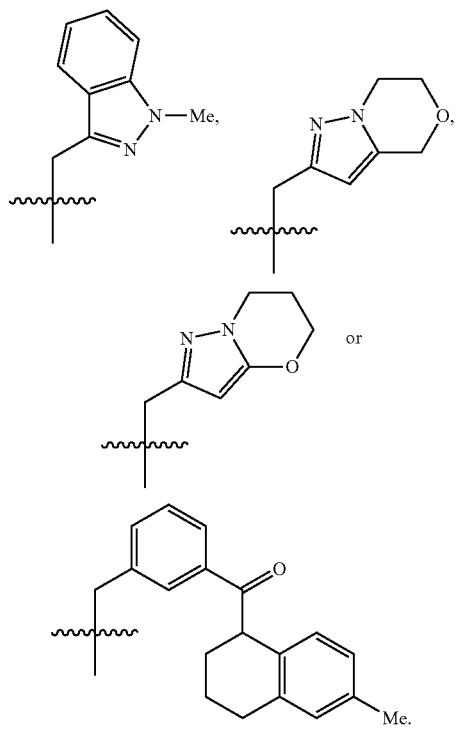

7. A compound according to claim 1, wherein the compound is of Formula (Ic) or (IIc):

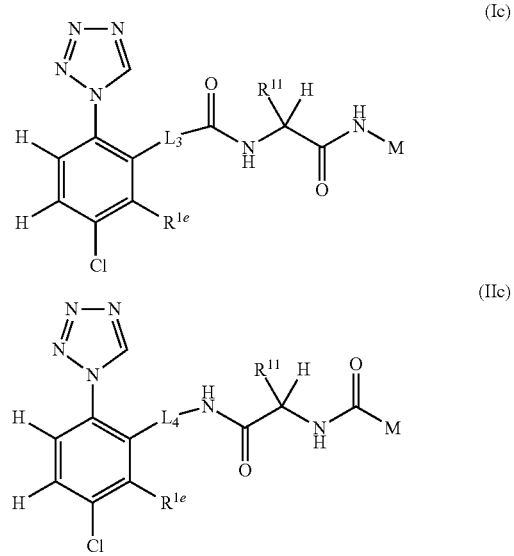

or a stereoisomer, a tautomer, or a pharmaceutically acceptable salt thereof.

8. A compound according to claim 6, wherein:

L$_3$ is —CH$_2$CH$_2$—, —CH=CH—, —C≡C— or —S(O)CH$_2$—;

L$_4$ is —CH$_2$CH$_2$—, —CH=CH—, or —COCH$_2$—;

M is substituted with 0-2 R$^3$ and is selected from the group consisting of: phenyl, pyridyl, thienyl,

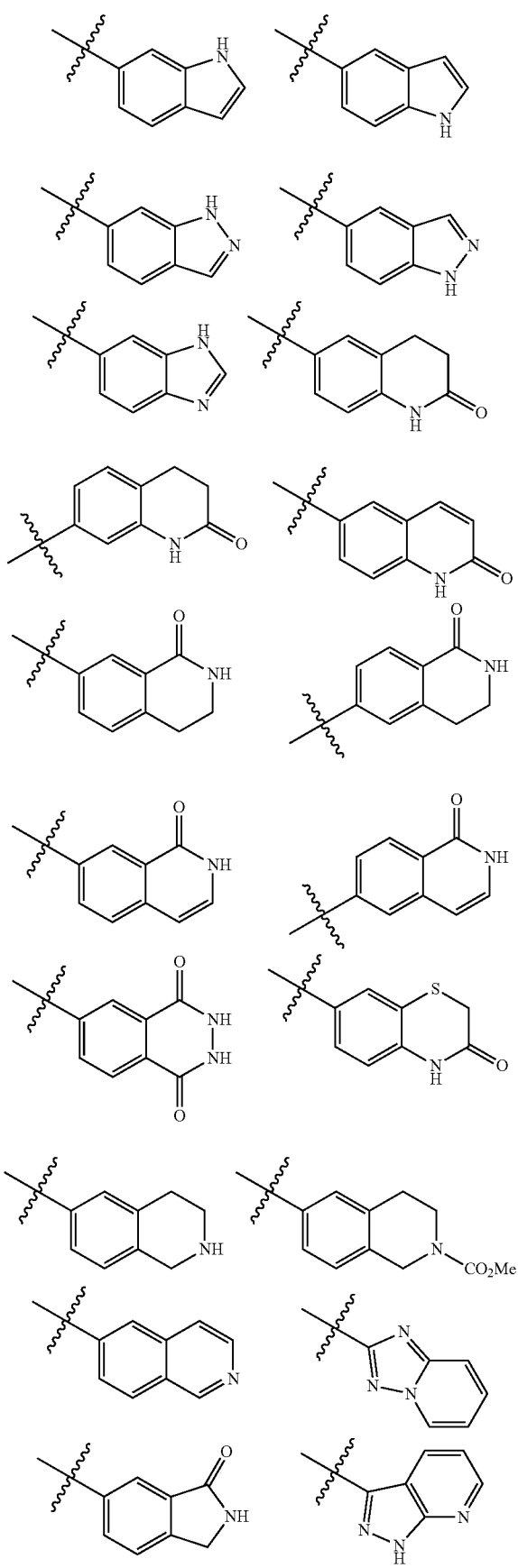
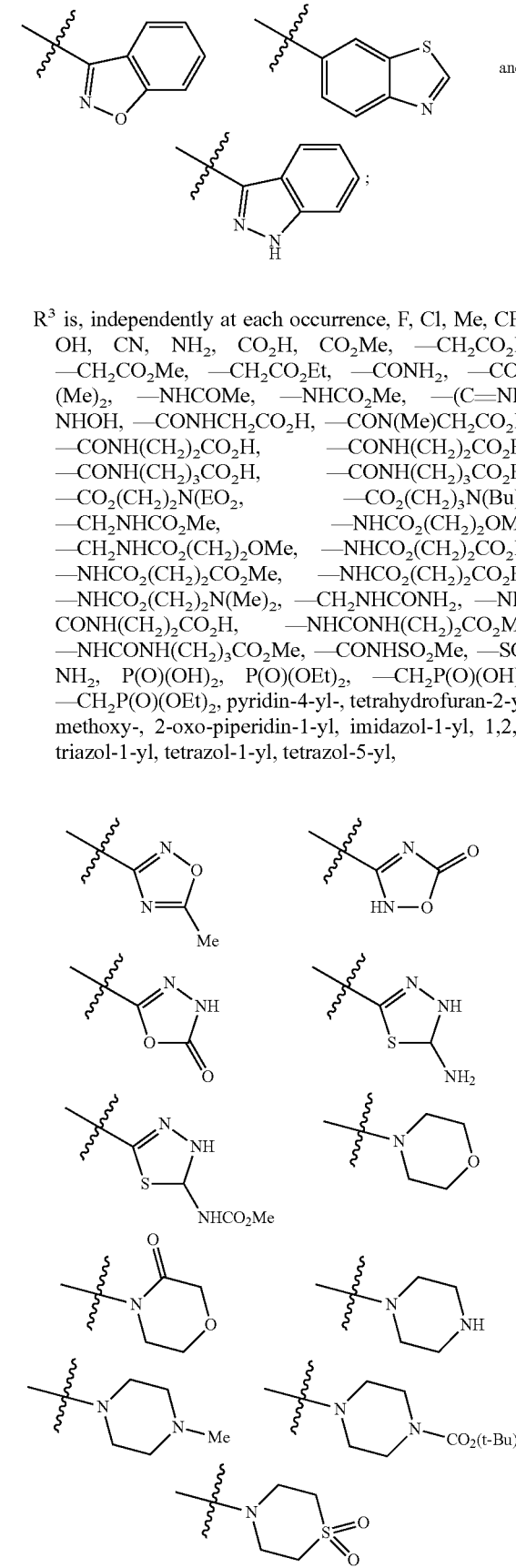

$R^3$ is, independently at each occurrence, F, Cl, Me, $CF_3$, OH, CN, $NH_2$, $CO_2H$, $CO_2Me$, —$CH_2CO_2H$, —$CH_2CO_2Me$, —$CH_2CO_2Et$, —$CONH_2$, —$CON(Me)_2$, —NHCOMe, —$NHCO_2Me$, —(C=NH)NHOH, —$CONHCH_2CO_2H$, —$CON(Me)CH_2CO_2H$, —$CONH(CH_2)_2CO_2H$, —$CONH(CH_2)_2CO_2Et$, —$CONH(CH_2)_3CO_2H$, —$CONH(CH_2)_3CO_2Et$, —$CO_2(CH_2)_2N(EO_2$, —$CO_2(CH_2)_3N(Bu)_2$, —$CH_2NHCO_2Me$, —$NHCO_2(CH_2)_2OMe$, —$CH_2NHCO_2(CH_2)_2OMe$, —$NHCO_2(CH_2)_2CO_2H$, —$NHCO_2(CH_2)_2CO_2Me$, —$NHCO_2(CH_2)_2CO_2Et$, —$NHCO_2(CH_2)_2N(Me)_2$, —$CH_2NHCONH_2$, —NH-$CONH(CH_2)_2CO_2H$, —$NHCONH(CH_2)_2CO_2Me$, —$NHCONH(CH_2)_3CO_2Me$, —$CONHSO_2Me$, —$SO_2NH_2$, $P(O)(OH)_2$, $P(O)(OEt)_2$, —$CH_2P(O)(OH)_2$, —$CH_2P(O)(OEt)_2$, pyridin-4-yl-, tetrahydrofuran-2-yl-methoxy-, 2-oxo-piperidin-1-yl, imidazol-1-yl, 1,2,4-triazol-1-yl, tetrazol-1-yl, tetrazol-5-yl,

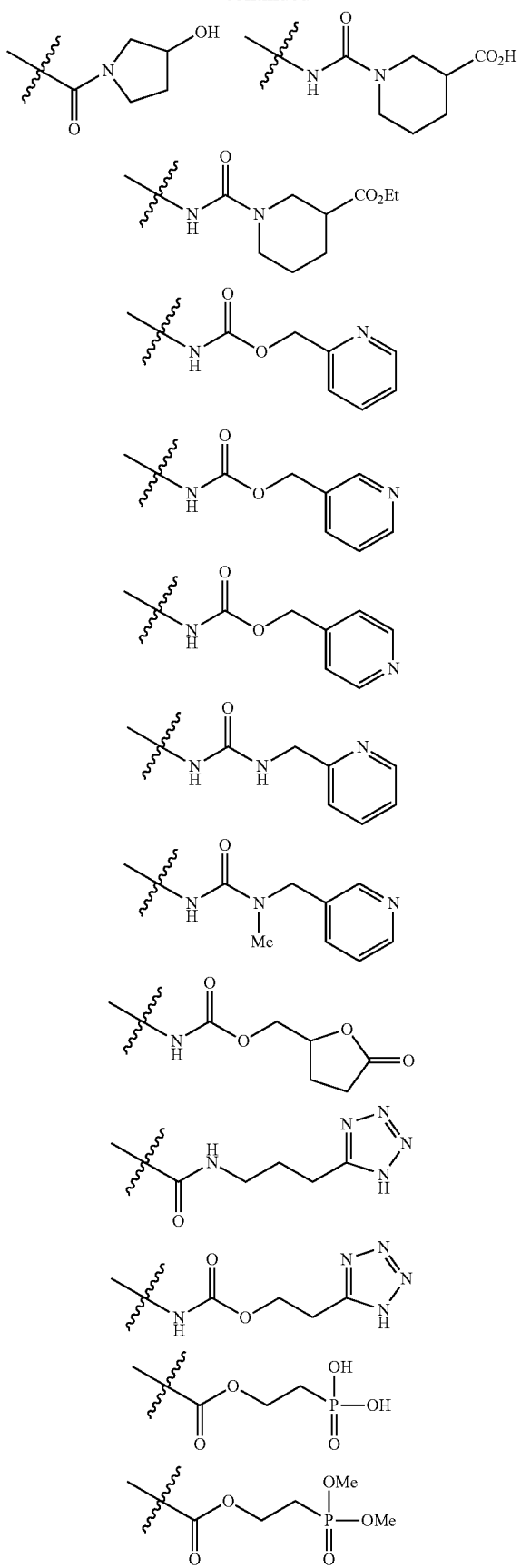
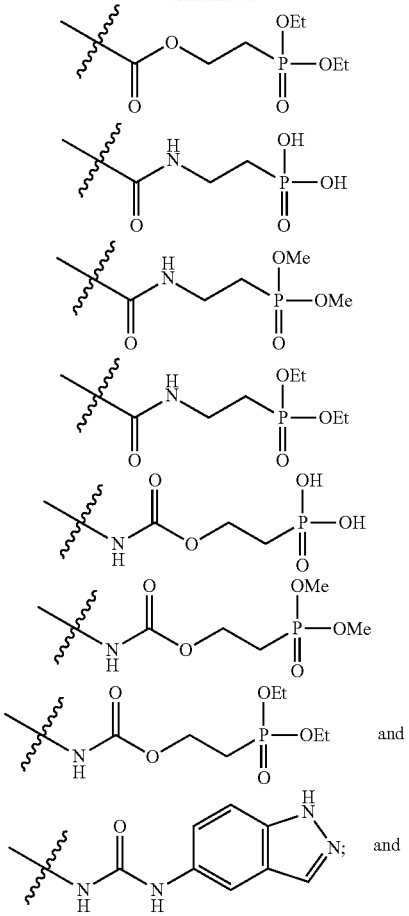

$R^{11}$ is neopentyl, —CH$_2$CO$_2$H, —CH$_2$CO$_2$Me, —CH$_2$CF$_3$, —CH$_2$CH$_2$CF$_3$, —CH$_2$CH$_2$SMe, —CH$_2$S(t-Bu), —CH$_2$CH$_2$S(O)Me, —CH$_2$CH$_2$S(O)$_2$Me, —(CH$_2$)$_4$N(Me)$_2$, —CH$_2$C(O)N(Me)(CH$_2$)$_2$N(Me)$_2$, —(CH$_2$)$_3$NHC(NH$_2$)=N(NO$_2$), phenylcarbamoylmethyl, benzyl, 2-fluorobenzyl, 3-fluorobenzyl, 4-fluorobenzyl, 3,5-difluorobenzyl, 3-carboxybenzyl, 3-carbamoyl benzyl, 3-(morpholin-4-ylcarbonyl)benzyl, phenethyl, (dimethylamino)-carbonylmethyl, 3-(N,N-dimethylcarbamoyl)-benzyl, thien-2-ylmethyl, (1-methylpyrazol-3-yl)methyl, (1,3-dimethylpyrazol-5-yl)methyl, (1,5-dimethylpyrazol-3-yl)methyl, (1-ethylpyrazol-3-yl)methyl, (1-(2-hydroxyethyl)-5-methyl-1H-pyrazol-3-yl)methyl, (1-methyl-5-(methylsulfinyl)-1H-pyrazol-3-yl)methyl, (1-methyl-5-(methylsulfonyl)-1H-pyrazol-3-yl)methyl, thiazol-2-ylmethyl, thiazol-4-ylmethyl, 1H-imidazol-4-ylmethyl, 1-methyl-1H-imidazol-4-ylmethyl, 1-methyl-1H-imidazol-5-ylmethyl, azetidin-3-ylmethyl, (1-acetyl-azetidin-3-yl)methyl, (1-CO$_2$Me-azetidin-3-yl)methyl, pyrrolidin-2-ylmethyl, pyrrolidin-3-ylmethyl, (1-acetylpyrrolidin-3-yl)methyl, (1-CO$_2$Me-pyrrolidin-3-yl)methyl, (3-(2-ethoxyethoxy)pyrrolidin-1-yl)carbonylmethyl, (1-benzoylpyrrolidin-3-yl)methyl, piperidin-3-ylmethyl, piperidin-4-ylmethyl, piperidin-4-ylethyl, (1-acetyl-piperidin-4-yl)ethyl, (1-CO$_2$Me-piperidin-3-yl)methyl, (1-CO$_2$Me-piperidin-4-yl)methyl, tetrahydro-2H-pyran-4-ylmethyl, pyrid-2-ylmethyl, pyrid-3-ylmethyl, pyrid-4-ylmethyl, N-oxide-pyrid-2-ylmethyl, N-oxide-pyrid-3-ylmethyl, N-oxide-pyrid-4- ylmethyl, (2-hydroxy-pyrid-5-yl)methyl, morpholin-4-ylcarbonylmethyl, 4-methylpiperazin-1-ylcarbonylmethyl, 4-methylcarbonylpiperazin-1-ylcarbonylmethyl, (1,1-dioxo-1$\lambda^6$-thiomorpholin-4-yl)methyl, (1,1-dioxo-1$\lambda^6$-thiomorpholin-4-yl)carbonylmethyl, N-(pyrazin-2-ylmethyl)aminocarbonylmethyl, 1H-indol-3-yl, quinoxalin-2-ylmethyl,

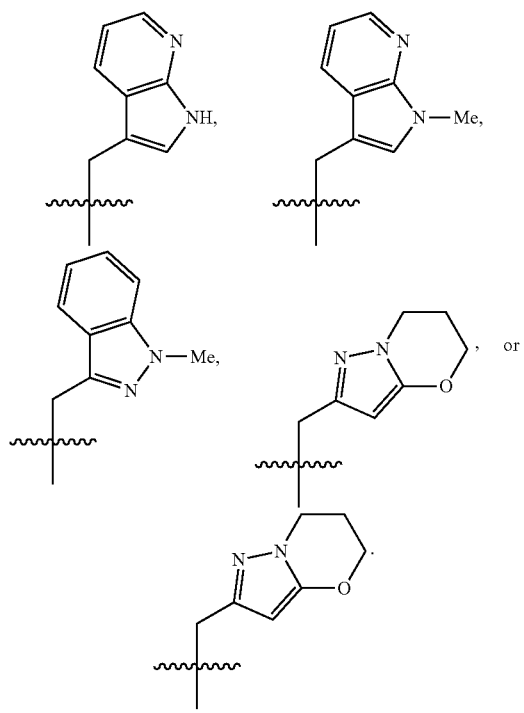

9. A compound according to claim 8, wherein:
M is substituted with 0-2 $R^3$ and is selected from the group consisting of: phenyl, pyridyl, thienyl,

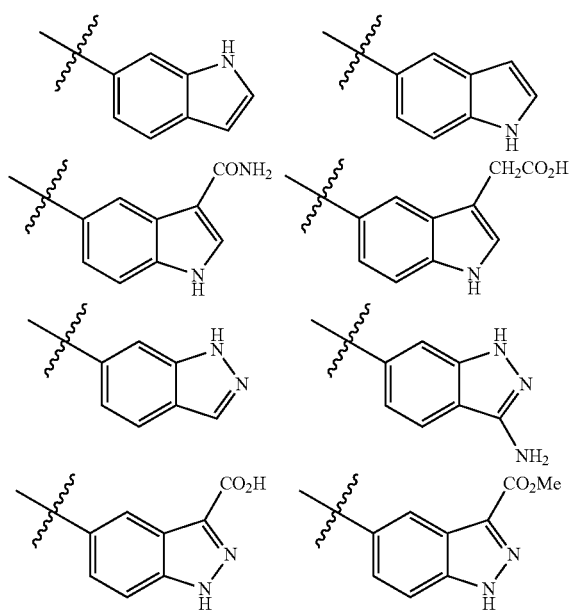

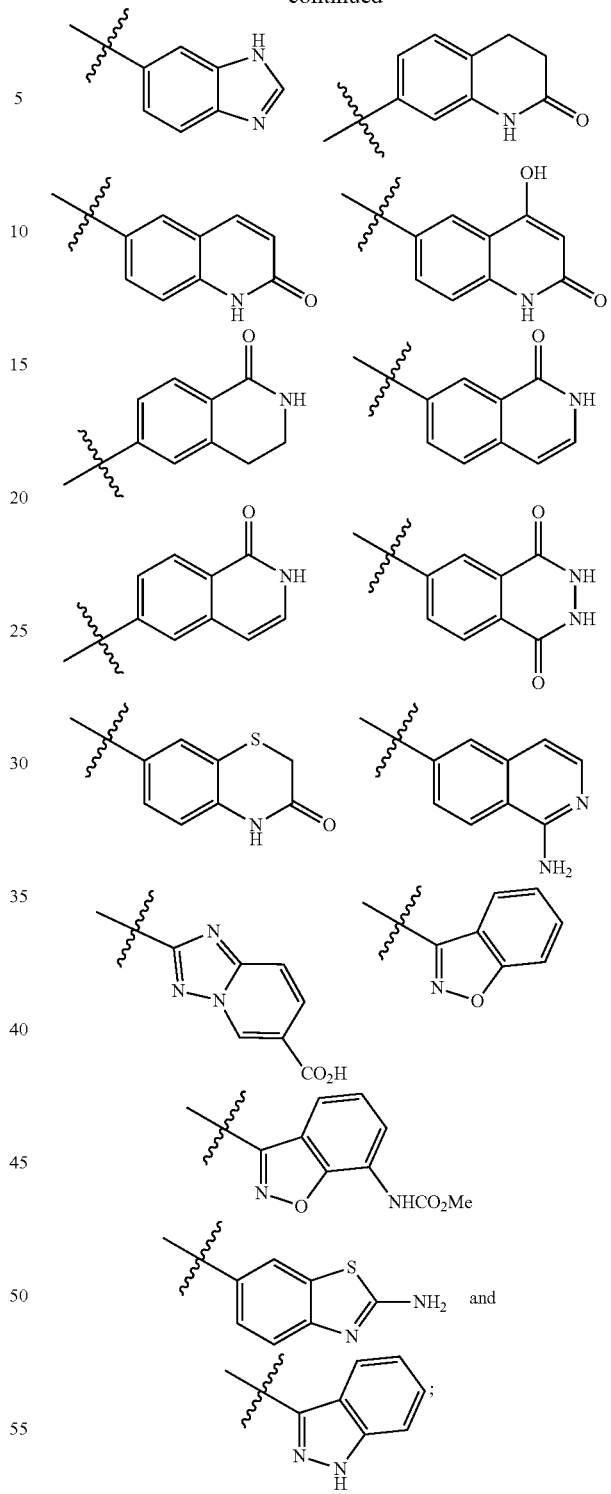

$R^3$ is, independently at each occurrence, F, Cl, CN, $CO_2H$, $CO_2Me$, —$CH_2CO_2H$, —$CONH_2$, —$NHCO_2Me$, —(C=NH)NHOH, —$CONHCH_2CO_2H$, —$CONH(CH_2)_2CO_2H$, —$CONH(CH_2)_3CO_2H$, —$CONH(CH_2)_3CO_2Et$, —$CH_2NHCO_2Me$, —$NHCO_2(CH_2)_2OMe$, —$CH_2NHCO_2(CH_2)_2OMe$, —$NHCO_2(CH_2)_2CO_2H$, —$NHCO_2(CH_2)_2CO_2Me$, —$NHCO_2(CH_2)_2CO_2Et$, —$CH_2NHCONH_2$, —$NHCONH(CH_2)_2CO_2H$, —NHCONH(CH$_2$)$_2$CO$_2$Me, —NHCONH(CH$_2$)$_3$CO$_2$Me, —CONHSO$_2$Me, P(O)(OH)$_2$, P(O)(OEt)$_2$, —CH$_2$P(O)(OH)$_2$, —CH$_2$P(O)(OEt)$_2$, pyridin-4-yl-, tetrahydrofuran-2-ylmethoxy-, imidazol-1-yl, 1,2,4-triazol-1-yl, tetrazol-1-yl, tetrazol-5-yl,

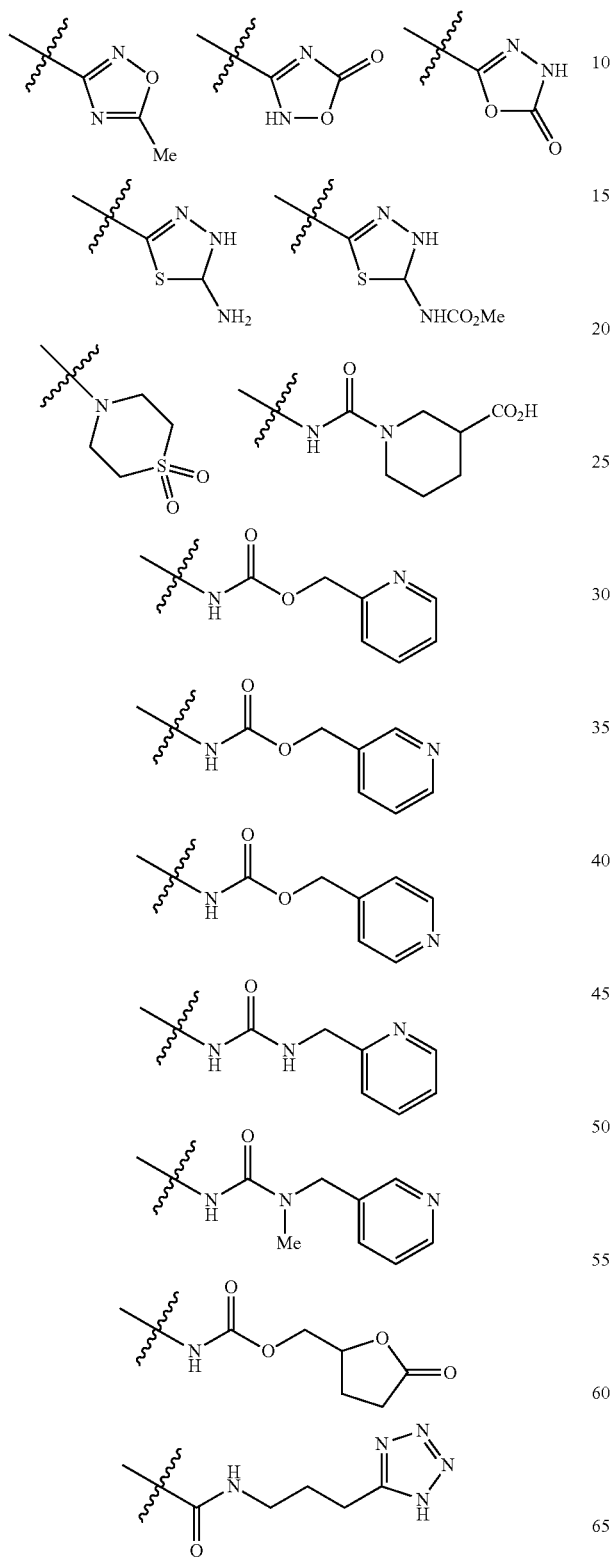

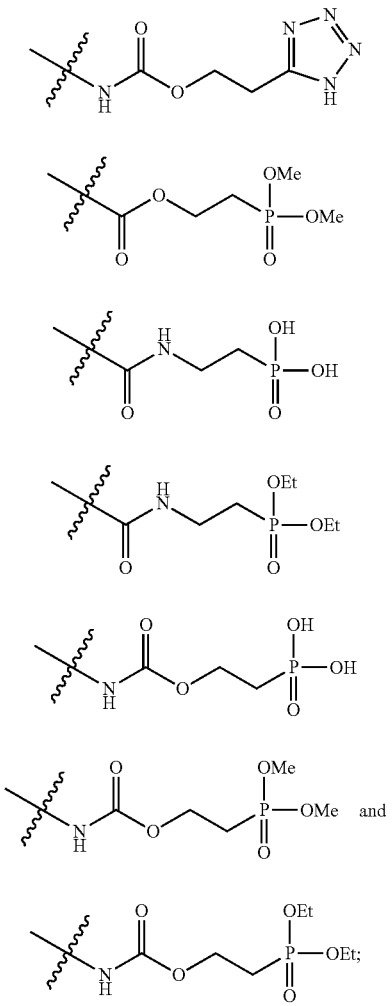

$R^{11}$ is —CH$_2$CO$_2$Me, —CH$_2$CH$_2$CF$_3$, —CH$_2$CH$_2$SMe, —CH$_2$CH$_2$S(O)Me, —CH$_2$CH$_2$S(O)$_2$Me, —(CH$_2$)$_4$N(Me)$_2$, —(CH$_2$)$_3$NHC(NH$_2$)=N(NO$_2$), benzyl, 2-fluorobenzyl, 3-fluorobenzyl, 4-fluorobenzyl, 3,5-difluorobenzyl, 3-carboxybenzyl, 3-carbamoylbenzyl, 3-(morpholin-4-ylcarbonyl)benzyl, (dimethylamino)carbonylmethyl, thien-2-ylmethyl, (1-methylpyrazol-3-yl)methyl, (1,3-dimethylpyrazol-5-yl)methyl, (1,5-dimethylpyrazol-3-yl)methyl, (1-ethylpyrazol-3-yl)methyl, (1-(2-hydroxyethyl)-5-methyl-1H-pyrazol-3-yl)methyl, thiazol-2-ylmethyl, thiazol-4-ylmethyl, 1H-imidazol-4-ylmethyl, 1-methyl-1H-imidazol-4-ylmethyl, 1-methyl-1H-imidazol-5-ylmethyl, azetidin-3-ylmethyl, (1-acetyl-azetidin-3-yl)methyl, (1-CO$_2$Me-azetidin-3-yl)methyl, (3-(2-ethoxyethoxy)pyrrolidin-1-yl)carbonylmethyl, (1-benzoylpyrrolidin-3-yl)methyl, piperidin-3-ylmethyl, piperidin-4-ylmethyl, piperidin-4-ylethyl, (1-acetyl-piperidin-4-yl)ethyl, (1-CO$_2$Me-piperidin-3-yl)methyl, (1-CO$_2$Me-piperidin-4-yl)methyl, tetrahydro-2H-pyran-4-ylmethyl, pyrid-2-ylmethyl, pyrid-3-ylmethyl, pyrid-4-ylmethyl, (2-hydroxy-pyrid-5-yl)methyl, (1,1-dioxo-1$\lambda^6$-thiomorpholin-4-yl)methyl, (1,1-dioxo-1$\lambda^6$-thiomorpholin-4-yl)carbonylmethyl, N-(pyrazin-2-ylmethyl)aminocarbonylmethyl, 1H-indol-3-yl, quinoxalin-2-ylmethyl,

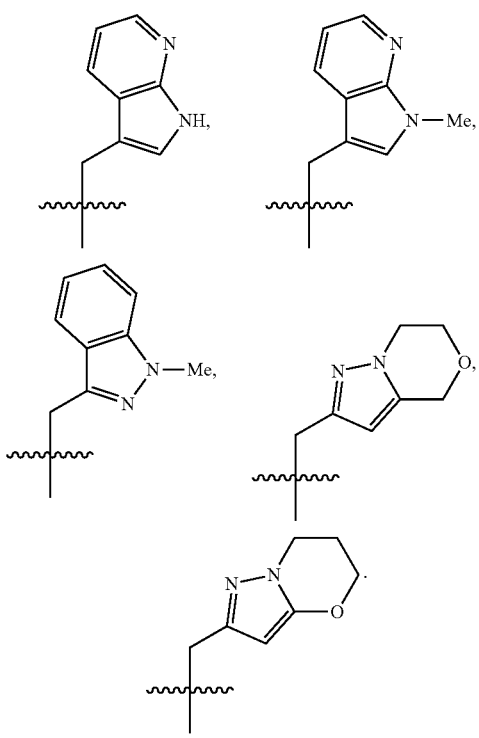
10. A pharmaceutical composition, comprising: a pharmaceutically acceptable carrier and a compound of claim 1, or a stereoisomer, a tautomer, or a pharmaceutically acceptable salt thereof.
11. A compound selected from the group consisting of:
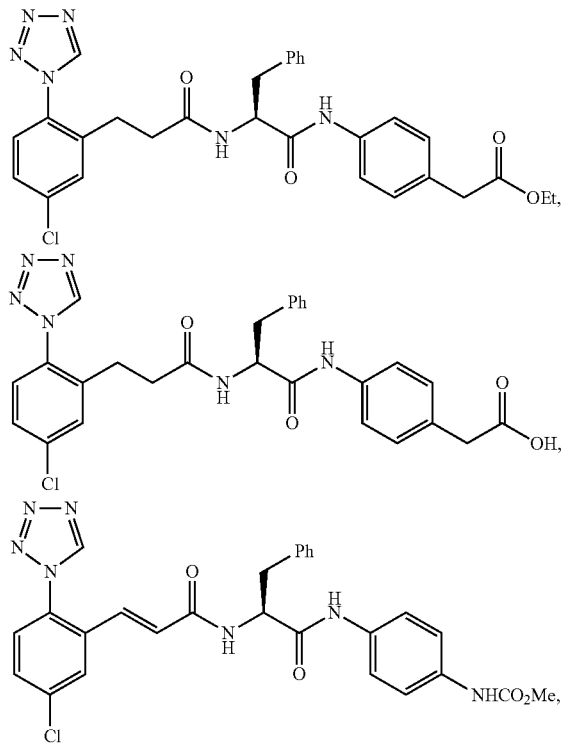
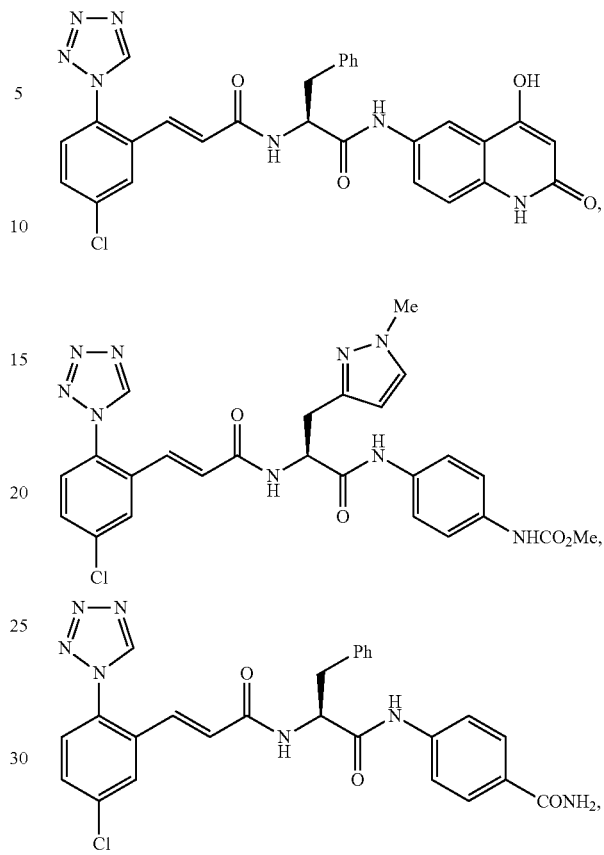
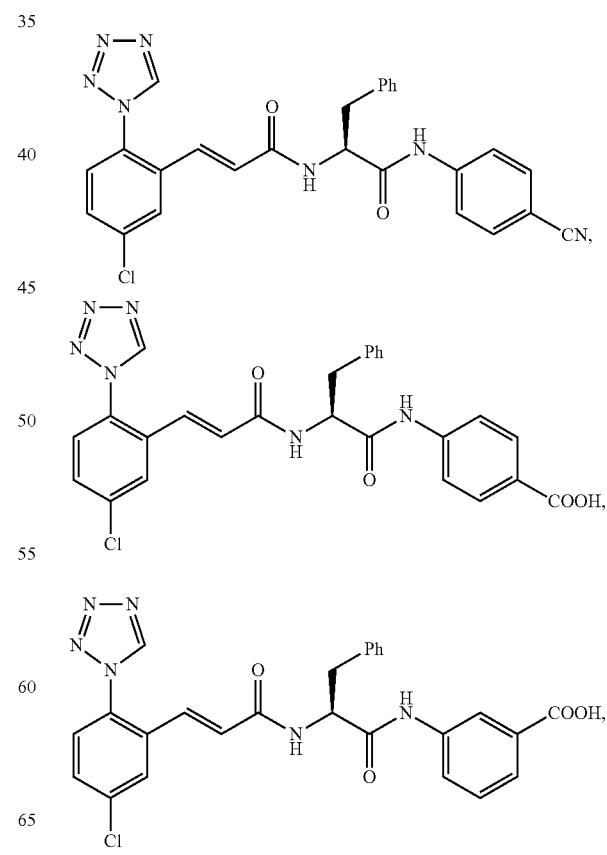

279
-continued
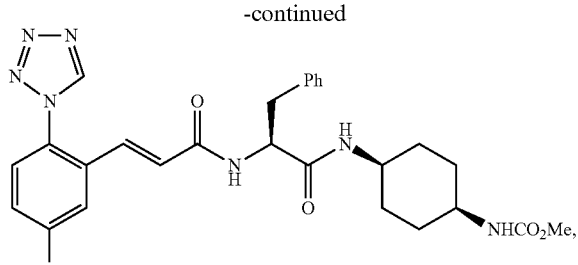
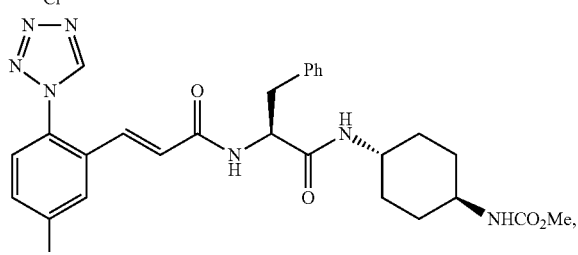
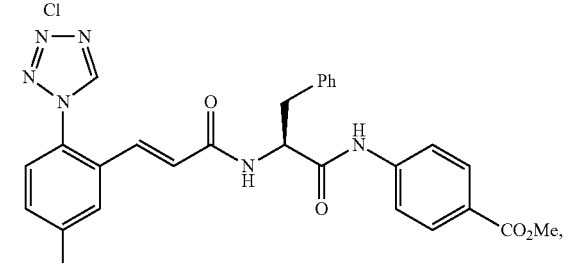
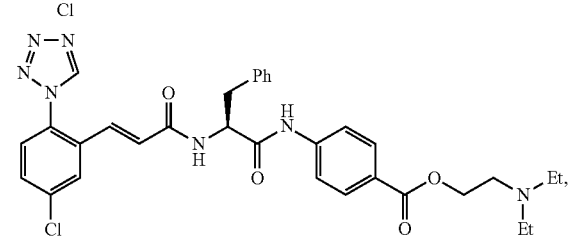
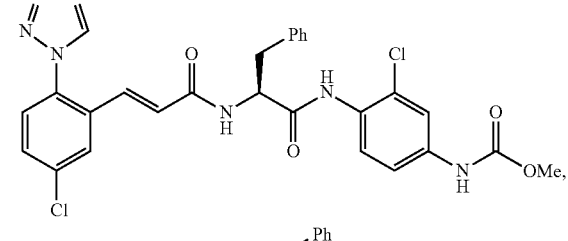
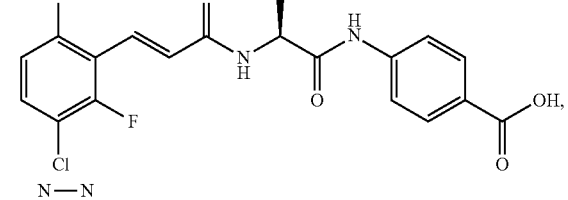
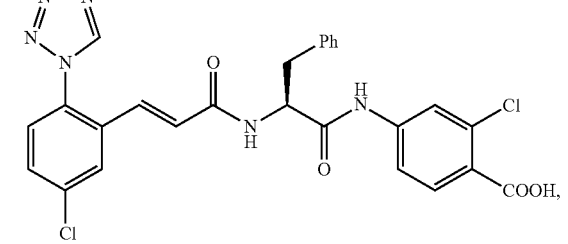
280
-continued
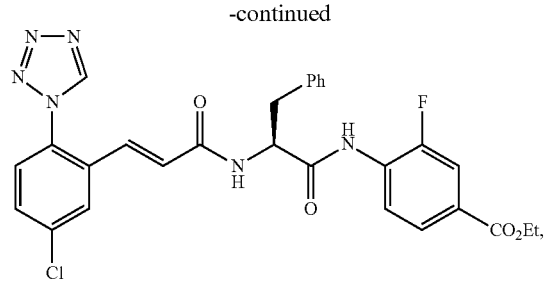
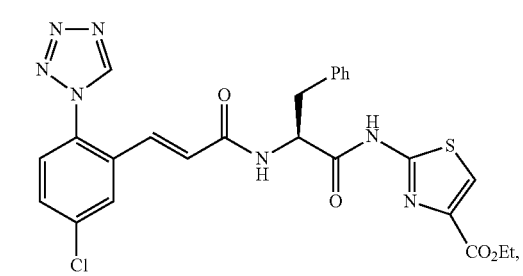
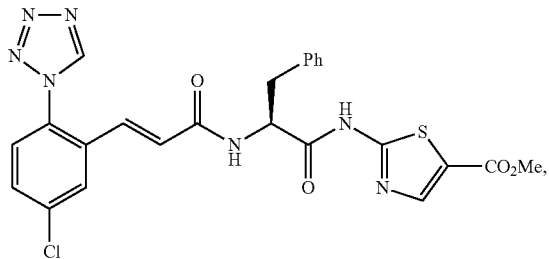
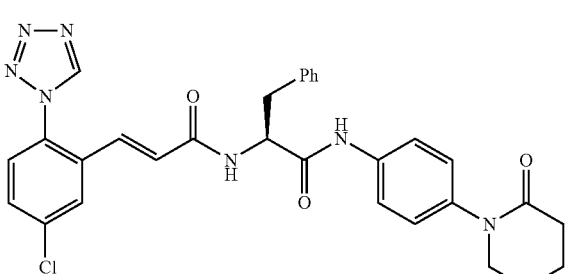
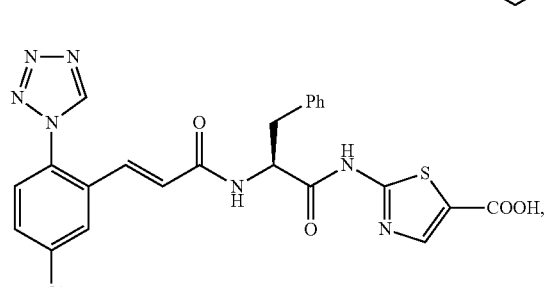
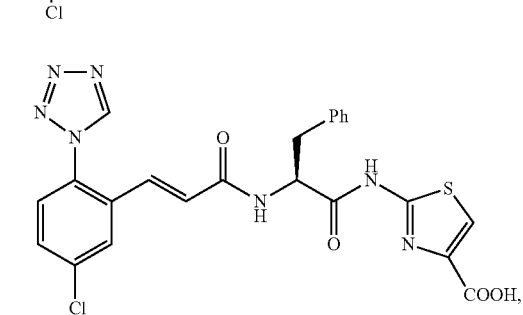

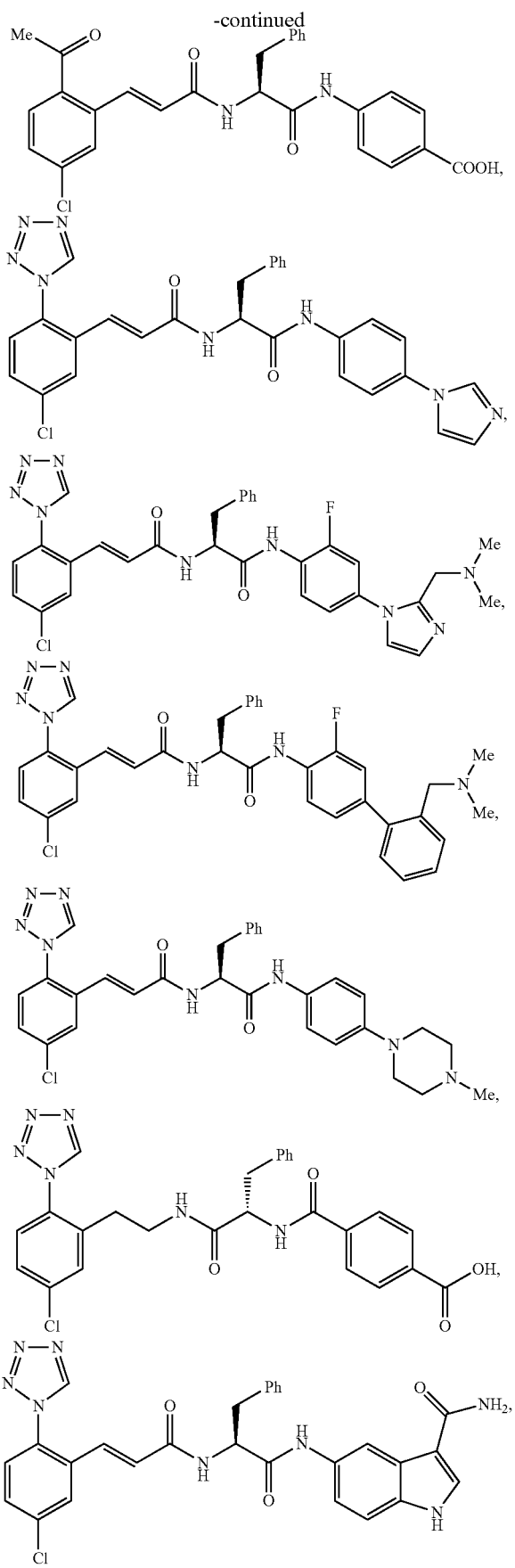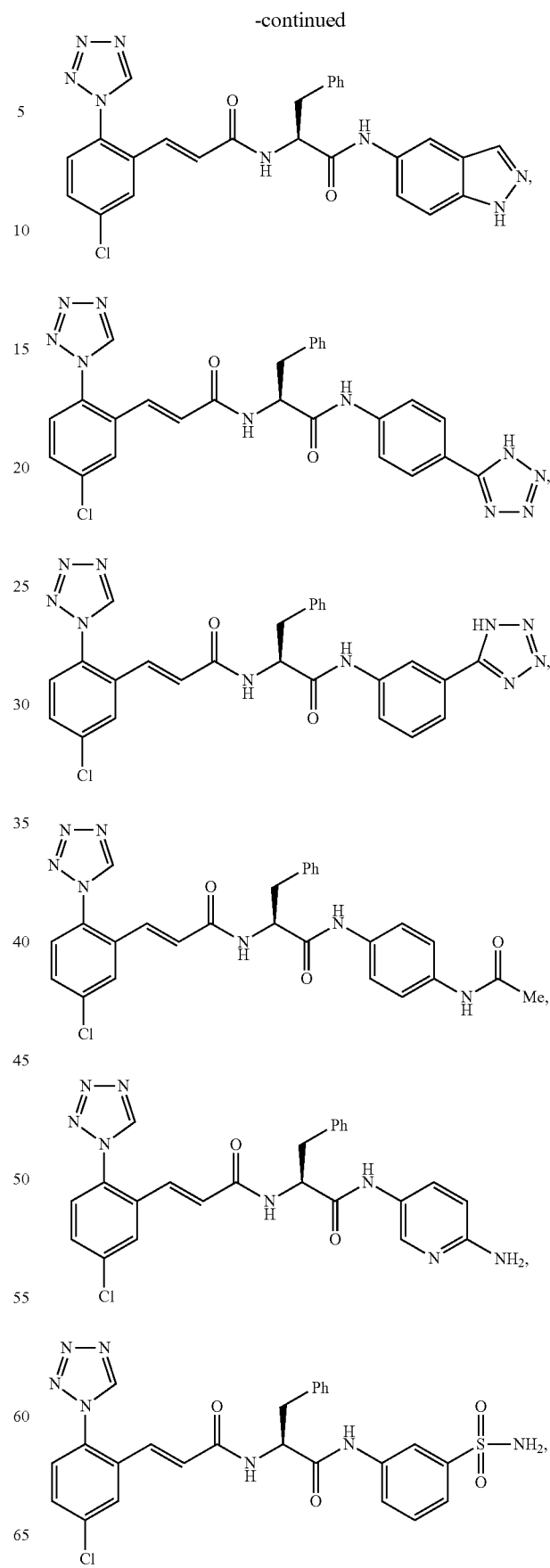

283
-continued
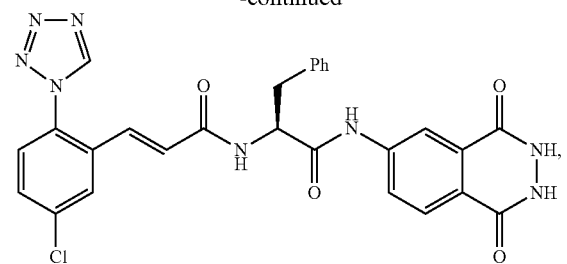
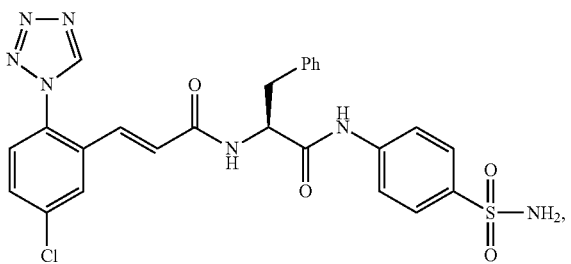
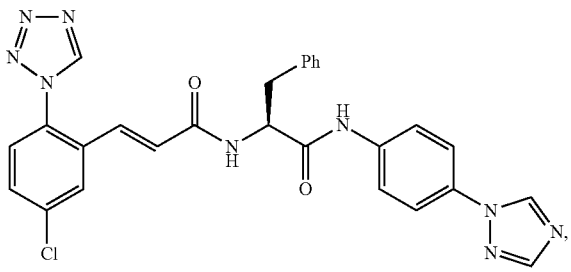
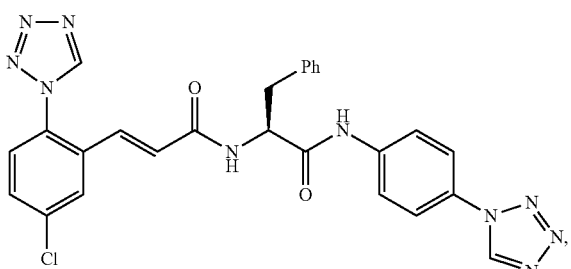
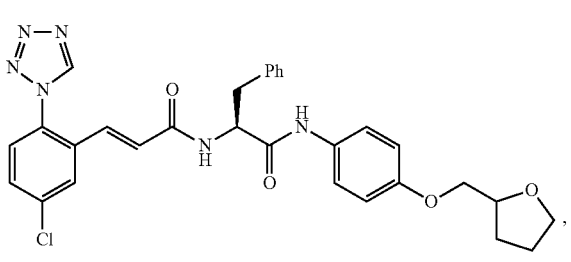
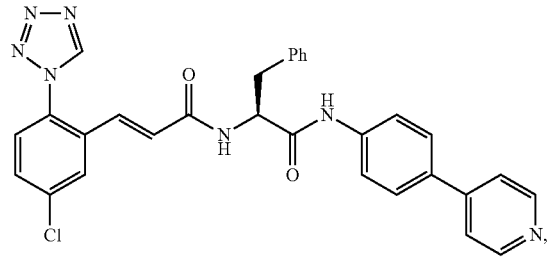
284
-continued
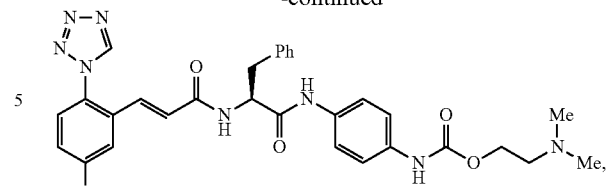
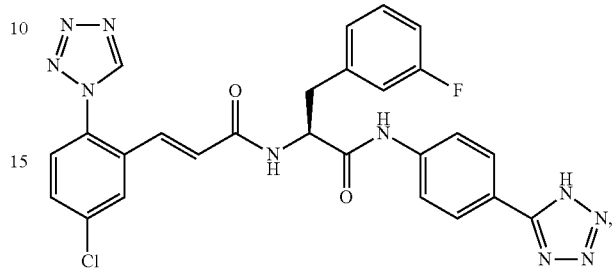
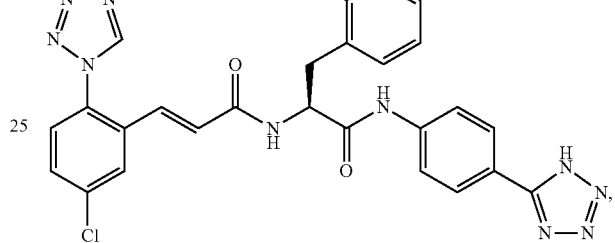
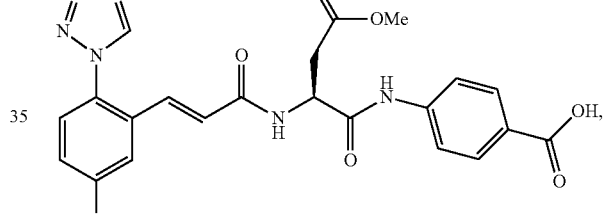
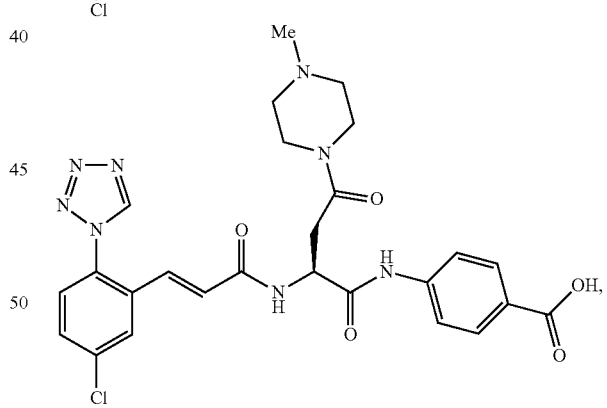
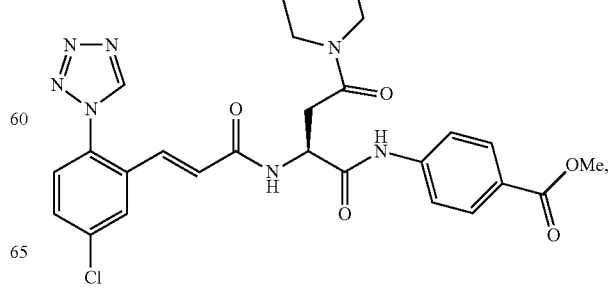

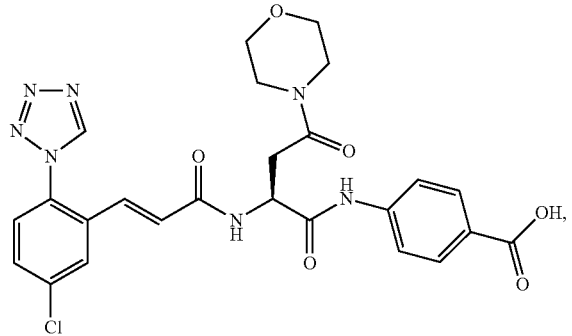
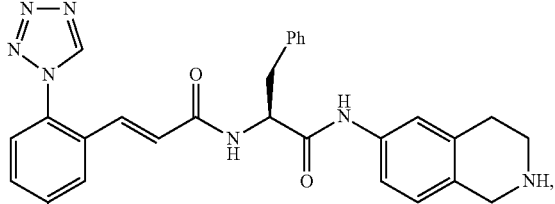
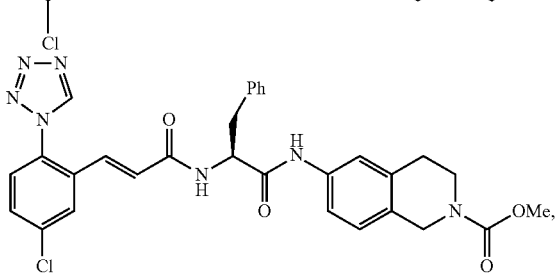
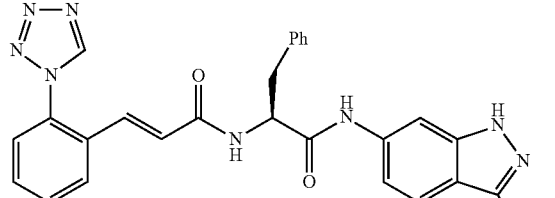
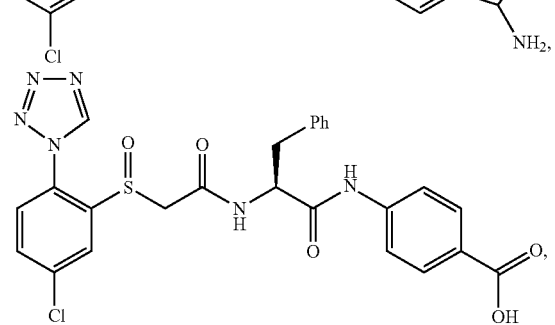
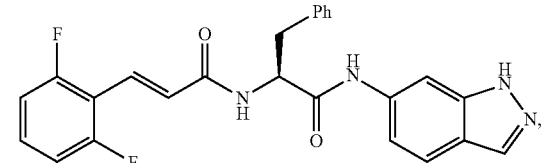
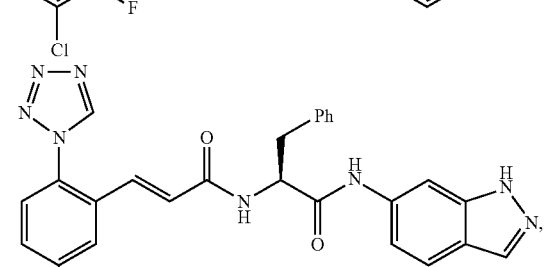
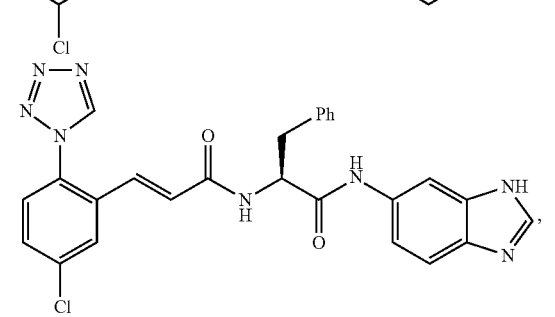

287
-continued
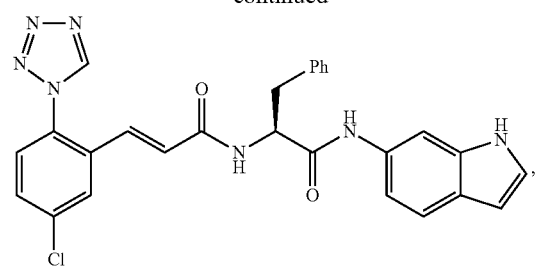
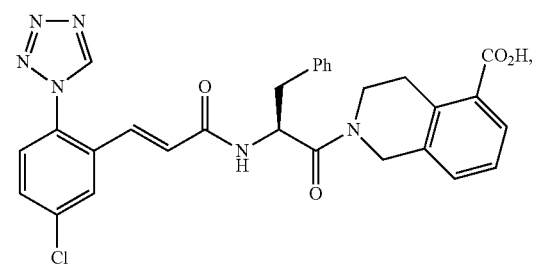
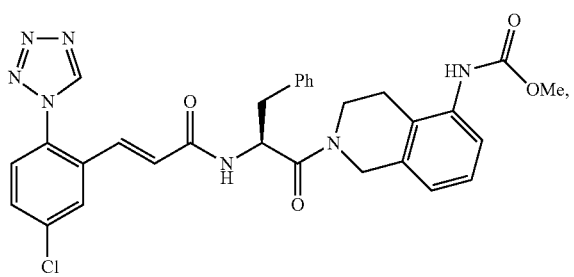
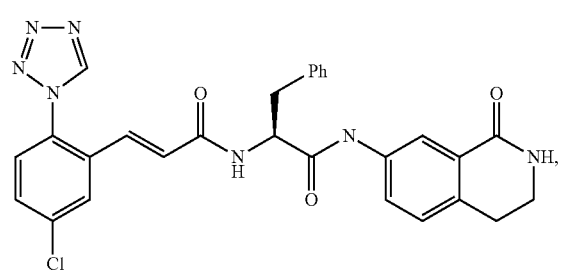
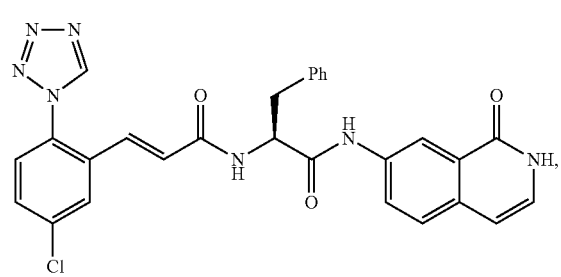
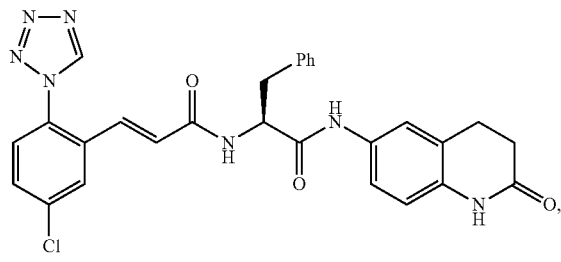
288
-continued
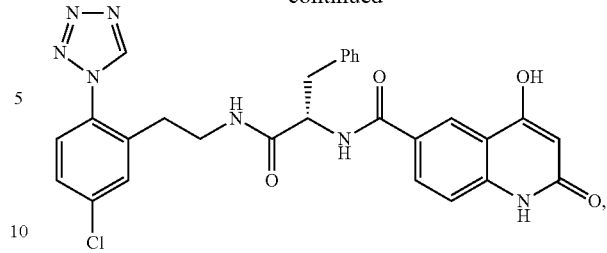
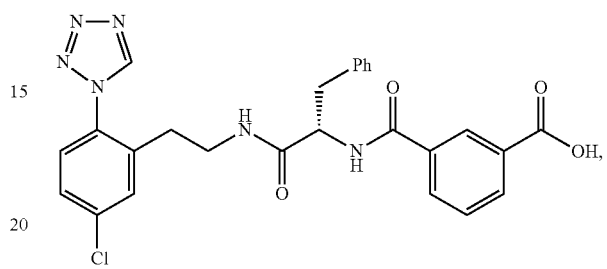
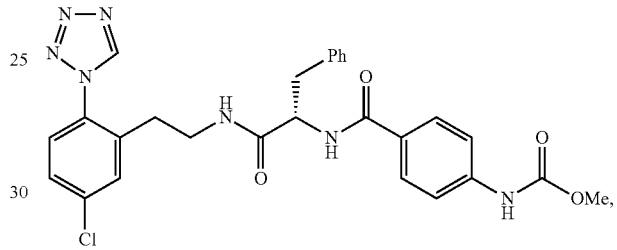
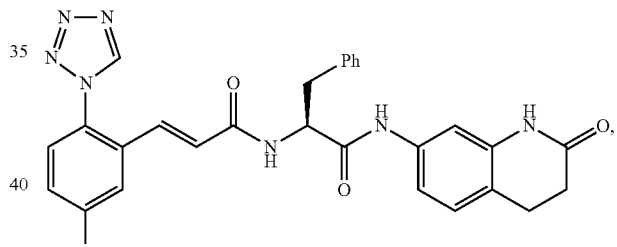
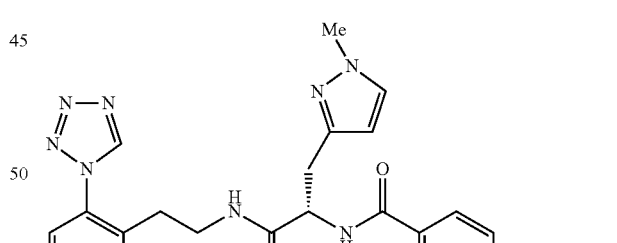
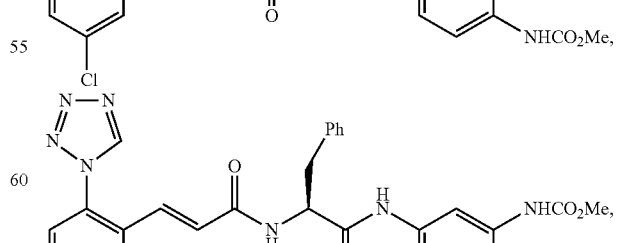

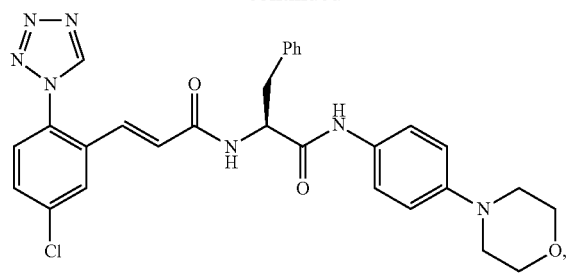
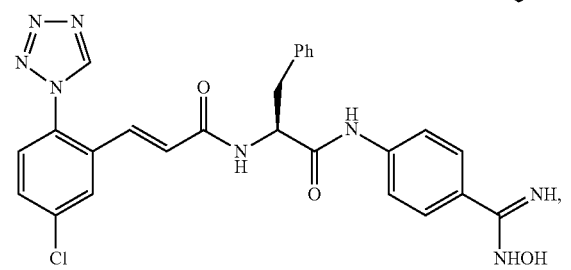
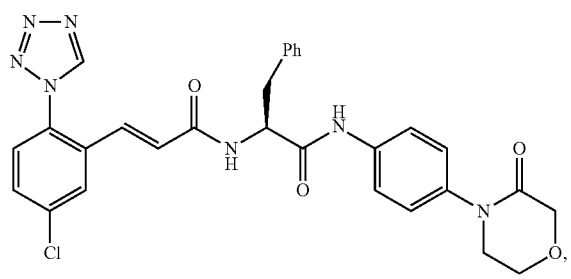
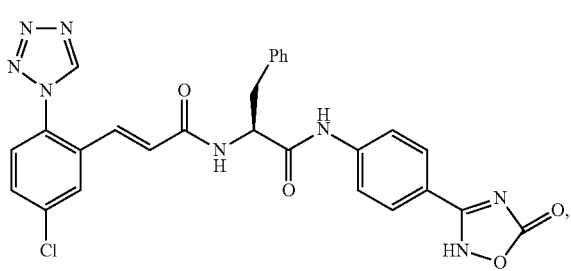
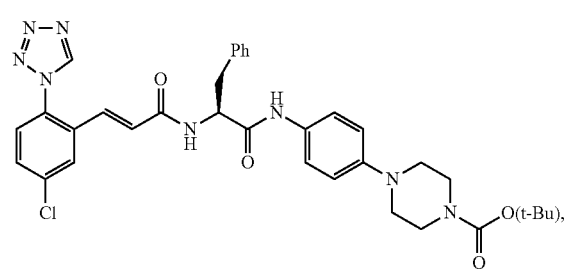
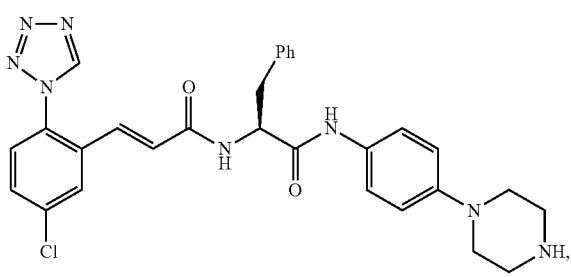
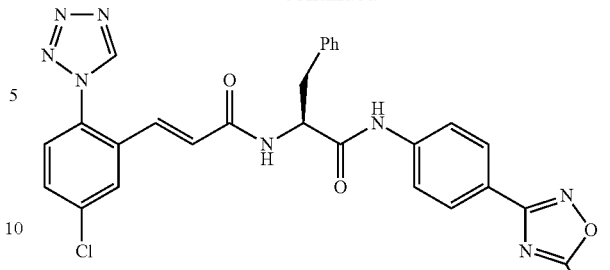
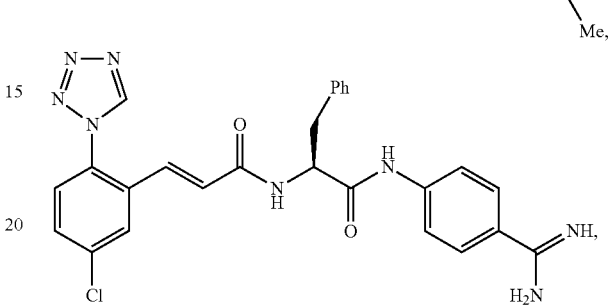
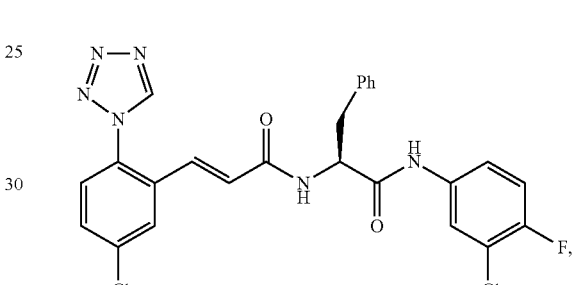
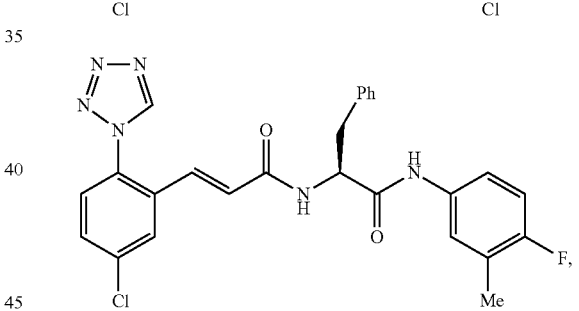
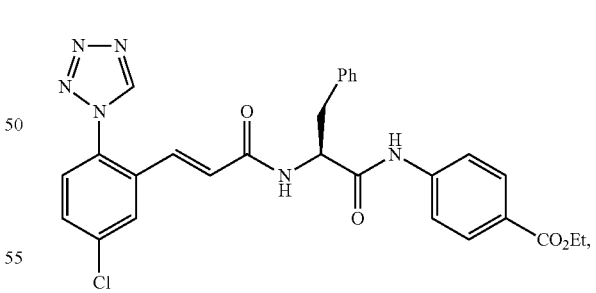
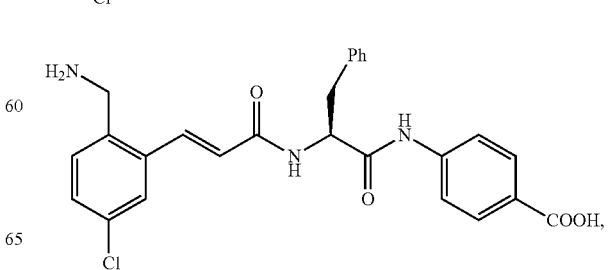

291
-continued
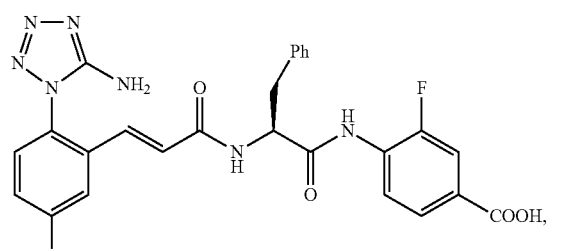
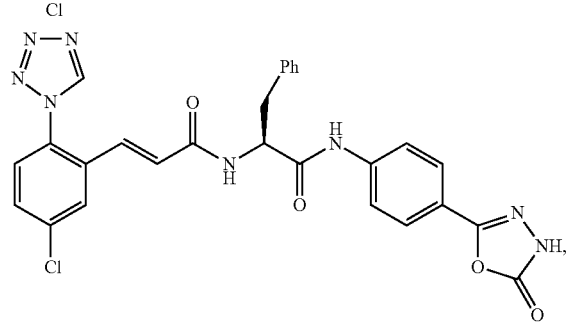
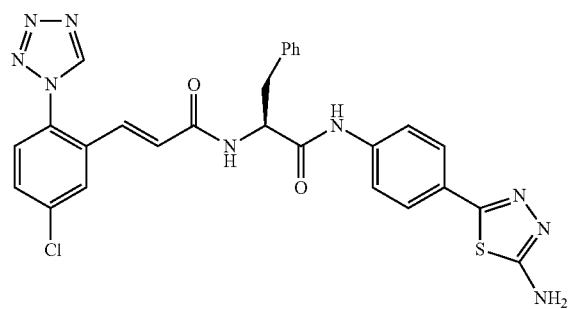
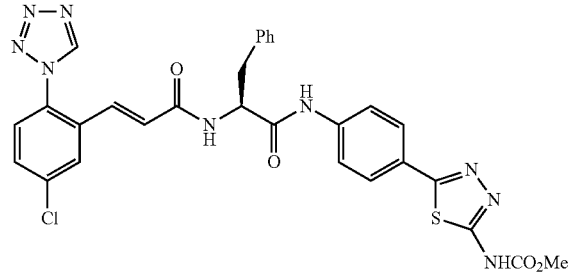
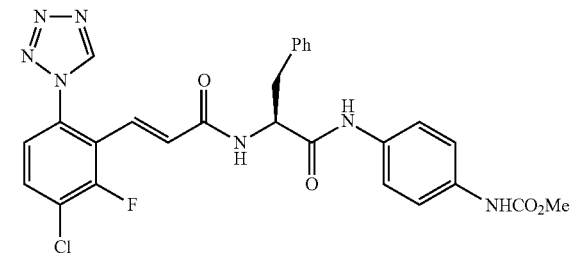
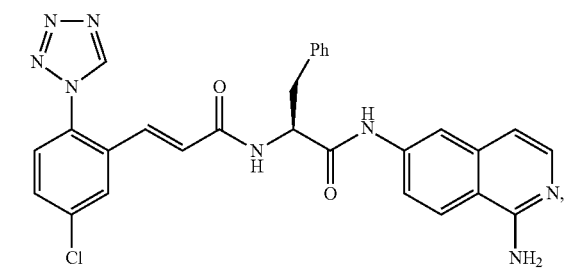
292
-continued
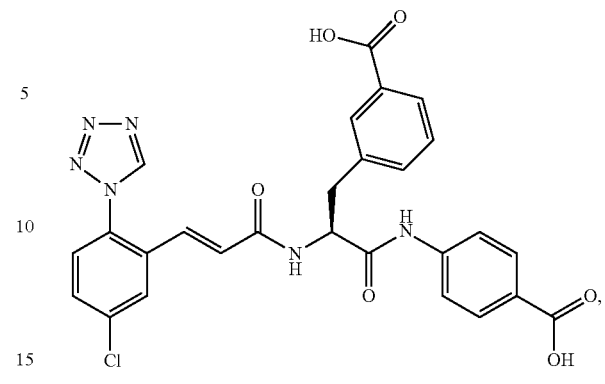
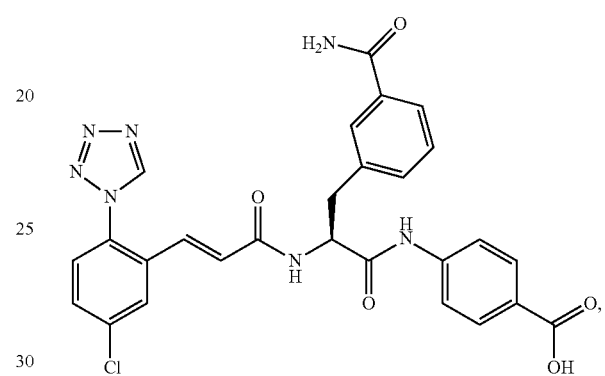
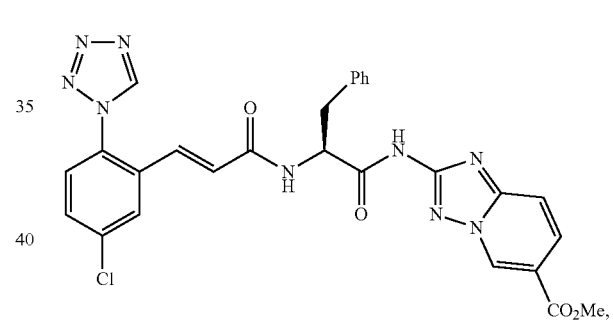
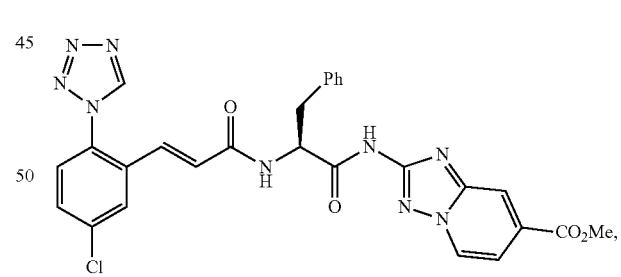
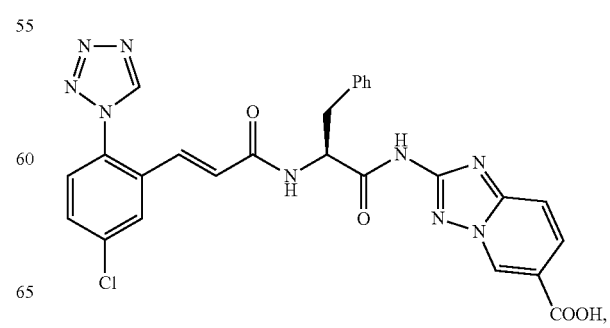

293
-continued
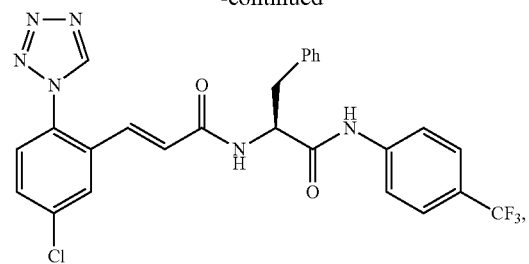
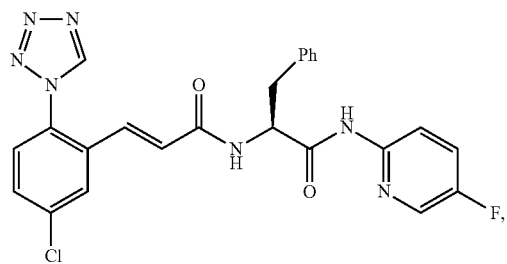
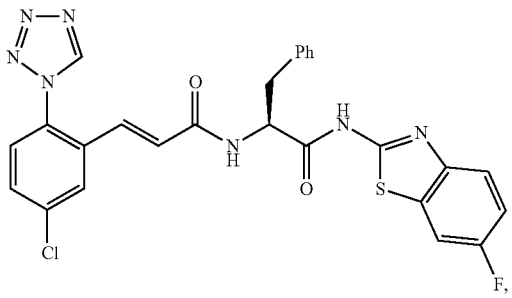
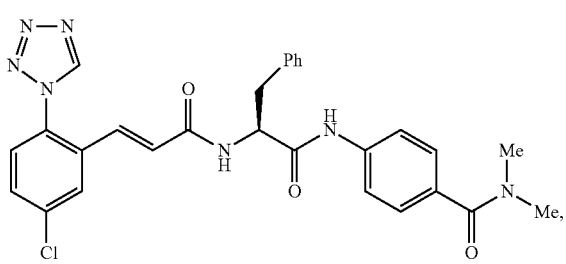
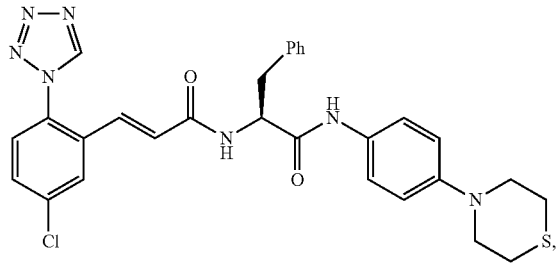
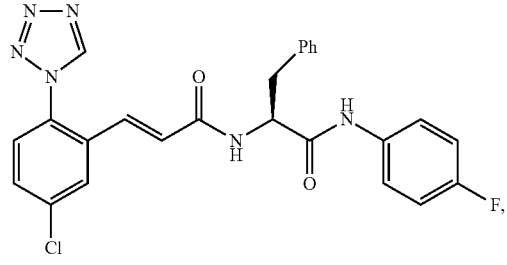
294
-continued
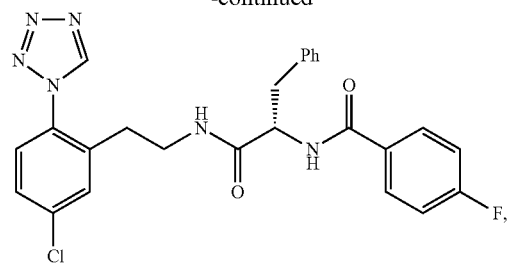
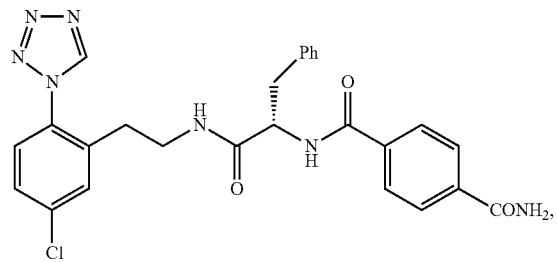
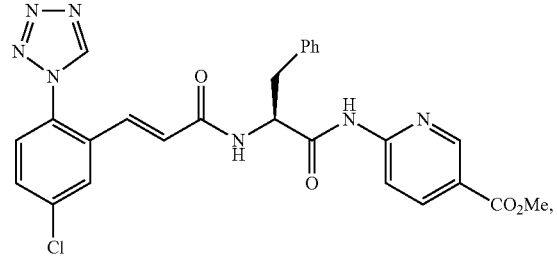
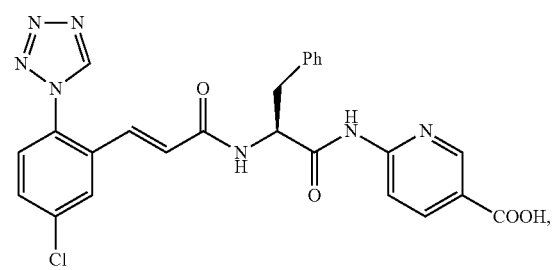
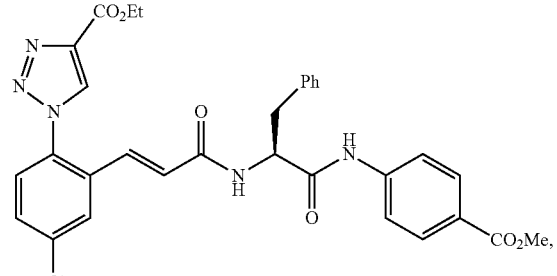
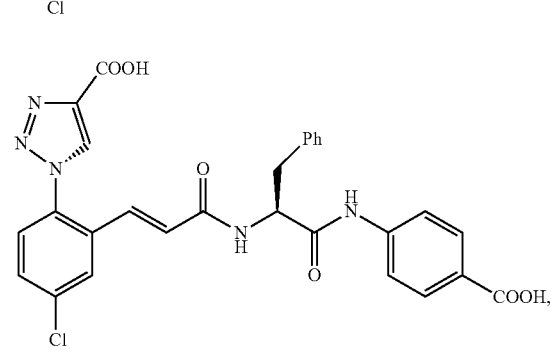

295
-continued
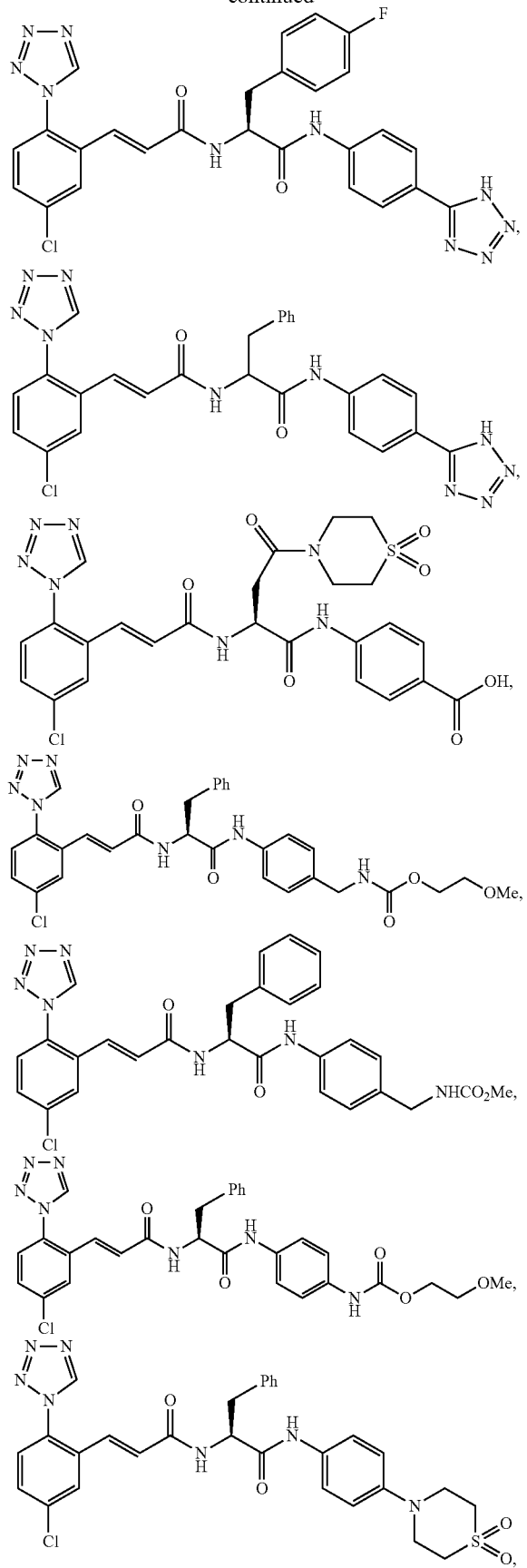
296
-continued
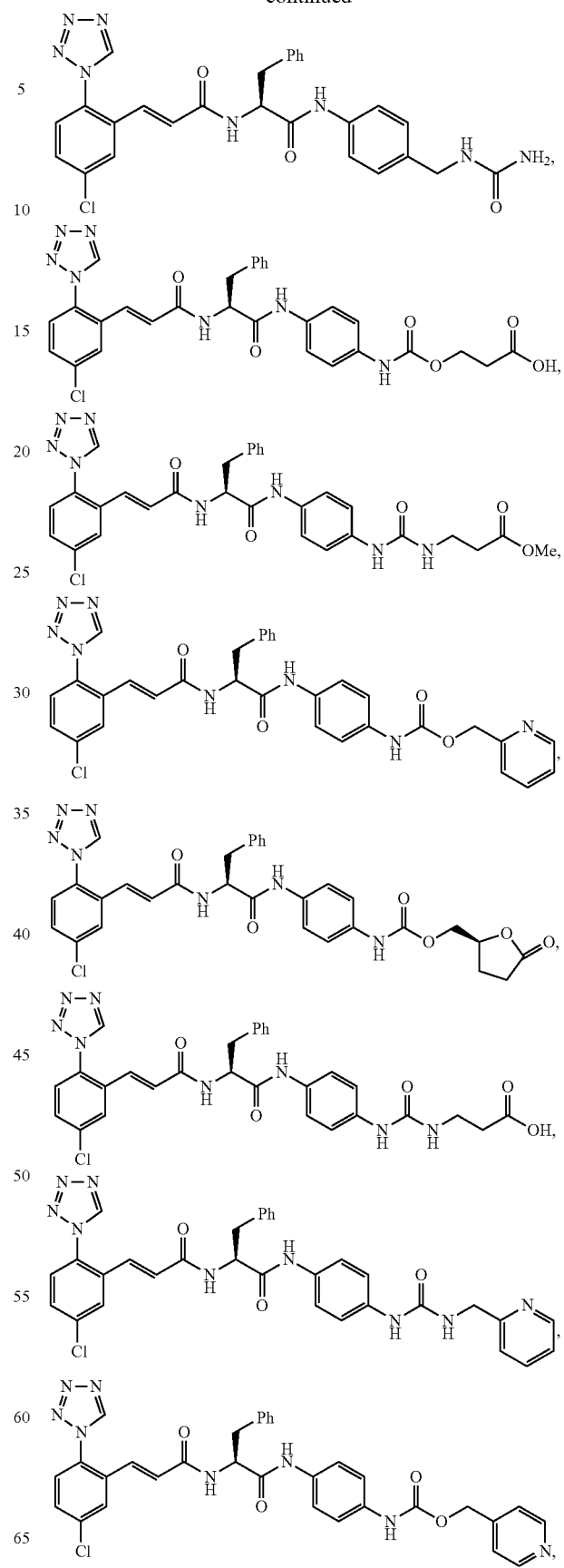

297
-continued
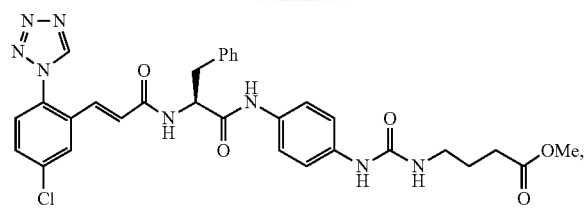
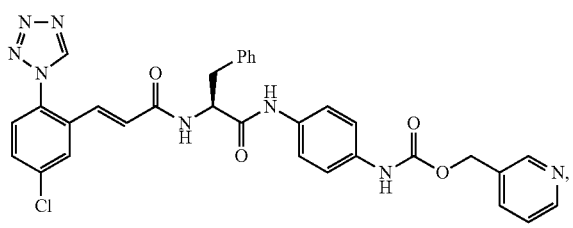
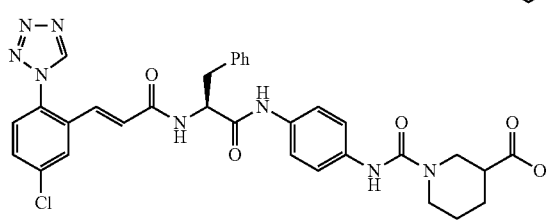
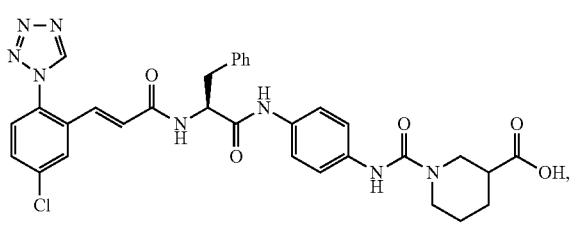
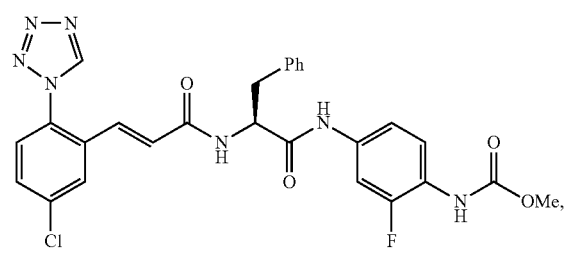
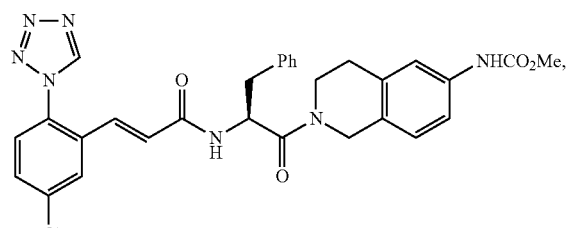
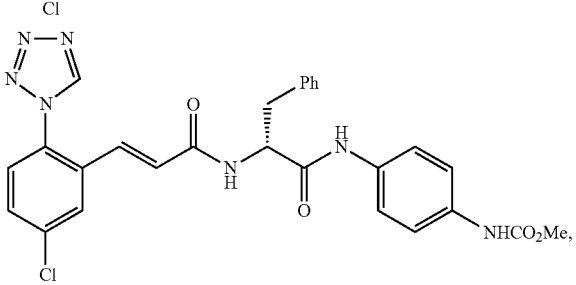
298
-continued
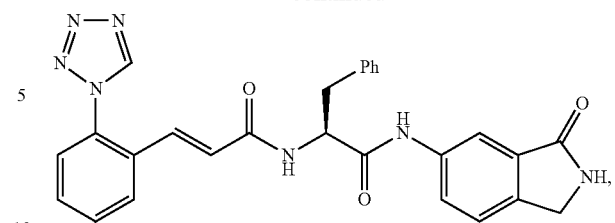
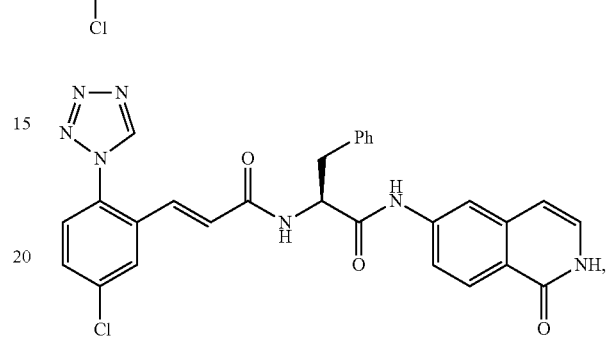
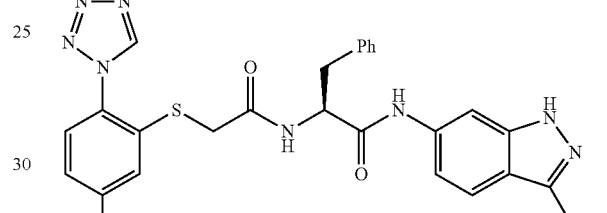
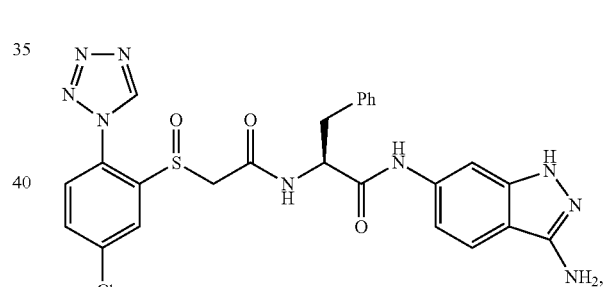
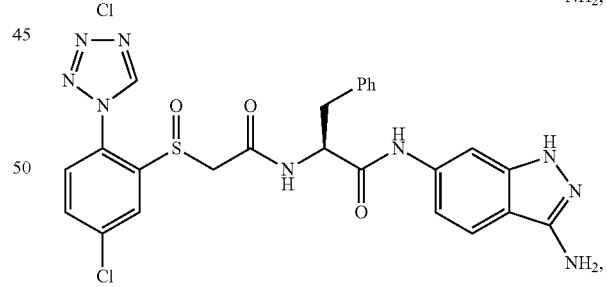
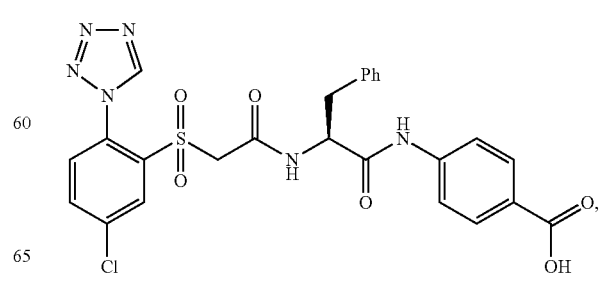

299
-continued
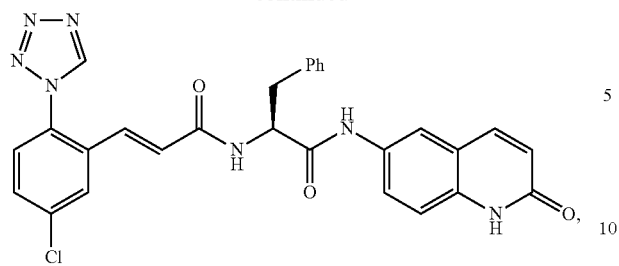
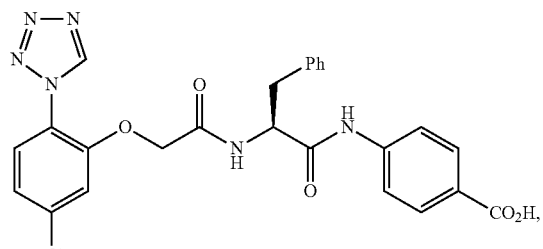
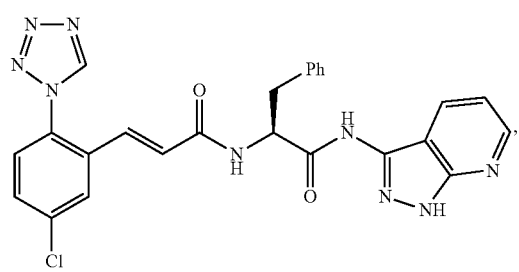
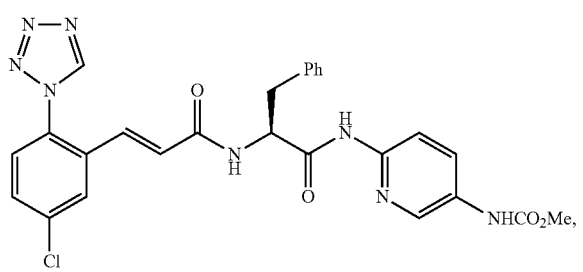
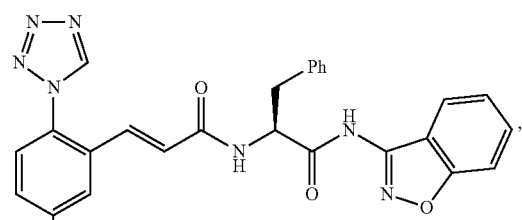
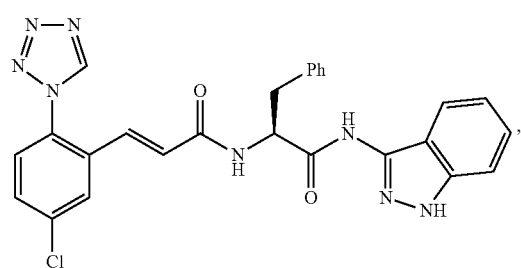
300
-continued
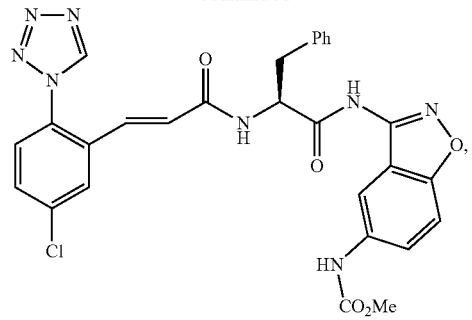
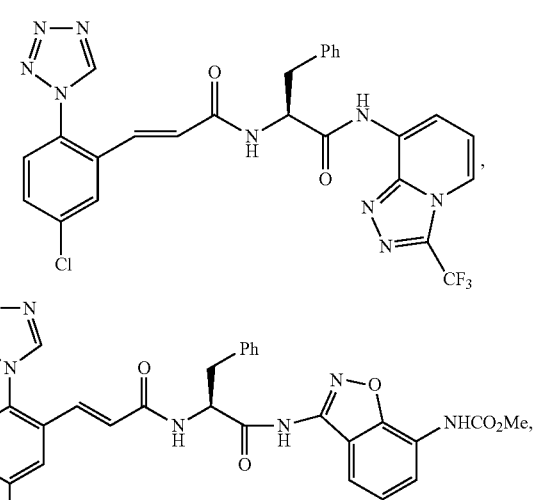
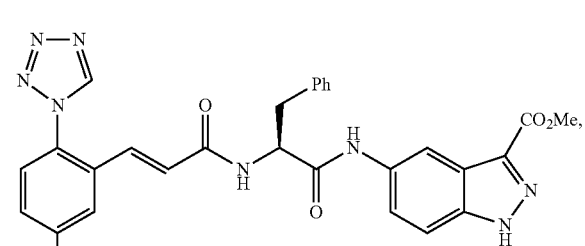
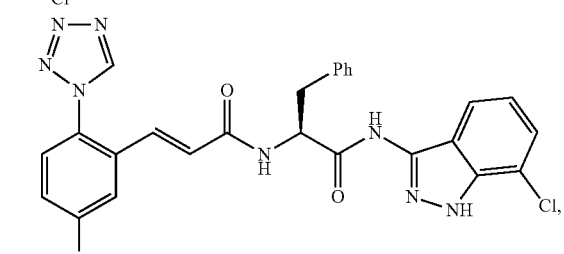
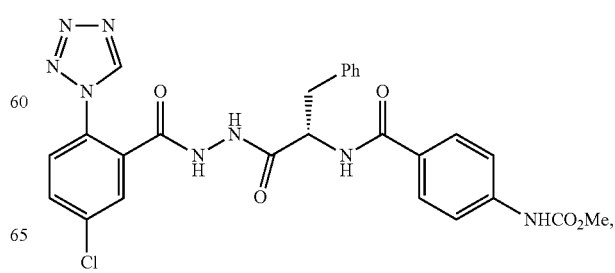

301
-continued
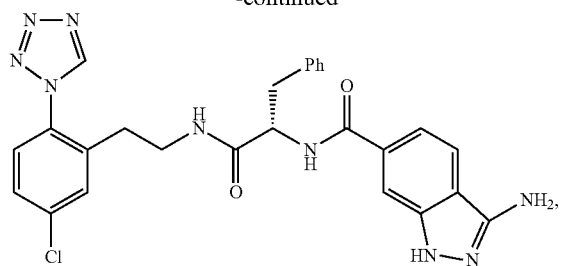
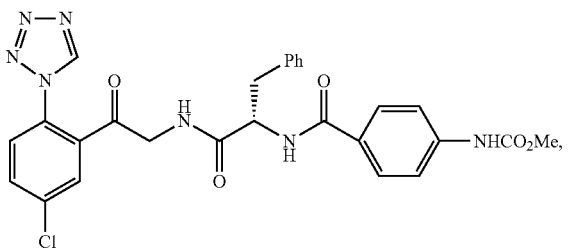
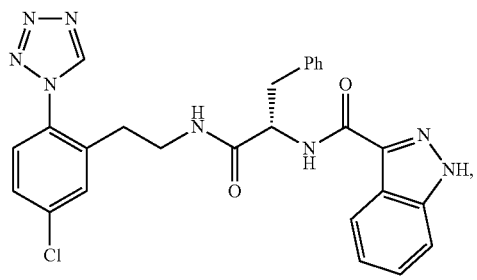
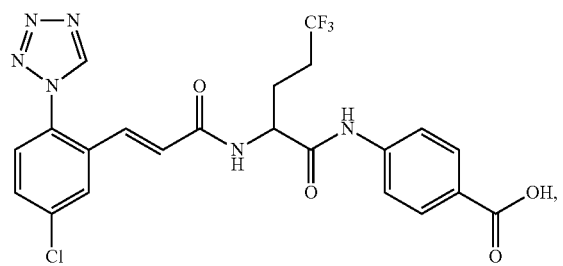
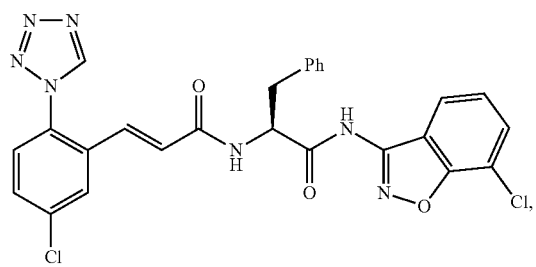
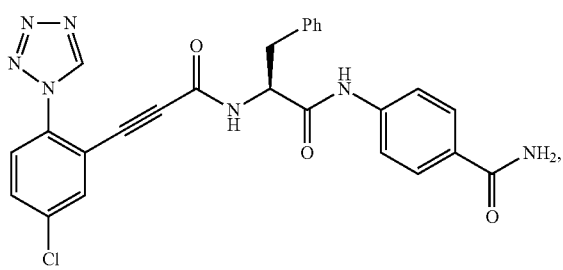
302
-continued
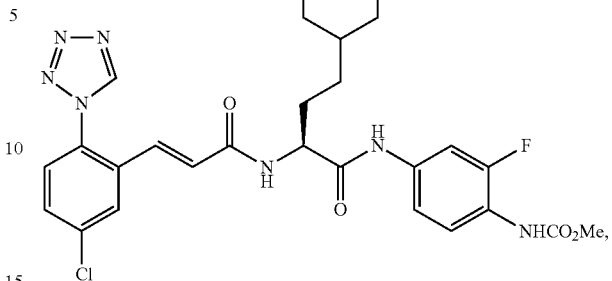
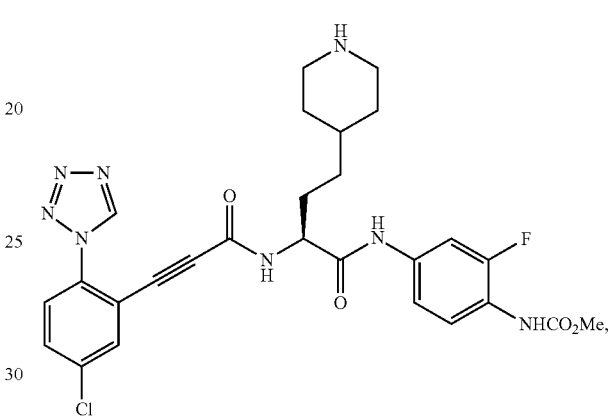
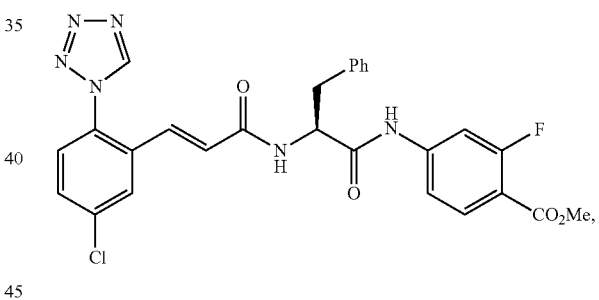
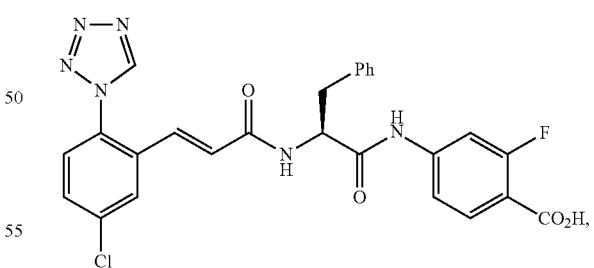
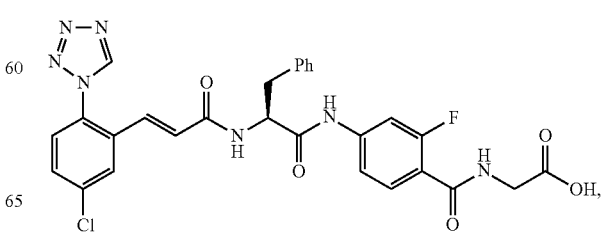

303
-continued
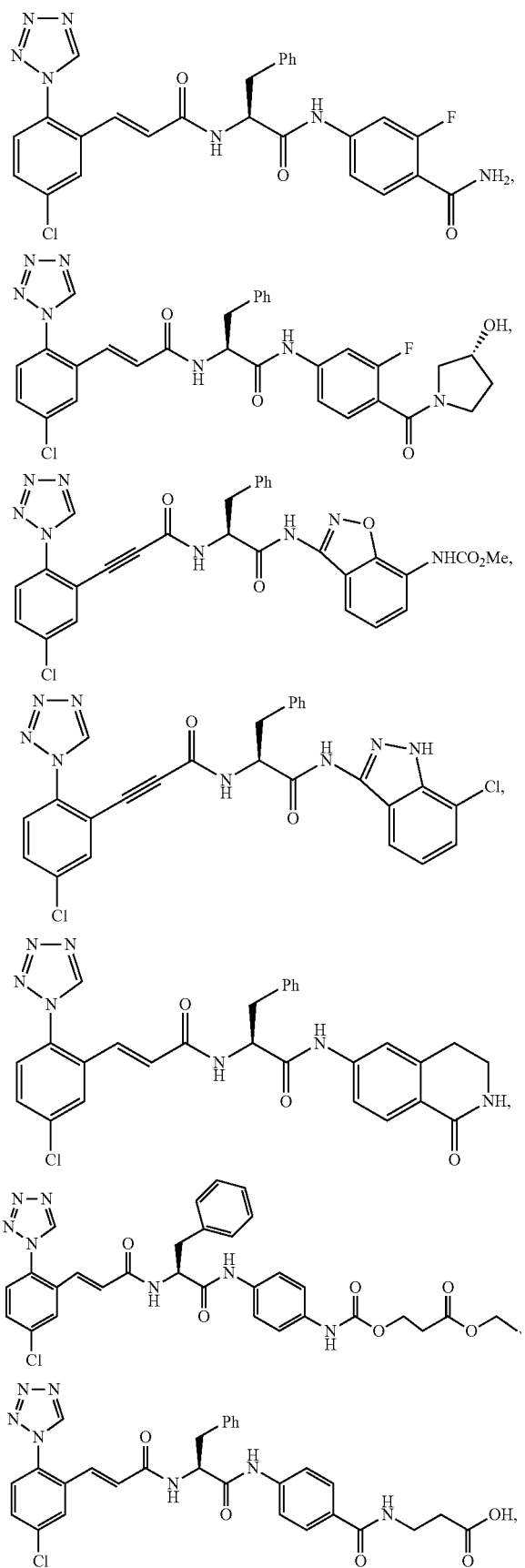
304
-continued
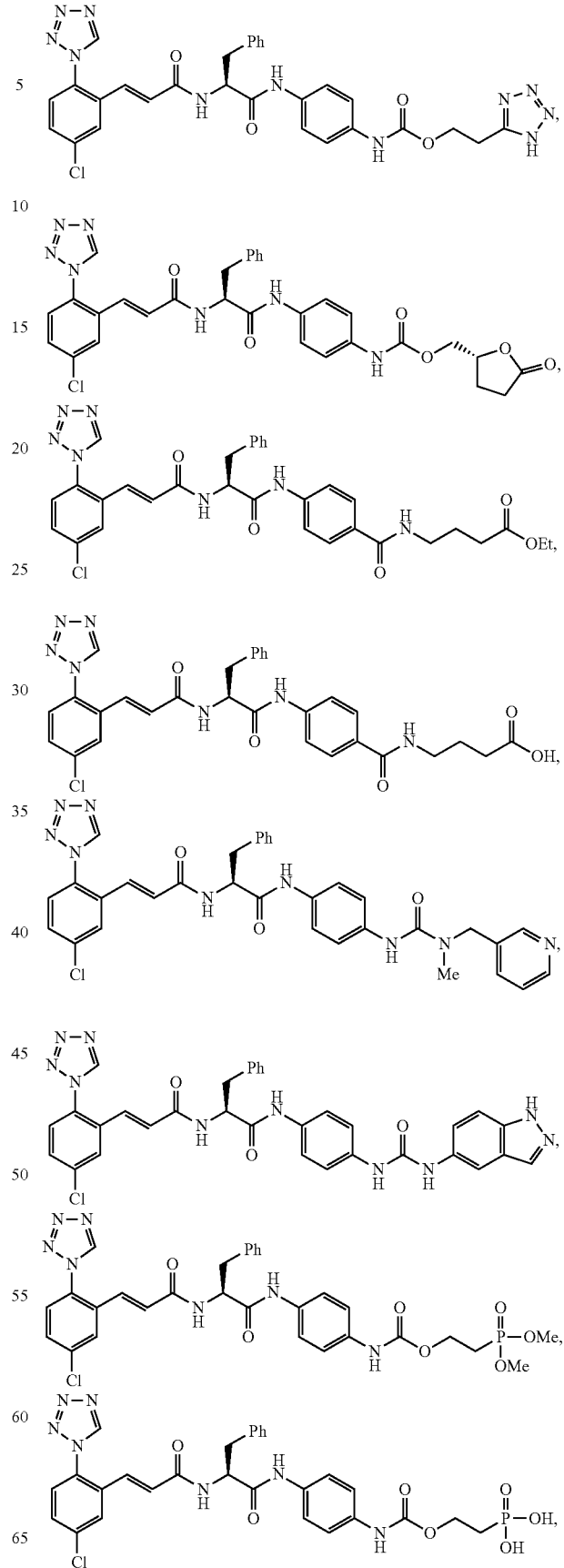

305
-continued
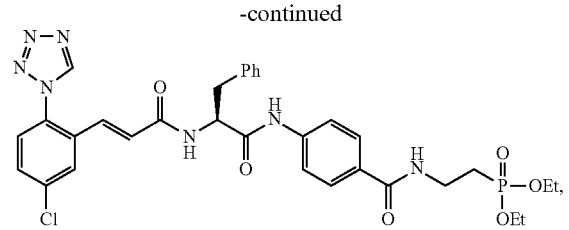
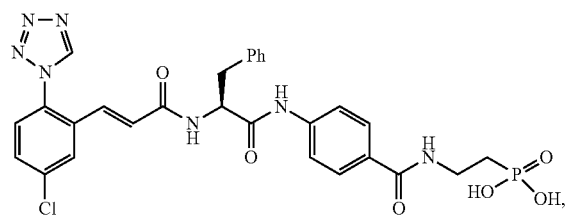
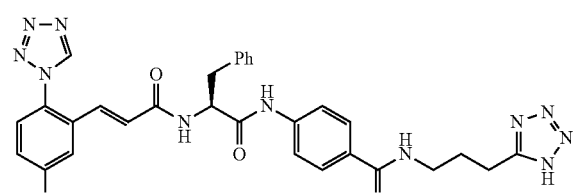
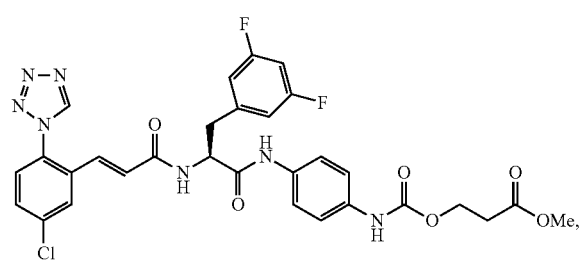
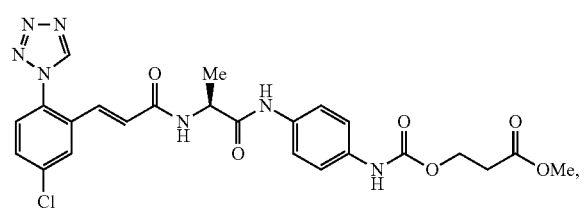
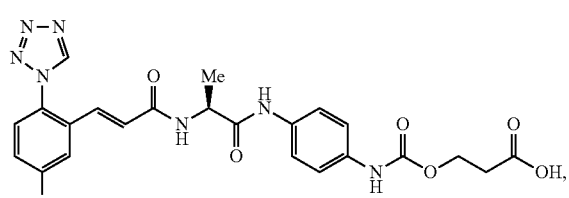
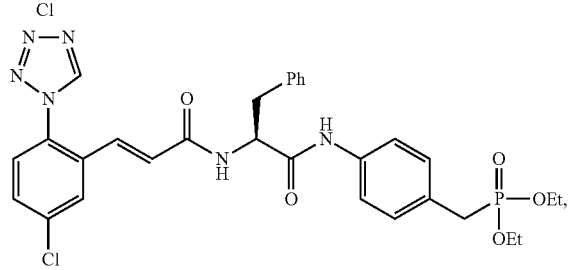
306
-continued
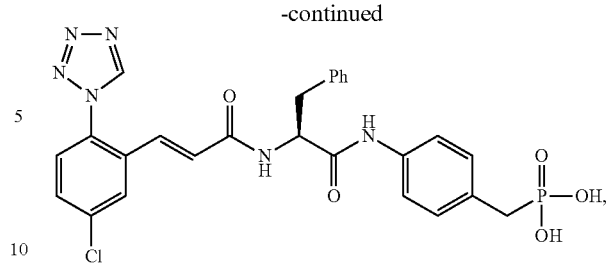
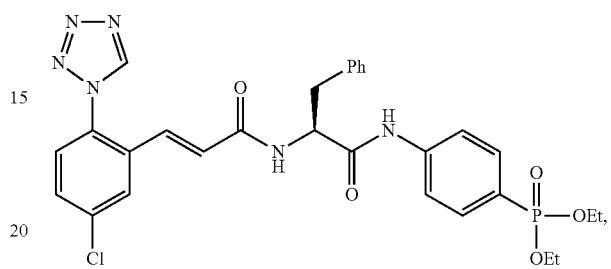
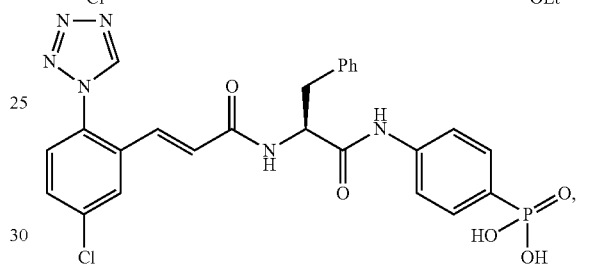
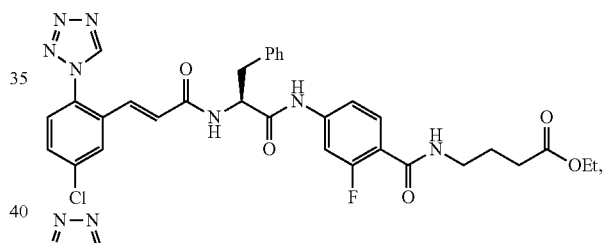
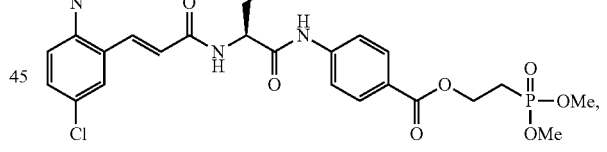
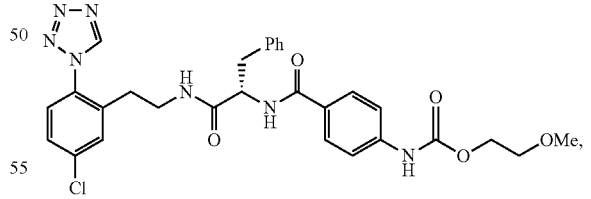
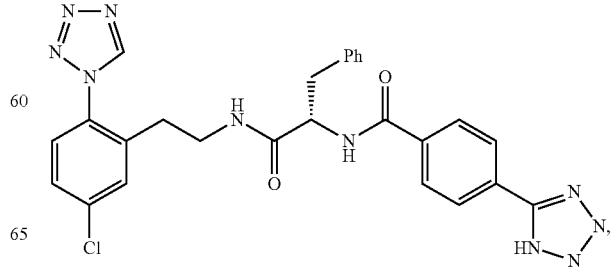

307
-continued
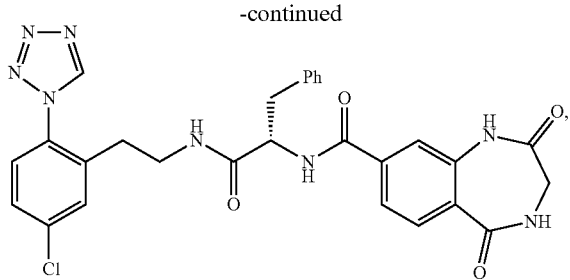
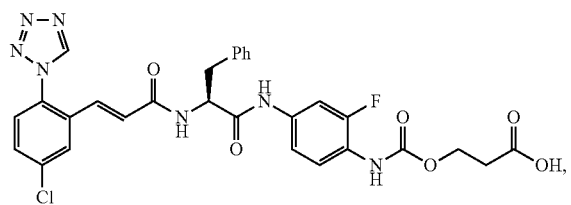
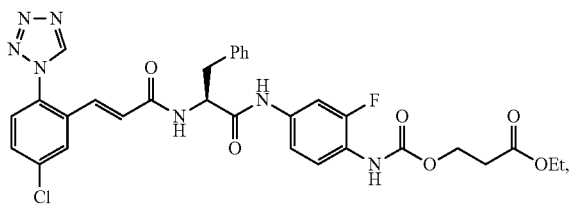
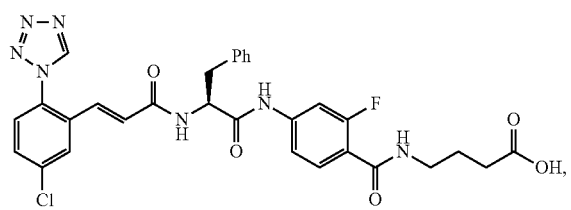
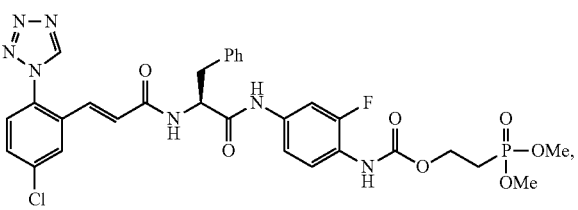
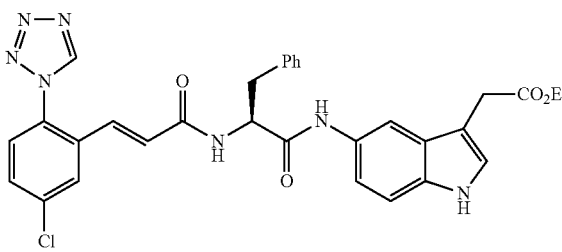
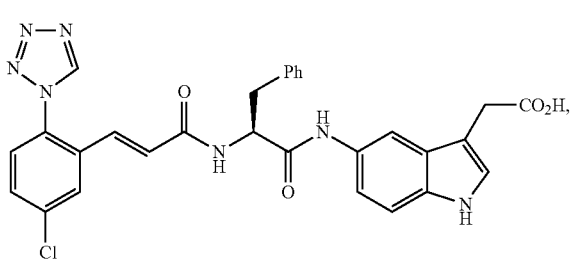
308
-continued
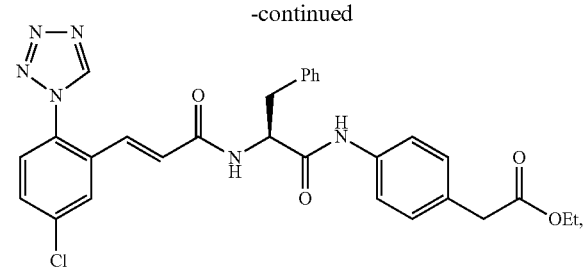
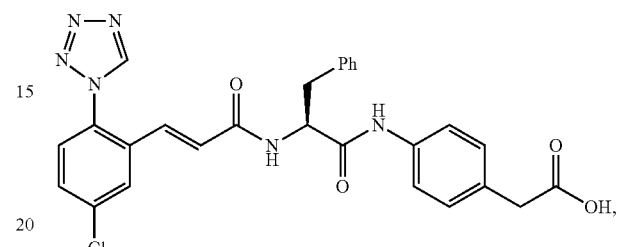
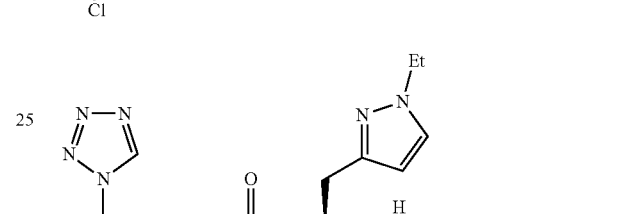
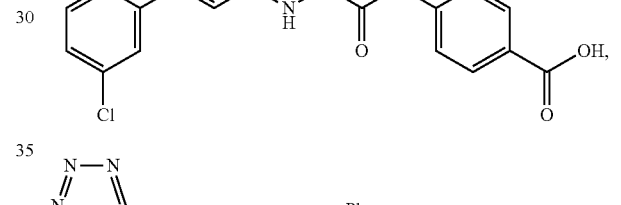
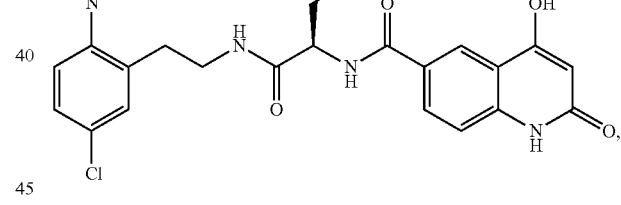
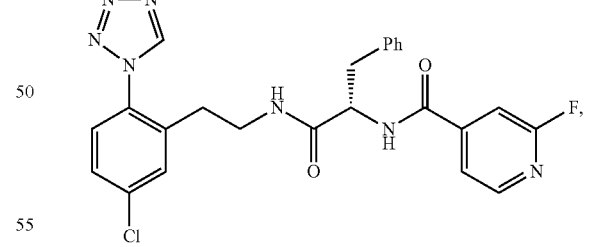
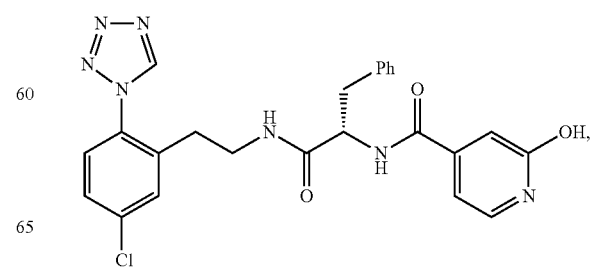

309
-continued
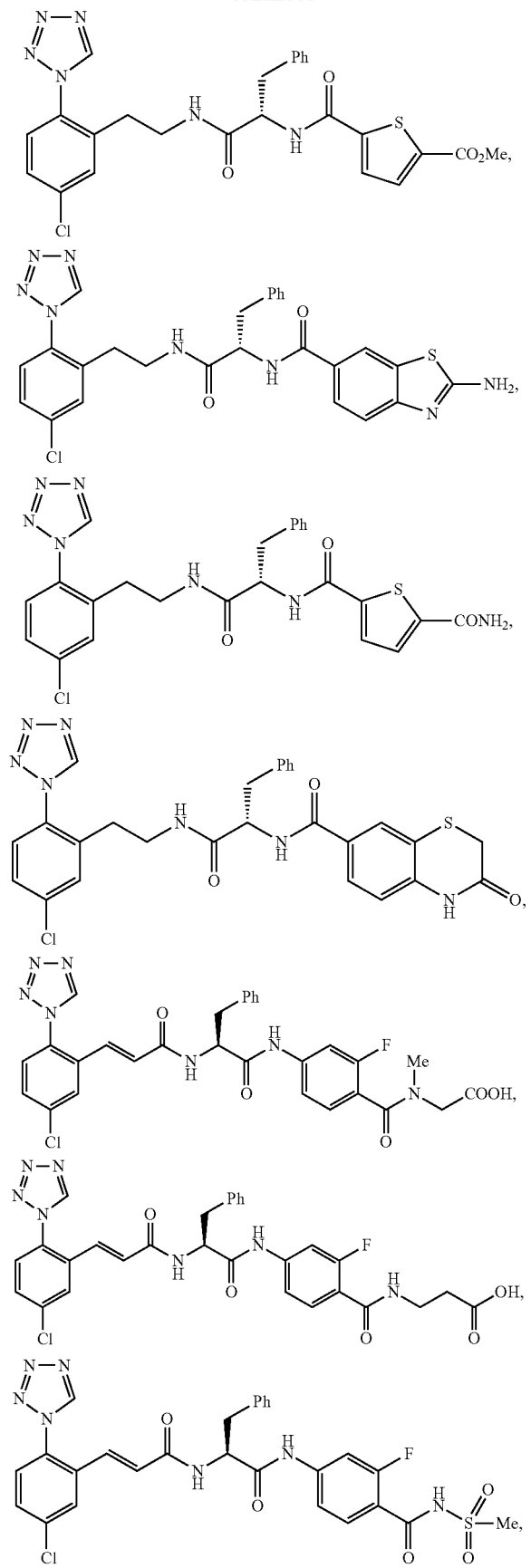
310
-continued
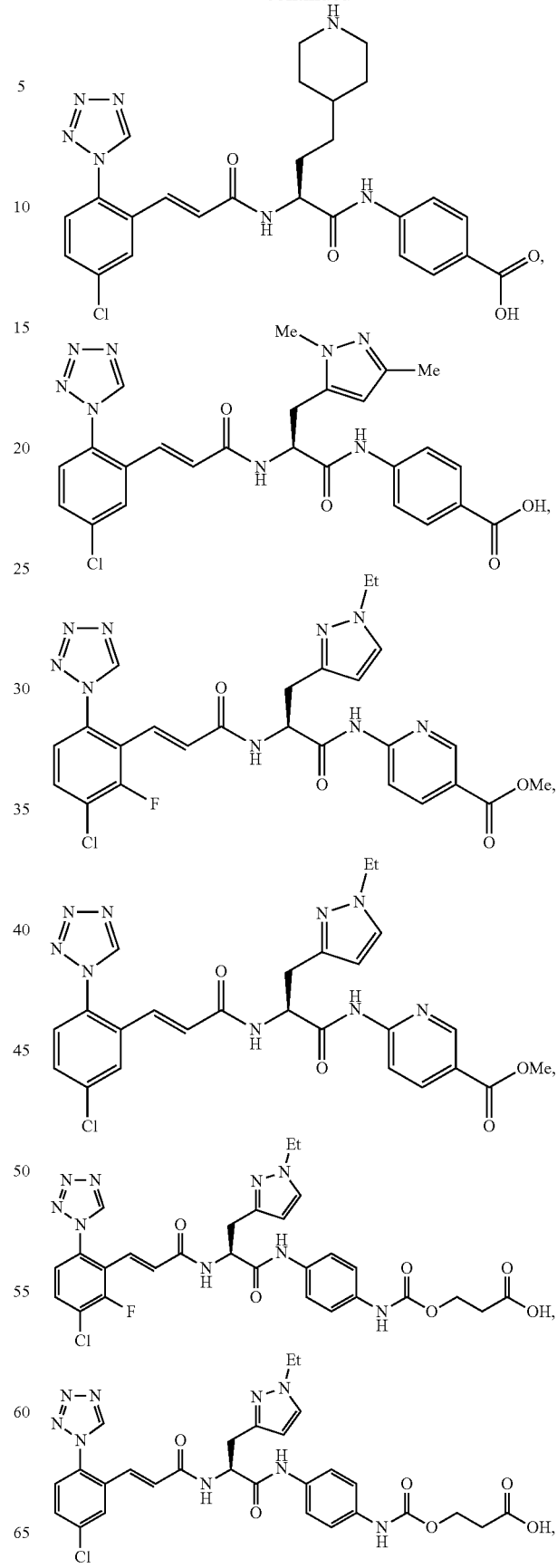

311
-continued
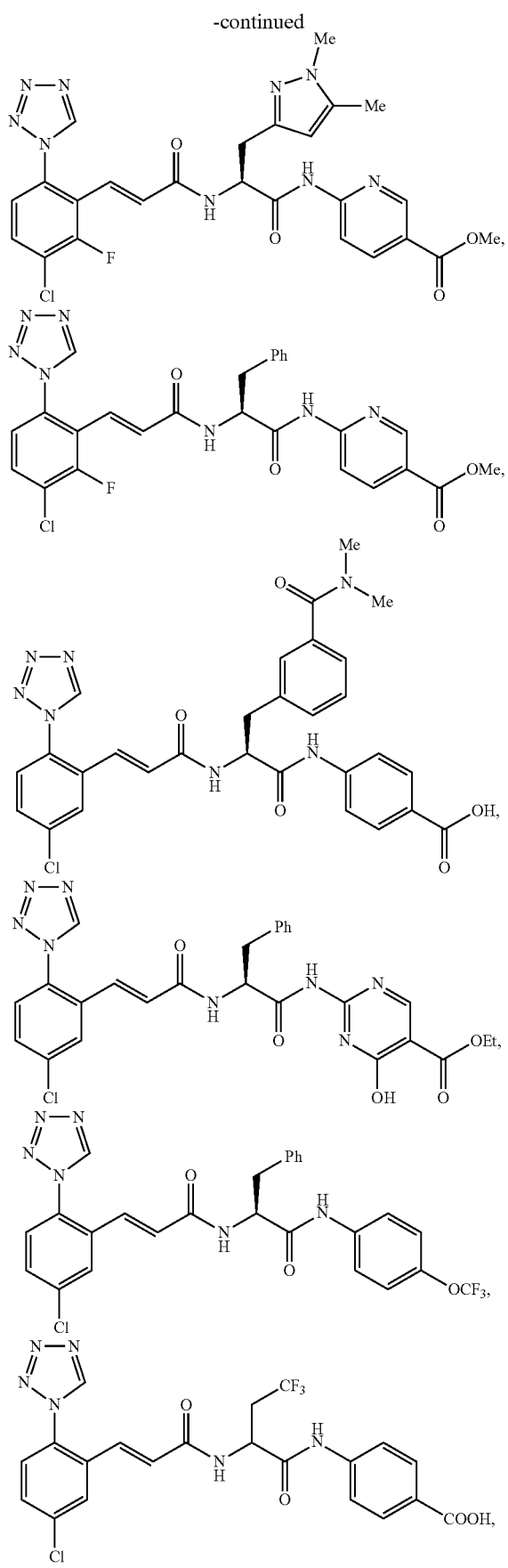
312
-continued
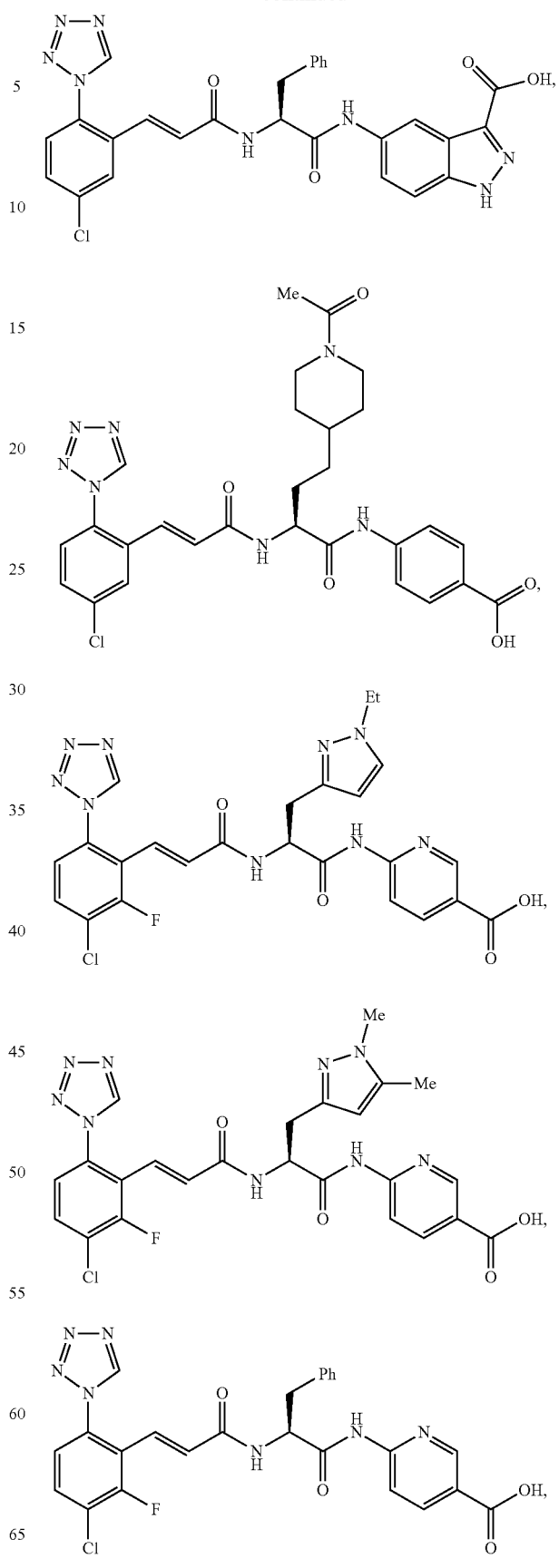

313
-continued
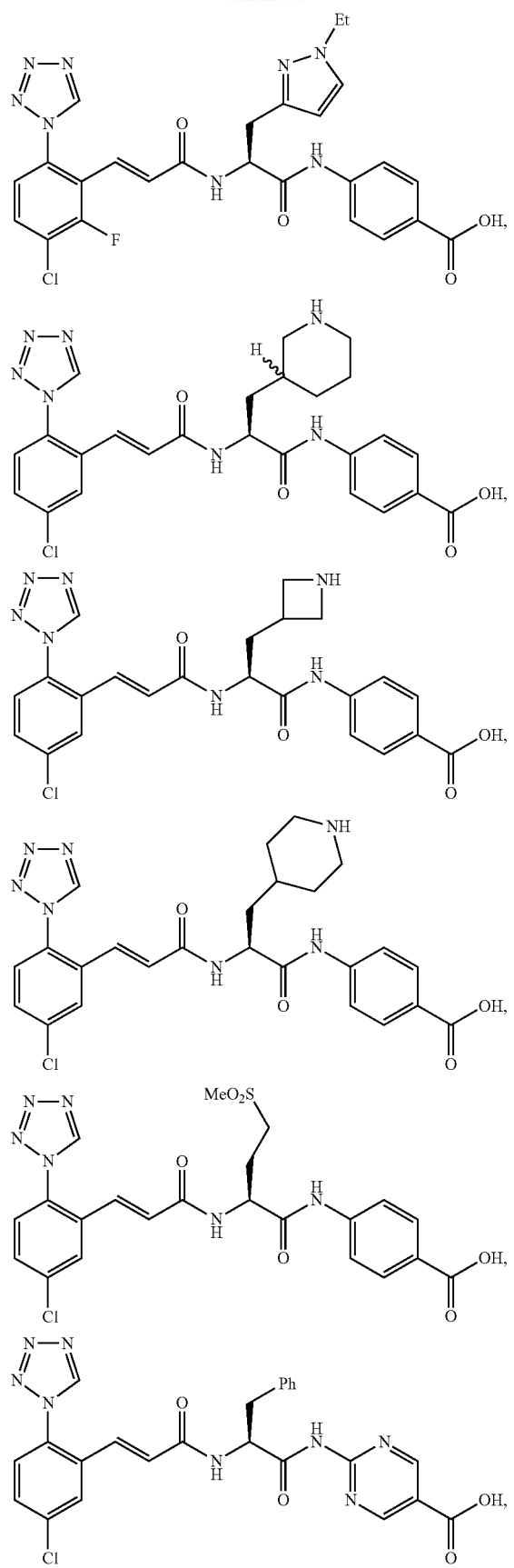
314
-continued
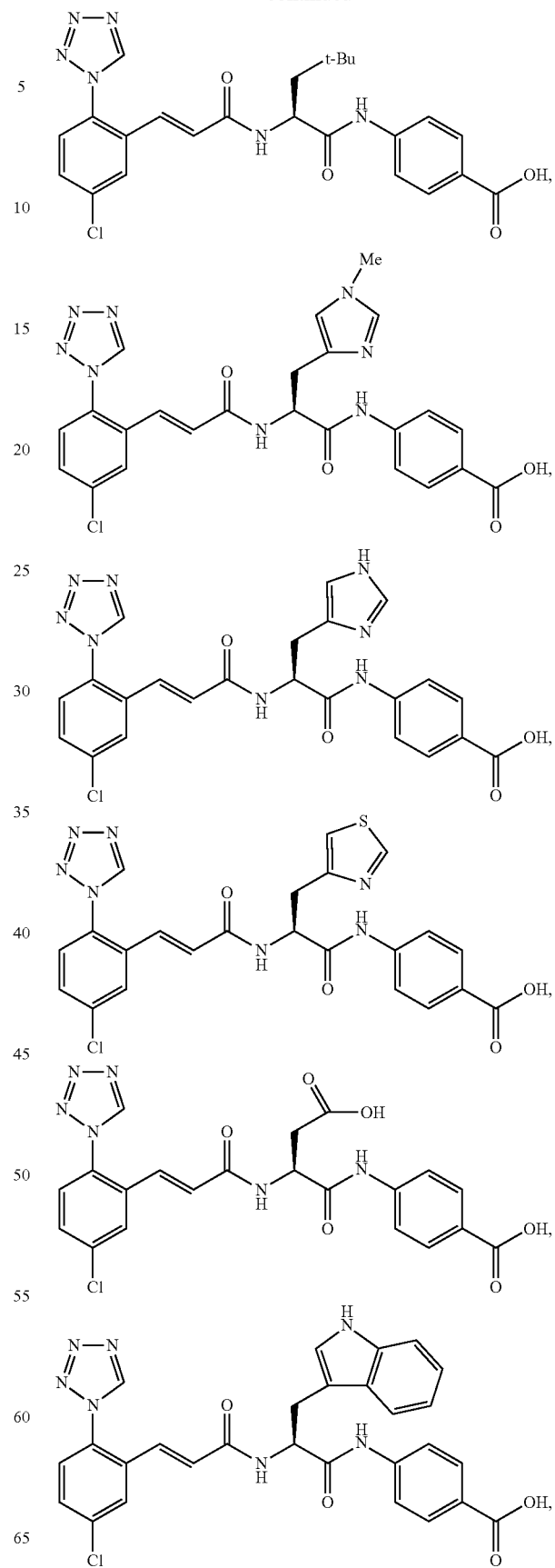

315
-continued
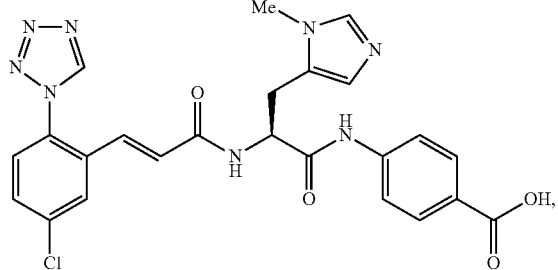
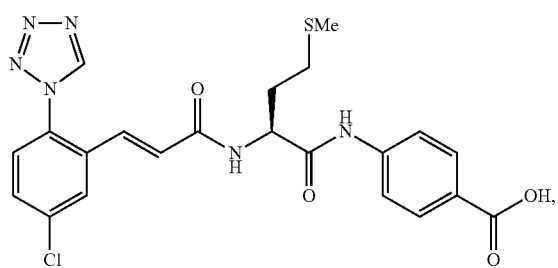
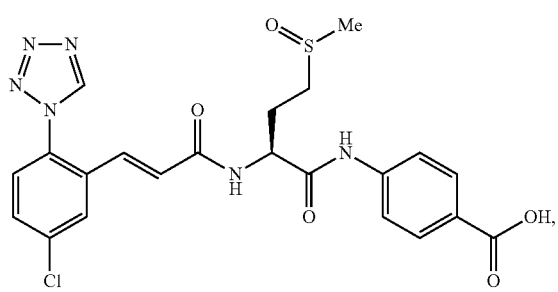
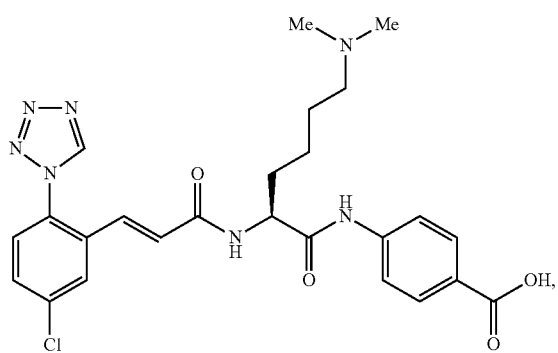
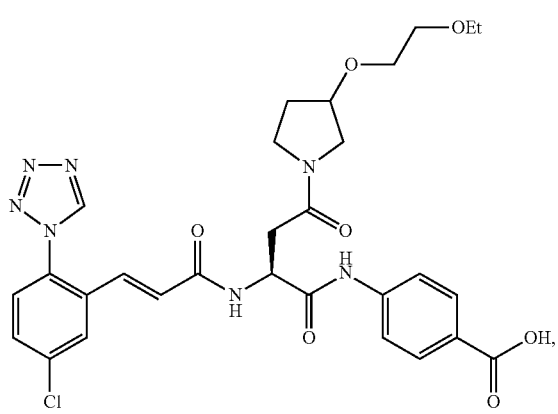
316
-continued
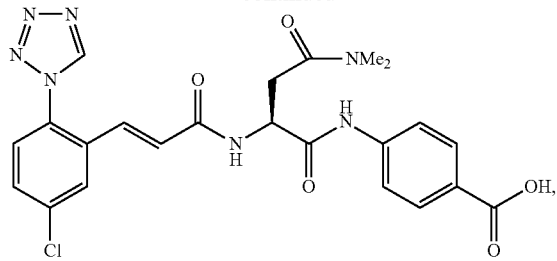
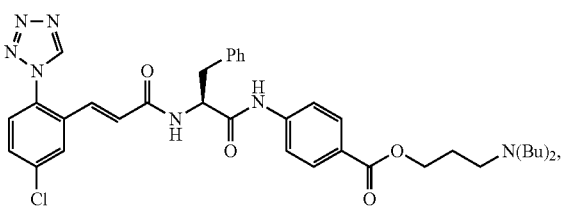
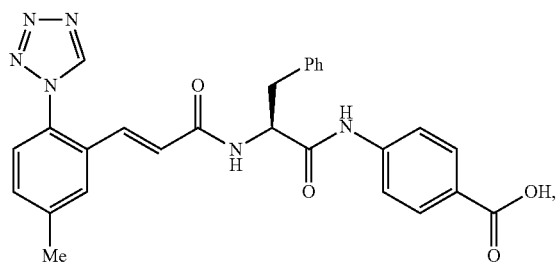
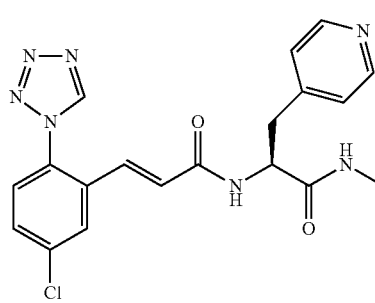
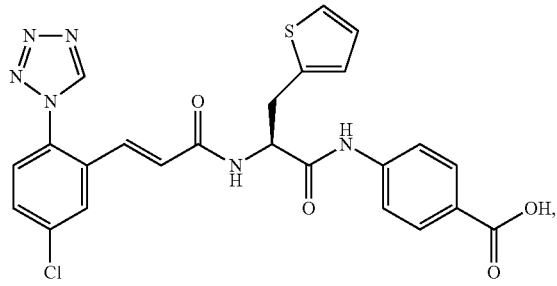
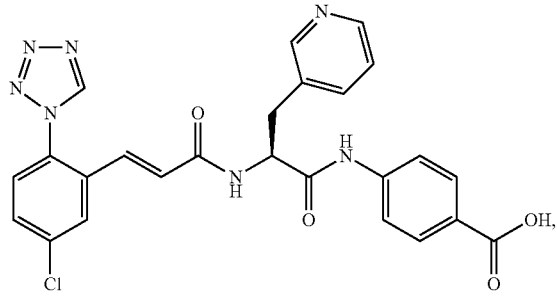

317
-continued
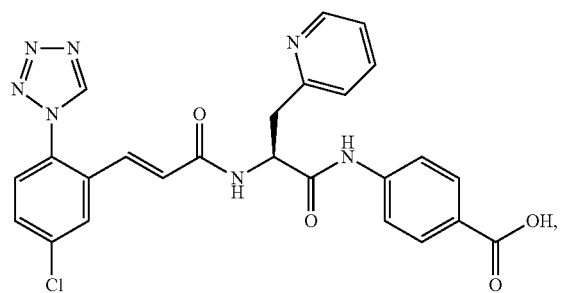
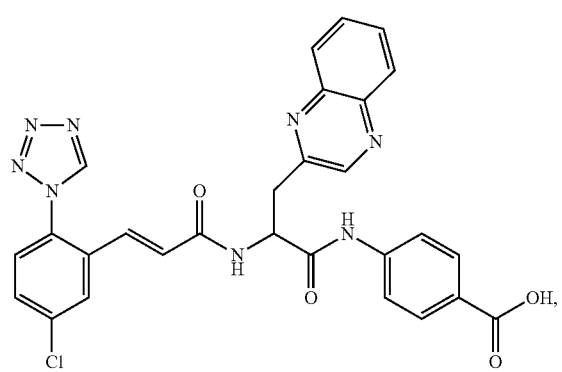
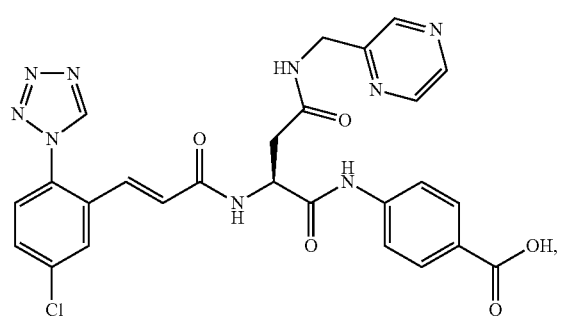
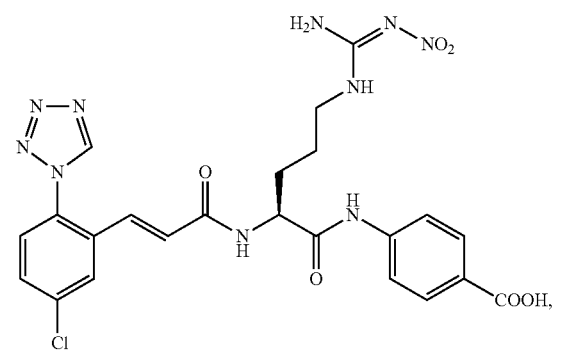
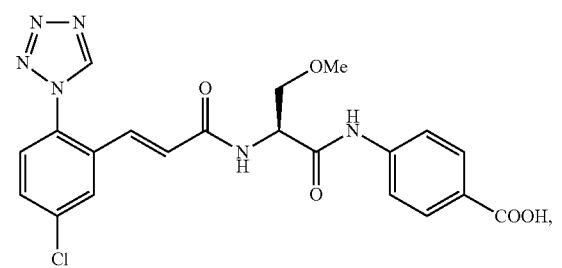
318
-continued
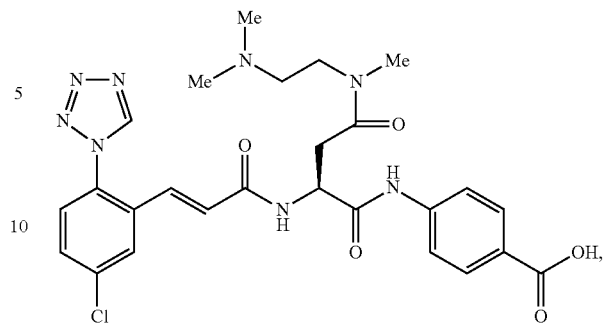
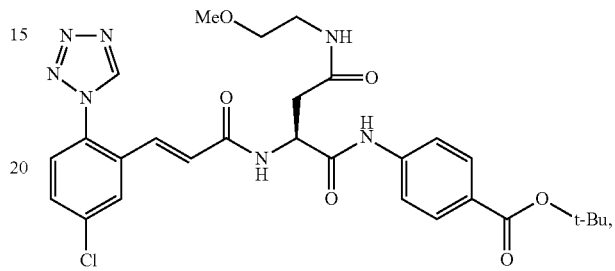
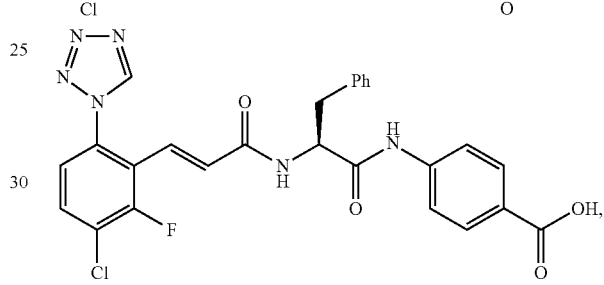
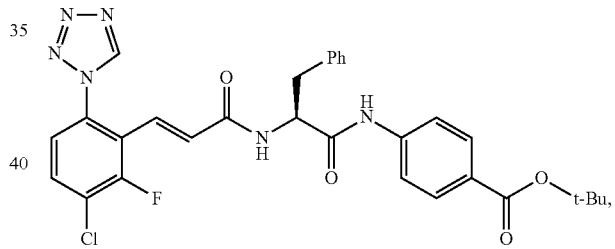
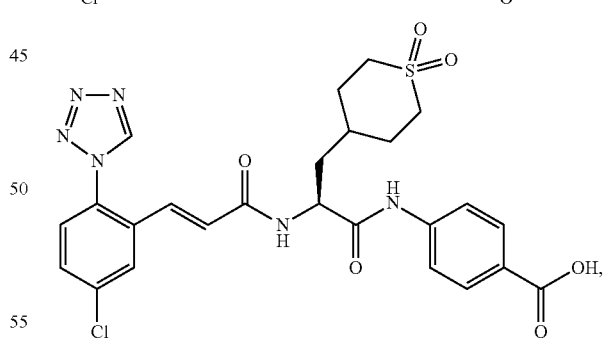
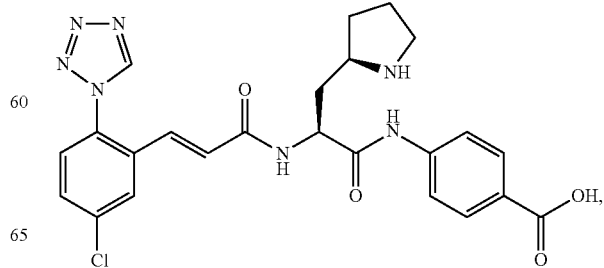

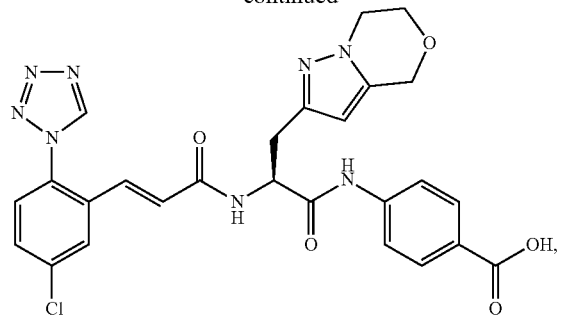
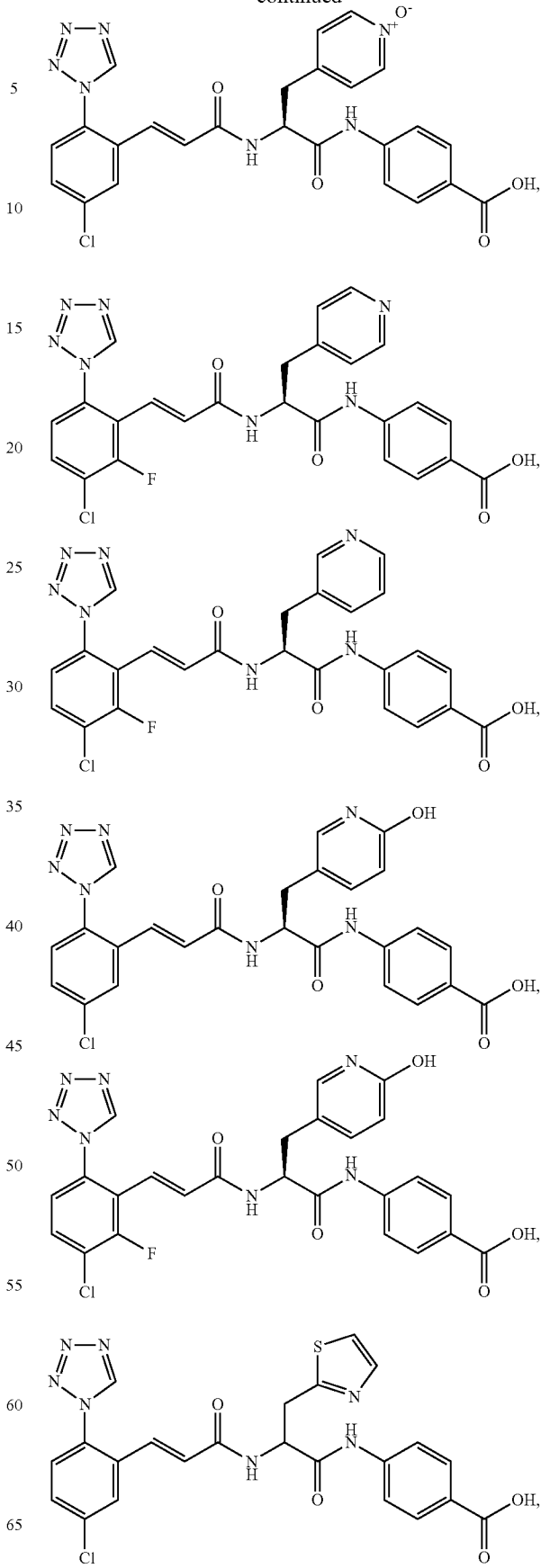

321
-continued
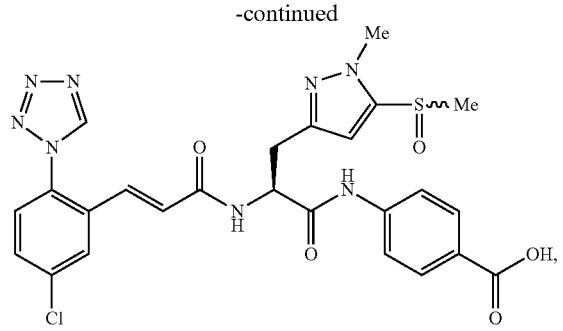
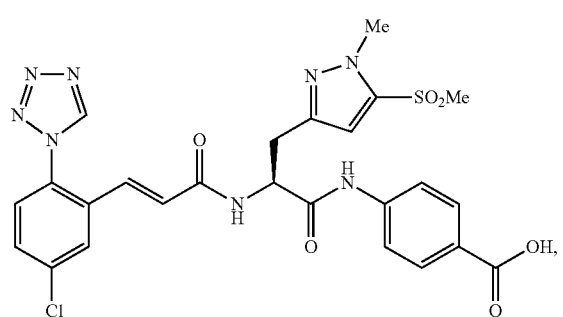
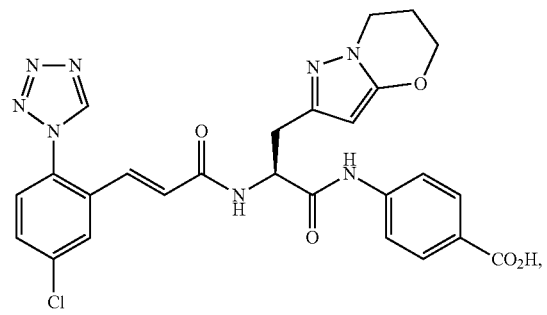
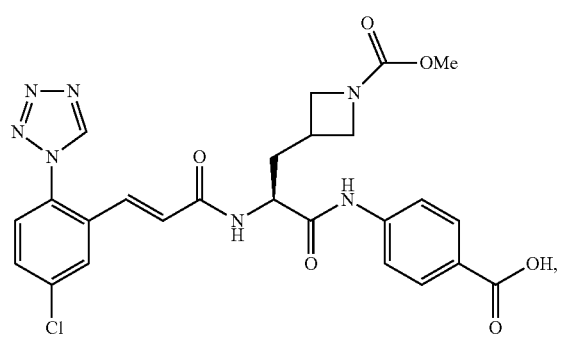
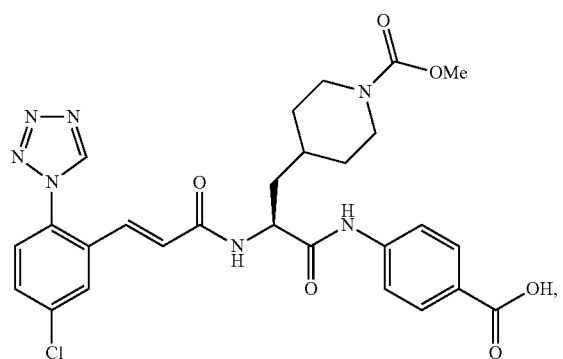
322
-continued
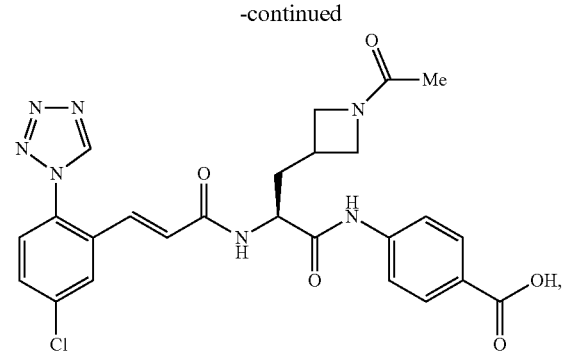
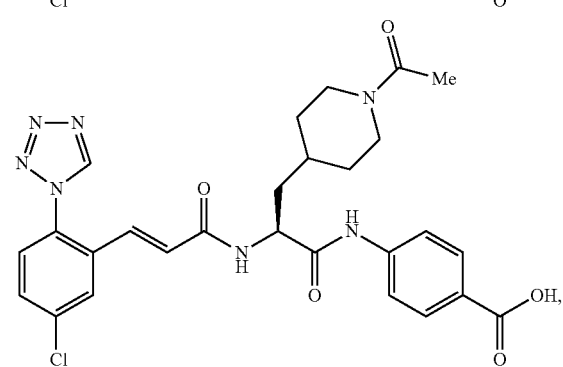
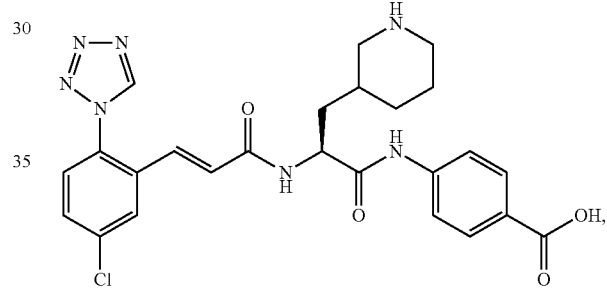
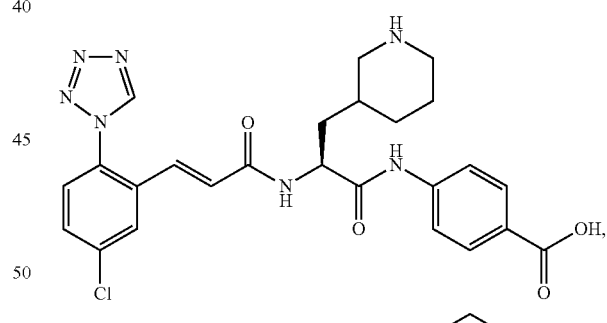
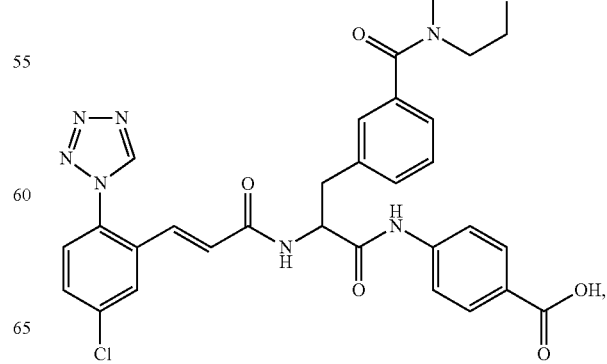

323
-continued
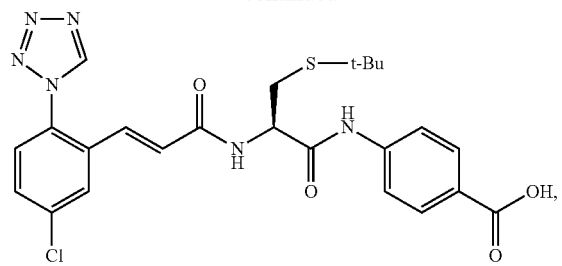
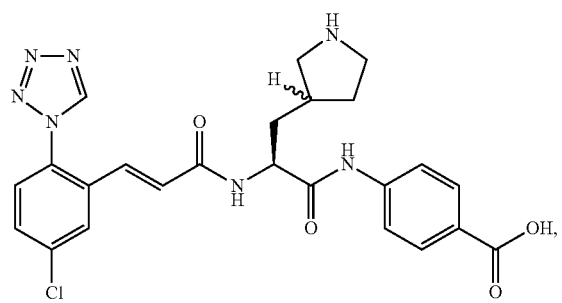
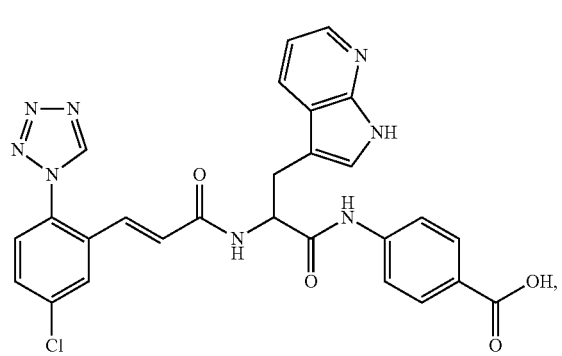
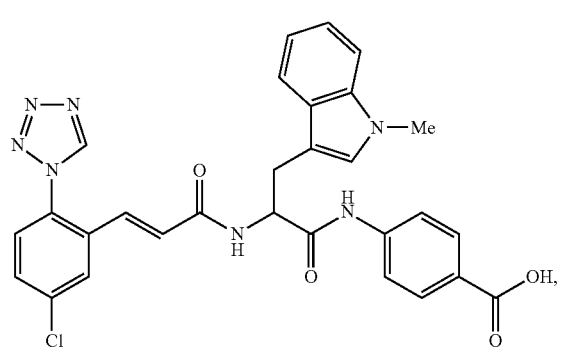
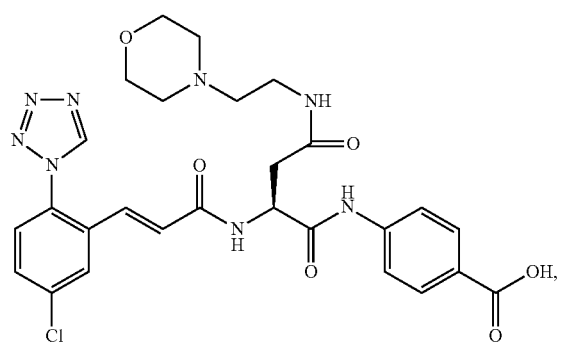
324
-continued
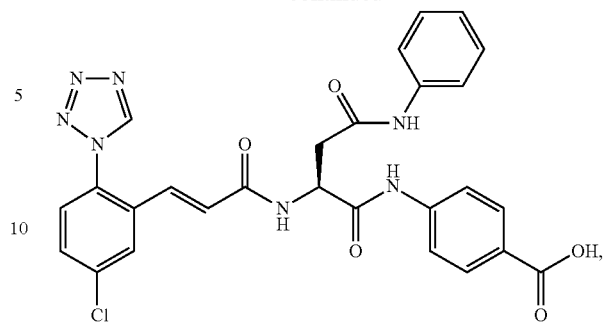
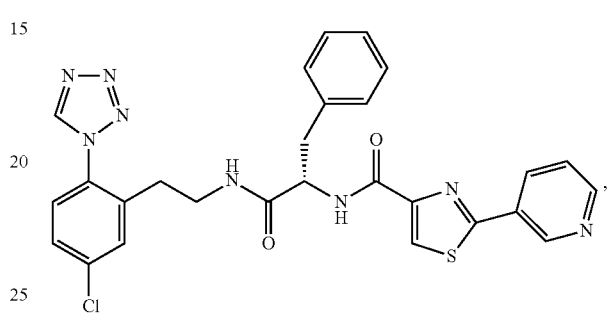
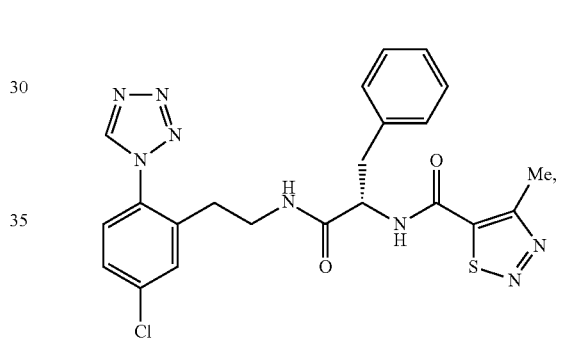
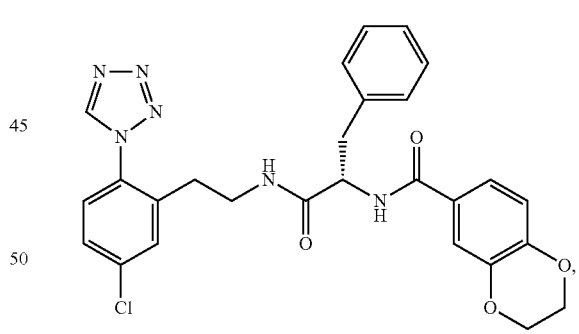
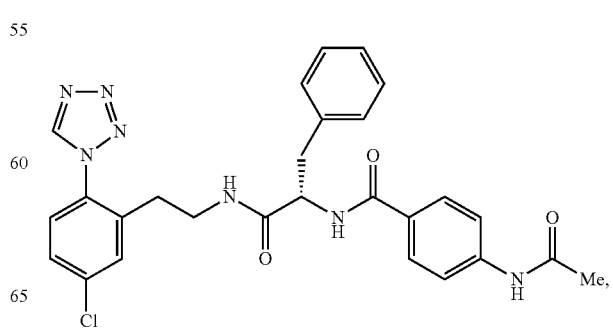

325
-continued
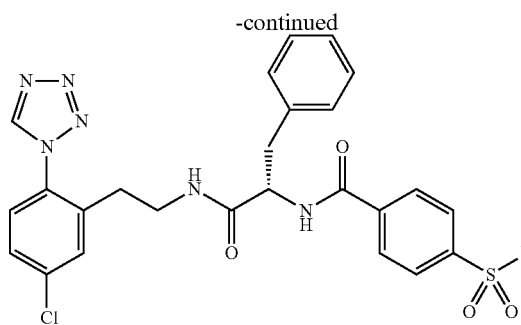
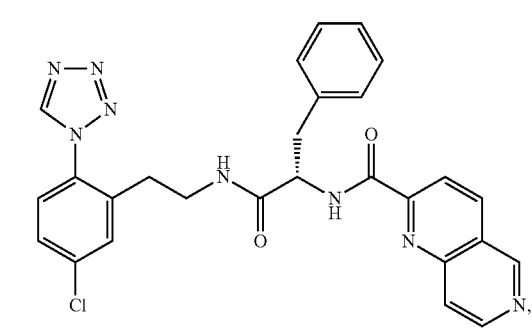
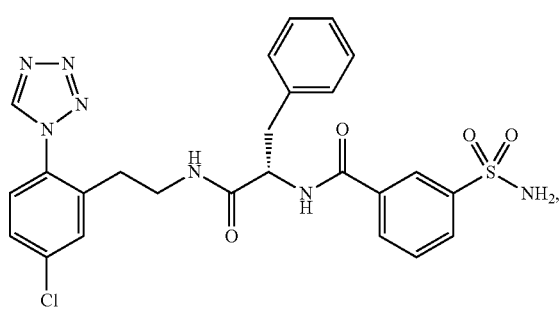
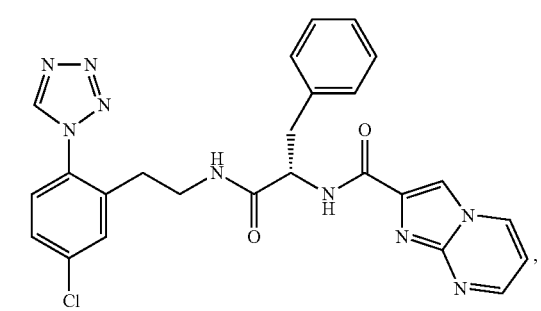
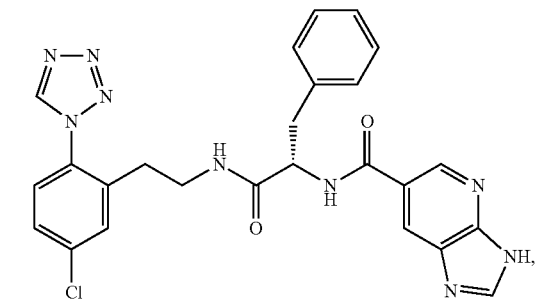
326
-continued
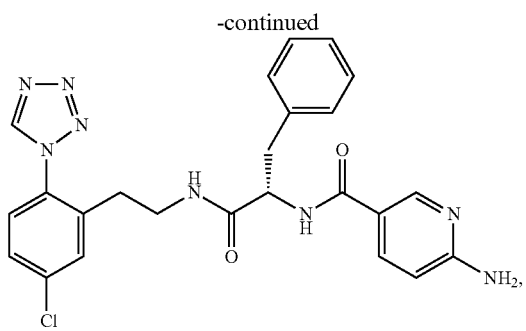
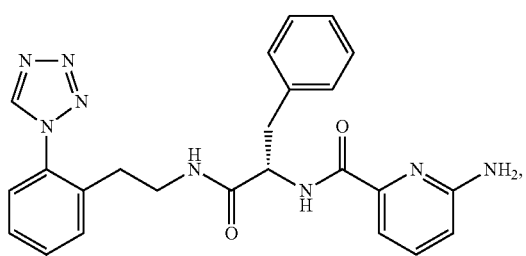
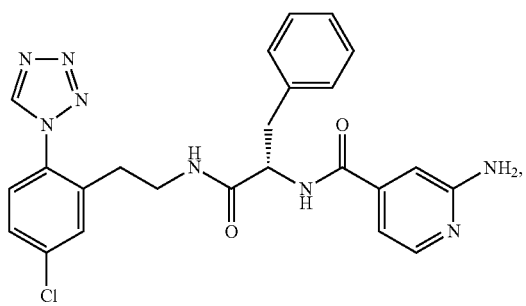
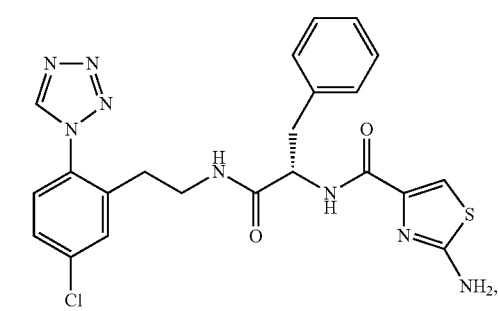
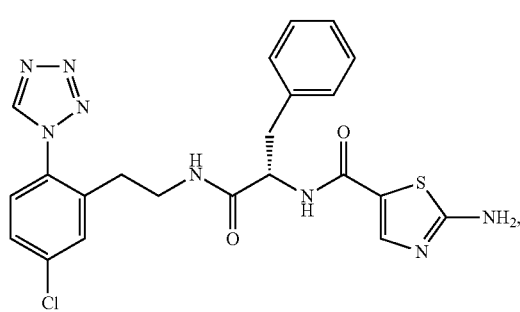

327
-continued
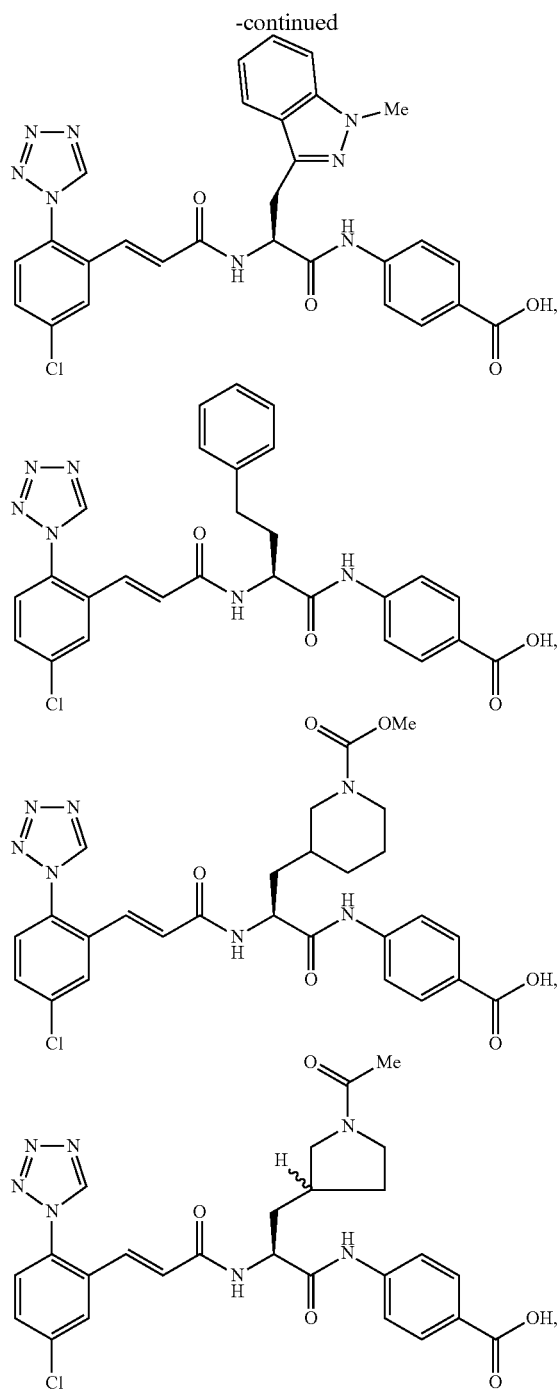
328
-continued
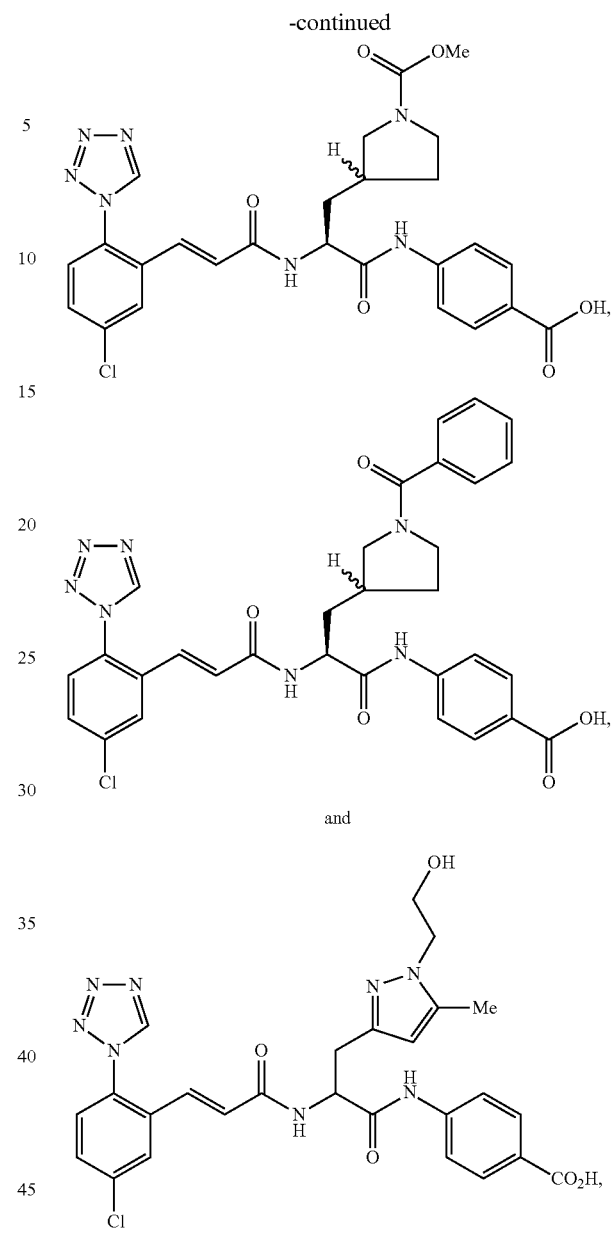
or a stereoisomer, a tautomer, or a pharmaceutically acceptable salt thereof.
* * * * *

UNITED STATES PATENT AND TRADEMARK OFFICE
CERTIFICATE OF CORRECTION

PATENT NO. : 8,367,709 B2
APPLICATION NO. : 12/663861
DATED : February 5, 2013
INVENTOR(S) : Donald J. P. Pinto et al.

It is certified that error appears in the above-identified patent and that said Letters Patent is hereby corrected as shown below:

On the Title Page:

Item (56), References Cited, under OTHER PUBLICATIONS:

Column 2, Coleman, R. reference, line 2, change "Antiagiogenic" to -- Antiangiogenic --.

In the Claims:

Claim 1:

Column 254, line 43, change "—$(CH_2)_r5$-" to -- —$(CH_2)_r$-5- --.

Column 255, line 7, change "—$CONR^{81}R^c$," to -- —$CONR^8R^c$, --.

Column 255, line 49, change "—$NR^8C(O)R^d$, —$NR^8C(O)OR^d$," to -- —$NR^8C(O)R^c$, —$NR^8C(O)OR^c$, --.

Column 255, line 50, change "—$NR^8S(O)_pR^d$," to -- —$NR^8S(O)_pR^c$, --.

Column 255, line 51, change "—$S(O)_pR^d$," to -- —$S(O)_pR^c$, --.

Column 255, line 58, change "ORE," to -- $OR^a$, --.

Column 255, line 61, change "—$NR^8S(O)_pR^d$, —$S(O)_pR^d$," to -- —$NR^8S(O)_pR^c$, —$S(O)_pR^c$, --.

Column 255, line 63, change "—$(CH_2)_rC_{3-10}$" to -- —$(CH_2)_r$-$C_{3-10}$ --.

Signed and Sealed this
Seventh Day of April, 2015

Michelle K. Lee
*Director of the United States Patent and Trademark Office*

CERTIFICATE OF CORRECTION (continued)
U.S. Pat. No. 8,367,709 B2

In the Claims:

Claim 1 (continued):

Column 255, line 64, change "—(CH$_2$)$_r$5-" to -- —(CH$_2$)$_r$-5- --.

Column 256, line 8, change "—NR$^8$C(O)R$^d$," to -- —NR$^8$C(O)R$^c$, --.

Column 256, lines 8 and 9, change "—NR$^8$C(O)OR$^d$," to -- —NR$^8$C(O)OR$^c$, --.

Column 256, line 10, change "—NR$^8$S(O)$_p$R$^d$," to -- —NR$^8$S(O)$_p$R$^c$, --.

Column 256, line 11, change "—S(O)$_p$R$^d$," to -- —S(O)$_p$R$^c$, --.

Column 256, line 21, change "—(CH$_2$)$_r$C$_{3-7}$" to -- —(CH$_2$)$_r$-C$_{3-7}$ --.

Column 256, line 29, change "—(CH$_2$)$_r$5-" to -- —(CH$_2$)$_r$-5- --.

Claim 6:

Column 267, line 6, change "3-carbamoyl benzyl," to -- 3-carbamoylbenzyl, --.

Claim 8:

Column 270, line 22, change "—CO$_2$(CH$_2$)$_2$N(EO$_2$," to -- —CO$_2$(CH$_2$)$_2$N(Et)$_2$, --.

Column 272, lines 44 and 45, change "3-carbamoyl benzyl," to -- 3-carbamoylbenzyl, --.